US009057066B2

(12) United States Patent
Hung et al.

(10) Patent No.: US 9,057,066 B2
(45) Date of Patent: Jun. 16, 2015

(54) COMPOSITIONS AND THEIR USES DIRECTED TO HUNTINGTIN

(71) Applicants: Isis Pharmaceuticals, Inc., Carlsbad, CA (US); CHDI Foundation Inc., New York, NY (US)

(72) Inventors: Gene Hung, San Diego, CA (US); Janet M. Leeds, Encinitas, CA (US); C. Frank Bennett, Carlsbad, CA (US); Susan M. Freier, San Diego, CA (US)

(73) Assignees: Isis Pharmaceuticals, Inc., Carlsbad, CA (US); CHDI Foundation Inc., New York, NY (US)

( * ) Notice: Subject to any disclaimer, the term of this patent is extended or adjusted under 35 U.S.C. 154(b) by 0 days.

(21) Appl. No.: 13/708,839

(22) Filed: Dec. 7, 2012

(65) Prior Publication Data

US 2013/0189782 A1 Jul. 25, 2013

Related U.S. Application Data

(63) Continuation of application No. 12/618,470, filed on Nov. 13, 2009, now abandoned, which is a continuation of application No. 11/627,921, filed on Jan. 26, 2007, now abandoned.

(60) Provisional application No. 60/836,290, filed on Aug. 7, 2006, provisional application No. 60/762,954, filed on Jan. 26, 2006.

(51) Int. Cl.

*C07H 21/02* (2006.01)
*A01N 43/04* (2006.01)
*C12N 15/113* (2010.01)

(52) U.S. Cl.

CPC .......... *C12N 15/113* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search

None
See application file for complete search history.

(56) References Cited

U.S. PATENT DOCUMENTS

| | | | |
|---|---|---|---|
| 5,595,756 A | 1/1997 | Bally et al. | |
| 5,700,922 A | 12/1997 | Cook | |
| 5,801,154 A | 9/1998 | Baracchini et al. | |
| 5,998,148 A | 12/1999 | Bennett et al. | |
| 6,043,060 A | 3/2000 | Imanishi | |
| 6,147,200 A | 11/2000 | Manoharan et al. | |
| 6,582,908 B2 | 6/2003 | Fodor et al. | |
| 6,670,461 B1 | 12/2003 | Wengel et al. | |
| 7,320,965 B2 | 1/2008 | Sah et al. | |
| 8,658,608 B2 * | 2/2014 | Glazer et al. | 514/44 A |
| 2001/0053519 A1 | 12/2001 | Fodor et al. | |
| 2003/0109476 A1 | 6/2003 | Kmiec | |
| 2003/0144242 A1 | 7/2003 | Ward et al. | |
| 2003/0228597 A1 | 12/2003 | Cowsert et al. | |
| 2004/0092465 A1 | 5/2004 | Dobie | |
| 2004/0096880 A1 | 5/2004 | Kmiec | |
| 2004/0137471 A1 | 7/2004 | Vickers et al. | |
| 2005/0042646 A1 | 2/2005 | Davidson | |
| 2005/0096284 A1 | 5/2005 | McSwiggen | |
| 2005/0191638 A1 | 9/2005 | McSwiggen | |
| 2005/0255086 A1 | 11/2005 | Davidson | |
| 2005/0255487 A1 | 11/2005 | Khvorova et al. | |
| 2006/0051769 A1 | 3/2006 | Barts | |
| 2007/0031844 A1 | 2/2007 | Khvorova et al. | |
| 2007/0099860 A1 | 5/2007 | Sah | |
| 2008/0015158 A1 | 1/2008 | Ichiro | |
| 2008/0039418 A1 | 2/2008 | Freier | |
| 2008/0274989 A1 | 11/2008 | Davidson et al. | |
| 2009/0092981 A1 | 4/2009 | Swayze et al. | |

FOREIGN PATENT DOCUMENTS

| | | |
|---|---|---|
| WO | WO 94/26764 | 11/1994 |
| WO | WO 01/79283 | 10/2001 |
| WO | WO 03/013437 | 2/2003 |
| WO | WO 03/064625 | 8/2003 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/105995 | 11/2005 |
| WO | WO 2005/116204 | 12/2005 |
| WO | WO 2008/018795 | 2/2008 |
| WO | WO 2011/097388 | 8/2011 |

OTHER PUBLICATIONS

Bennett et al., "Antisense oligonucleoties as a tool for gene functionalization and target validation" Biochimica Biophysica Acta (1999) 1489:19-30.

Boado et al., "Antisense-mediated down-regulation of the human huntington gene" *Journal of Pharmacology and Experimental Therapeutics* (2000) 295:239-243.

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" *Proc. Natl. Acad. Sci. USA* (2005) 102:11023-11028.

Branch et al., "A good antisense molecule is hard to find," TIBS (1998) 23:45-50.

Caplen et al., "Rescue of polyglutamine-mediated cytotoxicity by double-stranded RNA-mediated RNA interference" Human Molecular Genetics (2002) 11(2):175-184.

(Continued)

*Primary Examiner* — Jennifer McDonald
(74) *Attorney, Agent, or Firm* — Casimir Jones, S.C.

(57) ABSTRACT

Disclosed herein are compounds, compositions and methods for modulating the expression of huntingtin in a cell, tissue or animal. Further provided are methods of slowing or preventing Huntington's disease progression using an antisense compound targeted to huntingtin. Additionally provided are methods of delaying or preventing the onset of Huntingtin's disease in an individual susceptible to Huntingtin's Disease. Also provided are uses of disclosed compounds and compositions in the manufacture of a medicament for treatment of diseases and disorders.

17 Claims, No Drawings

(56) References Cited

OTHER PUBLICATIONS

Chang et al., "Structural Analysis of Complementary DNA and Amino Acid Sequences of Human and Rat Androgen Receptors" PNAS (1988) 85:7211-7215.
Chin "On the Preparation and Utilization of Isolated and Purififed Oligonucleotides." Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Davidson et al., "Molecular medicine for the brain: silencing of disease genes with RNA interference" Lancet Neurol. (2004) 3:145-149.
Diaz-Hernandez et al., "Full Motor Recovery Despite Striatal Neuron Loss and Formation of Irreversible Amyloid-Like Inclusions in a Conditional Mouse Model of Huntington's Disease" *J. Neurosci* (2005) 25:9773-9781.
Eder et al., "Inhibition of LNCaP Prostate Cancer Cells by Means of Androgen Receptor Antisense Oligonucleotides" Cancer Gene Therapy (2000) 7(7):997-1007.
Gonzalez-Alegre et al., "Technology Insight: therapeutic RNA interference—how far from the neurology clinic?" Nature Clinical Practice 3:394-404.
Gryaznov et al., "Oligodeoxyribonucleotide N3'->P5' Phosphoramidates Synthesis and Hybridization Properties" *J. Am. Chem. Soc.* (1994) 116:3143-3144.
Haque et al., "Antisense gene therapy for neurodegenerative disease" *Experimental Neurology* (1997) 144:139-146.
Harper et al., "Ten years of presymptomatic testing for Huntington's disease: the experience of the UK Huntington's Disease Prediction Consortium" J. Med. Genet. 37:567-571.
Harper et al., "RNA interference improves motor and neuropathological abnormalities in a Huntington's disease mouse model" *PNAS* (2005) 102:5820-5825.
Hasholt et al., "Antisense downregulation of mutant huntingtin in a cell model" *Journal of Gene Medicine* (2003) 5:528-538.
Hersch et al., "Translating Therapies for Huntington's Disease from Genetic Animal Models to Clinical Trials" *NeuroRX* (2004) 1:298-306.
Hersch et al., "Neuroprotect on for Huntington's disease: Ready, set, slow" Neurotherapeutics (2008) 5(2):226-236.
Kordasiewicz et al., "Sustained Therapeutic Reversal of Huntington's Disease by Transient Repression of Huntingtin Synthesis" Neuron (2012) 74:1031-1044.
Liu et al., "Specific inhibition of Huntington's disease gene expression by siRNAs in cultures cells" *Proceedings of the Japan Academy. Series B, Physical and Biological Sciences* (2003) 79B:293-298.
MacDonald et al., "A novel gene containing a trinucleotide repeat that is expanded and unstable on Huntington's disease chromosomes" Cell (1993) 72(6):971-983.
Machida et al., "rAAV-mediated shRNA ameliorated neuropathology in Huntington disease model mouse" *Biochem. Biophys. Res. Commun.* (2006) 343:190-197.
MacMillan et al., "Molecular analysis and clinical correlations of theHuntington's disease mutation" Lancet (1993) 342:954-958.
Maher et al., "Comparative hybrid arrest by tandem antisense oligodeoxyribonucleotides or oligodeoxyribonucleoside methylphosphonates in a cell-free system" *Nuc. Acid. Res.* (1988) 16:3341-3358.
Martin et al., "38. Ein neuer Zugang zu 2'-O-Alkylribonucleosiden and Eigenschaften deren Oligonucleotide" *Helv. Chim. Acta* (1995) 78:486-504.
Nellemann et al., "Inhibition of Huntington synthesis by antisense oligonucleotides" *Molecular and Cellular Neurosciences* (2000) 16:313-323.
New England BioLabs, Inc. Catalogue (1998): 121, 284.
Nguyen et al., "Clioquinol down-regulates mutant huntingtin expression in vitro and mitigates pathology in a Huntington's disease mouse model" *PNAS* (2005) 102:11840-11845.
Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.
Reynolds et al., "Rational siRNA design for RNA interference" Nature Biotechnology (2004) 22:326-330/.
Sanghvi et al., "Heterocyclic Base Modifications in Nucleic Acids and Their Applications in Antisense Oligonucleotides" Antisense Research and Applications (1993) pp. 273-288.
Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.
Sheehan et al., "Biochemical properties of phosphonoacetate and thiophosphonoacetate oligodeoxyribonucleotides" *Nucleic Acids Research* (2003) 31:4109-4118.
The Huntington's Disease Collaborative Research Group "A Novel Gene Containing a Trinucleotide Repeat That Is Expanded and Unstable on Huntington's Disease Chromosomes" Cell (1993) 72(6):971-983.
Uhlmann et al., "Antisense oligonucleotides: a new therapeutic principle" *Chemical Reviews* (1990) 90:543-584.
Vickers et al., "Efficient Reduction of Target RNAs by Small Interfering RNA and Rnase H-dependent Antisense Agents. A comparative analysis." J Biol. Chem. (2003) 278:7108-7118.
Wang et al., "Clinico-pathological rescue of a model mouse of Huntington's disease by siRNA" *Neurosci. Res.* (2005) 53:241-249.
Woolf et al., "Specificity of antisense oligonucleotides in vivo" *Proc. Natl. Acad. Sci. USA* (1992) 89:7305-7309.
Yen et al., "Sequence-specific cleavage of Huntingtin mRNA by catalytic DNA" Annals of Neurology (1999) 46(3):366-373.
Office Action from U.S. Appl. No. 11/627,916 dated Dec. 11, 2008.
Office Action from U.S. Appl. No. 11/627,916 dated Apr. 19, 2010.
Final Rejection from U.S. Appl. No. 11/627,916 dated Aug. 12, 2009.
Office Action from U.S. Appl. No. 11/627,921 dated Aug. 21, 2008.
Office Action from U.S. Appl. No. 11/627,921 dated Jun. 9, 2009.
International Search Report for Application # PCT/US2007/002215 dated Nov. 16, 2007.
International Search Report for Application # PCT/US2007/002171 dated Sep. 26, 2007.
International Search Report for Application # PCT/US2010/048532 dated Jan. 26, 2011.
Anderson et al., "An Overview of Psychiatric Symptoms in Huntington's Disease" Current Psychiatry Reports (2001) 3:379-388.

* cited by examiner

SEQUENCE LISTING

```
<160> NUMBER OF SEQ ID NOS: 369

<210> SEQ ID NO 1
<211> LENGTH: 11155
<212> TYPE: DNA
<213> ORGANISM: Homo sapiens

<400> SEQUENCE: 1

taatggagag cttgacctca tctgatacct tcactgaagg aaacaactta gtgtcttttg      60

tgttgaacac tgaggtaaaa aattggaata gttgattata tgaactctgc taaaattgag     120

tgcattttac attttttaag gccttgttgg gccctggtta aataattatt tttaaaaatc     180
```

-continued

```
cttaaggagc ctattataaa cagatctgtg gtcttaatga aatgtgatta atactgtgca    240
ttattttaag aacttttgac ttttcaaaaa acttttacaa catttcccat ttgatagcgg    300
cataggttta agcacttctc atctctaagt tagtggacaa aaaaccctca tggatagtct    360
aataatgttt gctacaagtc catgttgagt tttatactcc attttatttt cagttttaaa    420
aactgtggtt aaatatgtgt aacataaaat ttatgttctt aaccattttt tgcgtataca    480
gttcgctggt attaaataca tttaaataat gtcatggaat cattgctacc acccatctct    540
gtaacctttt gatcatgtaa cactgaagct ctgttcccat tgaactctat tcctcctttc    600
ccgccaagtc cctggcaacc acgattcttc tttctgtctt ctgaatttga ctactttggg    660
ttctcatata ctttaggagt cacacagtat ttgttttact tagcataatg tccccaaagc    720
tcatgcatgt tgtagcctat gttagaactt cctaatgttt caggccaaat actattccat    780
tgtatggata ggccacattt tgcttttcca ttcctctgtc catggacact tgtattgctt    840
catgttttag ccattgtgaa tcatgctgtt atgaacgtgg gtgtacagat agctcctgga    900
gactctgctt tccatttttt tggctaaata cccagaaatg gagttgcttt tacattccaa    960
ttttaattta aaacattcat atcattgagt gttttactta atagtatagt agttaacaaa   1020
cttaataaaa tagtattttg gtaataattt gctggtagtc cattgttcag ttttttttagg   1080
taaattacac aggacatttc aagtggacat gaaacatctt gtgatgtgga atcatgcccc   1140
aagctgatgg ctaaacatat gaaataccat accctaaatt tagtagattt agtctttgca   1200
atttaggaga taacctgtta tattgttagg tttttgtcga aaagctttgt cctcatattt   1260
ccaacttgct gtaaaatttg tttgtgaaga caaatatttt tgtatgggtt ttttcttttt   1320
catattaaaa agaaatgtcc acattggaat ttttttggag tttttagagc taatagagct   1380
tttcataatg tagtgggaat gagtgatcag taagctctta gcagtttcca tgcgtgcatt   1440
tctgtgcctt gaaataaatg acagatgagt acatttgtgt tctgtgtgta aaatgtgctc   1500
tttcctcatt gcacttccat gttggagggc ttgtctcttg gtgatcacac ttcaaaattc   1560
tcacagcccc ccttgaaccg tttaggtgtt agacggtacc gacaaccagt atttgggcct   1620
gcagattgga cagccccagg atgaagatga ggaagccaca ggtattcttc ctgatgaagc   1680
ctcggaggcc ttcaggaact cttccatggg tatgtggact acaggtgatg cgctacaaag   1740
tggtttgtat tcagacctgg acatcttaat tatatctttg cttccaagaa gaagtccttt   1800
gatactgttt tctgagttct gaatagctga tgaaaatgac caattgagga ataatcatac   1860
tttttcttga tctaaatctt atacttttga gttatcttag cataaatgta taattgtatt   1920
ttaagtggaa atttgtcact taatcttgat ttctctgttt ttaaagccct tcaacaggca   1980
catttattga aaaacatgag tcactgcagg cagccttctg acagcagtgt tgataaattt   2040
gtgttgagag atgaagctac tgaaccgggt gatcaagaaa acaagccttg ccgcatcaaa   2100
ggtgacattg gacagtccac tgatgatgac tctgcacctc ttgtccattg tgtccgcctt   2160
ttatctgctt cgtttttgct aacaggggga aaaaatgtgc tggttccgga cagggatgtg   2220
agggtcagcg tgaaggccct ggccctcagc tgtgtgggag cagctgtggc cctccacccg   2280
gaatctttct tcagcaaact ctataaagtt cctcttgaca ccacggaata ccctgaggaa   2340
cagtatgtct cagacatctt gaactacatc gatcatggag acccacaggt tcgaggagcc   2400
actgccattc tctgtgggac cctcatctgc tccatcctca gcaggtcccg cttccacgtg   2460
ggagattgga tgggcaccat tagaaccctc acaggaaata cattttcttt ggcggattgc   2520
attcctttgc tgcggaaaac actgaaggat gagtcttctg ttacttgcaa gttagcttgt   2580
```

-continued

```
acagctgtga ggaactgtgt catgagtctc tgcagcagca gctacagtga gttaggactg   2640
cagctgatca tcgatgtgct gactctgagg aacagttcct attggctggt gaggacagag   2700
cttctggaaa cccttgcaga gattgacttc aggctggtga gctttttgga ggcaaaagca   2760
gaaaacttac acagaggggc tcatcattat acagggcttt taaaactgca agaacgagtg   2820
ctcaataatg ttgtcatcca tttgcttgga gatgaagacc ccagggtgcg acatgttgcc   2880
gcagcatcac taattaggct tgtcccaaag ctgttttata aatgtgacca aggacaagct   2940
gatccagtag tggccgtggc aagagatcaa agcagtgttt acctgaaact tctcatgcat   3000
gagacgcagc ctccatctca tttctccgtc agcacaataa ccagaatata tagaggctat   3060
aacctactac caagcataac agacgtcact atggaaaata acctttcaag agttattgca   3120
gcagtttctc atgaactaat cacatcaacc accagagcac tcacatttgg atgctgtgaa   3180
gctttgtgtc ttctttccac tgccttccca gtttgcattt ggagtttagg ttggcactgt   3240
ggagtgcctc cactgagtgc ctcagatgag tctaggaaga gctgtaccgt tgggatggcc   3300
acaatgattc tgaccctgct ctcgtcagct tggttcccat tggatctctc agcccatcaa   3360
gatgctttga ttttggccgg aaacttgctt gcagccagtg ctcccaaatc tctgagaagt   3420
tcatgggcct ctgaagaaga agccaaccca gcagccacca agcaagagga ggtctggcca   3480
gccctggggg accgggccct ggtgcccatg gtggagcagc tcttctctca cctgctgaag   3540
gtgattaaca tttgtgccca cgtcctggat gacgtggctc ctggacccgc aataaaggca   3600
gccttgcctt ctctaacaaa cccccccttct ctaagtccca tccgacgaaa ggggaaggag   3660
aaagaaccag gagaacaagc atctgtaccg ttgagtccca agaaaggcag tgaggccagt   3720
gcagcttcta gacaatctga tacctcaggt cctgttacaa caagtaaatc ctcatcactg   3780
gggagtttct atcatcttcc ttcatacctc aaactgcatg atgtcctgaa agctacacac   3840
gctaactaca aggtcacgct ggatcttcag aacagcacgg aaaagtttgg agggtttctt   3900
cgctcagcct tggatgttct ttctcagata ctagagctgg ccacactgca ggacattggg   3960
aagtgtgttg aagagatcct aggatacctg aaatcctgct ttagtcgaga accaatgatg   4020
gcaactgttt gtgttcaaca attgttgaag actctctttg gcacaaactt ggcctcccag   4080
tttgatggct tatcttccaa ccccagcaag tcacaaggcc gagcacagcg ccttggctcc   4140
tccagtgtga ggccaggctt gtaccactac tgcttcatgg ccccgtacac ccacttcacc   4200
caggccctcg ctgacgccag cctgaggaac atggtgcagg cggagcagga gaacgacacc   4260
tcgggatggt ttgatgtcct ccagaaagtg tctacccagt tgaagacaaa cctcacgagt   4320
gtcacaaaga accgtgcaga taagaatgct attcataatc acattcgttt gtttgaacct   4380
cttgttataa aagctttaaa acagtacacg actacaacat gtgtgcagtt acagaagcag   4440
gttttagatt tgctggcgca gctggttcag ttacgggtta attactgtct tctggattca   4500
gatcaggtgt ttattggctt tgtattgaaa cagtttgaat acattgaagt gggccagttc   4560
agggaatcag aggcaatcat tccaaacatc tttttcttct tggtattact atcttatgaa   4620
cgctatcatt caaaacagat cattggaatt cctaaaatca ttcagctctg tgatggcatc   4680
atggccagtg gaaggaaggc tgtgacacat gccataccgg ctctgcagcc catagtccac   4740
gacctctttg tattaagagg aacaaataaa gctgatgcag gaaaagagct tgaaacccaa   4800
aaagaggtgg tggtgtcaat gttactgaga ctcatccagt accatcaggt gttggagatg   4860
ttcattcttg tcctgcagca gtgccacaag gagaatgaag acaagtggaa gcgactgtct   4920
```

-continued

```
cgacagatag ctgacatcat cctcccaatg ttagccaaac agcagatgca cattgactct   4980
catgaagccc ttggagtgtt aaatacatta tttgagattt tggccccttc ctccctccgt   5040
ccggtagaca tgcttttacg gagtatgttc gtcactccaa acacaatggc gtccgtgagc   5100
actgttcaac tgtggatatc gggaattctg gccattttga gggttctgat ttcccagtca   5160
actgaagata ttgttctttc tcgtattcag gagctctcct tctctccgta tttaatctcc   5220
tgtacagtaa ttaataggtt aagagatggg gacagtactt caacgctaga agaacacagt   5280
gaagggaaac aaataaagaa tttgccagaa gaaacatttt caaggtatgc tttctatctg   5340
agcctataac taacccatgc cttttgggaa gtcacgtgat gtttcacagt cagtaagtct   5400
ggaataatac ctggtcttgc ttcacttctg agttgggtaa agaagtctgt atcagtgtaa   5460
ttttctaatc cgtcctgcat tatctatggc tcttggttca tacctgtctt gaagttctgt   5520
catgttctgt ctcttgtcct cagtagagat gctacagcag tggctcgcct caggcagggc   5580
agggcagtgg ggtggctgtc ctgggggcag gcagtagggg cacgctgacg tcagggaagt   5640
tgaaacccaa gagaagccag taaaagtgag tctcagattg tcaccatgtg ctggcagttt   5700
tacacgctgt cagtaataaa aatcttctcc ctgcagggca gcctgcctcc aataaatacg   5760
tgtagtatca aatcctgtct tccctcataa attgtttgga agctccccaa ggacagtgat   5820
gaggcactcg taagtgcttg ctgcctagat gggtccctct ccacctttgc tagattctga   5880
gcattcactg agttagagct gcttctgcaa atgtgctgct tctgctaagt ggctgtgact   5940
tcatgcagcc ttcacttggt ttgtcatcag tggagatgcc ctgtgttgtc gaaggagata   6000
agcccagtaa gcctgctggg caccttttgg tttgcaggtt cagcaggcag cccatggctt   6060
tccctgtgtc gcattgaagc agctggctaa aattgatgat acattaaatt cctgtgacag   6120
atgatcagct tgtatttgtg taatggtgta cagttcacaa agcttaaaaa aatgctacct   6180
gccatttcat cctcagcgag gaaggtgata cacagagaga ccaagtgact gtgtccacgg   6240
cgacggcgct ctgcatttca ctttagcggt taatgtactc tacctatatt tttactttat   6300
atttaccata tatcttttca tgtatacttg gcgtaagtgc tttatagtag tcacctaatt   6360
cactgtcatc ttttttgttt cttggaaggt ttctattaca actggttggt attcttttag   6420
aagacattgt tacaaaacag ctgaaggtgg aaatgagtga gcagcaacat actttctatt   6480
gccaggaact aggcacactg ctaatgtgtc tgatccacat cttcaagtct ggaatgttcc   6540
ggagaatcac agcagctgcc actaggctgt tccgcagtga tggctgtggc ggcagtttct   6600
acaccctgga cagcttgaac ttgcgggctc gttccatgat caccacccac ccggccctgg   6660
tgctgctctg gtgtcagata ctgctgcttg tcaaccacac cgactaccgc tggtgggcag   6720
aagtgcagca gaccccgaaa agacacagtc tgtccagcac aaagttactt agtccccaga   6780
tgtctggaga agaggaggat tctgacttgg cagccaaact tggaatgtgc aatagagaaa   6840
tagtacgaag aggggctctc attctcttct gtgattatgt ctgtcagaac ctccatgact   6900
ccgagcactt aacgtggctc attgtaaatc acattcaaga tctgatcagc ctttcccacg   6960
agcctccagt acaggacttc atcagtgccg ttcatcggaa ctctgctgcc agcggcctgt   7020
tcatccaggc aattcagtct cgttgtgaaa acctttcaac tccaaccatg ctgaagaaaa   7080
ctcttcagtg cttggagggg atccatctca gccagtcggg agctgtgctc acgctgtatg   7140
tggacaggct tctgtgcacc cctttccgtg tgctggctcg catggtcgac atccttgctt   7200
gtcgccgggt agaaatgctt ctggctgcaa atttacagca tggcccagtt gccaatggaa   7260
gaactcaaca gaatccagga ataccttcag agcagcgggc tcgctcagag gtttcgtctc   7320
```

-continued

```
tccaccatgc aagactcact tagtccctct cctccagtct cttcccaccc gctggacggg   7380
gatgggcacg tgtcactgga aacagtgagt ccggacaaag actggtacgt tcatcttgtc   7440
aaatcccagt gttggaccag gtcagattct gcactgctgg aaggtgcaga gctggtgaat   7500
cggattcctg ctgaagatat gaatgccttc atgatgaact cggagttcaa cctaagcctg   7560
ctagctccat gcttaagcct agggatgagt gaaatttctg gtggccagaa gagtgccctt   7620
tttgaagcag cccgtgaggt gactctggcc cgtgtgagcg gcaccgtgca gcagctccct   7680
gctgtccatc atgtcttcca gcccgagctg cctgcagaac cggcggccta ctggagcaag   7740
ttgaatgatc tgtttgggga tgctgcactg tatcagtccc tgcccactct ggcccgggcc   7800
ctggcacagt acctggtggt ggtctccaaa ctgcccagtc atttgcacct tcctcctgag   7860
aaagagaagg acattgtgaa attcgtggtg gcaacccttg aggccctgtc ctggcatttg   7920
atccatgagc agatcccgct gagtctggat ctccaggcag ggctggactg ctgctgcctg   7980
gccctgcagc tgcctggcct ctggagcgtg gtctcctcca cagagtttgt gacccacgcc   8040
tgctccctca tccactgtgt gcacttcatc ctggaggccg ttgcagtgca gcctggagag   8100
cagcttctta gtccagaaag aaggacaaat accccaaaag ccatcagcga ggaggaggag   8160
gaagtagatc caaacacaca gaatcctaag tatatcactg cagcctgtga gatggtggca   8220
gaaatggtgg agtctctgca gtcggtgttg gccttgggtc ataaaaggaa tagcggcgtg   8280
ccggcgtttc tcacgccatt gctcaggaac atcatcatca gcctggcccg cctgcccctt   8340
gtcaacagct acacacgtgt gcccccactg gtgtggaagc ttggatggtc acccaaaccg   8400
ggaggggatt ttggcacagc attccctgag atccccgtgg agttcctcca ggaaaaggaa   8460
gtctttaagg agttcatcta ccgcatcaac acactaggct ggaccagtcg tactcagttt   8520
gaagaaactt gggccaccct ccttggtgtc ctggtgacgc agcccctcgt gatggagcag   8580
gaggagagcc caccagaaga agacacagag aggacccaga tcaacgtcct ggccgtgcag   8640
gccatcacct cactggtgct cagtgcaatg actgtgcctg tggccggcaa cccagctgta   8700
agctgcttgg agcagcagcc ccggaacaag cctctgaaag ctctcgacac caggtttggg   8760
aggaagctga gcattatcag agggattgtg gagcaagaga ttcaagcaat ggtttcaaag   8820
agagagaata ttgccaccca tcatttatat caggcatggg atcctgtccc ttctctgtct   8880
ccggctacta caggtgccct catcagccac gagaagctgc tgctgcagat caaccccgag   8940
cgggagctgg ggagcatgag ctacaaactc ggccaggtgt ccatacactc cgtgtggctg   9000
gggaacagca tcacacccct gagggaggag gaatgggacg aggaagagga ggaggaggcc   9060
gacgcccctg caccttcgtc accacccacg tctccagtca actccaggaa acaccgggct   9120
ggagttgaca tccactcctg ttcgcagttt ttgcttgagt tgtacagccg ctggatcctg   9180
ccgtccagct cagccaggag gaccccggcc atcctgatca gtgaggtggt cagatccctt   9240
ctagtggtct cagacttgtt caccgagcgc aaccagtttg agctgatgta tgtgacgctg   9300
acagaactgc gaagggtgca cccttcagaa gacgagatcc tcgctcagta cctggtgcct   9360
gccacctgca aggcagctgc cgtccttggg atggacaagg ccgtggcgga gcctgtcagc   9420
cgcctgctgg agagcacgct caggagcagc cacctgccca gcagggttgg agccctgcac   9480
ggcatcctct atgtgctgga gtgcgacctg ctggacgaca ctgccaagca gctcatcccg   9540
gtcatcagcg actatctcct ctccaacctg aaagggatcg cccactgcgt gaacattcac   9600
agccagcagc acgtactggt catgtgtgcc actgcgtttt acctcattga gaactatcct   9660
```

ctggacgtag ggccggaatt ttcagcatca ataatacaga tgtgtggggt gatgctgtct 9720
ggaagtgagg agtccacccc ctccatcatt taccactgtg ccctcagagg cctggagcgc 9780
ctcctgctct ctgagcagct ctcccgcctg gatgcagaat cgctggtcaa gctgagtgtg 9840
gacagagtga acgtgcacag cccgcaccgg gccatggcgg ctctgggcct gatgctcacc 9900
tgcatgtaca caggaaagga gaaagtcagt ccgggtagaa cttcagaccc taatcctgca 9960
gcccccgaca gcgagtcagt gattgttgct atggagcggg tatctgttct ttttgatagg 10020
atcaggaaag gctttccttg tgaagccaga gtggtggcca ggatcctgcc ccagtttcta 10080
gacgacttct tcccacccca ggacatcatg aacaaagtca tcggagagtt tctgtccaac 10140
cagcagccat acccccagtt catggccacc gtggtgtata aggtgtttca gactctgcac 10200
agcaccgggc agtcgtccat ggtccgggac tgggtcatgc tgtccctctc caacttcacg 10260
cagagggccc cggtcgccat ggccacgtgg agcctctcct gcttctttgt cagcgcgtcc 10320
accagcccgt gggtcgcggc gatcctccca catgtcatca gcaggatggg caagctggag 10380
caggtggacg tgaacctttt ctgcctggtc gccacagact tctacagaca ccagatagag 10440
gaggagctcg accgcagggc cttccagtct gtgcttgagg tggttgcagc cccaggaagc 10500
ccatatcacc ggctgctgac ttgtttacga aatgtccaca aggtcaccac ctgctgagcg 10560
ccatggtggg agagactgtg aggcggcagc tggggccgga gcctttggaa gtctgcgccc 10620
ttgtgccctg cctccaccga gccagcttgg tccctatggg cttccgcaca tgccgcgggc 10680
ggccaggcaa cgtgcgtgtc tctgccatgt ggcagaagtg ctctttgtgg cagtggccag 10740
gcagggagtg tctgcagtcc tggtggggct gagcctgagg ccttccagaa agcaggagca 10800
gctgtgctgc accccatgtg ggtgaccagg tcctttctcc tgatagtcac ctgctggttg 10860
ttgccaggtt acagctgctc ttgcatctgg gccagaagtc ctccctcctg caggctgggt 10920
gttggcccct ctgctgtcct gcagtagaag gtgccgtgag caggctttgg gaacactggc 10980
ctgggtctcc ctggtggggt gtgcatgcca cgccccgtgt ctggatgcac agatgccatg 11040
gcctgtgctg ggccagtagc tgggggtgct agacacccgg caccattctc ccttctctct 11100
tttcttctca ggatttaaaa tttaattata tcagtaaaga gattaatttt aacgt 11155

<210> SEQ ID NO 2
<211> LENGTH: 916
<212> TYPE: DNA
<213> ORGANISM: Homo sapiens

<400> SEQUENCE: 2
acctgaagtc aagctccccc accattcggc ggacagcggc tggatcagca gtgagcatct 60
gccagcactc aagaaggaca caatatttct atagttggct actaaatgtg ctcttaggct 120
tactcgttcc tgtcgaggat gaacactcca ctctgctgat tcttggcgtg ctgctcaccc 180
tgaggtattt ggtgcccttg ctgcagcagc aggtcaagga cacaagcctg aaaggcagct 240
tcggagtgac aaggaaagaa atggaagtct ctccttctgc agagcagctt gtccaggttt 300
atgaactgac gttacatcat acacagcacc aagaccacaa tgttgtgacc ggagccctgg 360
agctgttgca gcagctcttc agaacgcctc cacccgagct tctgcaaacc ctgaccgcag 420
tcgggggcat tgggcagctc accgctgcta aggaggagtc tggtggccga agccgtagtg 480
ggagtattgt ggaacttata ggcaagttat tagcaaggtc tactcttaca attaactttg 540
cagtaatact agttacactc tattgattat gggcctgccc tgtgctaagc agtctgcatt 600
ccatcttcct tgccaaaact tataatacaa atttcatctt tatcttatac atagggggaa 660
gttgggctag ggtgtggtag gctcacgcct gtaatttcag cactttggaa ggatcgcttc 720
aggccaggag tttgagacaa cctggccaag tgagacctgt ctctacaaaa aaaaaaaaaa 780
aaaacccggg ctctttttcc ggctgcggca aacacgaggt atacacatcg gcctggcctt 840
gtcgtttctc gacccctttc tgtccagggg gaatccgcgg tccaaaggag gcgataatcc 900
aaccggcaga aataaa 916

<210> SEQ ID NO 3
<211> LENGTH: 10348
<212> TYPE: DNA
<213> ORGANISM: Homo sapiens

<400> SEQUENCE: 3
ttgctgtgtg aggcagaacc tgcgggggca ggggcgggct ggttccctgg ccagccattg 60
gcagagtccg caggctaggg ctgtcaatca tgctggccgg cgtggccccg cctccgccgg 120
cgcggccccg cctccgccgg cgcacgtctg ggacgcaagg cgccgtgggg gctgccggga 180
cgggtccaag atggacggcc gctcaggttc tgcttttacc tgcggcccag agccccattc 240
attgccccgg tgctgagcgg cgccgcgagt cggcccgagg cctccgggga ctgccgtgcc 300
gggcgggaga ccgccatggc gaccctggaa aagctgatga aggccttcga gtccctcaag 360
tccttccagc agcagcagca gcagcagcag cagcagcagc agcagcagca gcagcagcag 420
cagcagcagc aacagccgcc accgccgccg ccgccgccgc cgcctcctca gcttcctcag 480
ccgccgccgc aggcacagcc gctgctgcct cagccgcagc cgcccccgcc gccgcccccg 540
ccgccacccg gcccggctgt ggctgaggag ccgctgcacc gaccaaagaa agaactttca 600
gctaccaaga aagaccgtgt gaatcattgt ctgacaatat gtgaaaacat agtggcacag 660
tctgtcagaa attctccaga atttcagaaa cttctgggca tcgctatgga actttttctg 720
ctgtgcagtg atgacgcaga gtcagatgtc aggatggtgg ctgacgaatg cctcaacaaa 780
gttatcaaag ctttgatgga ttctaatctt ccaaggttac agctcgagct ctataaggaa 840
attaaaaaga atggtgcccc tcggagtttg cgtgctgccc tgtggaggtt tgctgagctg 900
gctcacctgg ttcggcctca gaaatgcagg ccttacctgg tgaaccttct gccgtgcctg 960
actcgaacaa gcaagagacc cgaagaatca gtccaggaga ccttggctgc agctgttccc 1020
aaaattatgg cttcttttgg caattttgca aatgacaatg aaattaaggt tttgttaaag 1080
gccttcatag cgaacctgaa gtcaagctcc cccaccattc ggcggacagc ggctggatca 1140
gcagtgagca tctgccagca ctcaagaagg acacaatatt tctatagttg gctactaaat 1200
gtgctcttag gcttactcgt tcctgtcgag gatgaacact ccactctgct gattcttggc 1260
gtgctgctca ccctgaggta tttggtgccc ttgctgcagc agcaggtcaa ggacacaagc 1320
ctgaaaggca gcttcggagt gacaaggaaa gaaatggaag tctctccttc tgcagagcag 1380
cttgtccagg tttatgaact gacgttacat catacacagc accaagacca caatgttgtg 1440
accggagccc tggagctgtt gcagcagctc ttcagaacgc ctccacccga gcttctgcaa 1500
accctgaccg cagtcggggg cattgggcag ctcaccgctg ctaaggagga gtctggtggc 1560
cgaagccgta gtgggagtat tgtggaactt atagctggag gggttcctc atgcagccct 1620 gtcctttcaa gaaaacaaaa aggcaaagtg ctcttaggag aagaagaagc cttggaggat 1680
gactctgaat cgagatcgga tgtcagcagc tctgccttaa cagcctcagt gaaggatgag 1740
atcagtggag agctggctgc ttcttcaggg gtttccactc cagggtcagc aggtcatgac 1800

-continued

```
atcatcacag aacagccacg gtcacagcac acactgcagg cggactcagt ggatctggcc   1860
agctgtgact tgacaagctc tgccactgat ggggatgagg aggatatctt gagccacagc   1920
tccagccagg tcagcgccgt cccatctgac cctgccatgg acctgaatga tgggacccag   1980
gcctcgtcgc ccatcagcga cagctcccag accaccaccg aagggcctga ttcagctgtt   2040
accccttcag acagttctga aattgtgtta gacggtaccg acaaccagta tttgggcctg   2100
cagattggac agccccagga tgaagatgag gaagccacag gtattcttcc tgatgaagcc   2160
tcggaggcct tcaggaactc ttccatggcc cttcaacagg cacatttatt gaaaaacatg   2220
agtcactgca ggcagccttc tgacagcagt gttgataaat ttgtgttgag agatgaagct   2280
actgaaccgg gtgatcaaga aaacaagcct tgccgcatca aaggtgacat tggacagtcc   2340
actgatgatg actctgcacc tcttgtccat tgtgtccgcc ttttatctgc ttcgtttttg   2400
ctaacagggg gaaaaaatgt gctggttccg gacagggatg tgagggtcag cgtgaaggcc   2460
ctggccctca gctgtgtggg agcagctgtg gccctccacc cggaatcttt cttcagcaaa   2520
ctctataaag ttcctcttga caccacggaa taccctgagg aacagtatgt ctcagacatc   2580
ttgaactaca tcgatcatgg agacccacag gttcgaggag ccactgccat tctctgtggg   2640
accctcatct gctccatcct cagcaggtcc cgcttccacg tgggagattg gatgggcacc   2700
attagaaccc tcacaggaaa tacattttct ttggcggatt gcattccttt gctgcggaaa   2760
acactgaagg atgagtcttc tgttacttgc aagttagctt gtacagctgt gaggaactgt   2820
gtcatgagtc tctgcagcag cagctacagt gagttaggac tgcagctgat catcgatgtg   2880
ctgactctga ggaacagttc ctattggctg gtgaggacag agcttctgga aacccttgca   2940
gagattgact tcaggctggt gagctttttg gaggcaaaag cagaaaactt acacagaggg   3000
gctcatcatt atacagggct tttaaaactg caagaacgag tgctcaataa tgttgtcatc   3060
catttgcttg gagatgaaga ccccagggtg cgacatgttg ccgcagcatc actaattagg   3120
cttgtcccaa agctgtttta taaatgtgac caaggacaag ctgatccagt agtggccgtg   3180
gcaagagatc aaagcagtgt ttacctgaaa cttctcatgc atgagacgca gcctccatct   3240
catttctccg tcagcacaat aaccagaata tatagaggct ataacctact accaagcata   3300
acagacgtca ctatggaaaa taacctttca agagttattg cagcagtttc tcatgaacta   3360
atcacatcaa ccaccagagc actcacattt ggatgctgtg aagctttgtg tcttctttcc   3420
actgccttcc cagtttgcat ttggagttta ggttggcact gtggagtgcc tccactgagt   3480
gcctcagatg agtctaggaa gagctgtacc gttgggatgg ccacaatgat tctgaccctg   3540
ctctcgtcag cttggttccc attggatctc tcagcccatc aagatgcttt gattttggcc   3600
ggaaacttgc ttgcagccag tgctcccaaa tctctgagaa gttcatgggc ctctgaagaa   3660
gaagccaacc cagcagccac caagcaagag gaggtctggc cagccctggg ggaccgggcc   3720
ctggtgccca tggtggagca gctcttctct cacctgctga aggtgattaa catttgtgcc   3780
cacgtcctgg atgacgtggc tcctggaccc gcaataaagg cagccttgcc ttctctaaca   3840
aacccccctt ctctaagtcc catccgacga aaggggaagg agaaagaacc aggagaacaa   3900
gcatctgtac cgttgagtcc caagaaaggc agtgaggcca gtgcagcttc tagacaatct   3960
gatacctcag gtcctgttac aacaagtaaa tcctcatcac tggggagttt ctatcatctt   4020
ccttcatacc tcaaactgca tgatgtcctg aaagctacac acgctaacta caaggtcacg   4080
ctggatcttc agaacagcac ggaaaagttt ggagggtttc tccgctcagc cttggatgtt   4140
ctttctcaga tactagagct ggccacactg caggacattg ggaagtgtgt tgaagagatc   4200
```

-continued

```
ctaggatacc tgaaatcctg ctttagtcga gaaccaatga tggcaactgt ttgtgttcaa   4260
caattgttga agactctctt tggcacaaac ttggcctccc agtttgatgg cttatcttcc   4320
aaccccagca agtcacaagg ccgagcacag cgccttggct cctccagtgt gaggccaggc   4380
ttgtaccact actgcttcat ggccccgtac acccacttca cccaggccct cgctgacgcc   4440
agcctgagga acatggtgca ggcggagcag gagaacgaca cctcgggatg gtttgatgtc   4500
ctccagaaag tgtctaccca gttgaagaca aacctcacga gtgtcacaaa gaaccgtgca   4560
gataagaatg ctattcataa tcacattcgt ttgtttgaac ctcttgttat aaaagcttta   4620
aaacagtaca cgactacaac atgtgtgcag ttacagaagc aggttttaga tttgctggcg   4680
cagctggttc agttacgggt taattactgt cttctggatt cagatcaggt gtttattggc   4740
tttgtattga aacagtttga atacattgaa gtgggccagt tcagggaatc agaggcaatc   4800
attccaaaca tctttttctt cttggtatta ctatcttatg aacgctatca ttcaaaacag   4860
atcattggaa ttcctaaaat cattcagctc tgtgatggca tcatggccag tggaaggaag   4920
gctgtgacac atgccatacc ggctctgcag cccatagtcc acgacctctt tgtattaaga   4980
ggaacaaata aagctgatgc aggaaaagag cttgaaaccc aaaaagaggt ggtggtgtca   5040
atgttactga gactcatcca gtaccatcag gtgttggaga tgttcattct tgtcctgcag   5100
cagtgccaca aggagaatga agacaagtgg aagcgactgt ctcgacagat agctgacatc   5160
atcctcccaa tgttagccaa acagcagatg cacattgact ctcatgaagc ccttggagtg   5220
ttaaatacat tatttgagat tttggcccct tcctccctcc gtccggtaga catgctttta   5280
cggagtatgt tcgtcactcc aaacacaatg gcgtccgtga gcactgttca actgtggata   5340
tcgggaattc tggccatttt gagggttctg atttcccagt caactgaaga tattgttctt   5400
tctcgtattc aggagctctc cttctctccg tatttaatct cctgtacagt aattaatagg   5460
ttaagagatg gggacagtac ttcaacgcta gaagaacaca gtgaagggaa acaaataaag   5520
aatttgccag aagaaacatt ttcaaggttt ctattacaac tggttggtat tcttttagaa   5580
gacattgtta caaaacagct gaaggtggaa atgagtgagc agcaacatac tttctattgc   5640
caggaactag gcacactgct aatgtgtctg atccacatct tcaagtctgg aatgttccgg   5700
agaatcacag cagctgccac taggctgttc cgcagtgatg gctgtggcgg cagtttctac   5760
accctggaca gcttgaactt gcgggctcgt tccatgatca ccacccaccc ggccctggtg   5820
ctgctctggt gtcagatact gctgcttgtc aaccacaccg actaccgctg gtgggcagaa   5880
gtgcagcaga ccccgaaaag acacagtctg tccagcacaa agttacttag tccccagatg   5940
tctggagaag aggaggattc tgacttggca gccaaacttg gaatgtgcaa tagagaaata   6000
gtacgaagag gggctctcat tctcttctgt gattatgtct gtcagaacct ccatgactcc   6060
gagcacttaa cgtggctcat tgtaaatcac attcaagatc tgatcagcct ttcccacgag   6120
cctccagtac aggacttcat cagtgccgtt catcggaact ctgctgccag cggcctgttc   6180
atccaggcaa ttcagtctcg ttgtgaaaac ctttcaactc caaccatgct gaagaaaact   6240
cttcagtgct tggaggggat ccatctcagc cagtcgggag ctgtgctcac gctgtatgtg   6300
gacaggcttc tgtgcacccc tttccgtgtg ctggctcgca tggtcgacat ccttgcttgt   6360
cgccgggtag aaatgcttct ggctgcaaat ttacagagca gcatggccca gttgccaatg   6420
gaagaactca acagaatcca ggaatacctt cagagcagcg ggctcgctca gagacaccaa   6480
aggctctatt ccctgctgga caggtttcgt ctctccacca tgcaagactc acttagtccc   6540
```

-continued

```
tctcctccag tctcttccca cccgctggac ggggatgggc acgtgtcact ggaaacagtg   6600
agtccggaca aagactggta cgttcatctt gtcaaatccc agtgttggac caggtcagat   6660
tctgcactgc tggaaggtgc agagctggtg aatcggattc ctgctgaaga tatgaatgcc   6720
ttcatgatga actcggagtt caacctaagc ctgctagctc catgcttaag cctagggatg   6780
agtgaaattt ctggtggcca gaagagtgcc ctttttgaag cagcccgtga ggtgactctg   6840
gcccgtgtga gcggcaccgt gcagcagctc cctgctgtcc atcatgtctt ccagcccgag   6900
ctgcctgcag agccggcggc ctactggagc aagttgaatg atctgtttgg ggatgctgca   6960
ctgtatcagt ccctgcccac tctggcccgg gccctggcac agtacctggt ggtggtctcc   7020
aaactgccca gtcatttgca ccttcctcct gagaaagaga aggacattgt gaaattcgtg   7080
gtggcaaccc ttgaggccct gtcctggcat ttgatccatg agcagatccc gctgagtctg   7140
gatctccagg cagggctgga ctgctgctgc ctggccctgc agctgcctgg cctctggagc   7200
gtggtctcct ccacagagtt tgtgacccac gcctgctccc tcatctactg tgtgcacttc   7260
atcctggagg ccgttgcagt gcagcctgga gagcagcttc ttagtccaga aagaaggaca   7320
aataccccaa aagccatcag cgaggaggag gaggaagtag atccaaacac acagaatcct   7380
aagtatatca ctgcagcctg tgagatggtg gcagaaatgg tggagtctct gcagtcggtg   7440
ttggccttgg gtcataaaag gaatagcggc gtgccggcgt ttctcacgcc attgctcagg   7500
aacatcatca tcagcctggc ccgcctgccc cttgtcaaca gctacacacg tgtgccccca   7560
ctggtgtgga agcttggatg gtcacccaaa ccgggagggg attttggcac agcattccct   7620
gagatccccg tggagttcct ccaggaaaag gaagtcttta aggagttcat ctaccgcatc   7680
aacacactag gctggaccag tcgtactcag tttgaagaaa cttgggccac cctccttggt   7740
gtcctggtga cgcagcccct cgtgatggag caggaggaga gcccaccaga agaagacaca   7800
gagaggaccc agatcaacgt cctggccgtg caggccatca cctcactggt gctcagtgca   7860
atgactgtgc ctgtggccgg caacccagct gtaagctgct tggagcagca gccccggaac   7920
aagcctctga aagctctcga caccaggttt gggaggaagc tgagcattat cagagggatt   7980
gtggagcaag agattcaagc aatggtttca aagagagaga atattgccac ccatcattta   8040
tatcaggcat gggatcctgt cccttctctg tctccggcta ctacaggtgc cctcatcagc   8100
cacgagaagc tgctgctaca gatcaacccc gagcgggagc tggggagcat gagctacaaa   8160
ctcggccagg tgtccataca ctccgtgtgg ctggggaaca gcatcacacc cctgagggag   8220
gaggaatggg acgaggaaga ggaggaggag gccgacgccc ctgcaccttc gtcaccaccc   8280
acgtctccag tcaactccag gaaacaccgg gctggagttg acatccactc ctgttcgcag   8340
tttttgcttg agttgtacag ccgctggatc ctgccgtcca gctcagccag gaggaccccg   8400
gccatcctga tcagtgaggt ggtcagatcc cttctagtgg tctcagactt gttcaccgag   8460
cgcaaccagt ttgagctgat gtatgtgacg ctgacagaac tgcgaagggt gcacccttca   8520
gaagacgaga tcctcgctca gtacctggtg cctgccacct gcaaggcagc tgccgtcctt   8580
gggatggaca aggccgtggc ggagcctgtc agccgcctgc tggagagcac gctcaggagc   8640
agccacctgc ccagcagggt tggagccctg cacggcgtcc tctatgtgct ggagtgcgac   8700
ctgctggacg acactgccaa gcagctcatc ccggtcatca gcgactatct cctctccaac   8760
ctgaaaggga tcgcccactg cgtgaacatt cacagccagc agcacgtact ggtcatgtgt   8820
gccactgcgt tttacctcat tgagaactat cctctggacg tagggccgga attttcagca   8880
tcaataatac agatgtgtgg ggtgatgctg tctggaagtg aggagtccac cccctccatc   8940
```

```
atttaccact gtgccctcag aggcctggag cgcctcctgc tctctgagca gctctcccgc   9000
ctggatgcag aatcgctggt caagctgagt gtggacagag tgaacgtgca cagcccgcac   9060
cgggccatgg cggctctggg cctgatgctc acctgcatgt acacaggaaa ggagaaagtc   9120
agtccgggta gaacttcaga ccctaatcct gcagcccccg acagcgagtc agtgattgtt   9180
gctatggagc gggtatctgt tctttttgat aggatcagga aaggctttcc ttgtgaagcc   9240
agagtggtgg ccaggatcct gccccagttt ctagacgact tcttcccacc ccaggacatc   9300
atgaacaaag tcatcggaga gtttctgtcc aaccagcagc catacccccca gttcatggcc   9360
accgtggtgt ataaggtgtt tcagactctg cacagcaccg ggcagtcgtc catggtccgg   9420
gactgggtca tgctgtccct ctccaacttc acgcagaggg ccccggtcgc catggccacg   9480
tggagcctct cctgcttctt tgtcagcgcg tccaccagcc cgtgggtcgc ggcgatcctc   9540
ccacatgtca tcagcaggat gggcaagctg gagcaggtgg acgtgaacct tttctgcctg   9600
gtcgccacag acttctacag acaccagata gaggaggagc tcgaccgcag ggccttccag   9660
tctgtgcttg aggtggttgc agccccagga agcccatatc accggctgct gacttgttta   9720
cgaaatgtcc acaaggtcac cacctgctga gcgccatggt gggagagact gtgaggcggc   9780
agctggggcc ggagcctttg gaagtctgtg cccttgtgcc ctgcctccac cgagccagct   9840
tggtccctat gggcttccgc acatgccgcg ggcggccagg caacgtgcgt gtctctgcca   9900
tgtggcagaa gtgctctttg tggcagtggc caggcaggga gtgtctgcag tcctggtggg   9960
gctgagcctg aggccttcca gaaagcagga gcagctgtgc tgcaccccat gtgggtgacc  10020
aggtcctttc tcctgatagt cacctgctgg ttgttgccag gttgcagctg ctcttgcatc  10080
tgggccagaa gtcctccctc ctgcaggctg gctgttggcc cctctgctgt cctgcagtag  10140
aaggtgccgt gagcaggctt tgggaacact ggcctgggtc tccctggtgg ggtgtgcatg  10200
ccacgccccg tgtctggatg cacagatgcc atggcctgtg ctgggccagt ggctgggggt  10260
gctagacacc cggcaccatt ctcccttctc tcttttcttc tcaggattta aaatttaatt  10320
atatcagtaa agagattaat tttaacgt                                     10348
```

<210> SEQ ID NO 4
<211> LENGTH: 13495
<212> TYPE: DNA
<213> ORGANISM: Homo sapiens

<400> SEQUENCE: 4

```
gctgccggga cgggtccaag atggacggcc gctcaggttc tgcttttacc tgcggcccag     60
agccccattc attgccccgg tgctgagcgg cgccgcgagt cggcccgagg cctccgggga    120
ctgccgtgcc gggcgggaga ccgccatggc gaccctggaa aagctgatga aggccttcga    180
gtccctcaag tccttccagc agcagcagca gcagcagcag cagcagcagc agcagcagca    240
gcagcagcag cagcaacagc cgccaccgcc gccgccgccg ccgccgcctc ctcagcttcc    300
tcagccgccg ccgcaggcac agccgctgct gcctcagccg cagccgcccc cgccgccgcc    360
cccgccgcca cccggcccgg ctgtggctga ggagccgctg caccgaccaa agaaagaact    420
ttcagctacc aagaaagacc gtgtgaatca ttgtctgaca atatgtgaaa acatagtggc    480
acagtctgtc agaaattctc cagaatttca gaaacttctg ggcatcgcta tggaactttt    540
tctgctgtgc agtgatgacg cagagtcaga tgtcaggatg gtggctgacg aatgcctcaa    600
caaagttatc aaagctttga tggattctaa tcttccaagg ttacagctcg agctctataa    660
```

-continued

```
ggaaattaaa aagaatggtg cccctcggag tttgcgtgct gccctgtgga ggtttgctga    720
gctggctcac ctggttcggc ctcagaaatg caggccttac ctggtgaacc ttctgccgtg    780
cctgactcga acaagcaaga gacccgaaga atcagtccag gagaccttgg ctgcagctgt    840
tcccaaaatt atggcttctt ttggcaattt tgcaaatgac aatgaaatta aggttttgtt    900
aaaggccttc atagcgaacc tgaagtcaag ctcccccacc attcggcgga cagcggctgg    960
atcagcagtg agcatctgcc agcactcaag aaggacacaa tatttctata gttggctact   1020
aaatgtgctc ttaggcttac tcgttcctgt cgaggatgaa cactccactc tgctgattct   1080
tggcgtgctg ctcaccctga ggtatttggt gcccttgctg cagcagcagg tcaaggacac   1140
aagcctgaaa ggcagcttcg gagtgacaag gaaagaaatg gaagtctctc cttctgcaga   1200
gcagcttgtc caggtttatg aactgacgtt acatcataca cagcaccaag accacaatgt   1260
tgtgaccgga gccctggagc tgttgcagca gctcttcaga acgcctccac ccgagcttct   1320
gcaaaccctg accgcagtcg gggcattggg gcagctcacc gctgctaagg aggagtctgg   1380
tggccgaagc cgtagtggga gtattgtgga acttatagct ggagggggtt cctcatgcag   1440
ccctgtcctt tcaagaaaac aaaaaggcaa agtgctctta ggagaagaag aagccttgga   1500
ggatgactct gaatcgagat cggatgtcag cagctctgcc ttaacagcct cagtgaagga   1560
tgagatcagt ggagagctgg ctgcttcttc aggggtttcc actccagggt cagcaggtca   1620
tgacatcatc acagaacagc cacggtcaca gcacacactg caggcggact cagtggatct   1680
ggccagctgt gacttgacaa gctctgccac tgatggggat gaggaggata tcttgagcca   1740
cagctccagc caggtcagcg ccgtcccatc tgaccctgcc atggacctga atgatgggac   1800
ccaggcctcg tcgcccatca gcgacagctc ccagaccacc accgaagggc ctgattcagc   1860
tgttacccct tcagacagtt ctgaaattgt gttagacggt accgacaacc agtatttggg   1920
cctgcagatt ggacagcccc aggatgaaga tgaggaagcc acaggtattc ttcctgatga   1980
agcctcggag gccttcagga actcttccat ggcccttcaa caggcacatt tattgaaaaa   2040
catgagtcac tgcaggcagc cttctgacag cagtgttgat aaatttgtgt tgagagatga   2100
agctactgaa ccgggtgatc aagaaaacaa gccttgccgc atcaaaggtg acattggaca   2160
gtccactgat gatgactctg cacctcttgt ccattgtgtc cgccttttat ctgcttcgtt   2220
tttgctaaca gggggaaaaa atgtgctggt tccggacagg gatgtgaggg tcagcgtgaa   2280
ggccctggcc ctcagctgtg tgggagcagc tgtggccctc cacccggaat ctttcttcag   2340
caaactctat aaagttcctc ttgacaccac ggaatacct gaggaacagt atgtctcaga   2400
catcttgaac tacatcgatc atggagaccc acaggttcga ggagccactg ccattctctg   2460
tgggaccctc atctgctcca tcctcagcag gtcccgcttc cacgtgggag attggatggg   2520
caccattaga accctcacag gaaatacatt ttctttggcg gattgcattc ctttgctgcg   2580
gaaaacactg aaggatgagt cttctgttac ttgcaagtta gcttgtacag ctgtgaggaa   2640
ctgtgtcatg agtctctgca gcagcagcta cagtgagtta ggactgcagc tgatcatcga   2700
tgtgctgact ctgaggaaca gttcctattg gctggtgagg acagagcttc tggaaaccct   2760
tgcagagatt gacttcaggc tggtgagctt tttggaggca aaagcagaaa acttacacag   2820
aggggctcat cattatacag ggcttttaaa actgcaagaa cgagtgctca ataatgttgt   2880
catccatttg cttggagatg aagaccccag ggtgcgacat gttgccgcag catcactaat   2940
taggcttgtc ccaaagctgt tttataaatg tgaccaagga caagctgatc cagtagtggc   3000
cgtggcaaga gatcaaagca gtgtttacct gaaacttctc atgcatgaga cgcagcctcc   3060
```

-continued

```
atctcatttc tccgtcagca caataaccag aatatataga ggctataacc tactaccaag   3120
cataacagac gtcactatgg aaaataacct ttcaagagtt attgcagcag tttctcatga   3180
actaatcaca tcaaccacca gagcactcac atttggatgc tgtgaagctt tgtgtcttct   3240
ttccactgcc ttcccagttt gcatttggag tttaggttgg cactgtggag tgcctccact   3300
gagtgcctca gatgagtcta ggaagagctg taccgttggg atggccacaa tgattctgac   3360
cctgctctcg tcagcttggt tcccattgga tctctcagcc catcaagatg ctttgatttt   3420
ggccggaaac ttgcttgcag ccagtgctcc caaatctctg agaagttcat gggcctctga   3480
agaagaagcc aacccagcag ccaccaagca agaggaggtc tggccagccc tgggggaccg   3540
ggccctggtg cccatggtgg agcagctctt ctctcacctg ctgaaggtga ttaacatttg   3600
tgcccacgtc ctggatgacg tggctcctgg acccgcaata aaggcagcct tgccttctct   3660
aacaaacccc ccttctctaa gtcccatccg acgaaagggg aaggagaaag aaccaggaga   3720
acaagcatct gtaccgttga gtcccaagaa aggcagtgag gccagtgcag cttctagaca   3780
atctgatacc tcaggtcctg ttacaacaag taaatcctca tcactgggga gtttctatca   3840
tcttccttca tacctcaaac tgcatgatgt cctgaaagct acacacgcta actacaaggt   3900
cacgctggat cttcagaaca gcacggaaaa gtttggaggg tttctccgct cagccttgga   3960
tgttctttct cagatactag agctggccac actgcaggac attgggaagt gtgttgaaga   4020
gatcctagga tacctgaaat cctgctttag tcgagaacca atgatggcaa ctgtttgtgt   4080
tcaacaattg ttgaagactc tctttggcac aaacttggcc tcccagtttg atggcttatc   4140
ttccaacccc agcaagtcac aaggccgagc acagcgcctt ggctcctcca gtgtgaggcc   4200
aggcttgtac cactactgct tcatggcccc gtacacccac ttcacccagg ccctcgctga   4260
cgccagcctg aggaacatgg tgcaggcgga gcaggagaac gacacctcgg gatggtttga   4320
tgtcctccag aaagtgtcta cccagttgaa gacaaacctc acgagtgtca caaagaaccg   4380
tgcagataag aatgctattc ataatcacat tcgtttgttt gaacctcttg ttataaaagc   4440
tttaaaacag tacacgacta caacatgtgt gcagttacag aagcaggttt tagatttgct   4500
ggcgcagctg gttcagttac gggttaatta ctgtcttctg gattcagatc aggtgtttat   4560
tggctttgta ttgaaacagt ttgaatacat tgaagtgggc cagttcaggg aatcagaggc   4620
aatcattcca aacatctttt tcttcttggt attactatct tatgaacgct atcattcaaa   4680
acagatcatt ggaattccta aaatcattca gctctgtgat ggcatcatgg ccagtggaag   4740
gaaggctgtg acacatgcca taccggctct gcagcccata gtccacgacc tctttgtatt   4800
aagaggaaca aataaagctg atgcaggaaa agagcttgaa acccaaaaag aggtggtggt   4860
gtcaatgtta ctgagactca tccagtacca tcaggtgttg gagatgttca ttcttgtcct   4920
gcagcagtgc cacaaggaga atgaagacaa gtggaagcga ctgtctcgac agatagctga   4980
catcatcctc ccaatgttag ccaaacagca gatgcacatt gactctcatg aagcccttgg   5040
agtgttaaat acattatttg agattttggc cccttcctcc ctccgtccgg tagacatgct   5100
tttacggagt atgttcgtca ctccaaacac aatggcgtcc gtgagcactg ttcaactgtg   5160
gatatcggga attctggcca ttttgagggt tctgatttcc cagtcaactg aagatattgt   5220
tctttctcgt attcaggagc tctccttctc tccgtattta atctcctgta cagtaattaa   5280
taggttaaga gatggggaca gtacttcaac gctagaagaa cacagtgaag ggaaacaaat   5340
aaagaatttg ccagaagaaa cattttcaag gtttctatta caactggttg gtattctttt   5400
```

-continued

```
agaagacatt gttacaaaac agctgaaggt ggaaatgagt gagcagcaac atactttcta   5460
ttgccaggaa ctaggcacac tgctaatgtg tctgatccac atcttcaagt ctggaatgtt   5520
ccggagaatc acagcagctg ccactaggct gttccgcagt gatggctgtg gcggcagttt   5580
ctacaccctg gacagcttga acttgcgggc tcgttccatg atcaccaccc acccggccct   5640
ggtgctgctc tggtgtcaga tactgctgct tgtcaaccac accgactacc gctggtgggc   5700
agaagtgcag cagaccccga aaagacacag tctgtccagc acaaagttac ttagtcccca   5760
gatgtctgga gaagaggagg attctgactt ggcagccaaa cttggaatgt gcaatagaga   5820
aatagtacga agaggggctc tcattctctt ctgtgattat gtctgtcaga acctccatga   5880
ctccgagcac ttaacgtggc tcattgtaaa tcacattcaa gatctgatca gcctttccca   5940
cgagcctcca gtacaggact tcatcagtgc cgttcatcgg aactctgctg ccagcggcct   6000
gttcatccag gcaattcagt ctcgttgtga aaacctttca actccaacca tgctgaagaa   6060
aactcttcag tgcttggagg ggatccatct cagccagtcg ggagctgtgc tcacgctgta   6120
tgtggacagg cttctgtgca cccctttccg tgtgctggct cgcatggtcg acatccttgc   6180
ttgtcgccgg gtagaaatgc ttctggctgc aaatttacag agcagcatgg cccagttgcc   6240
aatggaagaa ctcaacagaa tccaggaata ccttcagagc agcgggctcg ctcagagaca   6300
ccaaaggctc tattccctgc tggacaggtt tcgtctctcc accatgcaag actcacttag   6360
tccctctcct ccagtctctt cccacccgct ggacggggat gggcacgtgt cactggaaac   6420
agtgagtccg gacaaagact ggtacgttca tcttgtcaaa tcccagtgtt ggaccaggtc   6480
agattctgca ctgctggaag gtgcagagct ggtgaatcgg attcctgctg aagatatgaa   6540
tgccttcatg atgaactcgg agttcaacct aagcctgcta gctccatgct taagcctagg   6600
gatgagtgaa atttctggtg gccagaagag tgcccttttt gaagcagccc gtgaggtgac   6660
tctggcccgt gtgagcggca ccgtgcagca gctccctgct gtccatcatg tcttccagcc   6720
cgagctgcct gcagagccgg cggcctactg gagcaagttg aatgatctgt ttggggatgc   6780
tgcactgtat cagtccctgc ccactctggc ccgggccctg gcacagtacc tggtggtggt   6840
ctccaaactg cccagtcatt tgcaccttcc tcctgagaaa gagaaggaca ttgtgaaatt   6900
cgtggtggca acccttgagg ccctgtcctg gcatttgatc catgagcaga tcccgctgag   6960
tctggatctc caggcagggc tggactgctg ctgcctggcc ctgcagctgc ctggcctctg   7020
gagcgtggtc tcctccacag agtttgtgac ccacgcctgc tccctcatct actgtgtgca   7080
cttcatcctg gaggccgttg cagtgcagcc tggagagcag cttcttagtc cagaaagaag   7140
gacaaatacc ccaaaagcca tcagcgagga ggaggaggaa gtagatccaa acacacagaa   7200
tcctaagtat atcactgcag cctgtgagat ggtggcagaa atggtggagt ctctgcagtc   7260
ggtgttggcc ttgggtcata aaaggaatag cggcgtgccg gcgtttctca cgccattgct   7320
caggaacatc atcatcagcc tggcccgcct gccccttgtc aacagctaca cacgtgtgcc   7380
cccactggtg tggaagcttg gatggtcacc caaaccggga ggggattttg gcacagcatt   7440
ccctgagatc cccgtggagt tcctccagga aaaggaagtc tttaaggagt tcatctaccg   7500
catcaacaca ctaggctgga ccagtcgtac tcagtttgaa gaaacttggg ccaccctcct   7560
tggtgtcctg gtgacgcagc ccctcgtgat ggagcaggag gagagcccac cagaagaaga   7620
cacagagagg acccagatca acgtcctggc cgtgcaggcc atcacctcac tggtgctcag   7680
tgcaatgact gtgcctgtgg ccggcaaccc agctgtaagc tgcttggagc agcagccccg   7740
gaacaagcct ctgaaagctc tcgacaccag gtttgggagg aagctgagca ttatcagagg   7800
```

-continued

```
gattgtggag caagagattc aagcaatggt ttcaaagaga gagaatattg ccacccatca   7860
tttatatcag gcatgggatc ctgtcccttc tctgtctccg gctactacag gtgccctcat   7920
cagccacgag aagctgctgc tacagatcaa ccccgagcgg gagctgggga gcatgagcta   7980
caaactcggc caggtgtcca tacactccgt gtggctgggg aacagcatca cacccctgag   8040
ggaggaggaa tgggacgagg aagaggagga ggaggccgac gcccctgcac cttcgtcacc   8100
acccacgtct ccagtcaact ccaggaaaca ccgggctgga gttgacatcc actcctgttc   8160
gcagtttttg cttgagttgt acagccgctg gatcctgccg tccagctcag ccaggaggac   8220
cccggccatc ctgatcagtg aggtggtcag atcccttcta gtggtctcag acttgttcac   8280
cgagcgcaac cagtttgagc tgatgtatgt gacgctgaca gaactgcgaa gggtgcaccc   8340
ttcagaagac gagatcctcg ctcagtacct ggtgcctgcc acctgcaagg cagctgccgt   8400
ccttgggatg gacaaggccg tggcggagcc tgtcagccgc ctgctggaga gcacgctcag   8460
gagcagccac ctgcccagca gggttggagc cctgcacggc gtcctctatg tgctggagtg   8520
cgacctgctg gacgacactg ccaagcagct catcccggtc atcagcgact atctcctctc   8580
caacctgaaa gggatcgccc actgcgtgaa cattcacagc cagcagcacg tactggtcat   8640
gtgtgccact gcgttttacc tcattgagaa ctatcctctg gacgtagggc cggaattttc   8700
agcatcaata atacagatgt gtggggtgat gctgtctgga agtgaggagt ccacccccctc   8760
catcatttac cactgtgccc tcagaggcct ggagcgcctc ctgctctctg agcagctctc   8820
ccgcctggat gcagaatcgc tggtcaagct gagtgtggac agagtgaacg tgcacagccc   8880
gcaccgggcc atggcggctc tgggcctgat gctcacctgc atgtacacag gaaaggagaa   8940
agtcagtccg ggtagaactt cagaccctaa tcctgcagcc cccgacagcg agtcagtgat   9000
tgttgctatg gagcgggtat ctgttctttt tgataggatc aggaaaggct ttccttgtga   9060
agccagagtg gtggccagga tcctgcccca gtttctagac gacttcttcc caccccagga   9120
catcatgaac aaagtcatcg gagagtttct gtccaaccag cagccatacc cccagttcat   9180
ggccaccgtg gtgtataagg tgtttcagac tctgcacagc accgggcagt cgtccatggt   9240
ccgggactgg gtcatgctgt ccctctccaa cttcacgcag agggccccgg tcgccatggc   9300
cacgtggagc ctctcctgct tctttgtcag cgcgtccacc agcccgtggg tcgcggcgat   9360
cctcccacat gtcatcagca ggatgggcaa gctggagcag gtggacgtga accttttctg   9420
cctggtcgcc acagacttct acagacacca gatagaggag gagctcgacc gcagggcctt   9480
ccagtctgtg cttgaggtgg ttgcagcccc aggaagccca tatcaccggc tgctgacttg   9540
tttacgaaat gtccacaagg tcaccacctg ctgagcgcca tggtgggaga gactgtgagg   9600
cggcagctgg ggccggagcc tttggaagtc tgcgcccttg tgccctgcct ccaccgagcc   9660
agcttggtcc ctatgggctt ccgcacatgc cgcgggcggc caggcaacgt gcgtgtctct   9720
gccatgtggc agaagtgctc tttgtggcag tggccaggca gggagtgtct gcagtcctgg   9780
tggggctgag cctgaggcct tccagaaagc aggagcagct gtgctgcacc ccatgtgggt   9840
gaccaggtcc tttctcctga tagtcacctg ctggttgttg ccaggttgca gctgctcttg   9900
catctgggcc agaagtcctc cctcctgcag gctggctgtt ggcccctctg ctgtcctgca   9960
gtagaaggtg ccgtgagcag gctttgggaa cactggcctg ggtctccctg gtggggtgtg  10020
catgccacgc cccgtgtctg gatgcacaga tgccatggcc tgtgctgggc cagtggctgg  10080
gggtgctaga cacccggcac cattctccct tctctctttt cttctcagga tttaaaattt  10140
```

aattatatca gtaaagagat taattttaac gtaactcttt ctatgcccgt gtaaagtatg 10200
tgaatcgcaa ggcctgtgct gcatgcgaca gcgtccgggg tggtggacag ggcccccggc 10260
cacgctccct ctcctgtagc cactggcata gccctcctga gcacccgctg acatttccgt 10320
tgtacatgtt cctgtttatg cattcacaag gtgactggga tgtagagagg cgttagtggg 10380
caggtggcca cagcaggact gaggacaggc cccattatc ctaggggtgc gctcacctgc 10440
agcccctcct cctcgggcac agacgactgt cgttctccac ccaccagtca gggacagcag 10500
cctccctgtc actcagctga gaaggccagc cctccctggc tgtgagcagc ctccactgtg 10560
tccagagaca tgggcctccc actcctgttc cttgctagcc ctggggtggc gtctgcctag 10620
gagctggctg gcaggtgttg ggacctgctg ctccatggat gcatgcccta agagtgtcac 10680
tgagctgtgt tttgtctgag cctctctcgg tcaacagcaa agcttggtgt cttggcactg 10740
ttagtgacag agcccagcat cccttctgcc cccgttccag ctgacatctt gcacggtgac 10800
ccctttagt caggagagtg cagatctgtg ctcatcggag actgccccac ggccctgtca 10860
gagccgccac tcctatcccc aggccaggtc cctggaccag cctcctgttt gcaggcccag 10920
aggagccaag tcattaaaat ggaagtggat tctggatggc cgggctgctg ctgatgtagg 10980
agctggattt gggagctctg cttgccgact ggctgtgaga cgaggcaggg gctctgcttc 11040
ctcagcccta gaggcgagcc aggcaaggtt ggcgactgtc atgtggcttg gtttggtcat 11100
gcccgtcgat gttttgggta ttgaatgtgg taagtggagg aaatgttgga actctgtgca 11160
ggtgctgcct tgagaccccc aagcttccac ctgtccctct cctatgtggc agctggggag 11220
cagctgagat gtggacttgt atgctgccca catacgtgag ggggagctga aagggagccc 11280
ctcctctgag cagcctctgc caggcctgta tgaggctttt cccaccagct cccaacagag 11340
gcctccccca gccaggacca cctcgtcctc gtggcggggc agcaggagcg gtagaaaggg 11400
gtccgatgtt tgaggaggcc cttaagggaa gctactgaat tataacacgt aagaaaatca 11460
ccattcttcc gtattggttg ggggctcctg tttctcatcc tagctttttc ctggaaagcc 11520
cgctagaagg tttgggaacg aggggaaagt tctcagaact gttggctgct ccccacccgc 11580
ctcccgcctc ccccgcaggt tatgtcagca gctctgagac agcagtatca caggccagat 11640
gttgttcctg gctagatgtt tacatttgta agaaataaca ctgtgaatgt aaaacagagc 11700
cattcccttg gaatgcatat cgctgggctc aacatagagt ttgtcttcct cttgtttacg 11760
acgtgatcta aaccagtcct tagcaagggg ctcagaacac cccgctctgg cagtaggtgt 11820
cccccacccc caaagacctg cctgtgtgct ccggagatga atatgagctc attagtaaaa 11880
atgacttcac ccacgcatat acataaagta tccatgcatg tgcatataga cacatctata 11940
attttacaca cacacctctc aagacggaga tgcatggcct ctaagagtgc ccgtgtcggt 12000
tcttcctgga agttgacttt ccttagaccc gccaggtcaa gttagccgcg tgacggacat 12060
ccaggcgtgg gacgtggtca gggcagggct cattcattgc ccactaggat cccactggcg 12120
aagatggtct ccatatcagc tctctgcaga agggaggaag actttatcat gttcctaaaa 12180
atctgtggca agcacccatc gtattatcca aattttgttg caaatgtgat taatttggtt 12240
gtcaagtttt gggggtgggc tgtggggaga ttgcttttgt tttcctgctg gtaatatcgg 12300
gaaagatttt aatgaaacca gggtagaatt gtttggcaat gcactgaagc gtgtttcttt 12360
cccaaaatgt gcctcccttc cgctgcgggc ccagctgagt ctatgtaggt gatgtttcca 12420
gctgccaagt gctctttgtt actgtccacc ctcatttctg ccagcgcatg tgtcctttca 12480
aggggaaaat gtgaagctga accccctcca gacacccaga atgtagcatc tgagaaggcc 12540
ctgtgcccta aaggacaccc ctcgccccca tcttcatgga gggggtcatt tcagagccct 12600
cggagccaat gaacagctcc tcctcttgga gctgagatga gccccacgtg gagctcggga 12660
cggatagtag acagcaataa ctcggtgtgt ggccgcctgg caggtggaac ttcctcccgt 12720
tgcggggtgg agtgaggtta gttctgtgtg tctggtgggt ggagtcaggc ttctcttgct 12780
acctgtgagc atccttccca gcagacatcc tcatcgggct ttgtccctcc cccgcttcct 12840
ccctctgcgg ggaggacccg ggaccacagc tgctggccag ggtagacttg gagctgtcct 12900
ccagaggggt cacgtgtagg agtgagaaga aggaagatct tgagagctgc tgagggacct 12960
tggagagctc aggatggctc agacgaggac actcgcttgc cgggcctggg cctcctggga 13020
aggagggagc tgctcagaat gccgcatgac aactgaaggc aacctggaag gttcaggggc 13080
cgctcttccc ccatgtgcct gtcacgctct ggtgcagtca aaggaacgcc ttcccctcag 13140
ttgtttctaa gagcagagtc tcccgctgca atctgggtgg taactgccag ccttggagga 13200
tcgtggccaa cgtggacctg cctacggagg gtgggctctg acccaagtgg ggcctccttg 13260
tccaggtctc actgctttgc accgtggtca gagggactgt cagctgagct tgagctcccc 13320
tggagccagc agggctgtga tgggcgagtc ccggagcccc acccagacct gaatgcttct 13380
gagagcaaag ggaaggactg acgagagatg tatatttaat tttttaactg ctgcaaacat 13440
tgtacatcca aattaaagga aaaaaatgga aaccatcaaa aaaaaaaaaa aaaaa 13495

<210> SEQ ID NO 5
<211> LENGTH: 172001
<212> TYPE: DNA
<213> ORGANISM: Homo sapiens

<400> SEQUENCE: 5
cctgcagggg cctctccagc tcactggggg tggggtgggg gtcacacttg gggtcctcag 60
gtcgtgccga ccacgcgcat tctctgcgct ctgcgcagga gctcgcccac cctctccccg 120
tgcagagagc cccgcagctg gctccccgca gggctgtccg ggtgagtatg gctctggcca 180
cgggccagtg tggcgggagg gcaaacccca aggccacctc ggctcagagt ccacggccgg 240
ctgtcgcccc gctccaggcg tcggcggggg atcctttccg catgggcctg cgcccgcgct 300
cggcgccccc tccacggccc cgccccgtcc atggccccgt ccttcatggg cgagcccctc 360
catggccctg cccctccgcg ccccacccct ccctcgcccc acctctcacc ttcctgcccc 420
gcccccagcc tccccaaccc tcaccggcca gtcccctccc ctatcccgtc cgcccctcag 480
ccgccccgcc cctcagccgg cctgcctaat gtccccgtcc ccagcatcgc cccgccccgc 540
ccccgtctcg ccccgcccct caggcggcct ccctgctgtg ccccgccccg gcctcgccac 600
gcccctacct caccacgccc cccgcatcgc cacgcccccc gcatcgccac gcctccctta 660
ccatgcagtc ccgccccgtc ccttcctcgt cccgcctcgc cgcgacactt cacacacagc 720
ttcgcctcac cccattacag tctcaccacg ccccgtcccc tctccgttga gccccgcgcc 780
ttcgcccggg tggggcgctg cgctgtcagc ggccttgctg tgtgaggcag aacctgcggg 840
ggcaggggcg ggctggttcc ctggccagcc attggcagag tccgcaggct agggctgtca 900
atcatgctgg ccggcgtggc cccgcctccg ccggcgcggc cccgcctccg ccggcgcagc 960
gtctgggacg caaggcgccg tgggggctgc cgggacgggt ccaagatgga cggccgctca 1020
ggttctgctt ttacctgcgg cccagagccc cattcattgc cccggtgctg agcggcgccg 1080
cgagtcggcc cgaggcctcc ggggactgcc gtgccgggcg ggagaccgcc atggcgaccc 1140

-continued

```
tggaaaagct gatgaaggcc ttcgagtccc tcaagtcctt ccagcagcag cagcagcagc   1200
agcagcagca gcagcagcag cagcagcagc agcagcagca acagccgcca ccgccgccgc   1260
cgccgccgcc gcctcctcag cttcctcagc cgccgccgca ggcacagccg ctgctgcctc   1320
agccgcagcc gcccccgccg ccgcccccgc cgccacccgg cccggctgtg gctgaggagc   1380
cgctgcaccg accgtgagtt tgggcccgct gcagctccct gtcccggcgg gtcccaggct   1440
acggcgggga tggcggtaac cctgcagcct gcgggccggc gacacgaacc cccggccccg   1500
cagagacaga gtgacccagc aacccagagc ccatgaggga cacccgcccc ctcctggggc   1560
gaggccttcc cccacttcag ccccgctccc tcacttgggt cttcccttgt cctctcgcga   1620
ggggaggcag agccttgttg gggcctgtcc tgaattcacc gaggggagtc acggcctcag   1680
ccctctcgcc cttcgcagga tgcgaagagt tggggcgaga acttgtttct ttttatttgc   1740
gagaaaccag ggcgggggtt cttttaactg cgttgtgaag agaacttgga ggagccgaga   1800
tttgctcagt gccacttccc tcttctagtc tgagagggaa gagggctggg ggcgcgggac   1860
acttcgagag gaggcggggt ttggagctgg agagatgtgg gggcagtgga tgacataatg   1920
cttttaggac gcctcggcgg gagtggcggg gcaggggggg ggcggggagt gagggcgcgt   1980
ccaatgggag atttcttttc ctagtggcac ttaaaacagc ctgagatttg aggctcttcc   2040
tacattgtca ggacatttca tttagttcat gatcacggtg gtagtaacac gattttaagc   2100
accacctaag agatctgctc atctaagcct aagttggtct gcaggcgttt gaatgagttg   2160
tggttgccaa gtaaagtggt gaacttacgt ggtgattaat gaaattatct taaatattag   2220
gaagagttga ttgaagtttt ttgcctatgt gtgttgggaa taaaaccaac acgttgctga   2280
tggggaggtt aattgccgag ggatgaatga ggtgtacatt ttaccagtat tccagtcagg   2340
cttgccagaa tacgggggt ccgcagactc cgtgggcatc tcagatgtgc cagtgaaagg   2400
gtttctgttt gcttcattgc tgacagcttg ttactttttg gaagctaggg gtttctgttg   2460
cttgttcttg gggagaattt ttgaaacagg aaaagagaga ccattaaaac atctagcgga   2520
accccaggac tttccctgga agtctgtgtg tcgagtgtac agtaggagtt aggaagtact   2580
ctggtgcagt tcaggccttt ctcttacctc tcagtattct atttccgatc tggatgtgtc   2640
ccagatggca tttggtaaga atatctctgt taagactgat taatttttag taatatttct   2700
tgttctttgt ttctgttatg atccttgtct cgtcttcaaa gtttaattag aaaatgattc   2760
ggagagcagt gttagcttat ttgttggaat aaaatttagg aataaattat tctaaaggat   2820
ggaaaaactt tttggatatt tggagaaatt ttaaaacaat ttggcttatc tcttcagtaa   2880
gtaatttctc atccagaaat ttactgtagt gcttttctag gaggtaggtg tcataaaagt   2940
tcacacattg catgtatctt gtgtaaacac taaacagggc tcctgatggg aaggaagacc   3000
tttctgctgg gctgcttcag acacttgatc attctaaaaa tatgccttct ctttcttatg   3060
ctgatttgac agaacctgca tttgcttatc ttcaaaatat gggtatcaag aaatttcctt   3120
tgctgccttg acaaaggaga tagattttgt ttcattactt taaggtaata tatgattacc   3180
ttatttaaaa aatttaatca ggactggcaa ggtggcttac acctttaatc cgagcacttt   3240
gggaggccta ggtggacgaa tcacctgagg tcaggagttt gagaccagcc tggctaacat   3300
ggtgaaaccc tgtctctact aaaaatacaa aaattagctg gtcatggtgg cacgtgcctg   3360
taatccaagc tacctgggag gctgaggcag gaaaatcgct tgaacccggg aggcagagtc   3420
tgcagtgagt tgagatcacg ccactgcact ccagcctggg tgacagagcg agactctatc   3480
tcaaaaaaaa tttttttaa tgtattattt ttgcataagt aatacattga catgatacaa   3540
```

-continued

```
attctgtaat tacaaaaggg caataattaa aatatcttcc ttccacccct ttcctctgag   3600
tacctaactt tgtccccaag aacaagcact atttcagttc ctcatgtatc ctgccagata   3660
taacctgttc atattgtaag atagatttaa aatgctctaa aaacaaaagt agtttagaat   3720
aatatatatc tatatatttt ttgagatgta gtctcacatt gtcacccagg ctggagtgca   3780
gtgatacaat ctcggctcac tgcagtctct gcctcccagg ttcaaatgct tctcctgcct   3840
cagccttctg agtagctggg attacaggcg cccaccacca tgtccagcta atttttgtat   3900
ttttagtaga gatggggttt caccatgttg gccaggctgg tcttgaactc ctgaccttgt   3960
gatctgtcca cctcggcctc ccaaagtgct gggattacag gtgtgagcca ccatgcctgg   4020
ctagaataat aacttttaaa ggttcttagc atgctctgaa atcaactgca ttaggtttat   4080
ttatagtttt atagttattt taaataaaat gcatatttgt catatttctc tgtattttgc   4140
tgttgagaaa ggaggtattc actaattttg agtaacaaac actgctcaca aagtttggat   4200
tttggcagtt ctgttcacgt gcttcagcca aaaaatcctc ttctcaaagt aagattgatg   4260
aaagcaattt agaaagtatc tgttctgttt ttatggctct tgctctttgg tgtggaactg   4320
tggtgtcacg ccatgcatgg gcctcagttt atgagtgttt gtgctctgct cagcatacag   4380
gatgcaggag ttccttatgg ggctggctgc aggctcagca aatctagcat gcttgggagg   4440
gtcctcacag taattaggag gcaattaata cttgcttctg gcagtttctt attctccttc   4500
agattcctat ctggtgtttc cctgacttta ttcattcatc agtaaatatt tactaaacat   4560
gtactatgtg cctggcactg ttataggtgc agggctcagc agtgagcaga caaagctctg   4620
ccctcgtgaa gctttcattc taatgaagga catagacagt aagcaagata gataagtaaa   4680
atatacagta cgttaatacg tggaggaact tcaaagcagg gaaggggata gggaaatgtc   4740
agggttaatc gagtgttaac ttatttttat ttttaaaaaa attgttaagg gctttccagc   4800
aaaacccaga aagcctgcta gacaaattcc aaaagagctg tagcactaag tgttgacatt   4860
tttattttat tttgttttgt tttgtttttt ttgagacagt tcttgctcta tcagccaggc   4920
tggagtgcac tagtgtgatc ttggctcact gcaacctctg cctcttgggt tcaagtgatt   4980
ctcatgcctc agcctcctgt ttagctggga ttatagacat gcactgccat gcctgggtaa   5040
ttttttttt ttcccccgag acggagtctt gctctgtcgc ccaggctgga gtgcagtggc   5100
gcgatctcag ctcactgcaa gctccgcttc ccgagttcac gccattctcc tgcctcagtc   5160
tcccaagtag ctgggactac aggcgcctgc caccacgtcc agctaatttt tttgtatttt   5220
taatagagac ggggtttcac cgtgttagcc aggatgatct tgatctcctg acctcgtcat   5280
ccgccgacct tgtgatccgc ccacctcggc ctcccaaagt gctgggatta caggcatgag   5340
ccactgtgcc cggccacgcc tgggtaattt ttgtattttt agtagagatg gggttttgcc   5400
atgatgagca ggctggtctc gaactcccgg cctcatgtga tctgcctgcc ttggcctccc   5460
aaagtgctag gattacaggc atgagccacc atacctggcc agtgttgata ttttaaatac   5520
ggtgttcagg gaaggtccac tgagaagaca gctttttttt tttttttttt tggggttggg   5580
gggcaaggtc ttgctcttta acccaggctg gaatgcagta tcactatcgt agctcacttc   5640
agccttgaac tcctgggctc aagtgatcct cccacctcaa cctcacaatg tgttgggact   5700
ataggtgtga gccatcacac ctggccagat gatggctttt gagtaaagac ctcaagcgag   5760
ttaagagtct agtgtaaggg tgtatgaagt agtggtattc cagatggggg gaacaggtcc   5820
aaaatcttcc tgtttcagga atagcaagga tgtcatttta gttgggtgaa ttgagtgagg   5880
```

-continued

```
gggacatttg tagtaagaag taaggtccaa gaggtcaagg gagtgccata tcagaccaat   5940
actacttgcc ttgtagatgg aataaagata ttggcattta tgtgagtgag atgggatgtc   6000
actggaggat tagagcagag gagtagcatg atctgaattt caatcttaag tgaactctgg   6060
ctgacaacag agtgaagggg aacaccggca aaagcagaaa ccagttagga agccactgca   6120
gtgctcagat aagcatggtg ggttctgtca gggtaccggc tgtcggctgt gggcagtgtg   6180
aggaatgact gactggattt tgaatgcgga accaactgca cttgttgaac tctgctaagt   6240
ataacaattt agcagtagct tgcgttatca ggtttgtatt cagctgcaag taacagaaaa   6300
tcctgctgca atagcttaaa ctggtaacaa gcaagagctt atcagaagac aaaaataagt   6360
ctggggaaat tcaacaataa gttaaggaac ccaggctctt tctttttttt tttttgaaa   6420
cggagtttcg ctcttgtcac ccgggctgga gtgcaatgat gtgatctcag ctcactaaaa   6480
cctctacctc ctgggttcaa gtgattcttc tgcctcagcc tcccaagtaa ctgggattac   6540
aggcgtatac caccatgccc agctaatttt tgtgttttta gtagagatgg ggtttcacca   6600
tgttggccag gctggtctcg aacttctgac ctcaggtgat ccactcgcct cagcctgcca   6660
aagtgctggg attacaggtt tgggccactg cacccggtca gaacccaggc tctttcttat   6720
acttaccttg caaacccttg ttctcatttt ttccctttgt atttttattg ttgaattgta   6780
atagttcttt atatattctg gatactggat tcttatcaga tagatgattt gtaaaaactc   6840
tcccttcctt tggattgtct ttttactttc ttgatagtgt cttttgaagt gtaaaagttt   6900
ttaattttga tgaagtcgag tttatctatt ttgtctttgg ttgctgtgct tcaagtgtca   6960
tatctaagaa atcattgtct aatccaaagt caaaaaggtt tactcctatg ttttcttcta   7020
agaattttag agttttacat ttaagtctga tccattttga gttaattttt atatatggtt   7080
caggtagaag tccaacttta ttcttttcca tgtggttatt cagttgtccc agcactgttt   7140
gttgaagaga ctattctttc cccatggaat tatcttagta cccttgttga aaattaatcg   7200
tccttaattg tataaattta tttctagact gtcagttcta cctgttggtc tttatgtcga   7260
tcctgtgcca gtaccataca gtcttgatta ctgaagtttg tgtcacagtt taaattcatg   7320
aaatgtgagt tctccaactt tgttcctttt caagattgat ttggccatgc tgggtccctt   7380
gcatttccgt acgaattgta ggatcagctt gtcagtttca acaaagaagc caagtaggat   7440
tctgagaggg attgtgttga atctgtagat caacttgggg agtattcgca tcttaacaat   7500
attgtcttcc acctatgaac atgggcaaac tttgtgtaaa tggtcagatt gtaagtattt   7560
cgggctgtgt gggcacagtg tctctgtcac agctacgcgg ctctgccatt gtagcatgaa   7620
agtagccata agcaatatgt atgagtgtct gtgttccaat agaattttat taatgacaag   7680
gaagtttgaa tttcatataa ttttcacctg tcatgagata gtatttgatt attttggtca   7740
accatttaaa aatgtaaaaa catttcttag cttgtgaact agccaaaaat atgcaggtta   7800
tagttttccc actcctaggt taaaatatga taggaccaca tttggaaagc atttcttttt   7860
tttttttttt tttttttttt gagacggagt ttcactcttg ttgcccaggc tggagtgcag   7920
tggcgcgatc tcggctcact gcaacctctg cctcccaggt tcaagacatt ctcctgcacg   7980
gcctccctag tagctgggat tacaggcatg cgccaccaca cccagctaat tttgtatttt   8040
tagtagagac ggggtttctc catgttggtc aggctggtct tgaactcctg acctcaggtg   8100
atccacccgc ctcagcctcc caaagtgctg ggattacagg gtgtgagcca ccacaccctg   8160
ctggaaagca tttctttttt ggctgttttt gttttttttt taaactagtt ttgaaaatta   8220
taaaagttac acatatacat tataaaaata tcttcaagca gcacagatga aaaacaaagc   8280
```

-continued

```
ccttcttgca agtctgtcat ctttgtctaa cttcctaaga acaaaagtgt ttcttgtgtc   8340
ttcttcccag attttaatat gcatatacaa gcatttaaat gtgtcatttt ttgtttgctt   8400
gactgagatc acattacata tgtatttttt tacttaacaa tgtgtcatag atattgttcc   8460
atagcagtac ctgtaattct tattaattgc tatgtaatat tttagaattt ctttttaaaa   8520
gaggactttt ggagatgtaa aggcaaaggt ctcacatttt tgtggctgta gaatgtgctg   8580
gtgacatatt ctctctacct tgagaagtcc ccatccccat cacctccatt tcctgtaaat   8640
aagtcaacca cttgataaac tacctttgaa tggatccaca ctcaaaacat ttagtcttat   8700
tcagacaaca aggaggaaaa ataaaatacc ttataaagca ctgtttaata ttgtattaaa   8760
ttggatcaat ttgggggcta gaatgtatgt tagagacatg atatgtccat aggtccttgc   8820
tatcacagtg aggtctcagg gacagtcgtt tggtatcatt tgggatctca taagcagact   8880
ctctctgctt gacctgacaa atcagagtct gtgttttaac aggttcagtg agtgacttac   8940
atgcacattg gagtttggga agctccactg taggtgctta gaccttacct ttgttgttgc   9000
taataacaat gcaagcattt gggaggaaga cctgtgttgc tcatatgtgt ccaggtgtag   9060
ctgaggtggc cttgcttatc tgctgtaggg ccgttgagca tttctgtagc tgtgatgagt   9120
gagctgaggt gagcctgcgg agagctccca gccattggta gtgggactcg cttagatgaa   9180
ctggaaggac cctttcatct gagcagccac tatggagaaa aacaaccgaa tgaggggaga   9240
gacaatgtgc aattttattt agggcacaaa ggagagctgt ggttagaagg tgacatttga   9300
gtggaaaggg ggcaagccat gtgtatagcg ggagaagaga ggtccaggca gagttaacag   9360
aaggcagaaa tgctttccat gtttgagaac cagtaaggag gccagtggct gaagtaaggt   9420
gaagggcaga aataaggatg aggctgcgag agatgagagg ttagagacga gcgtcttgtg   9480
caccaagata agcttgtgtg gtcaaaacaa gtagtttaat ttatgttttt aaaagatcat   9540
tttggctggg cacaatggtt catgcctgta ataccagtag tttgagacgg tgtggtggga   9600
ggattgcctg aggccagacg accagcatag ccaacatagc agcacctata aggtctctac   9660
aaaaaacttt aaaaaattag ctgggcatag tggtgtgtgc ctgtagtccc agctactcag   9720
gaggctgagg aggctggagg attgcttgag tccaggagtt tgaggctgca gtgagctatg   9780
attatgccac tacactacaa cctgggcaag agagtgagac cctgtctcta aatatacaca   9840
cacacacaca cacacacaca cacacacaca cacacacaca cacacacaca catatatatg   9900
tatatatatg catttagatg aaaagatcac tttgacaata ccacatgctg gtgaggattt   9960
agaaaaacta ggtcacttat tgctggtggg aatataatat agtacggcca ctctggaaaa  10020
cagtttggca gtttgtcata aaactgaaca taccgttagt atacagccca gcagcaacta  10080
caatcctggg cattaatcct agagaaatga aaccttaatg ttcacataaa aacctatact  10140
caagtatgca tagcagcttt acccataata tctaagaact ggaatcagct cagatgtcct  10200
tcaacaggtg aatggttaaa ctactcagta ataaaaagga atgagctact gatagcatgc  10260
aacagtttag gtgaagttat gctaatgaaa aaagccaatc ccaaaaggtt atacatactg  10320
tatgattcta tgtttttttg caatggcaca gttttaggga tggagaatag attagtggtt  10380
gcctggggtt agagatgggg tagtagagta ggttagtggt ggcagaggag agaaaagaga  10440
gggaggtgaa tgtggttata aaaggacaac acaggggaat acttgtaatg gaaatgcttt  10500
gtcttttttt tttttttttt ttttttggcg acagagtctt gctctgttgc ccaggctgga  10560
gtgcagtggc atgatctttt ctcactgcaa cctctgcctc ctgggttcaa gtgatacttg  10620
```

-continued

```
tgtctcagtc tcccatgttc agagtgaaac aaaccagagg taatgttcat ccaaataatc  10680
caacacacat gacattaaaa catcaagatc aggtcggacg tggtggctca tgcctgtaat  10740
cccagcactt ttgggaggcc aaggtgggca gatcacttga ggtcaggagt tcgagaccag  10800
ccgggccaac atgatgaaac cccatcttga ctaaaaatac aaaaattagc cgggcatggt  10860
ggtgtgcacc tgtagtccca gctacttggg aggctgaggc aagagaactg cttgaacccg  10920
aggggcagag gttgcagtga gctgagagtg cgccattgca cttcagcctg tgtgacagag  10980
taagactcca tctccaaaaa aaaaaaacca agatcaatta aaatacagca ttactgggcc  11040
gggtgtggtg gctcacacct gtaatcccag cactttggga ggccgagatg ggcagatcac  11100
gaggtcagga gatccagacc atcccggcta acacggtgaa accccgtctc tactaaaaaa  11160
tacaaaaaat tagccgggta tagtggtggg tgcctgtagt cccagctact tgggaggctg  11220
aagcaggaga atggtgtgaa cccgggaggc agagctggca gtgagctgag atcgcgccac  11280
tgcactccag cctgggcgac agagcaagac tccgtctcgg gggaaaaaaa aaaataaata  11340
aatagaatgc tgtagtgtcc ttgagtttac atgcccctcc ttacgcttgt gtgcccgtgc  11400
agattgcttg attacacaat tagaggaggc tggcggagga ttgttttaat tttttttttt  11460
ttgagacagt ctggctctgt tccccaggct agagtgcaat ggcgcaatct tggtgcactg  11520
caacctctgc ctcctgggtt caagcagttc ttctgccgca gcctcccgag tagctgggat  11580
tataggcgcc cgccaccacg cccaactatt ttttgtattt ttagtagagc agcgtttcac  11640
catgctggcc aggctggtct cgaactcctg acctcagatg atctgctgcc ccagcctccc  11700
aaagtgctgg gattacaggc gtgagccaca cctggccgtt tgttttaatt ttgaaggtga  11760
agtgaaagtg actacattta ccaaaagtga ttgaaaagcc aggactgttc ttaccctgtt  11820
tttccagttc ttgctcagag caaggtggtt tctttttcac ttaatcacca tacttacttt  11880
tcatgtagaa caagtcagtt tgagttatca gttcatcatc ttaactaaat tccatggggg  11940
aaggaattag ttttagtttc ttaaacttcc aggtttgctt attggacaaa atgagatagc  12000
aaggcagtgt ttttaagtta gattttttat ttctttggta atacaatttt ctcagaaact  12060
tagtagtctt ttagtttagt tgtttttagt tggtcctatg ttttggatca cccctctcta  12120
ctttattttg atagtgccaa ctgtgaagac atctgaagcc ataggtttgg atgggaagga  12180
ggcatcttta gcctgatcat cttcgccagg ctgtttatct ccttttgctt ggctgagaag  12240
tcttaatagg aggcttattc ccagctattt ggggacatag aagcagttag ccattgctta  12300
tattttactg aggtctgtgt ggtatgttga ttgtagtcag ttaacgattt tgagaactga  12360
aggcagcctg gtatatatag agtaggtatt agactgtgtt tcttctaatt gaatttccca  12420
tctcttgtaa tctatgccat catcttctgt actgctgaga aagaaagaaa gtttctaatc  12480
aaactatacc actggttgta agatgcagtt tggctttagt gatgttaaca catgattcaa  12540
acgtgaaatt gattgagtat tggtgaaata cagaggagat ttaaagccag aagacctggg  12600
tttaaatgct ggctgtatga cttcatatct gtgtgatctt gggcatgtca tggttggcac  12660
ttcaatttct tctctctata atgggggaag tgaggccagt catggtggct catacctata  12720
atcccagtgc tttgggaggc caagatggga agatcgcttg aggccaggag tttgagcaat  12780
tgggcaacat cgtgaggccc cgtctctaca aaatattttg aaaaaattag ccaggcccag  12840
tggtgcgtgc ctgtggtccg cgccactcag gaggctgaga cgggaggatc ctttcagcct  12900
aggagtttaa ggctaaagtg agccatgatt gtgctatcgt actccagcct gggcagcaga  12960
gcaagatcct gactctaaaa aaaagtaaaa taaagtaaaa tgggggaaat gaactgcttt  13020
```

-continued

```
agtaacatca tctgtttttt ctgtgagcag cgtagcttga cagccattgg tgaactcgtg  13080
ccctgtgctt ccctgtccag atccccattc tgcccgcaac atggagtata acggtttatt  13140
catagtagtc gagaaacact cactgaatga atgaatgagg tgtagaacta agtggagtgg  13200
gtaattcaac acatattaat ttccttcttt tttttatttt tagaaagaaa gaactttcag  13260
ctaccaagaa agaccgtgtg aatcattgtc tgacaatatg tgaaaacata gtggcacagt  13320
ctgtcaggta attgcacttt gaactgtcta gagaaaataa gaactttgta tattttcagt  13380
cttaatgggc tagaatattc tttgtgtccc agctatttta aatggattca gaaatccatt  13440
taagatgaag aaggaccctt ttcccatatt tctggctata tacaaggata tccagacact  13500
gaaatgaata atgttccctt tttgtaatct tttatgcaaa aattaaaacc attatggtaa  13560
ttgaacaaca tgtttatgtt tagttaacac ccttagcaac tatagttatt ttaaaaccat  13620
ctatggtttg atatttttgc atttgttgca atagtaggaa cagcacaaga cagttcagtt  13680
tgtctctctt atttgctttt tcttggcagt ttgctgtcct attgtacctc tgctcctagc  13740
agtggctgga gcccactcct ctgtgcttcg ggattagtgg ggatcgtggg gcattgactg  13800
taggtcagct ttccttgctt gatctttctc actgggatga actagcagca ccttcttttg  13860
tagctgcttt gcttttgact atctttctga ccgttgttcc tagtagctgt agatggtaaa  13920
tatatttagg cctgtttcca atggctcagt aggagacata ttcacctatg atatctgaat  13980
tctgttaccc acatgggcat gcgtgaaata gttgccttgc cttactttcc cttggaataa  14040
ataattcatg ttattctcct ggtagaagct agaaaaagcc tttatagtca gtcagaaaaa  14100
aatttttaga caaataatct tgattttagt actgacaaaa acgtgtggtg attctttttt  14160
taattttttt ttgagacgga gtttcactct tgttgcccag gctggagtgc aatggcgtga  14220
tctcggctca ctgcaacctc tgcctcctgg gttcaagtga ttctcctgcc tcagcctccc  14280
aagtagctgg agttacaggc atgtgctact gtgcccagct aattttgtat ttttagtaga  14340
gatgttggtc aggctgatct cgaactccca accttaggtg atctgcccgc ctcagcctcc  14400
caaagtgctg ggattacagg cgtgagccag ggcgcccggt gattcatttg tttttttcaaa  14460
aaatttcctc ttggccattg cttttcactt ttgttttttt tttttttttg agacggagtc  14520
acgatctgtc acccaggctg gagtgcagtg gcatgatctt ggcttactgc aagctctgcc  14580
tcccaggttc acgccattct cctgcttcag cctggcgagt agctgggact acaggtgctc  14640
gccaccacac ccggctaatt ttttgtattt ttagtagaga tggggtttca ccgtggtctt  14700
gatctcctga cctcatgacc cgctcaactc agcctcccaa agtgctggga ttacaggcgt  14760
gagccaccgc gcccggccct ctcttgtctt tttattgtgg taaaatgcac ataaaattga  14820
ctgtcttaac catttttagg ggtacagttc agtatatata ttcgtaatgt tgtacagcca  14880
tcactgccat ctacttcata agtttttctt ctgtcaaaac tgaacatctg tcttcattaa  14940
actccctatc atccattctt tcctgtagtc cctttctact ttctgtctgt atgagtgtaa  15000
ctgctctgga gacctcatgt aagtggattc ctacaggatt tgtgtttttt ttttggtgat  15060
ctgcttattt ttaatgcctc tgtgcatttg tattatatac tttcaaagtg atttcacaaa  15120
accgtttcat tttaggttaa ctcatttctg ttgtttgtga aatactgtgt atgattctgt  15180
tctgtttctg tctaatttgt ggaaatgttg tgggaagaaa atgaaataac aaatgagcat  15240
atgtcctgaa aataaaaata taaaaattct aagttagcat gctattgtag aatacaacgc  15300
tatgataaaa gtaggaaaaa aaaaggtttg aattctatct ctgctacctg tgtaagctgg  15360
```

-continued

```
gtgactttag ataagctgta acgtgtttga gccttactgg ctcatttttg aaatgtaatc  15420
cctagttaca cagttcttgt gggatcagat ggtacatgtg aaacactgtg aaaaagcaac  15480
tgcatagata tgttcattag ccacctgagc gggaagcgta tcccattgcg atgcccatca  15540
tccaaagcta tatgttatct ttactttttt ttttttgaga cagagtcttg ctctgttgcc  15600
caggctagag tgcagtggtg caatctcagc tcactgcaag ctccacctcc cgggttcacg  15660
ctattctcct gccccagcct cccaagtagc tgggactaca ggcacccgcc accatgcctg  15720
gctaaatttt tgtattttta gtagagatgg ggtttcaccg tgttagccag gatggtcttg  15780
atctcctgac ctcgtgatcc gcccgcctcg gcctcccaaa gtgctgggat tacaggcgtg  15840
agccactgcc cctggccatc tttacttttt ttgtgaaatg actttaaata cttggcaaac  15900
atttggtcat tgttcatctg atctccacca tccaggtctc agagaacata atttctctct  15960
gaaagcttat tgacccagga aataagatct ctttcaatct gagtgcgtca ggctttattc  16020
ttgtcatttt gtcttttgat aattttcaaa tggaattcat ggaatgttgg cttatattca  16080
tatattagta aagtatgttg agacatctta agattgattt gtggttctat atgccatatt  16140
aaatcaaaat aatagctgtt aatggttttc acattagtct gtctcttgtt tttatggagt  16200
aatgctgaga gttcattatg cttgttctac agaagagcat gttaaaagga gtttttggag  16260
tcagagaggt tattcttggt ttcataggat acactctata ctttttaggg atttcagagt  16320
atatagctga aggtgatatt ttatgtaaat atgttttatg gaaacttatt gctcatcgct  16380
gtttcctgtt aactctccta aaatataatt aaactttttgg aactttttta tagcttttgt  16440
gctagactaa tttttgtctc taatgaggtt atataaatgg cagcttctga cgttttcaat  16500
gtaggaagtc atttaaaact tcatgtatat tgtgaaaatg tagtctgctt taagctctct  16560
aaagtggtct aagttactgg ttcctaagta tggatgagca tcaaaatcat ctggaaaatt  16620
tgttaaaaat acagtaatga aggcacctca ctgtcctttt tcccaaacat acttctgcat  16680
tctgtttgag taggtaggga ctacacattt ttcacaagta tcctcttggg aatacccagg  16740
aatgcttact tgagcaacct cttactaata tgtaccttga taaggtggct aggtaaacat  16800
aaatatacaa aaatccatag atctcccata tattagcata aatcagctag aaaatataac  16860
gtttaaagat ctagttcaca gtagcaccaa tatatcgaac tctaaggaat cgataaatat  16920
gcaaaaactt tataaaaact tctgttaatg tttctgaaag atataggtga ccactttcta  16980
gataggaaga ttttatatta ctaagttgaa ttttctctaa attaacacag aaatttaaaa  17040
taatcttgat caaaattcta gtagaggtat ttttgaactt gttcactgca agaataaata  17100
cataattgca aagaatatct caaaatcatc accaggcctg gtgtggtggc ccatgcctgt  17160
aatcccagca ctttgggagg ctgaggcagg cagatcacct gaggtcaaga gtttgagacc  17220
agctggacca gtgcggtgaa acactgcctc tactaaaaat acaaaaatta gctgggtgtg  17280
gtggtgcatg cctgtagtcc cagctacttg ggaggctgag gcaggagaat tgcttgaacc  17340
caggaggtac aggttgcggt gagcctagat cgcaccactg cattccagcc tgggcgacaa  17400
gagcaaaatt ctgtctcaag aaaaaagaga aaaaagaaaa agaaatcaac actaatatgg  17460
tgagacttaa tgtatgtgac attaaaatag tgattggatg ttaaaacagg tatagaacag  17520
aaagaagagt gtatgtgtgt atctgtatga atttatgatg ggtgtaacat atatgtatta  17580
gggaaatgag ggaaatgata catttctctg actttgggag aacattatat ctctacctca  17640
tattgcaaac aaacataaag ttcagattaa ttacctaaat gtgaaaaaat gaaataattt  17700
ctttaaaaaa tgtaatctta gtttgaggaa ggttaacatt ataaaggaaa aaactgtttt  17760
```

-continued

```
gagtggaata tagttcaata tgtcaaaatc caccttcaac aaaattgaaa gtaaattgaa  17820
cttggggaaa gtattgacag catatagatc aaaggttact agcctgtgta aagagcagtt  17880
ataaatatcg ttaagaaaaa cactgtcgac ctgtcggcac cttgttctcc gactcccagc  17940
ctccagaact gtgacgagta agtgcttatt gtttaaacca cccagtctgt atgtggtatt  18000
ttgttataga aactcaagct gattaggaca ctagtaatca gtagactgaa actgaaacaa  18060
aaataagaac ctttttacc tgtcaaattg gcaaacatta agaatattca gatttttgtc  18120
agaggtgata caaccttcta agaaggcaat ttgggaaaat ataaagcttt agattattat  18180
atgtctgacc tagcagtttt acctctaggg tgcttacccc taggaaagtg tgtaatgata  18240
ttggtgcagt gcccttcatc ccattagaaa attaaaaata accttaatgg cctaccacta  18300
aaaggggatt gaaaatttaa gatatattta tttatgtgtt tattgagatg gagtcttgca  18360
ctgtccgcct gggccagagt gcaatggtgc gatctcggct cactgcaacc tctgcttccc  18420
gggttcatgt gattctcctg cctcagcctc ctgagtagct gggattacag gctcacacca  18480
ccgcacccgg ctaatttttt gtatttttag tagagatggg gtttcactgt gttggccaga  18540
ctggtctcga actcctgacc tcatgatccg cgcccctcgg cctcccagtg ttgggattac  18600
aggtgtgagc cactgcgcct ggccagatac atttatacaa gagaatgtta gttaacattc  18660
atagatattt atattttgtt tactttttat taaaaaaatt tttttagag acaggatctt  18720
actctgtcac ccaggcagga tgcagttgca caatcatagc ccactgcagc ctgaactcct  18780
gggcttaagt gatccttctg cctcagcctt ttgagtacct gggggacttt aggcagtgct  18840
actataccctg gctaattttt aaatgtttta tagatgagat cttgctgtat tgcccaggct  18900
ggtctagaat tcctgggccc aagtgatcct cccaccttgg cctcccaaag cgctgagatt  18960
acaggcatga gccaccactt ctgaccaata gatatttata tttgtgactg gaaaatatat  19020
taacaatgtg ttaaaaaatt cagttaaaaa ataatgaaag atttttgctt ctggctaaga  19080
tagaataaca aggacagcat ttatcttctt gccttgaaat agttgaaaac ggaagaaata  19140
tatgtaacag tggttttcaa gttattgggc atcaggcaaa gaagaatagt tatcccagga  19200
aaatgaatgt ggagagccct acaatttcct tacattactg cctggtcatg gcaagaggaa  19260
aaactgagag gagactgagg ctgagccagt ggtttgctgg gttgaggagg cagagctggg  19320
agtgcagaga tgcaaggtgg tgagagccca tatggaagaa taccagggaa gagagctgca  19380
gagggagctc cggagacctg caccctgccc tctcagtacc ctgtcatgtg tgtagctgag  19440
tactgacgag cacttgcttg tgcggaaatg acccagggct ggaggtagag ccacctgaaa  19500
ggattagaag gaacagttgc tgaaagtcac acagggccag gaagaatttc taatcacacc  19560
agttggagtg gaaaacctca gctctcatag agcaggtagg gtactcagaa gggtttgccc  19620
acctagcccc agactaagtt tcgttactct gaccctacct aatattaaaa agagattaat  19680
taaattgttc gcaacaaaaa taatatattt cagtgtttgt aacacgtaga agtgaattgt  19740
atgacaatag cataaaggct ggaagagcag aaattgacat gtatttgcgc tgggcagaat  19800
aatgctcccc tctttcccca aaagatatca agtcctaatc cctggagcct gtaaatatta  19860
ctttatatgg aaaattgttt tatgatgtga ttaaattcag gatcttgaga tgagggggct  19920
atcttggatg atctgggtag gcactaaatg caatcacata tatataaaaa ggaggcagag  19980
ggagatttta cacacagaga gaaggccctg tgaagatgga acagaaagat ttgaaggtgc  20040
tggccttgaa aattggagtg atgaagctat aagccaagga atgcagcagc caccaaagct  20100
```

-continued

```
ggaagaggca cggagcagtt ctcatttaga gcctactcca gagggaatgt ggtgctgcca  20160
attccttttt ttttttttt tttaagatat catttacccc tttaagttgg ttttttttt  20220
ttttttttt ttttagtatt tattgatcat tcttgggtgt ttcttggaga gggggatttg  20280
gcagggtcat aggacaatag tggagggaag gtcagcagat aaacatgtaa acaaaggtct  20340
ctggttttcc taggcagagg gccctgccac gttctgcagt gtttgtgtcc ctgggtactt  20400
gagattaggg agtggtgatg actcttaacg agtatgctgc cttcaagcat ctgtttaaca  20460
aagcacatct tgcaccgccc ttaatccatt taacccttag tggacacagc acatgtttca  20520
gagagcacgg ggttgggggt aaggttatag attaacagca tcccaaggca gaagaatttt  20580
tcttagtaca gaacaaaatg gagtgtccta tgtctacttc tttctacgca gacacagtaa  20640
caatctgatc tctctttctt ttcccacatt tcctcctttt ctattcgaca aaactgccac  20700
cgtcatcatg gactgttctc aatgagctat tgggtacacc tcccagatgg ggtggcggcc  20760
gggcagaggg gctcctcact tcccagatgg ggcggccggg cagaggcgcc ccccaacctc  20820
ccagacgggg cggcggctgg gcgggggctg ccccccacct cccggacggg gcgggtggcc  20880
gggcgggggc tgcccaccac ctcccggacg gggcggctgg ccgggcgggg gctgcccccc  20940
acctcccgga cggggcgggt ggccgggcgg gggctgcccc ccacctcccg gacggggcgg  21000
ctggccgggc gggggctgcc ccccacctcc cggacggagc ggctgccggg cggaggggct  21060
cctcacttcc cggacggggc ggctgctggg cggaggggct cctcacttct cagacggggc  21120
ggctggtcag agacgctcct cacctcccag acggggtggc agtggggcag agacattctt  21180
aagttcccag acggagtcac ggccgggcag aggtgctctt cacatctcag acggggcggc  21240
ggggcagagg tgctccccac ttcccagacg atgggcggcc gggcagagat gctcctcact  21300
tcctagatgg gatgacagcc gggaagaggc gctcctcact tcccagactg ggcagccagg  21360
cagaggggct cctcacatcc cagacgatgg gcggccaggc agaaacgctc ctcacttcct  21420
agacggggtg gcggctgggc agaggccgca atcttggcac tttgggaggc caaggcaggc  21480
ggctgggagg tgaaggttgt agtgacccga gatcacgcca ctgcactcca gcctgggcaa  21540
cactgagcac tgagtgagcg agactccgtc tgcaatcccg gcacctcggg aggccgaggc  21600
tggcagatca cttgcagtca ggagctggag accagcccgg ccaacacggc gaaaccccgt  21660
ctccaccaaa aaacacgaaa accagtcaga catggcggtg cgtgcctgca atcccaggca  21720
cttggcaggc tgaggcagga gaatcaggta gggaggttgc agtgagtaga gatggtggca  21780
gtacagtcca gccttggctc ggcatcagag ggagactgtg cgagggcgag ggcgagggcg  21840
agggaattcc ttaatttcag tttagtgata ctaattttgg actctggcct ctaaaactgt  21900
gaaagaaaaa attttttgtt tgtttgtttc ttttaagcca catagtttgt ggtaatttgt  21960
tacagcagct gcaggaaact aatttatgct gcatgtgaaa tggtgtaata aggtagattg  22020
tgatgaagat acatagtata aacaattaag caacaactaa aagcacaaca aggaattata  22080
gctaatgaac caaaaaagga gattagaata ataaaaatgg tgaatcccaa agaagccaga  22140
aataggggaa gaggcaaata aaggaaagaa agagcttgat ggtagatttc aacctaacta  22200
tgtcaaaaag gacattacat gtaaaaggca gcgatttttc agattgaatg gaaaagtaag  22260
actcggtata tgctgctgcc tgcaagaaac acattctaaa tataaaggca aaaataacct  22320
acaggtaaca gaacggaaag aagttcactg tgcttacaag aattagatgc aagctagact  22380
ggttctgtta atatcagaca aagtggattt caaagcaaag gctcttgccc aggatgagat  22440
ggtcatttca taatgatgaa ggggattcgt tcatcagcct ggcatagcaa gctgaaatgt  22500
```

ttatgcaccg gactacagag ctaaaataca tgaagcaaag cctgacagaa ctacaagtag 22560
aaacagacaa atccacagtg atagagattt cagtagccgc tctcaatgat ttgtagaaca 22620
cgtagccata atatctggat ctagaacact tgaccaacac tgtcccctgt gcaacctcat 22680
tggcatttac aggacactcc acccagcacc agcagaagag acactctctc aagtgctcac 22740
agaatgtttg ccaagataga gcagatgctg ggccataaaa caagtctcta aattaaaagc 22800
attcaaatta ttcagagtat gttttctgac ctcagtatca ttaagttgga atatattata 22860
ggaagataac ctggaaaagc ctcagatatg tggaaaaacc catttccaca tggcccatgg 22920
gtcagaagtg aagtcaaaag ggaaatttga aagtcttttg gattgactga tataaaaaca 22980
atagatttct aaacttgtgg ggtgctgtta cagcatagta aatggaaatt tctagcatta 23040
aatgcctgtt ttaggaaaga aagatttcaa atcaatgacc tcagcttcta cctttggaaa 23100
cttgaaaatg acaagcaaat ggaatccaga gttaccagaa gggccaggta cggtggctta 23160
tgcctgcagt tctgccactt tgggaggccg aggcaggtgg attgtttgag actggcagtt 23220
gaagaccagc ctgggcagcc tagggagacc ccatatctac aaaaaacaaa aaaattagcc 23280
aggtgtggtg gcatgtgcct gtagtcccag ctaaccagga gtctaaggtg ggaggattgc 23340
ttgagtctgg gaggttgagg ctgcagtgaa ctgtgattgt gccactgtgt tccatcctgg 23400
gcaacagaat gagaccctgt ctcaaaaaca aaaacagtta ctagaagaat ggacatcata 23460
aagataggag cagaagtcag taaaatagaa aacaaaaata cataggaaat caataaaacc 23520
aaaagctggt tcatcaagaa catcaataaa ttggtaaagc tgataggaaa aacagtgaag 23580
tcacaaatta gcaatatcag gaatgaggga gatgacagta gtatagatta tatagatatt 23640
aaaaggactg tatgaggcag gtgtggtggt tcacgcctgt aatcccagca ccttgggagg 23700
ccgaggtgga cagatcacct gaggtcagga gtttgggacc agcctggcca acatggtgaa 23760
actctgtctc tactaaaaat acaaaaatta gttggtcgtg gtgctgtgtg cctgtaatcc 23820
cagctacttg ggaggctgag gcaggagaat tgcttgaacc tgggaggcgg aggttgcagt 23880
gagctgagat tgtgccgttg cactccagcc tgggtgacag agcaagactc catctcaaaa 23940
caaataaata aataaaaagg actatatggt aatattatga acaactttat gccaataaat 24000
ttgacaactt atagatgaaa tggatgagtt ccttgaaaga cacagaaact attaaagctc 24060
tctcaagaag atatagataa gctgattagc cctatatcta ttttattgaa tttaaatgta 24120
aaaatcaata tttagttact ggaaaacttt taagtgtggt tggaaatggt atacgaactt 24180
tttcaactga attttatgaa gtctaatcac aggtaaaggt tttctgatga aaatttagtg 24240
tctgaattga gatatactgt aaaaaatgtt atatatctta attatttctt cacattaatt 24300
acatgttgaa ataatacttt gggtgtattg ggttaaatta aatattatga aaatcttgcc 24360
tgttttcttt ttacttttga tgcgtcagct aggaaatata aaagtgtagc tcacattctg 24420
tttctgttga cagtactgct ttggagcaca gtgtttgaat gatctatcat ttcaaagacc 24480
tttcctcagt tcgttattca tggctgtctg tattccacat agataaggtc tgaaatactg 24540
ctaagtggca tgttttgttt tatgctttta taagtttgtt gatcattact gatgtggact 24600
tttggtgcct cttaggctca ttgctatctt ccaaccattg tttgcaattt ttacctagag 24660
ataaagagaa agagacattt ggtttcagag tagttagatt gggatcatga aagagcaacc 24720
tcattttgat gcttcaaaaa tagcacatcc cccgtattac tgggatttgc tattcttggg 24780
attacttcaa gaacatcctt gtgttactgg tttggatgct tctgaatgct gtgaagtcag 24840
tttcatgtac atggctcatc agtttagctc tctcttggct ttgtttagac agttggagca 24900
tgatggccta aacagcttct ttcaattaaa cattttaaaa tagtttacaa atagtaaaca 24960
aactccagtt tttgtgactc tttgtctcgc acaacaaaaa cacaatctga ccatgatcat 25020
ctggcatctt agggtgaaat atggttatac tttggcccat accgaaagca agattaaaaa 25080
ggggcaggag agatagactg ctgaactgat tttcaaggtt ccaagaatat tgtaggttaa 25140
gagtaaaagt aaactttgg tagaaagcag tgggttgtct aggattgaag tatctgaagt 25200
ttttaaacga aaatttaaaa agaaaaatga gaattgcctt acaagtacaa tctcttcttt 25260
tttaaaaaat aaactttatt ttgaaatagt tttagattta tagaaaaaaa ttagataggg 25320
taggaagttt tcatataccc tacatccagt taccccagtt attatcatcc taatttagtg 25380
tgagacattt tcatgtttaa tgaatcaata ttgatatgct attaacttaa gtccagactt 25440
tattcagatt ttcttaattt ctatgtaatg tcctttttct gttccagaat tccatgcagg 25500
acaccggata cctcattaca tttcattgtc atgtcacctt aggctcctct tgacagtttc 25560
tcttcttttt ttgcttagaa attctccaga atttcagaaa cttctgggca tcgctatgga 25620
actttttctg ctgtgcagtg atgacgcaga gtcagatgtc aggatggtgg ctgacgaatg 25680
cctcaacaaa gttatcaaag taagaaccgt gtggatgatg ttctcctcag agctatcatt 25740
gttgtaggct gagagaagaa gcgatcattg agtgttcttc tgttttgagt ccctgaggat 25800
gtctgcactt ttttcctttc tgatgtatgg tttggaggtg ctctgttgta tggtttggag 25860
gtgctctgtt gtatggtttg gaggtgctct attgtatggt ttggaggtgc tctgttgtat 25920
ggtttggagg tgctcttgta tggtttggag gtgctcttgt atggtttgga ggtgctctgt 25980
tgtatggttt ggaggtggtc ttgtatggtt tgcaggtgct ctattgcatg gtttgcaggt 26040
gctctattgt atggtttgga agtgctcttg tatggtttgg aggtgctctt gtatggtttg 26100
gagatgctct attgtatggt ttgcaggtgc tctattgtat ggtttggaag tgctcttgta 26160
tggtttggag gtgctcttgt atggtttgga ggtgctctgt tgtatggttt ggaggtgctc 26220
tgttgtatgg tttggaggtg ctcttgtatg gtttggaggt gctctattgt atggtttgga 26280
gatgctctgg tatctgcctg cattgcttgc cacacctgcc cggtcagaag gcgctatgtt 26340
gacaattgtg cctgcacggt gcctaggtca atgaagggaa ccgatggtag ccactggatg 26400
ctcctgggaa aatgtcacta caggcaccag agaagccaga gctatgccca aatttctatg 26460
agtctcagtt ttcttaacca taaaatggga tcaatgtttt tgtggcatgt gtatgagtgt 26520
gtgtctgtgt atgtgtgagg attaaattgt gtatgtgtga ggactaattg ccactactgg 26580
atcctcaaag tggtaagaag tgttcttatt aataatgaca tccttacact cttacccagc 26640
aagattgatg ggtgtggcac tgcttctctt tttccatcac atggtttcca tggtatcctt 26700
ttgcccaggg aatctttgct ttgtggctag cactttgttg tttggctaat cacgctttct 26760
gtggtcagga cgctggcttc tctggagcca tgggattcta gctccctgtc ttgtccctag 26820
agtggtcact gtcttctctc tccgcttgca attcctgctt tgctcgcatc tcacttatgc 26880
agtgacgtat atcagtttca ccttgttctc cgtgcctgct gatcattggc accacttgca 26940
tggtgccatt tagggcctgc ttccagttaa gcttgcttct ccacaggcct aaatatcctt 27000
gcttgcttct tttattctca ctggcaggac cagggcggtc tgtctttgca tgagacaggg 27060
tctcgctcag tcacccaggc tggagtgcag tggctgatca cggctcattg cagccttgag 27120
ctaccgggct caagctatcc tcctggcttg gccccttgag tagctgggac tacaggcgtg 27180
caccaccatg cccagctaat ttttaaaatt atttgtagag atgggatctc gccaggttgc 27240

-continued

```
ccaggctggt cttgaacgcc tgggctcaag tgatcctccc tccttggttt cccaaagtgc  27300
tgggatcaca ggtgtgagcc actgtgcctg gcccttgatg tttcagttct tgatatttga  27360
tcctcagagt cagaaaatct aaaaagaggg ctatcccagg ttgccttggt tcatggcaaa  27420
tgggacgtta agagggcaga gagaatatga acagaaactg ttctaatatt ggtcatttaa  27480
tgtgtaagta ttgttctttt ttaaacctcc ttcatttttt ttccaggaat tgctggacac  27540
agtggcttgg tgtgtgtctg aggactgtag gccatggccc taggttgtgg ttttaggtct  27600
caggtgctct tcctggctgt ctccttgctt ctttcccatg tcctcttctt tgtttccagc  27660
catttctccc ttatgcttaa gtttggtgca gcagggtttg gctgctctca gattcctgct  27720
tcctcagatg ctgtagttgt caggcccagc gggctggcag cgggatcagg atctggctag  27780
gtttgctctc actgtggcag agtaggggga ggcgtgggag agcacgtgtg accccaggcc  27840
agctgtaggg agcataggca tggtcacgta gccttcaggt cctagacttt gtcttctcat  27900
gagtatggct gtgtgtgtat ggtgaaaact aggttctact tagcccaaga aaatgggcac  27960
attttgcatg tggtttctgt agagaaatgc actgggtatc tgacatagcc tggcagcatg  28020
cctccctcag gtaggttagt ctcaggcggt gaagcacgtg tgtccagcaa gaacttcata  28080
tgtggcataa agtctccgtt ctgtgaggtg ctggcaaatc accaccaccg tcaagaggct  28140
gaagtgattt ttgtctaggg aggcaggaaa ggcttcctgg agtcagcagc cagtaggtga  28200
aagagtagat tggagacctt cttaatcatc accgcctctt gtctcaaggg gtgccaggaa  28260
gctgtggagg ctgaacccat cttatgctgc cagagagtgg gacaccatga gggtcaggtc  28320
aaggggttgt accttgtttg gtagagaatt aggggctctt gaagactttg gatgtggtca  28380
ggggagtgta tcatttagga agagtgaccc ggtgaggacg tggggtagag gaggacaggt  28440
gggagggagt ccaggtggga gtgagtagac ccagcaggag tgcagggcct cgagccagga  28500
tggtggcagg gctgtgagga gaggcagcca cctgtgtgtc tgcggaagca ggggcaagag  28560
ggaagaggcc agcagcgtgc tgccatcacc cagcgactgg cgtagattgt gagagaccat  28620
tccctgctct taggaggggc tgagttttag ttttctcttg ttatacaata agcttggtat  28680
ttgtttacaa aacatttgta aagctaaatc aaggtttgat aaggcttcta gttttattta  28740
agaagtaatg ttgaaataaa tgtttgtcca attcgctttg ctcatttaag gactttcagt  28800
acaaactgca acaacaggat taggatttaa acgtttctga gatgttttta ctcctcagaa  28860
tttcccagaa tgtgatctgg ttttgatttt caagcttgct gacccaatag gttaacccac  28920
aagttttacg aagaccatct cagtccactt acatcaactg cccatgccac ggttaaagag  28980
atcatcgact gatgtttggc acagcttcct ccctcttggg tgggcaagca tttggaagag  29040
aaggctccta tgggtgagag tggggcacca aagtcttccc tgtcccatcc cctagcttga  29100
gaagcccttc tctaatgtgg actttgtgcc gttagcatcg ttactagctt gaagttgacc  29160
atctggacgt actttctggt ttagcctcac aagtgagcaa ggagggttga gagatgtgct  29220
gtgaggaatg tggggcccca gctggcagca ggctctgggt cagggggggca gggaccacgg  29280
gcatacctga cagtgaggag gggccacacc tgcagaaaag gatgcaggac tccgccttgg  29340
gaagtgttct aggccagagc gagggtctgt ggtttataag tacacccaca gtgctcggga  29400
ccctgcagat gtccagggtg ccgtctgagc ccgtatcatc caacagaatg ttctgctagt  29460
gaagattaaa gatttactcc aggggcttta ggatttatta tatatatata aatcctatat  29520
atataatttt tttttttttt ttttttgaga tggagtttcg ctcttgttgc ccaggctgga  29580
```

-continued

```
gtgcaatggc gtgatcttgg ctcactgcaa cctccgcctc ccgggttcaa actattctcc  29640
tgcctcagcc tctcgagtag ctgggattac aggcgcccac caccacaccc ggctaatttt  29700
tgtatttttt agtagagacg gagtttctcc atgttggtca ggctggtctt gaactcctga  29760
cctcaggtga tctgcccgcc ttggcctccc aaagtgctgg gattacaggc atgagccacc  29820
ccacctggcc aggatttatt gtatttgaac catctaccat tttaattttg atgttatgta  29880
gtatttgatg ataatgaaag ttaaattgtt tttctttcca tttttctgtt taagtgaatg  29940
acctgtatct agtttattca gtaacttcct gcatatattt gtttctttca ttcttaatga  30000
atatattctt aatttagttg ctattatgtt ttgctttgcc ccaaaattga aatcttagtt  30060
tccttttagc tcgttttaga actagtgatg ggatgtgtct tccataaatc tcttgtgatt  30120
tgttgtaggc tttgatggat tctaatcttc caaggttaca gctcgagctc tataaggaaa  30180
ttaaaaaggt gggccttgct tttctttttt aaaaatgttt taaattttaa atttttatag  30240
gtacacgtat tttgtaggta catgtaaatg tatatattta tggggtacat gagatatttt  30300
gatacaggta tacaatacat aataatcaca ccatggaaag ttggatatcc atgccctcaa  30360
gcatttatcc tttgtgttac aaacaatcca gttacatgct ttacttattt tattttattt  30420
ttgagacaga gtcttgcttt cacccatgct agagtacagt ggcatgacct tggctcactg  30480
caacctccgc ctcccgggtt caaccgaact ttgggctggt ctcgaactcc tgacctcagg  30540
tgatccgccc gcctcggcct cccaaagtgt tgggattaca ggcgtgagcc actgtgccgg  30600
gcctgattgt acattttaaa ataactaaaa cagtcagggc acagtggctc atgcctgtaa  30660
tcccagcatt ttgggaggct gaggcaggtg atcacctgag atcaggagtt cgagaccagc  30720
ctggccaaca tggagaaacc ctgtctctac taaaaataca aaaattagcc aagtgtggtg  30780
gcgggcgcct gtaatcctgg ctactcggga ggctgaggta ggggaatcgc ttgaacctgg  30840
gggtggaggt tgcagtgagc cgagatcacg ccactgcatt ccagcctgag cgacagagtg  30900
agactttgtc tcaaaaaaata aaaatgaaat aaaattgggc cgggtgtggt ggctcacacc  30960
ttagtcccag cactttggga acctgaggca ggtggatgct tgagaccagg agtttgagac  31020
cagcatgggc aacatggcaa aacgctgtct gtacagaaat tagctgggtg tggtggtgca  31080
caactatagt ctcagctact tgggagattg aggtgggagg attaattgag cctggaaggt  31140
tgaatctata ggtagctgag attgtgccac tgcccttcag cctgggcgac caagtgagac  31200
cctgtctcaa aagaaaaaca aaaaaacaaa aaacaaacca ctattatcga ctatatatta  31260
ttgtctatga tccctctgct gtgctgtcga ataccaggtc ttgggccctt atttccatca  31320
ctgagcaaac ttcactctgt taagcagcag gtgtgggatt tcatcgttat tcagtaattc  31380
acaatgttag aaggaaatgc tgtttggtag acgattgctt tacttttctt caaaaggtta  31440
ctctttatta gatgagatga gaattaaaaa tggtaactta ctttatatct ttataattga  31500
agcccactag accttaaagt agttaccaga tgttttatgc atttaaatgg ccttttctct  31560
aaaattagaa agtaacaagg aaagaaaatg cttcgtttct atgcaaccct cttggtgact  31620
agtatgtgac tcttaatgca accctcattg caccccctca gaatggtgcc cctcggagtt  31680
tgcgtgctgc cctgtggagg tttgctgagc tggctcacct ggttcggcct cagaaatgca  31740
ggtaagttgt acactctgga tgttggtttt tgtcgggggc cagctgctac tgatccttta  31800
tgtctcagct cagatgtcat ttcaaaagtc tgctctgccc tctccaaatt gcagtcgacc  31860
ttgccctgtt tatgtttccc tcatagcact aatccatgtc agaaattgtc acgtacagtc  31920
tatctgtgtg cttgtttatt ttctatccca cccttccgca agagacttat gggatgtgtg  31980
```

ccccaggaca gcaggggtct tactgtctta tgctctgttg cagcccagca gcgataacag 32040
tgtctgcaca tagtacttgc ttaaaagata cttgccaaat tgttgaaggt tgaggtacca 32100
atttcattat tgctgactat aggagttata gcaaaatatc catttgtctg ttacatgagt 32160
taaaaatatg gttgttgcac tgtgaatagt ttggtttagt caaaacagtt gtatcttaac 32220
ggattgagaa acaaaagcag gaccactttt catcagctcc ctccttctcc ttaaccagca 32280
atacatgctg atgctgatat cccatagacc ctcagctcca tcctgagtca ctgggaatgt 32340
ggtctaaacc ctcactatta atatgaactg agtttcaata agaatcttat atgggtcggg 32400
catagtggct catacctttg atcccagcac ttcaggaggc caaggcaggt ggattgcttg 32460
acccagacta ggcaacatgg tgaaacgccg cctctacaaa aaatacaaaa cttagccagg 32520
catggtggtg cgtgcctgtg gtcacagcca ctcgagaggc tgaggtggga ggatcacttg 32580
agcctgggag gtggaggtcg tgttgagcca agatcgcacc actgcactcc agcctgggca 32640
acagagtgag acctgtctca aaaaaaccaa aatccagaaa agaacttata tggctgcaga 32700
ggtataatca ctaaggaaat ttccttttgt ataatctttt ttcttttact atcatttaaa 32760
aaaatgtgtt atatttctga agcaacacat ccaggttctg cacatagcag ccaaagtgac 32820
cttaaagaat ataactgggt cttgtcattc ccttatttaa actcttgtac ccatttccca 32880
gtgccgttta gatagagatt ccagactcgt caatggctct gtcacctcag acaccctgca 32940
ttgactcatt agtctgatta gagtcaggtt tttcttcctc ctgatggttt tttttcccc 33000
cttagttctc agcggaacag tcacttcctt agggaggttt ccccagccac cctctgaggc 33060
cgtgcttgtt gccagactct gccactagag ggcagggctg caccactcct ggcacctcgc 33120
acccggcctg ccctgtcact ctgtgtgttg ggtgaattcc tgtgatctgt gactcactgc 33180
tctgtgtcct acacattcgg cttttcttct ctccccacaa ccccatttta taattctcct 33240
ttttcaggaa agctttattc ccatttaaaa atttttgttt ttaaaatggt attttcttac 33300
acttattttc taattaaaaa tgagtgtttt aagaagtatt atgatttact gcaaataatt 33360
tttaaaccca gccttttaga tcctctgtga tcataagaga aatgaaggat gtctcccaac 33420
acttgagctt catccacatt tcatcctcct gttctttcag ctgagttttc cccatcccat 33480
tagggactgt tggaatataa aactggcttt tccctaacag ggaatgaatt gcttctgttt 33540
ctcctgaagg agagctggaa gaatgacttg cgttcttttg catacacagg ccttacctgg 33600
tgaaccttct gccgtgcctg actcgaacaa gcaagagacc cgaagaatca gtccaggaga 33660
ccttggctgc agctgttccc aaaattatgg cttcttttgg caattttgca aatgacaatg 33720
aaattaaggt atgattgttg cctcaggtca caaacatgcg agtgatgctg tgagtgagtc 33780
tgtggagggt gagggcttct gaacagggag tcctgtggga gtgcttcttg ggtatgttg 33840
tatgtcgtaa tttagactac catcatttgt gttatttttg aggcacctaa ggacttcttt 33900
ccacttctca tttcttactg tggggtgaag agttgaattg ggagatggtt tctagatgca 33960
aattgaaaag gcatttttcc agagcagatt tgttttcggc gtactagagt gactctttaa 34020
cctagctgcg ggaagatgac tgtgccaaga ctgcaggtag gagaaagctc actgacgagg 34080
ccttgtgggt ctgaacgtcc tgcagctatc agagcctgtt ggcttcctgt tgtgcattcc 34140
aacaaatcat cttcaaaccc actttagtgt tttgtttata atgtccagaa atagtgaccc 34200
tgtcacatgc tctacagatt acaggattct tagcctcttc ctttttggta ggtcagtcct 34260
gggtttgagc ccaagtgacc ctcctgggag gtgatgatac acactgggta gagtggaatc 34320

-continued

```
agatggactt ggattagaat tctgtcctct ttactagtta ttttcctcta ggcaaactgc  34380
ccaacagctc taagctattt ccttcgtatt ctgaaaaata agccttaatg ggacccatat  34440
agggcaactc tgagagtaaa ataaaggaat atgtgttaga gtgtagcata gtcacccacg  34500
ggaagggctt agatgttagc tgctactgct cttattagct gaatgatttg gaataaactg  34560
ttagcctctc tcatgttttt tctcttgagc ttcgaagttt tcttgttaat actaaggaga  34620
tattcaaact agtcatgggg ttttggaatg acgaagggag atgatgaatc taaagaattt  34680
agtgtaatat ttcttcatgc tcagtaaatg gtagtttctg ctgctgttat ttttattacc  34740
atctctttgg aatgggagta ggtgctcctt tgtggtcaga ggctgtgaga gctccacagc  34800
gccagtttgc ccatctgtac actggggtct gttgaaggca gtcccctctg tgatatctct  34860
ggctgtcaga gctcagatga tagatggtat ttttgtactc ttagttctca tcattttcat  34920
gatttcgatc accatttgag tatgatgatg ctaacacttt gttgaacgta gaatccgtta  34980
attacttcct tcctgaacct ttggcattaa aaaaaatcta ttctgctacc tctctgctca  35040
tttatggtta ttcaaattta ttatcaagag cctggtacag tggcttgtgc ctataattgt  35100
agctacttgg gaggctgagg taggaggatt gcttgaggcc aggagtttga gaccagcctg  35160
ggcaagatag tgagacccta tctctaaaaa aactgaaaaa aaattagctg gacatgatgg  35220
catgtgcctg tggtcctagc tactcaggag gctgagacag gaggctcggt tgagcccagg  35280
agttggagtt cgaggctaca ctgagctgtg attgtgccac cacactccag catgggtggt  35340
aaaacaagat gccatttctt aaaaaaaaaa aatatatata tatatattat caatgaaatt  35400
cagtagtacc aacaggatta taaacaaaga tagtagttcc cttcctactt tttctcttaa  35460
tccttgtgtc tcacaggcaa acataactct tagtatttct tccaatattt actttcatgt  35520
ttctttcttt ctttcttttt ttttctttga gatggagttt tgctcttgtt gccaaggctg  35580
gagtgcaatg acgcaatctt ggctcaccac aacctctgtc tcccgggttc aagcgattct  35640
cctgcctcag cctcctagta gctgggatta caggcatgca tcaccacgct cggctaattt  35700
tgtactttta gtagagatgg ggtttctccg ggttggtcag gctggtctcg aactcctgac  35760
ctcaggtgat cctcccacct cagcctccca aagtgctggg attacaggcg tgagccactg  35820
cgcccagcaa cttccacatt tctaaataac atgcttctac tgctattttt tttttcaatt  35880
ttagacattt ttttactttc actatagttc tatcagaatt cagtgtgtac gttattatgc  35940
ctaagtaaat agtcatggtt gcttacgtat tatatttctt tgattgtgtt tcttatttga  36000
tgagaaagct gtgtttttg ctctgggttg aaactggaga gaggacctgg ggaggaggag  36060
gaggacagat gaagttggtg actgtacctt catggccata gctgggttct cagcacccgg  36120
ggatctgctg atcacctact cataggccag gcccctatcg aagttctagg tgacccagtg  36180
ctggggacgg gggggccacc tgcaaggtct aatcatggag gtgggggcta cagtgttggc  36240
ttgtgctggg gccagcatcc ttaggaaggc atcttggagg tggaggagac agccgcccac  36300
ttcttgattg gggccttcag cagcaccagc ttcttgggca ggctggtgct ggctttcatc  36360
accatgtcgt gttcaatctt cttccagatc ctgacttcta ggttcagctt tcctcagacc  36420
ctggttcctt tcagaggcca ttgctgctgc cttgctcttt gctggcttgt gccttgatta  36480
tatgtctttg tacaactttt tgttttcctg gagttaatct tcacatctgt tttcttggag  36540
ttaatcgtta cctctatatc gcttgcttat tattctttgg cctttttgtc ttctcacacc  36600
ttccaacttc tttgtaatat gtgtttagta caatttttca tgacaggtag tttactgaat  36660
cagtttttcc ccagtgtggt catccaactt gagttatcca gctctctgcc ccagtctggg  36720
```

```
caggttgatc ttcaggtctg tagtacactt gtatcctagg acttctcttt gccattagcc  36780
tggaatttcc tttgcagttc tcccgttgga tgcccagttc ctagatgcca tatgtttttc  36840
tatcgtctag tagcttcctg agagaagatg aatgggaggg aaattgtatg aggttttgca  36900
ttcataaaaa tgccattttt tttcctgtac acttggctgg gtatggtgtt ctggggtaga  36960
aatcattttc cctcagaaat gcaaagtctt tgccctgttg tcttaaaatc tccaacgtga  37020
cccgattcct taacctatga atgtactttt ctttggaagc tttccatttt tggggaggtg  37080
aagtgctagg tacttagtag gccttttaat ttggaaactt acatcccttc agttctggga  37140
aaattttctt aacatttctc tgagaagttc ttgcctttta ttttctgtgt tctctcctga  37200
aattggttag ttggatgttg gtcctcctag attgactcac atcttacctt tttcttttct  37260
ttttctggta ctttttagat atccatctca aactcttcta ttcattgtta tgtttttaac  37320
ttctttcttt tctttgtctc ttgatggggt cttgccctgt tgcccaggtt gtggtgcagt  37380
ggtgcgatca tagctcactg cagcctcaaa ttcctgggct caagcagctg ttctgcctca  37440
ccctcccaag tagttgggac tacaggtatg caccaccacg tccagctatt ttctttactt  37500
tttttttttt ttttttgaga tggagtccta ctctgtcgcc caggctagag tgcggtggtg  37560
ggattttggc tcacttaagc ctctgcctcc caggttcaag cagttctcct gcctcagcct  37620
ctcaagtagc tgggattaca ggtgtgcacc accatgcccg gctaattttt gtatttttag  37680
tagagccaga gtttcaccat gttggccagg ctggtctcga acgcctgacc tcaggtgatc  37740
cgcctgcctt ggcctccgaa agtgccggga ttacaggcgt gagcccatca ttagatcttt  37800
aaataccagt atctataagt cttttcctct tgagtcagct agtatccctg gaaggaaatt  37860
actcattttc ctgcttggag gctataagct tggctatgtt tatcctgcaa ccggggactg  37920
gaagggaggg gactgacagt gttgctggtc agggtgccct cttacttttt gttttctgtg  37980
tgcatctcac gtctgtcctc agcctatgta aacacctctt gagattatcc ctctcaatct  38040
ttgccggagg tgggggaggg gctgcttcct gggctgcctt ggattggagg gaagacctca  38100
ggtgagtggg tgggaatttg cccaaggagc catgagacca gccactattt caccctctcc  38160
atccctccac tttcagatgt atgtggcgcc tccaaagccc gagctcttct tggcgtctgt  38220
ggcttcaata agcttgcttt ttgctggtat ccctcctacc ctcccctgtc cccagcaaag  38280
cttgcatttg aacttcttcc tacgggctaa caaatcagtc agttatgtag ctcttgttac  38340
tttttagctt ccgaagtttt gttgacaccc gtagtctgct aatgtccctg ttctgttctt  38400
tctgttcgtg taaatatatg ctttatacaa cttctttaca tgatttttgt ggggtttctg  38460
ggtagcagag cttcacaagt tcaatccagc gtgttggatt agaaatctcc caccctctgg  38520
tttattctta ttctcaaaat tacctgccaa acactgatac tcccttgttt ttcctttttcc 38580
tgacaggaaa tgtacatacc atacaggaca gaaatcatta gtgtatccct tggtgaataa  38640
ccacaaagtg aacttaaccc ttgtaaccgc cacccaggtc aagacagaat attaccaagc  38700
actcagaagc ctctccccta ttcccccgtc actgctcctg ccttcctccc caaggtcatg  38760
actgctggct tctaattcca gagtctgttt ttaaattctg tgtacataga ccatggatta  38820
agtgttcttt ttgtctggtt tattttggtc gacattaagt tcatgagagt cttctatatt  38880
atcgtgtgta ttagtattcc tgtagtttta ggagcttcat agcattccat tgtagggata  38940
taccacagtt tattcattgt attatcactg ggttgtttct agttcttggc tattgcgagc  39000
agtgctactg tgaccactct taggtgtgtc ttttggagta catgtgcagg tttccatctt  39060
```

```
gcacagctag aggtggagtt gttgggtgat agggtgtgtg catctcagct gcagtagaaa  39120
ctgccaaata gctttccttg agtgcttgta ccagctcacc cttttgccac tgtgtatggg  39180
gattccagga gctctggtcc tcgctagcac ttggaattgc tgatgctttt actcttagcc  39240
ttcctgatgg gtgttttctg gaatcacatt atgattttaa tttccattcc ttaaagtacc  39300
cttggctctg aagtttaatg attcatgcat ctcttccctt ttgaagtact cttacaggta  39360
tgttgtgcat gtgttgaaaa gtggcactat ctattctaaa atacagtatg cctcctctgt  39420
gtttgaacag ttgtagcgtg gccttggggc ctcctgttag ctggcttgga gaagggattc  39480
ttgggattgt agagattaga cctgaggagg ccccttggag ctctctgact aaattttatt  39540
ctttattatt ccaaactatt taagctcacc gtgtgctgac tcatcataat aatgagtagc  39600
tctcattgtg cttgtctatt tggactcata caatgatttt tttttttct ttgagacaga  39660
gtcttgctct gttgcctagg ctggagtgca gtggcacaat ctcggctcac tgcagcctcc  39720
acctcccagg ttcaagtgat tcttgtgcct cagcttctca agtagctgag actgcaggtg  39780
cgtaccacca tgcctggcta atgtttgtat ttttagtaga gacggggttt caccatgttg  39840
gccaggttgg tctcaaactc ctgacctcaa gtgatctgcc ttcttcagcc tcccaaagtg  39900
ctgggattac aggtgtgagc cactgagctt ggccaaagta gttttttaag atgttagtat  39960
cttttcttgc agctaaaaaa gtttgtcaga gatgattcta ctttgttctc caggtgtttt  40020
ctcagggaga aattggaggc agtaagccac tgggggagtc ctgtggctgg ggggtggggt  40080
agtcctgtgg ctccttgtca gggagtcctg tggctggcaa ggagagaagt cctgtggctg  40140
ggttgggagg gagtcctgtg gctggggtct catcctgtgc ctaacagtgt ccagaggtgc  40200
cgagaccagc tcagtcgggg agaccctaac ccagcagcgc tagaggaatt aaagacacac  40260
acacagaaat atagaggtgt gaagtgggaa atcaggggtc tcacagcctt tagagctgag  40320
agccctgaac agagatttac ccacatattt attaatagca aaccagtcat tagcattgtt  40380
tctatagatg ttaaattaac taaaagtatc ccttatggga aacgagggga tgggccgaat  40440
taaaagaaga ggttgggcta gttaaccgca gcaggagcat gtccttaagg cacagatcgc  40500
tcatgctatt gtttgtggct taagaatgcc tttaagcggt tttccaccct gggtgggcca  40560
ggtgttcctt gccctcattc ctgtcaaccc acaaccttcc agtgtgggca ttagggccat  40620
tatgaacatg ttacagtgct tcagagattt tgtttatggc cagttttggg gccagtttat  40680
ggccagattt tggggggcct gctcccaata cagaggtctc gtgtaaattc cctgggaggc  40740
gataagcctc tgagaaacag actatgctaa ccacgccatg aaagagaaac ttatttataa  40800
atcagatgcc agttactagt ttactgctta tttgcccagg cgtagctctg acagagtccc  40860
cgactcatag tgcttgctca gtgcatgctg aacaatgatt ggaatcaagt catggctcag  40920
agcatagttt tgaataatgg gaaatggatg ttcttaagta acatagtcac caagataatg  40980
cgactagctg ggtcacccct tttcaatttt aggatatttt tatcaagatt taaatggcca  41040
tcattagagt tatagcactt tctcctttgg attgtcctag aggcccatga gaaagtattc  41100
cctaatttct taggagaaca gtttgtgggt agtatgcggt catgtccagt taaattgcag  41160
atatttccga tcgaagatgt tccagtcctg agaacttcgt gacattagca ggacttctac  41220
aagccatctc ttagggtggg gcatttactg cagttggcta gtactctttt ctccttaact  41280
ttgtcatttg ttgatttttt tttaactgtc cccaaatact gtgggcagag tgtatctaga  41340
attgaggcct ccaccattgc ggagaggaca tggatgctga gcagtcccct gagtgaaggt  41400
tataaagaag caaatagact acacatgtct gtaaactgct cttgagtgtc ccaaatttgg  41460
```

ggtacttcag ttcagctgta ggaaaagcct caaactgttt atactttgca agaattggaa 41520
acttctaatt cacgttaagt tttatgtaat acatgataag cttcatagga gcttcatctt 41580
ttatctactt ggacttttgc ttccgtaggt tttgttaaag gccttcatag cgaacctgaa 41640
gtcaagctcc cccaccattc ggcggacagc ggctggatca gcagtgagca tctgccagca 41700
ctcaagaagg acacaatatt tctatagttg gctactaaat gtgctcttag gtaaggtgga 41760
ggcatatgag tggaagagtc tccagcatgt actcaagata gacctttgaa ataaataaaa 41820
ccagatgatc cctcagcttc tagaccaggc tatttggcac tggttgattg aatgtgaact 41880
gcactggggc tgctgtgagc ccgcatgggt ctctgtgacc ctgcagatgc agccgtgccc 41940
agggactggg cagtgggtgt gggctggtgt gagccctgtc tgccacccag ggcctggccc 42000
tctgtctgtg tcggccatga ctatggtgag tcttgtaggc ttgagactgt gcctcgggtt 42060
cctgcgggtt ctctgtaggt cagttgacag tttctcctgt tgtttgggta actgtggaaa 42120
cgaacactgg caagtgctga agcgagcatg tggacgtgcg atatgaaata acgacctggc 42180
tttcaaaggc agtgaggctc tctggaaagg accttgctga gctagggatg tgggtgtgta 42240
gccattccca gtgggcctca tggcgtactc gttcatgatc atgtttgtgc catcttgatc 42300
tctcaggatc tcttcttttt taacagatta agccgggaat ctccaaacag tgagtcagat 42360
gttaagatgt cttgcttcca cccccacagg cttactcgtt cctgtcgagg atgaacactc 42420
cactctgctg attcttggcg tgctgctcac cctgaggtat ttggtgccct tgctgcagca 42480
gcaggtcaag gacacaagcc tgaaaggcag cttcggagtg acaaggaaag aaatggaagt 42540
ctctccttct gcagagcagc ttgtccaggt aggagcacag ggtttactct aggccctgca 42600
tgtgaatgac tgacattcaa agaaccgatt aatttggaag agaagcggca gaaccgagag 42660
ttagaggtgt ggactctgga gctgcgctgc tcgtttccaa ccctaggtgc tgacctctag 42720
ctgtcttccc tctgtatgtc cctgtcaccg tgagtcaaat gcgggtgatg cctcctcagg 42780
tgccgtgtta cctaagcctc tcagagacca ctgctaccct gtttctaaaa ccagaggtca 42840
cgatatgtgt tcatccaccc agtaaatact gattgagcac ccactgtgtg ctaggctctg 42900
ggataggggc tgggtataca atggtgagta tttcagctgc agcttctgcc ccgtggaggc 42960
tgtggcctag cacactggtc taggcacggt ggtatatgct cactcaagga gatagggacg 43020
tggtcgtttg gggtgtcgga acaaaatgtc ggaacttctc tttccaatgc agagaaacct 43080
tgcagtaatt ctaatgtact gtgattggca gttgacttca gttctttgta gcacgcttac 43140
tcaggttatt tcactaacta tgtaaccatg cagcctcatt ttaagcaatt ggattttttg 43200
aactttactt aaaatgttat gtcagggttt ttattgtgct taatgtgtgc catttagcta 43260
agttttgtag gatacgaaat tgtaagtggc ttaaaatgat tcttaataga atcatgaatt 43320
gaagataatg ctaataattt aagcactgag ttaggtagtg tttgtaaaat gcttagaatg 43380
cttcctggca catgttaagg ccatgtaagt gctgcgtgtt gataaacagc tgagcaaaag 43440
tggactctta agaaagtatt ggggctgaga gttctgttcc aaccagctgc cctttggtta 43500
tttttcagaa taaaagcaga gtctcatggg atatgacatt tatatttcct tcacaaaaaa 43560
cactgctgag tgttttgttg agtaaaaagg gtgtagccat ggtaataata catttaaaat 43620
atagtttatt tcatctttac cttgccttgt ttttttttta agctagcttt ttattgagaa 43680
ttccacacat acaaaagtat caactcatga ccagttatat ttcatttata atcctacttc 43740
tccctttttt tattatttga aagcaaaccc caattatcct cttatttcat ctataagtat 43800

```
ttcagtatct ctatagatga ggactcttct ttatttttaa aactttattt ttaaaatgat  43860
ggtcagatgc agtgttcatg cctgtaatcc cagaactttg ggaggccaag ctgggcggat  43920
cacttgaacc tgggagtttg agaccagccc gggaaacatg gcgaaacccc atgtcttaaa  43980
gaaaaaaatc agccaagtgt ggtgatgcat gcctgtagtc ccagctactt gggaggctga  44040
gatgggaggg tcacatgagc ctggaagatc aaggctgcag tgatccatga ttgtaccact  44100
gcactccatc ctgggtgatg gagcaagatt ctgtctcaaa aaaacaaaac tgcaaaacaa  44160
cgtcacaaaa cagtgccatt gttagacctg aaaatattaa acatttccta catcaaatac  44220
ccaccaactc attatcaatt tttctctcta ctcttttgga atcagcatct aaataaaatt  44280
ggtcgataag gattgtaaat ctctttgatg aactggttcc cctccatccc agtttttttc  44340
ccttagagtt catttattga gaaaccagat tgtttgtctt ctaagttttc ctgtggtctg  44400
atatactgct tccatctcca ctgtgtaaat taacaccttt ttctcttctc tgtatttcct  44460
gtaaatcaat aattggagga aaagccttgt cagatttagt gtatatttta tatctgagtc  44520
cagtatttct tatataatat tttaagataa gtgtactctt ttaaaaagta ttgaaactat  44580
atgctcaatt ttttttaact gatgctttta agaaggctgc ttgatcataa aagtttagag  44640
atcattggtc tgatgggaaa agcaaataat tactaaaccg tttagcaagg ttgaggtgca  44700
catggtgggg cctggagaag ttcagtcatg agccgtcact tatgggcacg tggaatctga  44760
cccggcacag agttgggaga agacaggagc tttatagaca gaaaatgtgg tctttgctaa  44820
gtcccaggag tgaaagggtg agacagtgct cacagcacac gagtgtgggt gcgtagacag  44880
agcaagggtg ggtcctgaaa aggcctgcag gctttctcat agattagcaa gagtgctggt  44940
tacggaggtt tctaacattt gtgaacagat cgaaactgtg ttaaattggg attgcagtaa  45000
tcctggaagg acagggatag agggtgaagg ggaaaaaagg gtatggatgt gagacttaat  45060
tgctgatttt cttaagacct ttctccaaag taaataaatg atgtggcaca tttttgaact  45120
ggcaaattct aaactctaga tatgattatc tctataacat atcttactcc atcttctttt  45180
gactaaaaac tgttcttaat taaattacca tgagacgttc aattcagcaa atgtagtttg  45240
gctaaccata tttaattaga atttaatata atcctaggcc tggccaaact attaagcaag  45300
tgtgggcaaa atattgataa ttttagatat gcaggaactt agtttgcttt ccatgtgtgc  45360
ttttcgaaaa aggaataaat tgaaaaatag aggaagccct gaaatccaag aagcaaactc  45420
tctcacctag gcatgcagta aaagcaattc taggatgatt gctgtttggc gcgtagttcg  45480
tattagaaac cattcttctt gaataaatag tatgtttaag aagctgggca gagggaaggc  45540
atatgcatat attatcaaca aggagggaga aaaaggcaat tagtaaccat ccataggagg  45600
gtcagcaaga tttataaagg aaatttgtga tccaagtatg aagcaaaata aggtgcagaa  45660
taaattttaa gcaagtaata gattagagta agagaaccca tttgaccatt aaccttggga  45720
cattctcttt caaatgacat ggagtagtac tgaaatcttt ctttctttct gagtctaggt  45780
tattgtgact ggactcagaa agaaatattt cattattgca gtgaataaca tttgtgaaca  45840
ttattgttca taaattatgc agtgaataac atttatgaac acgtgatgtg taagatacat  45900
actgtttatt tttagttaag ttttttggct caacttctag gcagagaaca ttaaatgtaa  45960
atagtgttac ctaggagcat gtaaatggaa atctccatag tatgaaagca gtgctgttgc  46020
taacagaatt taggaggggg cagatgaggt gaaggaaatg tgggtgctga tttccttatt  46080
acattgagag gagccaggag attctttgtt caaaatggat ggcttaagaa gtcaaagtat  46140
aagctgatta cgtagagcag gtacccaaaa atgttttgtg taaggggcca gatagtaaat  46200
```

```
attttcagtc ttgcaggcca tcccaagtct gtggcagcta ctcaacacta cctttgtagc  46260
atgaaagcag ccacaggcag cccataaatg tggctctgtt ccggtgaaac tttaggtaca  46320
aaagcaggtg caggccagac ctgacctgtg cactgtggtt tgctgacctg ggattcaggg  46380
gtatagaagt taccatcaga agagctaaaa gtgagacttt ttactttata ctcttctaca  46440
ctgtctgatt ttgaaaaaaa gaaacatgta ttttataata ttaaagatag ggttggcaaa  46500
tagcaaataa aaatacagaa taccagtgaa atttgaactt cagatacatt atgagtaatt  46560
ttatggtgta agtatattcc aaatcatgtg ggacatactt acactacaaa attatttgtt  46620
gtttgtttac agtttaaatt tgagtgcctt gtattttatc tggcaactgt aattaaaggg  46680
aaaaagaata aattcattat gttcatataa tgtgatatag caggggtccc caaccccccag  46740
gctgcagagt ggtactggtc catgggtccc caaccccccag gctgcagagc ggtattggtc  46800
catggcctgt taggaaccag gctgcccagc aggaagtgag cagcaggtga gctggcattc  46860
ccacctgagc accgcctcct gtcagatcag tggcagcatt agattcccat aggagtgcaa  46920
accctattgt gaactgcaca tgtgaggggt ctaggttgtg cgctccttat gagaatctaa  46980
tgcctgatga tctgaggtgg aacagtctcg tcttgaaacc atcccctggc cctgtggaaa  47040
aattgtctcc catgaaacca gtctctggtg ccagaaaggt tgggtagcac tgtgatatag  47100
tattaaaagt gctaataaat atggcatact gcctttaaaa tgtctggtag ctctttctca  47160
gtggcactca taatagtgtt ttttgatttt taaatgtgtg tcaagctgac tctcccctcc  47220
gtgtatgctg ggctttattt tccctttcct agtcaccagt tttgggaaat agagatcttc  47280
attctcatgc tgctcctcta gtgcaagtgc tccatttatt tttaaggaat taatataaca  47340
aaaaatcatg ggaatttaga aaacaacatg gaagctaatg atcacattgg tggaagtgat  47400
agggaaatat ttagggggag aagttaaggt ataaactttg tcaatgaagt cctattaaaa  47460
acaacaaaaa agtgaagctt aggatgcatt tttataaactc tgaccagaac acctgtgttt  47520
ctctgtttct aggtttatga actgacgtta catcatacac agcaccaaga ccacaatgtt  47580
gtgaccggag ccctggagct gttgcagcag ctcttcagaa cgcctccacc cgagcttctg  47640
caaaccctga ccgcagtcgg gggcattggg cagctcaccg ctgctaagga ggagtctggt  47700
ggccgaagcc gtagtgggag tattgtggaa cttataggca agttattagc aaggtctact  47760
cttacaatta actttgcagt aatactagtt acactctatt gattatgggc ctgccctgtg  47820
ctaagcagtc tgcattccat cttccttgcc aaaacttata atacaaattt catctttatt  47880
ttataaatag gggagttggg ctgggtgtgg tggctcacgc ctgtaatttc agcactttgg  47940
aaggatcgct tcagcccagg agtttgagac aacctggcca agtgagaccc tgtctctaca  48000
aaaaaaaaaa aaaaaaaaaa attagctggg catggtggca catgcctgta gtcccagctg  48060
ctttggaggc tgaggtggta ggattgctta agcccaagag gttgaggctg cagtgaatct  48120
tgatggcagc tgcactgagc ctggtgacag agcaagatgc tgtctcaaaa taaatttaaa  48180
aataaaataa gagaattaaa gtttagcagg ttgggtggca aaatgaggcc acacatttaa  48240
agcccctcct cctgattctt ttctctgcct tggctgcctc ctgtggcatt ttaggtgctg  48300
agaaatgaaa acagtaggga aaatagttcc aggatcctca tgttaatttg ccagaaatgg  48360
catcttcaag tcgtcagagg gatctgagag ttccttcctg gcctgacttg agaaaatccg  48420
tctgtcccca gctctgcgtc tgcctccact gcccagtcac ctcctctcca tgctcttggg  48480
gctgggccct accccaccat gcagtgctgc cctggagcag tgagcttggt gggtcctgtc  48540
```

```
tggcatgaga gctgcctttg ggagctggat cccagcctct accactgggt ctggtgccta  48600
gcaggctatg gataaacttc tgctgactcc ggcctctcct aagccactgc aacgtggtcg  48660
gtgtagtgca cagtgtgtgt gcagcgtggc cttactcaca gcctccacat tagagagaat  48720
ctgactgaag tcttactgct gcctcgtgtg aacataaatg tttgccagaa ccatgagcag  48780
gaaatgttaa tctgccttgt ttcctgtcct ttacacggaa gaattttttt ctgtatggaa  48840
tgcgtgcctt acaaataatg agtggaaata cccatcgcta atgaaaagtt atacttgact  48900
gttagtcagc taaataatct gagatttcta atacttttaa tttggctttt acaatgcaat  48960
ttatcttagc tttttgatt tcttaggtca tatctttaga actatatatt tgaatgttaa  49020
tgtaattttc atattgaaat taaaatgttg aactgcgatg ttaagtgttt cctgtggaaa  49080
aacgttcaca ttttctctag ttttaaagtt gaatcaagct gtttgaagat tttcacattt  49140
cttctagatt ttatcagctt gttactttat ctgtcacttt ctgtgatttg cagctggagg  49200
gggttcctca tgcagccctg tcctttcaag aaaacaaaaa ggtgattatt tcagaaatca  49260
gagtcttgtg ttgaatctta ctgattttct tgtatttctg taatgtaatg tatcttgtat  49320
ttcttgtaat actgtattgg actctgtgta tatctcttct cagatgagtg attatatgtg  49380
tgaatgttgc tggaatctga taaccaggcc tgaatagttt tgtagggtgg cttttaaaaa  49440
ttactttcat atcagaattg ctttgtcata aattttgaac gcatcataaa tttctaatgt  49500
tcggggtcag cagacttttt ttgtaaaggg acagagtgta aacatcttag ctttatgggc  49560
catatggtct cttttgcaac attcagctct gccctgtgac aggaatgcag ttgtaaagac  49620
atgagctact ggccagctat gttccagtag aactttactt acagaaacag acaggctgta  49680
gtttgccaat acctgcctta gggaatgtgt tgttatattt tgtgagttac cttctcagta  49740
aattttattt agtattagtc aggaatatta ttaagtagct tcttttccag cctggtcaac  49800
atagtgagac ccggtctcta ccaaaacaaa acaaaacaaa aaaacagcca cgcatgtggc  49860
atgtgcctgt agcctcagct gctgctcagg gggctgaggc aagaggattg tttgagccca  49920
ggagtttgag gtcacagtga gctgtagtca tgccactgca ctccagccta ggcaacagaa  49980
tgagaccttg tgtcttaaaa aaaaaaagtt tcctttgttg ggttatttta atttggacct  50040
ggttatcatt tttcagccat atttaacttt gtacatatca gaatgttctg ataaaactta  50100
acttttatta aagtgtttgt gatataatct gctagttttg gtacacatta tcttttgcaa  50160
tgccagttat tttcttttcc agtgtgggtt tgcataggaa aagaattgct gtcactttct  50220
attttgaaat cttaaaagac tgatcctttt ttgtgtcatg atttgagtat ttaattgaga  50280
gcctaatgcc taatattatt tgcagtatta aatgggatct taacaggaat agcattctag  50340
ccttcattga attaagtaaa catttcttaa gagaacttgg aatctataat atttgcgtca  50400
tcatagtatg agatacttaa tcaagtttga gattttagtg aaacattgtt tagaagccaa  50460
aaggattcta ggaaaaatta atgtctatat tcttgaatta ggagagattt tgggacgtgt  50520
gactaagtta cgctgacact tgtttgtttc ttagtcgctt tttccagtgg cggtgagaac  50580
gaagatgact gattcacatt gctcagatga gtttatcctc ttctggctgg gacatgggat  50640
atatcctgtc tcttttaagc ctttttggta tttttccccc attgagagct gtgtcttcaa  50700
actcttctgt tatagctgga aaatcctttt taagtgaaat ctgcccaaat tataagacag  50760
atgaaggtag agttgtgttg gatataggat tagggtgaaa gtagtggggg tgtcctggag  50820
cctctcttct ggtggcagcc tagctcttgt gcctttgagg aaattaccct ggggacggct  50880
ctgtggaaca tatttgcaaa ccactgattt ggaagataga gatggctttt gttaagatct  50940
```

```
gaattcacct ttttggcatt ttatttgatt tctcaaggta aagaacttat tttgtaataa  51000
agtttcctat tatttagtag ataggccaag ttgctgtgtt aattccatgt agattttggg  51060
tttcctttgc tcatttttc actcttaatc tcacatcatt gtaagtttat ggaagttatc  51120
atacttctga ctttttcttt gaagagcaga aattagaaat tcccaataat tattttgata  51180
gtgtcattta atgacactca catgtgatgt agccacaaag atttaatgag ttcagtttta  51240
aatcatatta agactgttgg tttcatttgt tctcattaat gtaattctga agatgaacaa  51300
taaaatgtat ttttagaact ttcaaatgaa atattatttc atccttccag atcatataat  51360
gcttaagttc tgattgttaa tcataaagtc tagaaaatta aaagataata aaatgaaagt  51420
gacttttagg tattagagtt ttattataaa ttctggtgtg tcattggagc tatgacatga  51480
atatttcaaa ggccaatagc attggatctt tacagttata acttaccatt tttaagttta  51540
agtagtaata tagattattt aataatcaaa atcaataaat attaattatt aaaatgtttt  51600
gtggtatagt ttgagaatca ttgcttttaa ctttttccat ataggtttat tgactttaat  51660
agcattctaa acataacatc tctacattct ttgtgtttaa tactgtggag gtataaaaat  51720
acttatatat gatgataaac tatattagag taaattaaat attcttatga gtttcatttt  51780
agagtgcatt tacttaattt tgaagtcctt atttttagca aactaaaagg aatgttggta  51840
cattatttac taggcaaagt gctcttagga gaagaagaag ccttggagga tgactctgaa  51900
tcgagatcgg atgtcagcag ctctgcctta acaggtagtt ctcactagtt agccgctggt  51960
gtggaccttc actgtctgcc ttccacccct tgcccttcct gctcgtcccc ctgcacctgg  52020
tggacagcac gactgggggc agcagtggag ccaggttgct taaatggggc atattcgggc  52080
ttcttttata atacttactc tgaagcttgt gtgtctgtgg tgtttgcatc atatatttgt  52140
tgttttccat ggtttaggct gttttaaaat taggtttatg gcttgagcat agggctttgt  52200
gagtagggga tggcaggtcg aaacatctca tgagttggat gggttatgct gggggttggg  52260
aaatgggatg aaaaattatg ggatgaaaaa ttgcctatgg atagtttaac ttgaaagaat  52320
ctgcctttgt ttacagatag ttatcttttt tcttttttga gatagagtct cacactgtca  52380
cccagtgcag atacccagtg tcactggagt gcagtggtgt gctcttggtg cactgcagcc  52440
tccgccttct gggttccagc gattctcctg cctcagcctc ccaagtagct gggactacag  52500
gtgcccgcca ccacgcttgg ctaatttttg tatttttttg tggagacggg tttttgccat  52560
gttggtcagg ctggtcttga actcctgacc tcaagtgatc tgcctgcctc agcctcccac  52620
agtgccggga ttacaggagt gagccactgt gcccggccag ttacagatac ttatctaatg  52680
aaattctctg tgtactttat aaaagatgag gattaactga aggtactaat aactggatta  52740
tatgagggtg gttttggttg tataatccta tctaaaagaa tattttagct ataactgaaa  52800
gtaagactta aatatttaga gaggaaaatc tgaataattc tagtagtaat tatttattta  52860
caaaataaaa atagattttt ttttgattac acaaattaaa caacaataaa acatcacagc  52920
aatccggata ctataaagct cacatgctta ccgacccaac tgccccagga gtgaccactg  52980
ccaacagctt catgtcgacc tttttgccat aatttttata tagccttttt tgtttttaaa  53040
tggtaattta gaaagtcaac taggaaaatg tgttacaggt ttatcttcca ggagaatagg  53100
actggagtcg agatcttgaa tgtggcttgg aagaaggcaa gcccacccca gagagatgag  53160
ttgacagttg tttctgacca ctgcttgctt agagggcctg cgtgtctgtg accgcctagc  53220
tttgcgcccc tgactaggct gccccttaat tacaaatgtc tttatatatt gctccagcta  53280
```

-continued aggcttggag tagtcggtta agaacttgaa cttcggtttt tgcagtgaaa cagcatttga 53340
gaatatcacc ttctgataag ccttatttta taaggtgggt actgtagtgg gaggcagtgt 53400
gagagatgct tgaaggatgc actgctgtcc tgcatttcag catcttcagg atgctgtgca 53460
gctgaaacat ttgataacgg tggaactgtt cgttattttg caagcctgtg attccctatt 53520
gaatgttttc tctcgccatt tgacaaatga gtgtttctct gtcttcagcc tcagtgaagg 53580
atgagatcag tggagagctg gctgcttctt caggggtttc cactccaggg tcagcaggtc 53640
atgacatcat cacagaacag ccacggtcac agcacacact gcaggcggac tcagtggatc 53700
tggccagctg tgacttgaca agctctgcca ctgatgggga tgaggaggat atcttgagcc 53760
acagctccag ccaggtcagc gccgtcccat ctgaccctgc catggacctg aatgatggga 53820
cccaggcctc gtcgcccatc agcgacagct cccagaccac caccgaaggg cctgattcag 53880
ctgttacccc ttcagacagt tctgaaattg taagtgggca gaggggcctg acatcttttt 53940
ttttattttt tatttgagac agagtctcac tccatagtgc agtggaggcc gggcacaggg 54000
gctcatgcct gtaatcccag cactttggga gactgaggca ggcggatcac ttgaggtcag 54060
gagttcgaga ccagcctggc caacatggtg aaaccctgtc tctactaaaa atacaaaaat 54120
tagttgggcg tggtggcaca tgtctgtagt cccagctgtt agggaggctg aggcaggaga 54180
attgcttgag cctgggaggc agaggttgca atgagccgag atcgtgacac tgcactccag 54240
cccgggcaac agagcaagac tccatttcaa aaaaaataaa aaaataaagt gcagtggctc 54300
gttctcagcc cactgcaact tctgcctccc aggctcgagc gattctcccg cctcagcctc 54360
ctgagtaggt gggattacag gtgggcacca ccacactcag ctaatgtttg tattttcagt 54420
agagacaggg tttcaccatg ttggccaggc tggtctcaaa ctcctgacct tagatgatcc 54480
acccaccttg gcctcctaaa gtattgggat tatagttgtg agccaccatg cccggccctg 54540
ccacctgcca tcttttgagt tcttccctgg agacctagac ctgaaccctc ctgcttgttc 54600
tcttgttatc taatacccct attgacagcg cagcttagat cattaatgga gagcttgacc 54660
tcatctgata ccttcactga aggaaacaac ttagtgtctt ttgtgttgaa cactgaggta 54720
aaaaattgga atagttgatt atatgaactc tgctaaaatt gagtgcattt tacatttttt 54780
aaggccttgt tgggccctgg ttaaataatt atttttaaaa atccttaagg agcctattat 54840
aaacagatct gtggtcttaa tgaaatgtga ttaatactgt gcattatttt aagaactttt 54900
gacttttcaa aaaactttta caacatttcc catttgatag cggcataggt ttaagcactt 54960
ctcatctcta agttagtgga caaaaaaccc tcatggatag tctaataatg tttgctacaa 55020
gtccatgttg agttttatac tccattttat tttcagtttt aaaaactgtg gttaaatatg 55080
tgtaacataa aatttatgtt cttaaccatt ttttgcgtat acagttcgct ggtattaaat 55140
acatttaaat aatgtcatgg aatcattgct accacccatc tctgtaacct tttgatcatg 55200
taacactgaa gctctgttcc cattgaactc tattcctcct ttcccgccaa gtccctggca 55260
accacgattc ttctttctgt cttctgaatt tgactacttt gggttctcat atactttagg 55320
agtcacacag tatttgtttt acttagcata atgtccccaa agctcatgca tgttgtagcc 55380
tatgttagaa cttcctaatg tttcaggcca aatactattc cattgtatgg ataggccaca 55440
ttttgctttt ccattcctct gtccatggac acttgtattg cttcatgttt tagccattgt 55500
gaatcatgct gttatgaacg tgggtgtaca gatagctcct ggagactctg ctttccattt 55560
ttttggctaa atacccagaa atggagttgc ttttacattc caattttaat ttaaaacatt 55620
catatcattg agtgttttac ttaatagtat agtagttaac aaacttaata aaatagtatt 55680

-continued ttggtaataa tttgctggta gtccattgtt cagttttttt aggtaaatta cacaggacat 55740
ttcaagtgga catgaaacat cttgtgatgt ggaatcatgc cccaagctga tggctaaaca 55800
tatgaaatac cataccctaa atttagtaga tttagtcttt gcaatttagg agataacctg 55860
ttatattgtt aggtttttgt cgaaaagctt tgtcctcata tttccaactt gctgtaaaat 55920
ttgtttgtga agacaaatat ttttgtatgg gttttttctt tttcatatta aaaagaaatg 55980
tccacattgg aatttttttg gagtttttag agctaataga gcttttcata atgtagtggg 56040
aatgagtgat cagtaagctc ttagcagttt ccatgcgtgc atttctgtgc cttgaaataa 56100
atgacagatg agtacatttg tgttctgtgt gtaaaatgtg ctctttcctc attgcacttc 56160
catgttggag ggcttgtctc ttggtgatca cacttcaaaa ttctcacagc ccccccttgaa 56220
ccgtttaggt gttagacggt accgacaacc agtatttggg cctgcagatt ggacagcccc 56280
aggatgaaga tgaggaagcc acaggtattc ttcctgatga agcctcggag gccttcagga 56340
actcttccat gggtatgtgg actacaggtg atgcgctaca aagtggtttg tattcagacc 56400
tggacatctt aattatatct ttgcttccaa gaagaagtcc tttgatactg ttttctgagt 56460
tctgaatagc tgatgaaaat gaccaattga ggaataatca tactttttct tgatctaaat 56520
cttatacttt tgagttatct tagcataaat gtataattgt attttaagtg gaaatttgtc 56580
acttaatctt gatttctctg tttttaaagc ccttcaacag gcacatttat tgaaaaacat 56640
gagtcactgc aggcagcctt ctgacagcag tgttgataaa tttgtgttga gagatgaagc 56700
tactgaaccg ggtgatcaag aaaacaaggt gagggacata ggcttgagac gacttggtgt 56760
ttctgagctt gtgtgaggat ttaaaatcgc cctggctact gtctacttta ttgctttccc 56820
atccctgggc ctttaaattt cccctttaaa taccagctct tcccaggcct gttgttttct 56880
gcctttccag gtactaccca cagccttgag aattgcctga gttctgcctc ctttgagagt 56940
gtgccccaga caaatctatt ctgtactgaa tgtttccttg tctgatttct tggatcattc 57000
atttgatggt tgcgtatggc ctgcaacgtt tcttgttttg gttctactga actgttctaa 57060
aagtctctct tcatattatc tttttacatg taaatgtaac tgtcttcact tttaattcct 57120
caaggacaag gaatagcgtt tcacagttcg tcccatcaat cagaattata gcctttggca 57180
tctccctatc taccaggccc acttcctctt agatttgggc ttccccaggc tgttgccttt 57240
ccccaagtag cttctgcttg tcctgtagaa gacctttcat gctttgcttc tgcagcagcc 57300
gttcctgaat gcctagtgtc aactgccttc ttaccacgcc caccctccct gcatgctgca 57360
tttatcccct gccacagccc tgtgaccctg tgtcctgctg cctctgactt gtctgtttct 57420
gcttggccat ggtctctgtg aggtcaggtg tgcatatggg cacaaaccag ggcatctctt 57480
tatccccagc acctggctta agtgctgctc tggaactatc tgttgaatga actaatgcat 57540
gaatgtattg ttgagtatga gacaaacaag tgtcattgtc tcctttctag ccttgccgca 57600
tcaaaggtga cattggacag tccactgatg atgactctgc acctcttgtc cattgtgtcc 57660
gccttttatc tgcttcgttt ttgctaacag gggggaaaaaa tggtgagtac aaaaggggat 57720
gtgcacagtt gaaggaaata actaggtttc agaggtcagc ttggtggcct gtttttgcct 57780
tgcgtgcagc agaggaagta gaatctgagg atgagtttgg ttttcactag ccgaggggag 57840
ggaggaaatg atgggagcag gtaggttatt gggtctggtt ttgttcattt gaaaacaatc 57900
tgttgtttga ggctgaaggt ggcttgggtg atttcttggc agtgctggtt ccggacaggg 57960
atgtgagggt cagcgtgaag gccctggccc tcagctgtgt gggagcagct gtggccctcc 58020

-continued

```
acccggaatc tttcttcagc aaactctata aagttcctct tgacaccacg gaataccctg  58080
gtatgttaaa agttcacatc ttattttctc agatttaatc attattgtaa aaactatttc  58140
agtattgact attttagttt tagagcagta agtgttttga gttcatttgg gatatttgac  58200
ctgcgttgta gctcttcaga aaacacatga atagtgaagt tctttgtttc atgggttccc  58260
tttagatgaa acccatagag gagaaaagta gaaacctcag cacgtaagag ccaacatata  58320
tacacatcgg atttaaacct aaagcacaaa ttgtgcctgg tcgcagtggc gctgagtcgc  58380
actcagccag gccaggcatt cacactcagg gtgagtggga accaggactg gctgaggcag  58440
cagtggaccc aagtctccat cgcgcccatg cttactatgg agccttctcg ttctctcttt  58500
ttctttgggt gagagggtac acttgtgttt ttgaatttat atgaggtaag tgtgtaatag  58560
ggttttttct aatctttttt aagtggaatc tggaatttta atcagattta ttatctgaca  58620
acctagaatt ataatccaga aagtctgtgg tattgaggac atattggcaa tatgatgaat  58680
ctctaattct taaatcctga aacttttttt tttttaatca cttagggtta ttatagtgaa  58740
gtcatttctg aatttggatc ttctcttcac acctcttttt ctctttcctg agaattaagc  58800
ttttgtttcg agttagaaag ttgatagtag ggaattgttc catggctgag caatttatct  58860
ccacagagga acagtatgtc tcagacatct tgaactacat cgatcatgga gacccacagg  58920
ttcgaggagc cactgccatt ctctgtggga ccctcatctg ctccatcctc agcaggtccc  58980
gcttccacgt gggagattgg atgggcacca ttagaaccct cacaggtaac ggccagtttt  59040
tcagctgtgt tttttctagt tatgcttact aaggtttaag tttagatgat gatgtttgtt  59100
gcttgttctt ctggttagga aatacatttt ctttggcgga ttgcattcct ttgctgcgga  59160
aaacactgaa ggatgagtct tctgttactt gcaagttagc ttgtacagct gtgagggtga  59220
gcataatctt ctgtggaacc atttcttcac ttagtggaca ttttatcatt gctacaatta  59280
aaattggagc ttaataggaa atatttccat gcactctaaa gctgtaacca gtaataccca  59340
ccatgtatcc atctctcagc tttagaaaga aaacgttgcc agtaaagtta atgcttcata  59400
aacttcagtt taagttctaa ttctcagaat atttgtttga aatagacctc ttcctaaagg  59460
atatatttag aaataaccta tcattaagtg taaagtctgt tgaatatgct gggcacggtg  59520
actcacacct gtaatctgac cactttggga ggccaaggtg gaaggattgc ttgagcccag  59580
gagttcaaga ctatgggcaa catagttgac cctgtcccta cagaaaatta aaaaaaaaaa  59640
aaaaaaaagt agctgggtat ggtggtgcat acctgtagtc tcagctactc gggaagctga  59700
ggtggagggg ggattgcttg agccccagag atcaaggctg cagtaaggcg tggttacacc  59760
actgccctct agcctgggca acagagtgag actgtctcaa aaataatagt aataataatc  59820
agttgaatta aaaaaaaaaa aaaaaaaacc actgtgctag gcccatagta tggtaagagt  59880
taaagtgagc cttagggatt atttactcaa cctctgtttc tgtataaagt ggaataggct  59940
caattcttta agtgatagca tgttgaacct ttccatacca actggctcat aagtcacaac  60000
tggccagtca acaagagtaa aaattaactg gtaaaaatca aagcaaaaaa cctacaattg  60060
tcaaatttgt gggataactc cccttttaa aatgtcatgc ctgacagtaa tttctctcta  60120
gtttccaggt tttcagtcag ttgtgtcttt tttgagcaga aggaagcatg ctaagagctc  60180
aatcttgtgg ctagctgggg gtctttgtgt cagccatgca tgtgatggtg cccctgggtg  60240
cttggggctg caggggaggg gtacagcagt aggggcctgt tctgttctct cgtgctgtgg  60300
agtacatagt gacatagtgg ggtggtcctt ggtgtaggtc ccttgttcct acccctgggt  60360
ctgagattta tttagaagtg gtgttggggc tgtgcggcag gcccctctgt aactgatcaa  60420
```

```
tgtttgtgaa gttgctgttt gagagttgaa accatgacat aagcagaaat ggaaggaaga  60480
aagaaccagt tatgtgaaag ggacacattt acttttaagc ttgtatttac tgagataaag  60540
tattcttaat caatgttctt gagaggtgtg ggaaaaatgc aacatcctgg ttgcagttaa  60600
acccagaaca ttgtgtgttg aagagtgacg gttctcaaac cgtcaagacg cgggtactga  60660
gtgggactaa cctgctgtcc tcttgccttg gaccttgtgt tccagaactg tgtcatgagt  60720
ctctgcagca gcagctacag tgagttagga ctgcagctga tcatcgatgt gctgactctg  60780
aggaacagtt cctattggct ggtgaggaca gagcttctgg aaacccttgc agagattgac  60840
ttcaggtaag tgagtcacat ccattagatt tcatgaacta agctcaattg aaagttctgg  60900
gatcacttga tgcaaggaat gatgttatca agtaccctgt ccatcagaaa tccgagtggt  60960
ttaggtagat gacagtgatt ttctcctccc agtggctttt tgctgaactt tgccctatgc  61020
ttggaatttt attttatttt attatttatt tagagacaag atcttgctct gtcgcccagg  61080
cttgaatgca gtagcacaat catagctcac tgaagctttg aactctagga ctcaagtggt  61140
cctcctgcct cagcctcccg attagctagg agaataggtg tgtgccgtca cactggctaa  61200
tattttttgt agaaatgggg tcttgctatg ttgcccaggc tggtctcaaa ctcctgggct  61260
tgattgatcc tccatcttgg cctcccaaag tgctgggatt acaggcatga gccactgtgc  61320
ctggcctaga attttaaaat ataagtagaa gagtagattt tttttttgg tagtcctcgt  61380
catttaagta ttctggatag tgggaataaa agagcttaga atttttcatc tttgtcttaa  61440
acttttaaaa aaatgtagct tatattaatt ctgcttgttt aaaaagaata tactcttcat  61500
tatactgaac ctaggtaaga cagctggttt atattttgtt gcaattaaaa aacgtgagct  61560
gtggttgcag tgagccaaga ttgtggccat tgcacttcag cctggcaaca gagtgagact  61620
tggcctcaaa aaaaaaaaaa taacatgagc tgtgttggca ctttcatttt ctaagagtag  61680
ttttggctgg agaagttttc tttcagtact ttcttttaga agggaaattt tcctttataa  61740
tttagggttt gttttttttt tttccaagcc accttttata gagcccttgt gggttatttc  61800
atttaatcct tagaatgttt ataaatctgg gcttgttctc ggctccaccc acagataggg  61860
acgctgagcg tgcatgagtg ggcagcaaga tagcaggtta tggagggccc agctcacccc  61920
ttctgtggct tgagccaatt ttatagggca cttacagagt cttttgaaat agtatttatt  61980
ttgaagaaaa agaaaaacag tttactgagt actgtcttat tgagtctgga attgtgagag  62040
gaatgccacc tctatttatt taaagccatt ggcctttttt gttgttttga gtaagtgctg  62100
cccaaggtcc ttccagggca cctggatgag cctgctctgg agcaagctgg cggtaagtgt  62160
ttactgagta actaaatgat ttcattgtta aatgtgctct tttgttaggc tggtgagctt  62220
tttggaggca aaagcagaaa acttacacag aggggctcat cattatacag gggtaagcgg  62280
tttatttttg tgagatgctg ttttaccttc aagaaggtga aagtgaggct ttccttgtgg  62340
aatttctcta aatgcattcg tcatgtttta gatgtttatt tcacagttta tatcatgaaa  62400
gttataatct tgtcatatgg atttaagtct agtaatgttg agttctttct cactagcttt  62460
ccaaaatatc ttacctaaaa tttagtcaaa tacaagatta tgtttatttt tattatcctt  62520
ctctctaaag cttttaaaac tgcaagaacg agtgctcaat aatgttgtca tccatttgct  62580
tggagatgaa gaccccaggg tgcgacatgt tgccgcagca tcactaatta ggtatttacc  62640
aatattttat ctcttttcct tttttggttg aagtactaaa agatacgaga atggaaagag  62700
agggaagaat tcaaaggatg tagagcagta ttcctgaatc tgagctcatt tcagccattc  62760
```

-continued

```
tattcttaaa ctataatgaa aaaaaaatcc aaaaaagtct aaaattataa ttaaaaaaac  62820
aacaaaatac taactgtcca ttgtaaaaag taatgcactt tcattgtaaa aattttggac  62880
tatagagaat agtactaaga agaaaaaaaa aatcaccttc aattctgctg ccacctggag  62940
gtaatcactg ttaatatttt gctatatact ctatgagttt cttgttcaaa atcaggtcaa  63000
aattacatgc aattttgtaa tctgacaatt tccacttaat attttattag cattttcctg  63060
ttatgaaaca gtaattttag ttatgggtcg ttgttttgct atgcggttgg gataaaattt  63120
tatatacttt ttttggcaat tacttattat acataaatgt ttgtgtatag ttttcttttt  63180
ctgagaattc ctggaagttg agttaccagg cccggctttg aatttttttt tttatttttt  63240
ttttgagaca gagtcctgct ctattgtcca ggtgctatct cggctcactg caacctctgt  63300
ctccctggtt caagcgattc tcctgcctca gcctcccgag tagctgggat tacaggggca  63360
caccaccacg cccaattaat ttttgtattt ttagtagaga cagggtttca cgatattggc  63420
caggctggtc tcgaacttct gaccccgtga tccacctgca ttggcctccc aaagtgctgg  63480
gattacaggc gtgagccatg gcgcctggcc aggctttaaa tttaaaacaa atcttctaat  63540
agctttatgg aggttataat ttacatttct tgaaatgtac tcactttgag tgtatagtaa  63600
actccaattt tatcacattt ctgtcacccc aaatgtatcc ttgtgcccat ttgctgtaac  63660
ctccggttcc tgccccaact cctaggcagc cactcatcta ttttctgtcc cttaagattt  63720
gtgttttcgc caggcgctca tgcctgtaat cccagcactt tgggaggccg aggttggtgg  63780
atcacttgag gtcaggagtt cgagaccagc ctggccaaca tggtgaaacc ttgtctctac  63840
taaaaataca aaaattagtc ggatgtggtg gcacacgcct gtaatcccag ctactcggga  63900
ggctgaggca ggagaatcac ttgaacctgg gaggcggagg ttgcagtgag cagagatcgc  63960
gccactgcct tccaacctgg gcaacagaga gagactgtct caaaacaaac aaagatttgt  64020
attttctgga cattttatag tactggggtc atagtataga tggacttttg catttggctt  64080
cttttactta attgtgagat tggttcttgt tgtagcatgt atcagtagtt tgttcatttt  64140
tattggcgaa agtattctat tatatgaata ataccatatt ttatctatcc atcagatgga  64200
tattatagag ttcatgtttt ggctaattta tgaattatgg tactgtgaac atttgcctgc  64260
aagattttgt gtagacatgt cttcatttct cttgagtaga tcacctagaa gtggattttt  64320
aaataatttt ggtacttact gtgaaactgc tcttcaaaaa cataccattg ttccttcctt  64380
ccttccttcc ttccttcctt ccttctttcc ttcctccctt cctccctccc ttccctactt  64440
ccctctccct ttccctttcc cttccccttt tcccttcccc ttcccgcctg cctgcctgcc  64500
tgccttcctt ccttccttcc ttcgtttctt tctacatata cacatttttt taaatttcaa  64560
tggtttttgg ggtacaagtg gtttttggtt acatggctga attttggtta catggtgaag  64620
tctgagattt tagtacacct gtcacccgag tagtgtacct tgtacccaat atgtagtttt  64680
ttgtccctca ccttccagcc ttccgccttg tgagtctcca atgtccatta taccacactg  64740
tatgcccttg cgtacccaca gctcagctcc cacttctgag aacatatagc agaaacatgc  64800
caaagtatac tcccactacc agaatgtgat tgtgcctgat tcttctcacc agtacaaata  64860
tttcaaaaaa agttaaatat gtatcagttt tttgggcaga agttgatact tctctttatt  64920
tatttatttt ttttgagata gggtctcatt ctatgatgcc caggctggag tgtggtggtg  64980
cgatctcggc tcactgcagt ctctgcctcc caggttcaag tgattcccac gtcagcctcc  65040
caggaagctg gaattacagg cgagggccac cactgccagc taatttttgt atttttttggt  65100
agagatgggg tttcaccatg ttggccagac tggtctcaag ctcctgacct caagtgatcc  65160
```

-continued

```
acctgccttg gccttccaaa gtgctgggat tacaggcgtg agctaccaca cccggctgat  65220
atttcttttt aaaataactt accttctttt gaaagtaata catgtttaat gaacagaatt  65280
taaggaaaat ataaaaaaac gaaataatct ttgtaatcaa actactgaaa agaaaaccaa  65340
agttacattt tggtgcatat tctttttcat tttcatcatt gtaatttgca tttctttgat  65400
tacttgtgag acactccttt catttactta ataggtttat atgacttgcc tattcagaga  65460
ttttgcagct ttaccatttt ctgcaaatga tagcaacttc tttttgtttg tttgtttgtg  65520
gagacagagt ctcgctctgt cactcaggca ggaatgcagt ggtggaatct tggctcattg  65580
caactattgc ctcctgggtt caagcgattt tcctgcctca gcctcccaag tagctgggat  65640
tacaggagtg tgccaccatg cccggctaat ttttgtatct ttagtagaga tggggttttg  65700
ccatgttggc cgggctgatc ttgaactcct ggcctcaagc ggtcccccctg tctcggcctc  65760
ccaaagtgct gggattacag gcgtgagcac cgtacccagc cagtagttac ttcttatatt  65820
ctagaaaaaa ttctactcat gatcaagtct ccatgaggaa agagacttta attgaagatc  65880
atggggcttg cagaccaata tgataaaata gttcattgtt tctaaaagta ttactgagtg  65940
ttgatggcag atatgaaccc ttttgttttt gtaggaaaat gttacccgta ttctccattt  66000
gaattcagtt tagatttgtt aggaatcgca gcttaagctt tgccatctgg gagtgtttgg  66060
gacagttttg cagacaaaat tgcaaaagtg cctaaggaat gcagctggca ttcagacctg  66120
ctctgtgctc agtactctgt ggacagacac tgttcagcac ttgttgatca gaaggtttag  66180
aaagagaact ttcaaagttg gtttttaatt aaagcattta atagtgtaaa tagaaaggga  66240
ttaaatttta tgacagacaa aagaaagtac agcacccagc tgggcgtggg ggctcacgcc  66300
tgtaatccag cactatgggg ggctgaggtg ggtggatcac gaggtcagga gttcaagagt  66360
tcaagaacag cctggccaag gtgatgaaac cctgtctcta ctaaaactac aaaaattagc  66420
cgggcgcggt ggcaggcgcc tgtaatccca gctactcagg aggctgaggc aggagaatca  66480
cttgaacctg gacggcagag gttgcagtga gccaagattg caccattgta ctccggcctg  66540
ggccacagag tgacattctg tctcaaaaaa aaaaaaaaaa gaaaaaaaga aagtacagca  66600
cccagttatg tccgagtggg tgcatgagag tgaccctgag attggagaca acgctgtcac  66660
gtgcttgaag aacgccacct gagaaagggg gcgagaagtg gtgtccgctg gtaaccagag  66720
gtgttggctt agccatctgc agggaggagg gtggtctatc acaggtgagt ttcatctact  66780
ttcttaagca aattaacctt acttttgtgt taggcttgtc ccaaagctgt tttataaatg  66840
tgaccaagga caagctgatc cagtagtggc cgtggcaaga gatcaaagca gtgtttacct  66900
gaaacttctc atgcatgaga cgcagcctcc atctcatttc tccgtcagca caataaccag  66960
gtatgctgac ccagtggcat cttcacattg tcgggaaaat gccctttcct gatgcctttc  67020
tttaggcttt aattgaaaac attttatttt ctagaaaaaa gcttcagctc aggatgtttg  67080
agtgtaggtc agtcctttga taggatatta tcattttgag gattgaccac accacctctg  67140
tatttaagct ctgccacaat cactcagctg tgacactgta aatctcttaa tagtttatta  67200
cattccatgt gctgacagtt gtatttttgt ttgtgacact tacgtattat ctgttaaaac  67260
attttcactt tagttgtgtt acctttaaag aggattgtat tctatcatgc ctgttgattt  67320
tttggtgagc gggctattaa agtcagtgtt atttagggtt atccactagt tcagtgattt  67380
gcgagattat cattcacatt tattgtggag cttttgaata tcgtgtcaaa tggccacata  67440
tatcccattc ttatctgctt cttaggtgag tgggacacag tgctttaatg aagctataat  67500
```

```
cttcagaatt ctagcttgca gagaagattg cagaagtgat aagacttgtg ctttttaatt  67560
ttgtctttta aatgttattt taaaaattgg ctttatatga tactcttttt ttctgctgag  67620
taacagtgtt ttacaaaact tggactaaat gacttctaag cttaaatgat cacttgatgc  67680
ttttttctg aattaggaac tcagcttatc aaatatcaaa gtcataattc ctgaataaat  67740
aacgtctttt ttcatgtaaa gactgcttta aaaaacacat ggaaggctgg gtgcggtggc  67800
tcacgcctgt aatcctaaca ctttgggagg cccaggtggg caggtcgctt gagctcaggg  67860
gttcaagacc acccagggca acatggcaaa acccacctct actcaaatac aaaaaattag  67920
ccaggcgtgg tggcgggccc ctgtaatccc agctactcgg gaggctgagg gatgagaatc  67980
acttgagccc cggaggcaga ggttgcagtg agccaagatt gtgccattgc actcccagct  68040
tgggctacag agtgagactc tgtctcaaaa aaagacacac acacaaacaa aaaaaacatg  68100
gagacatttt tttggccacc ttaatatttc ccctcagata atttcctttg tttaaactca  68160
gaactggcat tttctctctt ggagaagatt caggacaaat actcctttaa gataagtaga  68220
agcagtgaaa gaggatttga ttatcaggaa tttgataagc ttagaataaa ttgttgcttc  68280
ttaatgtcat ttcagaagat gaatatttat taatagatgc caactgagat atcattaaaa  68340
ttgattacta actactactt ggaaaagtct cccagttcca aacttcagca ggcctcttga  68400
caattcagct gtggtcaatt gggtcttgcg tgatagatac aatgaccaat tgtgcagcag  68460
agtgtgctgc ttagctgcct attctgttag cattcatgtg ttaacttaaa atcataatct  68520
ccttagtttt gttgagtgtc tccgtggaca agacactgtg agggatacaa aatcagattg  68580
gctttattca aaccactggg gtattataat tcatttataa tttattttat tttttgcctt  68640
ttttccatgt gttctaaagg aattagagtt tgtatataac tataatgggg gatagaaatt  68700
gacatgtgcc atgaagggaa tgcaaaaaag tgccgtggga gatgagaagt ggagaaagga  68760
atttcttttt tcttggaagc aggaataact tcatgaagca tgtatttcaa cttaaacaga  68820
tagtaggcaa cgctgtaagg ggagtatggc tgcagcaaaa gtgttcgggg cagactggga  68880
ggaagggagg gaataaattc agccattgtt atggaataat gatcaaaatt tattttcagc  68940
ccgtttcact taaaagttga gactgcttaa cttttttaa tctttaatct taaactttta  69000
aatgccattt gatctttaaa aatatatgtt ttaatagtgt attttaagtc tctatatttt  69060
tgttattaga atatatagag gctataacct actaccaagc ataacagacg tcactatgga  69120
aaataacctt tcaagagtta ttgcagcagt ttctcatgaa ctaatcacat caaccaccag  69180
agcactcaca gtaagtctct ttcttgatcg gtcttactga cattgtaata gtttttggta  69240
gcttgtatgg ccagttagtt gtatggtcat cttacggtga ggtgcttgtc ttacagctct  69300
tacttatcca tgaggcttgc taagaaattg tgcttctgtg aaaagaatct cagcttactc  69360
caggaatgta aatgactatg ttttttctga ttattaaagt aatacacgcc caaaataaaa  69420
aaattcagcc aatttaggaa gacacaacaa ttaaaataag ccaggcatgg tggctcatgc  69480
ctgtaatccc agcactttgg gaggccaagg ttgggggctc acttgaggtc aggagtcgga  69540
taccagcctg gccaacgtgg tgaaacccca tctctactaa aaatacaaaa attagctggg  69600
cgtggtggcg ggcgcctgta atcccagcta ctcaggaggc tgaggcagga gaatcgcttg  69660
aacctgggag gtagaggttg cagtgagctg aggtcaagcc actgcactcc agcctgtgca  69720
atagagcgag actctgtctc aaaaaaaaaa aaaaaaaaag aaaagaaaaa agtaaactac  69780
tgtcacctgc attggtaatg tatcagaagt ttaaaatgtc tagattataa ttaactcagt  69840
gacctggtaa tatatactaa gggaaaaata tttataattt acatttttac atttttattt  69900
```

ttttaatttt attatttttt ttttgagaca gagttttgct cttgttgccc aggctggagt 69960
gcaatggcat gatctcagct caccacaacc tccacctccc gggttcaagc aattctcctg 70020
cctcagcctc ctgagtagct gggattacag gcatgcacca ccatgcccgg ctaattttgt 70080
atttttagta gagacagggt ttctccatgt tggtcaggct ggtctcaaac tcccaacctc 70140
aggtgatccg ccctcctcga ccccccaaag tgctgggatt acaggtgtga gccaccatgc 70200
ctggccttac atttttataa taagaattta tgttgctgac attagaaaag aaccataata 70260
tccaagaatc caagaataat taaattatgt acatatgcta gtatatagtg tgatgctttg 70320
gagaattttt aacaatatgg agatgtataa tctggattgt aatattgagt gaaaaaaggc 70380
agaatacaaa cctggtgggg gtatagtcgg atttcagtta agaaaaataa tatttacata 70440
tatacatttc tcacactggc agataatcac caagataaat tttgggattg tggatgattt 70500
ttttcttctt tatatttttc agatattctc aaattttcta aaatgagcaa gtataacttt 70560
tgttatcaga aaaaaataat atacaaaagt aatgttaatt tgctggtgac caggttaaac 70620
ctttttattt ttattttttg agatggaatc tcactctgtt gcccaggcta gagcacagtg 70680
gcatgatctt ggctcactgc agcctccgct tcctgggttc aaatgattct ctggccccag 70740
cctcctgagt ggctggaatt acaggcgtgt ggcaccacac ctggctaatt tttgtatttt 70800
tagtagaggt agggtttcac caggttggtc aggctggtct cgaactcctg acctcgtgat 70860
ccacccacct cggcctccca aagtgctggg attacaggcg tgagctactg cgcccagcca 70920
gaccttttta ttttatttga caaaagaaat acttccatgt tatagaagac taaatattgt 70980
ttgggctgtc tgcagtatgg tcttcccttg atttgttcaa aatatcgtaa actttgctta 71040
tttattttta ttgtggccga ctgtgtcggg cactgttgta ggcttgggat ggaaaaacag 71100
gattcctgcc cttagggttt ctgcaggctg gtcagggaga cgatgtggta agctggagct 71160
cagctcctaa ggatgtgcag gggcagttga gaggcggaag ggtgggagat cattccaggg 71220
tgtgggcagc acaggaacct ctcttcattg ggatataatt gccattctga taacacgtgt 71280
ttgaggtgtc taaagtagga agttgtacca tggtgggaca gatatcctgt ggttatcata 71340
cacagatctc agttttcttc tcattgtttg tactttttat aaagggtaac aggagatata 71400
attcaataaa cctttgtggt gtttgggtgt gattttattg tttctttctt ctcagtttgg 71460
atgctgtgaa gctttgtgtc ttctttccac tgccttccca gtttgcattt ggagtttagg 71520
ttggcactgt gggtatgtat tttcctcagt atatattaat agttgtctac aacagtatga 71580
cataaacata gttattagga tgcccttttt ctttcttttt aagtctttta tcaatttggc 71640
tttttggaaa aatatctgat ggaatacttg tttctgctat attagctgtg tgagactagt 71700
gacaggagct gtgggaaatg aatgccaaat gttcttaggc attgatggga atttcagggt 71760
gtggtcttca agttcattta agggaatttt catatgctgg caaaaggctt ttctcattag 71820
cttgactctt tccaaaatta tttgctgtga attagaagtt taggaacctt ttttcactta 71880
attgtgacct agcatacgaa atggtgatga tttaggaact actgttcttg tattaacagc 71940
ttttatttaa aaatgatttt cctccagtag atggccctac tagcatctgg gaaataattt 72000
caagtcttct ccagcattca ggaataggct ttcattttgt gtatcaatta ctgagaatga 72060
ttttggtgac tcacatcaca tttgagaagt aaacctgcag atttcttgtg tgtgtcagca 72120
aatgaccaac tgatatttgc ttgaagtgga ttacattatc tgctctagaa tgattgcttt 72180
cccaccttcc tcacatacag actgagcagc tacggtttct aatcataggt ctggcactag 72240

-continued

```
acttcacttc tgggcaactt tggcattgga gtaaaatgta ttaatttaaa gaaagttaaa  72300
aatccgttca agtaaacata cagttctaat actttttaca atttaaaata tagatttaaa  72360
tgataaaata aaaaagaaaa tatgggtaga caccataatc ctcgtttctg catctgttca  72420
caaggggttg atatttatga gttctattct ccatatccat tctatgttct cttaatgctc  72480
agtcagcacc tcaggtggtt ggagttcaat gcttggtagt ttgacttaca ctgtcttttc  72540
taggggattg agccctgggt agtcctgctt atttgaggtt gcaatttgtc tttcaataac  72600
ttttactaca agatatggcg tgttaaagga taccattggg gaaccaacat aataatatca  72660
ggaaaactaa ccacgtcaga cctgccccat tgtgtatcaa gtacactatt tttccatagt  72720
aataaagagt tcaccccagc caattctctt ttattttgtg cctgtttact caatggcatt  72780
aacatgccca aatgtctggg tagctgtctc atctccagtt cagcagaacc attgtcatat  72840
gccctagtaa aagcattcct tcattggaca cttaggcccc aatactttca ttcagatcta  72900
ctacctgatt tcatttctca aatgattttt atggagctct gatttatagg aaagatgtta  72960
gttgattaaa aataaaacaa tttctgagct ggtataaaat gtattgtgac atgccttcct  73020
cttggaattg caagagaaag gaagactgtt gtttgcttaa aaattgtcta taatttgact  73080
ttgcaaatgt ctgcttccag agtgcctcca ctgagtgcct cagatgagtc taggaagagc  73140
tgtaccgttg ggatggccac aatgattctg accctgctct cgtcagcttg gttcccattg  73200
gatctctcag cccatcaaga tgctttgatt ttggccggaa acttgcttgc aggtactggt  73260
actgagttga aacagggact ccaggacttg gattttgatt tccttagggg gaatgggggt  73320
ggtgagcata tgaggggaaa atactataag gtcattgcca gtgatggctt gtccctttag  73380
tcaaatttca gatgttacct atatgcataa acacatgcag ttggcagctg ttctgtgctg  73440
agtattttaa agtagcctct tcccaatata gcccctcagt taactacaag taaactcatt  73500
ttgaatttca ttttaatggg caccatatgc cagtactccc tcgggcactg ggatgttaag  73560
aaagtataat gtatggactt cattctcaag ttagttttag attagagggg gatacacgta  73620
aacaaaagtg cagtggtcac acagagtggc cctaatcact ctccttgggc agatttatgg  73680
gctggtagga aagagcacaa cacggagagg gtgtagcacc ttggcgatga taatggagga  73740
tgtggccagc aaggaagacg gagtccattg aaattgattt tgggagaagt tgccaatctc  73800
catgaaagaa ttggggcctg tgctatttgc ttcagggggc tataggagag tttcgtgaaa  73860
gggactaaaa gatgagtatt ttaataagat cattcatcca acttgaacat gggctggagg  73920
agaaggtagg gagactcagg agattaatgt tgatgctaag gcaagataat ggctttggga  73980
ctgtagggaa gacactgatt gtaagagaat gaaggaggca gaattgccag gcctggttca  74040
ccaactgaac ttcggttgtg aagacaaaga aacctgggat gacttcacat cctgggcagg  74100
tgtgtggtgg tgacagtcat ggaaattggg aacacagatt tgtgcgggaa acatcagttt  74160
cagtttgagt ttggcttatc agttgaatat caggcacaga tgtctggcca actctcaaca  74220
tagggtctta aatgacttca gttccccaag caatttgtcc ttcccatgct attggggtgg  74280
agaggtaatg tctgtgccca tatcacagcc agtgctccca aatctctgag aagttcatgg  74340
gcctctgaag aagaagccaa cccagcagcc accaagcaag aggaggtctg gccagccctg  74400
ggggaccggg ccctggtgcc catggtggag cagctcttct ctcacctgct gaaggtgatt  74460
aacatttgtg cccacgtcct ggatgacgtg gctcctggac ccgcaataaa ggtaatgtcc  74520
cacttgggtg ctggattcat acagccttaa tgactatggg tttccagact acctttgttt  74580
agtaatctgt cccttcttta ttctcttttt gctttaaatg aacaaaattg ctcagattgt  74640
```

```
gacactaaat ttaacatcaa aatgtgacca tgtggatggg tgcagtggct cgtgcctgtt  74700
attccagcac tttgggagac tgaggcaagt ggatcacttg aggccaagag ttcgagacca  74760
gcctgggcaa catcacgaaa ccccctctct actaaaaata caaaaaatta gatgggttgg  74820
gccgggcgtg gtggctcaag cctgtaatcc cagcactttg ggaggccgag gtgggcggat  74880
cacgaggtca agagatcaag accatcctgg ctaacacagt gaaaccccgt ctctactaaa  74940
aatacaaaaa aattatctga gcatggtggc gggcgcctgt agtcccagct gctcgggagg  75000
ctgaggcagg agaatggcgt gaatccggga ggcggagctt gcagtgagcc gagatcgtgc  75060
cactgcactc cagcctgggt gacagagcga gactccgtct caaaaaaaaa attagatggg  75120
catggtggtg cgtgcctgta atcccagcta cttgggaggc tgaggcaaga gagttgcttg  75180
aacctgggag gcggagtttg cagtaagcct tgattgtgcc gctgcactcc agcctgggtg  75240
acagagtcag actctttcca aaagaagaaa aaaatgtgac catgtgtttt atagctcttt  75300
tagtatcatc agtcactgtt atccctaaga gggaaatacc tagctttagt tttaggtttc  75360
cagcattagc caagaaagct cagaattgat gttcctggcc aagtacctca ttgctgtctc  75420
cttaaatctt ggttaatggc tactgtcctg gctagcatag ttatggagca tttccatggt  75480
tgtagaatgt tctgccaatc tcagggacag ttttgctttt ctgtgaagca ataaaatcaa  75540
cttcaaaaca aatgttaact atttgtacaa tggatttaag atagaccagt tcacatactt  75600
ttttttttt ttttttttga gatggagttt cattcttgtt gcctgggctg gagtgcaatg  75660
gtgtgatctc agctcactgc aacttctgcc tcctgggttc aaacgattct tctgcctcag  75720
cctctcgagg cagattacag ctgggattac aggcatgcac caccacaccc agctaatttt  75780
tttgtagttt tagtagagac ggggtttcac catgttggtc aggttggtct caaactcctg  75840
acctgaagtg atctatccgc ttcggcctcc caaagtgttg ggattacggg catgagccac  75900
cacgcccagc ctaagataga ccagttcact tactgtttat atctgattac tctctctttg  75960
ccttgtcttc tacctttaaa aatctcccta ctaacttccc attctccttt agctgccatc  76020
agtcttctcc cttctctgca aacatctctg gagagtccca gcctcagccc acagagcttc  76080
ccactgctct gaggtggacc ttgtttgcaa ggcttctttg gctctcttgg cctggaccct  76140
gtctactact tcagccatcc ttccttaacc cctgctggtg gtttctgttg ccacactcca  76200
tagcagcgtt tcccgcccag atcatgtctt tacatctctg ggcactgctc tggtcctgcc  76260
tgcctttccc tctttgtatc ctgcaggctg ctacccccat cttgagtgtc ctcttcagtt  76320
ggctttcaga gggcctcctg ggtgttccct tacccacttg ccactcccca gtcactgggt  76380
tcagtccttc ctgcccacca gcacatgctt tctaggctct gtcctaggcc gtcttctctc  76440
tttgtagtct ctgggccagt gctgttctag agagtggcag aattttctat aaccatggca  76500
gtgctccata gctatgccag gcaagacagt agccactaaa cacatatagc tgttgagccc  76560
ttgaaatgca gctagtgtga ctgaagaact gaaccccgat tcggtttaat tttcattaaa  76620
tttaaattta aataacctta tgtgggtagt ggctccagta ttgggcaggg cagcctgaga  76680
gtcggggctg ttctcctgtc ttcagtgtct agatgaggga cctcagagga cctgtctctg  76740
gagctgcagt tcaatgtagc cagctgcccc gtgacactta catatagctg atttgtggat  76800
atgtcagaca cggtgtgatg agctcagctt tctgtcctcc tccccacatc tgcccctgcc  76860
ccatttaccc cactttgtgt cttatcaagc tagaaacagg tcaccacaag tcttcatttc  76920
cactcaccaa gtcttttgtt tcccctacta aatattttgc gagaagaaag tgtgtacctt  76980
```

-continued

```
tgtattcaca tacatgtaca tgcacatata catgcacata tgcaggggtc cccaacctct  77040
gttaaaaacc ggactgcagg ccgtgcgtgg tggctcacgc ctgtaattcc agaactttgg  77100
gaggccgaga ccagtgcatc acaaggtcag gagatcgaga ccattccggc tcacacggtg  77160
aaaccccgtc tctactaaaa atacaaaaaa aaattagccg ggtgtggtgg cgggcgccca  77220
tagtcccagc tacctgggag gctgatgcag gagaacggcg tgaacctggg aggcggagct  77280
tgcagtgagc cgagattgtg ccattgcact ccagcctggg cgacagagcg agactctgtc  77340
tcaaaaacaa aacaaaacaa aaaaaaaaaa aaccaggctg cacaggaaga agtgagcaag  77400
cattaccatc tgagctctat ctcctctcag gccagtggtg gcattagatt ctcataggag  77460
cgtgtatgag ttcgttctca cacttctgta aagacatacc tgagacatat aaagaaaaga  77520
ggtttaattg gctcacagtt ctgcaggctg tacaggcttc tgtttctggg aaggcctcag  77580
gaaacttgca gtcatggcag aaggtgaagg ggaagtaggc acatcttcac atggcccaca  77640
ggaaaaagag agaaggagag agagagagag acagagagag agagagaaaa agaaagattg  77700
agagggagag aggagggaga aaggagagtg cctgtagggg gagttgctac acaaaggagc  77760
accaggggga tggtgctcaa ccattagaaa ctaccccccat gatccaatca cctcccacca  77820
ggccccacct ccgacactgg agattacaat tcagcatgag atttgggtgg ggacacagag  77880
ccaaaccata tcagagcatg aaccctattg tgaactgcac atttgaggga tctaggttgc  77940
atgctcctta tgagaatcta atgcctgatg atgatttgag gtggaacagt ttcatcccga  78000
aaccatcccc cgccaaccct ggtttgtgga aaaattgtct tccacagaac cggtccctgg  78060
tgccaaaaag tttggggacc tctgcacata tgcatgcacc tgtacatgga cacataatac  78120
atgtacatat gcatacttta tattctctgc cacttctggt ccagactgat atactatctc  78180
atttggatta ctgcactagc cttttgtttt ggaaacagca ttttttaaaa aatttaattt  78240
aatttttttg agatagggtg tcattctgtt gcccagcttg gagtgcagtg tcatgatcat  78300
agctcactgc ggcctcgatc tcccaggctc aagtgatcct tctgcctcag ccttctcagt  78360
agttgggact acaggcatac ccaccatgcc cagctaattt tttgattttt tttttttttt  78420
gagacagagt ctcagcctgt cgcccaggct ggagtgggtt ggcgcgatct cagctcactg  78480
caacttctgc ctcccaggtt caagtgattc tcctgcctca gcctcccgag tagttgggat  78540
tacaggcgcc tgccaccaca cccagctaac tttttgtatt tttagtagag acggggtttc  78600
accatgttgg ccaggctggt ctcgaacttg tgacctcgtg attagcccgc ctcggcctcc  78660
caaagtgctg ggattacagg cgtgagctac cgctcccagc caggaaacag cattcttgag  78720
ataattcata taattcaccc atttaaagta tataattcat tctctttagt atgcccacag  78780
agttgtacag ccatcaccag aatcagtttt agaacccata aaggaactct gtactcttta  78840
cccaaaacct ccatgcctcc agctgcaggc agccactaac ctgccttctg tctctgtgac  78900
tctacgtctt ctggacatta ctgtggatgg gctcatacag tcagtgagct tgtgactggt  78960
gccttctacc aagcagggtt ttcagtgtag cagcctctct gtttttcttt ttttttttaaa  79020
ttgtgacgga acttctgcct cccgggttca agcgattctc ctgcctcagc ctcccgagtg  79080
gctgggacta caggcccatg tcaccatgcc tggctaattt tttttttttt tttttttagt  79140
agagatgggt ttcaacatgt tagccagggt ggtctcgatc tcctgacttc atgatccgcc  79200
tgcctcggcc tcccaaagtg ctgggattac aggcgtgagc caccatgccc ggctaacctt  79260
tcatttactg tctgcatttc ttccctgatg ccttccagtc catgcacccg attgtagcca  79320
ttcatcctat tatggtttaa ggtgactgtc ttagtcagca tgggttgcca taacaaaata  79380
```

```
ccatagcctg ggtggcttca acaacagaat ttacttctca cacttctgga ggttgggaag  79440
tccaagatcc aggactttcg ccttgccctc atgtggtgag ggggtgagga agctctgtgg  79500
ggcctcttat atatggatgc taatctcatt catgaggggt ctgccctcat gacccagtca  79560
cctcccaaag gccccacctc ctaataccat caccctggta attaagtttc agtgtataaa  79620
tttgggggac tatagacatt gaaaccataa caagcacttt tctaagatca gggagtgagt  79680
aagtagcaga gctaggacct caattccaca tgtcagtcat cttgccttca ctctgctcca  79740
tgatggctgc ctcctagagc attgggagtc tcgatgttct atatgctctc atgtgttgtg  79800
tattggagat agttgaggct ttatgaatac atctggattt gttgacttct agctttgctg  79860
gtaaccagct gtgaccttga ataagttact tcatctctga gcctgtttcc tcttttagaa  79920
acaggagttt aaaatgctgc tttgggttgg gcacggtggc tcatgcctgt aattccagca  79980
ctttgggagg ctgagatggg aggatcactg gagcttggag ttcgagacca gcctgggcat  80040
catagtgtga gatcctgtct cctcaagaaa ttaaaaaatt agctgggtga tgtggcgtgt  80100
gcctgtggtc ccatctactc tggaggctga ggtgggagga ttgcttgagc ccaggaggtt  80160
gaggctacaa tgaaatatga ttgcacccca tcctgggtga cgagtgagac cctgtctcaa  80220
aaaagaaaaa aaaaatgctg ctttgtaccc ctttcatgtc atggcgtcat ggccaacata  80280
gaatgccctg gttgtttgct gttggagggc atgggcctgg gggctccctg agggctcctt  80340
ccatcttcaa ctcattctct gtgcacctgt taggaagttg tgggccagtc cctaccatgt  80400
atcattgtgt gggtaaaagt aaataaaatg tgtacagtgt ctgaactgta catatcaggg  80460
tccaagaaca aaatgagtga catgggttag ctctttttaa taaatggtaa aaccaaatat  80520
tctaattttc agttttgtta tacttccatc acatgttttt gttttttgt tttttgtttt  80580
tgtttttcta ttttaggcag ccttgccttc tctaacaaac ccccttctc taagtcccat  80640
ccgacgaaag gggaaggaga aagaaccagg agaacaagca tctgtaccgt tgagtcccaa  80700
gaaaggcagt gaggccagtg caggtaggaa acagcgtggg gaagggaggg acatgagtgc  80760
agcatctgtc atgtagaaac ataggattta agtaacttgg tgttttagag aaataaatat  80820
aatacacatc agtaaagtga gagaaagttt ctccaggtgc ggttcaagat attagaaact  80880
aatgactgat gtacacagac caccttttgg tctgaagcat ttctaagtgc cactggctga  80940
catgcagccc ctacagcctc caggcttcca gccctagcat ggagcatcac tctcctatgc  81000
ttccctggtt gcaggtgatg gctggagagg cctcctgatt ttcagtaagg gaagtggtgt  81060
agatgcttag gaatagatgt agtgagtgaa aaaactgatt ctgatatgtc aaaaattctg  81120
attggaaatg gaatatttac atttggaaga gctaaaggcg agagaaagtg gggataaagt  81180
catctgagtt ggaggagctt aaaccattca caagtttgga ggaccttttt ttacccatga  81240
aaaggtcaga acagaagggg ctaggattta ggtgtgactg cagtttattg aattcccatc  81300
catactgctc tcggtgggca gtggcagggg caggagagga gcctggcaaa gcatgaagtg  81360
actgctgctg cctctgctat ctgggacgcc tggccacctg tctgtacagt ctccctccag  81420
acccattctc acgctgtctc ttggcaccca ggggccagtg atggttctcc catttgtttt  81480
gtgtatatag catttatatc aaggctattt atttatttat ttattttatt tatttatttt  81540
tttgagacag agtctcactc tgtcacccag gctggagtgc agtggtgcaa tctcggctca  81600
gtgcaagctc tgcctcctgg gttcaagcaa ttctcctgcc tcagcctcct gagtagctgg  81660
gactacaggt gtgcaccacc acacctggct aatttttttgt atttttatt agtggagacg  81720
```

-continued gggtttcacc ttgttggcca ggatggtctt gatctcctga cctcgtgatc cgtccacctc 81780
agcctctcaa agtgctggga ttacaggcat gagtcactgt acccggccta tttatttatt 81840
tttaattgac aaaattgtat atatctgtaa tatacaacat gatgtttgaa atatgtgtac 81900
attggccagg cgtggtggct cacacctttt atcccagcac tttgggaggc tgaggtgggc 81960
ggattacgag gtcgggggtt taaggccaaa ctggccagca tggtgaagag gtgcccctac 82020
taaaaatacc ccaaaaaaaa aaaaaaaaaa aaaaagccgg gcatggtggc tcgcgccagt 82080
cgtcccagct acttgggagg ctgaggcagg agaattgctt gaatctggca ggtggaggtt 82140
gcagtgagct gagttcatgc cactgcactc tagcctgggc gatagagcga gactccgtct 82200
caaaaaaaaa aaaaaaagaa gaaatacata tgcattgtgg aatggctaat taacctgtgc 82260
atcacctcac gtatcattgt tttgtggtga gaacacttaa aatctactct ttcagtgatt 82320
ttcttgcata tggtacattg ctattaactg cagtcaccat gctatacagt agatctcttg 82380
aactcattcc tcctgtctat aaatgaaatt ttgtatcctt gaccaacaca ttcaaggttt 82440
tttttgagat ggagtcttct tcacccaggc tggagtacca tggcacgatc tcatctcact 82500
gcaacctccg cctcccaggt tcaagcaatt ctcctgcctc agcctcctga gtagctggga 82560
ttacaggcac atgctactgc acctggctaa tttttgtatt tttagtagaa gtggagtttc 82620
accatgttgg ccaggctggt ctcgaactcc tgacctcaag tgatccgcct gccttggcct 82680
gccaaagtgc tgggattaca ggtgtgagcc actgcacccg gcctcaagcg ttttaaaaga 82740
tgctcttttc taaggattga ctgtagtaca ggaggaagat tgacctgttg aaaagcctca 82800
gcctttacaa gtgtaaaatt atcagtatat tactatcatc tttctgatga attaaataaa 82860
ctaaggactc caagtcaaaa gtcttcaaac tgaagtagaa tagttgtata tagtgcttgg 82920
cactttaata tttagtatcg gtttaatgat aatgtttgtg cctttgccgt ctttaaaaca 82980
tttttacatc atccctgttt gattacttgg tgtgctcatg aagttgttgg ccactaagga 83040
atcttaggct cagagaggtt ctggaattgg ccagtggtcc ttgaatcagc tgctcctatg 83100
attctctaac tgatttctca caaagcaaac aagcaatcat aacaaaacaa ctgtgcacac 83160
tgctcttctt attttgttat ttaaaaagta cttaggctct acttatgttt gttagtcaat 83220
ttctcattac ttctagttaa tcaaaaggtc agaggaaata cttgaatatt ttcatactag 83280
aatactttaa aaaatcatga tttccagtaa tctctttaaa acttggcaag ttattttgat 83340
ctaaaagttt atcttttgtg tgcatatttt taaagcttct agacaatctg atacctcagg 83400
tcctgttaca acaagtaaat cctcatcact ggggagtttc tatcatcttc cttcatacct 83460
caaactgcat gatgtcctga aagctacaca cgctaactac aaggtatggg cctctgcatc 83520
ttttaaaaat atatatgcac acatacttac gtctaatgga tagttgatgt ttttcttatg 83580
atttgtagga tgtataagcc ctttgagata tgagttacat ttagtttttt caagtttgtt 83640
tgtctttcag ctttgtttat gatagcttct atcatacagg tgttttggat tttcatattg 83700
tttgtactca cagctaagat tgattacagt gacagagcta ggatgtgcag ccaggttata 83760
gggggaagtg gccctggtgg agtctggagg gatccgtgta caggcttcct tccctcccgt 83820
gaggctcaca caaaaataca gcaacatgct ggtcctgcag gtaccctctg cctaacatga 83880
gccacaattc cagactcaca gaagaaaagc aggtgttcgg cataaaccat gtgtttcaaa 83940
tagtctgggc atggtgagcc acttgttatc agctagggaa agtttatgtc agcgtaagaa 84000
actgttcacc agataccccc aagagccagc ctttctgtct agggatgttt tagtttttta 84060
gttcattttt ttttttaact ttaaaatttt ctgttcatct gcaatttgtt agatatgaag 84120

-continued

```
tatgtgtcta atttaatttt tgtttttggt tgtccccaat aatgtttaca gaagaatttt  84180
tctgcactaa ttggcttgag ttacttacat tctcatagtt ctctagtttc agtagtttca  84240
tttattattt tgttatatca atctatctgt ctgctcatct attagaagca tccttgtttt  84300
tttttttct tttttagaca gagtcttgct ctgtccccag gttggagtgc agtggtgcaa  84360
ccatgcctcc ctgcagtctc agggctcaag tgatcctccc acctcagctc ctgagtacct  84420
gggactaccg gcatgtgcca ccacacccag ctaattttta catttttttgt agagacaggg  84480
tctccctaag ttgcctgggc tggtctcaag ctcctggctt aagtaatcct ccctccttgg  84540
cctcccaaag tgctgggatt acaggtgtga gcaactgcac ccggctacaa gtatacttct  84600
taattattgt agcttaatgg tatttatgag gggatcagtt cccctgttgt tctttagaat  84660
tttctggata ttcttcttta ttgattttgg gatgtgaaca atagaatcaa cttctacttg  84720
tagattgatt tagggagaac ttatacctca gatgttaagt caccctgtcc agaatgtggg  84780
atgctttcct atttgttcag aactttttaa attacctcag aagcacatga aatttaaagg  84840
attttaaaaa aaacttaaag attatttcac atagctcttg cacatttctt gataaatgaa  84900
tcctcaggta ttcctctgtt tttgttacta atagttactt cttatgggtt tttttcccc  84960
tgaaaatcat ttatcaaacg tatgtggctt attttctgaa ggatgtttga taattttgga  85020
agatatgaaa gtcttcatat tttacaaggt ttgaggtctc tttaagctgc atggttctca  85080
tgtcagctcc caaagcagaa gacggcatgt tgaaaaatgc cgtagagaag atacttcttt  85140
tccacctgtt ttcaactcat atcatcttga atttcagggc acctttccat gctcctagtg  85200
cttgctatct gtttattatt ttccttcctg aataccctga actccagcat gttctgctgt  85260
aattctggcc tccctggcat cttggactcc tgtttccttt gctctgtcat ccccgcggtc  85320
agctcctgct gcgcagcttc tcagctgaag tgcgtttgga gtgcctggcg tgtcttgctg  85380
gatctttgag tattgcctct ggtttccttg gttccttctg ctgagttgct cagcgtctcc  85440
actccccatt tcttgtgtgg cccttcctgc actcctctga ttccttttgt cttccctggt  85500
ttcttgcttt ggtttcgagt ctccacagaa cttttgcagc tcttctgaag acctggaagc  85560
tttttcatct taattctcat ctcatgacct cttttccctt ctttgagagc tagaacttcc  85620
catggtgaac ttctctttcc agaattccat gccttctttt ccctcccact tacctgttgt  85680
ccaggagagg tcagattgct gtgcatattg gaggagaacc ctttcttccc tgggctcttc  85740
atctcacatg acatcaccac atcacctcgt tccttggacc ctcagtggtg tcactgctgg  85800
atttttcttt cctttggctg gccttagggc acacccaggt tgactagcgt agtcatggta  85860
tttagatcca ctcacatttt cagtttctgt gtctgtctct tgcctgcttc tgacttcgcc  85920
cagagaaagc ttctctttca caagggttct tagatttatg ttcactgagc accttctttt  85980
ctgaggcagt gttttaccaa tatttatttt cctagtcagt ctcgccttac ctttcttgtt  86040
atgcatgtct ttggtcctga cccattctct gagtctgtaa aatagaattg ctgtataatt  86100
taattacatg aaatccttta gaatcttaac acatcttaca cctgatttaa tattttattg  86160
tatccaaatt gaaccaaccc tatgtgaatt tgacagtgat ttctcccagg gatcctagtg  86220
tataaggaat aggacttagt attttctatt ttttgatata ccacatacca gatactgatt  86280
atgatggaca tttaaccctt ttttctcatt atgaaagaaa gttaggaatt atttcttcca  86340
gtagcgccag tgtaacctga aagcctttga aagagtagtt tttgtatagc tatctgaaag  86400
gaatttcttt ccaaaatatt tttccagtgc tgacaacaaa cacgcagaca caccctgcaa  86460
```

-continued

```
ggtgagtgta cggcgccgca cagtggaggc atctgctgca gccgtcgatg tttgtgtctt  86520
tggttgtaca ttatgagatc gtgacagggc cagtaaccgt gtgttctctc cttcaccttc  86580
ccaaggtcac gctggatctt cagaacagca cggaaaagtt tggagggttt ctccgctcag  86640
ccttggatgt tctttctcag atactagagc tggccacact gcaggacatt gggaaggttt  86700
gtgtcttgtt ttttctcctt gggttgtggc tggcacactt gatgtgcgtc ttctgggctg  86760
agttcatcta ggatggagcc tggttctcca gggtgcctcc gggagactcc tccctgcccc  86820
acgtgcttgc gtcacaggac ccaagtctga ctctgcctta gccatgaagt ttagggggaa  86880
gtttctattt gtattctatt tttgtctgtt atcatgtatt agcttagacc cagtttagtt  86940
tggaaaatca gtgggtttca aaatgtgttt gtagagtcct ttatttctta acttgacctt  87000
ttcaagtgga aaggggcaaa acagacgggt aagggggcgg ggcgggaggt gtgacttgct  87060
cttttgtgcc tgaggaagta acagagctgg ggttgacagt catattctct gacacagata  87120
gtctctgact tatctcacag aaagtcagcg gcagagcctg agttaaaagt ctcgtagatt  87180
ttctttttct ttttttggt ggctaatttc agttttattt atatttgttt atttatttat  87240
tatactttaa gttctgggtt acatgtgcag aatgtgcagt tttgttacat aggtatacac  87300
gtgccatgat ggtttgctgc acccatcaac ccatcaccta cattaggtat ttctcctaat  87360
gttatccctc ccccagtccc ctcactcccc atgggccccg gtgtgtgatg ttctcctccc  87420
tgtgcccatg tgttctcatt gttcaatttc cacttgtgag tgagaacatg cggtgtttgg  87480
ttttctgatc ttgtgatagt ttgctgagaa tgatggtttc cagcatcatc catgtgcctg  87540
caaaggacat gaactcatcc tttttttatgg ctgtatagta ttccatggtg tatatgtgcc  87600
acatttctt aatccagtct atcattgatg gacattcggg ttggttccaa gtctttgcta  87660
ttgtgactag tgccacaata aacatacatg tgcatgtgtc tttatcgtag aatgatttat  87720
aatcctttgg gtatatgccc agtaatggga ttgctgggtc aaatggtatt tctagttcta  87780
gacctttgag gaatcgccag actgtcttcc acaatagttg aactaattta cactcccacc  87840
aacagtgtaa aagtgttcct atttttccac aacctctcca gcatctgttg tttcgtgact  87900
ttttaacgat cgccatccta actggcgtga gatggtatct cattgtgatt ttgatctgca  87960
tttctctaat gaccagtggt gatgagcatt ttttcgtatg tctgttggct gcataaatgt  88020
cttcttttgc gaagtgtctg ttcatatcct ttgtccattt tttgatgggg ttgtttgctt  88080
ttttttcgta aatttgttta agttctttgt agattctgga tgttaatctt ttgtcagatg  88140
ggtagattgc aaaaatttta tcccattctg taggttgcct gttcactctg atgatagttt  88200
cttttgctat gcagaagctc tttagtttaa ttagatcccg tttgtcaatt ttggcttttg  88260
ttgccattgc ttttggtgtt ttagacatga agtctttgcc tatgcctatg tcctgaatgt  88320
tatggcccag gttttcttct aggattttta tggtcctagg tcttatgttt aagtctttga  88380
tccatcttga gttgattttt gtgtaaggta taaggaaggg gtccagtttc agttttctgc  88440
atgtggctag ccagttttcc caacaccatt tattaaatag ggaatctttt ccccattgct  88500
tatgtgtgtc aggtttgtca aagatcagat gattgtagat gtgtggtggt atttctgagg  88560
cctctgttct gttccattgg tctatatatc tgttttggta ccagtaccat gcagttttgg  88620
ttactgtagt gttgtagtat agtttgaagt caggtagtgt gatgcctcca gctttgttct  88680
tctagcccag gattgtcttg gctatgcagg ctcttttttg gttccatatg aagtttaaaa  88740
tagttttttc caattctgtg aagaaagtca gtgatagctt gatgggggga tagcattgaa  88800
tctataaatt actttgggca gcaaggccat tttcacgata ttgattcgtc ctatccatga  88860
```

acatggaatg tttttctatt tgtttgtgtc ctctcttatt tccttgagca gtggtttgta 88920
gttctccttg aagaggtcct tcacatccct tgtaagttgt cttcctaggt gtttcattcc 88980
cttagtagca tttgtgaatg ggagttcact catgatttgg ctctctgttt gtctgttatt 89040
ggtgtatagg aatgcttgtg atttttgcac attgattttg tatcctgaga ctttgctgaa 89100
gttgctaatc agcttaagga gattttgagc tgaaccaata gggttttcta aatatacaat 89160
catgtcatct gcaaacaggg acagttttac ttcctctctt cctatttgaa taccctttat 89220
tgctttctct tgcctgattg cgctggccag aacttccaat actatgttga ataggagtgg 89280
tgagagaggg catccttgtc ttgtgccggt tttcgaaggg aatgcttcca gtttttgccc 89340
attcagtatg atattagctg tgggtttgtc ataaatagct cttactatgt tgagatacgt 89400
tccatcgata cctagtttat tgagagtttt tagcatgaaa ggctgttgaa ttttgtcaaa 89460
ggccttttct gcatctgttg agataatcat atggtttttg ttgttggttc tgtttatgtg 89520
atggattacg tttattgatt tgcgtatgtt gaaccagcct tgcattccag ggatgaagct 89580
gacttgattg tggtggataa gctttttgat gtgctgctgg attcagtttg ccagtatttt 89640
attgaggatt ttcacatcga tgttcatcag ggatattggc ctaaaattct cttttttttgt 89700
tgtgtctctg ccaggctttg gtatcaggat gatgctggcc tcataaaatg agttagggag 89760
gattctctct ttttctattg attggaatag tttcagaagg aatggtacca tctcctcttt 89820
gtacctctgg tagaattcgg ctgtgaatcc atcctggact ttttttggtt agtaggctat 89880
taactattgc ctcaagttta gaacctgtta tcagtctatt cagagattca gctttttttct 89940
ggtttagtct tgggagggtg tatgtgtcca ggaatttatc catttcttct agattttcta 90000
gtttatttgg gtagagatgt ttatagtatt ctctgatggt agtttgtatt tctgtgggat 90060
cggtggtgat atccccttta tcgtttttat tgagtctatt tgattcttct ctcttttctt 90120
ctttattagt cttgctagcg gtctacctat tttattgatc ttttcaaaaa accagcacct 90180
ggattcattg attttttttg gagggttttt tttcgtgtct ctatctcctt cagttctgct 90240
ctgatcttag ttattttttg tcttctgcta gcttttgaat ttgtttgctc ttgcttttct 90300
agttctttta attgtgatgt tagggtgtta attttagatc ttttctgctt tctcttgtgg 90360
gcatttagtg ctataaattt ccctctacac actgctttaa atgtgtccca gagattctgg 90420
tatgttgtgt cttcgttctc attggtttcc aagaaaattt ttatttctgc cttcatttcg 90480
ttatttaccc agtagtcatt caagagcagg ttgttcagtt tccatgtagt tgtgtggttt 90540
tgagtgagat tctcaatcct gagttctaat ttgattgcac tgtggtctga cagacagttt 90600
gttgtgattt ctgttctttt acatttgctg aggagtgttt tacttccaac tatgtggtca 90660
gttttagaat aagtgcaatg tggtgctgag aagaatgtat gttctgttga tttggggtgc 90720
agagttctgt agatgtctat taggtccgct tggtccagtg ctgagttcaa gtcctggata 90780
tccttgttaa ttttctggct cattgatctg cctaatattg acagtggggt gttaaagtct 90840
cccactatta ccgggtggga gtctctttgt aggtctctaa gaacttgctt catgaatctg 90900
ggtgctcctg tattgggggc gtgtatattt aggatagtta gctcttcttg ttgaattgat 90960
ccctttacca ttatgtaatg gccttctttg tctcctttga actttgttga tttaaagtct 91020
gttttatcag agactaggat tgcaatccct gctttttttt tgctttccat ttgcttgtta 91080
gatcttcctc catcccttta ttttgagcca atgagtgtct ttgcatgtga gatgggtctc 91140
ctgaatacag cacaccaatg ggtcttgact ctttatccaa tttgccagtc tgtgtctttt 91200
aattggggca tttagcccat ttacatttaa ggttaatatt gctatgtgtg aatttgatcc 91260
tgtcattatg atcctagttg gttattttgc ccgttaactg atgcagtttc ttcatagcgt 91320
cagtagtctt tacaatttgg catgtttttg cagtggctgg tactggttgt tcctttccat 91380
gtttagtgct tccttcagga gctcttgtaa ggcaggcctg gtggtgacaa aatctctgca 91440
tttgcttgtc tgtaaaggat tttatttctc gttcacttat gaagcttagt ttggctggat 91500
atgaaattct gggttgaaaa tacttttttt aaagaatgtt gaatattggc tcccactctt 91560
ttctggcttg taggatttct gcagagagat ctgctgttag tctgatgggc ttccctttgt 91620
gggtaacccg acctttctct ctggctgccc tttccttcat ttcaatcttg gtggatctga 91680
tgattatgtg tcttggggtt gctcttctcg aggagtatct ttgtggtgtt ctctgtattt 91740
cctgaatttg aatgttggtc tgccttgcta ggttggggaa gttctcctgg ataatatcct 91800
gaagagtgtt ttctaacttg gttctattct ccccatcact ttcaggtaca ccaatcaaac 91860
gtagatttgg tcttttcaca tagtcccata tttcttggag gcttggttca tttcttttca 91920
ctcttttttc tctaatcttg tcttctcgct ttatttcatt aatttgatct tcaatcactg 91980
atatcctttc ttctgcttga ttgaatcggc tgtcgaagct tgtgtatact tcacaaaatt 92040
ctcgttctgt ggtttttagc tccatcaggt catttaagct cttctctaca ctggttattc 92100
tagccattag tctaacattt ttttcaaggt ttttagcttc cttgtgatgg gttagaacat 92160
gctcctttag ctcggagaag tttgttatta ccgaccttct gaagcctact tctgtcaatt 92220
catcaaactc attctccatc cagttttgtt cccttgctgg tgaggagttg tgatcctttg 92280
gaggagaaga ggtgttctgg tttttggaat tttcagcctt tctgctatgg tttctcccca 92340
tcattgtggt tttatctacc tttggtcttt gatgttggtg acctacggat ggggttttgg 92400
tgtgggtgtc ctttttgttg atgttgatgc tattcctttc tgtttgttag ttttccttct 92460
aacagacagg cccctcagct gcaggtctgt tggagtttgc tggaggtcca ctccaggccc 92520
tgtttgcctg ggcatcacca gcagaggctg cagaacagca aatattgctg cctgatcctt 92580
cctctggaaa catcgtccca gagcacgaag gtgtctgcct gtatgaggtg tttgttggcc 92640
cctactggga ggtgtctccc agtcaggcta catgggggtc agggacccac ttgaggcagt 92700
ctgttcatta tcggagcttg aatgccgtac cgggagaacc actgctctct tcagagctgt 92760
caggcacgta tgtttaaatc tggagaagct gtctgctgcc ttttgttcag atgtgccctt 92820
cccccagagg tggaatctag agaggcagta ggccttgctg agctgcagtg ggctctgccc 92880
agttcgagct tccctgctgc tttgtttaca ctgtgagcat agaaccacct actctagcct 92940
cagcagtggt ggacacccct cccccagcca agctcctgca tcccaggtcg atttcagagt 93000
gctgcgctag cagtgagcaa ggccccatgg gcgtgggacc cgctgagcca ggcacaggag 93060
agaatctcct ggtctgctgg ttgtgaagac tgtgggaaaa gtgcagtatt tgggcaggag 93120
tgtactgctc cttcaggtac agtcactcat ggcttccttt ggcttggaaa gggaagtccc 93180
ccgacccctt gtgcttccca ggtgaggcaa caccccgccc tgcttcggct tgccctccgt 93240
gggctgcacc cactgtccag caagtcccag tgagatgaac taggtacctc agttggaaat 93300
gcagaaatca cctgtcttct gtgtcgatct cactgggagc tgtagactgg agctgttcct 93360
attcggccat tttggaagca tcccttgttt tttgaggtgg agtcttgctc tgtcgcccag 93420
gctgacgtgc atcggcacaa tctcggccca ctgcaacctt tgcctcctgg tttcaagcga 93480
ttctcctacc tcagcctccg gagtagctgg gattacaggc acctgccacc atgcctggct 93540
aattttttgt atttttagtg gagatggggt ttcaccacat tggccaggct agtctcgaac 93600
tcctgacctt gtgatccacc cacctcagcc tcctagagtg ctgggatcac aggtgtcagc 93660
caccacgccc agccatattt tcagatctcc ctctctttgc cctaaaccac tgtgcttaat 93720
aagtagtttt tagtggccag cagtctccat gtataacaca ttttagcaaa atggaaaata 93780
ctatatgttt taaatttgaa cgtgagatta tactgaaata aaaatcatct aactgggatt 93840
ctttaaatag taagattttc ttttttgtat gtgggttttt ttttaacctt attattatga 93900
ctgtcatata tagaaatggc tgtttttcag ttacagtcag tgaatgtatc aaatgctgcc 93960
ttatccaaat aataaaagta aattattaat aagtcacaat ttaatgaaga ttgatgttag 94020
ttgatcttta tattcttgaa atcagccata tggttgtgtg tgtatgtata tatttttaaa 94080
ggtacataaa gataataagc tcatctctga aaatttttac atttggcata agaataactg 94140
gataattaag catcttattc tctggcctgt gtctttacag ttaaaggtag atttactcac 94200
ctctcctttt ttgtttttct aagttcatct tttttgctgt ttcaagacag aggcccattt 94260
tagctttctc gcatatcctt ttgtttgtac tttggaagcc tcacctgctt aattgttgag 94320
tttttatccg tggtctttta gagggggata tgtagggtag aagctttcac aggttcttgt 94380
ttgcacttgg cccctgactg ttttgaggaa tctccctcac tgactcacag catggcaagg 94440
tttcagatct ctttctgcca cacagcagtt ctgaggcagc tggaaagata tccagatgct 94500
tagattgtca ggccaggctt gagatataca aactattgag ccttatctgt gaccttgctt 94560
aggtgaaggc atcagagccc ctgcaccaac atgcataggc ctctgcatgt gtgcggggct 94620
gggtgttgag gtctgagcac aagtgtagct ggagaggtga gcttgatgtg gcgacgggta 94680
tgagcaggtt ttcttcagac ttctgtgagt ttacctagtt ccaggattta aaggcacaga 94740
gactttagaa ttaaaataga atcattttct ttttctaaat agcaacacta ggaataaaaa 94800
ataataattc cacattcttg acaggtaatg ttttttcttg tcttctaatc cttatttatt 94860
ccatactcat ttttatacat aattgaaatg tattatgcat tggatttttc ttttgcatta 94920
tattatagac gatttttcat gtaactcctt actgttccat tttatatgtt ttgtctggtt 94980
taagacttta tctgcaaacc gggaaactgt ctctacaaaa agaaaaaacaa aaatagttgg 95040
ccgcagtggc atgcgtctgt ggtcccagct actcggggct gaggtgggag gattgcttga 95100
gccttgggag gttgaggctg caaagagcca tgatcatgcc attgcactcc agcatgggtg 95160
acagacttta tactgtctgt tttgggtgat ttgataatga tatgccctga tgtagttttt 95220
ttatatcttg tgtttcttgt gcctgggttt attgaggttg ggtctgtggc ttcatagtat 95280
ttttaaagtt tggaaaattt taggccattc tttctttctt tctttctttt tttttttttt 95340
gagacagtgt ctcgctctgt cgcctgcgtt ggagtgcagt gacactatct tggctcactg 95400
caagctctgc ctcctgggtt cacgccattc tcctgcctca gcctcctgag tagctgggac 95460
tacaggcgcc tgccaccacg cctggctaat tttttgtatt tttagtagag acgaggtttc 95520
actgtgttag ccaggatggt ctcaatctcc tgacctcgtg atctgcccgc ctgggcctcc 95580
caaagtgctg ggattacagg cgtgagccac tgcacccagc taggccatta tttcttcaaa 95640
gatttttttt ctgccctgcc tccctccttt tttccctctc ttaaaggggc tgtgatttcc 95700
tgaatgattg cttagtgttg tcccatagct tactgatgct cttttcagtg tttgattgtt 95760
ttatgtgttt tctgttttgt atagtttcta ttattgtgtt ttcaagttct ctgatctttt 95820
cttctacagt gtctactctg ttgttaatct gttaatctgt tgttaatcct gtccagcgta 95880
tttttttttt tgtttttgaa acagtctcac tctgttgccc aggctggagt ttagtggtgc 95940
gatatcagct cactgcaacc tccacctccc aggctcaagc aattcttctg cctcagcctc 96000
ccgagtagct gggactatag gcacgtgcca ccacacctgg ctaatttgtg tatttttatt 96060
agagatgggg tttcaccatg ttggccaaac tggccttgaa ctcctgacct caggtgattc 96120
atccgcctcg gtctcccaaa gtgttgggat tataggcatg agccaccgtg tctggcccct 96180
gttcagtgta tatcactaat tttgttttta tctctagaag tttgatttag gtcttttaaa 96240
aatgtctccc tgtgtttctg tttagctttg tgaacacaat tgtaataact gttttaatat 96300
ccttctctgc tagttctaag atcttctaat aacttcccag ttcttggtgt ttctcattgg 96360
ttgattgata ctcctcgttt tgggttgtat tttcctgcct ctttgtatgg ctgccaattt 96420
tttattggat gcccaacctt gtgaatttta ctttgttgga tgctatatat ttttgtgttc 96480
ccatagatct tcttgagctt tgttctgagg ttagttgagt tacatataga tggtttactc 96540
ttttgggtct tgctttataa tttgtcagat gggttggagc agtgcttagt ttaggactaa 96600 ttttttttt ggactaatta ttcctcttta ggaataatta ggtaccatgc ttaggaggca 96660
agaccatcct gagtactcta cctaatgaac cagaaagttt gggtttccca gtccgcctgc 96720
tgagaacagt gactttctag ccctgtgtga gcgctgagct ctgctccttc taatcctttc 96780
caatgcttct ttccctggcc tcagggagtt ttctcacaca catatctctg ctgagtactc 96840
gagagggacc ttccccagat ctccagagct ctctctgtct tgttttctct tctctggtgc 96900
tctgtcttat gaactgtggc tgtcttggtc tccttagatt ctcagcacct cttcaattca 96960
gagggttgcc tgtccctcct ccttgtgcca cagcctagga actctctcaa agcagcgagt 97020
tggggcagcc atagggctga cttagtctct cgtctcccag ggatcactgt ccttcattgc 97080
tcatgtccag tgtcttgagg actctgggtt ttgtctgttt tgttttttgg tttgctttgg 97140
ttgtctcagg caggagggta aacccagtcc ctcaccctca ttgtgctcag tagtggaagt 97200
ctcactctat tacattagat attagtattt gtagcagagc cctggttccc tggtacttgg 97260
ggagctcttg aaaggccaga aacagcatgc tttctcacct tttccagggc ttcagtttct 97320
ggtgcacatc aagcattcca tacacatttg ttaaagtcct ttgttagaca agtagtgatt 97380
cacaggttct atttgtaatt ttttcagtta acatgtattg ggtatctgct gggagctagt 97440
aaaaacaaaa agtggtgtgt gacaaattca attctgacaa gaacaacctt aaacacttag 97500
aatatacttt gagcatatca gaattttaaa aatgtgtggc ccttgagtat ttgaaaccaa 97560
caagaatcta ttgcttatta gtagaggata ttttgttaaa caagtggaga gagaggcatt 97620
ttcagtctaa ttggtgttgg cttttagcag ctgatggaaa ccagttcgtg attagccagg 97680
cagtggtgaa acaggctgtg cattctgaat gcctaggtat ctaggcattc agaatggtgg 97740
cgctctttga gttagcatct tcttctttct tgattctttt tttttttttt ttgagatgga 97800
ctttcgctct tgttgcccag gtaacaactc cagtgcaatg gcgccatctc ggctcactgt 97860
aacctctgcc tccctggttc aagcgattct cctgcctcag cctctcaagt agctgggatt 97920
acaggtgtgc gccaccacgc ctggctaatt ttgtattttt ggtagagatg gggtttcact 97980
atattggtca ggctggtctt gaactcctga cctcaagtga tgcacctgcc tcgatctccc 98040
aaaatgctgg gattacaggc gtgagccacc actcccagcc ccttcttgat tcttgaaaag 98100
gacattgggt gctgtacatc tcgttataga tgttgataaa aatgcttgtg agaagagtaa 98160
cattaaggta gttatttggt catttttgca gattatttta agacaattct aggactgatt 98220
tgtggtaaat cacacattgc tgtatcatag ttgtgttcac tgaacatatt caggggctct 98280
acagatgcag ggctcttagc tgctttgcac acttctgaat tcctgccctg cgaacaggac 98340

```
tggatacccta atagacaaca ggtacttgat aacagtttat tgaattaatg agtgaatgaa  98400
cagatacata aatgcatgaa agaatggttg taatgtatat aacttggatt tcaagacttt  98460
ttactgactg ttcaaaataa gaaattgaaa actttcctct gattttcctc tactatttac  98520
acaatttaaa tggaagttat cttgtacctt caatttctgt ctaggattcg tacaataacg  98580
ggtcatctct gagtcgctta atgtctcact tgtctttcta cagtgtgttg aagagatcct  98640
aggatacctg aaatcctgct ttagtcgaga accaatgatg gcaactgttt gtgttcaaca  98700
agtaagagct tcattctttt cctcttctgt taagacgttc gggtatgaca gcaaaacgct  98760
gctactcctt aagaggcagg cgctgttggc ataatcagct gggaggattg tggggtccag  98820
cgcagcactt tttggctcag tccatgattg agccaagagg ccatccttcc cttcactccc  98880
caggaggacg aggtctgtca ctgtggaggg cagaggacac cagaagctcc tctgcaacct  98940
cgctagttaa cttccagtcc ctcggagttt ctgtttagaa tgctcaatct catttagaat  99000
tgcaaggaaa cccaaaacgc ctatttaagg tacaaacagc acttcataca atatctcatg  99060
aggtattaat agtgattcac aggaagaatt tcacgctgtg agtctttgct aacatatcca  99120
gttatttaca gatggatttg atatttgtgt gggagattct taaaagtgtt gttcacgcca  99180
cattgttgat gcctcatttt tttcactgta gttgttgaag actctctttg gcacaaactt  99240
ggcctcccag tttgatggct tatcttccaa ccccagcaag tcacaaggcc gagcacagcg  99300
ccttggctcc tccagtgtga ggccaggctt gtaccactac tgcttcatgg ccccgtacac  99360
ccacttcacc caggccctcg ctgacgccag cctgaggaac atggtgcagg cggagcagga  99420
gaacgacacc tcggggtaac agttgtggca agaatgctgt cgttggtgga agcacgaaag  99480
agcaagcagg aaatactttg taaaagaata aaaacgaaaa atgttagcga acatcttcta  99540
atagtctgct gtattcagag aactctagga gatatatatg gttgatgcaa agatgattta  99600
aggcatagcc cggccttcca agaagtgtgt ggccagtgag tgagatgggc ttgggactta  99660
cacatctcag aggtgggggt agaggaggag gaacactgag tgggctgaga agcagccagc  99720
tctcattgcc aaagtgtgtc agcaaaccag aatgcagttc ataatgtccc cacccattca  99780
aagcacagga cctgtagagt ggtgtggcat gtgttggtgg cacttttcag gcctgtaaca  99840
aggatgaaag aacagcttca tagcagcaca gtagtgctgg tgttcagagg tgtgtgaagg  99900
ccatagaagc atcttggata tattaccttg tgttttgtca gctttatgac tagaagtctc  99960
ttttcactta aatttgtttt tttttttttt gagacggagt cttgctctgt cgcccaggct 100020
ggagtgcagt ggtgcaatct cagctcactg caagctctgc atcctgggtt catgccattc 100080
tcctgcctca gcctcccgag tagctgggac tacaggcgcc tgccatcacg cctggctaac 100140
tttttttttgt atttttagta gagacggggt ttcaccatgt tagccaggat ggtctcgatc 100200
tcctgacctc gtgatctgcc cgtcccggcc tcccaaagtg ctgggattac aggcgtgagc 100260
caccgcgccc ggcctctttt cacttaaatt tatgtttgtg tttttaatgc ctagtataca 100320
ggacttctta aattgcctta agtatgaaca ggtatttgag ttgctaatct gtatagtagc 100380
aataatagaa tcccttgttt ttccttttat aaatttagcg attaaatagc tacaattaaa 100440
acactagagt caggagtcaa ggaaaatacc catgttccag gctgtatgtt agtgatgtac 100500
ttactatata ttggagtttc aggagtaagt ctgtttcaat gctttctgta accatttggg 100560
gtattaataa gcatgtgagt gtgtgcatgt ttgggttaat ttcatatatg tttcttagaa 100620
gggatatcat tgatgtaaat attttaaagg cttgtcctcc aaaaaaatca tgtaatttct 100680
```

-continued

```
tctaaattac tgatctttta aatgaccttc acctttctct caaatctcac ttaagactgg 100740
gctgagtagt cagtttcctg tagcagaaaa aagctcagac ttgagtagcc ttctgcgagt 100800
gaggagactt gatggctgtc aggcagctgt aaactctaaa tagagtgtca ttatctgaag 100860
agggcgatgc tgccacactg agtggccttt caagttgttt ctcaatctga cacgttctga 100920
tcgtgtgaat gtgaaattgg tttgagcagg agtatatctg agtgcagagg agattattta 100980
aagatattct cattctctgc ttccctttta ttcccatttg gcagatggtt tgatgtcctc 101040
cagaaagtgt ctacccagtt gaagacaaac ctcacgagtg tcacaaagaa ccgtgcagat 101100
aaggtaaatg gtgccgtttg tggcatgtga actcaggcgt gtcagtgcta gagaggaaac 101160
tggagctgag actttccagg tattttgctt gaagctttta gttgaaggct tacttatgga 101220
ttctttcttt cttttttct tttttataga atgctattca taatcacatt cgtttgtttg 101280
aacctcttgt tataaaagct ttaaaacagt acacgactac aacatgtgtg cagttacaga 101340
agcaggtttt agatttgctg gcgcagctgg ttcagttacg ggttaattac tgtcttctgg 101400
attcagatca ggtttgtcac ttttatcttt catccatcat acctgttcct aatttagtac 101460
aaattaccct aaaagacact gaaatctact ttaaagaaat gtggtctgca tgtttccctc 101520
atcagttgct gctgcttatc tttttcatgc acctagctgg tgcagaaggc ctggggcata 101580
gccagcctca gcaagtcagc atccttgccc cagctccctg gactcaaggc taacctgggg 101640
ttggctgtta gggatttcca aaggtttgtc ccatccactt gcctcccctc caaaataagt 101700
ttgaatttaa attgtgagat acaattaaga tttattgttt ggggaacatt tttgcaaaat 101760
ctagagttag tttaaacaga ttatcaatta ttaccataat tgatcatctg cagtttcaag 101820
ctatctaaca ggttcactta cctctttaaa aaggaatgga atttagcagg acagtaactg 101880
agacccgtgc tcctggagtc catgtgggag ctgtgtggct ctgcacaagc atttgcacgc 101940
ttcccctctt gactgcatta ccttcctcct atagttgctg tgggcaccag attctggcta 102000
gtcctgtccc ttcatgatgc acattttcct caagattcgt cccagttaaa tcactgcaga 102060
tgaaactgcc ttttcatcgt caaaatttaa ctgtcatttt tgagccgtga tcttgggcta 102120
ctttcttatg tggggtagga atatttgtga gttagaaata ttacacttct ctatttcctt 102180
ctagacgtaa atctgttaat cctgtcagca ctgttactca cctgaaaggg tctgtttccc 102240
taggagaact gagggcactc ggtcaacact gattttccac agtgggtatt ggggtggtat 102300
ctgcttgttt tttttgttgt tgttgtttgt tttttttgt ttttttttg agatggagtc 102360
tcgctctgtc acccaggctg gagtgcaggg gtgcgatctc ggctcactgc cagctccgcc 102420
tcagaggttc acgccattct cctgcctcag cctcccgagt agctgggact acaggcaccc 102480
accactacgc caggctaatt ttttgtattt ttagtagaga cgaggtttca ctgtgttagc 102540
caggatggtc tccatctcct gacctcgtga tctgcccgcc tcggcctccc aaagtgctgg 102600
gatgacaggc gtgagccacc gcgcccggcc tggggtctgc ttttaatgaa ggaggcatca 102660
aggggtgggc tttgcgttgg cctgatgctt tcatctttct ttcacaaaac ctgtccgaag 102720
aaaatccgtc taaatgggcc attgctctcc tcaggaaata gtcattggga acttcttttc 102780
ctttcctttg acactaggag gctgactggg gagaagccct ggtctatggc tgtgggcagc 102840
aggggctgag aggagcaggc tctcaggggg gcacgggtac cccaagggaa gccagagccc 102900
tgatttgttc cattctagta agaacaaaga ctgctctggt ttcatgtttg ttctgattgc 102960
ctttcatcaa ccggtcccct ttctcccagt tcttaagatt cagtacagtg acagttttat 103020
gaacaagaat agaacactag aacagacaaa ccattgaact ctatgctgat aaagatttat 103080
```

tgagctcctg ctgtatgttt gcattctgcc cagaggctct gagaaaacca ggccatatgc 103140
tccatgcttt atccatggaa gctccccgtc aggttgggaa agctgacagc tgcagggaat 103200
acagtgtgac acaaaactgg ctcccatgca gcccttacgt gtcgcctctc agatggttgg 103260
gggacgaagg tcgactcctt tgggtatctt attactaaac cagtttcagg gaatctgtgc 103320
caccctatct gccattaacg tgaacagatg agtccccaag gtgtaatttt gggtattgtc 103380
tgatgtctct tggaatttat tatttgtttt tccaatgaga tttcacctca gggtatagta 103440
aagttgttga ggggattcct ggatgtgttc tgcaattatc taggctgatt tcagaataga 103500
gttatgctta tagtcaaatt tatcagctgt caagaatttt atttaaaatt tatgcagata 103560
agcaggagga aaagaagcct ggtttttaca ttttaatcct attattgatg tgaaatttta 103620
ttttccttcc tgtaggtgtt tattggcttt gtattgaaac agtttgaata cattgaagtg 103680
ggccagttca ggtaatagca ttttattatt ttagattttt ttcttcttct tgtgtactta 103740
catgtaattt aggttattaa gtgaatgttt aaactactgt taggcatttt tgctgttttc 103800
tttaaatgga aatctgacta acatactgtg catttttgct tctcttaaaa attaatgtat 103860
atctcaagac ttgtttggaa gtagttatgt atctgaaaat tccatatgtt gtcagtattc 103920
attgcacatt tcaaagcatt taattgtgtt gacagatggt ggaatgaaat cttgtggtgg 103980
agcactagtt tttaaatctt cttagagaaa gcagttttat ataatgttgt ctttagtaat 104040
tattatgcat ttgtattctc tgcagctttt tcttgctaga tgttgaggtt ttaatacttc 104100
ttgctagtcc attacaggtt tataattatt aaaagttaaa attcttttag tacctaaaat 104160
gcttaataaa cattgtaatt aggaaaattt agtgcagaag gaaagtgttc ccagattccc 104220
tggggtctgg aaacatagtg tttattctaa ttacatgaca cctccactgt gttttggggc 104280
aagttactgt ttctcttttg agtttcaatt tcttcaagag caaagaggca gaggagagct 104340
aggaagatcg tagctgctgt gcccctgtgc cgtcgggtgc cttctacctg ctgcctccga 104400
acctttacac atgtccctgc tctgcgcgag ggcacagatg ggatgcactg tggcaggggt 104460
ggggttagag tagatcacgg acacctgtta gcttgatgtg tgcttgctgt caaggttgaa 104520
tcatgaatta ttttatgttg cttatattga tatgtatctt aattttaaaa gaaaggtcta 104580
aatggatgtt tttgttttta gggaatcaga ggcaatcatt ccaaacatct ttttcttctt 104640
ggtattacta tcttatgaac gctatcattc aaaacagatc attggaattc ctaaaatcat 104700
tcagctctgt gatggcatca tggccagtgg aaggaaggct gtgacacatg gtaacgggac 104760
acacctttca ctgtcgtctt cggtgtcgtg atgtgcttgg cagtgttcgt tttcatatac 104820
ccactttgaa cgttgtcagt ggcagccatg tgcttctcag gctctgcatg tgtgtctgtg 104880
tatgtgaagg tactggttag agacgtttca aaagagaaga gagcatattc tttactctca 104940
gcaatttgta atcttctcag ggaaaaaaat tcaagaaaca gtaagataac ctaaggtaca 105000
gatagattct gaatataaag ttcctgttca ttcacatgaa acgctaaaag ttcttcactt 105060
gatcttagcc aaaaggccaa gaagcgatgc aacactaaaa attcttaaat cgaacttgcc 105120
gtgaattaaa ttttgatctc tcatccagtg gtattggaga tatagtttga cttgggttca 105180
gggctttctg ttttgcctga tgattttgct ggagcttaaa taaggaaccc aggagatggc 105240
cagctgtgca agcccccagc ctgtggaagg agctagtgtg gttttatgaa tgagttgcaa 105300
atctttcttt gagctttttg aactgatctt ccagcattgc cctattgacc cctccctgac 105360
tcctttgctg gaatctgtag gcttttgaac tttgacaggg acacatccta agacccttgc 105420

-continued aaactcccag atgtgagaat ggcactacta cttagagtct tttcgactca gcgtgtgtgc 105480
agaagagcat caaccgggct gtgttgcgag gcagggcctt ggctgacctc tcagtgttta 105540
catagctaag ccagttagtg tttgccacgg cctcacaagg gcttcagatt cacacagcca 105600
aagtatagat tattaaaggc ataggtgttt ggtttcctgg acttggaggg tctttggaca 105660
gaaaatcagt aggcaaccac acccagtact ttgtgctggg aagcttggtc atctgtgaga 105720
gggtcagaga gtatacccat gcgtgcatgc caccgaaggg tcagtgagta ttcctgtgtg 105780
tgcatgtctc agggccggag agagtatgtg tcactgagag gtcagagtgt ttgtgtgtgt 105840
gtcaaagagg gttgcattgt gcccttcact gaggggtcag agggtgcctc gcgtgtgtgt 105900
gtgtgtacgt gtgtgtgtgt cactgagggg tcagagtgtg cctgtgtgtg tgcttgtgtg 105960
tgcgtacatg tcactgaggg gtcagagtgt gcctctgtgt gtgtgctcat gtgtgtgcat 106020
acgtgtcact gaggggtcag agtgtgcctc tgtgtgtgct catttgtgag cgtatgtgtc 106080
actgaggggg tcagagtgtg cctctgtgtg tgtgctcatg tgtgagcgta tgtgtcactg 106140
agggggtcag agtgtgcctc tgtgtgtgtg ctcatgtgtg agcgtatgtg tcactgaggg 106200
gtcagtgttc ctatgtgctc atgacattga gggtcagagt gtgcctgtgt gccaatgaaa 106260
ggcatttctt atattttttt atatgtggtc atagtagacc agttaattta ttttgactcc 106320
tgtgttagac caaaataaga cttgggggaa agtcccttat ctatctaatg acagagtgag 106380
tttacttaaa aaagcataat aatccagtgg ctttgactaa atgtattatg tggaagtctt 106440
tattgtcttt tcagatgaat caagtagatt attcttgaga ccaggaatgt tgctgttttg 106500
gttatttgga aagttttatc attttcaaat tgacttttga atttgagtca cctttttca 106560 gaagtggtgt taaattatag gagccctagg ttttttttct tttttagaa gtcatcacaa 106620 aatgatcagt gttcagagga agagctttga ccttccacat ggtataatga ttgataacct 106680
taattcatct cttaccataa accaagtatg tgtaagggtt ttctttattt cttgaaagca 106740
ttttgtagat gttgagagca gttttccaaa tgtaatttcc atgaaatgcc tgataagggt 106800
acccttttgt ccccacagcc ataccggctc tgcagcccat agtccacgac ctctttgtat 106860
taagaggaac aaataaagct gatgcaggaa aagagcttga aacccaaaaa gaggtggtgg 106920
tgtcaatgtt actgagactc atccagtacc atcaggtaag aggaatgtat gttggaactg 106980
tcgtggatac tttattgacc cgtgcagatg gaaggaagtg ccatgtggta acgctcactg 107040
ttaactgtgt tactttgaac caggtttggg ctttctgggg cctgggtaga tgccggtgca 107100
gggggatggg gagggaggcg gggggtgggg gggtgtggtg gagttgggga ggtgcagtgg 107160
caggaggtgt tgttggtgtg tatccttttt tttttttga gatggagtct ctctccgtcg 107220
cccaggctgg agtgtggtgg cacgatcttg gctcattgca agctccacct cccgggttta 107280
agcaattctc ctgcctccac ctcccgagta gctgggatta caggcatgca ccaccatgcc 107340
cagcaaattt ttttttttgt atttttagta gagatggggt ttcaccatga tggccaagct 107400
gtttcgaact cctgacctca agtgatcctc ctgccttggc ctcccaaagt gctaggatta 107460
caggcgtgag ccaccatgcc cagcctggtg tttatcttta aagtgggcac agccacagga 107520
gttcacctga ctcctggtct gagagtcacg agatcgttca agatagtgag gccctctttt 107580
ccaaaacgag gaccaaaaat caattgacag tgttggtcaa gatggtagaa accttaaaat 107640
gatagaaatc tcaactctga aataaaaact ttatttgtat atttatttac cactattttg 107700
acatagggct aaggtctttt tctttgagct gatttctggt tttgttttct taaagtggca 107760
taagaattca aagacatttt gaggaaggct gagtgcagaa atctctcttt ttaaatgact 107820

-continued tctcctttct tttaacttgc actgttgtct agccctcact tattttgtca attcttttta 107880
gctgtttgtc tttgaatctt cataaagcca tagcttttct cataagaagc agcactttct 107940
ttgttcattc atattttaat gaacccctgt agtatttaat taaatactta atgcctaatt 108000
aaatcacata attgcaatgc aaaagtacat gtatcataaa gaggtctgaa aatgagcaac 108060
tggcaagcag gtggtggcag gcagagctgc ttgggtgggt gggtgtcatg gagaggagtt 108120
catcagccac atgttcagtg agctctggat atgtctgttt agaaatgatc actaataaac 108180
ttgtgctcaa ccatgtatac ctctgggaag caggtgctct tcagtagatt gcctctgcag 108240
agaacacaga attgaagtga atgtccacaa aggcaatgag ccacctgcag aatagtttag 108300
tcaaggctgt gtttgaagtt tgccaaagat taatatacat ttgattttca tgttgtgcct 108360
tttctctgat tgtgaaatat tacaaattct atacaaataa caatgatggc aaatcctcct 108420
gagcaaagtg tgcaccttgt atgtgcccta gaggaacttg tgtttcgttc tgattcccct 108480
acatttctca tgtcatagag tgggggttgc attagtgtcc ccctgtcctc gctgggatca 108540
catctgtttg gatcctagag tcttccagct gaactgggac aagtataaca gacggacacg 108600
taggggtgga aaggcgtctc ttggcagcag actttctaat tgtgcacgct cttataggtg 108660
ttggagatgt tcattcttgt cctgcagcag tgccacaagg agaatgaaga caagtggaag 108720
cgactgtctc gacagatagc tgacatcatc ctcccaatgt tagccaaaca gcaggtttgt 108780
ccccgcagcc ttggcttgtt gttgcatagt gatggtagct taaggtcctt gtgaaaggtg 108840
ggtggctgga atcagctctt ccttcagtcc taatctgtgc cttgatagca gttctccgtg 108900
ctagtcatgg gacagctgac ttcatttctt ctcacaatgc catctcaggt tggtattgcc 108960
cacctacttt acagggggga tcccacagct ccgagaggtt atggaggtga tcaggcagca 109020
cacagcttta gagtgctggg gtgagggcgg gccaaggcta actctaaagc ccgaaccctt 109080
acctcctaca ctgcctcctg cattctggtc aacccagtgt tttatttggt ggttagattt 109140
ttgtttttgt taccttactg cttgtaattt agcagttttc ctttcctttc ccttcctttc 109200
ctttccgaca gggtctcact ctgtcaccca ggctagagtg cagtcgtgta atctcactgc 109260
aacaacctct gcctcccagg ttcaaccaat tctcccacct cagcctcctg agtagcaagg 109320
accacaggtg tgcaccacta cgcctggcta gttttttgta tttttagtag agatgaggtc 109380
tcgctgtgtt gcccaggctg gttttaaact cctgggcgca agtgatccac caaccttggc 109440
ctgccaaagt gctggcatta caggtgtgag ccacctcgcc tggcctattc atcactaatc 109500
agaatttcta tgatcaaatg acatgaatca ttgtttccac aactgcagtg gaaggaaatg 109560
gcctggcagt gccagtttca gaagcagcct gcccccagtc aggcacaggc cactgtgccc 109620
ccagtgtagc agcacctctg tagctcacag agaagggtgg tggggacctc cttgaggcag 109680
ctctgccaga aaatctcatg agctgcctgg cacagcttga ggttgccttt taagtggact 109740
cagcaaatac atgtttgttc atcttgatta tacacaataa acaactactc tgtatagtac 109800
gagtagtccg tggtttttgg catttgattt aaacttagag gcatgtgata ttgatgttac 109860
tgccttcatg actgcacccc cattctgatt tcataatgga atgttatctt gagaccagtt 109920
agacaacagg acagggatct tggcttctgg tgagattgac agcagtttta gtgtggtcag 109980
ggtctccctg cctacagatg gttttagaat ggtgccctgg aagctttatc ccattctttt 110040
ctgtgcgtaa tctgagtaga gtggagatcg aaggcctgaa tacatagtaa atacctgact 110100
taatatctgc cgcaatggaa attgtgtgat acaacattta tgaaacgctt agtgcagcac 110160
ctgccaggta gctcaccaca ggtgcatgtt gcattcagaa gtagtgctag atactatcct 110220
gttactggca gtgcatacat cagtgatcaa agcagattaa agaaagaccc cctgccttct 110280
tggagtgaag attttgttgg gatgcgggta aggggacaga caatagaaaa gcaagtgagt 110340
gaagtctata ccatggcggc tgatcaggaa caccgtacag aagaatccag gagggaagag 110400
agttaggtgg tgtctgcggt gggagtggca ttgttcagct ggtgatgaga agaagctttg 110460
gtgatctggt gacatttgag tgaatttgca gaaaggaaag atacaagcct aggagatacc 110520
tggggaagga acattccagg cagagcaaat agcagtgcaa aggccctggc ggggggcgga 110580
catgctgtta gggtacaagc aatgagggtg gaggagtggg gcagccatgg ggagggaagg 110640
gagtgaggcc tggtggggtg aggccagtgt ggaggagcct tgagagggtt tgcgctgatg 110700
tggtgtaggt tttagcagga tcattcttat tcctgagttg agaatagcct tgaggggga g 110760
gtgagggcag agcagggcca cccatgtgag acccggcact ggagtggaat ggcccaagtc 110820
agcatccctt ggcagcatga aagcaaaacc agcaaggttt gctggtggct tagatgtggc 110880
atgtgagaga gagcagggct ttgggggtga tttcagggtg aggacagggt ggctgtggac 110940
aaggtagggc agacattggg ggcagcagga ggtcagagcc tgtctggatg tagcagttga 111000
gaccccatag gtgcctaatg aggtgaggcc agcatcaggt gtatgagcct ggagttgtcg 111060
agagactgtg gggcaggggg tcagcatctg agatgtccac tcacagtgga cccagactgg 111120
ctggagagga ggaggagctt gaataccgag cctgctgagt cccagctcca aggtcaggta 111180
ggtgagggga gccagtgctg gggcaggggg agtaggcagg tgtggggttc ctaaagccaa 111240
gattttttt aaggcatttt gtgcaggagg gcgacatctg ctgtcagcac cttgggaact 111300
tggcccaggt ttggcagcac cgagggcact gatgagtgct tttggaggag caaagggagc 111360
caaaccctaa tgggaatgtg ttcctgaaag gacaggagag agacttggga aaaggtttta 111420
cttgaagagg gaacggagaa atagggcagt agccagagga ggagaggagt cggcaatggg 111480
ttaagttggc agaaatgaag gcctgtttac gcactgaggg cagaagcaac agggaggatc 111540
agttcatgac acaggagaca caaatcgccg ttgtggtgtt cacagacatg ggttaggatt 111600
ggctgcatgg atgacagagc actgtgggtt ctcccagagt tgctggggag gaggcagagt 111660
tggtgagcac aggcgagggt ccaggatgca ggaatcctgg agctcaagtc agttgttccc 111720
ttgttgtaag atgtggccag tgttgtgagc ttcacatctg tgccttgaaa aacaccacat 111780
ctgtttgcag agttgtttac tatgtataca cactcagtag aaacaaaaat tggaaacagt 111840
cagtgcccac catcaataag taatggttga acacactgtg gtataagctt agactatttt 111900
agcttgggct attttgcatg attaaaaatg ttctggccag gtgtggtggc tcatgcctgt 111960
aatcccagca ctttgggagg ccaaggcagg cagattgctt gagctcagga gtttgagacc 112020
agcctgggca acatggtgaa accctgtctc tactagaaat acaaaaagta gctgggtgtg 112080
gtggtgtgcg cctgtagtcc tggctaactc aggaggctga ggtgggagga tcacttgagc 112140
ccattcgtgc gccactgcac tcctggggca cagagtgaga ctctgttaga aagagagaga 112200
gagaaagaag agagagggag ggaggaagga aggaaggaaa taaatggaag aaatggaagg 112260
gaggaagggg agggaggaag gaagaaagga agttcagcca gttgccttgg gagttctcca 112320
ttgcactggg ttaagtgaga agagcagaga cgtttatgat ttttcaaaac aactaaaaca 112380
aaacctctgt gggtgagggg gcaaggatat ggctatagga acatggggca gattaagaaa 112440
gggatataca cacaccactt agcatttgtt acaactgttg tgggagggat ggagtgcaga 112500
aaaagaaaaa aaaaagtgca caccatccca tgtatgtgta tacaaaggga cgcttggaag 112560
actggtcccc aaaatgttgg taatgattgt gtcagggtgc tgcagtgcta gttgattttt 112620
tttcacactt ttgtatattt gagtctttta cagaaagcat ttattattta tgtaataaaa 112680
atctaaatga caagatttct gttatgggaa aaatgtagct atacagtgtt gttgtaaaaa 112740
tgtttgcttg gttcaccact gaacttaaaa tgcttttaaa tgagggaagg tgacgatgag 112800
atgattatga tgatttgccc ttgagttaca tagctggtgt acaggaagct gtcgtttctt 112860
ttggcttacg tagaaatgtt tgtggtgtct aattccacag atgcacattg actctcatga 112920
agcccttgga gtgttaaata cattatttga gattttggcc ccttcctccc tccgtccggt 112980
agacatgctt ttacggagta tgttcgtcac tccaaacaca atggtgagtc tctcgcctgg 113040
ctcagcagat gaatctggac ggcttgttca ggctctgatt actgggacca cccccagaat 113100
gtctgagtca gtcagtttgg gtagggcttc ttgagagttt gctttttttt tttttttttt 113160
ttttggtgtg ggggtggtgc ggaacagagt ctcactctgt cgcccaggct ggagtacagt 113220
gtcatgatct cggctcactg caagctctgc cttccagctt cacaccattc tcctgcctca 113280
gcctcccgag ttgctgggac tacaagcgcc caccaccacg cccggctaat ttttttgtat 113340
ttttagtaga gatggggttt caccgtgtta gccaggatgg tcttgatctc ctgacctcgt 113400
gacccgccca tctcagcctc ccaaagtgct gggattacag gcgtgagcca ccgcacccgg 113460
ccttttttatt tttttggag atggagcctt gctctgtcac ccaggctgga gtacagtggc 113520
gctacctcga ctcactgcaa cctccgcctc ccgggttcaa gcaattttcc tgcctcagcc 113580
tcccgagtag ctgggactac aggtgcgtgc cactgtgccc ggctaatttt ttgtattttt 113640
agtagagacg gggtttcact gtgttagcca ggatggtcgc gatctcctga ccttgtgatc 113700
cgcccgcctc ggcctcccaa agtgttggga ttacaggtgg ctctcgcacc aagccaagag 113760
tttgcatttt tagcaaattc ccaggtgaaa ctaatgcctg cttttctggg agcacacttt 113820
gggactcagt gatagagagg tttattggta ggatagtaaa ataggagtta ttttctttca 113880
caaaattggc aattggggga aatttaatct tcctttttc ttcagctgtg acttatgtat 113940
tatgtttatt ttaggcgtcc gtgagcactg ttcaactgtg gatatcggga attctggcca 114000
ttttgagggt tctgatttcc cagtcaactg aagatattgt tctttctcgt attcaggagc 114060
tctccttctc tccgtattta atctcctgta cagtaattaa taggttaaga gatggggaca 114120
gtacttcaac gctagaagaa cacagtgaag ggaaacaaat aaagaatttg ccagaagaaa 114180
cattttcaag gtatgctttc tatctgagcc tataactaac ccatgccttt tgggaagtca 114240
cgtgatgttt cacagtcagt aagtctggaa taatacctgg tcttgcttca cttctgagtt 114300
gggtaaagaa gtctgtatca gtgtaatttt ctaatccgtc ctgcattatc tatggctctt 114360
ggttcatacc tgtcttgaag ttctgtcatg ttctgtctct tgtcctcagt agagatgcta 114420
cagcagtggc tcgcctcagg cagggcaggg cagtggggtg gctgtcctgg gggcaggcag 114480
taggggcacg ctgacgtcag ggaagttgaa acccaagaga agccagtaaa agtgagtctc 114540
agattgtcac catgtgctgg cagttttaca cgctgtcagt aataaaagtc ttctccctgc 114600
agggcagcct gcctccaata aatacgtgta gtatcaaatc ctgtcttccc tcataaattg 114660
tttggaagct ccccaaggac agtgatgagg cactcgtaag tgcttgctgc ctagatgggt 114720
ccctctccac ctttgctaga ttctgagcat tcactgagtt agagctgctt ctgcaaatgt 114780
gctgcttctg ctaagtggct gtgacttcat gcagccttca cttggtttgt catcagtgga 114840
gatgccctgt gttgtcgaag gagataagcc cagtaagcct gctgggcacc ttttggtttg 114900

```
caggttcagc aggcagccca tggctttccc tgtgtcgcat tgaagcagct ggctaaaatt 114960
gatgatacat taaattcctg tgacagatga tcagcttgta tttgtgtaat ggtgtacagt 115020
tcacaaagct taaaaaaatg ctacctgcca tttcatcctc agtgaggaag gtgatacaca 115080
gagagaccaa gtgactgtgt ccacggcgac ggcgctctgc atttcacttt agcggttaat 115140
gtactctacc tatattttta ctttatattt accatatatc ttttcatgta tacttggcgt 115200
aagtgcttta tagtagtcac ctaattcact gtcatctttt ttgtttcttg gaaggtttct 115260
attacaactg gttggtattc ttttagaaga cattgttaca aaacagctga aggtggaaat 115320
gagtgagcag caacatactt tctattgcca ggaactaggc acactgctaa tgtgtctgat 115380
ccacatcttc aagtctggta ggtgaatcac attagtcttc ctggagtgtc tcgttcccca 115440
ttctgcacta tacactctca gagtgtagga gctgtgctgc ccggtagaaa ctctgccttg 115500
cccagtgtgc cagttgaaaa tatttgttgc tgtaagagta cacctgatac catgtgaccc 115560
agcagttcca ctcttgggta tatacccaaa agaatggaaa gcagggtggt gaaaagatat 115620
ttgcatgcca gcattcatag cagcattatt cacgatagct aaaatgtgga accaactgaa 115680
gtgtccctcg atggatgaat ggataagcaa aatctggtgt atatttacag tggaatatta 115740
ttcagcctta aaaaaaggac attctgacac atgctacaac atgggtgacc cttaaggaca 115800
ttatgctaaa tgaaataagc cagtcacaaa aggacaaata ctatgtgatt ccacttacat 115860
gagggacctg gagtagttaa ttcatagata tagaaagtag aatggtggtt gccaggggct 115920
gcaggggagg ggagttattt ttacaagatg aagagagtta ttctagaaat gaatggtggt 115980
gatggttgta taacattatg aatgtactta atgctactga actgtacagt taaaaatagt 116040
taagaggacc aggtgtcatg gctcatgcct gaaatccaag cactttgaga ggccaaggca 116100
ggaggattgc ttgagccaag gagtttgaga ccagcctcag caacatggta ggaccccatc 116160
tgtacaaaca aactagccgg ggatagtggt gtgcatgtgg tcccagctac tcaggagact 116220
gaggctggag gatcgcttga gcccaggagg ttaagtctct agtgagatgt gttcatgcca 116280
ctgcactcca gcctcggcta tagagtaaga ccctgcctca aaaaaacaaa acaaaacaag 116340
acaagagcca aaaatggtta agatgggcca atcacagtgg cttatgcctg taatcccaac 116400
actttgggag gtcaaggtaa aaggatcact tgaagccagg agcttgggac cagcctgagc 116460
aacatatcga gacccctatc tctacaaaga aaatcaaaaa ctagctagat atggtgggca 116520
catgcctgta gtcccagcta cttgggaggc tgaggtggga ggatctcttg agctcaggag 116580
ttcgaggctg cagggagcta ttattgcact ccagcctggg ctacagaatg ataccctgcc 116640
tcttattaaa aaaaaatcca aaaaaaaaaa aaagtaaacc tgagagcttc ctcctcctgt 116700
gttaaatttg gaggccaaga tgtttttgtt acttttacaa atgatcaagg acggtgaagg 116760
ttgggcatgg tagctcacac ctgaaatccc agcactttgg gaggctgagg cggggtgatc 116820
gcttgagctt gagaccagcc tggacaacat agcaagagac cccatctcca caaaaataaa 116880
aaaataaaaa aaaatagcca ggagtagtgg catgagcctg agcccaggag gtcaagctgt 116940
agtgagccat gatcatgcca ctgcactcca gcctgggcga gatcgagacc atgtctctag 117000
agaaagaaaa tgacaaggac agtgaaccca agaaagtcat aagatgccag ctgtgcagca 117060
agcatggaaa gcagccagtc caaattagga cagtgtgttt tccaagaaga acgatcgttt 117120
gtaatgagaa tgctttgctt taaataaatg actaaatagc tagaagccta gttctagggg 117180
ataggcacgt ctttcttctc tcaagaaaat agaaaggcaa ttctaatttc tagtaacagc 117240
aaacagcatt aagtcatggt ccaaatatga ggcaaaccaa aatgtggctt gattgttcag 117300
```

-continued cagttgatct gttggaagcc cttgatatta aaaaggttct cctttaagcg gcttaggagt 117360
cacgatcaaa gacctataga aagagatgcc atccttctag gatccttggc tctcttggga 117420
actagattca gatagtcata atgtaaatac tgcttgagct ttctttcttt ctttctttct 117480
ttcttttttt ttttgagaca gagtttcact cttgttgccc atcctggagt gcaatggtgc 117540
catctcggct caccgcaacc tctgcctccc aggttcaagc aattctcctg cctcagcctc 117600
ccgagtagct gggattacgg gcatgcacca ccacgcctgg ctaatttttt gtatttttag 117660
tagagacagg gtttctccat gttgaggctg gtctcgaact cctgacctca ggtgatccac 117720
ccgcctcggc ctcccaaagt gctgggatta caggtgtgag ccaccgcacc cggcccgagc 117780
tttcattttt gaaatcaatg tatgactgaa acactgaaga cttactgact taattatggt 117840
ttcagaacag aatgaaaatg tcttcggttc tgatgaatat aaaaggaaaa ctaaccaagt 117900
taatttggca agtagatggt agagatagag gtggggagtg gaaggggaac taaaatcttc 117960
acctagcatt gttgggatta tatggttaca tcatctgaag ttgacagacc aaaatataga 118020
ggcttcagag gtctccaaat agaactaaac atgtaattca gattgttagg aggtagtata 118080
aatgagctaa atctcatctt tattacggta gagttaatgg gtgatgtcta aagttgtctg 118140
aagtctataa atcatgacaa attatgatgt ggtgattgta ttcaacagtc tttcagttgc 118200
agggataaaa ccccagttta aactagagta agagaaagaa tgtgttggtt taagctcctg 118260
gaaagtgcag gcaagggtag ttggtaggac tgcatctagt gttgtaattc tgtggtctgc 118320
attgtatatt tatgcatctc agctctgctt tcttcttttc atttatataa tttttaaatt 118380
ttattttaaa gatagggtct cactttgtcg cctaggctga agtgcagtgg catgaagtgc 118440
agtgcgaggc tcactctagc ctcgaactcc tgggctctag agttcttcct gcctcagcct 118500
tctaagtagc tgagacaata ggcatgtacc aacatgcctg gataggtttt aaaatttttt 118560
tgtagaaatg gaagtcttgc tgtgttgccc aggcgggtct ttaactctta gcttcaggcg 118620
atcctcctgc ctctgcctcc caaaatgctg aggttatagg tgtcacccac cacgcccagt 118680
ctcatctctg cttcctgtgt tagttttgtt ctctggtggg ctgttttcac atgaccgaag 118740
atgacctcta gcaggctgtg ttctcagccc ctcaagtagg cctatgtgat tggccttgca 118800
tgagtaatat gggtgaccat aaacccctga atgctctggt ccacatgggc caaatgggag 118860
actggacagc attccattga tgaggaggtg gggctggtct ccgggagtaa gggagaggag 118920
cacatgcagt aactgatggt ctgctgcaag ggatagcagc acagcagtta gaattttgga 118980
ggtaactacc agaactgaaa acagaaatga taacaagtag ttgccttaaa aagggatggg 119040
agcagggtgc ttttgtgatc aaagctcctt tctcttactg gatttttgta cacattttgc 119100
atacatatct tagagtaaaa gatagcattt tcagccttgg tccatttgag gatactcttg 119160
gcgtggcccg cctccatgct agcaggctct ggttgtgcca agttcagttg agcatcctgg 119220
ctcttgcctg cacggaactt ccagtcagtg cgtcagtatc acaagtcttg atatttccta 119280
tgaagaagaa cagtagtgca gtgacagacg aaatgggtgg gcaggcagag gcaggatttc 119340
tgagggagag aagtagctag ctttttgcag agaagagttc cggcacccaa gagagcagct 119400
gagagtacag gcaggcaggc aggatgccgg tagggcccgg ccgcacggcg ccacagaatc 119460
ctggagaaag gggcctcttc atggcctctg cattcagctg ctgtcaccct ccgcacaggc 119520
catggccaaa atttaatttt catagtggac tctagttttt gagccttact tgctattatt 119580
gaaataattt tcttgtttct ttttaaagat cttcggatta tgcttcactg accactgtaa 119640

-continued taagtttaaa gttgagaaaa tatggcttgt taatgaatga taggtcaatt ttagtatgtt 119700
ggtcatttta atattttgcc accagttggt ttggatttga tgccaggagg agacagcctc 119760
atttctaagg actagtcttg cctttgtggg ataagggtgg tgtgttctgt gtccttctac 119820
atgtccgagc gatctctgtg cagctcaaat gtggtcactg tcttattgcg ctgatttcct 119880
ctccttccat ctcacaattg aggcaaaata ttgttactgt tgaagtgttg tccaatagga 119940
cttccagcag agacaggatg tctgcactgt ctaatttagt tgcctttagc cacatgtggt 120000
gttctgtacc tgaaatgtgg ctggtctgat tggatagctt aatttataat tttatttaat 120060
tttaattaac ttaaatttaa acagctctgt gtggatagtg gctcctgtat gagacagtgc 120120
aggtctgttg agaagcagct ttactggtgg gagtggaggg cttggagagg gcacgtgggt 120180
ttcctgctgg tatcttttga ccttatttaa tctgcccaac atttgcaagt aagttgtgtg 120240
tgtgtgtata tataaatgtg tgtttctgtc ttcttgtttc ctttgactgc atttatttga 120300
aagacactag gtggcagaat tactgtattt gattggtttc aagataagag ttgaaataat 120360
tcatctcgtg tttttatata agtaaggtgt gtttagcatg taaaattggt aatatgtatt 120420
cacgtactgc ttaaacaaag gctatgaatt ccacccataa accgaaaatg aagaccttta 120480
aatttgtcca tttcaggcgt gggtacttct taaataatac ctggttcagg aactagtcag 120540
aatggcaccc ttgacttttt gtttcctgct tttcctcttg ttgggagagg agggtattca 120600
tcccaaagtg gtttgcctat ttcacattcc atctaggata agcagaatag ccaagaaaga 120660
tagctgtcct cctgtttaca acatttgggg taaccagcat ccctctcttt tggtccaaga 120720
tagactggtt tagaaacaga tgatggcacc agaggcccag gaggtggaaa catcagcttt 120780
gtttgttgtc catgtggctg aattagagct gtctggcctt gtagcctcaa cacggccttc 120840
cagctttgct caccgtgatt ttcaaggaca catcttgtgc tcttccctgc ctgccatcca 120900
gactataccc agtcagggtg gcaggagctg ctgccccttc ctccctgagt cctggtcgtg 120960
ggtggtggag atgtgccatg acgctcacgg aggcatgctc accccttcct ctgtggcaga 121020
ggggatggct gcacgacagc tcttccctgt cctttccaaa gcgtctgtgg ttccactttt 121080
tggggcaaag caggaatact ggaagagaga gaaagtggtc ctttctatag taataaagtt 121140
gacattgatt caagttcatg cttggggaaa ggacagggct actaacaatt ataatgctgg 121200
gagcaatgga attttctcat gggtatgtgg taggtttaat tttaattatc ccagttaatt 121260
cttagaactg ctctgtgaag tatttcccgc tttgtgctta agttctaaaa gatcctgtgc 121320
caaaaccaag aatgaaaacc caagcattct ttcttgccca tcgatctttc tctcatcagg 121380
ccacttcttg ggttgatagt ggtgagtgta gccgctgcca ctttcagaat acccaccatg 121440
ggccccagtc actgtgtggc gtggagaaga gatggttctc tctgtgtcat agctgaacaa 121500
gcccagccca gagaggtttc tgccctagga gctctcgatg gtggaattgg gatgcgatcc 121560
cacatcctgc ctgttttgaa aacagcattc tttatttcca attcctgctt ccattgttcc 121620
ttttaatatt tctttgttta gctcacaaaa acacggcttg cggagctgct gcgtgcagct 121680
gtagctgttt ctctgggtgc agcctgcatc cgccttcctg cccgcctcct ttcctgcact 121740
gccatcgtgg tctccgggca cttggtccct ttctcttccc ctgagtccct ttggctcccc 121800
tgtgccaccc ttgtgatcca caggctctgc cttctttctg tctcagactg ctgctcatca 121860
ctactcggga ccctaggaag ggaggttcca ccgagaagca tcttctcatc tcagccacgt 121920
tctcagtgcc actgttgtct ttgttaggta atggtagcta ctgtaacaaa taaaccaaca 121980
tttccatggc ttcacaccag agaaggttgt ttcttggttt tatgacaatg tattgagggt 122040
gttcttggtt cacggatggt tttcctccat gtgggaattc ggggacccag gctcctttcc 122100
ttcttttggt tctgttctcc aggccttcac atcctctgtg tctggttggg gacaaggaga 122160
gggaaggtaa agaaggcttt gtggccttgg ataagtgaca ggcatgcctt tgctggtgtt 122220
ctctcgtggt gacaggtcac agccccaccc tgtaaaaggg gactgagaga cgtcgtcctg 122280
ctgcttccca gcagcagcac tgtggtctct gatgtgtttt ctgtgaggat aaaaacaggt 122340
gattccagga tgaggaaagt cagggaaacc cttggaagga ggggaccagg cgggtgtcac 122400
catgggatta gtggtggctt cagaatgagc tgcagcgagt gccatgcctt ctaaagcttt 122460
tgctattctg atatgcccac accatgccca gcaggtgtct gccttgctct ccgcagagag 122520
agtgatgaat ccttctcatg agcctctgtc cagttgttcc tccctccacc tggaagggac 122580
cctgggttcc tcataacatc ccagcggaac aggggacctt ctatcctgtc cccaagttca 122640
tcctcatcct cctgccggct tcctggcccc tcttatgtct gcttcctgac gccacatcct 122700
tctggattct ctggaattga attttgcctt tgatgcttat ttaaaaatat ccattgcagg 122760
ccaggtgtgg tggctcacac ctgtaatcct gtgcactttg ggaagccaag gtgggcagat 122820
tgcttgagcc caggagtttg agattagcct gagcaacatg ttgaaatcct gtttctatag 122880
aaaatacaaa aattagctgg gcatggtggc gcacacctat actcccagct actcaggaac 122940
ctgagacagg aggatcaatt gagccccgga ggccaaagct acagtgggct gtgatcgtgc 123000
cactgtactc cagtctggtc aaacagagtg agaccctgtc tgaaaaaaaa aaaaaaatcc 123060
attgcatact tcaccgtagc gaaacatgta tgtcttacct ttcctttcct gcctgtagct 123120
gctcttttac acttaacagc cacactaagc cagccttaaa tgaaaaacaa accagcactt 123180
cctgtgccct cctgcttcct tcatgagggg tccctccctc tgtgtacact ccattctcat 123240
tgcccatggt ggtttgtttc cctcttgttt ctcaagccat ggcagcctgc ctcttgccct 123300
ctttactaaa aaggcctttg cagaggctgc ctgtgttctt tctttctagg tctctctcat 123360
cctaggccct ccagcttgat tctgtggagc tgccctcttg tcactcagta gcttgtgggg 123420
tcttctctgt ctagccactt aattgattgt gttcctcgag ttgctgtcca tggtctctcg 123480
ttactgtttt ctctgtgttt ctgcctctct ccttggcctt ggtaggtcca tccccttttgt 123540
gaccttggct gttgctctca tggacaactt tctcttgctg gtccttgtag tcctggcatc 123600
cagcttctcg acacgggact tgtcctgcca gtacctcaga cttgcactta aaattgaact 123660
agcaccactg tcactctcca gggcctcttc ttgttaatta gatcattagg gatgttcaga 123720
atcccagcat catagtatgt tcctcctccc gctaccccag gaaccctaac cttacctcct 123780
cctctctatc tactaggagg tggccctcag agtccgtctc atcttccacc tgaacttccc 123840
taataggctc cagcagctgc caccccgggg gctgagtact tcctccatgc cttgtgcagt 123900
gctgagccct ttacctgggt tctcctgttt gctccttatt acagccctgc gaacagatac 123960
tgctcttaat tccatcttac acctaaggaa gctgaggccc caggtaaggt gcatccaagg 124020
tcacccaggt agtagacagt agagccacga tctgaaccag gcagtctgat tcagagcctg 124080
tgttgacact cagccaccta gaacacagct tggattgtgg gtttctatta cctgttcaaa 124140
acccctacat cccgggtctg tccctgcacg tgctctgtgg cctggctgca tcttccttga 124200
aggcagtgca tgcctcttca ctcagggggc ccatgcagga acagagggcc ccacagaagg 124260
atgaggccag tgcagaatgg gctggagggg acaatgctga ccaggaagca agtgtagaga 124320
aatcccagga aacctggagg agccagagac aaggcattag aactcctcgt cgtgacctgg 124380

-continued

```
tctgcattct ctgagtgtgc tgcttctgtt agctcgcttc cttggtctca ggttatagtt 124440
taaggcattg tggagcccta aaaagcctgt actctgtttt tacctgtttt aggacccttt 124500
cactttgggg atgtgttgat tttttttttt tttttttttt tttttttgag atagagtctc 124560
gctccattgc ccaggctaga gtgcagtggc acgatcttgg ccactgctgc ccctgcctcc 124620
tgggttcaag caattcttgt gctcccgcct cccaaatacc tgggattaca ggcacccgcc 124680
accacactcg gccaattttt gtatttttag tggagacagg gttttaccat gttggtcagg 124740
ctggtctcga actcctgacc tcaagtgatc tgcccacctt ggcctcccaa agtgctgtga 124800
ttataggcgt gagccaccac acccggcctg aaatttaaat cagaaataaa attttgatcc 124860
caacagtgat gccaggcagc ccagatctgg gggagagggt ggccttggcc agctgggcct 124920
ttctctgttt cccaagtctt gctgcctctc cctgctgggc tttgcagcct gtgcatgtct 124980
ctgtgccttt gaccttgttt atccaaagga gaggatagaa tgaagtcatg attcctggag 125040
ccctgagaag gatgctgtgg agaaatttgc cggtagaatc tagctgagtg tgttgctgag 125100
gtgccagcat tgtgtgtggg gaggctgacc gcttggcctg cctaggccca ggatgctcca 125160
tggccgggca cagaggccac ttggctgtca ggtgtcagga gcctgcagag ggcacacaga 125220
gcctggaccg cagggggtc ctgctttctc acctggcctc cttcagcatt tctgtccctc 125280
agtccttagc aagcccagga gctgttgagt ttggcaggtg ccgagtgctg ttcctgcctg 125340
tgtagctgtg gctcagtcct gtgggggccc cgctgtggcc cgagtgcagt gattcgaggc 125400
gctgagtgtt ccctgactcc ttctccagga gctgtgttca gactttcgca gctcttggct 125460
tggagctcct ggagggcttg gcattgccga ccaatgtgga ggtcgacagt gagagaggag 125520
gaatgctagc tttcttgacc agtccattaa ataagtggga tattggccag gcacggcggc 125580
tcacgcctta atcccagcac tttgggaggc tgaggcgggt ggatcacgag ctcaggagtt 125640
caagaccagc ctggccaaca tggtgaaacc ccctctatac taaaaataca aatattagct 125700
gggcgtggtg gcaggcgcct gtaatcctag ctacttggga ggctgaggca ggagaacagc 125760
ttgaaaccgg aaggtggagt ttgcagtgag ccaagattgc gccactgcac tccaacctgg 125820
gcaacaagag caaaactcta tctcaaaaaa aaaaaaaaaa gtaggatatc tgtttctgct 125880
tagaaaaatc agaattttct aaatgccagg tgttctgaat acgtaagtat gggagacgac 125940
tcagcctgtt tcatttttat gtaaaatctt cgcgtagcca tgtggcactg gaccgagatg 126000
aaagcaaaga catttctcct taactttgtt tctaggaatg ttccggagaa tcacagcagc 126060
tgccactagg ctgttccgca gtgatggctg tggcggcagt ttctacaccc tggacagctt 126120
gaacttgcgg gctcgttcca tgatcaccac ccacccggcc ctggtgctgc tctggtgtca 126180
gatactgctg cttgtcaacc acaccgacta ccgctggtgg gcagaagtgc agcagacccc 126240
gaagtaggtt cataatgccc cacagcccag ggcgccagcc cagcaccctg tcctgagact 126300
cccagtaacc tgagctttgg ccaccgttaa agcattttca ttttccattt tttgtgaggg 126360
cttgtgaaat ttctgctgca tattaatatt cctttcatgg acagcatatt attgggacaa 126420
acatgcggtc cagctaaagg cattcaaaat agcagttgct ttctaaatgc gattttcttt 126480
ggcaggttct ttgacaccat tgcatcttgt gggatatgct tgtcatgctc tgtggctcct 126540
actaagttct agtccttaaa ttggttccat agccagacat gttgcaatgt cttaacctca 126600
ttataaagta aatgtggttc tggttatcct tagataatga agtaacagtg tagcaaattt 126660
caaaacctct tggaaatgtt attttaccat tcaaaaaggc ttactaaggt tctcgttatg 126720
ggtggccctc tttttgcaaa aggttttcag gcttaagctc catttctagg tgctccaaca 126780
```

ctccattatt tgtatatgta tggaaataaa agctgtgacc acccccaacc ctggccccccg 126840
cccagctgaa tcctcagcac agtatttctg gaaggctcaa gatcccacgc tggggaaaag 126900
aagttctgga gacaaaagag ggcaggtgct gccgtgcctc tctgctcagt atggatactg 126960
gaccttgtgc tgccagggct cccagtaggg ccagttcatg gcactcagct ggaaagtcca 127020
ctgttgggag gcattcttaa ccatccactc tgtgccgtat gtagtggggt ctggtcattc 127080
tgttggagga gacagaccag tgacgacatt tgaaatgctt ggtggatgtc ttaggcctgt 127140
tacgatgact gagcactgtg gggcaggag acagaaagtc agtgtctcct agttctgtgc 127200
tgctttaacg tgcatagaaa tcagctgcgg attcagcaga tcactccttt tctgacagat 127260
gggcctgctt actctgatgt tatatcagaa agctctgaat ctgggaattg tgtcccctga 127320
attggagtaa cagaaatgct tagatgatga gtgtttaaaa gaaataaacc aaaggtaaat 127380
ttagtttgga attcagcaag cgtcttcatt cagccctctg agggcaaact acagcttttt 127440
gtaaatgtag gtaaattctg tgactgtttc gtgacccccct ctgatccagt tttcctttat 127500
aaccttctgt attgttcctt ctattatcct gaaataacat taatagatta ggctgggcgt 127560
ggtggctcat gcctataatc ccagcacctt gggaagccaa ggcgggcaga tcacctgagg 127620
ccaggacttc gagaccagcc tggccaacat gatgaaatgc tgtctctact gaaaataaca 127680
aaaattagcc gagcatggtg acaggtgcct gtagtccctg ctactcagaa ggctgaggcg 127740
ggagaatcgc ttgaacctag gaggaaaagg ttgcagtgag ctgagatcgc gccactgcac 127800
tctagcctgg gtgacagagt gagactccat ctcaaaaaaa aaaaaaaaaa aaaaaaaatta 127860
atggatcaat ggatttttaa cctaataatt aaatttcaaa aaatatcgtt ctttaatggt 127920
aatgtaaagg taaaattaag ataatatgta acaagcatgt gagtgtctaa ggtgtccccg 127980
tggtggaagg aaaaaataaa tccccataag tgtccaagat gcccatagag agcagagctg 128040
ttctggttta aacccctgct cttagcactg tgtttttcca gctgtgggtg gtgggggatg 128100
agtatctttt tatttccatg agatgagaaa aatgaattac tagaagtgtg aaatacaaaa 128160
cacagctgct cttttttttag ccatagactc agcagccata aaattgctgt atccagttgc 128220
agaaattcct gctgcttact cttgaccctc tctcggtttg tgtgcatctc ctctcaggct 128280
ggctcccaga tgggagctgg ctccaggcga cactgggtgc tctgctccag gaggtcctta 128340
tgtgggtcct gccctagcct agcccctctc ttatggactc tgtcactgtg ggtttatgat 128400
tcactctcaa tctgtcttac ctcttggtga actgttagag tcctgcctat actttggcgc 128460
ttgtgggtgt gttgtggtac acatgatgtg ttggtcactt cccagctcat cttgttctga 128520
gtcaccctag atttgggaca ttcattcgcc accagtaccg ggcggtgtat ggcctgagat 128580
ttgggggggc ttgtgctgct acaaattggg gctgaatttg agttgacagt ggaccttctt 128640
tatgtctact gctcatattt gaattgcaaa tactgcctct tctctttcag aggctcatta 128700
ccctatagct gtattattgc aaagtgcaca attacagctt gagtgtaagt cacactgcgc 128760
tggcaggacg gcccactgag aaagggcacg tttcctgttc gttagttttc acattgacac 128820
ataatttaca atacagtaaa atgtactttt ctatcaactg tagtcagtaa cagccccccct 128880
cccccaacca catcaagata tagaggagtg ctgtcacttc aaacagttcc ctcttcctct 128940
gccacatcct gcccctcccc aggtctaacc accaatccgt gctctgtccc tctgttcagc 129000
ccattgcaga aggccataga aatagaatct ataggctagg tgtggtggct catgcctgta 129060
atcccagtat tttgagaggc tgaagtggga ggatgacttg aggctgggag ttcaagacta 129120

-continued

```
gcctgggctg cctagcaaga ccccatctcc agaaaaaaaa aatttaaaaa ttacaatcac 129180
gtccctgtag ttcagctgct tgggaggctg aggcaggagg atcacttgag ctcaggagtt 129240
agaggttaca gtgagctatg atcgtgccac tgtgctccag cctaggtgac acagcaagac 129300
gttgtctctg gggaaaaaag aaagaaacgg aaccacgcgg tgtgcagcct tctgagtctg 129360
gccccttcg gtgagcagtg tctaaagttc tgtcgcgtgt tgcccacgcg tcggtggctc 129420
gctccttgca actgctgagc attgtatggc taggctgtag tttgttttca cttcaccagt 129480
tgggaaacag agaaaaggca ctttttaaaa agtttaaatc tgtagaattt tggtttttac 129540
cagttctctt ctaaatcctg agggattaca ggaaaagttg ttgtatttca gaatattctt 129600
agcttgatgt gacctctgtc cccgttaagg ccctttgccg caatgggaag gacgtcgctc 129660
ggtcagaccc tgaaggtcag aggggcagtt tgggagtgtg tcaacatttt aactgtatgg 129720
actagagcca agagtctcaa ggtttataat tcccacgtat tcaaaaagaa aaaaacaata 129780
aagtgagaag tcagtgtaga gtgaaataac ctgtgttagt ggggaagaag tgtttttaaa 129840
caggatttcc ataacgtata acatcaacat gtttagagtg gtgatgtttc attgggaaac 129900
gaacagtaaa acatgaaagc agggaggttt tcattctggc agttggcaac tttcacggca 129960
gatggagaat ttcaaaagca attgctcaat tatcaaacat agccagtgtg agttctgaaa 130020
taaaggtgct gattgaatgt gcagctttat ggtggatttt gctattcagg caagcatttt 130080
aattttctgc ctgttaaatt ctgttttctt tagtttttca tatgtggttt attgtagctt 130140
aggaatagat aactgagagt atatattaca catacaacat tctgatatgg caatatttaa 130200
aacaacttgt ctgttttaga actagaatta aacataatca tcttcagtat tttgcaaata 130260
agctcactgc catccagaaa cattgtcaat gcatctgttg ctccttctag aagacacagt 130320
ctgtccagca caaagttact tagtccccag atgtctggag aagaggagga ttctgacttg 130380
gcagccaaac ttggaatgtg caatagagaa atagtacgaa gaggggctct cattctcttc 130440
tgtgattatg tcgtaagttt gaaatgcctg taaacggggt tgagggaggt ggggaccagg 130500
agaacatcct gtgtagatga cacttgcatg gaccctctgg aacccagacc gcccggtgtc 130560
ctgccaagct ccatcgaaac taaatctaga atgaatgttt acttctgctg tgacatataa 130620
ttggagacca ggcctggcct tccagtcact ggattctaag ttggactgtg agagtttttg 130680
cagctgactc atttatcaaa tgcccggcta ttggctcacg cctacatgat gctgggtatg 130740
tttgttaatt tgagggaagc aatggaataa taataactaa tgatttaaaa aacaaagtaa 130800
gtgcattgac tgtagtgggg ttctgatttt aaattttttt aaaaattaat accaggagca 130860
gtggcttatg cctaaattcc agcaactcga gaggctgagg taggaagatc acttgagccc 130920
aggagtttga gacaagcctg ggctatggtg tgagacaccc atctctaaaa aaataaaaaa 130980
taaaaaatta tccaagtgtg gtggctcgtg cctgtaatca cagctctttg agaagctgag 131040
ggcggaggat ggcttgagcc tgggagttcg agaccagcct ggcaacacag agaaaccctg 131100
cctctaccaa aaaaagaaag agaggaagaa agaaaaatta gcctggcgtg gtggtgcatg 131160
cctgtggtcc cagccacctg agagactgag aagggaggat tgcttgagcc cagaagtttg 131220
aggctgcagt gagctgtgac tgtgtcactg cactccggcc tgggtgacaa ggcgagaccc 131280
ctgctctaaa ataatttttt taagttaatt tgtagaaaag gtgttagatg ttctttgtca 131340
cattttatga tggattcctg tttaaatgcc gttctcttta aagaaaaaaa aataacttgt 131400
gggagttttt aaccataaaa ctagcatcac atatttacca tggagaattt acaaaaaaac 131460
aaataaacgg aggaaaataa aacctcctgt aatcatacta ctcagagata acttgctgtt 131520
```

agattttggt ctagatttaa tactttttct atatttatat taaaaatatt taaaacatat 131580
gcatttcttt gtcacaaaca tggtatctta tagatactac tgtcacatag caaaacagtg 131640
ttaaatattc tgaatcagaa aaggaagccg actctccaac tgaaagaggt gttatcctag 131700
agactttttc tggtgatgac aatttattaa tagtcacttt ttgctttact ttctctattg 131760
aagtagtttt tctattttgt tctactttta aggataatat aatttataat gctgtttttc 131820
acagaaatat aagaaaaaag atactaattt tataagttaa taaagtttga tcatcccaaa 131880
tccaaaaatc tgaaatccaa aatgctccaa attctgaagc tttttgagtg ctgacattat 131940
gttcaaagga aatgttcatt ggaaggtttc agattttcgg atttagggag ctcaacaaat 132000
aagtataatg cacatatttc aaaacctgaa aaaaatccta aattcagaat acttctgatc 132060
ccaaacattt cagataaggg ttattcaacc tgtactgtca gatgatccca aatgaaaaat 132120
attaatcgtt aaccaaatat caaggaattg atcacatttt acagtttctg cctaggatta 132180
tgaatcaaga tgaaaaggct ctgcatgttt aaaaatatat atttttattt tcttataaat 132240
cttaaatatc tacacttaag atttatttga tatgtgggat ccattcatat tttggattca 132300
acagttctgt caaaactgtg gcagtgatag gggattcttt ttttcccact gaactatcac 132360
aaaattggaa aaagagtaat tggagaaccc cactggctta gccggcccga agcccgggag 132420
agggcaggca gtgctgtgga tggggtcatc ccagcgcaac gctgcccctg ctacctgcgg 132480
atctcgctga ggcctgcctt tgtcctttga cccttggcca tttgttagtg tctctgagag 132540
ctggactgct gtaccctact tccccagggg gcctaacttc acacagcctc tgccgcagtg 132600
cgtggttgga ggtgacggcc ttggtaaatc gagtttccta cctcctcaat tatttgtgct 132660
catacactgt atatttttag tgaggtttat atttgggatg tgttttctcc ttcttaccct 132720
ttctggcctt tctatggcat taatacctgg tctcttcttg tgtacttgaa aatgaatctc 132780
tcatcatatt tttccttagt gtcagaacct ccatgactcc gagcacttaa cgtggctcat 132840
tgtaaatcac attcaagatc tgatcagcct ttcccacgag cctccagtac aggacttcat 132900
cagtgccgtt catcggaact ctgctgccag cggcctgttc atccaggcaa ttcagtctcg 132960
ttgtgaaaac ctttcaactg tacgtcttca tcctgccgac tattgccagt tgcagttttc 133020
cctgccttaa aaatggagta ttgaaatttt taactttaat ttctgatttg caaaatagtc 133080
atcttttgtt cttttccttc ttgctgttag ccaaccatgc tgaagaaaac tcttcagtgc 133140
ttggagggga tccatctcag ccagtcggga gctgtgctca cgctgtatgt ggacaggctt 133200
ctgtgcaccc ctttccgtgt gctggctcgc atggtcgaca tccttgcttg tcgccgggta 133260
gaaatgcttc tggctgcaaa tttacaggta ttgggaagag aaaccctgat attgatttat 133320
attgaaaatt tagcaggcca agcaaaacag gtggctggct ttttcctccg taagtatggt 133380
cttgacatgg tcaccgatag aaacatggaa acatctgcaa acttgccgtt actcgtgtgt 133440
ccgatctgac tgtttcttgt attttttct agtctgccct tactaggatg aactgtacac 133500
atcagttcat cctttttaaa tgagcatgag gttattttgg gttgttaggt gttacaaaca 133560
cactaatgtg tttttgtcta ttagagcagc atggcccagt tgccaatgga agaactcaac 133620
agaatccagg aataccttca gagcagcggg ctcgctcaga ggtaatgctg gaaacacagg 133680
tcgtccttgt gttaggacaa cccaggatat aaaggatata gatttgtacg ggaataaatt 133740
cacaggacaa gaaatcgatg tgccttatag gtgggtttac tgcagaagtg ccataataga 133800
accttcctac ttttaaaaca accagatctc actttctaaa gagtaaagga tgaccggcag 133860

-continued

```
gatcacgtct gtgacgtgag tggaggcagt ttgcactcct ggtggctgtt tgagaggtag 133920
catttagaat gcctgtattc actgtcctgt gatgagtggg aaaataggtt atcaggttta 133980
tcttagcaaa atcaaagcat gtcatctaat tgctaaacaa gagttggcaa atctgagaga 134040
cattactcaa tccttggcat gcaggactta catctgcatc ctgttgccat tttatgtctt 134100
caaagcattt aatcatttag ttgtgtttgc aaagtctttg agaagccttt gtcagaaatc 134160
cctacatctc ctatgtgagt gtatttccat gactgcagaa taagttaaac ttttaccttt 134220
ttccttccct tgcggggcgg ggtgggggc agggattgtg tgtgtgagag ggagagagag 134280
acagcagaga aggagaatat aattatcatg ctgtgtactt tgagctgaaa ctgcaaaaaa 134340
ggaaaaacac acaaaaatta ttatgctttt cagtctttag agtaccttgt ctattatgct 134400
tttcagtctt tagagtacct tgttgatggt gtttttaaat gggattgggc acaattaggt 134460
ggacagtttg ggatgatttt tcagtctgta gggccaagct cttttgtaat ttgcattatg 134520
aagttgtcac tctcatagca gatggcggga gataaactat tattactttt tgaccctaga 134580
cttagtcttc agtccagatg agggagatta aaagattata aatatcttgt gccagatgag 134640
gtgattttat tttgaaatga ccatgaattc ctatcagttg tcttactggg atatttgata 134700
gtggaatttg tgcatttgag tcttagatga tctgttttac atttattaag aaagccttta 134760
ttagctttta tactgtgtat tgcctgttgc agtgtttgag tataaatgaa atttctggaa 134820
aatattaatg gagtacaaac tgtgatactt aaaagtaaac tagggcctgc atttgtatca 134880
tgacctgttt gagtattgat gagaagatag ctgtgaagaa aaaggtttaa acaagtgtat 134940
tttcctttaa gaagccacta atagtgcatc tccttagagt gtatatttct agaatcctag 135000
tgtgcagagt ttagactaag actaaaaaaa aaaaaaaaca aattatactg taatttcatt 135060
tttatttgta ttttagacac caaaggctct attccctgct ggacaggttt cgtctctcca 135120
ccatgcaaga ctcacttagt ccctctcctc cagtctcttc ccacccgctg gacggggatg 135180
ggcacgtgtc actggaaaca gtgagtccgg acaaagtaag tgtccagcgt gtctgcatgg 135240
gaggcacagg gcgctgagtg cctctgtcac ctgtggcaga tacagagagt gcagaggagg 135300
tgccgtggac ccaaggagtt ctggcgctcg gctcggctca gtgaagctgt ggttagagac 135360
gtggggggcc atcaaggtct gagggagcca agcagtgctg atgtgggacc cttttggtag 135420
gagtgtgggg tgagtagtta gtgggtgaat caaggaatag tcggccgtgg cctgcaggcc 135480
cctgactgca caggccttca agcacatgtc aatgccgtta gcctccctcc atctcctcat 135540
accttctggc cacctgtgag ttgcactgcc actgccagcc attctggtat gttgtcagca 135600
cctccactgc tcatacctca tggttaggga ccacctggag ccttggtaga gccttggtag 135660
agccttggta ctctactttc ctggacaaag ttcagcttat gaatatgaat ttagatttca 135720
aaaaccagca gcccaagtat aagaaagcga aggttcagtc ctgccttctt aggctctatt 135780
cgctaagcac ctgccctgcc ctggttgctg gggagagatg agtaaagcag acaacccagg 135840
agaggatggc aaaggggccg ctaaccctta gtggtttagc tatatttgga aggcctattg 135900
gaagttcacc aggtgaaggg ggaggctgtg agggtgccca ggcaggtaac agaagtccaa 135960
aggggaaaac ctgtggtgtg gtgagccgta tagccacagc ctgccggccg gcagccctct 136020
cagcctagtg cggtgttccc aagcactggc ctaggcctgt agctccaggg atgtgaagtc 136080
cccttgaacg ccgcccatca tgttcccctt atccattttt ttcttcccag gactggtacg 136140
ttcatcttgt caaatcccag tgttggacca ggtcagattc tgcactgctg gaaggtgcag 136200
agctggtgaa tcggattcct gctgaagata tgaatgcctt catgatgaac tcggtacggg 136260
```

-continued

```
gggagcagtg gaggcaagga atcctcagct tttcttgtga cttccaagtg ggatttgtct 136320
catcatcatg tgacccactt gttgacaaca catgttgggg actccagtct gggcagggac 136380
gggatgtcgg agagactcca ctctgaatgg ggccgggaag tggggaggac tccatttcag 136440
atggggtcgg gacatggggg ttatgctgat cgagacagaa aagcacattg tttcagccac 136500
attagaatcc acggaggtgt tgttttgaaa tccagctggc cccaaggctg ggtgtatggt 136560
ttgggatgag aactatctgg cctccactgg aggaacaaac acaggatgtt atcatctaag 136620
ctccatggcc aagacagaat ggaagtcaag gttgcgtatt tgccgtagac ttcaacacag 136680
tgtcgtaatg cgtgacgtca ataacttgtt tctagtgtct tggaagttga tctttagtcg 136740
taaaagagac ccttggatgc agcgagattt cctctactca cacctctgtt agatgtagtg 136800
aggttcttca ccccccaacc ccagatgtca gagggcaccc tgcgcagagc taggaggcca 136860
tgcaaagcct tggtgtccct gtccctcacc cgtgggcagg tcctgtgagc agtggggggg 136920
ccacctcttg ggtatggtgc agccatggcc caagcagggc ttcttctcag acctactagg 136980
acgggagaaa cctcctggtg ctttagccct gcgttgatat gcagcaaatg ggagggaagt 137040
gggcacctgg gaggacaaat gcctgtagag gccgggagtg acggcaggtg ttcatgaaaa 137100
gagaccttgt ggggagggca acacaacagt gtgttctgat gtactgaaga gctcaactga 137160
aaacaacagg agaattagcc caaaatccat ttactaaaat tgtttatctt tttttttttt 137220
tttgagacaa agtctcgctg ttgtccccca ggctggagtg caatggcgct atcttggctc 137280
actgcaacct ccgcctcctg ggttcatacg attctcctgc ctcagcctcc caaatagctg 137340
gtattaacag gcatgcacca ccacgcccgg ctaatttttg tatttttagt agagacggga 137400
tttcaccatg ttggccaggc tggtctcaaa ctcctgacct caggtgatcc gcccacctcg 137460
gcctcccaaa gtgctgggat tataggcctg agccaccacg cccggcctaa aattgtttat 137520
cttaagattc atgcagtgaa agctaactta ctgagtgata aatttgctta gtgatctgtt 137580
tattaggttt tccaaatttg ctaattgggc tttgaacagc tgtaaaagtt ctgactgtaa 137640
aagaaagctt caacttttgg cattcatgat gcttttctga gtattaaact aagatagatg 137700
ttttacctga aggatcggcc accaatcttt aaatggctaa acaaaagggt tgctaaaaca 137760
taatccaaat tgacataaga aataccattt ttccaaccaa aattttggca ttcatatggc 137820
tacttttacg tatttcagct gcatttgaac atctttttca aactttaggg tggttggtgt 137880
atcactgagg tcttggatga cactttagct ttgattttgt ttttatgaat taaaattgtc 137940
ataccaaaat ttttatttca agcaaatcca agagcataaa aaattaaaat attacttaaa 138000
atactaagag agaacagata tatattttac taagcatatg ttgaatgaaa ttgttcaaat 138060
atttataaca ggcatagagt agaattttct taaaaatatt tttgatggta taccaatttg 138120
tattttctca gaaacatttg ccttattctt ttttctgttg tgtttttctt acctgattga 138180
aagctcataa tctgttgtta ttgtttgtta acctttaatg ctctgatttc aggagttcaa 138240
cctaagcctg ctagctccat gcttaagcct agggatgagt gaaatttctg gtggccagaa 138300
gagtgccctt tttgaagcag cccgtgaggt gactctggcc cgtgtgagcg gcaccgtgca 138360
gcagctccct gctgtccatc atgtcttcca gcccgagctg cctgcagagc cggcggccta 138420
ctggagcaag ttgaatgatc tgtttggtaa ttaaaattaa aatttatctt atttttaaaa 138480
agcattccag ggccagtata gtactttgca ccaagtaaat gtacaataaa ggcagtggat 138540
ctaatacatt gaaagcgttt acagaggtag ctaaagagca gcacgggtgt cctcggctca 138600
```

gaatttcttc ctgtgtgttt gccactttgc cattcattga catggtcatg gacatagggc 138660
tctaagccct tgaggaaggc tgggccagac ctcaggggag atgcagcccc aaaccacgtg 138720
cagtcctgtg gacggatgtg tagatgtgcc actgaggaac aatgtcttga gctttcatca 138780
gattctcaga gaattgcttg actgcctttc gaagttgatg catctgtgct cacgtttgca 138840
cccacccacg aggtccttct gtttcagggg atgctgcact gtatcagtcc ctgcccactc 138900
tggcccgggc cctggcacag tacctggtgg tggtctccaa actgcccagt catttgcacc 138960
ttcctcctga gaaagagaag gacattgtga aattcgtggt ggcaaccctt gaggtaagag 139020
gcagctcggg agctcagtgt tgctgtgggg agggggcatg gggctgacac tgaagagggt 139080
aaagcagttt tatttgaaaa gcaagatctc tgaccagtcc agtcactttt ccatctcagc 139140
ctggcagtaa gtcttgtcac cgtcaagtta ttgtagccat ccttcaccct cacctcgcca 139200
ctcctcatgg tggcctgtga ggtcagccag gtcccccttct catctgcacc taccatgtta 139260
ggtggatcct aattttagag acatgaaaaa taatcatctg gaagtacttt atgtcttaag 139320
ttggcctgga catgtcagcc aaggaatact tacttggttt gtgttagtgc ttgtaattcg 139380
cccccagaat gtgtacacgt tctggatgca ttaaagtctg gcctgtatcc ttaaagggcc 139440
atcgctgtgc tgcctgccct cagcaaggac acactttgca gacccacaga ggctccgcct 139500
ccacctcaca ccaaagaaag ggaggagtcc aaagggcatc agtgccatta ctcacaaaat 139560
gataaataca cccttattct gaaccacgtg gagtcatatg gtttgtgatc cctgtccttc 139620
aggtttcagc ttagtgggga agtgggaaag tcagcgtgtg atcacagcac agggtgattg 139680
ctgctgatta tattatgtgc ctgctgtatg caggatgaaa tactttatat gcgtcatctt 139740
atttgactct cacaaccccc tgtgagatag gctctgttac tcccatttga caggtgagga 139800
aagcaaggct tagagaattt cagtgacttg cccaggtcct ctgagctagg aagtagccat 139860
tctggcattt gaacccaagg cctgctatcc ctagaaccca cgctctcaaa ttcaacctat 139920
gacagaggca agccctggtg ctgtgggagc cccaaggaag agcctctggc ctggtggcca 139980
cgtagcccag gagagatttc tacaggagcc cacagcgctg aaggagagag aggcagcaga 140040
gtaagggggc tttgtggcag agaggggact ggcactttgg ggaataggtg ggtcaggact 140100
gaatgtaatg gagccatgtc agagctgtcc ttctggaagg gcaagggcac ctggacgcgc 140160
tgcccctcag tgctttggac ggttccacaa ctgtgattca cacggcttcc ccaaacgaag 140220
gtacacgagt gggcattctg tgactcggta cttccctta ggccctgtcc tggcatttga 140280
tccatgagca gatcccgctg agtctggatc tccaggcagg gctggactgc tgctgcctgg 140340
ccctgcagct gcctggcctc tggagcgtgg tctcctccac agagtttgtg acccacgcct 140400
gctccctcat ctactgtgtg cacttcatcc tggaggccgg tgagtccccg tccatgaacg 140460
gtgggttcct atcatagttc ctgtctgctt caccatgttt ttattttgtg ctgcctgttt 140520
gccaggtact aagctaggaa ttggggatgg agaggtagat aaaatatgca tcaggaaggg 140580
ctgggcccca tctcttactc tccaatatat tggagtctac actggaattt aactggaatt 140640
tgctttttta gtcattttat ttagattttg aagtttcagc tttcatcaaa aatacctcta 140700
aactttatgt ctctgtgatc tttggtctta gctgttttat gtatttagtc ttatatgatc 140760
ataagattaa taacattaca ttcagaagat tatttgtttt ctgtcagagt taaaatgttt 140820
gtttttatac tgcattgtaa tattaacgta ctgtaaaata aaagtggctt gttcttttca 140880
aggaacagta tcctcaacaa gggtcattag ccacaatttt taaaaaattg gacgtcatag 140940
tttacatgtt agagggcgtt ttgaagcttt gtatttttaa attaaatgtt atagagtgat 141000

-continued gttttcatgt ttcataattg ttttcatctg tgcatttgta gccaacttga aaacaaagat 141060
ccagggatta ctacttaaaa gccagacttc ttggaggtta tagtgatgat tttgatagta 141120
tcttgagccg tctcataata acctcagggt gagagatggc caacaggaga cagtcgaggg 141180
acttagaaat ctgaatgaaa tctgaagttc aaatcttcag acatatacca ctaaccaaga 141240
gattggtacc tcagtctagt attgtctgtt tgtctaaaat tggttctaag gaatctaggc 141300
tagtctgtct atccctttca acttttgtga ggctgcacaa atgtaaaatg ttgaataaaa 141360
agcactgatg gaagtgtgta gaaattcttc tctttgttct gttgtaattt tagttgcagt 141420
gcagcctgga gagcagcttc ttagtccaga aagaaggaca aataccccaa aagccatcag 141480
cgaggaggag gaggaagtag atccaaacac acagagtaag tctcaggacc catttttttc 141540
ttacatgttg ttcctccagg acttaaaaat cattcacaga gacgtgcacc gcggtgagtg 141600
tggactcctg gaagcgcacc gtagctccgc tgtgtcctgc tgctcctccc tagctgtcag 141660
ggaggctgta gtccattgct ttgccagctc ttttgtttcc gagtgaacac cttatccgta 141720
cacatgcggc tgtctctgac cctacagacc agctgggatg ccactggggg agcgctccct 141780
tccccccgca cttcccacac tctgcagtta ttctgagatc cttgagggca gggaacaggt 141840
ttgtcttctt tgtgttctca gaaattaatg ctcggcctct ggtcagcaag caacaacctt 141900
ttgttgagtg ataatgaata aataaatgtt tcccacatga gtattcagta acctcagtgt 141960
caggttcagc catctgtttt ggtggatatt taaaagaaaa ttccgctttt cctacagaaa 142020
aaaaaaaaaa tccaaatccc agtgatttaa gccagttata gacttagaca tatactacgg 142080
cttttcatgc actttcctcc caattctaga gtaggtattt tactaggaaa atggtggcag 142140
tgcctgttgg gaggaagatt ctttggccaa gtgtcttttg ttcttgccag ggcccctagg 142200
ctgctggggt gcttcagctt ctttagccca gtgtctggtg gggaatggcc cctgttgcct 142260
gtcccacaga ggtgggggtg cctcacctgg agcctgtcca cacattttac acagcacgct 142320
tacctggagc atcaggcatc ttttccatgc tctgtggctc aggaaacacg ccttttcaat 142380
catgagtgca ccagtgcttt tgggcttttt ctccccgctt ttgtgcaatc ctggttgtgg 142440
atggagtttt cctgtcttta gtcttctgca tagtactttt ctcttctggt tcccggttca 142500
aggttttgta attagagaat gacccagaag caatggcatt ttaatgcaca gccaaggact 142560
tctctgaatt tgtatctcaa acctctgtgg gtccttcagg cttcagtttg tgatttcatg 142620
atttcttgtt gctacctaag gaatatgaaa acacccacct ccctactctg catcttccag 142680
ccgagtggca cctcaggctg tggatcctgt gcttctgtgg tgaggataag aatagtgcca 142740
accgtgtgga ttgaaatcaa tcagttaatc cctccatgta aagcacctgg aacggatgac 142800
agtcttgtta tgaatactca acaaatgcta tcatgatttt tagttagatt tccattgctt 142860
taaaacagtt gagacatctt ggcggtttga gttagagcaa cgggccctga agtgggttct 142920
gtttgggtga agatgattat gcttattccc catggccctc tttaggcaag agtgggaagc 142980
tttctttgtt tttttaatca cctcgatagg acgttacttc ttaaaggtca tccaataaat 143040
attaataggc cgggcgcggt ggctcacgcc tgtaatccca gcactttggg aggccgaggc 143100
gggcggatca cgaggtcagg agatcgagac catcccagct aaaacggtga aaccccgtct 143160
ctactaaaaa tacaaaaaat tagccgggcg tagtggcggg cgcctgtagt cccagctact 143220
tgggaggctg aggcaggaga atggcgtgaa cccgggaggc ggagcttgca gtgagccgag 143280
atcccgccac tgcactccag cctgggcgac agagcaagac tccgtctcaa aaaaaaaaaa 143340

-continued aaatattaat aaagccaact cgttagcgtg gggcttaatt gcttaagtcc aatgagaagt 143400
ccttctctat cctaggaagt tgcccaaact gtagaatctc gtggcctgtg ggtaatagcc 143460
acgtaataca cactcactgc ctcaacaaat catattttag taggtatgat attctagact 143520
caagacacca ttctgtggat cttcccaagg gtgtgaagtg tccacagcgt ctgccttggg 143580
agtttccatg cccaccagaa ccatgcccca agcccctcaa gcactctgac ctaggaaagc 143640
cagtgaagca aggatgacaa catggccctt tgatactagc tgagggacag acacaggtcc 143700
tgggagacca gagaaagacg aggggcagag gaggtgtcct aaaggaagtc tgaggctgag 143760
gagccacagg atggcttcca gctgtcacag gctgctgctg gccttatcac agagagtggg 143820
ccagagggct gggaaccaag gccagagctc aggttcagga ccattccagc aatcccagca 143880
gaaaatgggg agaattgtat ggtataggcg gatatgaagg tagaatctgc aggccttcag 143940
tggccaactc agagtctaag tggattccac agttacagct tgagcagctg gttgtaggtc 144000
atgctttcta cactgggcat ataggatgtg ttttttaaaa agtcctctct taaccgttgc 144060
ttgtttagat cctaagtata tcactgcagc ctgtgagatg gtggcagaaa tggtggagtc 144120
tctgcagtcg gtgttggcct tgggtcataa aaggaatagc ggcgtgccgg cgtttctcac 144180
gccattgcta aggaacatca tcatcagcct ggcccgcctg ccccttgtca acagctacac 144240
acgtgtgccc ccactggtga gtctgctcgt tccttgcaga agaccaagta cggtgaaagg 144300
caccggtagg ccctgggctg ggcacacgtg agagggcggg acagaatccc cgcagcccag 144360
aggctgcctg ctgtggttct ggtgcccact gtggttctgg tgccaggctg ctttcctcag 144420
gcaccacgtg tggaggtcgc tagtagaaat actgggtttt ctaaaatgaa ctgaggccct 144480
acatccctaa gagattagtg ttagacctga ttctagagca actagaccac tttgcttaat 144540
agcagaccag aaaccacacc ccctcgagtg agtgagattt tcctttggag ataattcatg 144600
tttttctaca cagttttgca gttgtcttca gaattggttt aaagtaggtg ttattgccag 144660
gcgcagtagc tcatgcctgt aatcccagca ctttgggaag ccaaggtggg cggatcactt 144720
gaggtcagga tttcgagacc agcctggcca acatggtgaa accccatctc tactaaaaat 144780
ataaaaatta gccaggtgtg gtggtgtacg cctgtaatcc cagctactca ggagactgag 144840
acaggagaat cgcttgaacc caggaggcga aggttgcagt aagccgagat cgcgccactg 144900
cactctagcc tgggcaacag agcaagactc cgtctcaaaa aaaaaaaagg taggtgttat 144960
tgatcagaac ccttgtttca gataacatga ggagcttagc ttgaggagag tgagggttga 145020
tggaggggga ctgacttctg cccagtgaaa tggcatcatc tcccaccagc ccgctgaaat 145080
aagatgatgg ggcctgttcc ttagggcctg cagcatcctc aggcaggaaa gaaaggccga 145140
cctggcaggg tgtgagccag caggtgtagg tcagggagaa tggagccagg tcccagggaa 145200
gaggcttgtg gctgcctgag aagggtgcgt gcctgcctgt gtgtgtgtgt gcacgtgtgt 145260
gtatgtatgc tggagagtct agggaggctt gctccaagga cgcagtattg tttgatcctg 145320
agagataagg attctgccgc agggaatgaa ggtattccag atggcgggct tattccgaag 145380
aagaggccag tgcctggcgg tgctggaagc agttgcagaa cagggagttg taggctttcc 145440
tgggaagaga gcagcagggg tgctggagaa gcaggccaca cttgctgcat ggggttgctc 145500
tcggccccac tcttggtgca cagcgagtca ctgtgggttc attagcatct ggttatgaga 145560
cagtaactgc tcctttggag gggctcgtgg agaccatgca ggagggcacg gtcttgaggt 145620
catgccgtcc agagcacacc tgaggatagg ccaggacggg ctgcacgctg taggtaaaat 145680
tcctccagca agctcttcac tggcattgag gagttccctg agtgcggtca tctggaaggc 145740

```
agctgtaaca ggcactgcag tctctccctg ggtgggtacc agagaggagc ataggggagc 145800
ataaccgatt taaagagagg gctttcctgt ggtgaggtaa gagattagct ggtcattatc 145860
atagagcccc ctctgccttt gtgcagatgg gctgtgggaa tcctggggtt ccgttgggtc 145920
ctttgtcacc tcactgaagg catgtaagct gagctggcca gaccgtgagc tgatcctgcc 145980
acttgaacag catcaagcct gcctctggat tcttctgtgc atggcacttg tctgagcacc 146040
tcacgcacag agaactggac ttcagagttt acagaaataa gctgtatggt tcattttcat 146100
gcctgcttgc caataaacat atctgagctg aacctcattg aacgcctgcc tttattctag 146160
cacagcacct gctgtttgtg ggcgaggggt gctgtctcta actcctgcct gcttctccca 146220
gcactccctg agtggggtgt gccagcagcc tcaggatgag gacaggaagt gggagggcag 146280
agcagatttg ggagggccac ttgatgggga aggaagtccc aggaagcagt tggagctgtt 146340
ttctggggga gaaggtgcca gctctgggac agtgttgggg tagtgaggag ggagcccagt 146400
ggagagaagt cgggcttcct gcttcctcac agtatgtctg tcctgactca actcggatga 146460
tgtcacttcc ttttcatctt ctcaggtgtg gaagcttgga tggtcaccca aaccgggagg 146520
ggattttggc acagcattcc ctgagatccc cgtggagttc ctccaggaaa aggaagtctt 146580
taaggagttc atctaccgca tcaacacact aggtactctt ggggcctctc cttcaggtca 146640
ccattgtcgg acatctaccg ggaggaaatc cagagccccc agtactggga tcttctcatt 146700
tgactccaga aaagatttaa gcatgataat aatacaaacc tatgtgaata cattttgcag 146760
tgttggcaaa actcctttta tactgagaaa atagatccca gttcctgtgt tttgtggctt 146820
gaatcccagc tttgtgtatt ccgggcttgt ttgaagtcag gaaaggttca tgtgtagtgg 146880
acaacgtgag accaaattct gccttagatt ttgcatttag gctaaacagt ggcagcactt 146940
gtctcagaat gttttcttgt gttcaccagt ctgatcctgt tgtgtctcag tggtccattt 147000
tctcatatgg gaacaagcag acgggagcag atggagtcag gtttcttggc actcgccttc 147060
cccagagcct agaggcagca tggggagaaa gcaggcttgg ggctcagaca gtcctggtct 147120
gcttccagcc ctcctacctg agcagcgcag ggcaagtccg tctaacctct agagaccctc 147180
agttttgtca tatgtaaaat gggggtcgtg tctatttcat agaattgttg cagatttaga 147240
aattacattt ctaaacaaat gttacccctt atttctaaat aagtgtctaa atgaataagt 147300
caccactttt gcccctattt gatggcaaga ggtgtgatct tgtggtggga ctgtaatcag 147360
tcagttctca gtgactgtgc cctgctgtgg tgtttcctgg aatgttcctg tcttgtccta 147420
gaaagtctgg caggggcacc ctgactccac tgtccagtcc tctccccagt ccctcgggct 147480
tctgcagatt tgaggcttgt ttggatccca gaaggttgtg gcaggagaca ccttgcctct 147540
actttcccct ttataattca atgtccaaag agagccctga gcaggtacct cacgccagct 147600
gcctcacgga gctcctcctc ttcctggctg tgaggatcgg tatcagtggc ctcctgctct 147660
ctcccccttg cctaacacga gcacctttgc ttacttgggt gcccttgctc ttgaactgcc 147720
catcggacgt gcgtgaccca agactgtgcc gcagtccttg ccttgtctgt gctcattttc 147780
tttgttcatt tttttccctg taacgtaaat tgttatattt gtctgtatct gtgtctgaat 147840
cagtcctgca cgctctcctt ctctctgtct cttgttcttt ctttaccccg tttatcacgg 147900
ggaccccgat gtccattgct ctagttctcc tgtcctaagc accccatccc gtctctctgg 147960
ccttaccaca agtggcgtgg ctgcctcaga catcatgatg gggacatgaa gcacagctgt 148020
cagaaacaac tgttcgttag atacactcga atgcagctca tcaataggga tggagggtct 148080
```

-continued

```
gtcggatgta ttttcactga atccccgttc ctaccttgat acactctttt taatctattc 148140
ttctagacag gtcagaggaa ccattacttt gacttttaaa tttttagcag ctttattgag 148200
gtagaattca catactacag atttcaccca ctctaagcgg acagcttggt ggccattagt 148260
tttatccaca gagttgtgca gccagctgca cagtctcagg gctggactcc agggaagatt 148320
ttagcccatt tagtgagtgg ggcagaagtg gccctggccc tgcacgaggt tgcctgcatg 148380
ggcgtccctg ccctgtccct gtgtctgctc cactgggggt tgaccaggct gccagggccg 148440
acttgggcct gtgccacctg cctctcatgt gtctcggaca gtgcagccga tgtctatact 148500
tcggtttcct caatgatgaa atggagggga tagtgttccc cgcatcatag aactgtgtga 148560
ggtttaaggg actcactgcc cttggcgtgg agccttctcc aggggccgtg ctgtgtcggc 148620
gtagctgtca gctctccgtt acaggcttga gaagggttga cactctctca tgtaacattt 148680
atatttctag gctggaccag tcgtactcag tttgaagaaa cttgggccac cctccttggt 148740
gtcctggtga cgcagcccct cgtgatggag caggaggaga gcccaccaga agtaaggcca 148800
caccctgtgc tggttggcac atgggcagtt atggccgctt gcaggccttt ggtggggaat 148860
aaaataaggc agcaagctgg tgttcttttt ttctcttacc ttatttttga aagagtagct 148920
gaatggtgtc ttgactgata ttccagagca gggacaaagc ctgctgaggt ctgggggctg 148980
cgattaccaa tggctggaat gcattttatt acggtgcatt ccatgttaag gatcaatacg 149040
attgtgccct ttctggaaaa tatcttttag tttatcaata ttcagaggag tgtaggttga 149100
attaaaatga aaaggcactt tataaaggcc atgagtagta cctggtttca tttttctaat 149160
gtcttgcaga gattttatca ggcttcttga agtgttcacg tacattacgc taacacgata 149220
ttaataataa ctgtgctctg gtacagcgga gccagcagaa tgggaagttg tggaatgcag 149280
gcccttgatt ctgatagaag gtgtggtttg aactcacaga aatgacagtt tggagggtag 149340
acatatgtca caagtcatca agattgtctt taaattcatg catagaagct aacagggtgt 149400
cataagcaag gcctgtaaaa tgtatgaggg aattcaaaga taatttatta aaaagtaatt 149460
catgtttgga gttttgtgcc caaaggagtc cttgatttga aaaatgggct tttgcccatc 149520
agattgtttc agggcccgtg tgtgcggagg ccctgccttg tgccccgtga gctcagcctg 149580
acagaaatcc tttggtagca cttaaggctc ctcttcctcc cattgaggca gggaagactc 149640
tgggttctgc aggcagaggt ggttgtgggt gtcttgctgc tcttgttgac atgtgggctc 149700
tccttccagg aagacacaga gaggacccag atcaacgtcc tggccgtgca ggccatcacc 149760
tcactggtgc tcagtgcaat gactgtgcct gtggccggca acccagctgt aagctgcttg 149820
gagcagcagc cccggaacaa gcctctgaaa gctctcgaca ccaggtttgc ttgagttccc 149880
acgtgtctct gggacatagc aggtgctggg gacagtgggt tccccgctga agcgtccagc 149940
agcttcaacc aggccgtttt ccttcattgc tagaattgaa aacaccgtcc gtgtggcctg 150000
tgcaggagat gcagacccaa aggtggcctc ctggtcagtg agaagctgga aacgtgacag 150060
gaactgacgt ggggttattg agcatttagg ggaagacgtt agcagagcag gaatgagcag 150120
gcaactagta gaacacccac ttaagggctc acggacaggt gctcacttag gaagtgagtt 150180
tcatttggta ttacaccagg ttcctttagg caaagcggag ggaaagttct ggtgtttttc 150240
acttgtaaga ttttgaagga aacaaaacac tctttacctt ttttctaaaa tgtaggtttg 150300
ggaggaagct gagcattatc agagggattg tggagcaaga gattcaagca atggtttcaa 150360
agagagagaa tattgccacc catcatttat atcaggcatg ggatcctgtc ccttctctgt 150420
ctccggctac tacaggtacc tgagggaaag ggtgcggggg agcggttgta cttgggctag 150480
```

aatgagagaa gactggcatg ctcaccacac cagtgatgcg ggaagacctg agtgtggtct 150540
gagttggagg ctgtggtgct aaatacgctg ccccttttcat aagcaggagt cttagtcagg 150600
cccagggagg aagtaaaatc tggaaatgaa tgagaagcat tctctcctgc cagtcaagaa 150660
atgagaagcg aaagaattct cacgggctgt aagaccagca ggatttaaaa gttgaattag 150720
ttgcttatgt taagaactca accaagttca tctacacaag ctgaatctcc agcttttcct 150780
aagaaaccat gtgtggcagt ggctgcaggg cagggcacag ctgggcctga gcaccccgct 150840
ccctgcacct ctcccctccc tgggccctgc ctgtcactgc ccactctccc accaagcctt 150900
ccggttgtgt gcctgcccta tcacaggcat cggagcttgt cacctggttt aaaagaagag 150960
agttgtgtgg ggatttggga tgcacgtttt tcactcaaaa gtattttagc gtagagctct 151020
gtgattccgt agctatttag gagtttaagc accttgaagg ctttaattgc agaaagttct 151080
atgtggacgt gcaatgtgtt atacgcagtg tctatgagac tcaaatgttt attagggcgt 151140
tgaagtaaac tgagcacttg gagggccatg gatccagcct tcaaggagct cataagtcag 151200
gaggacccag gagcaatgac ctgtcataga aggcagaaaa gaggggcaca gaggtgggtg 151260
ggaggcatac acaggcagct cctggagctc caaggggagc aagtgcttcc agggaagggg 151320
gcgtggaggc ccctttggag gaggcaagtt gatctggggt ctggcagagg gttagctggg 151380
gacatttagc gggaggctgg tgcccgggaa ttggggggat gcccagcaga aagacatgag 151440
gaggctggcc tggggcgtgg gggggtgtga aaggttaagt gggggcatta tcctgctccc 151500
gctcctgccg gctgtatctg gtcagcctgg gcaccgaggt ggggttctgg aaggcactgt 151560
tcaccaaaat gcttatctgg gtcccccaga gagcttgcct gcctggactg tcggctcgcc 151620
tgcaactgct gactcctaag cttttgcagc tcagcccaca accagttcct attcacagag 151680
gtgggagctg aggggtgaca agtgactgct gcagtcttat ttgtcataga gaaaaagtga 151740
cagagtccag cttgcccact ggccctgcca gcttaactgg ttataaagtg acaaatcccc 151800
aagacccaca gggctctgca caacctgggc cctcctgcca gtggcggcga gggcaggtgg 151860
ctcacggctg ggtgcctgtc tgggcaggag ctgggctggt atggggtggg cctgcggccc 151920
tgcccccctg tgcagatcaa gactcagggt gctggtgttc acaggtgccc tcatcagcca 151980
cgagaagctg ctgctacaga tcaaccccga gcgggagctg gggagcatga gctacaaact 152040
cggccaggtc agtctcgcgc ccccgccgcc tggcctctgt ccgtttctgt cctcagactt 152100
tggcgcttga cacacccagg agaaaagctc agtgcacttt ttaaatgaaa ggaagttttc 152160
ctttttttta aaaaaaaatt taatgttcat tgtttttatc tgttttattc ctaggtcccg 152220
caagcagagg aagcattagt tttgttttta tttatgttct gtattccaga aagtagttaa 152280
gagacctcac atgtagcgat agagatgtgt gtaagagaca gtgagagggc gtgacttgga 152340
cttaagcaag gaccgtgaga cacaaaaagg ggggtgagga cagagtggag tcagctgaaa 152400
tgctcaggag gaagtagacg ccatgaaggg ccatggtatg gggggccgca ggcgtggccg 152460
tgagtgtccc tggggccagc tcttgggggg ctccctgagt gtccctgtcc ctgtggccag 152520
ttctgggtgg gagccccgtg tgcaggcaga cagctcggcc acttcctagc aggtcacatt 152580
ggtctgtgct tctgtttcct cctcagataa gtgaagggat tcaagggtct gggtgtggtg 152640
gctaacacct gtaatctata acattttagg aggctgaggc aggaggctta cctgagctca 152700
ggaggttgag gctgcagtga gccatgattg caccactgca ctccagcctg ggcaacagac 152760
cagtactctg tcccttaaaa aaaaatgtaa acagaaacgt agggccattt gcatatgatg 152820
gcacatggcg tggagcccta caggtgtatg ctgggcgggg cccggctgtg ctggccgact 152880
tgcacctttc cctccacccc ggtgctgtgt ctttcgctca ccgggttcct gatttagtga 152940
aagcagttgt gcaggacagt tctctttgta gcttttgttt ctgtggaaat gggtcagaat 153000
atggtgttta gaaacactta tgagctctga gagtttcctc ttctgagttc ctggcctgca 153060
gccttcacag cagaaaccct gtgatgtcac aagcctgttt ctgttccctg ctctctgcct 153120
gtactgtcct gttttgtgcc tgccggtttc agtgacagga agcagggagc tactggacca 153180
gcctgtattt ttctagacat agttggaaaa agaagtccca ctcttctgtc ctttcacctt 153240
tgacagatgt ttccacccca agataagtga aaatgaccaa taggatgcac tgtatttttc 153300
atgaaagtgt ttctgaaggg caggctgaga gtgagaggcc tggggctcac tgggtgcctc 153360
tggccttgtc ctgggcccag ggacactggt ctgtgcccga ggtattccct atccccccaa 153420
ccccgctgca tttggccaca tccttcaatg tttgcgttgt gtccagcgtc cgcaaaccaa 153480
ctgtcatggg atcatactgg ggctgaagta cggtcccacc cctgccctgt ctggggctga 153540
agtacagtgc cacccctgcc ctgtctgggg ctgaaggaca gtgccacccc tgccctgtct 153600
ggggctgaag tacagtgcca cccctgccct gtctggggct gaaggacagt gccacccctt 153660
ccctgtctgg ggctgaagga cagtgccacc cctgccctgt ctggggctga aggacagtgc 153720
cacccctgcc ctgtctgggg ctgaaggaca gtgccacccc tgccctgtct ggggctgaag 153780
gacagtgcca cccctgccct gtctggggct gaaggacagt gccacccctg ccctgtctgg 153840
ggctgaagga cagtgccacc cctgccctgt ctggggctga aggacagtgc cacccctgcc 153900
ctgtctgggg ctgaaggaca gtgccacccc tgccctgtct ggggctgaag gacagtgcca 153960
cccctgccct gtctggggct gaaggacagt gccacccctg ccctgtctgg ggctgaagga 154020
cagtgccacc cctgccctgt ctggggctga aggacagtgc cacccctgcc ctgtctgggg 154080
ctgaaggaca gtgccacccc tgccctgtct gggatgttta gcccctagat gccactggac 154140
tgagccgcta cttgcttttg ggaaagaggg gtgggggtta ggggtctggg cgaggggagt 154200
gcaggggctc ctccttggcc tgagagctgt tcatacagac tcctcgccca ctccctgcag 154260
ggtgctgggt cccagggggg aaatggccct tggtgccaag aacgtgagtt ggggctagtg 154320
ccagtgatga tggagaacag ctttttatgg gcacacagcc cacagcactg tgccaagtgc 154380
tcgaggcttc ccgagaacca ggcagaaagg aggacagtcg aggtgtgctg actgcgtggt 154440
ggctgcgtga tctagagcgc gggtcacaaa ggcgcgaggg agctctggcc ttgggtttac 154500
cgcaatgact gccagtgcgg gagactggaa aaggaatctc acgtattggt tccgtgtttt 154560
ggggactcca ttcagatgtc acttaggagt gaaagcatcc cttcgtagag cctctttctg 154620
tgtcaccctc ctcagctgct cctggggttg actggcccct gattcatgcc tttagcatgt 154680
gctggagctt cccagcagct gtccagcccc tgccccaccc tctctgtggg ctcccttgcc 154740
cgtaacctgg ggtgtctgaa cgacccttgc taaggggcag actgttagac ggtaggcatg 154800
tgctgagtcc cagtggccac acccacccac caggagcctg gcactgtggc cgcagcactg 154860
agcagtgccc cgtttctgtg gcaggtgtcc atacactccg tgtggctggg gaacagcatc 154920
acacccctga gggaggagga atgggacgag gaagaggagg aggaggccga cgcccctgca 154980
ccttcgtcac cacccacgtc tccagtcaac tccaggtttt ccaatggcct ttttcttttt 155040
aacagaaatt tgaaatttct tatcagtcat ttgatttgtt tgaggtgctt cttgaaatga 155100
gcctctcatc tcatgtactt ggaaaatacc catctcgcat attccacagg aaacaccggg 155160
ctggagttga catccactcc tgttcgcagt ttttgcttga gttgtacagc cgctggatcc 155220
tgccgtccag ctcagccagg aggaccccgg ccatcctgat cagtgaggtg gtcagatccg 155280
taagtgagcc ttcccattcc cctcacacct gcacgtgcca cacgcaccac acacgccaca 155340
caccccacac acacacaccg cccacacaca tgccacttgc acacacaccc ctcatgcatg 155400
caacacacac acaggccaca cgcaccatag acaccacaca cacatgccac atgcacacac 155460
atacacggca tgcaccatac acacaacaca cacagcacac atgccacaca cacacgccac 155520
accacatgca ccacacacat gccacatgca cacacactcc acatgcatgc accacacaca 155580
cacacacaca ccacacacac cacatgcacc acaccacaca ggttacatgc acacaacaca 155640
cacatgccac gtgcacacac cccacacacc acatgtatgt gccacacaca gcacacaacc 155700
acacacatgc accacacaca tgccacatgt gcatgcacca gacacatggc acacactaca 155760
cacacgccac gtgcacacac cccacacaca tgtacgcacc acacacatgc cacacacaca 155820
tgcaccacac acatgccaca tgtacacaca tgtatataca caccccacac cacacacaca 155880
ccacttgcac accacgcaca cacaccacat gcgcacacac acaccacata cgccacatgt 155940
acacaccata cacacaccat acatgcacca cgtgtaccac gcacccacac agacacagca 156000
cacgcataca ccacacacac acgcacacat gcgtcccgca cagtaatgtc tcttgggtgt 156060
aagaacacga cttgccagta gtagcgttct ggatgcgttg cctggattct aacagcgcga 156120
ttctcccctt gccctcctgg ttttccacat ctccagcttc tagtggtctc agacttgttc 156180
accgagcgca accagtttga gctgatgtat gtgacgctga cagaactgcg aagggtgcac 156240
ccttcagaag acgagatcct cgctcagtac ctggtgcctg ccacctgcaa ggcagctgcc 156300
gtccttggga tggtaagtga caggtggcac agaggtttct gtgctgaagc cacgggggcc 156360
catctgcctt gggacctggt gttggccaga ggtgccgggt gcggctgcct ccttccaaga 156420
gttgacccga accggactcc acggcccacg tgagctgcag tgcttctcag atggaggggg 156480
ttcagcgacg gtcagtgcca ttcacaggtc actgtgatgt gggttgtggc ggccaagcca 156540
tggtttgggg tcccgtatcc ctgggcttat gacatcattg tagtagccca tccccacaga 156600
accacggtgt gtggtggcgc tgaggcatcg tagatggtgg aaatgctact ggcttcccca 156660
tgctctgccc tgaggcctga ctgcctcact cccccttctca gttatgttcc aggccccccg 156720
agcttcctgg ctggacagct tctctcctgg gggccgtttt gtcacagtga ccctgtgttt 156780
ctagtcccaa atctgggtgc tatagtctct ttttagcgtg gtggttgtct tagtcttttt 156840
tggctgctac cacaagttac cttagactgg gtaatttata aacagtggaa atttacttct 156900
caccgttctg gggctggaa gttttcatgg tcaaggtgcc agcagatttg gtgtgtgatg 156960
agggctgctc tctgcttcat agatggcatc ttctggctgg gtcctcacgg tggaaggagt 157020
gaacaagctc cctcaggcct tttagaaggg ccccaatcca caagggctct cccatcatga 157080
cctcatcacc tcccaaggcc ccaccttctt gtactgtggc actgcaaatt aggtgtcagt 157140
gtaggagttt caggagggat agaaacattc agaccatccc agcggtcaag tgttcatcct 157200
cttgagttcc tccttattct gcttctggtt tatcaggatt cagccagtgc agcatggtac 157260
ctgtattctg tggcacatca ccacatggta tttgccaagt atccatcacc tgcacacgtg 157320
aaatcattgc ccgtgggtcc cgacatctgg cgaagcatat tcaaggatgg cagaactgtc 157380
agagctggca cctctggttc cttgtcatgt ggcattacct agtaatccat tttatgatag 157440
caatggaaac tcatttcttc aacaaacacc tgagtggctg ccgtgtgcca gccgtctggg 157500
gcccttggtg agaatggcat ggtggtgccc atcagggcct gcctagcccg tgctctggac 157560
gggctcctgt gtgtcaggaa cgacaatgct gtcatgacgg tgaatgattt tttttttgc 157620 catcactcca gccgctaaca tttgcggagc tcttcctccc gcacccccac ctgacaaggc 157680
caagggtgac cttggcccca ccctaggcgg ccaaggtcag aggttagctg gcttgtctgg 157740
gtcacacaaa atgcagcaga ggttgaggtg agcacatgtc cgtgacctgg agcctgactc 157800
cctctctgcg agtcttgact gctcttgcct agactctgtc ctccccgagc ccaaacgcca 157860
gtcatcttcc cttgtgggtg tccttcagcc tggtgccatg ctggtgactc agcagccgtc 157920
cagggagtgg aaacaattga gtgtgtgggt tccctgtgtg ggcatctctc ttcacggcga 157980
acaccctctg ggtgttgccc acacgatgtc aaagcggctc ttggaagggg tccttctcct 158040
ttgtgggaag tttcagctgc tgggctaact tgaattgtaa ctgtggtttt gtgctcaggc 158100
ccagatcccc ctaggcaagt gttgtgccat cagtaatcaa atgagaaata atcattttga 158160
aaagcagatc ctaaggcagg atggtcatgg acactcactc ccagctcttt gtgcactcat 158220
gctttctgga agatggccat cctctgtgaa ggttttcagc gcgtcatgct tggtacccac 158280
gtatccagag catgtcgttt tgaggtattt gcccaccgtt gtgaaatccg tgccacccga 158340
gagcaggtcc tgatgtgggg ctttcagaag tgggacctgg ggccgtacgc agtccttagg 158400
gaggggccgt gtggcgttgt gcgtgtgagg ggatagcaca gggtgaggtg ggggcccaag 158460
aaggaagtga cccacaaaga acagcctcct cttttggtcc ttgttcctgg gatggctggg 158520
agtggcttct gtgtcgtccg gccatttccc ctgcggagag gctcctacca ctgccgagaa 158580
cctcatcatt ccacaaaaac aagaggccgc ctggccatcc agcgctccat gggaattctg 158640
tgtccccata gtcttgggct gaaggagggt gacattcctt gctgacttct gcaggggtct 158700
cctcactgtt aaagagcaga ttgaaagtga agaacgtggg ctaagtgttt aggtcgatat 158760
ttaaccctgc taggttttgg atactaagtg aaattgaggc cattttggtt gaagttgaca 158820
gaaaccacta tcagggatcc ccaagactac cccaggcttt tctagaaaga ctctcagcta 158880
agatgtgtta tggtaaaagc acacaaaaca aaatcagcaa agaaaattag caagggcaga 158940
ggcccatggg gcgatgtccc gaggacacca ggcttgagct tccagaatcc tctcccagcg 159000
gggtcgtgca ggacgcactt aactccccgc acagtgagcc gtgacagcgc gtgtgcagtg 159060
tcgtcgccag gaaagcacac tagagactcg gtgccagggt ttttactggg ggctgggcac 159120
atgggcaccc tctgcctgcc tcgtgcccag actctggact cccggaggga aggcaagttc 159180
tcagcaccaa ccctggtgcc cacacaagca gctgagcaca gggagcccct cctcagtgag 159240
gatggtgggc accgtcccaa caccagccag gggccagcct tgcacacagg cctctcagga 159300
tggtctccgg cctgctgtgt agtctcttct gcacacaagc gtgagggcag cgcccccgcc 159360
tcggctgtgg ggaggagcca ctgggacgtg agctctggtg gcatgcagca gcttttgtct 159420
gtgtgtgcct aggacaaggc cgtggcggag cctgtcagcc gcctgctgga gagcacgctc 159480
aggagcagcc acctgcccag cagggttgga gccctgcacg gcgtcctcta tgtgctggag 159540
tgcgacctgc tggacgacac tgccaagcag ctcatcccgg tcatcagcga ctatctcctc 159600
tccaacctga aagggatcgc ccagtgagtg ggagcctggc tggggctggg gcgggggtct 159660
cagaatgagc tgtgaaggaa gcagcatcac cctctccaag tgcccaggct cctggccaga 159720
tggcaggcca ggtatcagtg ggaacccagg tgggtgccat ggctgaggtc agtgagacgc 159780
aagagcacag gtgcgtccta gaggcttcct cgggcacctc cagcgagctg gagctctcgc 159840
ctctgctgct gtctcatgtg gcgcttagca cactctccca cgtgcccatt cctgactctg 159900
ctctcgaggc catcggctct cattctctgc tcccagaacc ctgttattac ccaggctagc 159960
ctcctctctg caccttcccc gccctggccc agtacctccc tcttgtttcc actgtgattc 160020
cgacctcacc ttatcttaaa gctgctggac ggcaggttct gtacacacgt gtccttgaca 160080
aagcacggct ggtgccgcaa cccctcagcg agcaagtcaa gctcttcaca gcgatgtctt 160140
acaagcgcag agggctctgt gacaccctgg tctcaccgcc actcttccaa agtcgcagag 160200
gctttagcag agatgggccc agcctctctg agtcataggc ttctgcacac gggagctgtc 160260
tttagaggga gggtggaatt tcatcagcca cccacatggg ggagttgagg gcaagaatta 160320
ggagcaaaga tgggaagggg tctgggagga atggccagtg atccccttg acaagtgggc 160380 aggaaacggg ggctaggtca aagttgagtg gaagacctgg agggagacgg gaaggtctct 160440
gtaggcacag ttcagacagg agggaggtgt gagccagggc acatgccggt ggccgtctgg 160500
caggatttgg gacatgctgg agcagggaca gcggctcatc aggggccatt gccctcatcc 160560
aggccagagt gtcacaagcc cgtggggagg ccccttctcgc ctgtcatcct tgctgggcag 160620
tgggtgctgt gctagcagga caggcggacg gctggcaact gtctctgcat ccctggagcc 160680
tggcataggg ccaagtcaca cggggcacag gcctgcaaat caggcacata tgttggtgca 160740
gtgacgtgat tttggggggc agccccagaa caggccccag acacaggcca aagccctgcc 160800
tgtgctggtg tgttgggctg ttctatggct cttgctgtgg gcatggagga ctcagggaag 160860
gagagttgag gtggtccagg agttgcgttt gggatgcaga gagcttgtgg catccaggta 160920
gaaatggtgc gtggggctga cctcagcacc atgggcagag gggccgtgtc acgtgcctcc 160980
gaggtggagg tgggaccacg tggtgacaga tatacgcatc actgggcacg tttttgtggg 161040
tgttgggggg catcgtattg gctcctctgt tcacagtggc cactcattca gtccctggct 161100
accaggtcct cactgtgcca tggggaaggc cggcgctgtc gggggatcac agaaggcagc 161160
acgtcatgat ggcatgtgcc atgaaggaaa agcacagggc actcaggaag tagaggggac 161220
tggcctgggg tgtgggaatc tagggcctcg ttgagggaca gagagaggaa gtgtgtggtg 161280
gccagcatgg aggtggccac aggggaggct gagttaggcc gagagggcag ggcgttgggg 161340
aggtagacgg gctcagccac tcagggagtg gtcaagcaga ggctgaaggg tcaggccagg 161400
ttgcaggggc ctgggggagc cactcagggt aggcgctccc gggagcccgc ctggcccata 161460
gctctacact cccgcgtggg gccggacatg ctgtgaagcc ctctccacgt tggatggggg 161520
tggctgagcc tggatgctgt ctcccgtttt cagctgcgtg aacattcaca gccagcagca 161580
cgtactggtc atgtgtgcca ctgcgtttta cctcattgag aactatcctc tggacgtagg 161640
gccggaattt tcagcatcaa taatacaggt gagtgggccc tggctgtctt cctctgcaca 161700
cggggagtgg gcttcccttc tcttttcctt gcaggatcat accagtgggc cagttttgac 161760
ttggtcggga ggaggcatga acacctgaga ctgtgcagcg attctttgac acagaggcct 161820
ttctccctgt gcagatgtgt ggggtgatgc tgtctggaag tgaggagtcc accccctcca 161880
tcatttacca ctgtgccctc agaggcctgg agcgcctcct gctctctgag cagctctccc 161940
gcctggatgc agaatcgctg gtcaagctga gtgtggacag agtgaacgtg cacagcccgc 162000
accgggccat ggcggctctg ggcctgatgc tcacctgcat gtacacaggt gagcatgtac 162060
acggtgccca taaggccagc ccaagtcctg ttcaagggag gcaggagcat gctcactcaa 162120
gggacctcga ctaggtgccc tctgatttca cacttctggt gttgccccaa gccggcccca 162180
tcaccttgca agaaaggctc tggagccccc agggctggag tacctggtca gggttgaccg 162240
tccctgtggt cactcatccc atgtggctga gctgggctgg gtcctgggca agcaaggggc 162300
tgatatcacc tgctttcaga tctccaggga ctcactggac ccctgtgtac aaagcactgt 162360
ctacagagcc tattgggttg tatagaggta accttcgtac tgaacacttt tgttacagga 162420
aaggagaaag tcagtccggg tagaacttca gaccctaatc ctgcagcccc cgacagcgag 162480
tcagtgattg ttgctatgga gcgggtatct gttctttttg ataggtaaga agcgaagccc 162540
catccctcag ccgttagctt ccctagaact ttggcctgaa gctgtgcttt tgtgtgtgtc 162600
tgctgatccc ctggcgctgt tgctggagtc ctgccagtga ttccccacca cagcctgacc 162660
atgggctgcc ttggctcagg gttccactgg cgagctggtg gtccttggac cccagcactc 162720
aggtgtagcg ttgaccagtt ccaaggttgt cccagtgcct gcccatctct cctgagggct 162780
cagggacagt acctggcagt tgggggtgtg gcagggggca ggaatgacca gcctctggga 162840
gggtggggca gaagcctgta cagtgaggag gagctggctc agcctggctg cctatcgtga 162900
gaggggagcc cacggggctg tgggaggggg gccgtggtgc ctgtgagcag ggtgaggagc 162960
agcggcagga ggatgaaggt ggaacccaca catgcatctt tgagacccgt gtggtcagtg 163020
gcttctgccc cccaccaccc cccactgctg tgcgtgcata gaattggctt ccctcacctg 163080
ctctggaagt gggttaggag cttggtaggg ctttttctca aggacaaggg cccctgattt 163140
gctctcaggc ctcagtcctg gcgacatggt ggatctggag ccttgttgca ctgccttgcc 163200
tgtgctctcc aatcagggtg gccagtgggg agccatttgg cttttctcaa gagcatactc 163260
aggtggacct tgctccactg tttgaccaga tgaggcattc tgaacagcca agcctgtgct 163320
ggtctgtttt catgttgatt tttttttttc ttttcttttt gagatggagt tttttcccttg 163380
tcacccaggc tggagtgcaa tggtgtgatc tcggctcact gcaacctccg cctcccgggt 163440
tcaagtgatt ctcctgcctc agcctcccta gtagctggga ttacaggcac acaccaccat 163500
gcccagctaa tttttgtgtt tttagtagag acggggtttc accgtgttgg ctgggctggt 163560
ctcgaactcc tgaactcaag tgatccaccc tccttggcct cccaaagtgc tgggattgca 163620
ggcgtgagcc actgcgcccg gcccccatgt cgatttttaa atgcacctct gcatcgttct 163680
tcagtcccca tatgctcact gagcaccact gcgactggca gacgggcaca gggaggcgcc 163740
acgaccagtc ctggccttca aggggcttgt ggtctagtgg gcccaatgct aggtggcgag 163800
tgctccaaag agtgtggtgc acgccttccg cttgaccgct ctccagacgc cacagggagg 163860
cacctcgcag ctgaccacag atttctctct gtggagcagt gtcttcagag cggctgccat 163920
gccactgctg ggcgagggtc tgcgggcggg tagagccagg agcacctgtg aggaagtgca 163980
ctgccatttt cgtagctgct tcccgtgtgt ctcagttaca cacggctggc atgtgtgcac 164040
tgatgagacg ggaacgtgat ggttgctttt cagcactgaa agggatactg ctcagggggc 164100
gtgtttcagg atctggttag ggaagaagca gcgagagcac agatggggcc ctgtgtggta 164160
acaagaaaaa agtcctggtt gacaacagtg ccacgaagcg ttagaacaca tagggatgtt 164220
tgtggagcat ttgcatgtgg aaagcagcaa aaacataatg ggaacgggtt cttttgttat 164280
gatttttaaa aatctctttt gtaacatcct tcccgctgcg ccgtttctgc atattccttt 164340
atgtagcttt caaactcctc ttaggagttc tggtccctac agggcgtggg agcccaggct 164400
ttacgtagct ttcaaactcc tcttaggagt tctggtccct acagggtgtg ggagcccagg 164460
gcctgtgccg agcagcctgc ctccacgagc tagacagagg aagggctggg gttttgcctt 164520
tttagtctca aaattcgtac tccagttgct taggctctga ctttccccac ttggaaagtc 164580
cctcacggcc gagggtccct cccagccctg atttcacatc ggcattttcc ccagtattag 164640
agccaaggcc ctccgcgggc aggtggggca gctgtgggag ctggtgccag tctctgacct 164700
gcgtccctcc tcccaggatc aggaaaggct ttccttgtga agccagagtg gtggccagga 164760
tcctgcccca gtttctagac gacttcttcc caccccagga catcatgaac aaagtcatcg 164820
gagagtttct gtccaaccag cagccatacc cccagttcat ggccaccgtg gtgtataagg 164880
tgaggttgca tgtgggatgg ggatggagtg ggaaagcctg gaggtggagt tgcctccgac 164940
ttcccagcag attcgccagc agagcccagc tcctccgctt taaagcagca atgcctctgg 165000
cccccacccc acccccgcca cccaggcgca gcaggtgctt cccgtccccc cagccctgac 165060
actcaggcac ctgcttgctc cttgcaggtg tttcagactc tgcacagcac cgggcagtcg 165120
tccatggtcc gggactgggt catgctgtcc ctctccaact tcacgcagag ggccccggtc 165180
gccatggcca cgtggagcct ctcctgcttc tttgtcagcg cgtccaccag cccgtgggtc 165240
gcggcgatgt atcctctctg ggtccctggt gctggccccg tttcccttgt caacaccgag 165300
gctcatgttt catgataagg ttttgaaacc taacctttgc aaaaacccca cagatgccag 165360
ggtgacaggc cctcagcccc agggaagtaa aatgctgaca ggggtacaga aaggagcacg 165420
tccagacatt tgctgaccag ggcctctcag aggggccggt gtatggcagg agggtcgcag 165480
ctgaggggcc tttctgtgga gggcctgggt gaggggagcg agggtgggcg gtggtctctg 165540
cagacgtccc gcccactcgc gggctctgtg tggctgggct tctcctgaca ctgcttctca 165600
ttagctttgg tcattgtgcc tcgatcgccc tctcggggaa aggcttaagt aaagatccag 165660
ttcccacccc cagatgctgg ctgccaggag tttccctttc cacagccctt ccccaagaca 165720
gaccacaaga gcctccaagc agcacagttg tcctggtgct gacagcacag ccttgcccgg 165780
cgtgcctggc acggctctgc cctcactgca ttggagcagg gctagtggag gccagcggaa 165840
gcaccggcca ccagcgctgc acaggagcca ggccaggtga gtgctgccga gtgggtgccc 165900
tgcctgcagg gcatccagcc agccaagggt tgcaggaatg gaggtggagg cgctgatgca 165960
gctggaggca tccaggtggc ccttccgggg ctctgctcgc tctccaggct ccctggaccc 166020
ctttgtagac tgtttcagga gaggaactcc caggtgagga cagggaggca gcattcccct 166080
catttgccgg cctttttcct taactcctgc accagcctcc cacatgtcat cagcaggatg 166140
ggcaagctgg agcaggtgga cgtgaacctt ttctgcctgg tcgccacaga cttctacaga 166200
caccagatag aggaggagct cgaccgcagg gccttccagt ctgtgcttga ggtggttgca 166260
gccccaggaa gcccatatca ccggctgctg acttgtttac gaaatgtcca caaggtcacc 166320
acctgctgag cgccatggtg ggagagactg tgaggcggca gctggggccg gagcctttgg 166380
aagtctgcgc ccttgtgccc tgcctccacc gagccagctt ggtccctatg ggcttccgca 166440
catgccgcgg gcggccaggc aacgtgcgtg tctctgccat gtggcagaag tgctctttgt 166500
ggcagtggcc aggcagggag tgtctgcagt cctggtgggg ctgagcctga ggccttccag 166560
aaagcaggag cagctgtgct gcaccccatg tgggtgacca ggtcctttct cctgatagtc 166620
acctgctggt tgttgccagg ttgcagctgc tcttgcatct gggccagaag tcctccctcc 166680
tgcaggctgg ctgttggccc ctctgctgtc ctgcagtaga aggtgccgtg agcaggcttt 166740
gggaacactg gcctgggtct ccctggtggg gtgtgcatgc cacgccccgt gtctggatgc 166800
acagatgcca tggcctgtgc tgggccagtg gctgggggtg ctagacaccc ggcaccattc 166860
tcccttctct cttttcttct caggatttaa aatttaatta tatcagtaaa gagattaatt 166920
ttaacgtaac tctttctatg cccgtgtaaa gtatgtgaat cgcaaggcct gtgctgcatg 166980
cgacagcgtc cggggtggtg gacagggccc ccggccacgc tccctctcct gtagccactg 167040

-continued gcatagccct cctgagcacc cgctgacatt tccgttgtac atgttcctgt ttatgcattc 167100
acaaggtgac tgggatgtag agaggcgtta gtgggcaggt ggccacagca ggactgagga 167160
caggccccca ttatcctagg ggtgcgctca cctgcagccc ctcctcctcg ggcacagacg 167220
actgtcgttc tccacccacc agtcagggac agcagcctcc ctgtcactca gctgagaagg 167280
ccagccctcc ctggctgtga gcagcctcca ctgtgtccag agacatgggc ctcccactcc 167340
tgttccttgc tagccctggg gtggcgtctg cctaggagct ggctggcagg tgttgggacc 167400
tgctgctcca tggatgcatg ccctaagagt gtcactgagc tgtgttttgt ctgagcctct 167460
ctcggtcaac agcaaagctt ggtgtcttgg cactgttagt gacagagccc agcatccctt 167520
ctgcccccgt tccagctgac atcttgcacg gtgacccctt ttagtcagga gagtgcagat 167580
ctgtgctcat cggagactgc cccacggccc tgtcagagcc gccactccta tccccaggcc 167640
aggtccctgg accagcctcc tgtttgcagg cccagaggag ccaagtcatt aaaatggaag 167700
tggattctgg atggccgggc tgctgctgat gtaggagctg gatttgggag ctctgcttgc 167760
cgactggctg tgagacgagg caggggctct gcttcctcag ccctagaggc gagccaggca 167820
aggttggcga ctgtcatgtg gcttggtttg gtcatgcccg tcgatgtttt gggtattgaa 167880
tgtggtaagt ggaggaaatg ttggaactct gtgcaggtgc tgccttgaga cccccaagct 167940
tccacctgtc cctctcctat gtggcagctg gggagcagct gagatgtgga cttgtatgct 168000
gcccacatac gtgaggggga gctgaaaggg agcccctcct ctgagcagcc tctgccaggc 168060
ctgtatgagg cttttcccac cagctcccaa cagaggcctc ccccagccag gaccacctcg 168120
tcctcgtggc ggggcagcag gagcggtaga aaggggtccg atgtttgagg aggcccttaa 168180
gggaagctac tgaattataa cacgtaagaa aatcaccatt ccgtattggt tgggggctcc 168240
tgtttctcat cctagctttt tcctggaaag cccgctagaa ggtttgggaa cgaggggaaa 168300
gttctcagaa ctgttggctg ctccccaccc gcctcccgcc tccccccgcag gttatgtcag 168360 cagctctgag acagcagtat cacaggccag atgttgttcc tggctagatg tttacatttg 168420
taagaaataa cactgtgaat gtaaaacaga gccattccct tggaatgcat atcgctgggc 168480
tcaacataga gtttgtcttc ctcttgttta cgacgtgatc taaaccagtc cttagcaagg 168540
ggctcagaac accccgctct ggcagtaggt gtcccccacc cccaaagacc tgcctgtgtg 168600
ctccggagat gaatatgagc tcattagtaa aaatgacttc acccacgcat atacataaag 168660
tatccatgca tgtgcatata gacacatcta taattttaca cacacacctc tcaagacgga 168720
gatgcatggc ctctaagagt gcccgtgtcg gttcttcctg gaagttgact ttccttagac 168780
ccgccaggtc aagttagccg cgtgacggac atccaggcgt gggacgtggt cagggcaggg 168840
ctcattcatt gcccactagg atcccactgg cgaagatggt ctccatatca gctctctgca 168900
gaagggagga agactttatc atgttcctaa aaatctgtgg caagcaccca tcgtattatc 168960
caaattttgt tgcaaatgtg attaatttgg ttgtcaagtt ttgggggtgg gctgtgggga 169020
gattgctttt gttttcctgc tggtaatatc gggaaagatt ttaatgaaac cagggtagaa 169080
ttgtttggca atgcactgaa gcgtgtttct ttcccaaaat gtgcctccct tccgctgcgg 169140
gcccagctga gtctatgtag gtgatgtttc cagctgccaa gtgctctttg ttactgtcca 169200
ccctcatttc tgccagcgca tgtgtccttt caaggggaaa atgtgaagct gaaccccctc 169260
cagacaccca gaatgtagca tctgagaagg ccctgtgccc taaaggacac ccctcgcccc 169320
catcttcatg gagggggtca tttcagagcc ctcggagcca atgaacagct cctcctcttg 169380
gagctgagat gagccccacg tggagctcgg gacggatagt agacagcaat aactcggtgt 169440
gtggccgcct ggcaggtgga acttcctccc gttgcggggt ggagtgaggt tagttctgtg 169500
tgtctggtgg gtggagtcag gcttctcttg ctacctgtga gcatccttcc cagcagacat 169560
cctcatcggg ctttgtccct cccccgcttc ctccctctgc ggggaggacc cgggaccaca 169620
gctgctggcc agggtagact tggagctgtc ctccagaggg gtcacgtgta ggagtgagaa 169680
gaaggaagat cttgagagct gctgagggac cttggagagc tcaggatggc tcagacgagg 169740
acactcgctt gccgggcctg ggcctcctgg gaaggaggga gctgctcaga atgccgcatg 169800
acaactgaag gcaacctgga aggttcaggg gccgctcttc ccccatgtgc ctgtcacgct 169860
ctggtgcagt caaaggaacg ccttcccctc agttgtttct aagagcagag tctcccgctg 169920
caatctgggt ggtaactgcc agccttggag gatcgtggcc aacgtggacc tgcctacgga 169980
gggtgggctc tgacccaagt ggggcctcct tgtccaggtc tcactgcttt gcaccgtggt 170040
cagagggact gtcagctgag cttgagctcc cctggagcca gcagggctgt gatgggcgag 170100
tcccggagcc ccacccagac ctgaatgctt ctgagagcaa agggaaggac tgacgagaga 170160
tgtatattta atttttaac tgctgcaaac attgtacatc caaattaaag gaaaaaaatg 170220
gaaaccatca gttgttgctg tgtgaggctt gctttgcttc atgagaacct agaccttgct 170280
gagctggagt cttaggaagc agtctcctaa gtgcttctcc agcaggggca gaaactgtcc 170340
caccagctaa catctggcat tatggagggt cccccaggca gctgccagca gggacaggcc 170400
ccgtgttttc tgtagccagg gatgaggaag tggccccagg gcatgggcct ggctgggtgc 170460
ttctgcaagg gccttcccaa accacagtac aggtggtctt cctgccctgc agatgggagc 170520
tgtgggagct gctggagctg ctggagcctt catggtcaag tgacatcata agcttatatg 170580
acatacacaa gcctcaggac ttggcccatg gcactgaagc aggtcatcag gcccagcaca 170640
gagactagag ctgtgttctc acagggccca ccacccttcc acctccttgg ccattgacac 170700
ctgcgtccct ggcccagctg ctcccaggta acccccaaag cagctggcac atcccacctc 170760
tggtgtggcc ggggctgctg tgtgtccgca gggcctgccc cgtctattct agcttgtttg 170820
tcctgtctga accagcgcct actccaagaa gcctctgctc agcccagcgg ggatgcttct 170880
aagctccgga cgagcctctc ggaagccttg gtgattggtg gtgtagtcat cttgggatgc 170940
agatgtctta ccaacctgca agaacaaaaa ccctgtggct tcctctggtg cagggtattt 171000
agtcaatgtt tgctgaggtc ccgtctggtt ctggctaatt ggcaggggtc gtccacccat 171060
tctttccctg ctctgctgtc tgtgccagga gagacggggg ccagtcggcc aaggggccag 171120
ctcctgctgc ctgctcctct tgggcacgtg cgggggcccc ctttctctga gcagggatag 171180
ggatcagtct gccggaggga tgtggtggac aggcctaaag catttggggc ggggcatgcc 171240
acttgagctc cctaaatctg tctcctcata ggtgacaccg ctccagggcc ccccagtggc 171300
ctctcctttc agagctacct aaattctggt cacttcagag aaatggagca ccccccttctc 171360
cctggtccag gtgtggacag cctggcacac tgagcacacc tggcatggct ggtaatttca 171420
gaaagaagag gggccggggt ccagtgggaa gcagcggtga acccctcgtg agtgggcttt 171480
gcagtccctc cccatgccac ggcagagctg ccctcaacac agccttcctc ttcctcatcg 171540
gagagcacac cctgtcccct tgccgagctg tgccctgtgc cttcggtggt atttgatttt 171600
ggctgctact ggctttgttg ggatctggaa gtcgcttccc ctgcgtggtg cgtggagcac 171660
tgtaagtcag atgagggaag tagccagggt gaggtgagta ccgggtggag ccgccactga 171720
agggactggg tagggggcc ttgcctctac atgatgtgac acagccaacc gaggacagag 171780
gaagccccgt tcctgggggt gtggggtgca cccctcaggg aagcctgcag tggggcctga 171840
ggaaaggcat cctccgcgag cccacgagtc tggtccatga gcaccgtgac agtgtctgtg 171900
ggtagaggtg gacccggcct tgtgtcatca ccaggacctc ttttgggaaa ccatgtggac 171960
atcgcttgcg ggtcccccag gctctgcagc cccagcagcc t 172001

<210> SEQ ID NO 6
<211> LENGTH: 3059
<212> TYPE: DNA
<213> ORGANISM: Mus musculus

<400> SEQUENCE: 6
ggcactcgcc gcgagggttg ccgggacggg cccaagatgg ctgagcgcct tggttccgct 60
tctgcctgcc gcgcagagcc ccattcattg ccttgctgct aagtggcgcc gcgtagtgcc 120
agtaggctcc aagtcttcag ggtctgtccc atcgggcagg aagccgtcat ggcaaccctg 180
gaaaagctga tgaaggcttt cgagtcgctc aagtcgtttc agcagcaaca gcagcagcag 240
ccaccgccgc aggcgccgcc gccaccgccg ccgccgcctt cgccttaacc ccctcagccg 300
ccgcctcagg ggcagccgcc gccgccacca ccgtcgctgc caggtccggc agaggaaccg 360
ctgcaccgac caaagaagga actctcagcc accaagaaag accgtgtgaa tcattgtcta 420
acaatatgtg aaaacattgt ggcacagtct ctcagaaatt ctccagaatt tcagaaactc 480
ttgggcatcg ctatggaact gtttctgctg tgcagtgacg atgcggagtc agatgtcaga 540
atggtggctg atgagtgcct caacaaagtc atcaaagctt tgatggattc taatcttcca 600
aggctacagt tagaactcta taaggaaatt aaaaagaatg gtgctcctcg aagtttgcgt 660
gctgccctgt ggaggtttgc tgagctggct cacctggttc gacctcagaa gtgcaggcct 720
tacctggtga atcttcttcc atgcctgacc cgaacaagca aaagaccgga ggaatcagtt 780
caggagacct tggctgcagc tgttcctaaa attatggctt cttttggcaa tttcgcaaat 840
gacaatgaaa ttaaggttct gttgaaagct ttcatagcaa atctgaagtc aagctctccc 900
accgtgcggc ggacagcagc cggctcagcc gtgagcatct gccaacattc taggaggaca 960
cagtacttct acaactggct ccttaatgtc ctcctaggtc tgctggttcc catggaagaa 1020
gagcactcca ctctcctgat cctcggtgtg ttgctcacat tgaggtgtct agtgcccttg 1080
ctccagcagc aggtcaagga cacaagtcta aaaggcagct ttggggtgac acggaaagaa 1140
atggaagtct ctccttctac agagcagctt gtccaggttt atgaactgac tttgcatcat 1200
actcagcacc aagaccacaa tgtggtgaca ggggcactgg agctcctgca gcagctcttc 1260
cgtacccctc cacctgaact cctgcaagca ctgaccacac caggagggct tgggcagctc 1320
actctggttc aagaagaggc ccggggcaga ggccgcagcg ggagcatcgt ggagctttta 1380
gctggagggg gttcctcgtg cagccctgtc ctctcaagaa agcagaaagg caaagtgctc 1440
ttaggagagg aagaagcctt ggaagatgac tcggagtcca ggtcagatgt cagcagctca 1500
gcctttgcag cctctgtgaa gagtgagatt ggtggagagc tcgctgcttc ttcaggtgtt 1560
tccactcctg gttctgttgg tcacgacatc atcactgagc agcctagatc ccagcacaca 1620
cttcaagcag actctgtgga tttgtccggc tgtgacctga ccagtgctgc tactgatggg 1680
gatgaggagg acatcttgag ccacagctcc agccagttca gtgctgtccc atccgaccct 1740
gccatggacc tgaatgatgg gacccaggcc tcctcaccca tcagtgacag ttctcagacc 1800
accactgaag gacctgattc agctgtgact ccttcggaca gttctgaaat tgtgttagat 1860
ggtgccgata gccagtattt aggcatgcag ataggacagc cacaggagga cgatgaggag 1920
ggagctgcag gtgttctttc tggtgaagtc tcagatgttt tcagaaactc ttctctggcc 1980
cttcaacagg cacacttgtt ggaaagaatg ggccatagca ggcagccttc cgacagcagt 2040
atagataagt atgtaacaag agatgaggtt gctgaagcca gtgatccaga aagcaagcct 2100
tgccgaatca aaggtgacat aggacagcct aatgatgatg attctgctcc tctggtacat 2160
tgtgtccgtc ttttatctgc ttcctttttg ttaactggtg aaaagaaagc actggttcca 2220
gacagagacg tgagagtcag tgtgaaggcc ctggccctca gctgcattgg tgcggctgtg 2280
gcccttcatc cagagtcgtt cttcagcaga ctgtacaaag tacctcttaa taccacggaa 2340
agtactgagg aacagtatgt ttctgacatc ttgaactaca tcgatcatgg agacccacag 2400
gtccgaggag ctactgccat tctctgtggg acccttgtct actccatcct cagtaggtcc 2460
cgtctccgtg ttggtgactg gctgggcaac atcagaaccc tgacaggaaa tacatttttct 2520 ctggtggact gcattccttt actgcagaaa acgttgaagg atgaatcttc tgttacttgc 2580
aagttggctt gtacagctgt gagggtgagt acaatgcttt acataaactg ttccttgcct 2640
tagtgagctt accattgata cagttaaatt tggagcttaa taggtcacat ttccgtaagt 2700
tgtaaacagt tcttttccga aatttaccac tcagcctttg aaaaaacgtt gccatcatat 2760
taaaattcat taaaactttt aattcttgga ctccttattt gaaacgttct tttctctaaa 2820
gatagtgttt agaaatatac ctttgctatt ttgaaatata aagtttgttg aataattaca 2880
attactgttt taagatacta gaatgttgag ctgcaatgaa attatgggtg ttatttaact 2940
gggcctttac taaaagagcc ttgattcctc aagtgacagt aaggtgaaac atttcctatt 3000
agctgcatca taagtcacaa ttgggcattc agtagcagaa aatttaacta gagaaaatc 3059

<210> SEQ ID NO 7
<211> LENGTH: 1375
<212> TYPE: DNA
<213> ORGANISM: Mus musculus

<400> SEQUENCE: 7
tcataagtca caattgggca ttcagtagca gaaaatttaa ctagagaaaa tcaaaacaaa 60
aacagtgatt aagtctcagg aagggactat cattcttttt agaaatgtaa tggcctcaaa 120
gtagtgtttt tctagatcta attttttaaa aagattttat ttttttaatg gtgtatatgt 180
gtgtgtgtgt gtgtgtgtgt gtcagagtat gtcagagtgt gagtttctat ctgtgagggt 240
aatagcaaca gatgccagaa gagggcactg gatcccctaa aactggaatt ctaggtgact 300
atgagccacc tgatgtggat gctgggaacc aaactcgggt ccttcagaag agcagtaagt 360
aggcactttt gaccagtgag ccatctttcc agcccccagc accattgggt ttttttgctt 420 ttttttttt ttttttttt aagttaagtt ttagttagtt gtgtcttttg agcaatgaag 480
gcatgctgat agcacaggtg ctatgctgat agatataagt gtgttatcct tgtataggat 540
aactacagga taattaatgc ctttaagctc tgaggctgaa ggtcctatag caatataaga 600
tccaccttga ttccttcctt gtccatcaag aaagttgagt cacatctaag atactctttg 660
atatgggtct cttctcctta tgctggacct gagacttctt ttcacatgtg gcaggactat 720
gttgtgtcat cttcctctaa accagtggtt agtgttcctg agattgaggc tcaagagtca 780
aggcaagtaa tcagaggcag aaagaaacaa aatataatgg gcacatttac ttttaaactc 840
aagcataata agataaagat gtatcttgag tacttctggg aacctgtatt gcttcttgtt 900
gctgcttaaa gatagactag aacaaacagg tgcatgcata agagtgctgt tcaaagacgc 960

-continued ggtgcggtgt ctgacctgat gccttctgtg gtgggatggg ctttcagcac tgtgtcctga 1020
gtctttgcag cagcagctac agtgacttgg gattacaact gcttattgat atgctgcctc 1080
tgaagaacag ctcctactgg ctggtgagga ccgaactgct ggacactctg gcagagattg 1140
acttcaggta agggagccaa gttacaattc agaagttcaa attaaaaatt gaaagtcctg 1200
aggtctctgc agttggcatg gctgtcatgt gtactgtctg ttcagctcat ctccagttta 1260
gttagagaac atgtgatagt cacagtactt tttattgaac tctgaacttg gagattttgc 1320
tattttaaat gagataagtt tttctggttg tcctgttttt ctagatggta ggagt 1375

<210> SEQ ID NO 8
<211> LENGTH: 9992
<212> TYPE: DNA
<213> ORGANISM: Mus musculus
<220> FEATURE:
<221> NAME/KEY: misc_feature
<222> LOCATION: 3103
<223> OTHER INFORMATION: n is a, c, g, or t

<400> SEQUENCE: 8
ggttccgctt ctgcctgccg cgcagagccc cattcattgc cttgctgcta agtggcgccg 60
cgtagtgcca gtaggctcca agtcttcagg gtctgtccca tcgggcagta agccgtcatg 120
ggaaccctgg aaaagctgat gaaggctttc gagtcgctca agtcgtttca gcagcaacag 180
cagcagcagc caccgccgca ggcgccgcca ccgccgccgc cgcctccgcc tcaacccccct 240 cagccgccgc ctcaggggca gccgccgccg ccaccaccgc cgctgccagg tccggcagag 300
gaaccgctgc accgaccaaa gaaggaactc tcagccacca agaaagaccg tgtgaatcat 360
tgtctaacaa tatgtgaaaa cattgtggca cagtctctca gaaattctcc agaatttcag 420
aaactcttgg gcatcgctat ggaactgttt ctgctgtgca gtaacgatgc ggagtcagat 480
gtcagaatgg tggctgatga gtgcctcaac aaagtcatca aagctttgtt ggattctaat 540
cttccaaggc tacagttaga actctataag gaaattaaaa agaatggcgc tcctcgaagt 600
ttgcgtgctg ccctgtggag gtttgctgag ctggctcacc tggttcgacc tcagaagtgc 660
aggccttacc tggtgaatct tcttccatgc ctgacccgaa caagcaaaag accggaggaa 720
tcagttcagg agaccttggc tgcagctgtt cctaaaatta tggcttcttt tggcaatttc 780
gcaaatgaca atgaaattaa ggttctgttg aaagctttca tagcaaatct gaagtcaagc 840
tctcccaccg tgcggcggac agcagccggc tcagccgtga gcatctgcca acattctagg 900
aggacacagt acttctacaa ctggctcctt aatgtcctcc taggtctgct ggttcccatg 960
gaagaagagc actccactct cctgatcctc ggtgtgttgc tcacattgag gtgtctagtg 1020
cccttgctcc agcagcaggt caaggacaca agtctaaaag gcagctttgg ggtgacacgg 1080
aaagaaatgg aagtctctcc ttctacagag cagcttgtcc aggtttatga actgactttg 1140
catcatactc agcaccaaga ccacaatgtg gtgacagggg cactggagct cctgcagcag 1200
ctcttccgta cccctccacc tgaactcctg caagcactga ccacaccagg agggcttggg 1260
cagctcactc tggttcaaga agaggcccgg ggccgaggcc gcagcgggag catcgtggag 1320
cttttagctg gagggggttc ctcgtgcagc cctgtcctct caagaaagca gaaaggcaaa 1380
gtgctcttag gagaggaaga agccttggaa gatgactcgg agtccaggtc agatgtcagc 1440
agctcagcct ttgcagcctc tgtgaagagt gagattggtg gagagctcgc tgcttcttca 1500
ggtgtttcca ctcctggttc tgttggtcac gacatcatca ctgagcagcc tagatcccag 1560
cacacacttc aagcagactc tgtggatttg tccggctgtg acctgaccag tgctgctact 1620

```
gatggggatg aggaggacat cttgagccac agctccagcc agttcagtgc tgtcccaccc   1680
gaccctccca tggacctgaa tgatgggacc cagccctcct cacccatcag tgacagttct   1740
cagaccacca ctgaaggacc tgattcagct gtgactcctt cggacagttc tgaaattgtg   1800
ttagatggtg ccgatagcca gtatttaggc atgcagatag gacagccaca ggaggacgat   1860
gaggagggag ctgcaggtgt tctttctggt gaagtctcag atgttttcag aaactcttct   1920
ctggcccttc aacagacaca cttgttggaa agaatgggcc atagcaggca gccttccgac   1980
agcagtatag ataagtatgt aacaagagat gaggttgctg aagccagtga tccagaaagc   2040
aagccttgcc gaatcaaagg tgacatagga cagcctaatg atgatgattc tgctcctctg   2100
gtacattgtg tccgtctttt atctgcttcc tttttgttaa ctggtgaaaa gaaagcactg   2160
gttccagaca gagacgtgag agtcagtgtg aaggccctgg ccctcagctg cattggtgcg   2220
gctgtggccc ttcatccaga gtcgttcttc agcagactgt acaaagtacc tcttaatacc   2280
acggaaagta ctgaggaaca gtatgtttct gacatcttga actacatcga tcatggagac   2340
ccacaggtcc gaggagctac tgccattctc tgtgggaccc ttgtctactc catcctcagt   2400
aggtcccgtc tccgtgttgg tgactggctg ggcaacatca gaaccctgac aggaaataca   2460
ttttctctgg tggactgcat tcctttactg cagaaaacgt tgaaggatga atcttctgtt   2520
acttgcaagt tggcttgtac agctgtgagg cactgtgtcc tgagtctttg cagcagcagc   2580
tacagtgact tgggattaca actgcttatt gatatgctgc ctctgaagaa cagctcctac   2640
tggctggtga ggaccgaact gctggacact ctggcagaga ttgacttcag gctcgtgagt   2700
tttttggagg caaaagcaga aagtttacac cgaggggctc atcattatac agggtttcta   2760
aaactacaag aacgagtact caataatgtg gtcatttatt tgcttggaga tgaagacccc   2820
agggttcgac atgttgctgc aacatcatta acaaggcttg tcccaaagct gttttacaag   2880
tgtgaccaag gacaagctga tccagttgtg gctgtagcga gggatcagag cagtgtctac   2940
ctgaagctcc tcatgcatga gacccagcca ccatcacact tttctgtcag caccatcacc   3000
agaatctata gaggctatag cttactgcca agaataacag atgtcaccat ggaaaacaat   3060
ctctcaagag ttgttgccgc agtttctcat gaactcatta cgncaacaac acgggcactc   3120
acatttggat gctgtgaagc cttgtgtctt ctctcagcag cctttccagt ttgcacttgg   3180
agtttaggat ggcactgtgg agtgccccca ctgagtgcct ctgatgagtc caggaagagc   3240
tgcactgttg ggatggcctc catgattctc accttgcttt catcagcttg gttcccactg   3300
gatctctcag cccatcagga tgccttgatt ttggctggaa acttgctagc agcgagtgcc   3360
cccaagtctc tgagaagttc atggacctct gaagaagaag ccaactcagc agccaccaga   3420
caggaggaaa tctgccctgc tctgggggat cggactctag tgcccttggt ggagcagctt   3480
ttctcccacc tgctgaaggt gatcaatatc tgtgctcatg tcttggacga tgtgactcct   3540
ggaccagcaa tcaaggcagc cttgccttct ctaacaaacc ccccttctct aagtcctatt   3600
cgacggaaag ggaaggagaa agaacctgga gaacaagctt ctactccaat gagtcccaag   3660
aaagttggtg aggccagtgc agcctctcga caatcagaca cctcaggacc tgtcacagca   3720
agtaaatcat cctcactggg gagtttctac catctcccct cctacctcaa actgcatgat   3780
gtcctgaaag ccactcacgc caactataag gtcaccttag atcttcagaa cagcaatgaa   3840
aagtttgggg ggttcctgcg ctctgccttg gacgtccttt ctcagattct agagctggcg   3900
acactgcagg acattggaaa gtgtgttgaa gaggtccttg gatacctgaa atcctgcttt   3960
```

-continued

```
agtcgagaac caatgatggc aactgtctgt gtgcagcagc tattgaagac tctctttggg   4020
acgaacttag cctcacagtt tgatggctta tcttccaacc ccagcaagtc tcagtgccga   4080
gctcagcgcc ttggctcttc aagtgtgagg cccggcttat atcactactg cttcatggca   4140
ccatacacgc acttcacaca ggccttggct gacgcaagcc tgaggaacat ggtgcaggcg   4200
gagcaggagc gtgatgcctc ggggtggttt gatgtactcc agaaagtgtc tgcccaattg   4260
aagacgaccc taacaagcgt cacaaagaac cgtgcagata agaatgctat tcataatcac   4320
attaggttat ttgagcctct tgttataaaa gcattgaagc agtacaccac gacaacatct   4380
gtacaattgc agaagcaggt tttggatttg ctggcacagc tggttcagct acgggtcaat   4440
tactgtctac tggattcaga ccaggtgttc atcgggtttg tgctgaagca gtttgagtac   4500
attgaagtgg gccagttcag ggaatcagag gcaattattc caaatatatt tttcttcctg   4560
gtattactgt cttatgagcg ctaccattca aaacagatca ttggaattcc taaaatcatc   4620
cagctgtgtg atggcatcat ggccagtgga aggaaggccg ttacacatgc tatacctgct   4680
ctgcagccca ttgtccatga cctctttgtg ttacgaggaa caaataaagc tgatgcaggg   4740
aaagagcttg agacacagaa ggaggtggtg gtctccatgc tgttacgact catccagtac   4800
caycaggtgc tggagatgtt catccttgtc ctgcagcagt gccacaagga gaatgaggac   4860
aagtggaaac ggctctctcg gcaggtcgca gacatcatcc tgcccatgtt ggccaagcag   4920
cagatgcata ttgactctca tgaagccctt ggagtgttaa ataccttgtt tgagattttg   4980
gctccttcct ccctacgtcc cgtggacatg cttttgcgga gtatgttcat cactccaagc   5040
acaatggcat ctgtaagcac tgtgcagctg tggatatctg gaatcctcgc cattctgagg   5100
gttctcattt cccagtcaac cgaggacatt gttctttgtc gtattcagga gctctccttc   5160
tctccacact tgctctcctg tccagtgatt aacaggttaa ggggtggagg cggtaatgta   5220
acactaggag aatgcagcga agggaaacaa aagagtttgc cagaagatac attctcaagg   5280
tttcttttac agctggttgg tattcttcta gaagacatcg ttacaaaaca gctcaaagtg   5340
gacatgagtg aacagcagca tacgttctac tgccaagagc taggcacact gctcatgtgt   5400
ctgatccaca tattcaaatc tggaatgttc cggagaatca cagcagctgc cactagactc   5460
ttcaccagtg atggctgtga aggcagcttc tatactctag agagcctgaa tgcacgggtc   5520
cgatccatgg tgcccacgca cccagccctg gtactgctct ggtgtcagat cctacttctc   5580
atcaaccaca ctgactaccg gtggtgggca gaggtgcagc agacacccaa gagacacagt   5640
ctgtcctgca cgaagtcact taacccccag aagtctggcg aagaggagga ttctggctcg   5700
gcagctcagc tgggaatgtg caatagagaa atagtgcgga gaggggccct tattctcttc   5760
tgtgattatg tctgtcagaa tctccatgac tcagaacact taacatggct cattgtgaat   5820
cacattcaag atctgatcag cttgtctcat gagcctccag tacaagactt tattagtgcc   5880
attcatcgta attctgcagc tagtggtctt tttatccagg caattcagtc tcgctgtgaa   5940
aatctttcaa cgccaaccac tctgaagaaa acacttcagt gcttggaagg catccatctc   6000
agccagtctg gcgctgtgct cacactatat gtggacaggc tcctgggcac ctcctcccgt   6060
gcgctggctc gcatggtcga caccctggcc tgtcgccggg tagaaatgct tttggctgca   6120
aatttacaga gcagcatggc ccagttgcca gaggaggaac taaacagaat ccaagaacac   6180
ctccagaaca gtgggcttgc acaaagacac caaaggctct attcactgct ggacagattc   6240
cgactctcta ctgtgcagga ctcacttagc cccttgcccc cagtcacttc ccacccactg   6300
ggtggggatg ggcacacatc tctggaaaca gtgagtccag acaaagactg gtacctccag   6360
```

-continued

```
cttgtcagat cccagtgttg gaccagatca gattctgcac tgctggaagg tgcagagctg   6420
gtcaaccgta tccctgctga agatatgaat gacttcatga tgagctcgga gttcaaccta   6480
agccttttgg ctccctgttt aagccttggc atgagcgaga ttgctaatgg ccaaaagagt   6540
cccctctttg aagcagcccg tggggtgatt ctgaaccggg tgaccagtgt tgttcagcag   6600
cttcctgctg tccatcaagt cttccagccc ttcctgccta tagagcccac ggcctactgg   6660
aacaagttga atgatctgct tggtgatacc acatcatacc agtctctgac catacttgcc   6720
cgtgccctgg cacagtacct ggtggtgctc tccaaagtgc ctgctcattt gcaccttcct   6780
cctgagaagg agggggacac ggtgaagttt gtggtaatga cagttgaggc cctgtcatgg   6840
catttgatcc atgagcagat cccactgagt ctggacctcc aagccgggct agactgctgc   6900
tgcctggcac tacaggtgcc tggcctctgg ggggtgctgt cctccccaga gtacgtgact   6960
catgcctgct ccctcatcca ttgtgtgcga ttcatcctgg aagccattgc agtacaacct   7020
ggagaccagc ttctcggtcc tgaaagcagg tcacatactc caagagctgt cagaaaggag   7080
gaagtagact cagatataca aaacctcagt catgtcactt cggcctgcga gatggtggca   7140
gacatggtgg aatccctgca gtcagtgctg gccttgggcc acaagaggaa cagcaccctg   7200
ccttcatttc tcacagctgt gctgaagaac attgttatca gtctggcccg actcccccta   7260
gttaacagct atactcgtgt gcctcctctg gtatggaaac tcgggtggtc acccaagcct   7320
ggaggggatt ttgggacagt gtttcctgag atccctgtag agttcctcca ggagaaggag   7380
atcctcaagg agttcatcta ccgcatcaac accctagggt ggaccaatcg tacccagttc   7440
gaagaaactt gggccaccct ccttggtgtc ctggtgactc agcccctggt gatggaacag   7500
gaagagagcc caccagagga agacacagaa agaacccaga tccatgtcct ggctgtgcag   7560
gccatcacct ctctagtgct cagtgcaatg accgtgcctg tggctggcaa tccagctgta   7620
agctgcttgg agcaacagcc ccggaacaag ccactgaagg ctctcgatac cagatttgga   7680
agaaagctga gcatgatcag agggattgta gaacaagaaa tccaagagat ggtttcccag   7740
agagagaata ctgccactca ccattctcac caggcgtggg atcctgtccc ttctctgtta   7800
ccagctacta caggtgctct tatcaaccat gacaagctgc tgctgcagat caacccagag   7860
cgggagccag gcaacatgag ctacaagctg ggccaggtgt ccatacactc cgtgtggctg   7920
ggaaataaca tcacacccct gagagaggag gaatgggatg aggaagaaga ggaagaaagt   7980
gatgtccctg caccaacgtc accacctgtg tctccagtca attccagaaa acaccgtgcc   8040
ggggttgata ttcactcctg ttcgcagttt ctgcttgaat tgtacagccg atggatcctg   8100
ccatccagtg cagccagaag gaccccccgtc atcctgatca gtgaagtggt tcgatctctt   8160
cttgtagtgt cagacttatt caccgaacgt acccagtttg aaatgatgta tctgacgctg   8220
acagaactac ggagagtgca cccttcagaa gatgagatcc tcattcagta cctggtgcct   8280
gccacctgta aggcagctgc tgtccttgga atggacaaaa ctgtggcaga gccagtcagc   8340
cgcctactgg agagcacact gaggagcagc cacctgccca gccagatcgg agccctgcac   8400
ggcatcctct atgtgttgga gtgtgacctc ttggatgaca ctgcaaagca gctcattcca   8460
gttgttagtg actatctgct gtccaacctc aaaggaatag cccactgcgt gaacattcac   8520
agccagcagc atgtgctggt aatgtgtgcc actgctttct acctgatgga aaactaccct   8580
ctggatgtgg gaccagaatt ttcagcatct gtgatacaga tgtgtggagt aatgctgtct   8640
ggaagtgagg agtccacccc ctccatcatt taccactgtg ccctccgggg tctggagcgg   8700
```

ctcctgctgt ctgtgcagct atctcgtcta gacacagagt ccctgggcaa gctaagtgtg 8760
ggcagagtga atgtacacag cccacacagg gccatggcag ccctaggcct gatgctcacc 8820
tgcatgtaca caggaaagga gaaagccagt ccaggcagaa cttctgaccc cagccctgct 8880
acacctgaca gcgagtctgt gattgtagct atggagcgag tgtctgttct ctttgatagg 8940
atccgcaagg gatttccctg tgaagccagg gttgtggcaa ggatcctgcc tcagttccta 9000
gatgacttct ttccacctca agatgtcatg aacaaagtca ttggagagtt cctgtccaat 9060
cagcagccat acccacagtt catggccact gtagtttaca aggtttttca gactctgcac 9120
agtgctgggc agtcatccat ggtccgggac tgggtcatgc tgtccctgtc caacttcaca 9180
caaagaactc cagttgccat ggccatgtgg agcctctcct gcttccttgt tagcgcatct 9240
accagcccat gggtttctgc gatccttcca catgtcatca gcaggatggg caagctggaa 9300
ctaatggatg tgaacctttt ctgcctggtt gccacagact tctacagaca ccagatagag 9360
gaggaattcg accgcagggc tttccagtct gtgtttgagg aggaggcggc accaggaagt 9420
ccataccaca ggctgcttgc ttgtttgcaa aatgttcaca aggtcaccac ctgctgagta 9480
gtgcctgtgg gacaaaaggc tgaaagaagg cagctgctgg ggcctgagct ccaggagcct 9540
gctcaagctt ctgctggggc tgccttggcc gtgcaggctt ccacttgtgt caagtggaca 9600
gccaggcaat ggcaggagtg ctttgcaatg agggctatgc agggaacatg cactatgttg 9660
gggttgagcc tagtgctagg ttgaccaggt gtttgtcttt ttcctagtgt tcccctggcc 9720
atagtcgcca ggttgcagct gccctggtat gtggatcaga agtcctagct cttgccagat 9780
ggttctgagc ccgcctgctc cactgggctg gagagctccc tcccacattt acccagtagg 9840
catacctgcc acaccagtgt ctggacacaa aatgaatggt gtgtgggggc tgggaactgg 9900
ggctgccagg tgtccagcac cattttcctt tctgtgtttt cttctcagga gttaaaattt 9960
aattatatca gtaaagagat taattttaat gt 9992

<210> SEQ ID NO 9
<211> LENGTH: 8552
<212> TYPE: DNA
<213> ORGANISM: Mus musculus
<220> FEATURE:
<221> NAME/KEY: misc_feature
<222> LOCATION: 3103
<223> OTHER INFORMATION: n is a, c, g, or t

<400> SEQUENCE: 9
ggttccgctt ctgcctgccg cgcagagccc cattcattgc cttgctgcta agtggcgccg 60
cgtagtgcca gtaggctcca agtcttcagg gtctgtccca tcgggcagta agccgtcatg 120
ggaaccctgg aaaagctgat gaaggctttc gagtcgctca agtcgtttca gcagcaacag 180
cagcagcagc caccgccgca ggcgccgcca ccgccgccgc cgcctccgcc tcaacccccct 240 cagccgccgc ctcaggggca gccgccgccg ccaccaccgc cgctgccagg tccggcagag 300
gaaccgctgc accgaccaaa gaaggaactc tcagccacca agaaagaccg tgtgaatcat 360
tgtctaacaa tatgtgaaaa cattgtggca cagtctctca gaaattctcc agaatttcag 420
aaactcttgg gcatcgctat ggaactgttt ctgctgtgca gtaacgatgc ggagtcagat 480
gtcagaatgg tggctgatga gtgcctcaac aaagtcatca aagctttgtt ggattctaat 540
cttccaaggc tacagttaga actctataag gaaattaaaa agaatggcgc tcctcgaagt 600
ttgcgtgctg ccctgtggag gtttgctgag ctggctcacc tggttcgacc tcagaagtgc 660
aggccttacc tggtgaatct tcttccatgc ctgacccgaa caagcaaaag accggaggaa 720

-continued

```
tcagttcagg agaccttggc tgcagctgtt cctaaaatta tggcttcttt tggcaatttc    780
gcaaatgaca atgaaattaa ggttctgttg aaagctttca tagcaaatct gaagtcaagc    840
tctcccaccg tgcggcggac agcagccggc tcagccgtga gcatctgcca acattctagg    900
aggacacagt acttctacaa ctggctcctt aatgtcctcc taggtctgct ggttcccatg    960
gaagaagagc actccactct cctgatcctc ggtgtgttgc tcacattgag gtgtctagtg   1020
cccttgctcc agcagcaggt caaggacaca agtctaaaag gcagctttgg ggtgacacgg   1080
aaagaaatgg aagtctctcc ttctacagag cagcttgtcc aggtttatga actgactttg   1140
catcatactc agcaccaaga ccacaatgtg gtgacagggg cactggagct cctgcagcag   1200
ctcttccgta cccctccacc tgaactcctg caagcactga ccacaccagg agggcttggg   1260
cagctcactc tggttcaaga agaggcccgg ggccgaggcc gcagcgggag catcgtggag   1320
cttttagctg gagggggttc ctcgtgcagc cctgtcctct caagaaagca gaaaggcaaa   1380
gtgctcttag gagaggaaga agccttggaa gatgactcgg agtccaggtc agatgtcagc   1440
agctcagcct ttgcagcctc tgtgaagagt gagattggtg gagagctcgc tgcttcttca   1500
ggtgtttcca ctcctggttc tgttggtcac gacatcatca ctgagcagcc tagatcccag   1560
cacacacttc aagcagactc tgtggatttg tccggctgtg acctgaccag tgctgctact   1620
gatggggatg aggaggacat cttgagccac agctccagcc agttcagtgc tgtcccaccc   1680
gaccctccca tggacctgaa tgatgggacc cagccctcct cacccatcag tgacagttct   1740
cagaccacca ctgaaggacc tgattcagct gtgactcctt cggacagttc tgaaattgtg   1800
ttagatggtg ccgatagcca gtatttaggc atgcagatag gacagccaca ggaggacgat   1860
gaggagggag ctgcaggtgt tctttctggt gaagtctcag atgttttcag aaactcttct   1920
ctggcccttc aacagacaca cttgttggaa agaatgggcc atagcaggca gccttccgac   1980
agcagtatag ataagtatgt aacaagagat gaggttgctg aagccagtga tccagaaagc   2040
aagccttgcc gaatcaaagg tgacatagga cagcctaatg atgatgattc tgctcctctg   2100
gtacattgtg tccgtctttt atctgcttcc tttttgttaa ctggtgaaaa gaaagcactg   2160
gttccagaca gagacgtgag agtcagtgtg aaggccctgg ccctcagctg cattggtgcg   2220
gctgtggccc ttcatccaga gtcgttcttc agcagactgt acaaagtacc tcttaatacc   2280
acggaaagta ctgaggaaca gtatgtttct gacatcttga actacatcga tcatggagac   2340
ccacaggtcc gaggagctac tgccattctc tgtgggaccc ttgtctactc catcctcagt   2400
aggtcccgtc tccgtgttgg tgactggctg ggcaacatca gaaccctgac aggaaataca   2460
ttttctctgg tggactgcat tcctttactg cagaaaacgt tgaaggatga atcttctgtt   2520
acttgcaagt tggcttgtac agctgtgagg cactgtgtcc tgagtctttg cagcagcagc   2580
tacagtgact tgggattaca actgcttatt gatatgctgc ctctgaagaa cagctcctac   2640
tggctggtga ggaccgaact gctggacact ctggcagaga ttgacttcag gctcgtgagt   2700
tttttggagg caaaagcaga aagtttacac cgaggggctc atcattatac agggtttcta   2760
aaactacaag aacgagtact caataatgtg gtcatttatt tgcttggaga tgaagacccc   2820
agggttcgac atgttgctgc aacatcatta acaaggcttg tcccaaagct gttttacaag   2880
tgtgaccaag gacaagctga tccagttgtg gctgtagcga gggatcagag cagtgtctac   2940
ctgaagctcc tcatgcatga gacccagcca ccatcacact ttctgtcag caccatcacc   3000
agaatctata gaggctatag cttactgcca agaataacag atgtcaccat ggaaaacaat   3060
```

-continued

```
ctctcaagag ttgttgccgc agtttctcat gaactcatta cgncaacaac acgggcactc   3120
acatttggat gctgtgaagc cttgtgtctt ctctcagcag cctttccagt ttgcacttgg   3180
agtttaggat ggcactgtgg agtgccccca ctgagtgcct ctgatgagtc caggaagagc   3240
tgcactgttg ggatggcctc catgattctc accttgcttt catcagcttg gttcccactg   3300
gatctctcag cccatcagga tgccttgatt ttggctggaa acttgctagc agcgagtgcc   3360
cccaagtctc tgagaagttc atggacctct gaagaagaag ccaactcagc agccaccaga   3420
caggaggaaa tctgccctgc tctgggggat cggactctag tgcccttggt ggagcagctt   3480
ttctcccacc tgctgaaggt gatcaatatc tgtgctcatg tcttggacga tgtgactcct   3540
ggaccagcaa tcaaggcagc cttgccttct ctaacaaacc ccccttctct aagtcctatt   3600
cgacggaaag ggaaggagaa agaacctgga gaacaagctt ctactccaat gagtcccaag   3660
aaagttggtg aggccagtgc agcctctcga caatcagaca cctcaggacc tgtcacagca   3720
agtaaatcat cctcactggg gagtttctac catctcccct cctacctcaa actgcatgat   3780
gtcctgaaag ccactcacgc caactataag gtcaccttag atcttcagaa cagcaatgaa   3840
aagtttgggg ggttcctgcg ctctgccttg gacgtccttt ctcagattct agagctggcg   3900
acactgcagg acattggaaa gtgtgttgaa gaggtccttg gatacctgaa atcctgcttt   3960
agtcgagaac caatgatggc aactgtctgt gtgcagcagc tattgaagac tctctttggg   4020
acgaacttag cctcacagtt tgatggctta tcttccaacc ccagcaagtc tcagtgccga   4080
gctcagcgcc ttggctcttc aagtgtgagg cccggcttat atcactactg cttcatggca   4140
ccatacacgc acttcacaca ggccttggct gacgcaagcc tgaggaacat ggtgcaggcg   4200
gagcaggagc gtgatgcctc ggggtggttt gatgtactcc agaaagtgtc tgcccaattg   4260
aagacgaccc taacaagcgt cacaaagaac cgtgcagata agaatgctat tcataatcac   4320
attaggttat ttgagcctct tgttataaaa gcattgaagc agtacaccac gacaacatct   4380
gtacaattgc agaagcaggt tttggatttg ctggcacagc tggttcagct acgggtcaat   4440
tactgtctac tggattcaga ccaggtgttc atcgggtttg tgctgaagca gtttgagtac   4500
attgaagtgg gccagttcag ggaatcagag gcaattattc caaatatatt tttcttcctg   4560
gtattactgt cttatgagcg ctaccattca aaacagatca ttggaattcc taaaatcatc   4620
cagctgtgtg atggcatcat ggccagtgga aggaaggccg ttacacatgc tatacctgca   4680
aatttacaga gcagcatggc ccagttgcca gaggaggaac taaacagaat ccaagaacac   4740
ctccagaaca gtgggcttgc acaaagacac caaaggctct attcactgct ggacagattc   4800
cgactctcta ctgtgcagga ctcacttagc cccttgcccc cagtcacttc ccacccactg   4860
ggtggggatg ggcacacatc tctggaaaca gtgagtccag acaaagactg gtacctccag   4920
cttgtcagat cccagtgttg gaccagatca gattctgcac tgctggaagg tgcagagctg   4980
gtcaaccgta tccctgctga agatatgaat gacttcatga tgagctcgga gttcaaccta   5040
agccttttgg ctccctgttt aagccttggc atgagcgaga ttgctaatgg ccaaaagagt   5100
cccctctttg aagcagcccg tggggtgatt ctgaaccggg tgaccagtgt tgttcagcag   5160
cttcctgctg tccatcaagt cttccagccc ttcctgccta tagagcccac ggcctactgg   5220
aacaagttga atgatctgct tggtgatacc acatcatacc agtctctgac catacttgcc   5280
cgtgccctgg cacagtacct ggtggtgctc tccaaagtgc ctgctcattt gcaccttcct   5340
cctgagaagg agggggacac ggtgaagttt gtggtaatga cagttgaggc cctgtcatgg   5400
catttgatcc atgagcagat cccactgagt ctggacctcc aagccgggct agactgctgc   5460
```

-continued

```
tgcctggcac tacaggtgcc tggcctctgg ggggtgctgt cctccccaga gtacgtgact   5520
catgcctgct ccctcatcca ttgtgtgcga ttcatcctgg aagccattgc agtacaacct   5580
ggagaccagc ttctcggtcc tgaaagcagg tcacatactc caagagctgt cagaaaggag   5640
gaagtagact cagatataca aaacctcagt catgtcactt cggcctgcga gatggtggca   5700
gacatggtgg aatccctgca gtcagtgctg gccttgggcc acaagaggaa cagcaccctg   5760
ccttcatttc tcacagctgt gctgaagaac attgttatca gtctggcccg actcccccta   5820
gttaacagct atactcgtgt gcctcctctg gtatggaaac tcgggtggtc acccaagcct   5880
ggaggggatt ttgggacagt gtttcctgag atccctgtag agttcctcca ggagaaggag   5940
atcctcaagg agttcatcta ccgcatcaac accctagggt ggaccaatcg tacccagttc   6000
gaagaaactt gggccaccct ccttggtgtc ctggtgactc agcccctggt gatggaacag   6060
gaagagagcc caccagagga agacacagaa agaacccaga tccatgtcct ggctgtgcag   6120
gccatcacct ctctagtgct cagtgcaatg accgtgcctg tggctggcaa tccagctgta   6180
agctgcttgg agcaacagcc ccggaacaag ccactgaagg ctctcgatac cagatttgga   6240
agaaagctga gcatgatcag agggattgta gaacaagaaa tccaagagat ggtttcccag   6300
agagagaata ctgccactca ccattctcac caggcgtggg atcctgtccc ttctctgtta   6360
ccagctacta caggtgctct tatcaaccat gacaagctgc tgctgcagat caacccagag   6420
cgggagccag gcaacatgag ctacaagctg ggccaggtgt ccatacactc cgtgtggctg   6480
ggaaataaca tcacacccct gagagaggag gaatgggatg aggaagaaga ggaagaaagt   6540
gatgtccctg caccaacgtc accacctgtg tctccagtca attccagaaa acaccgtgcc   6600
ggggttgata ttcactcctg ttcgcagttt ctgcttgaat tgtacagccg atggatcctg   6660
ccatccagtg cagccagaag gacccccgtc atcctgatca gtgaagtggt tcgatctctt   6720
cttgtagtgt cagacttatt caccgaacgt acccagtttg aaatgatgta tctgacgctg   6780
acagaactac ggagagtgca cccttcagaa gatgagatcc tcattcagta cctggtgcct   6840
gccacctgta aggcagctgc tgtccttgga atggacaaaa ctgtggcaga gccagtcagc   6900
cgcctactgg agagcacact gaggagcagc cacctgccca gccagatcgg agccctgcac   6960
ggcatcctct atgtgttgga gtgtgacctc ttggatgaca ctgcaaagca gctcattcca   7020
gttgttagtg actatctgct gtccaacctc aaaggaatag cccactgcgt gaacattcac   7080
agccagcagc atgtgctggt aatgtgtgcc actgctttct acctgatgga aaactaccct   7140
ctggatgtgg gaccagaatt ttcagcatct gtgatacaga tgtgtggagt aatgctgtct   7200
ggaagtgagg agtccacccc ctccatcatt taccactgtg ccctccgggg tctggagcgg   7260
ctcctgctgt ctgtgcagct atctcgtcta gacacagagt ccctgggcaa gctaagtgtg   7320
ggcagagtga atgtacacag cccacacagg gccatggcag ccctaggcct gatgctcacc   7380
tgcatgtaca caggaaagga gaaagccagt ccaggcagaa cttctgaccc cagccctgct   7440
acacctgaca gcgagtctgt gattgtagct atggagcgag tgtctgttct ctttgatagg   7500
atccgcaagg gatttccctg tgaagccagg gttgtggcaa ggatcctgcc tcagttccta   7560
gatgacttct ttccacctca agatgtcatg aacaaagtca ttggagagtt cctgtccaat   7620
cagcagccat acccacagtt catggccact gtagtttaca aggtttttca gactctgcac   7680
agtgctgggc agtcatccat ggtccgggac tgggtcatgc tgtccctgtc caacttcaca   7740
caaagaactc cagttgccat ggccatgtgg agcctctcct gcttccttgt tagcgcatct   7800
```

-continued

```
accagcccat gggtttctgc gatccttcca catgtcatca gcaggatggg caagctggaa   7860

ctaatggatg tgaacctttt ctgcctggtt gccacagact tctacagaca ccagatagag   7920

gaggaattcg accgcagggc tttccagtct gtgtttgagg aggaggcggc accaggaagt   7980

ccataccaca ggctgcttgc ttgtttgcaa aatgttcaca aggtcaccac ctgctgagta   8040

gtgcctgtgg gacaaaaggc tgaaagaagg cagctgctgg ggcctgagct ccaggagcct   8100

gctcaagctt ctgctggggc tgccttggcc gtgcaggctt ccacttgtgt caagtggaca   8160

gccaggcaat ggcaggagtg ctttgcaatg agggctatgc agggaacatg cactatgttg   8220

gggttgagcc tagtgctagg ttgaccaggt gtttgtcttt ttcctagtgt tcccctggcc   8280

atagtcgcca ggttgcagct gccctggtat gtggatcaga agtcctagct cttgccagat   8340

ggttctgagc ccgcctgctc cactgggctg gagagctccc tcccacattt acccagtagg   8400

catacctgcc acaccagtgt ctggacacaa aatgaatggt gtgtgggggc tgggaactgg   8460

ggctgccagg tgtccagcac cattttcctt tctgtgtttt cttctcagga gttaaaattt   8520

aattatatca gtaaagagat taattttaat gt                                 8552
```

<210> SEQ ID NO 10
<211> LENGTH: 10081
<212> TYPE: DNA
<213> ORGANISM: Mus musculus

<400> SEQUENCE: 10

```
gcactcgccg cgagggttgc cgggacgggc ccaagatggc tgagcgcctt ggttccgctt     60

ctgcctgccg cgcagagccc cattcattgc cttgctgcta agtggcgccg cgtagtgcca    120

gtaggctcca agtcttcagg gtctgtccca tcgggcagga agccgtcatg gcaaccctgg    180

aaaagctgat gaaggctttc gagtcgctca agtcgtttca gcagcaacag cagcagcagc    240

caccgccgca ggcgccgccg ccaccgccgc cgccgcctcc gcctcaaccc cctcagccgc    300

cgcctcaggg gcagccgccg ccgccaccac cgccgctgcc aggtccggca gaggaaccgc    360

tgcaccgacc aaagaaggaa ctctcagcca ccaagaaaga ccgtgtgaat cattgtctaa    420

caatatgtga aaacattgtg gcacagtctc tcagaaattc tccagaattt cagaaactct    480

tgggcatcgc tatggaactg tttctgctgt gcagtgacga tgcggagtca gatgtcagaa    540

tggtggctga tgagtgcctc aacaaagtca tcaaagcttt gatggattct aatcttccaa    600

ggctacagtt agaactctat aaggaaatta aaaagaatgg tgctcctcga agtttgcgtg    660

ctgccctgtg gaggtttgct gagctggctc acctggttcg acctcagaag tgcaggcctt    720

acctggtgaa tcttcttcca tgcctgaccc gaacaagcaa aagaccggag gaatcagttc    780

aggagacctt ggctgcagct gttcctaaaa ttatggcttc ttttggcaat ttcgcaaatg    840

acaatgaaat taaggttctg ttgaaagctt tcatagcaaa tctgaagtca agctctccca    900

ccgtgcggcg gacagcagcc ggctcagccg tgagcatctg ccaacattct aggaggacac    960

agtacttcta caactggctc cttaatgtcc tcctaggtct gctggttccc atggaagaag   1020

agcactccac tctcctgatc ctcggtgtgt tgctcacatt gaggtgtcta gtgcccttgc   1080

tccagcagca ggtcaaggac acaagtctaa aaggcagctt tggggtgaca cggaaagaaa   1140

tggaagtctc tccttctaca gagcagcttg tccaggttta tgaactgact ttgcatcata   1200

ctcagcacca agaccacaat gtggtgacag gggcactgga gctcctgcag cagctcttcc   1260

gtacccctcc acctgaactc ctgcaagcac tgaccacacc aggagggctt gggcagctca   1320

ctctggttca agaagaggcc cggggccgag gccgcagcgg gagcatcgtg gagcttttag   1380
```

-continued

```
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
tgaggaccga actgctggac actctggcag agattgactt caggctcgtg agtttttttgg  2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa acccccccttc tctaagtcct attcgacgga  3660
aagggaagga gaaagaacct ggagaacaag cttctactcc aatgagtccc aagaaagttg   3720
```

-continued

```
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca accccagcaa gtctcagtgc cgagctcagc   4140
gccttggctc ttcaagtgtg aggcccggct tatatcacta ctgcttcatg gcaccataca   4200
cgcacttcac acaggccttg gctgacgcaa gcctgaggaa catggtgcag gcggagcagg   4260
agcgtgatgc ctcggggtgg tttgatgtac tccagaaagt gtctgcccaa ttgaagacga   4320
acctaacaag cgtcacaaag aaccgtgcag ataagaatgc tattcataat cacattaggt   4380
tatttgagcc tcttgttata aaagcattga agcagtacac cacgacaaca tctgtacaat   4440
tgcagaagca ggttttggat ttgctggcac agctggttca gctacgggtc aattactgtc   4500
tactggattc agaccaggtg ttcatcgggt ttgtgctgaa gcagtttgag tacattgaag   4560
tgggccagtt cagggaatca gaggcaatta ttccaaatat atttttcttc ctggtattac   4620
tgtcttatga gcgctaccat tcaaaacaga tcattggaat tcctaaaatc atccagctgt   4680
gtgatggcat catggccagt ggaaggaagg ccgttacaca tgctatacct gctctgcagc   4740
ccattgtcca tgacctcttt gtgttacgag gaacaaataa agctgatgca gggaaagagc   4800
ttgagacaca gaaggaggtg gtggtctcca tgctgttacg actcatccag taccatcagg   4860
tgctggagat gttcatcctt gtcctgcagc agtgccacaa ggagaatgag gacaagtgga   4920
aacggctctc tcggcaggtc gcagacatca tcctgcccat gttggccaag cagcagatgc   4980
atattgactc tcatgaagcc cttggagtgt taaatacctt gtttgagatt ttggctcctt   5040
cctccctacg tcctgtggac atgcttttgc ggagtatgtt catcactcca agcacaatgg   5100
catctgtaag cactgtgcag ctgtggatat ctggaatcct cgccattctg agggttctca   5160
tttcccagtc aaccgaggac attgttcttt gtcgtattca ggagctctcc ttctctccac   5220
acttgctctc ctgtccagtg attaacaggt taaggggtgg aggcggtaat gtaacactag   5280
gagaatgcag cgaagggaaa caaaagagtt tgccagaaga tacattctca aggtttcttt   5340
tacagctggt tggtattctt ctagaagaca tcgttacaaa acagctcaaa gtggacatga   5400
gtgaacagca gcatacgttc tactgccaag agctaggcac actgctcatg tgtctgatcc   5460
acatattcaa atctggaatg ttccggagaa tcacagcagc tgccactaga ctcttcacca   5520
gtgatggctg tgaaggcagc ttctatactc tagagagcct gaatgcacgg gtccgatcca   5580
tggtgcccac gcacccagcc ctggtactgc tctggtgtca gatcctactt ctcatcaacc   5640
acactgacca ccggtggtgg gcagaggtgc agcagacacc caagagacac agtctgtcct   5700
gcacgaagtc acttaacccc cagaagtctg gcgaagagga ggattctggc tcggcagctc   5760
agctgggaat gtgcaataga gaaatagtgc gaagaggggc ccttattctc ttctgtgatt   5820
atgtctgtca gaatctccat gactcagaac acttaacatg gctcattgtg aatcacattc   5880
aagatctgat cagcttgtct catgagcctc cagtacaaga ctttattagt gccattcatc   5940
gtaattctgc agctagtggt ctttttatcc aggcaattca gtctcgctgt gaaaatcttt   6000
caacgccaac cactctgaag aaaacacttc agtgcttgga aggcatccat ctcagccagt   6060
ctggtgctgt gctcacacta tatgtggaca ggctcctggg cacccccttc cgtgcgctgg   6120
```

-continued

```
ctcgcatggt cgacaccctg gcctgtcgcc gggtagaaat gcttttggct gcaaatttac   6180
agagcagcat ggcccagttg ccagaggagg aactaaacag aatccaagaa cacctccaga   6240
acagtgggct tgcacaaaga caccaaaggc tctattcact gctggacaga ttccgactct   6300
ctactgtgca ggactcactt agccccttgc ccccagtcac ttcccaccca ctggatgggg   6360
atgggcacac atctctggaa acagtgagtc cagacaaaga ctggtacctc cagcttgtca   6420
gatcccagtg ttggaccaga tcagattctg cactgctgga aggtgcagag ctggtcaacc   6480
gtatccctgc tgaagatatg aatgacttca tgatgagctc ggagttcaac ctaagccttt   6540
tggctccctg tttaagcctt ggcatgagcg agattgctaa tggccaaaag agtcccctct   6600
ttgaagcagc ccgtggggtg attctgaacc gggtgaccag tgttgttcag cagcttcctg   6660
ctgtccatca agtcttccag cccttcctgc ctatagagcc cacggcctac tggaacaagt   6720
tgaatgatct gcttggtgat accacatcat accagtctct gaccatactt gcccgtgccc   6780
tggcacagta cctggtggtg ctctccaaag tgcctgctca tttgcacctt cctcctgaga   6840
aggaggggga cacggtgaag tttgtggtaa tgacagttga ggccctgtca tggcatttga   6900
tccatgagca gatcccactg agtctggacc tccaagccgg gctagactgc tgctgcctgg   6960
cactacaggt gcctggcctc tggggggtgc tgtcctcccc agagtacgtg actcatgcct   7020
gctccctcat ccattgtgtg cgattcatcc tggaagccat tgcagtacaa cctggagacc   7080
agcttctcgg tcctgaaagc aggtcacata ctccaagagc tgtcagaaag gaggaagtag   7140
actcagatat acaaaaacctc agtcatgtca cttcggcctg cgagatggtg gcagacatgg   7200
tggaatccct gcagtcagtg ctggccttgg gccacaagag gaacagcacc ctgccttcat   7260
ttctcacagc tgtgctgaag aacattgtta tcagtctggc ccgactcccc ctagttaaca   7320
gctatactcg tgtgcctcct ctggtatgga aactcgggtg gtcacccaag cctggagggg   7380
attttggcac agtgtttcct gagatccctg tagagttcct ccaggagaag gagatcctca   7440
aggagttcat ctaccgcatc aacaccctag ggtggaccaa tcgtacccag ttcgaagaaa   7500
cttgggccac cctccttggt gtcctggtga ctcagcccct ggtgatggaa caggaagaga   7560
gcccaccaga ggaagacaca gaaagaaccc agatccatgt cctggctgtg caggccatca   7620
cctctctagt gctcagtgca atgaccgtgc ctgtggctgg caatccagct gtaagctgct   7680
tggagcaaca gccccggaac aagccactga aggctctcga taccagattt ggaagaaagc   7740
tgagcatgat cagagggatt gtagaacaag aaatccaaga gatggtttcc cagagagaga   7800
atactgccac tcaccattct caccaggcgt gggatcctgt cccttctctg ttaccagcta   7860
ctacaggtgc tcttatcagc catgacaagc tgctgctgca gatcaaccca gagcgggagc   7920
caggcaacat gagctacaag ctgggccagg tgtccataca ctccgtgtgg ctgggaaata   7980
acatcacacc cctgagagag gaggaatggg atgaggaaga agaggaagaa agtgatgtcc   8040
ctgcaccaac gtcaccacct gtgtctccag tcaattccag aaaacaccgt gccggggttg   8100
atattcactc ctgttcgcag tttctgcttg aattgtacag ccgatggatc ctgccatcca   8160
gtgcagccag aaggaccccc gtcatcctga tcagtgaagt ggttcgatct cttcttgtag   8220
tgtcagactt attcaccgaa cgtacccagt ttgaaatgat gtatctgacg ctgacagaac   8280
tacggagagt gcacccttca gaagatgaga tcctcattca gtacctggtg cctgccacct   8340
gtaaggcagc tgctgtcctt ggaatggaca aaactgtggc agagccagtc agccgcctac   8400
tggagagcac actgaggagc agccacctgc ccagccagat cggagccctg cacggcatcc   8460
```

```
tctatgtgtt ggagtgtgac ctcttggatg acactgcaaa gcagctcatt ccagttgtta   8520
gtgactatct gctgtccaac ctcaaaggaa tagcccactg cgtgaacatt cacagccagc   8580
agcatgtgct ggtaatgtgt gccactgctt tctacctgat ggaaaactac cctctggatg   8640
tgggaccaga attttcagca tctgtgatac agatgtgtgg agtaatgctg tctggaagtg   8700
aggagtccac cccctccatc atttaccact gtgccctccg ggtctggagg cggctcctgc   8760
tgtctgagca gctatctcgg ctagacacag agtccttggt caagctaagt gtggacagag   8820
tgaatgtaca aagcccacac agggccatgg cagccctagg cctgatgctc acctgcatgt   8880
acacaggaaa ggaaaaagcc agtccaggca gagcttctga ccccagccct gctacacctg   8940
acagcgagtc tgtgattgta gctatggagc gagtgtctgt tctctttgat aggatccgca   9000
agggatttcc ctgtgaagcc agggttgtgg caaggatcct gcctcagttc ctagatgact   9060
tctttccacc tcaagatgtc atgaacaaag tcattggaga gttcctgtcc aatcagcagc   9120
catacccaca gttcatggcc actgtagttt acaaggtttt tcagactctg cacagtgctg   9180
ggcagtcatc catggtccgg gactgggtca tgctgtccct gtccaacttc acacaaagaa   9240
ctccagttgc catggccatg tggagcctct cctgcttcct tgttagcgca tctaccagcc   9300
catgggtttc tgcgatcctt ccacatgtca tcagcaggat gggcaaactg gaacaggtgg   9360
atgtgaacct tttctgcctg gttgccacag acttctacag acaccagata gaggaggaat   9420
tcgaccgcag ggctttccag tctgtgtttg aggtggtggc tgcaccagga agtccatacc   9480
acaggctgct tgcttgtttg caaaatgttc acaaggtcac cacctgctga gtagtgcctg   9540
tgggacaaaa ggctgaaaga aggcagctgc tggggcctga gcctccagga gcctgctcca   9600
agcttctgct ggggctgcct tggccgtgca ggcttccact tgtgtcaagt ggacagccag   9660
gcaatggcag gagtgctttg caatgagggc tatgcaggga acatgcacta tgttggggtt   9720
gagcctgagt cctgggtcct ggcctcgctg cagctggtga cagtgctagg ttgaccaggt   9780
gtttgtcttt ttcctagtgt tcccctggcc atagtcgcca ggttgcagct gccctggtat   9840
gtggatcaga agtcctagct cttgccagat ggttctgagc ccgcctgctc cactgggctg   9900
gagagctccc tcccacattt acccagtagg catacctgcc acaccagtgt ctggacacaa   9960
aatgaatggt gtgtggggct gggaactggg gctgccaggt gtccagcacc attttccttt  10020
ctgtgttttc ttctcaggag ttaaaattta attatatcag taaagagatt aattttaatg  10080
t                                                                  10081
```

<210> SEQ ID NO 11
<211> LENGTH: 154001
<212> TYPE: DNA
<213> ORGANISM: Mus musculus

<400> SEQUENCE: 11

```
gggcatttga ttcttacagg tagcctgaag cttcattggg tttctcactg catggatcac     60
ctccagacag ctttttctga agccggaacg gttttgtttg tttgtttgag acagggtttc    120
tatgtagctc tggctgtcct ggaactcact ttgtagaaca ggctgaccta taactcagag    180
atctgcctgc ctctgcctcc agactgctga gattaaaggt gtgttctatc actgcttggc    240
tttttccttt tcctttttct tttgagacaa gttctgatac agcccatgct gacttgaatt    300
cactatgaag ccaaggaaaa cctggaactc ctgatcctcg ttctacctgc agagtacatg    360
attaccaccc ctggtttata aaatgcaggg attgaactca gagcttcgtg catgctactc    420
aaaaagcatt ctacaagtgc tgtgattaaa ggcatgcacc accatgcccg gttgaagcca    480
```

-continued

```
acactttttg ctgggcagac tgcaggggca gcttgggtgt atccacacca ttttcagctt    540
cctgctttaa ttgctcacct ttgggagatg gaggctctag agacaaggac ttcagcgctg    600
gtggcaatga gaccccttgt aggtcctggc tggttgccac agcactttcc agggtccgtg    660
tctcaatgta gagtgtgtga ccaaagttgc atgaaacaca gcctttcttt ggacagtaac    720
tactgctgcc tgcctgaaac cctttctcag ccttcgctgc ctgcttgaaa ccctttctca    780
gccttctcta ctgcagacac ttctggggct tcggggtcca cggatcataa agggttcttt    840
ggtcctgaat acaggtcact ctggttccct tctcattgca gggagctccc agcacgctgc    900
gttcgggaag ctcaggccac cacctggctt gtggaagaga gagctgcttt gggtttcggg    960
ttccgagctc cacaatcgct ttcccggtga ctccaggtgt agggtggctt tacgcaggaa   1020
aatttcttcg ctgtcattcc cctttccaac cttttcttcc ttccgggtct ccccaactcc   1080
tctgcccacc tcctcacttc ttttctatcg ctggtgccag ggagccgccc taaagcccac   1140
tctccgctca gctccgtccc tcatctagca gcccgccccg cccacctcat cctcttgctt   1200
ggccctcttc actaaggggg gctggctttt gcgggaaggg gcggggccac atcggcgggg   1260
cggagagtct taaactagca gaggccccgc aggcctgcgt cctgacttcg ggaaagagga   1320
cgacgcatcc gcctgtcaat tctgcgggtc tggcgtggcc tcgtctccgc cggcatgacg   1380
tcacgggacg cactcgccgc gagggttgcc gggacgggcc caagatggct gagcgccttg   1440
gttccgcttc tgcctgccgc gcagagcccc attcattgcc ttgctgctaa gtggcgccgc   1500
gtagtgccag taggctccaa gtcttcaggg tctgtcccat cgggcaggaa gccgtcatgg   1560
caaccctgga aaagctgatg aaggctttcg agtcgctcaa gtcgtttcag cagcaacagc   1620
agcagcagcc accgccgcag gcgccgccgc caccgccgcc gccgcctccg cctcaacccc   1680
ctcagccgcc gcctcagggg cagccgccgc cgccaccacc gccgctgcca ggtccggcag   1740
aggaaccgct gcaccgaccg tgagtccggg cgccgcagct cccgcccggg ccccgcgccc   1800
ctggcctgcg tgctgggcat ggccaacact gttccctgtc cagagggtcg cggtacctcc   1860
ctgaggccag gctttcccgg cccgggccct cgtcttgcgg ggtctctggc ctccctcaga   1920
ggagacagag ccgggtcagg ccagccaggg actcgctgag ggcgtcacg actccagtgc   1980
cttcgccgtt cccagtttgc gaagttaggg aacgaacttg tttctctctt ctggagaaac   2040
tggggcggtg gcgcacatga ctgttgtgaa gagaacttgg agaggcagag atctctaggg   2100
ttacctcctc atcaggccta agagctggga gtgcaggaca gcgtgagaga tgtgcgggta   2160
gtggatgaca taatgctttt aggaggtctc ggcgggagtg ctgagggcgg gggagtgtga   2220
acgcatccaa tgggatattc tttttccaag tgacacttga agcagcctgt gactcgaggc   2280
acttcgtact ctcctggcgt ttcatttagt ttgtggtgta gtgtagttaa accaggtttt   2340
aagcatagcc agagaggtgt gcttctgtgt gtctgcaggc agttggatga gttgtatttg   2400
tcaagtacat ggtgagttac ttaggtgtga ttattaataa aaaactatat gtgtgcatat   2460
atatgaaaga gtcgacttat acttaactgc ctatcgattt tttgttctat ataaaacgga   2520
tacattggtg gtgctcagtt ttcaccgggg aatgaatttt actagtgttg cagacaggct   2580
tgttttagaa cataggccac tctgactctg actttgtgcc agtaaaagtt cctgtttagt   2640
tctttgctga catcttatag atctttggaa gctagctgct tgtgactgga gagaatattg   2700
aaacagaaga gagaccatga gtcacagtgc tctaagagaa aagagacgct caaaacattt   2760
cctggaaatc catgctgagt gttgagccct gtgctctctt gcagctcagt cctttctctc   2820
```

```
aactctgggc attttatttc taatctggat ttgtataatt aataaggaga acttttggga   2880
acaacctact aaagaatgtc atcattaaaa ctcacttaga aaataagtgt tctggtgata   2940
tcattgagct atgttcccag tcctgagagt ttgttttttt tttttttttt aaataaagat   3000
ttggggagaa aaggtggctt acttgataga acaaaatata ggaataaaat ttccttctat   3060
aaggtgaaaa gtgtgaatag aaaacttctt atcctctaga taagtagttt ctttttgctt   3120
ttgagagtct cactatgtaa ctcttgacct gaactcagag agatccatcc tcctgcctct   3180
gcctcctctc tctgggatta aaggcatgtg gcaccatgct gggctgtcca agtatgccac   3240
agaccctcta ggtccctggt cttcgaggaa cgggatttct taggcagatg ggtaaggagt   3300
cggatgaaaa tgacaatcag ccacacacaa gagaggtgtt gaatctgaat gtaatgttct   3360
ggttgagctt cagacttata taacaacgaa ttatcagagg atacaaatca caaaaagaca   3420
agatacactg aaattcacca gttacagcag aaaggaattt gcagggacta attaaatgtt   3480
tacattaggg ataacaagcc ctgcctagga tcagcctaat gccaggcaag aatttcacac   3540
tttaaggtta aaagcatcag gggttgtta actcttgaca ggccttaaga gtaatgtgct   3600
atcactgagc tctaaattct taggtctagt aaaacttatc ctgtctggag agttccccct   3660
tatcagggta gtatatcaac ttatacttga catggaatga agcctgtagt aaaacatttc   3720
tatctcagtg agacttttag tctctatctg taaacagctg agtaaaatgg caagtgctta   3780
attgtttact gaatgggtta agctccttgc tgctatctgg aatctaagaa cactggggaa   3840
aggctttagc tatgttagaa tacaatatta aaaggcattt actataaggt gatgcttaat   3900
agagtgcacg tgaatctata cactagatta atgtggtgga aatttgaata taatgggtta   3960
gggaaagaga tgccataact ctgggaggaa aatttccctg gactcttatc ctcgtgaaac   4020
agcttccagg cttttcgcct gacaaaccga tccaaactgg agagttggct ttcgccagaa   4080
tatccaggag gagagtccta gaaattcatt tctcatgagc agctttttgg catttttgcc   4140
tcacaagctg actccaccag agtaccctga cacaagtatt gtctagttat tttgattatt   4200
accatgactc tgcctctggg tgagaggaat tgtggaagtt tacatattcc ccatatcttc   4260
tataaacctc tgtgtgtgtg tgtgtgtgtg tgtgtgtgtg tgtgtgtgtg tgtatgaggg   4320
agagagaggg agagagagag agggagggag gaagagagag agagagattg ttctgtgcct   4380
gcttcgaaca caaattagtt tgcaaaagta attcattaac atgatacagt cccaaagata   4440
aaaatggtta aataatgaaa acatctccct ccccattttc ctaactttgt acccaggagc   4500
aagctctgtt acacttcatt tgtccttcca gataaaattt gggcatatgt taggacagaa   4560
ttttaaatta tttacaaaca aaagtatttt ggaacaaaag cttttaaaag cttttatttt   4620
aataaaataa cttgttacta cactgtatat aactaactaa cattttccaa aattagctcc   4680
attagcatct atctcatatt tctatgtact ttgctgttga aaaaccaagt gttcattaat   4740
aataagtaac aaactcactg cttggaagct ttgatttttg gcattttgtc cacttgactc   4800
agttaaaagt ccttttttc gaaatgagaa cagccaaaac agttttagaa tgagtctgtt   4860
ctgcttttgt gactctcatt gtgttctgta gaaccagtgt cacagccata tgtgggcctc   4920
tgttgaagta gctgagaact tgttctctgc tctgctagct gctgtcgatc tgataggcct   4980
tgaacagttg acattcaccc ttaatagtcc tcattagtct tcctgagcat agtcattcat   5040
ttatcaatat ttgctgatca tctcctatgt gcctagcatt gttctagttg caggttttag   5100
cagggaacaa agtcatgtct catgaagcta aaattcttgg gagagacata gacagtaagc   5160
agaatagttt gttcatagtg agtgatgagg cgcatgcagt aaagtaggga aggggattag   5220
```

-continued gaaatgccag ggcttgacat gttttagaca gggtgtttaa ataatatctg cttagttgaa 5280
ggcttatttt tgaataaata tctgaagagt cagaaatcta ccaggagggt gtatggaaga 5340
ggagtattcc tgcaagggga agttgtcaaa ggctttcctg tgtggggatt agtgatgtca 5400
tgtttttgct ggatgaaatg agtgacggta agagttgtag tgggggtgaa gcaaagggtt 5460
gagggaggct tcattggtgt tatcagttac tgcatttatc tccaaataga gaacgtagca 5520
atgaaagcta cagagaacgg gaaaggtgag gatttattct aagacaaaat aagtgtagga 5580
agtttaacaa ttagatcagg agcacagact ccaagtctaa gtcttcattc ttgcacattt 5640
tttaaaaatt ttgttatgtg ttctggatac tatttcctta tgagatataa gtttaaaagc 5700
ctttctgtgg attgccttgc ctttgttgtt gttgtttgtt ttgttttgtt ttgttgagac 5760
aggtctctct atgtagcctt gactgtcctg aaaatcactc tgtagaccag gctggcctgg 5820
aactcagaga tctgcctgct tctgcttttc aagtgctgat attaaatgta tgtgccacca 5880
ctgccaggct aagattgttc tttcaatttc ttttttgtt ttcttttgag atcaaagttt 5940
gctatgtact tttggctggc ctggtatatt gtgtagtcta agttggcttc aaatcttcat 6000
ggcacagatt cccaagtact gggaccatag gtatggccca tcacagtggg gggttggggg 6060
ggccagtaca tctatctctt gaatggtgtg gagtgtatat atgtgttagg ggtttgcaga 6120
ggccaaaaga atattgagtg tcttcctcta ttgctcgcca cttctctgaa taaacctaaa 6180
gttaccaatg gatttctagt aagctgactg accagcaaat attggggatc tgtctgtccc 6240
tgttcaccat agtgaggtta cagacgtgaa taaccacacc cagttttaac gctgaatgct 6300
gaagagttaa actcaggatt tagacttgcc tcactttctt atgttcttca aagcatagac 6360
attttaagtt ttgatgaagt ttaattttgt ctttagctac ggtatgttag atacttaata 6420
aatcactctt ttatctgaaa tcacaaagat ttatttactc cctctttttc taagagttgt 6480
ttgtaagcct gactcatttt gaatttgtgg ttaaggtaga tgtctgactc ttttcttttg 6540
cacgtgtaat ttagcatttg gctaaagaga atgttttttt ctcattgaac tgtattgaca 6600
tctttgttga aaattattac ctgtccatat gtaaatgttt ctacttccat ttttgccatt 6660
gattgtgtgt ctgttctatg ccagtactat acagtcttga ttactggttt atatcatgat 6720
ctcaaatcat aaagtatgcc ccccaacatt gtctttttca atgttgcttt agttattctg 6780
ggtcccttgt gattctatcc atcaatattg gtgaacttca tgaccagata gtaaacggtt 6840
aaggctctgt ggctataatg ccatcacagc cagtcagctc tgccactgtg gcatgaaagc 6900
agccatagaa aatatgtaag agaatgagta catagaattg gaatttctta aaattttcaa 6960
gtcatgaaac attcttttat tattttttt taaagaaaat gttttattta ttctttgaca 7020
gtttcatgca tgtatacaat gtatctgaat ctcatgcagg gcccctacta tctccctccc 7080
atctacacct cagcatgtcc ttctcccaca gggtccctac tctctccctc ccatctatac 7140
ctcagcatgt ccttctccca cagggcccct actatctccc tcccatctac acctcagcat 7200
gtccttctcc cacagggccc ctactatctc cttcccatct acacctcagc atgtccttct 7260
cccacagggc ccctactatc tccctcccat ctacacctca gcatgtcctt ctcccacagg 7320
gcccctacta tctccttccc atctacacct cagcatgtcc ttctcccaca gggcccctac 7380
tatctccctc ccatctatac ctcagcatgt ccttctccca cagggcccct actatctcct 7440
tcccatctat acctcagcat gtccttctcc cacagggccc ctactatctc cctcccatct 7500
atacctcagc atgtccttct cccacctcca tgcctttttt taatgaccca ctgaatccag 7560

-continued

```
ttagtgttgc ttgctggaat ggaatgttga ctggtttttg tttgtttgtt tgtttttgtt   7620
tgtttgtttg ttttccctga ggcaggcttt ctctgtgtag ccctggctgt cctggaacta   7680
ctagctctgt agatcaggct ggcctcaaac acacagagat gagtgcttct gcctcccagt   7740
gtagggacta aaggtttatc tcccacccag ttcttgtgtg gtaaccataa ctgcagtgag   7800
tttattatta cagcagccat gccatgtctg gaaggcagaa tttcattgag ctctataaaa   7860
cctggctcat aaattctctc taccccttcc cttccctgaa cctgggtgtg gggtcaatt   7920
tagatgtcac atttaggctg acatttatca gtcacttatt ctcagtatac tatgagtttt   7980
tgagttgctg cccactgcag aaagaggttt ctttggccaa ggcctgacag tagcactagt   8040
ctgtaggtat aaatgtaaat atttactctt gtttgtttat ttggttggtt tgtttttga   8100
gactgggttt ttctgtagcc tggccatcct ggaactcact ttgtagacca ggctggtctt   8160
aaactcaggt tcacttgcct ctgcctccca aatgctggaa ttaaaagcat gcaccaccac   8220
atcgggctcc caaacataaa tatgtagaag gtagtctaac aacatgtcta cttagcaaaa   8280
cagcagtagt agggtcctgt tttaggacct gtaacctcct tcccctgagt catgggcttt   8340
tgactaggtg tgtacctttg gcgcacactt taagtctagt cagaaaactg tgggttatct   8400
ttgtattctt tacatcactg ttgcactagt ggtcacattt cgcctttgtc tatattatag   8460
cattcagggt ccagtgctta gtaagaccat tgatgtcttt tctcctccag tggcctgcaa   8520
aacacctggc attataaaac ctaaccagcc aagaggaagt tttcagatca gttctatctt   8580
gatttctcta tgtcttctat gcaaccaaag tgtgttgtat cttcatcaat agggttttac   8640
tattatatag ttacattggg caaccaagag tgatagaaat aacctgtgtt gtttggatag   8700
gaaggtgttt ctgggacctc catgactaat aacttgtaag aggtatctca tgcttagcac   8760
atgttttctg aggatacatt gtcatgtaca tacctatgtt gaaactcctt taaaaaacac   8820
ttatactttt aaattagctt tcaaaatagt ttctataagt ttttttaaaa aagattatat   8880
atatatatac acacacatat atgtatacac acacacacac acacacacac acacacacac   8940
acacacatat attgtagctg tcttcagaca catcagaaga aggcatcaga ttccattaca   9000
gatggttgtg agccaccatg tggttgctgg gaattgaact caagacctct ggaagagcaa   9060
tcagtgctct taacaattga gccatctctc cagctctata agttttttt cacacatcat   9120
ttacattctg taagtaatga ataatcacta cacaaaacaa caattgttct cctgaacatt   9180
aattctggag aatctaaaat taacagtctc ataaaacctg tatgcaaatg attaacagat   9240
ctaggggtaa tagcctcaag ctggaatcag tttagaagtc gtcaataggt agttaagcta   9300
cctaacaaca agaaggaatt cagctgctga tacctgcagc agctcaggta aatagtggag   9360
attataggcc attgagcaag ctgattccta atgcctactc attatatgat tttacttatg   9420
tatctttttt tcctgtaatg ttagatcttt ggttattttg ttttcccctt gtggcaaaat   9480
aacatcacat aaaacataac cattttgagt atacaatcta tgattgtaaa aacacagtgt   9540
tccattgtga ccaccagcca ccactgttac tcttcctttt taacattgct tttaaaagta   9600
tattacaaaa aaagtatatt acaattttca cttgacattg taattgtaca tgtctatgaa   9660
tagggtcatt tttttaaaat tatacattct agtatcttct gttgcattca gttaacttaa   9720
gagcaggaaa gactggtata gaagtccttt tctctctctc ttttttttct ttttcgagac   9780
agggtttctc tgtgtagccc tggctgtcct ggaactcact ttgtaaacca ggttggcctc   9840
gaactcagaa atccgcctgc ctctgcctcc cgagtgctgg gattaaaggt gtgcgccacc   9900
acacccggcg aagtcctttt ctatgataga gagtatatcg tgggcaaatc ctaggccttg   9960
```

-continued

```
gctctttagt caaccagcat ttgtatgatt aaataaaaca ttggtgtgtg tttgtgtgtt  10020
tgcacactgg gtacagcctt tcctttatta gccctgggtg tgattttctt ctctgctgat  10080
agatcctttc taagctgatc gcttcatact tagggtgggg atagttgtga ggactgagga  10140
ggtgatgtgc ggtcctgtcc ctttctcatt ttgctagtgt gactgatatg ttagttcttt  10200
gcatgtgtct cctactctgg aaggagctgg atgggaattg tttgtttttt agtcactaaa  10260
tctagactat caggttcatg gcaagttctc aggaagtact tattacatgt atagagttat  10320
aatctgaact tgattagaca tatggcactt ttcatactcc tacttttgtt tttcaagtta  10380
tttttttcta cttaccagtt tcatgtttta aaaacttgtt tctttttta aattttttta  10440
attaggtatt ttcctcattt acatttccaa tgctagccca aaaatccccc ataccctcca  10500
ccccactccc ctacccaccc actcccactt cttggccctg gcattcccct gtactggggc  10560
atataaagtt tgcaagtcca atgggcctct ctttccagtg atggctgact aggccatctt  10620
ctgatacata agcaactaga gacacgagct ccagggggta ctggttagtt catatcgttg  10680
ttccacctat agggttgcag atccctttag ctccttggat actttctcta gcctcctcca  10740
ttgggggccc tgtgatccat ccaatagctg actgtgagca ttcacttcta tgtttgctag  10800
gccccggcat agtctcacaa gagacagcta tatcagggtc ctttcagcaa aatcttgcta  10860
gtgtatgcaa tggtgtctgt atttggtggc tgattatggg atggaacccc tagatatggt  10920
agtctctaga tggtccatcc ttttgtctca gctccaaact ttgtctctgt aactccttcc  10980
atgggtgttt tgttcccaat tctaagaagg ggcaaagtgt ccacaatttg gtctttgttc  11040
ttcttgagtt tcatgtgctt tgtatcttgt atcttgggta ttctaagttt ctgggctaat  11100
atccacttat cagtgagtac ttgtttcttt taattaaaaa acaaaacaaa acaaacaaaa  11160
aactgtgtgt aggccgggcg tggtgcccct catacttaat cccagcactc aggatctctg  11220
tgagtttgag gccagtctgg tctacatggt gagttatagg acatctaggg caacatagtc  11280
agaccctgta gtcaaaaaga accaaaactg aaccaataca aaactttgtg agctagtaaa  11340
atagtgaagt gcttgctaac attctgagtt tgatctctgg gacccatgtg gtagaaagag  11400
aggaccagtt tccacaagtt gtcttttgat ctccatgtga gtgccaaagc acacatacat  11460
gtattaaaat gtgcatgtgt aattgtaaag tttcgttacc actgacagtc agaaacgagc  11520
tctggggcct cagggttctc ttccttcagt gctgtgggaa gtgcaccttt aaacaatctt  11580
atttgggttt cttttggaga caggagttat gacagagatt aaacttggct ttgagcaaat  11640
ttcatacaca tttaaccact gaatttaacc acagtgccta ttcagttttg aatatcacat  11700
gactagaatc gtagagctcc tcctattcat aactcacact gtgtcaaagc tccttttctt  11760
cagtgttgtt ggtcacccat ttagtttgtc tgttttgtat gaatatgccc tgtttttctc  11820
atcttattag tgcatgcttg ggttattaaa ctttgacaaa tgctgctgtg aggatatctc  11880
atatgctggc ctgtcttttc cctcacaaaa tggtgctttt taatgagcag ttcccatttt  11940
ggtgacttct aatttgtcat acttttccat tatggtaagt gcttttattt ctttttgat   12000
gaatttttca tcaacttgag atcatgagac gtttcctgat actgttgcat aaatggcata  12060
ttgatttgcc caatgaagtt gacttgtttt tgtgtgtggt gtaaaataga cttcttgttt  12120
gttcttctaa tgtgggtact tctttttca ccagtttcct ccatgttctg tgtgtatttc   12180
ctccctttta ttgttattaa gtttatatta ttaaaagaat tcacattaag taggtttttt  12240
tttaaaaaaa aaactttta ttaattcttt gtgagtttta tatcatgtac cccactcatc   12300
```

-continued

```
tccctgaccc gtttcccccc tctgcccttg catccccccc ttcaaaagaa aagaaaaacc  12360
acacaaacag aaaaaccaat aatgtataga aaacatctca tagtagaaac tgtatcatgt  12420
cacagtgtgt gccactgtat acccctctgt ctgcacatct tgacatgcag atgatcattg  12480
caatgagtca ctgatctgat tcaaggtctc tgacttatgt cacaccatta atattggatc  12540
ttctccagga ctcctcttgg tttattcagt tgttactctg tgtcatcaag ttcctgcagc  12600
tttggatcag caggaccggc tcttttatgt actccaacgg ttcacagatg atgtagatgt  12660
tggggtgcgc caactcaaag ccctggatct gggcctgggt ggtagttgtg ctggtcagcc  12720
tgctggctct cctgcatctg catcaccagg gctgttctcc agcactgcta ggccactcga  12780
tgctatcatt tgtaagaagc agggtcatga ggagggagga cacctccctg ccccaaaaca  12840
cacacacacc acccaatggc agatgagtga ccagtccagc tctccctcta tctcaccctt  12900
gaggctaggt cacctgtgca cctgccacca gggccagctc tactctgctg cccagttaag  12960
attcaggacc tactctcctg agtactgctg ctggtgagag gtgtgccagc tctctagagt  13020
gccaaagcca gttctgtaca gatacatggc tgcacagacc agggacatcc ccatggtttc  13080
tagtgataat gtgagtcacg acatcaacat caatccctgc cactgcatgg ccacagatcc  13140
agacatggtc ctcagtagca gcaggagttg gtacttcacc atggcttcaa gtggcagggc  13200
tagctactca caataggctc ttcctcttcc ccctcatgtc tcagttcctt ctctcttcat  13260
actgcgcagg ctgttctgct tctctttctc ttccttctgt ccaccacata cttgcacatt  13320
gcagagactc ctgctgcagg caagccatga tgctggtatg cctctgggtg atctcctctg  13380
cttgtgctgt ttggcatggt ggcatgcaga cctctaggtg tctacagcta cccatgtgac  13440
atggcagcag tgtcctcccc cacccctctc tgcagtgtgg caggcaggtc ttctggactt  13500
ttttccctgc cagtgccctg tgtcatggca gtgggatggc agtgggtggg tctctctctc  13560
tctctttttt ttaaacacag ggtttctctt tgtagccctg gctgtcctgg aactccctct  13620
gtagagcagg ctggcctaaa actcacagag atctgcctgc ctctgcctcc caagtgctgg  13680
gattaaaggt atgtgccacc accacaggca tggcaggttc ttttggcata attatttctc  13740
actttgttct ggggttgttt aggacagagt tttgtgttgt agctcatgct ggcctagagc  13800
atgctgtggt tctcctatct ctactccctg cattctagga gtgaagatgt tcaccatgtt  13860
tggttctagt tatcttaaaa taaggaccat ctcttgctaa taatactttt cattgtacag  13920
tacattatgc cccggtctgt cttagtattt gaagaacctt tgtccttcat actgattctt  13980
atgtctttcc tagatggcat cttctgtctc ccacatagac aatattgtca catcgttgtc  14040
cttagacaat attgtcatat tgttgtcctt tgctattgga agattgaagg gttttgttgc  14100
ttaaaagacc attttgatag tctaagtgtt gctgcatgat tttgtgtgtg tgaatatgtg  14160
tgtttaagtg tagtttttca gtattatcac ttcttgagaa agtatatcct atagttccaa  14220
atcagatgtt gatttaacct tttaaaaaaa tctttctggt gctggagaga tggttcagtg  14280
tttaagaaca ctaacttgct cttctagagg tcctgagtgt gattcccagg aaccacgtgg  14340
tggctcacaa ccatctgtaa tgggatctga tgccctcttc tggtgtgcct gaagacagct  14400
acagtgtact catatacatt taaaaaaaaa aatctttcta ctcaggtggt ggtggcagca  14460
catacccttta accccagcac ttggggagca gaggcagcta gatctctgtg agtttgaggc  14520
tagcctggtc tacagcgttt caggacagcc aggactacct gtctgtcttg aaacaagaca  14580
aaacaaaaac gccaaacctt tctgaaagtg gtctaagtgt tcagcaacac tgtcatgtaa  14640
ggataggact tgacaaaaat cagagagcaa ctgttgaaga atcagaagct atgcattcat  14700
```

```
gctccaggct gctgtgcttc ttataggcag gacagcttcc agacttcagt cttgcccccca  14760
gtatggagtg tacgttacat gtgttcgtgg agggggagga ggaagaggag gggagaggag  14820
gaagaggaag aagaggaatg ttttaaaatt ccttgagcgg ttcagtctac cctcttctct  14880
taatgtggaa tcacattgtt aagattttta tttttaatta ggtgtctata tatgtatctg  14940
tatggaagtc tatatgcaca tgagtgcatg taccctgaag agggtattgg atcctatgtt  15000
tctggagtta aaggtggttg tgagccacct gatataggtc ctgggtaact gaacttggag  15060
tttttttgga ttagcaataa gcactcagaa ccattgagcc atctctccaa gccctgtaat  15120
cacatattta aaagaacaat gagtgtaatt ctaaagttaa gaatttagat atgggggctg  15180
gagagatggt tcagtgatta agaacactga ctgttcttcc aaaggtcctg agttcaattc  15240
tcagcaacca catggtggct cacaaccatc tgtaatggga tctgacaccc tcttctggtg  15300
tgtctgaaga cacctacagt gtactcatat aaataaaata aataaatctt ttaaaaaatg  15360
aatttaatta tgaaggccaa atttatattt ttagaagtag ttcttaattt gttacagtgt  15420
gctctagagc ctggatttta catgccccca caattgtgag cctgtgtaga ttgctttgtt  15480
gcacttaaaa tagtttggct gaagcttgtt ttcattttga agatgtagtt tcaagtggtt  15540
gaagagccaa ggttgttttt accctattga tacagttcct accctgagct attttatttt  15600
tcataaaaaa caaatcagtc tgacttatct ctaaaaatcc catctaattt cataaggaat  15660
gaaatagcta cagatgttta tttatttatt ttatatcaga ttttcttatt ggacagaatg  15720
aggtagaaaa aaatgttatt tcaggctggg acctaggcta ggtgtggtgg tgagggctgc  15780
agttctagca ctaagagcca gagatgaggc aggaggatct tgacttcttg agagggctag  15840
actgggttcc aggccagcca ggagtgagag aagaagaggg gtgggtgctt tacagaactc  15900
agctggaaga tgtatgccaa acacctgcag ctttatcatt tctattctgt ctctcctctt  15960
tttaagctaa agtttaaagg gctagagtcc cctgcaggtt ggagaatcta aggaatgaag  16020
ttgaaaggta gcctgaggtc aaattgattt gttgttttga gacaaagtct tgcactgtat  16080
attcaaggct cttgtcaaat tcctgattct cctggttccg tctcttgaat gctgccaagt  16140
tataatattg ggatcgtgtt ctaattggct gagaagtctg tattagaagt tctagcttct  16200
gacctgcaga gtatagcaga aggattttca ttttctgata tttttggtta gtgtcatctc  16260
tgttctgaga gtgcattctg actctcatac tttaaataag agtacttggt atgctaagag  16320
gaaatgcttg ttataagact gtaaaactat cttttattct cctggagtaa ttgtctccaa  16380
ggcttactgc ctctgtccat taacctagac ttagtaccca aaggtgctag cctccataca  16440
atctaattta tgccgagact attttcaact tctgaaactt attgctccat aagctcaccc  16500
tttcttgttc tttctgatct ctggctgctg attcaattca gttagctgtt ctggctcaga  16560
ctcctctcca agctgactga ttgaatctgg tttctctctc ttggcttctc ctgcattgtt  16620
ctgcttggcc ttacactaac tttgacaatc tgttctaatt ttctggctcc ttcttattct  16680
ctggcttgtt ctagcttcac ctgtgtctag tttgtcctct ctctataacc tgtctctcta  16740
tcacggtcca gggaaaactg cctccttcct ctctctgccc tcctctgcaa gtagcttttt  16800
ttccccccttt ttcttctggt gagagttggg cagatcctat tctagcaaat ctttctctaa  16860
ttcatcactt tgtctgctat tcaattagac ttctataaac tacttttacc ctcattgatt  16920
gagattaaag ggtgtgtttg tattccagcc agaagtggct taggtgtatg ctaagggctt  16980
agccacacca caacgagaaa taagttttgt tgttgttgtt ggttttgttt tttgtttttt  17040
```

-continued gttttttgt cagtaaataa cacaatctta gagttcattg tgtgatcaaa tatcctgcaa 17100
cataaggtct ggatgttctg gcctgaattt taaatctggc accatgagag atagattctg 17160
atagaagagt tgtgctgctc ttagaatgta cagggccaga gaacagatgc atgatggata 17220
taagaaaaga ggaacaatat cattattgta agagcaagta gatggcttgc ttttcacaca 17280
aagcaggcac ttaataacta ttgtttgaat tttaagtcaa actagcaact attgggaact 17340
agcaaaattt tatgatatta ggaagggtca aatttttcct gaaaagggtt tagtttgttg 17400
taaatagttt gggatgaggt aaaagagaaa acttgagatt tgtcttttct ttggttgtct 17460
gtgatggttt attgtcccgt ttttgacagt gacctcttag tgatgtgaat ctgtgaacaa 17520
gtgatctttg cacgtgtatg tttgtatgtg tgtgtgctca tgtgagtgta cctgctgtgg 17580
gcctgtggaa gttagaggac aactttggag agttgcattg tttgtatttg tcagggttct 17640
ctaaaggagc tgaactgaaa agatgtatat gtgtgtgtgt atgtcttagt tattgttctt 17700
tagtgatgaa acactataac caaggcaact taaacagaag catttaattg gggcttgctt 17760
acagtttcag aggcttagtt cttatcatca tggcaggatt gtagagtcag gcagctatgg 17820
tgctgagaag tagctgagaa ctcacatctg actagcagtt tgcaggcagg gagagaaaga 17880
gagagagaga ggcagagaga gagagagaca gagagagaga gagagagtca gagacagaca 17940
gagacagaga cagacagaga cacagagaga gagacaaaca tagaaagaga tacagacaga 18000
caggtccatt aactagaacc aaacatttaa gcatgagtcc atggggccat tctcgttcaa 18060
actactatat atggtatata aaatgtgtat atatgtatat atacatatat atatatatat 18120
acacacacac acacatgtac atttttaaaa gggaattttt tatgttgctt tataagttgt 18180
ggtctgggta gtccaacagt gactttcctc tgacagaaag gccaagaatc caacagttgt 18240
tcaaattgaa tgtctcggca gtcccagtct gttgctggag tcctggaaga ttcctagaga 18300
ggtgtggggt ctttagtctg tgttggagtt ctgaaaaagt aggttccaat accagtggag 18360
gaatccctca gcaacaggat aaattagttc tcaacatttg gggggtccaa cggccctttc 18420
acacgggtca cctaagacca ttgaaaaaca cagatattta tgtggtgatt cataacagta 18480
gcaaaaatta cagttatgaa atactgtacg atgagaataa tgttatggtt ggggttcatt 18540
atgacttgag gaagcttatt aaaggatctc agcattagga tggttcgtaa ccactgtgat 18600
agatggatca gctgtggaga gtgagggcac gagggcaagc agcaaagtct tccttccatg 18660
tccatttatg tgagctgcca ccagaaggtg acctagattt agggtgggtc ttcccacctt 18720
cagtaatcca atcaagaaag tccctcacag atatgcccag tgcttgggtt ttagttgatt 18780
ccagatgatg tcagttaaga ttagctgtct ccttggtcct ttcctttctg ctgttttcaa 18840
cccctccctc ctggctttgt ccctctccac tccccccatct agtcaagcaa ttttcttacc 18900
agactaaaga atttgagttc aggacatttt agatgaagct ttattatttc tacctttctt 18960
tgatctcttg attttagata cataagtgta aagttaaaga tcattgtcct ttatcttcag 19020
agttgccgaa gattcaccca agaaactagt actgataatt tctgtaatgt attctcccat 19080
attgggaatt tacttcattt gatgagctct tgtggaactc tgtatagtat gggtactgag 19140
tgctagtaat atagataaga tatggtccct tcaccttcac ttctggggat acaatctaag 19200
gcacactgtc tgaagaagtg ccagcaggag ccagagaagg gcccttggta aataagagct 19260
tcccccaagg tgcccagtgc ctcaaaaaga attatgaatt ttcatttcat tgttaagatt 19320
ggtattgtct ataagtcata gtttgataag cttgactaag tcgaaggtgg caagccataa 19380
gaggtggtat catattcttt gttgccacct ttatcctatg gggttatctc atgaaggagg 19440

```
gagagcaaga atgaatacca gagaaaactt tttccaactc atttgtatta cttcaaagat  19500
gtaagataaa tgctccatag gcctacctag tttatcagac atgtagttcg tgtgaaactg  19560
ttgggttttt ttttttttaa tctttttttta acttgtggat gtgtgtggtg tttgtatgga  19620
ggcagacatg tgtgtatggt gtgttttaca gtatggaggc ctctaagatt gatgtcggga  19680
atctccctta tctttttgta ctttgttctt cgaggcagga tctcttagtc aaactcaggc  19740
tttgatagcc agctagctca aggactcaag tcccatctct cctttcaatg ctggattcac  19800
aagtggctgc tgcattgtca ctttgcattt aaatgggttt tggggatctg gatttggccc  19860
ctttgtttgt acagcaaatg ttaacactaa gtcatctttt caggtctgat tttttttccc  19920
cttaaattct ttattaatag ccacttcctc catgattcta ctaggtgata caactccatc  19980
agtaattttt aactacagaa aagttggcat gttgacatac tgcttctgtg gacacatgcc  20040
tcataaactt gtcaaagccc gaggggacgt tgggaatctc tttatgacaa ttcccgaggg  20100
cagtagtctt tcctcttgaa agtggatgag gcctagacct gtttatttgg gcagccatat  20160
accactgatc atggtggacc tgtcaaaagt acctatttac catgctgtct gagtttagct  20220
gagtcttgtc agttacaatt gggaaagttg gcgagagcaa agggacttgg ttagtttggc  20280
tttggatccg aggtgactga aaatctcaga taatgaatgt ttccataata aatgtaatta  20340
ggtcactgag ttcagtgttg tcagccttct ttttttgttt acactttttg ctttattatt  20400
taatgaatgt attagtgctg tgctgcatgt acaccagcat gccagaaaag ggcaacagat  20460
gcccttttttg atggtcagag ccaccatgtg gttgctggca attgaaggga attgaactca  20520
gaacctctgg aagagcagct ggtgtgctta attgctgagc catctcatca ccatcaggta  20580
gcctttttgt cactacttgg tactggtgta gcatgacccc tttaagacgt gtaatttcag  20640
ttcatttaaa acctgggaca gatttttcct gtgcaaatca aaggataatg ggttggtgct  20700
ttagtttgct tcctaaaatg tttaatgggg ttagtgttct ggaagcatcc taatggctat  20760
tttaaggtag gtaaaaacct aagctgttgc aacagaggct tattacaagt gatttagaga  20820
agaaagcatt ttattctcat agtattttct ttacagtgtg aggaaatgtt ctttttggta  20880
tacaattctg agatttaact aatgcaatcc ctgtgactac cataatcagg attcataaat  20940
ttactattat tatatggtgt gcatgtacat gtcaagtgtt tgagtgtgtg tttgcatgtc  21000
ccatgtgcaa aggaatgcgg gtggaggtca gaggacaaca ttagagttaa gtttttctat  21060
tgtgagctcc agggattgta ctggctagtt ttgtgtcaac ttgacacagc tggagttatc  21120
acagagaaag gagcttcaat tgaggaaatg cctccacgag atccaactgt aaggcatttt  21180
ctcaattagt gatcaagggg gaaaggcccc ttgtgggtgg gaccatctct gggctggtag  21240
tcttggttct ataagagagc aggctgagca agccaggtga ggcaagccag taaagaacat  21300
ccctccatgg cctctgcatc agctcctgct tcctgacctg cttgagttcc agtcctgact  21360
tcctttggtg atgaacagca gtatggaagt gtaagccaaa taaacccttt cctccccaac  21420
ttgcttcttg gtcgtgatgt ttgtgcagga atagaaaccc tcactaaggg atcacatgca  21480
gatcctcagg cttgtgtggc gagtcatttt accatctgag ctgtcttgct tccataatca  21540
ggagttaggt tggttctgtc gctacccgaa gctccctatg ctgctttgct gtcatctcct  21600
caccctgaca ttactggtca tattttaatt cttacagttt tgatttgttc taaaaataga  21660
atggccctgt gttggttgtc ggagtcttac taagttcttc ctcaagtgta gtgcattgtg  21720
atctgtcctt gtttcctgtt agtagttact tccttttctt agatacgttt ccattgtttg  21780
```

-continued

```
gctattgctt ttgtttatct ttcagcaggt ggatgaggag cgcttgctag atttccattc  21840
tagcattgct gcagtgagct tcttatgagg atgggaggtg tgggagcctg tgcttctgaa  21900
gatgataaag ggacccacga tgctgccgtg ctgctctgca ctcttcttat tgtctttatt  21960
tatataattg acactcgagt gttgggcatg tttgttctga ttggaggaag atagcttgga  22020
cattcagata caataggaat tctgtatatc acttgcattc ccaatacatt tatgggagga  22080
agttatgtgc ttgtgttagg caaattttgg tgggtgacca gcagtttacg tgaccggtca  22140
gaaaaagtct ctttctggga agacataagc tacttttttt tcacatgtct gacttttctg  22200
agtgtcgtgt gaggaagctc ttagtagacc tcatctgtcg tcatcccttc ctcatgctgc  22260
cctcttccca gcatggagtt tatgattcac tagtagtagc caaaacgtac ttaggaatga  22320
atgaaatata gaaacaaacg aagtagtcac ctcagtggat gctcatttct tttcctcttg  22380
ttttttgta gaaagaagga actctcagcc accaagaaag accgtgtgaa tcattgtcta  22440
acaatatgtg aaaacattgt ggcacagtct ctcaggtaat tggcttttta aaaaaaagat  22500
ttatatattt atgtatatga gtattctgct tgcatgcatg cctccatgac agaagagggc  22560
atcagatccc tttatagatg ggttgctggg tagccagtgc tgagccatct ccccagcctc  22620
ttcttttctt tttgttttg gttatttttg ttgttgtttt tctttttttg tttaaaagat  22680
ctctctggta attactgagt tgggtggtgg tggatatacc tgtaacctgg cattcaggag  22740
gcagaggcag gcagatcttg gtgagttcag ggatagcctg gactacagag ccagtaccag  22800
gacctacaca aagaaacctt taactcataa aaaacagaaa acaaagaaga agaagaagaa  22860
gaagaagaag aagaagaaga agaagaagaa gaagaagaag gaaggaagaa ggaaggaaga  22920
aggaaggaag aaggaaggaa gaaggaagga agaaggaagg aagaaggaag gaagaagaag  22980
gaagaagaag gaagaaggaa gaaggaagaa ggaagaagga agaagaagaa gaagaagaac  23040
aacaacaaca aactggttgc tgggctgtgg tagtgcattt ctttaatccc agcacaacaa  23100
caacaacaac aacaaactgg ttgctgggct gtggtagtgc atttctttaa tcccagcact  23160
tgggaggcag aaacaggtga ctctcaaggc caacctggtc tacagagtga gttccaggat  23220
ggctagagct tacacagaga aactctgtct tgaaactcca ccccacccca aactatatct  23280
aaatactctg tgttttcact attaatgcat taccatgttc tttgtacccc tagctatctc  23340
ttaaaagttc atttaggcta agcgtatttt ggtacatgct tgcaatccca gtatttggca  23400
ggctgagaca ggaggatctt gaatttggta ttagcctggg caacatagca aaaccctgca  23460
tcaagaaaaa tccatttaaa atcaggacgt tttaccacat ttgtagttgt gctataaggg  23520
tatctgggtt ctcttatagg aaatgttttc ttcttgtcat cttatatatg agaattttag  23580
tcatatgata attgaatggc atgttagtaa tttaatttgt attcttttaa ggtttattta  23640
tttttaaata aatgaatgag tgttttgtcc ctattttata tttgttccct gtatgtgcct  23700
ggcacccaca gagaccataa gaaggtactg gagttcctgg aactggaatt aaaagatggt  23760
cataagttgc tgtgtggatg ctgggaaaca aacttaggtc ctctctgcaa gaatagcaag  23820
tgctcttatc tactgagcct cctactttct gtttgtttgt ctgagacaag gtctcattta  23880
gcccaggatg gcttcaaact cactgtatag caaaagatga ctttgagttc ctgctcctct  23940
tcttctgcct cctgaatgct tagactatag acctgatctc ttagagtttc tattgctgtg  24000
atgaaatacc atgatcaaaa gcatctttca cttatacatg tgtgtaacag tctatcactg  24060
tagaaatcag ggcaggatct catacagact gtggaggggt actgcttgct ggcttattct  24120
tcatggcttg attggcctgc tttatagaag ccaggagcat gagcccaggg gtgttcccat  24180
```

```
ccacaatgag cctggccctt ccccaccaat cattatttaa gaaaatgcac tatagactct   24240

tctgcctaaa gtcccatttt atggaggcat tttctcaatt gaagtttctt caaagacgag   24300

tttagcttat gtcaccttgg tcagaaaact agctaggaca cttggcttta gaatatagct   24360

tcaatgtcaa aattcccat aatcaaaact gaaagtaaat tcaacttggg gattgtattg    24420

gcaatttata taaattaaag gcttaatagt ctgtagggtg aaccattaca gagcagagta   24480

ttatcctaat aagaaaatac ataacacaca cacacacaca atacacatat ttcaagaaag   24540

aaatttgact tggctactac tcaggcagag gcaggaggtt catgacttag agacttttta   24600

tagagccctc tttcaggctt tataaaagca tgacttcttc tcaaacaaaa aggaaagaag   24660

gaaggaatca gggtgggctc aatgtttatt tcgtgttttc tatattagaa gttcatcttt   24720

attagttatt atggactaaa tgtgtatctc cccaacccgt ctgtatgttg aagatctaat   24780

cccccattct gaaactgaaa ccaactatgc attttagtag gttaattcag tgttttcttg   24840

aagttaatct cacaacccac atagttatac agctttgtct catgggctgt tcttcatgta   24900

gtagtcacag gcttgtggga ggccactgag tgactaatct gagatttgaa tgacctttct   24960

ccttaggttg aggagtttgt ggtgtgctag cgtggcttgc agaactcaag aaaatactaa   25020

cattttctgg cttgctacaa agctatagct cagtagcagc cagattgtag agactcagag   25080

ggtaaggtat gggagggaag catggcccct ctgtgctctc ttcttccagt cttccatgtg   25140

tctcagcatg gacttctgtt accagaacca ggagcttgat atgtgttgta ctttaagcat   25200

caccattcac attggcaaca aaaatcatca gaattttttt cagagggaag acacttgggg   25260

ccataataga gacagattaa agtggtgtct taaaaataaa atctgaccac aataaaaatc   25320

aatcagaaat gcaacaaagt ataggaagtt acaatttgta acaagaacag ttagtcaatg   25380

ttggcccaga aattaaacta ggttagcata cacaagcact aaaacagtat aagaaacatt   25440

taaacagttt aacttttttt ttttttaatg tctaagaagc aaaaggttga gggtatggga   25500

agaagaaaca agacaggaaa aaggctgagc ctgaactaaa ataaggagac agcctacttc   25560

ttataggaaa tgcctgccaa aatccaggga agtgccatct gtaagtcatt ctatcctcag   25620

taaaaatctc ttgtaaaatg aaaaggtgaa ataaagaggt tctcagacat acctctgagg   25680

agtaccctct gtctgacaag cagtgagttt aagacatttt aaaggaagtg tttcaagcag   25740

atagaaaatt ataccagata gaatctggat ctgtccaaag gattgctagc agatggataa   25800

acataggaga tgtctgtctg tctgtctctg tccctctctt gatccctctc cccctcccct   25860

ctctcagaca agattatgta ctgatgtaga actagtgatc ctcttgcctg tgctgcttgg   25920

gtgctgggat tacagaaatg tgtctcatgc atgcagcagc aacctgttgc atgacagaca   25980

acataggaac aaatgtttgc tcaactcata gggaagcatt aacaaactaa agtatagatg   26040

cctctaaaat ccaatttggt gaaccagtgg atgcataagg gttacttaca gtggtatggg   26100

tgagtggttc cttataggat catggatgac tcaaaaggca tcaccaaaat cccaccctgg   26160

catgggacac agctcactaa agctagaacc ctggaactct ctgcgcaact tagacttcag   26220

cagttcagga atccccctcc cctcagcagt ccttactact tatataaccc aggagtctta   26280

gtcagggttt atattgttgt gataaaacac tgactaaaag caacttgggg agggaagggt   26340

ttatctcagc ctatccgtct acatcacagt ccactgaggg aaaggaactg atacagagat   26400

aatagaggag tgctgggggg atggatggct cagcaggtaa gagcactgac tgctcttctg   26460

aaggtcctga gttcatagca accacatggt agctcacaac catctgtaat gagatctgat   26520
```

-continued

```
gccctcttct gtggtgtctg aagacaccta cagtgtactt aaataaataa attaaaaaaa  26580
aaaaaaaaga gtagctctgc ttactggctt cctctcatgg tttgctctcc tgcttctttt  26640
ttatatgcca attgtgcagt tccttttttt tttatattgg atattttctt tatttacatt  26700
tcaaatgtta tcccctttcc cggtcccccc ccccagaacc cccctatccc atcctccctt  26760
ctcctgcttc tatgagggtg ttcctccacc cacccagcca cccaccaact cccacttccc  26820
tgcccttgat tcccctatac tggggcatct atcgagcctt cataggacca aggacctctc  26880
ctcccattaa tgcctgacaa ggccatcctc tgctacataa gcagctgaag ccatgtgtac  26940
tcctttgtta atggcttagt ccctgggagc tctgggggtc tggttggttg atattgttgt  27000
tcttcccatg ggttgcaaa ccccttcaac tccttcagtc ctttctccaa ctcctctatt  27060
ggggacccca tgctcagtcc aatggttggc tgcgagtatc tgcctctgta tttgtaatgc  27120
tctggcaggg cctctcagga gacagccata tcaggttcct ttcaacatgc acttcttggc  27180
atctacaata gtctctgggt ttgataactg tatatgggat gaatccccaa gtgggacagt  27240
ctctggatgg cctttcattc agtctctgct ctatactatc tccatatttg ttcctgtgag  27300
tattttgttc tcctaaggag gactgaagta cccacactta ggtctttctt cttcttgagc  27360
ttcatgtggt ctgtgaattg tggtctgtat cttgggtatt tggagctttt gggctaatat  27420
ccacttatag gtgagtgtat accatttgtg ttcttttatg attgggttac cacactcagg  27480
atgatatttt ctagttccat tcatttgcct aagaatttca taaattcatc atttttaatg  27540
actgatagta ctccattgtg taagtgtacc acattttctg tatccattcc tctgttgaag  27600
gacatctagt ttctttccag ctcctggcta ttataaataa ggctgctatg aacatagtgg  27660
aacatatgtc cttattatat gttggaatgt cttctgggta tatgcccagg agtggtatag  27720
ctgggtcctc aggtagtact atgtccagtt ttctgaggaa ccgccaaact gacttccaga  27780
gtggttgtac aagtttgcaa tcccaccagc aatggaggag tgtttccctt tctccacatc  27840
ctcaccagca tctgctgtca cctgagtttt ttatcttagc cattctgact ggtgtgaggt  27900
ggagtctcag ggttgttttg atttgcattt ctctgatgac taagggtatt gaacatttct  27960
ttaggtgctt ctcagccatt tgatattcct cggttgtgaa ttctttgttt agctctgtac  28020
cccattttta atagggttat ttggttctct tgagttcttt gtatatattg gatactagcc  28080
ctctattgga tgtagggttg gtaaagatct tttcccaatc tattggttgc tgtttttgtt  28140
gttgttgggt ttttttttgtt tgtttttgtt tttgtttaag gtcacatttt taaattcttg  28200
atcttagagc ataagccatt ggtgttctgt tcaggaaatt tggggacaga gagtcattgt  28260
gaatctgata aacttcaggg acttcctaag atttctgggc tgtttccttc cttgagtctc  28320
tttgtttctt tgtttgtttt ttgaaatgga gtttctttag tccagccagt ccttaaatgt  28380
actatttaga tcaggttggc cttgaactca cagagatttc ctacttcttt ctcctgagta  28440
ctgggattaa aggcatgtgc caccttgctc agccactttc tgagtcataa caagcattcc  28500
ttcagaagtc cctgactctg aaaaagcttg ctatacagca caatcttttc tttttctttt  28560
tttctttatt ttatgttgat tggttagttt tgtgtgtgtt atgtcaatgg gtatgcattg  28620
acatagtgct tgtgtgtaag tcagaagcca actttcaggt gatggttctc tttttatgat  28680
gtgtgttctg aatattgaaa tcaggttatc aggcaggcct gctgttattt gctgactaca  28740
tgtagaaagt atattttaga tatgtctgtt gagtaattag ccttacttct ttcttattat  28800
attgatgcta ctggaaggaa tcctgagccc atgcttagag ctgtcattaa tttctgtttt  28860
ggcactgcta agactgatgt ctgagggaaa gcctctagtg tcagactttc cgcctttcat  28920
```

cctagtttat tactgtattc ctttccagta aggtctatgg cattgctgag tgacatgtct 28980
ttttgctctg tatgtgttga gaattattga tcccttttct ttctcttagg tttatggatg 29040
tctttcaatg ccttttgagc cagagtctca ttgtgtagat ctagcttgcc tagaactcat 29100
aaagatcccc ctgcctctgc ctccctggtg ctgggattaa aatcacatgc tagaattttt 29160
taattagagg taaaagagaa ggtgactgta tagatcatag tcctttagat taagatccta 29220
gtacaacagt ctgcttttga tgttttagaa atggcatgcc ccattcttaa gtcaccagaa 29280
tcactttcaa atatgccttg tgttacaggt ttgagatact ttagagtttt ccactcaagt 29340
ggcccaccag cctcctcttc taatgggcgg gcttagcttg ttggatcatg acataccaaa 29400
caggttttct caactaaact tactaaaata ctttacaaat agtacccaga ttgtgatacc 29460
agtattcggt ttcttgcaac agaaaagcct gtaagcctgt ggaatctagg gaaatgtagt 29520
tggaccttta tgcacattga aagtaagatt gaaaagaaat aaaggagatg tattgacttg 29580
ctgggttttc aaggcttcaa ggatgctatc taaaagtaaa tctacctttt tacaaagcat 29640
atgattacct gagatttgag aatcctagac agtatcttct aaagatgttt caatgaaatc 29700
ttaaaaagaa aaggggatca gtaccaatat gctgctcacc acagtccacc tttacgccga 29760
tattcttaat ttttatgaaa tgttctttct tgtcctaaaa ttccatttag attgctcttt 29820
gcattttgtc atcagttctc ctagatctgt catgacgatg acaacctctc tctctctctc 29880
tctctctctc tctctctctc tctctttttt acttagaaat tctccagaat ttcagaaact 29940
cttgggcatc gctatggaac tgtttctgct gtgcagtgac gatgcggagt cagatgtcag 30000
aatggtggct gatgagtgcc tcaacaaagt catcaaagta agcgccccat aatgatgata 30060
atggtgatgc gtgctcctgt aattgtcatg ccttaagaga caaagctcca gatacctaca 30120
ttttttccat tttgggcatg tggcttggag gacctggggt attttcccat aaacagctaa 30180
atgtgttcct gcggaacttt tttttttttg cacccttata gttcataggt ccattctgaa 30240
gggcatctgt gtgaccactg gctgcctatt tcttaagagg aatgtctcta tgggctgcca 30300
cttttgtttg ggcattgctt ggagaacctc agagccctgg gggcacaaag gtgggtgtgg 30360
ggggaatgaa gtcttgcatg ccttccttca tttcttttcc tgcccctctt agtggaggtc 30420
agacaatact gcttgttggt gaagatgtag cttctcaggt taggttaatt ggaggtagca 30480
tgacctgaat ggggagagag gagagtacag acaggagaat ggagccagga agcaatagcc 30540
actcaggtgc agtgccagaa gaggtgaaaa ggctgggcac ctgtctcact atgtcattgc 30600
ttcctagtac tgagtgcaga ccactgcaac tccagtctgt ttctttgttc agttttctgc 30660
tatgaaagaa gattgaagtc ctccttcccc gccctcatcc taatgcaggt gggcattagg 30720
aagggcagag agaacaatgt gactctaaat tgaccatatc cttgttactt caagtgcaag 30780
cagcttttcc tctcaaacct ctcttctgcc gtggctgatg ctggtcaggt tggcttggtg 30840
catgtttgag gccacagacc actgttgtag cttgcagctt tatgttctgg atctttggct 30900
gcctatctcc actttcttcc tgtttctttg tggtttctag tcaatgtcag gaattccagc 30960
ttttacagca cagccctgag tcaggccaat cttcattctt tcccttctgc ttatagctgc 31020
tttcatgttt ctgccttttc aactgctgca atgttcagga taagccagta aggtggacca 31080
ggatccagct attcactatg atagaggaaa ggcgaggcaa gatgggagaa tgggatggct 31140
tcaggccaag tgtagggaat ggttcacttt ctagtctggg acttttcttt tcttgaaaga 31200
attagtgtat gtactataaa gaccaatttc tagccccgaa aatgggcaga tattacttgt 31260

-continued

```
cttttatgtt caaaatacat tgagttctga tagccaggat gtgtattcct gctttcaagt  31320
cttgggtggt aaagtgaatg tgtccagaac tcacccatgg tataaaatgc agagcagaaa  31380
gaaggtagta attttttttt ttcccaagaa gatagaagtg gtattctgga gtcaggaaag  31440
accctcccat ttttacctac tacctggagg tttgtctcag agaggagagc aggccctttt  31500
taggctgtga aaaatggtgt gtcttgaggg tcagtttaag tattttgtgt cttggtagaa  31560
aatgaaggcc tcttgcagat cactggcttt gtgtggaagc cagttttgat agggaatgaa  31620
aagaaggacc ccagctgagg ggaaggcatg agctaggatg gtgtcagagt gtgttttgtc  31680
agctatgtgt ggaggcaggt tgggagttgg gggtaaagga agctataatg agctctatta  31740
tcaccccatg aaggactcat ggaagagcca tgctctaccc ttaacagagt tgagcttttg  31800
ttttctctac tacaaaataa agtagatttt ggttcataaa catttatata gctcaaacag  31860
tatttgatgt actcttaaat ttcatttgaa agtagtcttt taatgtttgt cagcatggtt  31920
tgcttctttt gttcaaacta cagcagcaga atcagggtct gaaatttcct ggtggggcca  31980
gagagattgg ttaagaagag aagttactgc ttttgcagaa gacctgactt cagttcccag  32040
taccataaga tgtcgtataa ccacttgtaa cccaaatttc agggggtcct gtgccttctt  32100
ctgacctctg tatgttcctg tacatataca tacactcagg cacacataaa atgaattttt  32160
caaaaaaagt tggtagaatg ttatacttct tctgaatcaa ttttccaaag tgtgcctctg  32220
ttttaccttt gaaactcatg gcccagtgaa tgatccctgt gtcctagttt catctctttg  32280
gctatgataa atatcctggc aaaaaactga agggagaaag aacttgattt agaacttcag  32340
gtaacagtcc atcattctag tgaactcaaa gcaactagaa cgcaaagcag ttggtcacag  32400
tcgcagtcaa gggcagaaag gaaaagaatg tgtgtgtgct tgttgctcag ctgtcttcct  32460
ctactttaat ctgtcctagg tctaaaactt aggcagcggt gttactcatt ttcagcattg  32520
gtcatctcac atcaattaag gcaatcaaaa tagtccctca caaatatggc cacaggacaa  32580
cctgatctag acaggatctt aatgagacta ttcccaggta atctaggtta tgtcaggttg  32640
acacagctaa ccatctcatc tctccttggt ctctagatat caggtttgca tgtgcctgaa  32700
aaggagagct gggtcacttc ctcacatttt tttgacatgc cattttagaa gagaaagttc  32760
ttagggacaa gaatagggtg attttctcta atgtggactt tatgctatta gccttgattg  32820
tggctcgaag tcagatacat gaaccttatg ttttagttag agttttattg ctgtgaatag  32880
gcaccatgag tacagcaact cttgtaagga aaacacttag ttggggctgg gtcacagttc  32940
acaggtttag ttcatcatca tggtgggaag catggcagca tgcaggcagg catggtgcta  33000
gagaggtagc atagaattct atatctgcac tggcaatagg aagaaaagac tgccattggc  33060
cctgtcttga gcatctgaaa cctcaaagcc cacccccagt gacacacttc ctccaacaag  33120
gccccaccta ctaatagtgc cattccctat gggcctgtgg agccattttc agtcaaacct  33180
tcatacctta tttctgagtt agccccaaag tgatcaggaa aggtcaagaa atgagctctg  33240
aggactgtaa gacttcctag ctgacactga gacctgggtg ggtcagggag ttggggctgt  33300
gagcatcctc atcattttgc aagtttagaa cttcaaaaaa agatgattct gttgttacat  33360
gttccctgtc agagagaagg gctcagatcc tacaagtaca atcctcatat cttgcttact  33420
tagagacttt cacctgagct gtccaggtga gccagtgaag actgtgtgct tactctgaaa  33480
gctttagggt taattttaat ttgatattat atagtatttg attactataa atgttatctt  33540
ctgtttttat cctggtaaag acctgtattt agaatattct gtaattttta tatgtgttta  33600
ctttttctt aatatatagc ttcttattta gttgctgtta atgttacttt tccttaaaat  33660
```

ttgaactttt ggttaccatt tagctttatg ggtagaattt agatctatag gtagaatgta 33720
tcttctataa caagtctctt ctatttcttt gcaggctttg atggattcta atcttccaag 33780
gctacagtta gaactctata aggaaattaa aaaggtgggt gtttgctctg cattattgag 33840
aagatgatac tgttttactg ttgagtaccc tatgagattt ctaacttgca agttattaaa 33900
taacactgtt aggaagaagt gccatttggt gaagcagagt ttagttttct ttaaaaacgt 33960
actcctcatt ttcattaatt gaaatagaaa tttatagcac caccttaaat tttttaaaga 34020
ttttttttg ttttattata tgtgtatgag ttgcctgtgt gtacatctct gcaccgtgta 34080
tgtgcagtgc cttttgaggt cctctgcaag agcagcaagt gctcttaacc cctgagctgt 34140
aactcctagc aaccaagcaa ccaaccaaca acttacttct cttctctctt ctcttctctt 34200
ctctctctct ctctctctct ctctctctct ctctctctct ctctctctct ctctctagca 34260
tgaccccagc cagttctgag gttgaaggca ggtttccccc ccatctactt ttataatatt 34320
ttagttacat gcaagtaata aggttaagca gtacaataga cacaaacagt caaggaacaa 34380
gctaggcaat aaagaaagtc tcttgatcac tcccgtgatg actgtttcta agggcttatc 34440
tggatgacca aaatatctgg gcctacttcc ctgtcttagc tcaaagtcat attcatgcct 34500
gaagcctgtt ctagcctaaa attacattcc tgcctgagct tacttccttg tcatggccta 34560
gtgtcagatt tctgctaagt ggtcccaaaa agctctccac atctccccct tttttatttc 34620
ataaacaaga ctgcacctgt cttaggtggt tctaacaaga atgccttcct tacatgtcgt 34680
ggaatatcta ttatcaaagt cgtgcatttc tgtcttaggt tggtaaggct ctgtgcagaa 34740
cttacccgtc agcgtcaatg gctgccggcc tattaaatta ataattctgt ctgggggttc 34800
atttttagtt tcaaaccatg tattttggcc accaacatgt tgatgctatt aaaggcaagt 34860
tttattacag tgggcaggaa taaaaatatt cccaggacaa aaagggctat catgatcaag 34920
ctatatgtgc cattcttgaa gcttgaccaa gatggaaata ctgacatata ttcatgaata 34980
attttatcga caatacctgc agcgtcagag ctcagcagag taccattctt taaattcata 35040
atctcaatat gcaaaattaa aacatccaga gaggtgttag aattatgcca aatactcttc 35100
aagtgtcttt caattttccc aattatattg actctcattg taaattttag aagtaacaca 35160
aatcccttgg tatttcgcat aacacttgag atggcttctt actcttaaac tctaaacctc 35220
ctctcataat ttgaatatta tcaataaaga gcataaacca ttgtttcgga cacctatcta 35280
aatcaatctt tctttcgttc ttccttttct ttttttaaat ctgtattttt ataattgaag 35340
ccctctggat tttaaaaatc tttgaagtaa ttaccatcta tttcacactg ttaattttga 35400
ctttctctga ttaaattaac agagaaagag aatgtttaac tctccaagag aggatgcaag 35460
cagctccaat atcatagacc tagctgtaga aagtgcatgt gactcttaaa tgtaacacat 35520
cacttgttaa ctccacttag aatggtgctc ctcgaagttt gcgtgctgcc ctgtggaggt 35580
ttgctgagct ggctcacctg gttcgacctc agaagtgcag gtaagttgta cctctgtatt 35640
atttttaaga tttgtttggt aaatagctag tcctgcctgt cttttttgtt ccagtgcata 35700
tgtctacacc ttgagacatc attcttgtcc actctgtgtt gcctagctat gtcctgtctg 35760
gttgctgtca gcattttgtt cttatatttc tttccaaaga cccatctcta ttaggaatac 35820
tcttatgtcc tctattaatg tgcttctttc ttgtcccatc attccccaag agacttgtgg 35880
gatgtatttc cagagtaaca tagtctcacc atcttattct gtgcttcatt tccaacacga 35940
atgtagtgag cactcaatgt gttggttaag gaatacttac tggatgaatg acaactgtcc 36000

```
ctgatcccat cagcagcaga gttagcaatt attgaaaaat aatcatttgt atagtacttg  36060
ggttggagaa gtagatgaac tgtgcataaa atttgaactt gttgattgtc tttgactcct  36120
atggtgttag gtattaaatc caggagctca ggcatgctag gcaattgctt tactgctgag  36180
tctcattgtc agcccacaca tctggctttg tggcttgagt aacaaaacag gattgtagtt  36240
ataccgttct ttcctttttc tcctcagttg gtaaaatgta ctgcgtatgt cccaaagact  36300
gtatccgtga gaaacatagt agagtgctct aaatcttcac actaacaagg aacaatgatg  36360
tgttcaattt aggttaagtt tcagtaagaa ttttatgtgg ccagaaagat gtaaccacga  36420
aggaagtttc tttctataga acttttactt ttgctctgct gatatgttta tttttgtgtt  36480
ggctttggtg ctaaggctag gcatgcctaa gtgtgcgctt ccacacttcc acatttccag  36540
ctcaagtgcc ttactttgaa aattgtcata ttattgaggt aatacatccc aggtttacaa  36600
cacagcagac aaaatagctg ttcaaaagta tgactgtcct gtcacaggcc cttccttaaa  36660
ctctcttaat tattccctag tgttgtttag ataaaatcta gacttcccac tcaaggcaag  36720
agataattta gcctttgctg gccctttcct atctcatcac taaagaaata ctatattgat  36780
tcattgatcc aatttagttc ttcaaatagg ttttatttcc tcaagatagc ttgatgtctc  36840
agaaaataat cacctccttc tgcaagcatt ctagcctcct tatcttctaa gttgtaactg  36900
atttctgcct aacaaagatg gctgtagtat ctgtaggcct aattgctata taagagggcc  36960
ttggccccac tatagcagac accctactcc atcctcgttt ttctgtctaa ggtaaggaat  37020
tgttgtttga agtccccatt taatttgacc actttttac ccctagagat tgtgcagctc  37080
tcctggagag cataaaagaa acttgtgttg atttctaatt aaaagaagct gggttaccaa  37140
acaaaagtcc cataatgtct ggcatgccaa attaatgggt ttatttggct tatatacaaa  37200
agcacggaca acttataagt agctatgcct ttgaagcttc acctccagtt agtttgcctt  37260
ttacataact cagtccttct aaggttatgt atccctgtag tacaaaggaa tgatgattgg  37320
aatcttgggg tcttatgaca ttttcttttt ctccccaaaa gggagtatta tcagactatc  37380
ccatagacct aggcacctgc tctgtagttc tccttgcttt gttgtctgct tgtggctcca  37440
aggtctccat ataagtcacc acagctactc tgcttcatgg tagggatggt catgtcaagt  37500
gtacaggaaa cagctagccc acagtagctt ttaacatgac tttttcagta aaatgatgtc  37560
cacattttat tttgtttttc aaaagttact gtataagggt acataccagt acctgtatat  37620
agaaaggtaa gaggagtgtc attcctgggc atggttcctc aggagctgtc cagcttgttt  37680
gataagataa agtcttcact gccctaggat ctgctgatgc gacttggctg gctgcccctt  37740
aacctcagag aatcactggt ttctgacttc ctagtgcagg gattacaaat gagcactact  37800
atgtctgggt ttttatgtgg atgataggga tcgaactcat atcctgtgct tggtgcataa  37860
gctatctcct ttgttccctc cagtttgtgt ttttaaagta gtagttttta atctattgtt  37920
tcctatttaa attatatttt aataattgct ataatttgtg acaaattttt taaatattta  37980
tctttaatat ttttttacag tccagtcttt atccctctcc tgatctgccc tcccaaagtt  38040
tttcaaaccc aaaaaaagaa gaaaaagaaa ttggagagat cgtacattag taacttaaca  38100
gaatacctga aagccctaga acagaaagaa gcaaacgtgt ccaaaaggag tagacaggag  38160
gaaatagtca aactcagggc caaaatcaac caaagagaaa caaagaaact gataaaagaa  38220
tcaacaaaac caaaagctgg atctttgaaa atcaacaaga tagataagcc cctagccaaa  38280
ctaaggggca cagagacagt atccaaacta acaaaatcag aactgaaaag ggagacataa  38340
caacagaacc tgaggaaatc atcaggtcct actacaaaag cccaacaaaa ctcaacaaaa  38400
```

```
ctggaaaaat ctagatgaaa tggttgattt tctagacata taccatgtcc taaagttaaa  38460
tcaagatcat gtaaactatc taaacagtcc tatatcccct aaagaaatag aagacgtcat  38520
taaaaacctt ccaaccaaaa agaagcccag ggccagatgg ctttagtgca gaattctacc  38580
agaccttcaa agaggagcta ataccaacac tcagcaaata ataatttaaa tccaactttt  38640
taaattacat tttatttgtc tgtgtgtctt tatatgtgta ccatgccttt gggtgaggat  38700
aacttatagt taattcttcc tttcctctat gtgggtccca gagatcaaac ttgggtcttc  38760
aggcttctcc ttctttaccc acaaagccat cttgcttgtc cctacaccca gcttcttaat  38820
attctttgta actcatggga gagatgacag acaattgaac ttcatcagca tttatgcctc  38880
ctgtacttgt agttgagcat tgtggtctcc attgaggact aattcaccta taaaactagg  38940
tttttcctg acagggaacc atgagcttgt tgtttcttaa cagaggagac ctgaagaatg  39000
atgagtattc ctcttgcaca tacaggcctt acctggtgaa tcttcttcca tgcctgaccc  39060
gaacaagcaa aagaccggag gaatcagttc aggagacctt ggctgcagct gttcctaaaa  39120
ttatggcttc ttttggcaat ttcgcaaatg acaatgaaat taaggtatgg ctgttgcctc  39180
ttggcatgag tcttgtgtgg ctttggggag aaagtcattt gagattgctt ctggtgtcct  39240
tttggcttca ctgagagaca tctcaagaac ttctttttac ttctgctttc ctttcatggg  39300
gtaagttgtc aagggaaata gcttatagat gcaaattcaa aggcatttcc ccagagtgga  39360
tttaggtata ctgggttggc cacttgagcc agctaaggaa aagagacttc ataggaaaga  39420
gtgaagaaga gttaatgggc cttgtgggtg tgggcgccct aaagccacca ggactcgagt  39480
ttggttcata gtgcccagaa agcaacttat tacataattt gtgggttgca agattcttgg  39540
ctttgatttt atctttttga aaaagtattt tttttttaat ttatttattt attatatcgt  39600
tacggatggt tgtgagccac catgtggttg ctgggatttg aactccagac cttcggaaga  39660
gcagtcgggt gctcttaccc actgagccat ctcaccagcc ccagtttta tttttaaagt  39720
atttatttta tatgtttggg tgttttgtca atgtactgta tacatgccta ctgttctcag  39780
aagccagaaa agtgttggat atcctagaac taaagttata gatgattgtg cgccaccaca  39840
tgggtgctgc aaactgaatc tggatcctct gaaagagtaa ctagttctct taagccctga  39900
gcccactctc cagcttctac cttttctcat tgtttatctg tgtaagtgcg tgtgcgtgtg  39960
tgtatgtctg tctgtctgtg tgtctgtctg tatgagcctg tgtgtgaatg gaggctagaa  40020
gaaggtgcta ggtgtccgtc tttatcactc tctgcctgtt ctttttgagg ttgagtttcc  40080
ctgaacctga ggcttacttt tttttttttt ttaaattgga cattttattt gtttacattt  40140
caaatgttat cccctttccc agtttccctt ctgcaaaccc cctatcttat caccaccctc  40200
accctgcttc tatgagggtg cttatccacc cacccaccct cccactcact cctgcctcac  40260
tgccctagca ttcctctaca ctggggtatc aaacctttat aggaccaaag gcctcccctc  40320
ctattgatgt cagataaggc ccctttagct ccttcagtcc ttctcctatc tgctccattg  40380
gggtccctgt gctcagtctg atggttggct gtgagcctct gcatctgtat tggtcaggat  40440
ctggcgatac aggagatagc tgtatcaggc tccggtcagc aagcacttct tgacatcagc  40500
agtagtgtct ctgggtttgg tgtctgcatg tgggatggat ccccaggtgg ggcagtctct  40560
agatggcctt tccttcagtc tctgttccac tttttgtccc tgtatttcct ttagacagga  40620
gcaattcttg gttaatattt tggagatggg tgggtggctc aatccctcaa ccagggggcc  40680
atgcctaacc tctgaatatg gtctcaacag gttctctttc tcctttgtgg ggtatttcag  40740
```

-continued

```
ctaatgccat ccctgtgggg tcctgggagg ctcttgcttt cctggcatct gctgctgctg  40800
tcagtgttat tcctccctcc ttggaggggt ggaagctcct gatggtgcag aaatgagtac  40860
tgcaatactg tcaagagtct ctgtgataac tgctgtcaga gccaggggac aggtgtatac  40920
acacacacac acacacacac agtggttggt tctggatctt tccatgatat agatgccatt  40980
tgagtaaggt aatactttcc tttttttttt tttttttttt tttttttgta tgtatctgta  41040
gctgtacaga tggttgtgag cttcatgtgg ttgttgggaa ttgaatttta ggacttctgc  41100
ttgctctggt tggctgtact tgctccggtc aaccctgctt gctcaggccc aaagatgtat  41160
ttattattat taaaaaagta cactgtagct gtcttcagat gcaccagagg cagacatcag  41220
atctcattat gggtggctgt gagccaccat gtggttgctg ggatttgaac tcaggacctt  41280
tggaagagca gtcagtgctc ttatccactg agctatctct ccgccctccc ccccatactt  41340
actaactact tccttcatga acctgtgaca tttaagagat ctagtcattc ttctgcccat  41400
gtatcattgc tgtgctctag aaacaaatag tgccaccctg tcctacttat cttggttctg  41460
tgtcagaggc aaacaataat gcttgcttcc ctgggtttag atttttaaat tttacatttg  41520
ttttttaact gtagaagagg tgaatttggc tctaacactt gtttcttttt acaatagtcc  41580
tgtatatatt gaatatgtac tttattatgc ccttatcaat agtgatggct aatcgtatat  41640
gattttgaac accttttttgt tttctaaacc taataattat tggttgtttc tgaagtctca  41700
aacagaagtg ccatttctta ctcgttagct tgctcaatag atggcctatc tcctttggca  41760
gttatcgtcc cacatcctgc ttaatatggc cagtgattct tgagtttgta aattctgtca  41820
tcctggagac tcctttactg ctctcctctt tctggctgct gtcttctgtc taggtttgct  41880
tcccaaaggg ttgtgcagga agcagttggg atttgacatc cctaaaaatt cctttggtat  41940
gcagatcact ttttcctcag gagaattcaa tctttgtttt gtagtacaga actggaagat  42000
cctgtccaca ccaagaggca ggatccccaa ggagttaggt gtgtggtgta aagagggacg  42060
cctgtaagga ggctgcagcg gacagagtgt ctggagagat ggggttctag gtcttatgta  42120
gtagtggagt ctccacagaa tggacccaca gtaagaggac acttgcacac aggctgccat  42180
agtactgggg gtgatatcct gagagatgga actaggatga aaattgccag agtctcaccc  42240
tggtatggac tggggggggg gggggtgtcg tcctcacata aagtgtttct cggtaaacag  42300
gctgacatga aggaatgggg aagggctaga aggtagggct gagagggtcc acaggaaaga  42360
gtaactctga gtttcccttt ttaccattct tacgtgtgtg tttatttcta ttagcacttt  42420
tattggtctg aatatcattt gtggggtgtg tgggatgtgt gtgtgtgcac gtgcgcacgc  42480
gctatatcat catcagctag ccatacaaga tatacagaga catacttaca atcagttgca  42540
gccaccaatg aatgtatcac cagtggccct gaaactgaca atggcagttc tactatggaa  42600
tgtgctatga agtcaacagt tagttaggct aagtgtggaa atagtgagtg aatgagataa  42660
aggagggaca taggcaaatg aaacaaagac aagagagaca aggttaaata aatgaaagga  42720
gaaggtggag gggtcaggaa gaacattatg ggcttattct ggagattact aggaatatct  42780
tctctgtgat ttcttagaaa gtggtatgtg gtatgctgtc atgcctataa agttgcaggc  42840
ttccactcac agaggcacca gtctagggag gatgttttag tacagcagca cttctgcaga  42900
aaagtcttag gccagattat cactgtattt gtctagtgct ttttccttat tattgtcaag  42960
ttttttaaaa aatttatata gtgttcttac tacctctgtt ctggtatacc acgagtagcc  43020
tatagacact gagactgaca cagtgaacaa gttcctgatg aatgtgtgtg tgtgtatttc  43080
ttattcatgt gggttctgag gatggaactt aggccatcaa ccttggctac aaattccttt  43140
```

atcatttgac ctagcacaca gccttcctaa tgcgattaat aaggaagtaa atatactgct 43200
aataaatact tggtgactat tgaaaatttg gtatttttttg ctccatctat gaaaaatgtg 43260
tcatcttgtc acagttttttg tcctataagt tttagaattc tgtgaaatgt gtaataagct 43320
ccatgggagc ttcagttttc atcatcttgg ttttgtttgt tctcaggttc tgttgaaagc 43380
tttcatagca aatctgaagt caagctctcc caccgtgcgg cggacagcag ccggctcagc 43440
cgtgagcatc tgccaacatt ctaggaggac acagtacttc tacaactggc tccttaatgt 43500
cctcctaggt aagagagaaa gggcctgctg gcccagtctt agcatctgct caatcttcta 43560
aactacactg acccttgcca tcatgattag accatttgca gctgctgact gctaaatgtg 43620
aagtgtgtag gggatgttgc aagcccataa atggtctcgg agacttttca gctgcggctg 43680
tgtctctagg acacccagct ggtacacaac ctcatccacc ttcctgtcct tctgtatcag 43740
aggcctgagg ctatgcttca gcacgctgtg ggtactctag ggaaactgac attcccctac 43800
cccctctctc ctgtcaaaat caacatgaac aagtcttgct ggaatgagca tatggacatt 43860
tgatacaact ctctgaattc cacatggaca tttgatacaa ctctctgaat tccacataca 43920
gttccactcc ctataaggtc ctgccaagct aaggatatat tttatgctgc aaggctgctt 43980
ttgatctgag tgtgcacagc ctgtgtttct cagtctcgct tatgtcacct ttccctttta 44040
ctgctaggtt tacaacaggg cactcctgta ggtctccctt tttcaccagc atgtactgtg 44100
ggtctctgag cagtggactg gctgttgagc ccctttggtt gtctttgcag gtctgctggt 44160
tcccatggaa gaagagcact ccactctcct gatcctcggt gtgttgctca cattgaggtg 44220
tctagtgccc ttgctccagc agcaggtcaa ggacacaagt ctaaaaggca gctttggggt 44280
gacacggaaa gaaatggaag tctctccttc tacagagcag cttgtccagg taagggtgaa 44340
tagtgataag ttcatgtggg acatgaaaga agtagcatct ttccgcaagt gctgggacag 44400
aggaagtagc tgggagatgg tgtgttcctt ttgctgctga ggagtcagga gatgtgtgtc 44460
cacagatcag gtatgagttg tttgcttaaa acagggagca cacatgtttt ccacaaaggg 44520
ccagagtgta tgtgtgttaa gctttgcatt ccaactatct tcactgaact cccccagtga 44580
tgtagtttga gccacaaata gcccataaat gtggccatat tccagtgaga cttcatccac 44640
agaagcaggc acacaatgaa ggtacagttt tgtatgcctg tgaccccagt acttggggtg 44700
tcaagagaaa agtacaagtt ctgcaaatgc ctggcctatg taggaacccc aagctctctg 44760
tagctgtacg atgagactag atctcaaaaa agccaaaatg gggagtagaa agccagatgt 44820
ggctgtggct agcagtttgc cagtcaggat ttaggggcat gcatatgcat acaggttgcg 44880
tgagaagagc taaagctaag ccttaaggca gcttcctggg aggctttcgc tcttcctttt 44940
ttattctaca ccaaccttta aaaaataaaa tgcatggttt tggttttttt tattgtacat 45000
tggtgtttgg cctgcacata tatctttttg agggagttgg atctactgga agttgattta 45060
cagactgttg taaactgcca tgtgggtgct gggttccttt gcaaaagcag ctcttaactg 45120
ctgagccatc tctctagcct gcatttgttt attttttgct tttatcttac caactaatgc 45180
tagggttggc aaactttgca aagtaaaaat atagagtgcc tgtgaagcat tgattttata 45240
tagtgattgt ataagaatgg ttaaaattgt ccaggatata attatttata ttgcaaaatt 45300
atgtgttatc tgaaatcaag gtttaaactt gtgggctttt ttcccctggt aaatttaaag 45360
aaaaaactaa caaactcatt ctttctatag tatggtatag tattaaaaac accaaaaaat 45420
tttgactgcc atccttaaca tgtgtggcta ttttcccccct ggcattcaga gctgtgtttc 45480
tgatgatcgg atgtccccac ttgcttccat agcagtgtcc attgggatta ttgtcttttc 45540
tgttcatcag ttttgggaaa tgaagatcct gagtttgctt actggtgttc tagaggaagt 45600
gctctatgta tttccaagga gttactataa atgaaaatta aaaaccatag gaattcagaa 45660
aatagcacag acaataataa ccctacctat ggaagtaata ggtctttaca gggaaaaact 45720
aaggcacaat tttgttgaca aagaccagtg aaaacaaaag tgaaatctgg gatgcttatg 45780
tatttattaa ttttgttttt gtttttaagc attttaagat ttatttattt tctgtgtgtg 45840
ctctgtctgc atgtacacct ctgtgccaga agagggcatc agatcccatt gtagatggtt 45900
gtgagccacc atgtggttgc tggaaattga actcagaacc tctggaagca ccagggcagc 45960
ctggattgca gaatgagacc ttgtctcaac aaaagaacta aaaacttcca attcactaaa 46020
ccagcaaatg cattcttttc tatgacctga ttagcgctta gctgatgatg gatgttgtct 46080
ttgttggcag ctggggctga gtgacccatc tccttcaccc ccctgtcatt ccagcacctg 46140
ctttctctta accgctgagc catctctccc gccctgggat gcattttaaa catgatgtaa 46200
gacctgtgtt tctgctccta ggtttatgaa ctgactttgc atcatactca gcaccaagac 46260
cacaatgtgg tgacaggggc actggagctc ctgcagcagc tcttccgtac ccctccacct 46320
gaactcctgc aagcactgac cacaccagga gggcttgggc agctcactct ggttcaagaa 46380
gaggcccggg gccgaggccg cagcgggagc atcgtggagc ttttaggtgt gttctcagca 46440
aggtcttcta accattgtgc atggaggcat gtttccttct gttgctttat ggggctgtac 46500
tgcgctgagc tacccatgcc gaaattcctt gcccaagctt acaatgtagg cgtcttgctg 46560
cttttgcaaa taaatctaca gtttagaaag ctagatgaca caatgaggcc acacctttaa 46620
agcttggtct cctgcctttc tggcttgtca cctccatttt ggatgcagtg aaatagaaat 46680
attaggcagt ttccaggact ctcatgtttg attgtcaggg atgaatagat ttttatgtct 46740
ttttttggga atttagtgtt ctttttctac ttggatcctg actttagaga accctttcta 46800
ttcctcatcc ttgaagatac ctctttaacc tggtctcgtc tttttgatgc tcaaagagtt 46860
tgatccatag actaggcatt ggcagcctga cctgtctgac atgagctagt cttagatggt 46920
gggacagata ggaatctggg cttgccagcc tttagaagtg acctggcatt tagcaggctg 46980
tgacaaattc tgctgaccct gacttatcat ggcttgccac agtatataca ttgaggagcc 47040
atatttatta tagctacaca ttagagacag tctgcctggg aaatactatt gtgaccttgt 47100
gcgcttaaaa atttgcctgg actatgagca gaaactgttt tactgctgtc cttgttaaag 47160
aatttttatt tttgtggaaa gtatgtcata caccctggta actgtttcca atgaaagctt 47220
atgtctggcc tatgcttgtc caataatgtg agatcttaca gttttaattt ggcttttaaa 47280
gagcagttta tatgagcttt tttgacattc tagtcatatc tttaaaactg tgtatttgaa 47340
catgagtgta attttcacct ttaaagtgtg acactgtggt gtttaaacat gtcctatgga 47400
aatatgtcca cattgtctgt tttaggattt gagttaagct ttttgaggat ttttgaattt 47460
cttgcagatt ttagcagctt gtaatcttac tttcttgtta ctttctatga tttacagctg 47520
gagggggttc ctcgtgcagc cctgtcctct caagaaagca gaaaggtgat tatctcaaaa 47580
tctgagtctt gtgttgagtt gaactgctgt ttctgtgttt gcataatgca ctagattctg 47640
cttatatttc ctctcaggag atgaagtgta tggatattgc tggaatctga cattttctgc 47700
tgtttaaaaa ttgtttatat cacattatgt ctaatgttcg aggtcaaagg tcagcaaact 47760
ctataaggga ccagagaaca aatattttaa acatgcaggc tatagactct tttttgttt 47820
tgttttttgt ttttttggat ttttgagaca gggtttctct gtgtagccct ggccgtcctg 47880
gaactcactc tgtagaccag gctggcatcg aactcagaaa tccacctgcc tctgcctccc 47940
aagtgctggg attaaaggcg tgctccacca ccacccagcc atgctataga ctcttgcagc 48000
tgtttccctg gcttgtgact gctgaagaac aatggtatag aaactgctgt gtctagctgt 48060
tttccactaa aatcttaaag atgcagctgg gctcagcatc actttagaga gtgcaccact 48120
atactttaga aaagtaactt ctgtttttttg cttgtttctt tttaaacatt tatttatttg 48180
ttttatttat gtgagtacac tgtcgctgtc ttcggacacc agaagagggc atgcgattcc 48240
cattacagat ggttgtgatt cccatgtggt tgctgggaat tgaactcagg acctctggaa 48300
gagcagccag tgctctctcc aacctaactt ctcttcttga tgaattttat tattaggcat 48360
attaaatagt ttattttgtt tggttcttca ttttgttcat gcctagttat cagttttcag 48420
acatatttaa cttcttgcat atgtgttttc tgacctattt ttattccaga gtttctgata 48480
tgacctgata gttttatata cttggtcact ttgcagcagc tgaaatttca ttttatatta 48540
tgaatttctg tggaaaagaa ttgctgtcat ctttattttt aaaatcttaa aagatgagtt 48600
tgttttcttt gtcataattt gagcatttaa aacttaaagc tcagtattat ttgctatgtt 48660
aagtgagggt ttgtgtgttt ttcctttttt taagttttga gacggggcct tactgtgtag 48720
tgtgagctgg ccttgaactc agtatctctt cctgtacttc ccacttgcta ggatgacagt 48780
acacctcact tttgagtaag ttcttcccag gaaaaacatt gtagttgcca ttgaattaag 48840
agaacattta cttgaagaat ttgggagcta gatgttaccc ggaggctgag acagaagtct 48900
tttgggcaac tgggaagacc ttgcctctta aagagaaagc cgaatgtttg atccattgct 48960
gtaagaaata ctgattttag aaagcattgc caatgtttaa aggagagtag aattctaaga 49020
aatattactc tctattcttg atctaggaga gatcactggg cacttggtaa aatcactttg 49080
ataatttact ccacagtcac tttgtccaga gatggggaca aaggtgatgt tattgagata 49140
agttctcatc tttactattt cctgaatctc ctgatgattt tttatttaga ctggtgattt 49200
taaaactttt tttgttataa tgaagattct gttttttca agtgttgtgt tggctagttt 49260
ttgtcaactt gatacaaggt agagtcattt tggaagtagg aaccttagtt gaaaaaaatg 49320
tcctcattag aaaggtctgt ggacaaacct gttatgcatt ttcttgattg atgatataga 49380
aaggcccggc ttaaactctg ggcactgcca cccttgggct gttggttctg ggttctataa 49440
gaaagccaac tgagcaagcc agtaagcagc attctccaag gtctctgctt cagttcctgc 49500
ctccaggtcc cttccccaat tcccctcagt tttttcccaa gttactttttg gtcttggagt 49560
tttatcacag ctatagaagc cctaactaag acaagtgtaa tctgccagat ataagataga 49620
taaaaacaga gttgtggagc acatagacct cagcaaaggt caaagggggc caggagtctc 49680
ttctctgttg gcagcccctc tcctttttcc atcttcatgg gatctgccct gggggaactt 49740
ttcccagatc ataatcagcc actgacttgg agagtagaaa ctgcttcatt aaaattcaaa 49800
ttcactgttc ttgagtttta tttgattatt ttaaaccaca tgttttgtta ataaaaggtt 49860
ctgtttgtat ttatgtctag ttgctgtgtt gatttttgca tagatttgtg ttctctttgc 49920
taattagctt gtgcctttaa tgttatatca tgtaatttca tggaaagtat cacagctctt 49980
attacttgaa gaacagtaac atgagaagct aacagctaga tagtatctgg tttagttttc 50040
ccgtgtatga gaatatacct gaagtgaata acttcaaggg aaagatttac tttggccact 50100
gtttcagagg tcttggtctg tcacagcagg gcagatttgt tcgagcagca accagaaggc 50160
aggttgttat acctgtgttg gtgtgcttcc tctaagtttt ttatttcaac atgagaacaa 50220

-continued

```
tgctacccac accaagcacc agtcttccct tttagttaac cctctctgaa aattccctaa  50280
gtatatcttc tttcaatcaa gctgacaagt tcaaagtgta acttgatgtc aattaatgtt  50340
tatatataat gtaactgtaa agatattaaa tctgattttt cttcctaata taactatata  50400
agctataagg tatatttcta aaattctact aggaaatatt ttgtcttttc agatttttag  50460
ctactgtgta gactaaaaag ataataaaat gaaagtgact tatttatatg ttggagtttg  50520
acatacaact tcgtatttgc catggatatt ccattagaac atggatatcc caaggcctga  50580
ctgatagaat tggacctttt cagtcataag ctactcattc atttattaac tggtagtaaa  50640
ttatttaact acaacagtaa tctaaatcaa taaaaagtta ttatgtggta tagttcaata  50700
gtaattactt ctgcctctta attggtttta cagtattcta aaagttactc ttttatccat  50760
cctttaacat tgtagtaata tttaatttat gatggataaa ttgtactatg gtaaattaaa  50820
tatgcctgtg attttcaatt cagaatatat gcttatttga tttttgtctt ttgagataga  50880
gccattatat agctttggtt tggactaaaa ctcactgtgt agatggggct gacctcacgc  50940
tcatagaaac tggcatgctt tctatctcct gagtgttggg agtaaaagtg tgcaccatca  51000
tgcctgacta tttattcaag ctaaaaaaac ccaacattat ttttagcaaa actaaaaagg  51060
aatattgctg tattatttac taggcaaagt gctcttagga gaggaagaag ccttggaaga  51120
tgactcggag tccaggtcag atgtcagcag ctcagccttt gcaggtactc ggtggcagcc  51180
atgagctgcc agtgtcagcc tctagttatt atccgccatc tcgtgctcct ttcagcacct  51240
cagcctgcac acagcattgc gagcagcttt tataattcag ctgcttttat aatgttcact  51300
ctaaatgtgt ttggctatgt gcttttcttg ttttaggcta ttcaaatatt gatttattat  51360
ccttgagcat atccttttgg agtggatgat agatggagtt gtctcctgaa ttaaatggtc  51420
tatgatcagg acagtgggtt gaagaactgt ctgggtaatt taacttgaaa ggatatattt  51480
ttgctcacaa gtggttacat aagattcttt gtgttttcta taaaacacag gtattatttt  51540
aagacactaa taaatagata aaatgcaaac agctttagtt atgtttgctg ttaggtaaat  51600
aaagataaga caaagatcct tggggaggaa acctgaataa tgtcaatgga ttttccctgc  51660
ttacaagata aacaagtcac aggacagaaa ttttgggctg cctagactag tgtaaaactc  51720
aagtgcctct gacccagttt ccttcatcac aagccactgc tcataccttg ttcatggttt  51780
tgaagtgatt ttgtttttat atttaatgtt ttgttttata agacaaacca tcctgtcagc  51840
attctgaaag ctcgctttta ttggtataat ctcagtgttc ccaaccatca gaacctttca  51900
ttccctgcaa tgtaaatcaa ccccccccctt tttttgcaa gttcttccaa acgtctaagg  51960
atgaataaat gttacatact ggattttact attatagaat ggcactgaag tgactttgat  52020
ctcacatagt gtttgtaaga gggaatttca aaattaaact aggaaaagat ggagtgtgtt  52080
tatcctagag gaggttagga ttggagtgga gatgaacaac acgacttgga agaaagcaag  52140
ctgatcctaa agggtactgc gctcactagt gttctgttgt tgcctatgta gagtttctgg  52200
aagtctgctt gtccctgccc cagctgcttg tccctgcccc agctgcttct cagcaacaca  52260
cattctatgt gtggctttag agatgcagta agagcttcag cttgaaaata ttcacagcca  52320
tgaagaattc acttgttcac ccagctgaac tgtgctcctt gactttttct tcactatgct  52380
ccaagctgtt taatagttag aacattcaat acagtgaact ttttgtcatt ttgcacagtt  52440
ggattcctta gctacagttt cctctggcca tttgacaact gagtttctct gtgtctctag  52500
cctctgtgaa gagtgagatt ggtggagagc tcgctgcttc ttcaggtgtt tccactcctg  52560
gttctgttgg tcacgacatc atcactgagc agcctagatc ccagcacaca cttcaagcag  52620
```

-continued

```
actctgtgga tttgtccggc tgtgacctga ccagtgctgc tactgatggg gatgaggagg  52680
acatcttgag ccacagctcc agccagttca gtgctgtccc atccgaccct gccatggacc  52740
tgaatgatgg gacccaggcc tcctcaccca tcagtgacag ttctcagacc accactgaag  52800
gacctgattc agctgtgact ccttcggaca gttctgaaat tgtgagtggg cagagggtgc  52860
cctggttctt ttgtcttctg agcttattct tggatgccca cacttggacc ctcctgctca  52920
tttttctgt gttactacac ataatagtaa gaggccccca gctcagatgg ttaacagaga  52980
gccttgttgg atgtcttcac tgtagaaatt gcctagtatc atttgtattg agccatggag  53040
attaaagtga ggttacttat atgcaccttg tacacatgat atatttttaa tacctgatta  53100
ggcctgttta aataactact ttcaattttt caaggagctt gttattgaaa gtatctgtgg  53160
tcttaatgtg ggtggtgata ttagtactct gtattatttt tagcactttt tgacctctca  53220
atgtacttat accacattcc attttaaagt aggatgtgca tatttctatc cctgtgatgt  53280
ctgagttcat agacaggaat caccttaaag attatataat cagaaagttt ggtgcaagtg  53340
tgtgctgaat tgtggggtat tttttgtttg tttgtttgtg tgttttgttt ttttaaactt  53400
gcttgtcact ttgttttttt gttttatatt tctgaaacag ggtcctagcc caggctgacc  53460
ttaaatttga gatctgcctg cttaagcttt ggactcttgt gaatgtgggc atgaaccaca  53520
cttggcctgc attctaaata gtcattttct tctcctcttc ctctttctct tcttagtgta  53580
gtaaaatagc aaaattatct catagatcat tcctacagtt aagtggtata ttaatcacca  53640
ccatacacct ccattaagtc ttcatcttct gaaacctgac cttctgtaaa ggctgtgccc  53700
tcctggaagc cagtggtctg tttttttatag tacaagttta aggactgtag gtccttcatg  53760
cagtatgttt atcatgaagt attatccttc tatggctgac ttacttaaca taatgcctcc  53820
atgtagcatg tgtgagaatt ttcatttttt aagggatgat taatattcca ttgcatggat  53880
agaactacat tttgattatt gtctcatctg ttagaaaaca tgtgggttac tctcacatct  53940
tgacaattat ggataatgtc acaattatga ataataggtc tactaagtat ttcaaagact  54000
ctgttttcaa ttcttttggc tatacaccta aaagtagaat agtttctaca tccagcttta  54060
agtaatgtaa ttaaatgctt agctactata gaatatgcat atatcttgat atatatgtac  54120
tatagaatat aatagtctat atagaatata catatattac ataatatata acctatatat  54180
attctatata gagcctatac ataggtcttt ttgagacagg gtttctttgt ataatagccc  54240
tgagtgtcct ctacctactt tgtagaccag gctggttgaa ctcaaagaga tccacctgca  54300
tctccctccc aaatactggg attaaagggg tgagctatca cacccagcct agaatattaa  54360
aaaaaaaaaa aaaaaaaaaa aaagctggtc tttgtgacca cacacttttg taatcccagc  54420
tctgggaagg tagaaacacc caaatgggtg agctccaggt tcactgagag accttgactc  54480
aaaaatacca taaagaacaa ctgaggaaaa cacctgacat tgacctctca cctccacacc  54540
catgcttaca aatatgcata tacccactgt ttgcttgtgt taccactcca cctcaaacct  54600
cctccctcca ccccccatac acattccaca tacacagtct tagttcggat tttattgttg  54660
tgaagagaca ccatgacaaa gccaactctt tttgtttgtt tgtttgtttg tttgttgttg  54720
ttttgttttg tttttgtttt tcgaggcaag gtttctctgt atagccctgg ctgtcctgga  54780
actcactttg tagaccaggc tggcctcgaa ctcagaaatc cgcctgcctc tgcctcccaa  54840
gtgctgggat taaaggcgtg cctggctaca acaaaggcaa ctcttaagaa ggaaacatag  54900
ggctggagag atggctcagc agttaagagc actgactgct cttccagaga tcctgagttc  54960
```

aaatcccagc aaccacatgg ttgctcacaa ccatctgtaa tgagatctga caccctcttc 55020
ttgggtgtct gaagacagct acagtgttct ttaaaaaaaa aaaaaaaaaa aaaaaaaaaa 55080
aggaaacata attggggctg gcttacagtt tcagaggttc agtctattat catcatggca 55140
ggaagcaagg caccatgcag agcaagtggt gtctcttaag ttctgggcta ccttgatcta 55200
caattgagtt ccaggacacc cattggtaca cagataaacc ctgtgcctgt gtcaaaccaa 55260
accaaaccaa accaaccaaa caaaagaggt tgttaggtca catacacgtt aaagatgtcc 55320
taagaggttt taactatagg ctgcagttct atctttgagt tctcactggg tttactttgc 55380
tgttctttcc agcaactttt ttaccacaga atctgtctgg gcatgggaag tatatataaa 55440
tttaatgcag ataacctatt gttagactta tctggaagcc ttgtcttttt ttctaactta 55500
ttgtacagtt tgttcaggaa gacaaggttt taaaaatatt aactcattga gaattgcatg 55560
cttgtatttt gaggtttacc cctcatcttt ctgactaact actcccagat ctactttcca 55620
cttctctttc caaccttatg tctttttttt tcaatttttt tattagctat tttcttcatt 55680
tacatttcaa atactatccc gaaagtcccc tataccctcc ccccacccag ctcccctacc 55740
cacccactcc cacttcttga ccctggcgtt cccctgtact ggggcatata acgtttgtaa 55800
gaccaagtgg cctctcttcc caatgatggc cgactaggcc atcttctgct acatatgcag 55860
ctagagacac gagctctggg gtactgacta gttcatattg ttgttccacc tatagggttg 55920
cagacccttt cagcttcttg ggtactttct ctaactcctc cattgggagc cttgtgttcc 55980
atcttatagc tgactgtgag catccacttc tgtatttgcc aggtactggc atagcctcac 56040
aagagacagc catatctggg tcctttcagc aaaatcttgc tggcgtatgc aatagtatct 56100
gagtttggtg gctgattatg gaatggatcc ctgggtgggg tagtctctgg atggtccatt 56160
cttttgtctt agcttcaaac tttgtctctg tacttttgta atatcaaaaa tgtttacaaa 56220
cagaaatttc tttacgtttt ctagagctat aaaaggttgg tatgaccttc tcctgggga 56280
gacaaacaaa tatctgatta ccacagatag gataccagtg acagaccaaa gtaatgattc 56340
cacctaagtc tagtttgaca agccagttag tttatttaac actacttcaa aggaacacaa 56400
gccacggcta cccaccaggg catgcgcaac ttataaacat ctataccatt gaagagtatg 56460
tttatcccag cgatcattaa ccacttatat atccttagga aggagcaggg ttccacaagc 56520
ctatccccag aatgttactt cctatctagt gcaggccttg tccaggtggc atcccacagc 56580
aaagcttttc ttgccatagt agtgaagagc tcttgcttgt tgcttttaac acatgcattt 56640
acctgtggcc actgactagg taattgccct ttgcattctg tatgtgttac tgatgcaaca 56700
tggtctttgc attctgcgtg ctcagctctg ttggtggctt ttccttcatg ttgaagggct 56760
ttcccctgac agtccccctt tatctgtaca ggtgttagat ggtgccgata gccagtattt 56820
aggcatgcag ataggacagc cacaggagga cgatgaggag ggagctgcag gtgttctttc 56880
tggtgaagtc tcagatgttt tcagaaactc ttctctgggt aagctcttat atgatggaaa 56940
tgtttttagc cttagacatc tttatctttt cttgtttgtt tgtttgtttt tgtttgtcca 57000
gacggagttt ctctttgcag cattagctgt cctggaactt actctataga ccaagctggt 57060
ctcaaacttg gaagatcttt atgcctctgt catccaaatg ctgggattaa aggcatgaac 57120
caccactagc cagcgagact tttttatctt tatttcaaaa agaaaccttt tggtatcatt 57180
attttttaaa ttgaaaatgg cattaatttt catttcaatt caaaatgaaa atggcaattt 57240
aggtataatc agactgattt aaattggtac ttgtatatta tctctatata aatatataca 57300
tattttgatt ggacttgtca cttatttatg atttctattt ttaaagccct tcaacaggca 57360
cacttgttgg aaagaatggg ccatagcagg cagccttccg acagcagtat agataagtat 57420
gtaacaagag atgaggttgc tgaagccagt gatccagaaa gcaaggtgag cttcatagga 57480
aggaacagct tgtgtgtgag gggttggaat tgttctggct tttgccaatt ccatttgttc 57540
ctagcccatc tctggcttat ttctttcccc tagaaacact ggacactccc aggccttgtc 57600
tgtttatgcc tcaccaggga tacccaaact cttaacagtt gcattagttc tgcctccaga 57660
gactcctccc tacacagatg caccctgtgc tgagctccac cctgcctcat ttgaggcttg 57720
tgcagagctt tgcagcagtt cttgttttg ctcactcaac tgattaaaac acctctctct 57780
ttctctgttt gctttacaag catattacat ataaatttac agttaactta aattccttaa 57840
ggtcaggaat atgttttgtc atttaattgt atcatcaaaa ttacttcctt tgagagtgct 57900
ctaggttctt ttatatcctt tcgacctttt ttttttcag acagggtctc actatataga 57960
cctggctgga ctagaactca tagttttcag tagacaattg tgccttgcca atgtgaacag 58020
cctttcctga atgctatgtt ttagcacctt cctgtctagt gaaccttctc catactaagc 58080
ttgtctcttg ctgcatccta cggccctgtg ttttagggtt ccagttacgt tctgtttgag 58140
atcagctatg gggtggccca agcataggca tctctgtgtc tagcaccctg atgtggatta 58200
ctttcgtgac tgaactagtg aatcaaatgt ttacttctct gttctagcct tgccgaatca 58260
aaggtgacat aggacagcct aatgatgatg attctgctcc tctggtacat tgtgtccgtc 58320
ttttatctgc ttcctttttg ttaactggtg aaaagaaagg taagcatagc agagtaggta 58380
cagagttgag gggacactta caggttcagg agtcagtttg ttggtctgtt ggtgtctggt 58440
tattggggtc gtttactttc catttctgct gtcagaggga gggaatgaga gggtgagttt 58500
tgttccttgg aaaaggctaa aggggcctgg gtggttcctt tgcagcactg gttccagaca 58560
gagacgtgag agtcagtgtg aaggccctgg ccctcagctg cattggtgcg gctgtggccc 58620
ttcatccaga gtcgttcttc agcagactgt acaaagtacc tcttaatacc acggaaagta 58680
ctggtatgtt acaattcact ttttttcacc agctaatttg tacttaagct atctcacagt 58740
cttgccttct tttgtcttag agtagtgttt ctaggtagct tatatgtttc agctgtgtta 58800
gaactctcca ggtgtgcata tggtcatgtt cttagtccca tgactcccct atgtgtagtt 58860
acatacaaat gactacataa gtcataaagt agaaatctgg aaatgtgaaa gttatttata 58920
cacatactta tttcttctta aatcataagc tgcattgtta aattgctctg ggccacatcc 58980
atattaaatt gctctgggcc acatccatgt tcaggctaag cctggtcagg acagcaccgt 59040
gacactgggt ctgcttttgg acatagttgt tctggagtag aaagtatctg ccaccttctt 59100
tctttctttg agtgataagg caaatctgtg ttattgagtt taaagataac aaatatataa 59160
tagattgatt gtttctgatc tttattttca aaagaaatgt cagaagcttg attttatttt 59220
ttaatttttt tttttttatt tttggctttt cgagacaggg tttctctgtg tagccctggc 59280
tgtcctggaa ctcactttgt agaccaggct ggccttgaac tcagaaatcc acctgcctct 59340
gcctcccgag tgctgggatt aaaggcgtgc gccaccacgc ctggcttttt ttttaatctg 59400
acaacctgga atcacaattt agaaatcctg acgtattgag ataatttcaa cgtgagaact 59460
ctagaaacta aatcccaaac atcttttact acttaggaaa ttatagtcag gtcctttgca 59520
aatgttccct taagcttgct tcatttgtat ataaatttga tgatggaaga aggtacagct 59580
gggccattta tgtccgcaga ggaacagtat gtttctgaca tcttgaacta catcgatcat 59640
ggagacccac aggtccgagg agctactgcc attctctgtg ggacccttgt ctactccatc 59700

```
ctcagtaggt cccgtctccg tgttggtgac tggctgggca acatcagaac cctgacaggt  59760
aacgggacag tttgctctgg tgtcttttct ggatactctg cccatgttca tgtttctata  59820
gagatatttc ttgctcattt ttctggttag gaaatacatt ttctctggtg gactgcattc  59880
ctttactgca gaaaacgttg aaggatgaat cttctgttac ttgcaagttg gcttgtacag  59940
ctgtgagggt gagtacaatg ctttacataa actgttcctt gccttagtga gcttaccatt  60000
gatacagtta aatttggagc ttaataggtc acatttccgt aagttgtaaa cagttctttt  60060
ccgaaattta ccactcagcc tttgaaaaaa cgttgccatc atattaaaat tcattaaaac  60120
ttttaattct tggactcctt atttgaaacg ttcttttctc taaagatagt gtttagaaat  60180
ataccttttgc tattttgaaa tataaagttt gttgaataat tacaattact gttttaagat  60240
actagaatgt tgagctgcaa tgaaattatg ggtgttattt aactgggcct ttactaaaag  60300
agccttgatt cctcaagtga cagtaaggtg aaacatttcc tattagctgc atcataagtc  60360
acaattgggc attcagtagc agaaaattta actagagaaa atcaaaacaa aaacagtgat  60420
taagtctcag gaagggacta tcattctttt tagaaatgta atggcctcaa agtagtgttt  60480
ttctagatct aatttttttaa aaagatttta ttttttttaat ggtgtatatg tgtgtgtgtg  60540
tgtgtgtgtg tgtcagagta tgtcagagtg tgagtttcta tctgtgaggg taatagcaac  60600
agatgccaga agagggcact ggatccccta aaactggaat tctaggtgac tatgagccac  60660
ctgatgtgga tgctgggaac caaactcggg tccttcagaa gagcagtaag taggcacttt  60720
tgaccagtga gccatctttc cagcccccag caccattggg tttttttgct tttttttttt  60780
tttttttttt ttaagttaag ttttagttag ttgtgtcttt tgagcaatga aggcatgctg  60840
atagcacagg tgctatgctg atagatataa gtgtgttatc cttgtatagg ataactacag  60900
gataattaat gcctttaagc tctgaggctg aaggtcctat agcaatataa gatccacctt  60960
gattccttcc ttgtccatca agaaagttga gtcacatcta agatactctt tgatatgggt  61020
ctcttctcct tatgctggac ctgagacttc ttttcacatg tggcaggact atgttgtgtc  61080
atcttcctct aaaccagtgg ttagtgttcc tgagattgag gctcaagagt caaggcaagt  61140
aatcagaggc agaaagaaac aaaatataat gggcacattt acttttaaac tcaagcataa  61200
taagataaag atgtatcttg agtacttctg ggaacctgta ttgcttcttg ttgctgctta  61260
aagatagact agaacaaaca ggtgcatgca taagagtgct gttcaaagac gcggtgcggt  61320
gtctgacctg atgccttctg tggtgggatg ggctttcagc actgtgtcct gagtctttgc  61380
agcagcagct acagtgactt gggattacaa ctgcttattg atatgctgcc tctgaagaac  61440
agctcctact ggctggtgag gaccgaactg ctggacactc tggcagagat tgacttcagg  61500
taagggagcc aagttacaat tcagaagttc aaattaaaaa ttgaaagtcc tgaggtctct  61560
gcagttggca tggctgtcat gtgtactgtc tgttcagctc atctccagtt tagttagaga  61620
acatgtgata gtcacagtac tttttattga actctgaact tggagatttt gctattttaa  61680
atgagataag tttttctggt tgtcctgttt ttctagatgg taggagtaaa aaaaaaaatc  61740
agttatatta tttttaattt tgtccaaacc tgtctgtctg tattaggcat atgggtttgt  61800
gcacatgagt gcaagtgcct gagaagacca gaggcgtcat agcccctggg gcaaagtaag  61860
atggtttaag cctcttaaca tgtctgccga gactacactc caggtccctg gaagacctga  61920
acgcattttt aaatgctgag ctagctttct agccccactg agttgtttgt tttgagaaac  61980
cttgtttcag acttttaaaa taggctatca actctgcttg gttttttttt gttgttgttg  62040
tttttttttt taatgtacct ttattctgat ttaagggaga tagccgaata gtattttgtt  62100
```

gcagtttaaa aaaataactt gaggactggg gagatgggtg gtggccacac aagcagagct 62160
tgagtttgat agcagcacct acgtgaaagc aggtgtggtg gtaaccatag tgctggagaa 62220
gtggaggcag ctggctccat gggccttgct ggtcagccac tttgcctagc atagtaggga 62280
gagtccctgt ctcaaagaaa aaggtggctt ttcgccagca tggtgctgaa agtgaagtag 62340
agaactcttg cccctcccaa aactgaagtc aaagtgaaga cagggaaagt ttaaaaggca 62400
gtgtggaagg tgccctaaca tcagccacct tccccttggg cagtccacat accctcatca 62460
gaacactcct aggagaaatg aagcttgaca gtgccaccat aatctagtct gtcccctaac 62520
cagtcagtca tgaagaagct agaagacaag tatgttgatt gtggttgcca agaccaacaa 62580
gcacaggatc aaacaggcta taaacagctc tgggacactg atgtggtctg atggagagaa 62640
gacagcatgg ttgactactt cctgattatg atgctttggg tgctgcaagt aaaattgaga 62700
ttatctaaac tgagtccagc tggaaaattc taaatacaca ttttttaac cattaaatgc 62760
ccccactcca aaacaaaaac aaaaaaattc caaaatttag catattagat ctttcatttc 62820
cttagagcaa gttttagtta gcagttcttt taacagtccc ttttagaagg gcaatgttcc 62880
tttttttatt cactttttt gtgtgtgtgt ggttattgtt gtttgcttga ttttgttttt 62940
gttttgtttt tcctctatgt ctgtgtttgt accatatgca tgtagtgccc atggaatcta 63000
gaaaaaggaa gttgcaagcc ttggaactgg agttatagag ttgtaagctt ctgtagcttc 63060
tgggaattga accctgctcc tctggaagag cagcctatgc tcttaaccat ggagtcatct 63120
ctccagcctg tttgattgat tgttaaagcc actgtagacc ttgtgggtta ttgtgtctca 63180
tcttcagacg atctctgaaa gaaggattat tctgttgttg caattaggac tgtggaacag 63240
ggcacacagc tggtcacttg ggtgggagtt tcagtgtgct gtcctctctg tatttaagct 63300
cactcatgga acacttactc atgaagtagt aggtttgtat tttgatgaaa aacggtttat 63360
ccagtcttac ttgtttagtc aagaatttgt agaagacaaa ttgcctcagc tgcctctgag 63420
agactgtttt catgttgagc tgagagctac aggccagcac tgtgtctgct aagtgaatga 63480
catctctgtt gaatgtgctc ttttgttagg ctcgtgagtt ttttggaggc aaaagcagaa 63540
agtttacacc gaggggctca tcattataca ggggtaagca gttcattttg tgagactgtg 63600
ggcccctatc ttctggaaac attctgagca gggtctccct ggtggtatga atcctgctga 63660
aagcctgtgt tgtgctatat cttcaacact ttatgtcatg aaacttgtca gtatgtggca 63720
tggatttgaa ataagtcacc ctgagttctt cctgactagc tttccaaagt gccttcctta 63780
actaactaga tatagcagcc catgacttta attccagcac ttgggagaga gaggcaggca 63840
gatcttggtg agttcagcac tagccaacct tatctaatta gtgagtttca aatagccaaa 63900
gccacataat gagactgtat ttcaaaaaat ccaaattccc ccaaataaaa aaccaagaaa 63960
aacaacatta tagaaattaa aatattttta ttttctgtct ctaaagtttc taaaactaca 64020
agaacgagta ctcaataatg tggtcattta tttgcttgga gatgaagacc ccagggttcg 64080
acatgttgct gcaacatcat taacaaggtg ttttatcagt atttatttct ttactctttg 64140
gttgaaatat atagtaagag aatgggagag gcaaaaggaa tcccatttaa ttattttaaa 64200
aacttactaa agtgataatt tgaaaaaaca aatcactatc cttttattat aaaactaatg 64260
tgctttcatt gtcaaatttg tagtttagag atcagcacta agaatgaaag agagttctgc 64320
ttctttctac ctcctggatg taattgctgt gcacagctct gatggctgtc atgggcatag 64380
gttgggttag catctgggaa aaggtgtagt gacgggtgaa tttcacatac ctcctgagta 64440

-continued

```
gatcagtttt cctgtcacgg caggcttgtc ccaaagctgt tttacaagtg tgaccaagga  64500
caagctgatc cagttgtggc tgtagcgagg gatcagagca gtgtctacct gaagctcctc  64560
atgcatgaga cccagccacc atcacacttt tctgtcagca ccatcaccag gtacgctgcc  64620
cccagcacct tgctttgttc attaacagga tatttatctg agacaccatg gtttgccaca  64680
gccccctgtg acagtttaag tcccttctca gtcacataac ggtgatgtcc tcagtcttgc  64740
aatgagttct ttaaggtctt catctgataa ttgtattttt gcttgtgaat gtcacatgcc  64800
atctgaaaac cagtccatgg aaaagtttca ctcttttagt gaatttagct aatgagtggg  64860
tgggctgatg ccaagggtca gacggctgtg tgtagtcttg attctcaggc ctatattgct  64920
agcacatggg cagggtctgt tggccacgta acctcttcta cctggccagt agaatggcag  64980
agcaaaagat cacagtgaat gtactgggtt cgttggaaat ctagtttgta aggaagattg  65040
cagtaagagt agtaaaacat gcccttggga cacttgtctt ttaaattctt aagactggat  65100
atacaggata cctttctttt tttgatgatt tgaaacaaca aaaacacaac tcaaccaaaa  65160
gacttccaag ctcacctggt aatttgtttt ttggtttttt ttttccctga attgggaact  65220
caactcatca aattttaaag tcattactcc taaatgactc tcatcttttc tcatggaaaa  65280
aacaacttta aaaaaaaaaa aaatcaacca ccagcagcac acggtaatga gtgtgtaggg  65340
gcatctagtg aaggagaagt caggcctttt tttttttttt aatgatgaaa aacttattcc  65400
agtctttttg gaaagacctt ttgcatgcta agcaagcgct ctgctgctga gccagaccca  65460
gcctcattcc cagcctctgg tttactctaa agtcaatgct gctttccttt cttctggacc  65520
ttaatcatac acgtttaaat gtcatttgat catgaaaaat atatgctttt agagcctctg  65580
catttttctt actagaatct atagaggcta tagcttactg ccaagtataa cagatgtcac  65640
catggaaaac aatctctcaa gagttgttgc cgcagtttct catgaactca ttacgtcaac  65700
aacacgggca ctcacagtaa gtttctcgc ttgggcttaa gataattgcc ttgcacgtct  65760
tttacaatgg gaaggacctg tgtgaggcct ctctctcttg aggtgcttta taaaaaagtg  65820
tagttctttc aacagattcc aaagtagcac atactcattg taatattatc caatctaaat  65880
tgtaaattta tccaacctag aaagtcatca aataaaagtt ctaaaatggg ctggatgata  65940
ctggctcgtg cctttaatct tagcacttgg gaggcagacg caggtagaaa aaaacctaat  66000
atataagaat ccaataatgg ttatattcca attacaataa aatgctaaat aacatatagt  66060
aatatgttag acacgtgttg atgtgttgct ttggagaaac ttaatgatat agagacatgt  66120
aacctaagtt ttaatgttga atggcagaga tagaataaaa atgtcttgga aatgtagttt  66180
gattctaggt taaaaaagta atattcatat gtgtacagac agtctttaca aactcagaga  66240
aaggacaagc aaaaaattgc taggatgatt tttagggttg tgactaactt tcattttctt  66300
acatacagtt ttcaagtatt cataaatttt ctaaaataat cacatgtaac ttttaaaatc  66360
agaaatagaa tattatgcag aattattgtg taatggttcc tcaaaagacc tttatttgta  66420
caatggaaga aatacttgga cattgttgag agtcacacag ttgagatttc agctgtcttc  66480
taaatgcctt tcaaatttaa atttgttcaa gataggagat tcatttcaat tgtgatctgc  66540
acatgtcaaa gcatgggtct gatctggagg tttattttaa tcattttgag ctgaggtctt  66600
gagggaggaa gagagaacct tctagggaga ctttgagtct ccctggggaa ctagagttcc  66660
tagcagaagc tgctagctgc ctatctgtca gctgtaacag tgttttactg acagttgtgt  66720
ccagctcttt tgtttaaagt atgcagtgtc tagtggtagg atgactaccc tgtaattgct  66780
tactggtctc agttttcatt tcatttgttg tgtgtgtgtg tgtgtgtgtg tatgtgtgta  66840
```

```
ggtttaattc agtaagcctt tggtggtgtt tgggtatgat ttttccattc ctttcttctg  66900
cagtttggat gctgtgaagc cttgtgtctt ctctcagcag cctttccagt ttgcacttgg  66960
agtttaggat ggcactgtgg gtatgtacat tcctcagtgt acaagtcagc tacccaccca  67020
gagcaagcac agctgccggg tctctctttt ctactccaac ttcattcccc tttctccctt  67080
tccatcccct ccttttcctt ttatgttgga tctctttgcc tctttttttt tttttttttt  67140
ttttaatata tgctggaatc cttgtttctg ccgtgtgaga tgtgtgaaat tggtgagaga  67200
actgttgggg atgctgaagc agttgtgact cttatgaatg tcaggtgctt gaaagcatct  67260
ttaggggtct gagggtatca tctgtggact cattaaggca ttttcatata caggtaaaaa  67320
ctttctcatt agtttgattc tttctaaaat tactaggtaa ttttaaagtc agttagcatc  67380
cagagttgta atgagctata agagtgtgct ctattatgtt cccttacaaa ataatttctc  67440
cagtagatgg cctactgctg tctgggtata atttagtttt ctcagcacta ataagcaagc  67500
cttcatttgt gctgatgacc gagaaacttt ggggattcca atcatatctg aaaggaaatc  67560
taaagatttc ttctgagtgt aaaatatatg gccaactaat ggtctcatgc tttgtcatct  67620
agaatgattg ttctcttctt tgtgagaatc atgactcaac agttacaggt tccagtcata  67680
ggtcctgcac ttttgagcaa ctttgacatt ggagtctgct aagtcagaaa gggaagaaaa  67740
tttgaacttc atcagaataa tcattctagc tctctcaatg aactctattg tgtgatttca  67800
tttcccaagt gacttttgtg aagtcgtgat ttacaggaag agtgttagtt gattagcagt  67860
tttaaaatga taatggctca cacttgtaac ctcagtactt ggtaagcaga ggtaggaggt  67920
ttgacacatt ttgcagcaca gcactggcta catagtgtgt tccaggccat ggggactaca  67980
taaatgagag tgagacttaa gtaacccaaa ccacatcaac aaataaggta aaaaggtaaa  68040
atgggtggtt ctcgggggca ttaaagagca agactgtatg cttggaactt gatttttgac  68100
tttggaaatg tctgctttca gagtgccccc actgagtgcc tctgatgagt ccaggaagag  68160
ctgcactgtt gggatggcct ccatgattct caccttgctt tcatcagctt ggttcccact  68220
ggatctctca gcccatcagg atgccttgat tttggctgga aacttgctag caggtactga  68280
cagagataga ctattagact gagttctgat ttgctgctaa ggggtactca agttacaaga  68340
atacaattgt tattttggga gacagctggt ttccttaata cagatttgag atattgtctg  68400
tttatgtgaa tgtgtatgaa gggagtagtt atgtgctgag tatttttagg tgtgtgtgtg  68460
tgtgtgtgtg tgtgtgtgta ggttacaaga tgtttaattc agtgagcctt tggtggtggt  68520
gtttggatgt gattttattt tcttccattg cactgtggat aaaactgttt tgagttttgt  68580
tttctgggtg ctgtgtgcca ggcagtggct tggtctatag caggtagggt tgtattcttc  68640
aaggggttat agagtagcag gagatgcaga cagacaagca caggagcagc agagcagatg  68700
tacacttctt atttggtcag atttataggt taatagaaaa ggatacagca ggtgaggtat  68760
tgcatatgta aggatttgga gaactaaaaa gttatttaat attgaatata agttactgtg  68820
gatatcacct gaggacagga gtaagaatgg agaatacagc cagccaggtc tgaaaccagt  68880
gaatctactt ggggataggg taccaggtct tagtgaggaa tattgacttg ttctgtttgt  68940
cattgatatg ttttatggag atctcctgac ttgagtttgg gctggaattt gtagggagga  69000
tcaggtgttt atgggaaaag actgagccaa gagtgtactt taggtgtaga gaaaggggat  69060
agaaagcata atggaggcag catccccagg cctgatctcc agctgcatct cgattgtgag  69120
gatcacaccc atagctggag gagagtggtg actttgtgga agattgggtt ttgggggcca  69180
```

-continued

```
aatagcactt ttatgtaagt ttgagacatc tgtttagatg tagaggttca tccatatgtt  69240
agcacagatc agtgagaaac ttaggccaca acctcttccc acctaacaca ttgcgggtag  69300
agtaatgtgt gtgcctatgt ctcagcgagt gcccccaagt ctctgagaag ttcatggacc  69360
tctgaagaag aagccaactc agcagccacc agacaggagg aaatctggcc tgctctgggg  69420
gatcggactc tagtgccctt ggtggagcag cttttctccc acctgctgaa ggtgatcaat  69480
atctgtgctc atgtcttgga cgatgtgact cctggaccag caatcaaggt aactgttcct  69540
tgggggcagc cattatcatc tgcctaatga ctggacttcc tgaacatcat gctagttgtc  69600
tgtttcttct ctatttcttg ctataagtaa agcttattca gacactgtat ttaacataaa  69660
gatgtagtta ttttgttttg ttttgttttg atgtcagcca tgaagctcag aagtgataat  69720
ttccctttaa tccccaggtt ccttcacttg ctttctcttc cccatcacag caaagtcttt  69780
gaagaatcat cctagtcaca aagtccctcc atctgctcag gcatggactt gtgtgttgag  69840
gtctttggcc ctttctggca ggaaggaccc tgttcccctt cttgagccat ccattcttcc  69900
actccagtct gtctggcttc tgctgccccc tttcagagta cttcctgctg cggcagtcat  69960
gtcagttgta tggattcttt gacagccttc ctatcctctg ggctactttt taccccaagt  70020
gatatggctt tctgtgtttt ttttccaaca tcctctactg ttgggttcag tttttcttgt  70080
ccactgttaa aggtgctgtc ctgtggatca tctactttct ttttattctt gactttctgc  70140
tctagcggga attttccatg tccataccag ccacaacagt agtcactgac cacatgaggc  70200
acttgtgttt ttgaaatgtg gctgtgtgac ttaaactgaa ctgactaaat agactattga  70260
atcaggctgc cgatgtgcct gcatcctttg gggctggct tcaactctgt ggaaccttag  70320
tcctgtgtgc ctgctatatt gtagatgctc tgaggctgtc tcacatgtgt cagaagcctc  70380
agccagagcc tggccttctt atcttcttcc ctcctctgaa cctgcttctc ttctcacact  70440
ttgtacttta tcaggatagc aacgggagcc accatagttt tatttcagct cactattctt  70500
tatttttcct actaaatact ttgtttaaaa tttatataaa gtgaggtggt agtggtacat  70560
gcctttaatt ctagcacttg ggaggtagaa gtagatctct gagtttgagg ccagcctggt  70620
ctacagagtg agttccagga catccaaggc tacacagaga aaccctgtct cagaaaaaaa  70680
caaaacagct taagtatacc tacatatatg tgcacaaaca tccctttggt gttagtgtac  70740
atgttcattg attcatacct tctcttttct ggattctggt ataaactggt gtatctgcac  70800
tggcctattt ttggaaatca tattattgaa gtaattcata ttccataaca ttcaagtata  70860
caatttaatt ttgtttgagt ctaggccaac tgacctgaaa gttatgtatc ccagactgcc  70920
ctctgacaca tggtgattct ctcagttcaa cctcccaaat actggcattg cagtgtgagt  70980
caccacatgg tggtggcgct tgttattttt gttattgtgt tgttgttgtt ttaaattata  71040
ccacagagtt atatggacat gactacagtc aaccctgtaa ctgtaactga ctccaaaaac  71100
cttccatgcc cctgtctctg gatagccatt actctgcttt ttgtctgtgg gtgtgcttct  71160
cccggactat tttgctgatg gcctcataca cttggtggat ttgtcacagg ttctttatac  71220
caaaaatgtc ttcagtttga tagttcctca cctgcccccct gcagccttcc tgcctccttc  71280
catgcactgc ctgaccacag ccattcatcc tgatatgctg cttgtcttgt ctgcttgatg  71340
aggatcagag gtgcttagtg actcacgcag tctgggctac catcattaca gagcctcagt  71400
ggctacttat tctcccagtt ctaaaagctg agtattctga cccctggtaa gtctggcctt  71460
ctcatggaga atggggaatg ggaactgctg gagtctcttt tcataggagc aatgatccta  71520
tttatgaggg tcctgccccc atgacctcat tctgaagctc actcccttct gttgcatgct  71580
```

```
cttgatttca gcagatgagt agggcagagg ctgaggccag aaagggagtg aggagcacag  71640
caaagacctg atgtgcctgc cttttaccat gttgtgtcta tcctgtgcca cctttcttct  71700
ttgtgtgtag gagcctgatt gtcccgtgta tccttggggt tgcatattgg agagcatggg  71760
tcacatctgg gctgttgact tgttgggttt tagctatcac attgagcaag tggcttaatt  71820
cagaacattg tttcctcact taaaaatgaa aatgtaaatg tttcactgtg cttactcatg  71880
tgatgttcac ataaaatgtc ctgattgcct tctcttagag gggacatggc cggggtgcca  71940
gtgactttag gtccttttaa atccctggag gccctccctt ctccaaccca ttctcagtgc  72000
tggtatgagg aagttcagag ccatgcctgc catgtgcagt tatgtgggtg aaagtagaat  72060
taattatctc tagtatccca gctctttagt aggagctcaa aggccatgag tagcctgagc  72120
tagtactttc caatatgtgg ttgaactgta tattagtatt tttagggttt ggctcctgta  72180
ttaattttat cccattatat attttttat tttaggcagc cttgccttct ctaacaaacc  72240
ccccttctct aagtcctatt cgacggaaag ggaaggagaa agaacctgga gaacaagctt  72300
ctactccaat gagtcccaag aaagttggtg aggccagtgc aggtaggaag gcgtttctgg  72360
agggcagagg gctgcctgtg gtgcaggagt gtaagcaccg taagtaggaa agctggtcct  72420
ctgcagtaca gtcagggagg agttctctgg gtgcttcaga agtgtctgtg gtaaactgtc  72480
actttacaga gtcaagccat agaaaggagc ctgcttttct gtgcttactc tccccttctt  72540
gtaaggaaga actccgcatt attattaaag aggcaaagaa gatgtgtagg aatagatgtg  72600
gatggtgata gtcaaaaaca aacacaacaa atgatgatgg tatgggaagc gttctgataa  72660
ggcaaatgag gaatcagttt tgggagaggt aacaagacag tggaagccag agatgatgta  72720
tctttaatct aaccctcaga aggcagagtg gattgagagt ttgaagccac tttggtttat  72780
gaagtgagaa cttacctaaa acaaagagga cagtgacaga aagacacagt ggagatagtc  72840
atctgatttg gaggaatcta gaaatcacac agatgtttgg aggggctttt gtatttgggg  72900
agatatcagg tcaaagggcc agagttttgt catagtcgaa gtaacagagt cccatctatg  72960
ccccttttggg atgagaagca gagtgatgcc tctgtcttgt ggctactttc tttctgttca  73020
tgttcatctc acagcaggct ttgtagacaa gtacccaagg agttgaaggg atctgcaatc  73080
ctataggtgg aacaacaata tgaactaacc aataccccccc cagagctcgt gtctctagct  73140
gcatatgagt cagaaaatgg cctagtcggc catcagtgaa aagagaggcc cattagtcgt  73200
gcaaacttta tatgccccag tacaggggaa caacagagcc aagaagtggg tgggtggcgg  73260
agtgggtggg ggagcgtgtg ggggactttt gggatagcat tggaaatgta aatgaaataa  73320
ataccaataa aagaaaagaa aaaaaaaagc tacggacttg aaaatgtaac tgatgacccc  73380
tcaaaccaag ccctccaagt gagaaagcct tagaaattta gatagagatg aagagcagga  73440
gactgctctg cttgtcactt ggctctttag tctcagtgta gtaatgtata caccctttac  73500
agttttcaaa gcatgtccac agcacttaat gaatatccca gaactcgttt gtctcaaggt  73560
cagccccatg tacctcagga gccttactta gaccaagggg acctgtgttt ggcttcagcc  73620
cttcggtcag cagaggacag ctgaggccac agatgactcc atcagctgat gcccttctgc  73680
ccaccattcc tttccattct tttactctca ggctcttagg attttacttt attccttact  73740
acctcccaga gcacatactt cagaagtcag gggaaagact tgaatgtttc tgctagacca  73800
ttctgaaaag ttatcattgc agtaattgct gttaaactta ggaagttttt tccttagatt  73860
taaaagttta atttttgggt tttggtgttt ttgtttgttt ttttctaagc ctctcgacaa  73920
```

```
tcagacacct caggacctgt cacagcaagt aaatcatcct cactggggag tttctaccat  73980
ctcccctcct acctcaaact gcatgatgtc ctgaaagcca ctcacgccaa ctataaggta  74040
ctgctccttg cttatttctg aacatgtatt ccagcgggat gcatgtccat gtacccatgt  74100
tcatgcttac atagaaagaa gccctgtaac ataggattta aattttgctt ctcatttgtc  74160
ttctaggttt atggaagctt tacaaatatt taggaatttt gtatgagaac aaagatctgt  74220
ggtctctggg tgttgtttgt ttattgtctc cccaagaata cttggtttag aaagatatgc  74280
ctcaaggact cctggggctc agtacagagt cctgtttata ggtgaggctc attgccatgt  74340
cctgaagaca cacagccaag ccaagcaggt ttcatgtgcc ttctccctct atcagcctta  74400
aaagatagtg caactgccca actcaaacca aaattgtagc ttccggagag aaaagcagat  74460
gctcactata gacctataac cttggtgttc ttgtcagcta gggttttctg tcagtgtagg  74520
gactcttttg ccagatggtc ctgattcagc tttgtattgg ctattggatg attgtgtctg  74580
ggtttacatt cttttttttt ccccatgatt atcccagcat taaagaatga tttgtagatt  74640
tacccttatt gatttgaaat cctattttta tcaaatgtta agatctcatg attgtatagt  74700
ttcatttatg tttttgttac atcagttgtt cactcattta atagcacatt ttaatttttt  74760
tatttaatta atgaattatt tttgagactg gggcccaagc ttgactagaa ctggcctcaa  74820
acatcagtgt ctcaaactca cagtgaccca cctgcctctg cctcccaagt gctgggatta  74880
aaggcatgag acactatgcc ctgtagaagc acattttaaa attattgtgg tttcctgata  74940
taatccccat ttttctttag aattttctgg atattaccta tttttacatg tgaaaatttg  75000
aatagactgt ctaattctaa aaaccatgga aattctttcc ctttaggatc gtgtctgctg  75060
tgtgtcttcc ctcagacaga gctaatctaa gggaatggta gactgagatg gatgttttga  75120
tcacaggata cctttctgtt tgttaaagct cctttcctta cctcagaaat ctgagagtta  75180
aaagaatttt taaaagaact taatagatta ttcacatagc cctggtattt cttactgttt  75240
tccaggtgtg cagctgcttc attgagaact agtgataatg ttcagaactt ctgttcatga  75300
actctgtcag cccatgtaga ggagggcaca tgtggtgctt gctgtttgtg ctttcgtcct  75360
ctgtcattag gagccctttc ccatgcttcc caccttgatc ctctttttgt actgaaacct  75420
caagcatttg cttttagttt tggcctcccc aatatctcag atttctgttc ctttgctctc  75480
tggccctgct tctgtaacta actcttctgt aacttttaag tgttttgagt agctgttctg  75540
ccgtagtgtg tcttcttacc ttgtctttcc ttcactctta actctgagtc cctttcacta  75600
cccactcctc tcctgcttcc tcttgttcta tttctcctct tccccttcta tttcgccttc  75660
cttgttgtct gtgtcttagt tagggtttta ctgcaggcac catgaccaag gcaactctta  75720
caaaggaaag catttaattg ggactggctt acagggtcag aagttcagtc catatcatca  75780
aggcataagc atggcagcat ctaggcagat gtagggctag aggaactgag agttgtacat  75840
cttcatccaa aggcagacag gagaagactg gcttccagtc agttaggaca agggtctcaa  75900
tgcccacccc tacagtgatc cactttctcc aacaaggcca tacctcctaa tagtgccact  75960
ccctgggcca agcatattca aaccaccaca attgggaaag aagcatgatg ggagtgaagc  76020
cattcctcac taggcctttg atcccacata taacatcact gcattgttct gggctgtagg  76080
atctcaggtc tctctcactg ctggtgtccc ttcctgtccc tgacatactg aggctgattc  76140
cagtgcaccc cagacctaga cctgttagat tatataaaag cagtgtagag agacagagga  76200
tggaaagaaa taggcagaac catgttcatg gcagaggagt attttgtcac ctacaagtga  76260
tgcctaaaat gtctgtagaa gataggatgc tgccccttat aggccagaaa taactctcat  76320
```

agtctgcaag ggaagctggg aagtatagtc tttaagtggc aaaccatcat tcctaactct 76380
taagatgata taaaaaattc agagcagggg agttatgtat agctgtttaa tgctgaggag 76440
ggtttttgct ggaagcagta gttttgggtc taatgaagag gggttctctg gtcatgtatc 76500
agggagagtc ttaacttgat tagctgaggt ggatcgggct gttgtcttat atttctgaag 76560
agacttggaa aataattctc agagggcagt aagcagatga catggttaca gagtagaagt 76620
aaaagatttc caggaaggtt gaggagtagg gagaagcaga ggtagagtgg actggtaaga 76680
gacagtgagg atagaatgga ttcagggtgg cagtgactgc ttccattagc ataagtagca 76740
gataactaga gtagcaaagg aaggaataag aaacaataaa aagactctga ttaaagagtt 76800
gtacccagcc ggccatggtg gcgcatgcct aaatcccagc acttgggagg cagaggcagg 76860
aggatttctg agttcaaggc cagtttggtc tacaaagtga gttccaggac agccagggct 76920
acacagagaa accctgtctt gaaaaaagaa agaaaaaaaa aaaaagagaa agagttgtac 76980
ctggcctaaa gtgaaaggga cgatgttgct tttagtcagc ttgcctcagt atctaacaga 77040
tctttttata gatatatcag gagcaaatgt agctgttgta ggatgagggc tattgggaaa 77100
gcttacgtca aatatttagt ttaggtgtaa ggtaaagttc agtaagcaaa acatttaaaa 77160
gacaggtcaa aacataaata taagtataat aaggagaaaa agagtgatct aggggaggaa 77220
gcacggtggg agggaaccag aagcccacac gtaggaatag gcttgtagtg gacgcttttt 77280
caaagaagtt aagatttact ggcctggaaa cagcacgttc atagaagaga acacaaatct 77340
catcccagtg ttagacctag tccttttaaa ttttgaagta ctgcagcagt caaggagtca 77400
agctggccct aaaggatatt taagctgatc agagctgatg agacagaggg gttaatagat 77460
gcaaatgtct agagtggtaa gaagaaagat gagttagatg gccggtgccc attagttccc 77520
tctcagaggt gacccagatt gcttttatgg gcttaagggg gtggatcttt ataactacct 77580
caaggctgac ctctgagggg gcagcagtta gagtgtctca gatgagggtc catccaaggg 77640
gccacaataa aacctaacag atgacaaaga tgtagggcat aagtcagaag gtaatgactg 77700
tgcaaccttg tgaggaaatt aagagacaaa agttaaatga ataaaacttt gccatcaaga 77760
ttaacatgaa tcaaaataag gttaaattat aaatttaaca taaggttaaa tgcaatcata 77820
caactggctg gaccatgtac cagagctatg tagtaggata aagtaacttt tgttagccgt 77880
tggcttatat cagactcctg aatgaggaga gagcactcag gacctttgga aaagatgcca 77940
gttaaagtca gggtccaagg gaagcatccg aacagagcgt ctccgtgata gtcgctgctc 78000
ccaagtacga ggaattttgt atgttgtctc aaatattaat aataaggcta ttatttattg 78060
ttgcttagtt ccttgagttt gtaagctttc tattgttttg ttgttgatat ccatctttaa 78120
tccatggtag tttgatggga tacaagaagt tatttcattt ttcttgtata tgtggaagac 78180
ttgctttgta tccaagtacg tgtccattta gagaacgggc ttgagaagaa ggtgtgttct 78240
ttcgtgtttg gatgaaatgt tctgtaagca tctgttaggt ccacttgatt tctaatatct 78300
tagctccaac atttctctgt ttagtttttg tctggatgtc ctgtccgttt gtgagagtgg 78360
ggtattgaag ttttccctat aagtgtgtga gggtcaatgt gtgatttaag tttcagtaat 78420
gttcctttca caaaactgag tgcccttatg tttggggcat atgttggaca tagtcctgag 78480
ttcaattccc agcaaccaca tggtggctca caaccatctg taatgggatg ccctcttcta 78540
gtgtgtctga agacagctat agtgtactca catacataaa ataaataaat aattctttta 78600
aaaaaaaact gaaatgtcat cttggtgatt ttttttcttt gatgagtatg tagtgtactt 78660
cccatctctg tgattagttt tggtttgaag tctatcttgt taaatagtaa aatggctata 78720
ccagatcatt tacatataga tcatttatag attgcttcat agatccattt atttggaaat 78780
ttgtttccat tattggggaa ttgagaccat tgagagatat caataaccct tgattgttga 78840
ttcatgcatg ttatttcttg ttattatggt ggtggtggtg gtggtggtgg tggtggtggt 78900
ggtgtgcatc cattttgttt ttgctggtgt gagattgttt atttcctgtg ttttcatggg 78960
tgtagttaat gtccttggat ttttcttcta gcatcttctt cagtgctgga tttgtagatt 79020
catactcctt aaatttggtt ttatcggaga acttcttatt ttttccatct atggtaattg 79080
aaacgtttgc tgggtatggt agtctgggct ggcatctgtg gtctcttaga gactgcagca 79140
cttttgttca ggctcttctg ggttttaggg tttccattga gaagtcgagt ataattctga 79200
taggtcggct tttgtaggtt acttgacctt tttcccttgc agcttttaat attctttctt 79260
tgttctgtat gtctagtgtt ttgattatta tgtggccaga ggactttctt ttctttcttt 79320
tcaggaccaa tttatttagt gatttgtatg ctgcttgtac ctttataggc atctctttct 79380
tgaggttaga attttttttt cttctatgat tttgttgaaa atattttcta ggccttggag 79440
ctgggtttct tctccctcct ctattcttac tatccttaaa tttggtcttt tcatagcatc 79500
ccagatttcc tggatgattt atatcaggaa atttttaaac ttaacatttt ctttgactga 79560
tgtaccattt cttctgacat cttcaatgtc tgagcttctc tcttccattt ctcatattct 79620
attggtgaac cttgccatgt agtttctctt tgagttccta aatttttcat ttctagaatt 79680
ccctggtttt tttttttttt tttttttttg cttctatttc cattttcagg tcctgaatag 79740
ttttattcat ttccttcaac tgtttttttt attgttattg ttttccattt tcttgacttt 79800
cttttaagat attgttttca ttttttccaa ttgtttgtgg ttttctggca ttatttaagg 79860
gacttacttg ttttctcttt aaggatctct gtcaacttca tgtagttggt tttaagatct 79920
ttttcttgag cttcagctgt gttggaatat tcagggccta tggtggtagg acaggtgagc 79980
tctagtggag atttattgtt ctggctgtta ttgattgtgt ttctaacaca ggcttctagg 80040
tgtctgggtt tggtgtgatt ataggtctag gtgctgactt ctgtgtttgt ctttgttggt 80100
tgggtgcttt gttgcttgtt tctctggtgt gttcagctgg tgtgttccca gagtatgcct 80160
gatgttgttg gaagctggga tgtagtgaag agtagcagaa ggaggtcagg aggtgatggt 80220
ccatgggatg catgccctat ggcagcagtg gggaaggagg actgcagcag tgctagggag 80280
gagacggagg tttgtggcac cccacctggt tttctgacaa gcatgaccta ggtgagcagg 80340
aatgttgccc aagttagggg ctgggattca acaatgaatt gaggaaggga agccaggaga 80400
agatggtcta taggagccat ggataggggc aagaaagact gcagctggtg ttggctgcag 80460
tgcttcagag gagactgaag agttggctct aggtgaacag agagttctaa ggaatttctt 80520
gaacctgggt gtgtcctgcc agtgtgttat aaatttaatt cattttactt aagcattctc 80580
ttttcattat taattttata tacttgattt tgaatattgt tctacattaa tttaaacact 80640
gtaagtttac tttaaccttg ttttgagtta cctgtttcag gcttaatttt gacaatatat 80700
acagaatatt aggtgataga agatagaagt aactcaagct cggttgtgat ggcacacatc 80760
tttaatccca gcacttaggg ggcagaagta ggcagatctg agttcataca gcctggtcta 80820
cagtgtgagt tccagaatag ttagggcttc atagagaaac cctgtctata aaaaataaaa 80880
tgtaacaaaa caaaagttgg tttttccctc caactttata ttcctgtaaa tgaattaatt 80940
tttacttagc atgactacaa acatagttct gagcacattg agtaatttgt tcatttataa 81000
gataaccgag cattaacttg tatatcttag ttaattaaaa taatttacaa tatataagat 81060

-continued

```
tagggtttta taattttata tctgatatgt ttaaacttac atgtaaaaaa ttacacatac  81120
acacatatat tttttaatat caagtaaact ttaaacataa atacagtcca gagagactgg  81180
cctcttatag tgtactttta tatcagcttt ttatatgatt tagtttctcc aaatagctaa  81240
agcttaacaa agatagcaaa aatatcacag gttttttttgg atgacccagt tttaagacaa  81300
accatcttgg aagcctggtg ttgccttgtt agtccaaaaa aaataggata cagtggtaag  81360
cagagggata tgacatactt agctgaggtc acatgtcata ctttaaccct gatgaagtca  81420
ccaaccaaaa tgttgggaag gtgagccctt ctgcatttgc cttctgcatt tctaagctag  81480
agttgaatcc aatttacata catggtatgc tatagcacat taaggttagc tgaacataga  81540
cttttaccta ttaacccttt tttgttacaa attttaagtt aacttttgtt tggaatttta  81600
aaccatactt aatgaactta taaatcctga gatgcagaac tttacacagt gctcttataa  81660
agcctgagat gaaagaaggt ctatacttta gtaaagtttt agagctcaga tttcccattg  81720
gcaccatatg ttaaattgtt aaaggaattg tagagagatg gatggatgga tggatggatg  81780
gaagggaggg agggaggaag gaagaaagga aagaagaaag gaagggaagg gaaggaagga  81840
aaggagggag ggaagcttgg tttaacctta ggtgaccaca gtaaggggaa tatttttgtc  81900
acccacatgt ggggatggcc aaaatgccta gagaagatgg gataccgccc catactaggg  81960
cataagtgac ttccatagtc ctcaagggta gctggaaagt gtagtcattc aacaggaaac  82020
tatcaagacc cattctcatt ttctgttcag tatcttttcc ctgcatttgt ccagtattct  82080
cttcatcata ggaggttagg ttcaagttca gtggacagat tctcttgtaa agtttttttga  82140
actggttctt tgcatgatca gcccctcccc tgccatcaga atctgtagaa ataggggaat  82200
tgttatagac ttcagttaag ccaaagcttt tagaatcttc atcatcctaa gattaatttg  82260
actacatcta gaattgacag tgaccacctc ccaccccccac cccaccccccg ggatggtgag  82320
agtctaggtc agcatgaaga agcacctccc cgcagcagac ggcatttgtg tctttgttgt  82380
agataaccag acttcggtgg tgccagtaac cgtgtgctct ctccttccac cttgccaagg  82440
tcaccttaga tcttcagaac agcactgaaa agtttggggg gttcctgcgc tctgccttgg  82500
acgtcctttc tcagattcta gagctggcga cactgcagga cattggaaag gtttgtgtgt  82560
ggtctctttt ccttgaacct gggtcagagt acctcagatg atacctagtc acatggtgta  82620
ggcaggggag actgcatcct atttgtgtcc tagtactaca ggatgccagg gcacctgtgt  82680
taggtctgtt accagtgtgt caggtcttat tgccacagtt tttcattcag tctagaacat  82740
gttgaaaatt tgcttacaga atccttcttc tctcccttga gcttttaaat ggaaagagac  82800
aaaaccagat taacaaaggt aactgaccta ctccttccat agcccagaaa gcagatctaa  82860
gctcattcat gttctgtggt tctgagtaga ataaatcttc ctcccagccc atatgctcac  82920
acttaatcct gccattgcta acaattttgc ttgcactcca ctagaacatc tcgtttctaa  82980
tatactccac agtgagttag acagccatct tcaacttaca tcttcaagtg aaatatagtc  83040
cagggcctgc caaccactga tgtcaaaatc cattcatgct aacgctcctt atatgaaatg  83100
gtatcaaatt ttgaaagcct acccacatct gcttataaga ctgagtcatc ttgaaatgat  83160
ttacagcctc aagcatttgt aacagttccg tgtagttgtt attctgtatt gtttagggaa  83220
taatggtaag gaaagacacc tgcacaaatc cagtacagat tgaatcctgc ttttcttcct  83280
catttgtttg tttgtttgac ccatactatc aggcaacaca ctattttaca ttttcgtccc  83340
ttcattgcat gcagcagtgc ctgaactatt aacattcatc aaacatttgg tcagtaaaca  83400
```

```
gatactcttt tcaagaatca gtttgaaagt tgggtatagt gttcacatct ggtaagctag  83460
gtataatggc acatacccct ccgaggctga actgggggag ctgtggtagg agctaaaaga  83520
caatccatat caaaagcaaa tgaacaggga aaattgatgt gagtgtctca tagaccttag  83580
agccgtgctc catgtatgat tagtctgtgt catcacatga cattgataaa atgctttcct  83640
tttcccactg tccagatctt gttattccat actaattttt atacataatt gaatgtatta  83700
tgtgcgagtt ttgcttagat tatgtataat acacatttcc ccacatatct ccttactgtt  83760
ctgtattgtt ttcctatgac ttctcccaag acttcatact atttttgagt gattttacta  83820
tgatttagct tgatgtggtt ttcctttcag ttgtgtttct tgtactcagg tttgttgcgt  83880
ttcttggttt tgggcaagta tagttttcta cagtttagaa aggttggggc tacttcctta  83940
tatctctcca accttttccc ctcactctat ctcttaatta ccttctaaaa acccattctt  84000
ggttacttaa aattgctctt agtttactgt tgctcttttt aaggatttgg gtttgattat  84060
tctagattca tttttaccat ttttaatgtg tttgtgtgta tgtatgtgcg tgtgagtgga  84120
ggtgttggca gaattcagaa gagggcacca gagctgctga agttttagtt gttgggagtt  84180
gtgagccaat taatgtaggt gctgggaacc caactcaggt tctctgcaag aaagcatcgg  84240
ctcttaactg tctttccagc cctcctttt aggtctgttt gtttttaatc actatctact  84300
tttccttttg tagtttctgt tacagtcttt aggttctcta agttttcctt tccccacatc  84360
tgctctacta taaaatccca tctgttatat cttttatcat taacattata gcctttctca  84420
ctagaagttt gattatttct tttcaaatct cctatcttta tttaacttaa attatttgtt  84480
tattatttat ttgtgtgtgt gtgtgtgtgt gtgtgtgtgt gtgtgtgtgt gtgtgtgtat  84540
acacacgtgt ttgttacgtg ggcacctgtc cacatggagg ccagaaaagt gttagagtcc  84600
tccactacaa ctctcaacct atttctttaa ggcagagtct ttccctaaat tagacactcc  84660
catttttctt gctgttctgg aagccagcag gttcagcctt gtgtgagtgc ctactgctcc  84720
ttcaagttct tctgatgatt gcttctcagg ccttggtttt gttagctccc ttagtatctt  84780
tgaagtactc aaggaacatc ctccccccaat ctccaggggt ctctgaatga cttgttttct  84840
tggtgccata tcatttgagc tgccattttc ttggggtctt tggattcact gtgccctcac  84900
agcttgcctt ctgtcccctt gttgtgccac agcctgggaa tgctctcaga tccttatcta  84960
gggccatcct aggactttgt ctgtatttta ttttcaggat cactgatatc tatggcccga  85020
tgttcagtgt ttgaaaacta tgatatcaaa gctggaatct ttaaaataca ttttttgatc  85080
atttcaggca ggagagggta aatgcagaga tggaagtctc tcaatattac attgtatagt  85140
gatgcctgtg gtagtgtcct gattccctgt aaccctggag ctcctggaag gacaggaatt  85200
acattcttta tctgtatttg cagcacctgg tatcatttct acagcacaca aagtgttcta  85260
tacagactgt ggtgaggctc attggcagtg gctctcacag tgttctgttc agccgatcat  85320
atttaggact ctacaagtac agggcttttg actcctttgc acactccata atgcctgccc  85380
tgaaaacagg tattagatat agatacttga ttatttactg aatgattggg tgacagattg  85440
gttgtgtaaa tgtacaagaa agcagttttt acacaattgt agatacagga gttcttgtga  85500
ttgttaagat gattaattga aagcattact cagaatttct ctgacattta tatagtttat  85560
atggtcactg tctatttctg agtggcaaca ataatgggtc acctatgagt cactgatgtt  85620
gtcctcttcc tttcacagtg tgttgaagag gtccttggat acctgaaatc ctgctttagt  85680
cgagaaccaa tgatggcaac tgtctgtgtg cagcaggtgt gtgtcatttc ctatcttttg  85740
ggatttgagc taacccccttt gggccaagtg acaaagccta gttcctttttt ggaagctggt  85800
```

gctgtggtgt ggtatgagga agagtttggt gcccctagct atcactcccg cgtgctctgt 85860
gattgggact gtggggggag agggcatcaa gaagcagctc tggccctcac tgcttcgcct 85920
ttgccaccgc accccagtgg gcttgtttct cttagaacca cagagaatct caggcacagg 85980
ggaccacatg gtgcgatgga tcttctggga tgctaactcc tagggattca caacaaagcc 86040
ttccatcata cgttcctgct ggatttgcta ctgggaaagg attgtcccgg cggatgttta 86100
cttttgcttt tgtttttttc ccttttattt tttcattagt ggtactaatg gttgaacctg 86160
gcttatgcat tccaggaaag cactctatca ctgagacttt taaatttttg aaatatgatc 86220
tctgtagcag ttcccagtta atgctactca gtcgatcttg gtggctgtgg tggtgctcct 86280
ccttgctacc cacccaatat tttgggttcc tgaatgagag acacatacat gcagccttta 86340
tatttttata tgtcttaaac acctcaagaa ctgaaccact tcctaaccac catgtggcta 86400
acccaccctt tgatatcccc gagttattgc ttactacatc tatattttat ctttgctgcc 86460
ctggacccag atgtgtagtc ctcttggacc acaatcccct gattcctaca tggtggctat 86520
gttctctgtc aggcatggca tcttggttct tcctctccca acatagtgga tctctctttc 86580
ctttctctcc ctgtccccag ccctggaatc ctaaaagtcc cacctctgta tgccctgccc 86640
agccattggc tctcagcatc tttattgacc agccagaacc aactgtgggg agggtctctt 86700
ggtgtcttat gtgtgaggac actgcaaaca ggtttttaac atgattagca tacaagcatg 86760
cattagacca aacccacaac atttccccct ttttgtccat taaaaaggtc ttttctctca 86820
gatatatatt gaacataatt ataacagtta tgtaaaatat aaggtatgat atatattagt 86880
gtccagtcat tcaattttgt cagtttaaat aaattattct atcatctatc gtaacctaag 86940
ttgcccaggc tttcctggaa cttgcagatt gtctatttcc atcctgacca ctgtctatcc 87000
taaccgctgt ccactagctg gcattgcaga caggcctgtg ctgctcatct acattaaatt 87060
tatattaagt gaagtactga tgtttccatt ctttcattct agctattgaa gactctcttt 87120
gggacaaact tagcctcaca gtttgatggc ttatcttcca accccagcaa gtctcagtgc 87180
cgagctcagc gccttggctc ttcaagtgtg aggcccggct tatatcacta ctgcttcatg 87240
gcaccataca cgcacttcac acaggccttg gctgacgcaa gcctgaggaa catggtgcag 87300
gcggagcagg agcgtgatgc ctcggggtaa tatttatggt gcaagtttgt cactgatgat 87360
gcagacacga gttatgtgca gcccttcctt gaaagtcatt ggctgagtta tggtgtagtc 87420
agctatccag aggtgacagg ctagagagga ggaacccaag ctgcctgtga agcataggtt 87480
ctaagttccg aatcttgccc taaactagaa gtggcacact cactgtcctc acctgttgag 87540
agtgtttggt acttgcagtg tttatagtaa ggtggcttgt gtcagtggtg cttctctatg 87600
ctgtgactca gaggaccacc ttcaaaatgg cacacagtgg tgctcgtgtt tagaagtatt 87660
gaagggcata aaatagtctg gggtgtgttg tttttttatt tctatatgaa tttatgttaa 87720
tctttttcag tagctgaaat ttggaagtcc ttccgtccct ttctccttcc cttcagggct 87780
ttatatggta ggcgtgtact ttaccactga gctacattat agccctagaa ggtgttttgt 87840
aaacttcttt accataatta tcaaatactt gagatgttac tcagtgtagt aatgttagca 87900
gcattcttac tttccttttt tggatgacca gacaatattg gaatcaagga aaatgctcct 87960
tttcttggat ttatcttggt agtgtgcttt tatgtgtgtg ccataatacc tgctttgctg 88020
tcttttcaaa cattttatga gatggttctc tctctacatt gcctaggctg atgttgaact 88080
tgtgacctcc atcagtcttc ccccaagaaa accgaatgat atcacctatc tttgagttga 88140

-continued

```
ttttcacctc tctcaagccc tcttagagag tgtgctgggt agtgagtttt ctgtagcatt  88200
gcacactcaa ttgaatcctc ttgtctctag cacatgctac tcctaaaccc aatggccttt  88260
ctaactctca ttttgaaatg atctgatttt tttgaacatg aagttgaatt gatgtatggc  88320
tgagtagtac aggggagatg attaaagata tttgttttct gctttgggcc atttggcagg  88380
tggtttgatg tactccagaa agtgtctgcc caattgaaga cgaacctaac aagcgtcaca  88440
aagaaccgtg cagataaggt gaatggcact gcagctagag atgacatgcg gatatcactg  88500
gggtggaaac agagctcaga cttttctaga ttagttgcca gaagattcta attgcaactg  88560
tggtttcttt cactttttcc tatagaatgc tattcataat cacattaggt tatttgagcc  88620
tcttgttata aaagcattga agcagtacac cacgacaaca tctgtacaat tgcagaagca  88680
ggttttggat ttgctggcac agctggttca gctacgggtc aattactgtc tactggattc  88740
agaccaggtt tgtctctcgg ccttgtagtc actatacttt ctcctaactg aatacaaatt  88800
accctgaaaa gacaccaccc aagactggcc cgtactccag tggggttagg ctttagaaat  88860
ttccacaagt tttctacatc tgtataccca ctcataactt tataataagc tgtctttaac  88920
ttgtaagata gaattttaga tttattctgg tgggccaggt catttatgca aaattcagat  88980
ttctgtaaaa caggtgatca tcagccaaac agtggtggcg cacgccttta ttcccagaac  89040
tcgggaggca gaggcaggca gatctctgag ttcaagccta gcctggtcta cagaatgagt  89100
tccaggatac ccagggctac acagagaaat cctgtctcaa taaactaaaa ataaataaaa  89160
cagaaacaag tgatggcttt gctcagagaa gcttctttct cagaggacag tggtcacata  89220
agtaagtggt cgttgagtac tcaaccctaa atgggacatc aggcctcctc tcccctcagg  89280
gagcactgct gaagaggggg atggaaaaaa gagagagcta gagggtaggg aggaatgctg  89340
tgaagtgtga aatgccagag ctgtcatagt cacgaactca cagcagttgt ggtcacctgc  89400
acaagatcaa accagtcaac ctcccagcat gactgatgtt ggggctcagc tgatggctgt  89460
ttggggagga atgtcatttt tctttgcagg ggagtagcac ataggcagca ctaattcaac  89520
tcaatggatt ataagaaaaa taacattaaa acatcaagat atcatttaca gactatactt  89580
tcaagcactg atgtaatcaa caggcccaat cacttttaca ccattctggg ggctgtgtaa  89640
cttggatcag aacccctctt ctcaaactct ccttgccttc ctcttgcagt tcctgtggtc  89700
ataaagttcc aatagtcctg cttgtaatac aaattctatt cctagggaga tcttctatcc  89760
atgccttcac tgagaagaaa ttatctttag gttgttgaaa attgaccatc atttttgtgc  89820
tctgattgtg gcctaccctt tctgagtgag ttactaggat gagccagttg gggagactcc  89880
ttggccctct taggctcatg gtcatagtgc aaaatgtatt tagttcaact tcaaaagcat  89940
ttatagtctt gcagtcggaa agtacaaagt cctgtttgag atttctcaat tgtaataccc  90000
ttggatttgt aaaatcaaaa attacatatt tctactatac tatgatgtag aatatacatt  90060
cccattccga aatggaggaa tggggatata gtgaggaaat actggaccaa agtaagattg  90120
aaacctagca gggcgaactg taagacctga agttagcctg taagccccac ctacccaagg  90180
actaggtaac ttcccggaat actgagagtt gtagtattac aaaaaaaaca acgccacatt  90240
ggggcgagcg gggggtaggg ggggtgaggg ggggtgaggg ggggaggaac agatggcctt  90300
tgagtttgtc cttttgtgag atagagtcct accacgtagc ccaggctggc ctcaaacttc  90360
catctggctg ccttttgccc aagtcctgag aacttgcctg aggctataat taaaaaatag  90420
acaaatttct ttgataaagt gaatttcaaa gacagtataa cattgagtct gtggattggt  90480
tattacagat accttatgca ggtctacagt gaaaaagagc aattaggata gaaagagata  90540
```

atagagtttg gagagaaaaa gagcactggg aagttttgcg ttccacctca ctcatgcacg 90600
agctagggta gttggcatag gtaagtgctg ttaaccagag gcttccaggc ctacatctac 90660
ctgtctgcct tgaccactgt gttcccaaag gcatgactga aggcactctg cacttagctg 90720
acttcacagt agctttgaaa atgtggttat aaacaagcta atcttctgtg taggggcttg 90780
ggaacagtac acagatgggt tgaagaaatg acccccggtt tttgtgtaag cctgtgactg 90840
acggcagctt ttctctccct gcattaggtg ttcatcgggt ttgtgctgaa gcagtttgag 90900
tacattgaag tgggccagtt caggtactga tgcttagtta cttgagttgt tgtccttgtt 90960
atgtacacat gtgcagccct aggtccttac agtgacaggt gctttccact ttcacacatc 91020
tgaccacttg cagaaagcct ttctcaagac ttgcttagaa acaggtctaa tctagccatt 91080
agtgtgtttt catttcacat tcatagtatg tgatgatggt aacatgtcac taagtgccat 91140
cttacccagt gggtccctgt tccctaactt tagaggaagc acttttaggc cgtggtttag 91200
taaagggagt gattgtggtc tttagttgca ttatctgtag tttttcttgt tggacattaa 91260
agttttaata atcttgcagt atgtataaca gatttgcaat ttttgaaaat tacagttctt 91320
agcaagtagt ttgaaaggcg caacaatgga gagttttgtg agtttccctg agatcgagac 91380
tcagctcttg ttctgattat gtgacacctt gactctgtag ttttaaccag ggaacatttt 91440
ctcctcggtg tctgaatttt ttcaggagaa gaaaggaaag tgaagagcta gaaaggtctt 91500
acctgctagc atccagtgct taaggtgcag cttcacaccg taaccatcag gctctccatg 91560
tggcagaggc aggaagacca agggtacggg tgggactaaa tgaggtctca gagtctgctt 91620
taatttagga ctttctcctg ggcttgactt gtaacttttt tttttgtata tgtagattac 91680
acatcttatt ttttaaaaaa gaaatgtcta aatgggtgtt tttgtttcta gggaatcaga 91740
ggcaattatt ccaaatatat ttttcttcct ggtattactg tcttatgagc gctaccattc 91800
aaaacagatc attggaattc ctaaaatcat ccagctgtgt gatggcatca tggccagtgg 91860
aaggaaggcc gttacacatg gtaatgtgtg catctctgct tgttgtcctc ggtcatccac 91920
tttgactgca agtgctgtgt gtatgtgtat gagggctcgt catgcgtgca catgggttag 91980
agatgtttaa gaagaaaaaa ggaacacatt gcttactcat aaaatttgta aactacttgt 92040
agaaaccata aaaaatagtg acatcattaa ggtatagata gattctgata tgtgcctcta 92100
tttatgaaga aaaattttta ttttaccatc tttatttgct ttggtctttt ttttagagag 92160
ggcataggct cagatctggg ccctcacatg tgctaagcag tttacctcca atcacaccct 92220
aaactcacaa cattttacat ctagcttgtc acagtcaaat tttaactttt gtgttatgtt 92280
ttgtcttttg tttgttggtt ggtttgttgt ttgtttttca tttgtaaaaa cttgtttgga 92340
gtctgatagc tgtctctcat gagtcatttc cacctgtggt ctcacttgct ccctcttcgc 92400
gcctatagct atacctgctc tgcagcccat tgtccatgac ctctttgtgt tacgaggaac 92460
aaataaagct gatgcaggga aagagcttga gacacagaag gaggtggtgg tctccatgct 92520
gttacgactc atccagtacc atcaggtaag aggaaagcac agggataccc acatcacagc 92580
atggagagac acgccatagc cgggtcctgt gtgtggtgag cagtctcggg aacactgggc 92640
tctctggcgc gagggagaaa gtgcactagg ctaggagctg gcacagccca gaaggctagc 92700
agacatatgg ctgaccacta gagtttcagt cgagatgcta atgtcacagg ggctgtttat 92760
tctcaaatgt agctcaagga tcaagtaatt gacagtgtta atctaaacca ttaacatttt 92820
aaaaatagta aaaccgtcaa atctgaaata agtagatagc atatttacct ctatcttaac 92880

```
gtagtcatgg tttttgtttt ggtttggttt gttgttgtta ttgttgttgt tgttttgaga  92940
caggatttct ctgtataata gagtcctagc tgtcctaggc ttgccttcta gaccaggcta  93000
acctcaaact cacagagatt tgcctcccga gtgctgagac tgaaaccata caccaacgtg  93060
cctggccagc catgtttttt atttgtgctc atatagtctt gtgtctctta agcatgagca  93120
tggactttac atgcttcaat cagcccatgt gtagaaatag tttttaacat ttttgtcctt  93180
ttaaaacttg tacttttgat tattcctccc ttattttgtt agctcctttc agcagcctgt  93240
ttctgaaact tcataaaacc acaagctttt ctttttcttt ttctttttct tttttttttt  93300
tgagacaggg ttagcctttt tcaaagaaac agtactttct ttgtttcatt tatgttttga  93360
tcaatcttta taatagttaa ttaaatattt aatgcttagt taagccaagg cataaagtag  93420
tttgagagta agcacatgcc tttgctaagc acagtggagc tagtagtgcc ttgggaatag  93480
tatacgcctt gtgcatgctc atcagggtct gccccgtgga gatcctcgag ggcccaggaa  93540
ataagggctt gtgtgcatag gcagtgtaca tggaccttga agcaaggcag ctttggggat  93600
aaggtagttg ggctaggctt aacgttgtat attgtctctg aggtggtgtg catttttttgg  93660
ttttggtttg ggtttttga gacgaaaaga acagcttagt ttttgtggac ttcctgatct  93720
attgtagcac agaagtgaat acttgaccat gctcctctaa aatgctatct acaaaatggg  93780
cagtgggcca gatgtctctg ttaccagcct ttgccaggtc acaggtttat ctatttagaa  93840
tgaccaaaat gaccaccagt aaactcacac tcagctttgt atgactgttg gcaagtgagg  93900
gccactcaac aataaaatgc ctttgcaaag agcactgaag tggatttaaa gtacatagga  93960
atattagatt gttccacagt atttagtcaa gggagtgttt gggctctcct acagattaat  94020
gtaagtttga ttttcacttg atcccttctt tatgaaatgt cgaaatactc atcatgagtc  94080
ttccggagcc cagcacagcg cactcatccc cttggaggtt actgcatctc ttctatggct  94140
ttttgttccc ttcacattca catttcacag agtgaagatt gtgtgctttc ctcggtcttc  94200
cctggggatt atatctcttt gaaccttaga gttaccagct aagctgggac cggtgtggaa  94260
catggggaag ttgagggccc ctgggccagg aagcattctg atcctaccca aacattcttg  94320
caggtgctgg agatgttcat ccttgtcctg cagcagtgcc acaaggagaa tgaggacaag  94380
tggaaacggc tctctcggca ggtcgcagac atcatcctgc ccatgttggc caagcagcag  94440
gtttgtcttc attgccctgg tttgccatta tgtagtgtga tttatttcag agtggactga  94500
gatgcttatg aaggttggtt gtgatcatta tatcctgaca ggttcttgct ctgaaagttg  94560
gtcttggtgc tggttgtggg aaaagtggct tcttttattt ccattaccct ttgaggttga  94620
attgtcttct cactttccaa gtgagggaac acagagtcag agaggttatt gaggttttcc  94680
atcctcacag agctggaggg tgataggtct atagttgctt ggcccagtgt tgacttgaaa  94740
actaagtcct ttcttatttt attaccctga ctcctgtatt ctggtaagtc aggtatttta  94800
tttgatcctt agctttcttt tctttttttt tttattggat attttcttta tatacatttc  94860
aaatgctgtc ccaaaagttc cctataccct ccctccgctc tgctccccta cccacccact  94920
cccactcatt ggccctggcg ttcccctgta ctgaggcata taaagtttgc aagaccaagg  94980
gacctctctt cccagtgatg gccgattagg ccgtcttctg ctacatatgc agctagagac  95040
acaagctctg ggggtactgg ttagttcata ttgttgttcc acctataggg ttgcagaccc  95100
cttcagctcc ttgggtgctt tctctagctt ctccattggg ggccctgtgt tccatcttat  95160
agatgactgt gagcctccac ttctgtattt gccaggcact ggcataacct catacaagac  95220
agctatatca gggtcccttc agcaaagtct tgctggcata tgcaatagtg tctgcgtttg  95280
```

gtggctgatt atgggatgga tccccgggtg gggtattctc tggatagtcc atcctttcgt 95340
cttagctgca aactttgtct ttataactcc tttcataagt attttgttcc ctagtctaaa 95400
gaggaatgaa gtatccacac attggtcatc tctcttcttg attttcttgt gttttgcaaa 95460
tcgtatcttg ggtgtcctat gtttctgggt taatatccac ttatcagtga ttgattatca 95520
aatgacttcc tttgtgattg ggttacctca ctcaggatga tatcttccag atacatccat 95580
ttgtccagga atttcataaa tccattgttt ttaatagctg agtagtactc cattgtgtaa 95640
atataccaca ttttctgtat ccattcttct gttgagagac atctgggttc tttccagctt 95700
ctggctatta taaataaggc tgctatgaac atagtggagc aggtgttctt attaccagtt 95760
ggaacttctt ctgggtatat gcccatgaga ggtattgcgg gatcctccga tagtactatg 95820
tccaattttc tgaggaacct ccagactggt tgtacaagct tgtaatccca ccagcagtgg 95880
aggagtgttc ctctttctcc acatcctcgc cagcatctgc tatcacctgc atttttgatc 95940
ttagccattc tgactggtgt gaggtggaat ctcaggattg ttttaatttg catttccctg 96000
atgattaagg atgttgaaca ttttttcagg tgcttctcag ccattcaggt ttcctcaggt 96060
aagaattctt tgtttagctc tgaaccccat ttttaatggg gttatttgaa tttctggagt 96120
ccaccttctt gagctatttg tatatattgg atattagtcc cctatcagat ttaagattgg 96180
taaaaattct ttcccaatct gttggtggcc tttttgtctt attgacagta tcttttgcct 96240
tacagaagct ttgtaatttt atggggtccc atttgtcaat gctctatctt acagcacaag 96300
ccattgctgt tctgtttagg aatttttccc ctctgcccat atcttcgagg cttttctcta 96360
ctttctcctc tattaatttc agtgtctctg gtcttatgta gaggtctttg attcacttag 96420
acttgagctt tgtacaagga aataagaatg gatcaattct ccgatgctca tggattggca 96480
ggatcaacat tgtaaaaatg gctatcttgc caaaagcaat ctacagattc aatgcaatcc 96540
ccatcaaaat tccaactcaa ttcttcaacg aattggaaag ggcaatctgc aaattcatct 96600
ggaataacaa aaaacctagg atagcaaaaa ctcttctcaa ggataaaaga acctctggtg 96660
gaatcaccat gcctgaccta aagctgtact acagagcaat tgtgataaaa agctgcatgg 96720
tactggtata gtgacagaca agtagaccaa tggaatagaa ttgaagaccc agaaatgtac 96780
ccactcacct atggtcactt gatctttgac aagggagcta aaaccatcca gtggaaaaag 96840
ctggcacaac tggtagttat catgtagaag aatgcgaatt gatccattcc tatctccttg 96900
tactaaggtc aaatctaagt tgattaagga actccacata aaaccagaga cactgaaact 96960
tatagaggag aaagtgggga aaagcctcga agatatgggc acaggggaaa aattcctgaa 97020
tagaacagca gtggcttgtg cagtaagatc gagaatcgac aaatggggcc ccataaaatt 97080
gcaaagcttc tgtaaggcaa aagacaccgt caataagaca aaaaggccac caacagattg 97140
ggaaaggatc tttacctatc ctaaatcaga tagggaacta atatccaata tatataaaga 97200
actcaagaag gtggactcca gaaaatcaaa taaccccatt aaaaatgggg ctcagagcta 97260
aacaaagaat tctcacctga ggaataccga atggctgaga agcacctgaa aaaatgttca 97320
acatctttaa tcatcaggga aatgcaaatt aaaacaatcc tgagattcca cctcacacca 97380
gtcaaaatgg ctaagatcaa aaattcaggt gacagcagat gctggcaagg atgtggagaa 97440
ggaggaatac tcctccattg ttggtgggat tgcaagcttg tacaaccact ctggaagtca 97500
gtctggaggt tcctcagaaa attggacata gtactactag aggatccagc aatacctctc 97560
ctgggcatat atccagaaga tgttccaacc ggtaagaagg atacatgctc tactatgttc 97620
atagcagcct tatttatact agccagaagc tggaaagaac ccagatgccc ctcaacagag 97680
gaatggatac agaaaatgtg gtacatttac acaatggagt actactcagc tattaaaaag 97740
aataaattta tgaaattcct aggcaaatgg atggacctgg agggcatcat cctgagtgag 97800
gtaactcaat cacaaaagaa ctcaaatgat atgtactcac tgataagtgg atattagccc 97860
agaaacttag aatacccaag atataagata aaatttgcaa aacacatgaa gcttgggaag 97920
aacgaagacc aaggtgtgga tactttgccc catcttggaa ttgggagcaa ggcacctata 97980
gaaggagcta cagagacaga gtttggagct gagacaaaag gatggaccat ctagaggctg 98040
ccatacccgg ggatccatcc cataatcagc ctccaaacgc tgacaccatt gcatacacta 98100
gcgagatttt gctgaaagga ccctgatata gctgtctctt gtgagactat gccggagcct 98160
agcaaacact gaagtggatg ctcacaatca gctattgggt ggatcacagg gcccccaatg 98220
gaggagctgg aggaagtacc cagggagctg gggagatctg caaccctata ggtggagcaa 98280
caatatgaac taaccagtgc accaccacca ccaccaccac caccaccacc accaccacca 98340
ccaccaccac ccccagagct cgtgtctcta gctgcatatg taagaagatg gcctggccat 98400
cagtggaaga gaggcccatt ggtcctgcag actttatatg cctcagtaca ggggaacgcc 98460
aaggccaaga agtgggtgtg ggagggtgtg ggggacttgt gggatagaat tggaaataaa 98520
atacccaata ataaaaaaaa gtgtaaaaaa aaagaaaaaa aaagagtgga tcaatttgca 98580
ttcttctaca tgataactgc cagttgtgcc agcaccattt cttgaaaatg ctgtcttttt 98640
tccactggat ggttttagct cccttgtcaa agatcaagtg accatagggg tgaggattca 98700
tttctgggtc ttcaattcta ttccattgat ctacccatct gtcactgtac cagtgtacta 98760
tgcagttttt atcacaattg ctctgtagta cagcttaatg tcagacatgg tgattccact 98820
agaggttctt ttattgttga gaatagtttt tgctgtccta ggctttttat ttttccagat 98880
gaatttgcaa attgcccttt ctatctcagt gaagaattga gttggaattt tgatggggat 98940
tgcattgaat ctgtagattg ctttcggaag gttagccatt tttactatat taatcctgcc 99000
aatccatgag catgggagat ctttccatct tctgagatct tcaatttctt tcttcagagg 99060
cttgaagtta ttatcataca gatctttcac ttccttaggt agagtcactc caaggtattt 99120
tatattattt gtgactattg tgaagggtgt ttccctaatt tctttctttt tccgtttatc 99180
atttgtgtag aaaaaggcca ttgatttatt tgagttaatt ttatatccag ctacttcact 99240
gaagctgttt atcaggttta ggagttctct ggtggaattt ttggggtcag ttatatatac 99300
tatcatatta tctgcaaata gtgatatttt gacttcttcc tttccaattt gtatcccctt 99360
gatgtccttt tgttgttgaa ttgctctggc tagaacttca agcactatat tgaataggta 99420
gggagaaagt ggacatcctt atctagtccc tgattttagt gggattgctt caagtttctt 99480
tccatttagt ttgatgttgg ctactggtct gctgtagatt gcttttatta tgtttaggta 99540
tgggccttga attcctgatc tttccaaaac ttttatcatg aatgggtgtt agattttgtc 99600
aaaatctttt tcagcatcta acgagatgat catgtggttt ttgtctttga gtttgtttat 99660
atagtggatt acgctgatgg gtttccatat attaaaccat ccctgcatcc ctgggatgaa 99720
gcctgcttgg tcaggatgga tgattgtttt gatgtgttct tggattcggt ttgcgaggat 99780
tttattgagt atttttgcat cgatattcat aagggaaatt ggtctgaagt tctctttctt 99840
tgttgagtct ttgtgtggtt taggtatcag agtaattgtg acttcataga atgaagaata 99900
gggtagagta ctttctgttt ctattttgtg gcataatttg agattagttg gaattaggtc 99960
ttctttgaag atctgataga actctgcact aaacccatct ggtcctaggc tttttttggt 100020

-continued tgggagacta ttgatgactg cttctatttc tttaggggaa atgggaatgt ttagattgtt 100080
aatctgatcc tgatttaact ttggtatctg gtatatgtct aggaagttgt ccatttcatc 100140
caggttttct agttttgttg agtatagcct tttgtagtag gatctgatga tgttttggat 100200
ttccacaggt tctgttgtta tatctccttt ttcatttttg attttattaa ttaggatact 100260
gtccctgtac cctctagtta gtctggctaa gggtttatct atcttgttga ttttctcaaa 100320
gaaccagctc ctgatttggt tgattctttg aatagttctt tttgtttcca cttggtagat 100380
ttcagccctg agtttgatta tttcctgcca tctactcctc ttggatgaat ttgcttcctt 100440
tagttctaga gcttctgggt gtgctgtcag gctgctagtg tatgctctct ctagttcctt 100500
tttggaggca ctcagggcta tgagttttcc tcttagatct gccttcattg tgtcccataa 100560
gtttgggtat gttgtggctt cattttcatt aaactctaaa aagtctctaa tctatctctt 100620
tatttcatcc ttgacaagga atcattgaat aaagtattgt tcagtttcta cgggaatgtt 100680
gtatctgttg aggcctgttt tgtgaccaat tatatggtca gttttggagg aggtacgatg 100740
tggcactgag aagaaggtat atccttttgt tttaggataa aatgttctgt agatattaat 100800
taaatccatt tgtttcataa cttctgttag tgtccatgtg tctctgttta gtttctgttt 100860
ccaagatctg tccattggtg agagtggggt gttgaagtct cccactatta ttgtgtgagg 100920
tgcaatgtgt gctttgagct ttgctaaagt ttctttaatg aatgtggctg cccttgtaga 100980
gttcctcttg gtagatttta cctttgttga gtatgaagtg cccctccttg tctttttttgg 101040 taactttggt ttggaagtca attttattcg atattagaat ggctactcca acttgtttct 101100
tcggaccatt tgcttggaaa ttgttttcca gcctttcact ctgaggtagt gtctgtcttt 101160
ttccctgagg taggtttcct gtaagcaaca caatgttggg tcctgtttgt gtagccagtc 101220
tgttagtcta tgtcttttta ttaggggatt gagtccattg atattaagag aaattaaaga 101280
aaagtaattg ttgcttccta ttatttttgt tgttagagtt gggattctgt tcttgcggct 101340
gtcttctttt aggtttgctg aaggattact ttcttgcttt tcctagcgta tagtttccat 101400
ccttgtattg gtgttttccc tttattatcc tttgaagggc tggattcatg gaaagatatt 101460
gtgtgaattt ggttttatca tggaatactt tggtttcgcc atctatggta attgagagtt 101520
tggctgggta tagtagcttg ggctggcatt tgtgttctct tagggtctgc ataacatctg 101580
tccaggatct tctggcttta atagtctctg gtgagaagta tgttataatt ttaataggcc 101640
tgcctttata tgttacttga cccttttttcc ttaatgcttt taatattcta tctttattta 101700
gtgcatttgt tgttctgatt attatgtgtc gggaggaatt tcttttctgg tccagtctat 101760
ttggagttct gtaggcttct tttatgttca tgggcatgtc tttctttagg tttgggaagt 101820
tttcttctat aatttttgttg aagatatttg ctggcccttt aagttgaaaa tcttcattct 101880
catctactcc tattatccgt aggtttggtc ttctcattgt gtcctggatt tcctggatgt 101940
tttgagttag gatcttttttg cattttgcat tttctttgat tgttgtgcct atgttctcta 102000
tggaatcttc tgcacctgag attctctctt ccatctcttg tattctgttg ctgatgctcg 102060
catatatggt tccagatttc tttcctaggg tttctatctc cagcgttgcc tcactttggg 102120
ttttctttat tgtgtctact tccctttttta tgtcttggat ggttttattc aattccatca 102180
cctgtttggt cgtgttttcc tgaaattctt taagggattt ttgtgtttcc tctttaaggt 102240
cttctacctg tttagcagtg ttctcctgta tttctttaag tgagttatta aagtccttct 102300
tgatgtcctc tatcagcatc atgagatatg attttaaacc cgagtcttgc ttatcgggtg 102360
tgttggggta tccaggactg gctgaggtgg gagtgctggg ttccgatgat ggtaagtggc 102420
cttggtttct gttagtaaga ttcttatgtt tgccttttgc catctggtaa tctctagagt 102480
tagttgttat agttgtctct ggttggagct tgttcctctt gtgattctat tagcctctat 102540
cagcagacct gggagtctag ctctctcctg agtctcagtg gtcagagtac tctctgtagg 102600
caagctcttc tcttgcaggg aaggtgcacc aatatctggc gtttggactt gcctcctggc 102660
tgaagatgaa ggcccgatag agggcctgtc tcagaagctg tgtagcttct gtagtccaca 102720
ctctcacctg cgcagactag tctctgaggg aaccaggacg aaagatggct tccccaggtg 102780
ctccagcaga gcccttccag gcggggtgga tacctctcct ctgtcgggga aggtgcccag 102840
atgtctggat cccgaaatgg ggtctgtccc agaagctgtg tcgatcctta gctttcttta 102900
tgtttatttg ttttttcata gcacttacaa agtaacctag caataattta tgacttagtc 102960
agaatttctg taatcagatg acccttacta gttaattaag aaaatgcagt agtccggctg 103020
tgccatatct tgtggaaaca aagagccctg gctcctggac tgtgtggtcc tcagaacaca 103080
ggaacctgtg tgactctcac caaagcacca ttacaacaga agatagaaca cagagcctgt 103140
ctatacacag tcctaccagg aagtctgagc agctgccaga tggatctctg gctatgcttt 103200
gaatgaaact cctaacagat gacaaggcac tactttgaaa taggttctgt agaaagcaca 103260
agggagccat gtttctcggc atctcataaa ctcttttagg catactctat tggtagttgc 103320
tgtctgcata tgctaggcag aattgcaggc actgatagga aaaatttcac tgaagaaaat 103380
gtattgaaaa gcagtgttct cccacctaga taacaatgaa ataaatacac tattaaagta 103440
tatacaatat cagaggatag tagttttgat ggcagaggag gagggtagtg tagggtagag 103500
aatgcatttg ttgttctaac agtgacaaaa tgagaaagcc ttttttagga ggtgacattg 103560
agtaaacatg attctagcag ttacctgcaa gagagtgttt cagcagagca gagagaaaag 103620
caagtccctg ggattgcagc atgacatttg gatacaagct agtcccagga aaaggaagga 103680
tgggagggta gacatagaga aatagtgtcc tgaaactttg ctaaggttac tgctgagagt 103740
aaaatgcagt ggatacactg ctgaaagtaa aatgctttta acttttaact gcgaggatga 103800
tggtgattgt gtgccccaga ggcgcagtga tgacgtgtgt gaagctgcta ttcccatcgt 103860
attacagaca tatccatgat gcttaattcc acagatgcat attgactctc atgaagccct 103920
tggagtgtta aataccttgt ttgagatttt ggctccttcc tccctacgtc ctgtggacat 103980
gcttttgcgg agtatgttca tcactccaag cacaatggtg agtgtcacca tatgtttggg 104040
atgcactgga ggaagatccc agcccaggtc tgccacagct ggtgagggag gacttgaggg 104100
tttgcgtttt accaaatctc caaccgagtc tgatctgctt ctctgggacc atacttggaa 104160
ccagtgctct agggactttt ctgttgaatg attttcttcc atgggattga caagcaggga 104220
aaatttaatc tttccttagc tttagcatat gcattttctt tttctttttc ttttcttttc 104280
ttttttcttt ttaggcatct gtaagcactg tgcagctgtg gatatctgga atcctcgcca 104340
ttctgagggt tctcatttcc cagtcaaccg aggacattgt tctttgtcgt attcaggagc 104400
tctccttctc tccacacttg ctctcctgtc cagtgattaa caggttaagg ggtggaggcg 104460
gtaatgtaac actaggagaa tgcagcgaag ggaaacaaaa gagtttgcca gaagatacat 104520
tctcaaggta tgtttctgt ctgaacctgt aaactgacca tgtcttttag ctgatcctat 104580
ggtgtcgcag cagcagtagc caacaataat cactgttctt tagtgaggct gatatcactc 104640
acctagcttt tttttttta agaaaaaaat gaaaagattt gtttcttttt attgattgtg 104700
tatgagtgtt ttgcctatga gtaagtaagt atacttaggg tgtgtctcat acccatggag 104760

-continued gccaaaagaa ggcattgaat ctctggaatt gcagtttcag acagttgaag tgtcattctc 104820
tgaacccagg ttctctgcca gatcagcaag ttcttttgaa ccctgatttt tcttcttacc 104880
ttcctcacct tttttttcat gtctttccta aggtctgtcc ttgtgacaga cttgacaaga 104940
gtggctcacc atgattaagg aggggtggcc ttccctgcat gcagcccagt aaggggtgaa 105000
ttgcctgtag catggtcaaa gcctagggta agccactgag aagcagccct gtacttattt 105060
tcaccatgtg ctacttgaag gacctttcgt tgccaaggtc aatagcatct accagatacc 105120
tgcaggatca gctcacatgc tacacacaca cacacacaca cacacacccg gtgtgctagt 105180
gcctcaaggg cagtgacagg ggagactgct tatcaacgct ctgcacagag aagtatctgt 105240
gactcctaga gttttcacta agttagagct gtgctgcaga tgtgctcctt aggacctctc 105300
atttgcaggg gtaagcacct gtagtctctg ataaacacac gatgcctttg tgtttgcagg 105360
ttcaactggc agcccattgc tttccctccg ttaggttgaa ggagtggcta aaactgatgt 105420
tacactaagt ttcttttttt atttcttttt tttttaattg agtatttatt tcatttacat 105480
ttccaatgct atcccaaaag tcccatacac actcccccac cctcccactc ccacttcttg 105540
gccctggcgt tcccctgtac tgaggcatat aaagtttgca cgaccaatgg gcctctcttt 105600
ccactgatgg ccgactaggc catcttctga ttcatatgca gcgagagaca cgagctccgg 105660
tggggtgggg ggtattggtt tgttcatatt gttgttccac ctataggatt gcagatccct 105720
tcagctcctt gggtactttc tctcgctcct ccattggggc cctgtattcc atccgatagc 105780
tgactgtgag catccacttc tgtgtttgcc aggccctgga atagtctcac aagagacagc 105840
catatctggg tcctttcagc aaaatcttgc tagtgtaagc aatggtgtca gcgtttggaa 105900
gcttacacta agtttctatg gcgaattacc gtcttatatt tatgtaacac tcctacagct 105960
gataaagctt aaaaaaatac attgtcaatt tgccttgatg ggcctttgaa agtggtatga 106020
ttaccatttc acatttaaag aaggtaatag agagaaggag agactcagtc cacagtgatg 106080
gtctgaaaca tttcacttgg tttagtgtac tgtctttgtg ttttcttact ttacaaaaac 106140
caatggtctt tatttcacac tgtgcttagc acagctcact gatcatggcc taatctgctg 106200
ttatgtgctc cctttcttgg aaggtttctt ttacagctgg ttggtattct tctagaagac 106260
atcgttacaa aacagctcaa agtggacatg agtgaacagc agcatacgtt ctactgccaa 106320
gagctaggca cactgctcat gtgtctgatc cacatattca aatctggtaa gtggatccga 106380
ttagacttca taatactttg tgttccctgt ctccagcagt gcccgcttct catagaaact 106440
gttctccatg ttccttgtgc catgtgagaa aatgttgata gtaggagtga atctgatacc 106500
atgtggtcca gcaattacat tgataggcag atacctgaca ggatgaggag cagagtgctt 106560
ggaagatagc tgtatactaa tcttgatagt agcattcatt acatagctga aagaagcaac 106620
tctgacatcc aatgctcagc tggttgataa gccaaatatg gcatatacat aagttataga 106680
gtcaaatgtg tctatgtggg atatttttca gcctgaaaag gtaaaatagt tctgacataa 106740
gaaacaacat ggggtgttgg agacatagct cctcagttaa gagtatttgc tgttcttgca 106800
gaagaccctc cttcacttcc cagtgaagag gctcaccatt actgtaactc cagttccagg 106860
gatctgatgc ggtcttttag actctaccag caccagacat acacaagctg catatccata 106920
catgcaggca aaacactcat atacataaca tttaaaagcc aacataggtg acccttgaag 106980
acattgtgct aagcaaaata agccaggccc aaaaagacga tggatgagat actcagagta 107040
ctccaaatct agagacaaaa aacaaaatgg tagttgccag tggcttagga gaggatttaa 107100

-continued

```
tgactttgga ttttcagttt tacagatgat ggtgatattg tataacataa gtgcatttaa 107160
taccagaact gtatatttaa agattatcaa ggtggtaaat tttattttat atgtatttta 107220
ccacaataaa aaataattgg aggcccatag gccttagtag atagatgttt gtaagcaacc 107280
ctgacaacct aagtatgatc tctaagacaa acatggcaga aggagagaat gaactgcttc 107340
caagttattc tctgcctcca ggtacgtgca ccccaccacc accagtaaac aaataaacct 107400
aaagagtcat gctgggaatg cagtgaatcc attggtagtg attgccagac acgtacaaaa 107460
ccctggtttt gatctctacc taacctaaac gtgatggcac cccagagaat cagaagttca 107520
aactcatctt cagctgcata gagagtttga ggcaggacga tctacatgaa gacctgtctt 107580
agaacagaat attttttaaa cttgtttgtt taattggtgg ggtgtaggtg ggagtgtgat 107640
atggtggctt catcctgtag tcttcgtagc atatttccac attccagctt tagtttctat 107700
catggccttg ctctttgggg gactcatttc atgtggcaga agtagggcct ctagccaccg 107760
tggtctgagc ctctgaagta tgctgattag cctccattca cccatgtagg ccatatgagc 107820
tcctagctgc tccgaccaac ttgagcagcc ttcttttgaa gggggtgtgt tgcctcctgg 107880
gcagaaagga aaagaaacag atgatgagcg gatagtttgg gccagagaaa ctgttagaac 107940
actggaggca acttctagaa acccagccag aagtgccagg aaatggacga tgtggcagag 108000
tgtttctcca gtcagaaggt gtgctctgta tttggagttc tatgtgcatt ttatgtacat 108060
atcttggaga aaaaagtagt tattgtcctt agccttcatc caacaggact tatattctta 108120
cctgttgcta tactgggctc tgacgtactg ggttgagaca agcagatgtg ctttttgtgc 108180
ccttgtagag cttcacagtc agtggggagg gtagtacagc aatacacaac cactgtccca 108240
ggaagttcat tggtacacat ttctgagggt gcctggttta tctggtttac ccaaagaggt 108300
cagcagaatc aacctttgga gttggaagaa caaactagag aaatggagtt gagaagagag 108360
tagagagtaa agcaagctgc tcaggtgaac agagagaaag gcattatgta gactgcctcc 108420
cttgtatctg gcacccttgg catagtagtg tgccagaatt taattttgat aatgggtgtt 108480
agtttcaaac tatatttatt cctaatattg atttaggtat tgtttttttgt ctaaagattt 108540
atatacttgt ttgttgtgtg tgcaggagag agacaggcag gtcatgtgca tgccaggatg 108600
ggcaactcct caggaatctc ttctctcttt ccaccttgtt ttgaggccgc ttcttctgtt 108660
tctgtgattg cactgccaaa aagagctttt caccaatcct cctgtctctg ccttccatct 108720
tgccgtacaa attaaatgcc cacccccaca tctgacattt tccatgggtt ttggggatta 108780
agcttgtaca gtaagtgttt ttactaactg agccaactgt ctggccctta aagatctttt 108840
gatttatgct tcattggtca ctgtagcaaa ttgaaagtca agaagtatgc ctgtttatga 108900
atagcaagtt gtttttagtt tgttggtcac tttaatattt tccattggtt ggtttggatc 108960
tgataccaga agagctttct cttgccttct ttggatggta gatgtctatg ttgtgtcctg 109020
ctcacctggt gggctgccat gtgtggctgc tatatggttt cactacttac tatccagttg 109080
ctctagcttc tcttgcttcc tttttcagga acatcaaaga ggaaaaagat tcaagggcat 109140
atttttactg tgtgttgtgt cagtgttgtc cagcaaagtg acctttagct gcccagtgac 109200
tgggtagcta atgcagatag catatcttag gtactttgtg actttgttta acttcagaca 109260
caatggctta aatggcttca tgtggtcagt ggttccactt ttttttttt catcatgcat 109320
acatccttct ggaagaacat tcaatggtta gacatacagg ctttgcccta gtgctgatag 109380
attatatata aatgtctatt tcttatttag tatgacacta ggtgtcagaa ctactgtttg 109440
ggtatttgct tggtcttaag attgggttga agtaaacagc tatgtgttta taaagatata 109500
```

tatttaggtc tcttgacagt tatcctgttt gcttgggtag ccccttgtgc ttccgtctgc 109560
tggctgtggc tcagttctgt gttctcccag gtgtggcctg aatcctttcc cctgtgttgg 109620
ctggctcttt ctggccacct gtgtctaggc ctccacagca gctgttttgg ggctcctaaa 109680
gaatgtggca attgagcctg gcagtggtgg cgcacacctt caatcctagt acttgggagg 109740
cagagacagg gggatttctg agttggaggc cagcctggtc tacagagtga gttccaggac 109800
agccagggct acacagagaa accctgtctc tataccctgt ctcgaaaaaa caaaacaaaa 109860
agaatgtgtc aatcatcaga ggtgcaaaag tggactgact tgttaagtaa gttgtgcctg 109920
tttctgctta gaaaagttag agtttggggc tggggaaaac cctaatcaga gaagtgcttg 109980
cagtgcaaag tgtgagagct gagtttggat tgccagcacc ttattccaag cgttccttgg 110040
cagccagtat atctaatcag tgagctccag ctccaggttc agtgtaggag accttgtgtc 110100
aaaaaatcag atagagaagt aatattgacc ctacatcagc ttttaacttc agcacatatg 110160
tacccaggta cacacatgca tcctcacgta catagaagca caagtatgca cacacaaagg 110220
ccacaatttt ctaagtgcca agtgctataa aagtatggaa aaggacaatg aatagtcctt 110280
ggtcacctgg tactggacca ggtagaacag tagaggcata ccccataatc tgtttttctt 110340
atttttgttt ggttctagga atgttccgga gaatcacagc agctgccact agactcttca 110400
ccagtgatgg ctgtgaaggc agcttctata ctctagagag cctgaatgca cgggtccgat 110460
ccatggtgcc cacgcaccca gccctggtac tgctctggtg tcagatccta cttctcatca 110520
accacactga ccaccggtgg tgggcagagg tgcagcagac acccaagtag gtgcacagct 110580
ccccagggcc aggccccagc ccagtgtttg gcctgaggca aagctgctct gagagcattc 110640
tcattttcca ttctttataa agctttgtaa aattcaggct gcatattaat ctttctttca 110700
tgggtactgt tttgtaggga aatgtggtct ggctacaggc attcagacca aactgtttga 110760
ctgtgatttt ctttgacaag cgctttgaca ctgttccatc gtttgggcta tgcttgtcag 110820
gctctatccc tcctgccacg tcctacggct ctcattggtt ctacagccag acatgttgca 110880
atgtcttaac tttgttatga gtaaatgtgt tctgggtatt cttagataat gaagtaatta 110940
tttagcaaat ttcgaaactg attggaagta ttttattaat ttatttttac tattcagata 111000
gactgtttct ggttgtgggt ggccctcttt ttttttgcaa agagtttgta gtcttaaatc 111060
tcagtgccca ggtactaact gactgacttg ctcagtcagc tctatgagca tgtttgggag 111120
ctagaagctg tgagccccga tgagtcggtc ttcagtgtgc tttctggaca gtttatgaac 111180
acttgtgggg aaatttttcc taaggaaaag tataggtatt gttagctctt cagcttggtg 111240
tagggagacc agagcctccc atccagacat gcttttacat ccctgtgtcc ggcatttttt 111300
gcccatctgc tgtgtgctct ttataatgtc atctgcaaag gaaatagaaa cactacttcc 111360
tgcccccacg tgtgatcact tggagaggta cccacaacat catttgaaat gcttagagga 111420
tctcttaagc ctgtcacatt aactgatcat tataagagct aggacaggaa gccagctaca 111480
tagctctctg gttcttacat gtacatgtaa atcagccctg aaactgctta aagcatttca 111540
gtccaggaag cttcgtaggg gctaggagtt tgcacatatt ctaagcccct gctgctgcca 111600
gtgcggttgt tgcactgatg ctctagcaca gggacagctc agcaccacca gtgttccttc 111660
ctttcttctc tttctttctt ttctattttt tcagtttttt taaaattttt ataaaaatgt 111720
ttttatttga aatagaatca catcatttcc ccccttccaa ctaccctcca aagcctcctc 111780
tatacctctc ttctcacatt gatagccttt tctccaattt gttacataaa catgtaaatg 111840

-continued

```
gtatgtgtgt gtatgtacag tatatataag ttcaatttac tgtgtctgat tttgttattt 111900
gtgtttatat ggattcattg ttggctactc tacattagac agccagtaag caggctcatc 111960
cctggaagag gctaattctc ctttcaaaaa gttattagct acttatattt tttgtctagg 112020
gataagatct atgaaaactt cccccatcca tattaatata cccatgaaca ctgcctttat 112080
tgtagtctta tttgtgtatc catttctctc ctagaccgct tcacagcaga ctttctggta 112140
ttctggccct tacaatcttt ctgctcctct ttcataatgt tccctgagcc acagatgcag 112200
gaactgtgat gtagatgtat ccactgggct agactcccct acagtccatg gatctctagt 112260
tttgtccagt tgtggttttc tatgattgtc ttcatttgct ataaagagaa gtttctttga 112320
taagggtggt agctacaaat tgaagctcag agctgtgtat aatgaagtct atctttaatc 112380
tcagccttca ggaggcagaa gcaggtggac ctcagtcaat tcaaagccag cctgatctac 112440
aaaccaagtt ccaggcctgc cagtgctaca cagagtaaac ttgtctcaag taaataaaca 112500
aaaacctggc agctttgacc ttagtaagga gactcagtgc ataaaggaac ttcctgctaa 112560
gcctgagact tgagttctaa ccctaagacc cgtatggtaa aaagggaatc tgttcccata 112620
tgttgtcctc tgatatccac aggcacatgg gtgcacaggc acacaaatca tttgtttaaa 112680
ggcttaaaaa acaaaaataa ttggggcctg agaacttgca gtaggttccc aggacagtct 112740
agtaaacatc caagcctgag ttgtgttggg taagacacgg gagcctccat taactatgga 112800
tgagccaaga aggcaggaga aggtaagaat ggctttagcc cacagtaagc cataattctc 112860
agcaacatct gcccacccgg ttggtgtata atagtgttga agattaaaag acatactatg 112920
gtttgttcaa gaggaaaatg gattttgacc ttagctgatg gatcttttac caagatgtct 112980
actggacacg ctgaaacatc tgtggtaaaa gatgaaagtg ttatgttaat agaagaaaac 113040
aagtaggaca agtgaattta ttttagaatc cttggctgtg ctctggatct ggaatataag 113100
actgctagaa tgattattat tgggtagtca taaatataag gatgagtttt ctgtgagtga 113160
tggctttgta gctgtgaaca tgtttgggag acaactgctg cagagtttat agtgaagtgt 113220
gctctggaat cattcatccg tgttgcagcc aaagaaatgc atgtgtgcaa gtattcagac 113280
tgcaataacg tttcacatga gtgtgcagtg tgtgtagagt ccaagtagga tatttggtat 113340
gaacctagtc tgcatgtgta aagtgtgttc atgaattcaa acatgaccaa tattaatagt 113400
tgaatatagg caaaaatcaa gggctgttca ttgaattgtt ccttcaagct tttctgtttg 113460
acactttcaa taaaccgggg aagaaggtgg aaaagatagc aatcagagtc agctcttagg 113520
ccttactata aggggattgg aactatgaga attgggatca tagtttcttt tcatttatat 113580
ttgtgtgtgt ctctctctgt ctctctgtct gttttgtctg tctgtgtctg tgttaatgtg 113640
cctgagccca catgtagagg tcagaggaca actttgagga gtgactcagt cttcttcttc 113700
cactgtggaa tccagggatt gaactcaggt tgccaggctt gtgcagcaag tgcttttact 113760
tgttgagcca tcttgccagt tcaagagggg atttctagtg atagaaataa tagtaacatt 113820
tatccaaagg gctacagatt ggagtgtaca gaagaagctt ccttgagttg gtgaatgtgg 113880
gatttggaca caaacattgg ttttattgta gtagttattg gtagtttttc aaagttgaaa 113940
ttacagtttc tttctttcct tccttcttta ttatgtgtgt tggtattttg tctgtatgag 114000
ggtgagatca cctggaactg gagtgataga tagtagtagg ccaccatgtg ggtgcttgga 114060
attgaatcca ctggctggaa gaatagccag tgctcttcaa tactaagcca tctctctagc 114120
tccaaaatta ccacgtctca ccatacacaa tatattaaaa tgagaaacct atctatcact 114180
ttcagttttt agtgcagtat tcttcagaga agccgcccat gcttttcctc atttgcttag 114240
```

-continued

```
atctcaaggt ctgcacttag gtaacttctg ctcctcagta gcaaggtcat aattgagcat 114300
tatttgtgtg atgatttgat tagtagctgt ctcttctttc tatggttgct gttatattcc 114360
agtcagtacc atttcacatt caaaccataa caatgtctcc tgctaattat ttaattgcaa 114420
atttcaccta ttgtacgtga gtagttcttc gctgtacatg tggctatgag tgtaagctac 114480
aaagctccag ctgtgaaagg gcaggggttc tgtatatgtt tcctaactga cagagggtgc 114540
ctggtgaaat gccttttgta ccatctgttg tcagatacaa acagtaccat cattccagga 114600
agttccctct tgtcccttta tcaccatccc ttcccttgtc cataagaacc tccgtgaata 114660
ctctgtgccc agagcagaaa tccatggaaa tgaacactgc atccggttgt tgatcagcaa 114720
ccattgatca gtttaaagtt tatttccctg gtggtgatct gtggtctgct cctgcattac 114780
tgagttgatc ccactacaga tacactaggt tattcatcca tctgctacct aggaagcaga 114840
aatggttggc agctttaaca aacctttagc ttgcagcaca agttttatcg ataatctatt 114900
agtactgagg acttacagga ctggtcaaca aatttcaagt gtgctttctc tcctgtgact 114960
tctgtcccta ttgagactga gcaaaagact agaaatatgt cagacatggt cttttaaata 115020
tttggctata actgaaagtc tccagggtta tatttagaaa gatgcaatga gaaaggagta 115080
tgagtggagt aaccactgca gtagagaaga agcactttga acagtaattc cacaaccatg 115140
actttctcag taatgttttt gaaaattagt aggaaagtgt gaaatgaggc ttctccctgg 115200
cacttgaagg tgtttgtaga acatgagaaa tatcagaaca actgctccat tatcaaacat 115260
ggccagtgtg aattctggaa tggacatgct atttggaatt gcagccttaa atagtgggtt 115320
ttgcccttca gtcaagcact gtaatcatct ggctgctaaa ctctctgtgt ccttcaatga 115380
tttctaggga cagaagtctg aggtgcataa acacacacca ccagtctgat agagcaatat 115440
ctggaataac ttgtgggttt gagaaggaaa atccatcata gctttgttca atattgtgtg 115500
tctaagtttg tggctatccc agacattccc tcattgcata ttcatgcctt gtaggagaca 115560
cagtctgtcc tgcacgaagt cacttaaccc ccagaagtct ggcgaagagg aggattctgg 115620
ctcggcagct cagctgggaa tgtgcaatag agaaatagtg cgaagagggg cccttattct 115680
cttctgtgat tatgtcgtaa gtgcccacaa gagctcttat ggtagagggt ggcatagatg 115740
ctgcttatat gcacctgcta ggcaaccaaa ttattcactg tgccacagat atatcaaagc 115800
tgaggagagg tagcaatgtt tactctggag tttaattaga gcagtctggt gacatttttc 115860
cttgtattgg gcagctgtgt tttttgattc aagaactcta tcaaatctgt ggcatttaga 115920
gtctgttttc tttactaagc attgcagaca gagtaagtag aacagcccat gctaggctgg 115980
cctgcaacct ggtagcaagt tgtattccta catggggctt cctttgttcc catgcatgca 116040
aactccaggc cagtcgctag ggagggctac accagagtgc tcaccgtgct cctgtgggca 116100
tctacctctt gacttgtcca aggagccaat tctctgatat tgaggcattt gctggtgtct 116160
ctaggagctg gatgttgccc ttggttcttg gcttcctgtg gcctctacca catgtgatca 116220
gaggtgtaag gttctataag tttccttcct ttctctcatt tacttatact cagacacttg 116280
tcttcaccaa ggcaaaattt gtatttcaag tgtgtttttt cttacacttt gtagccttct 116340
tgtccacttg aaatatatct tttattatat ctttctagtg tcagaatctc catgactcag 116400
aacacttaac atggctcatt gtgaatcaca ttcaagatct gatcagcttg tctcatgagc 116460
ctccagtaca agactttatt agtgccattc atcgtaattc tgcagctagt ggtcttttta 116520
tccaggcaat tcagtctcgc tgtgaaaatc tttcaacggt aagtctttag cctgccagtt 116580
```

-continued

```
tgctttctcc aacttaaaaa tgggatactg ggattttgtc agtactagtt atcagtctga 116640
ggaataataa atttcgttcc ttctcaacat tagccaacca ctctgaagaa aacacttcag 116700
tgcttggaag gcatccatct cagccagtct ggtgctgtgc tcacactata tgtggacagg 116760
ctcctgggca ccccccttccg tgcgctggct cgcatggtcg acaccctggc ctgtcgccgg 116820
gtagaaatgc ttttggctgc aaatttacag gtactgaaaa tggtaattta tatcaaaact 116880
tagaaagtca atcaaaacat ttggtctatt gacctggtct tgattggcca ctgataaaga 116940
gcatgtatgt catatttgtt atttgtgtat ctgaccaacg gctcttttta gatatactgt 117000
gtatagtaat ttatcctttt taagtgggtg tgaggttgta tatcacaaaa gccctgatgt 117060
gttcttgtct gtgtagagca gcatggccca gttgccagag gaggaactaa acagaatcca 117120
agaacacctc cagaacagtg ggcttgcaca aaggtaagac tgcagcgtgg ggtcctggca 117180
cttgggcaac cagcgtatta acacatagat atgttcagga acaaataggt agacaaagga 117240
attagtgtac agtgagttta ctacagcaat gccagagtag aaaagactat ctaaatatca 117300
gatgaaattt agtcatgtct cactttagta gacatgaaga agtggcactc aaatacctgt 117360
tgcacagaga agggactcct gaactttgtg actgttgaag ggataagaag tatgtttgtt 117420
acctctgcta ctggaccctg actgagtggg aataaagcta gaacctaatt gccaggttgg 117480
agggagtaaa catgagagca ctacctggct cttggcatgt gcacattatg ttaagtgaca 117540
tctcttcata gctattcttt tgcctaattg tttgaaagtc ttttagaagc ctttattaga 117600
aacatttcca tctgtagtgt aagtgtagtt ccttgactac aagataaatt aagaaaagct 117660
ttcacctctt ttccattgct gaagggggaa gggagcattc gagagggtct ctcataactt 117720
taatcttcag aggatttttc atggtgtttc ataatgggac agggcatggt ctggatgatt 117780
tttctcaatc tgcagagcca catgatgctg acatttgatc atttgacata tgaagtatca 117840
cattgactct gtatagtaag agaataaatt atcattgtgt ttgacagtag ttgtagtcat 117900
agaccaagat aaggaagatt atgacttcat aaataattta ggccagatga aatggttttc 117960
tgtgaaatga ccatttctaa tggaatgaat tgtgtcatta ttggggatta aatggagttt 118020
gtgcacttgg atcttaaaat ttatctgttt tgcacacatt acaaatacga tggctaggat 118080
tatgtaattc agtggtaaag cacttgtcta gtgtgcacaa gtccctaggt tcaatctcta 118140
atattgccaa gaaaagaaag agtagaatag aatagctttg ttagcggtta tatagttcat 118200
tgcctaatgg aatgttgagc ataaatgaaa cttctggaaa atatcagtga ggtataaatt 118260
ttggtaattt aaagtaacta gggcgtaaat gtgcatcatg actttagaat gttgaaggga 118320
aagtccaaaa cctgttgccc tgtcttaaga agctcctagt gctccttggt attacatgtt 118380
tctagaactc atctgtgcaa aaactgagat ttcaaaccaa agaacaaact actctggctt 118440
ttttattcca gacaccaaag gctctattca ctgctggaca gattccgact ctctactgtg 118500
caggactcac ttagcccctt gcccccagtc acttcccacc cactggatgg ggatgggcac 118560
acatctctgg aaacagtgag tccagacaaa gtaagtgtcc cgaatgtcta agtgtgatga 118620
ccaggaaccc tgtggagaca atgacagcct ctgtctacaa tgaggatagt ggtggctgtc 118680
agtatacatg ggacctgaca ctcagctcag gtcattagat gccctgcttg ggattagagt 118740
gcaggatgga ggccaagagg tcctactgag aacaggagtg ctgatgtgag gcttttgtgg 118800
aggactgtgg gggcaagtca ggtggctagt cagcaagtca ggaaaagttg gttgtggtcc 118860
aggacctatg actgcagaca ttgtccagca catgctgaca aaacttggcc tgcctccccc 118920
tctgaacctt ctatctccta taaattgatg cacctactgc caccagctat ataatgtatt 118980
```

gtcatctgta ccctttctca ttcacacttg agaattagaa actgttaggg cctttgcctt 119040
ttaggcaagg agatgagatt ttagaagcct gcagcccatg acagaaaaca cacatttgcc 119100
ccaggctcac tctccagctt tgtgggaggc atttctttgg ctttggctgc tgggaaagat 119160
gagggaggca gatactccag tatagtatag atggtgcatc atctagagtg caggtagagc 119220
aaaaattgtg aacactgaga acttggctga gtttgcaagg actgctggaa ggtccacagg 119280
tggaaaagaa gagggcattc aagcacagaa caagagaggg aagactagct gtctagagag 119340
tgtaagccca agatgtgtct gatgtctgta cagccagccg tcggtgcttc tatcacagcc 119400
cagagaagcc gaagtgccta cccagtccca ttcaattttc ttttcttctc aggactggta 119460
cctccagctt gtcagatccc agtgttggac cagatcagat tctgcactgc tggaaggtgc 119520
agagctggtc aaccgtatcc ctgctgaaga tatgaatgac ttcatgatga gctcggtagg 119580
caataatccg ttgagtccag gaaatcctca gctctgcttg tcagaaagtt agatttgtgt 119640
cttagttagg gtttctgttg ctatgatata acactatgac caaaaagcaa gttggggaag 119700
aaagagctta tttggcttaa caccatcatt gaagaaagtc aggataggaa cttaacaggg 119760
ccagaacctg gagtcaggag ctgatgcaga ggccatagag gagtactgct tacttgcttg 119820
ttctccatag ttggtcagcc tactttctta cagaacccac gaccaccaac ccagggatga 119880
caccactcac tatgggctgg gtcctctgcc atctaccact aattaagaaa acacccacag 119940
gcttttgatg acattttttt tcttgtttgt ttgttttgag acagggtttc tctgtgtagc 120000
cctggttgtc ctggaactca ctttgtagat caggctggcc tcaaactcag aaatccacct 120060
gtctctggct cccaagtgct gggattaaag gagtgcacca ccaccccctg gcttggtggc 120120
attttcttat ctgaggtttc cgcctcttag atgactttag cttgtgccaa gttgataaaa 120180
ctagccagca caatttgtct catctttgtg tgattaatat atgggaaacc tgagttcaag 120240
caagggacac catcaagcaa agcacatggg aggctctaac aaaaaatggc acacgagagc 120300
tataatccag aatagctagc acatgagatg tgaataggat gccgttttaa acaaactaga 120360
atcctaaaag aagaaaattg ttttaacttg atctttcata cctttaaaga aaacgggtgg 120420
tcataggcta tggtcagttg atcattcatt tcctgactat aagaaagtat tgtgtgttca 120480
ttgtcttctg gaaattgatc tctagtaacc cctgtattaa ttactttctc gttgctgtga 120540
taagacactg aggaaaagca gttgagatga ggagggtttg ttttggctta cagttcaagg 120600
gtacaatcct tggcagggga agcatcacgg taagcttgat gtgtctggtc acattgtgcc 120660
cgtgaccaga aagcagagag aagtgactgc tagtgctgag tttgctctgc cctttgtgtt 120720
cagtccagga tccctgccca cagttaaagt gggtcttcct acctcaacct catcaagata 120780
ggcacaccaa gaggttatta tctcctcagc agttgtagaa ctgctacgct gacatcagta 120840
ttaaccatta cacccatcat gtagtgaggc accttgtccc tgtagataaa gaggcattct 120900
gtcatgtagt gaggtacccc gtcctctcta gatatagagg aattacctca tgtagtcaga 120960
tgccctgtac tgtctagata cagagcaatt ctcctccact taccccctcga ataccagaaa 121020 gcatactgag agctggtgca ggccttgaaa gcattcaatt cccttccttg tcttctttgc 121080
caagcactct taggccacta ccttagtggg gttctttgtt gcccagtgaa gacaaggacc 121140
tcattgcccc ttgatacatg ccaaatggtt atggggaagc aggaactgag caggttaata 121200
gaaggtgtgt gtgttgtgga gagagagggt tctcacatag gaagatatct aaagcacagg 121260
acccagtttg ttatattttc caagtcgtta ggtggactat tagcagcttg caagttccat 121320
ccatgaccat agaaatgttt gatttggggg aactaatgat gaaatacagt gtttaatatt 121380
aaagcttatg ttctacttga aaaaattgtg actctctcta aatccttaaa tggcttaaaa 121440
taagtttttg acaaaacata ataaaaactg tcatatgagg ccagacatgg tagtgcatat 121500
ctttaattcc aatacttggg agtcagacac ttgaggatct ctgtttgtga catgtctggt 121560
tgacttaagt tccaggccag ccagggctac atagtaagac tatctccaaa tcaaaaaaaa 121620
aaaaagaaaa ttaaaagttt ttggcatgtg aaatgttgtg tgtgtgtttt tttaagcaga 121680
tttttgtcta atataagatg ctctgtgtgc cttctcaggc tgcagcattg cttggcatcc 121740
cactggattc ttagatggca tattaaactt ggtgcgctgt ctacatcaat taagatttgt 121800
catcctagaa ttatttcaat gaaatataag atcataaaaa ttaaaaatat tgctctttct 121860
ctctttccct ccccctctc tccacgtggc catggccagt ctctctctct ttctaccttc 121920
tctcctttct ccctgacttt ctacaataaa gctctaaaac cattttaaaa aattaaaaat 121980
attactttaa aattcaaata tgacagtgac cagaaatatt tattaagcat gttaagtgga 122040
gttgttgata tatttattaa tatatataac ataggatata ctttttaaaa tagagaattc 122100
aacttagttt tatctgtctt ttaactttat ttgtagtcta agatcttttc tagagagtat 122160
ttcccacttt tattattata agttacttga gacaagctac atcataagag aaaaagattt 122220
attttgactg atagttctgc acatacaaca tccaagggct catctggtga tgactttact 122280
gtcagagtcc cagtgtggtg cagaaaacct cccatggcaa acaataagga gcttgagtgt 122340
ctctgtttct agaatattct cagaagcatt ccttacagtt ctttggtctg gattatctca 122400
gaaacaaatg cttattgcat taactgtgtg tgttccagcc tgaaggaaag cttactgtct 122460
ttgctgttgt ttgtcttgca tgtaaacttc tgacccagga gttcaaccta agccttttgg 122520
ctccctgttt aagccttggc atgagcgaga ttgctaatgg ccaaaagagt cccctctttg 122580
aagcagcccg tggggtgatt ctgaaccggg tgaccagtgt tgttcagcag cttcctgctg 122640
tccatcaagt cttccagccc ttcctgccta tagagcccac ggcctactgg aacaagttga 122700
atgatctgct tggtaattaa atacagttcc cttggatgct tgtctgtcta tcttctctgt 122760
cactctgtct ctctttatgg gtgataggaa tggcagtagc agaatggaca agccagaggg 122820
acactgagtc acacattgaa cctagagctg ccaactctgg tagatcagct gaccaagcct 122880
ctaggaccct cctgtctcag ccctaagtgc tgaggttaca ggtgtacacc cacagccagg 122940
ttttacataa gatcttaaat tccaaactca agtcctcatg cttgcacagg aagcacttat 123000
ccaccgactc atcctctcag ctcaagttat cttagtgttt tagttatttt atattatgtt 123060
atagttgtct gcatgtatgt cttcaccaga tgcatacagt gcccatggag acagaagatg 123120
gcatcaaatc ccatgggact ggaattacag gtggctgtga acacactatg tggcagctag 123180
agatttaact taggtcctct ggaagtgcag ctcatgctct cagctcccga gctgtctatc 123240
tagctacaag ttgtcaccgt ttttaaaagt attacagatt cagcaccgtg cttttcctca 123300
agcacgcata tagtcaggac tgttgatcta aaaggctgac aaaaatagct gagaaactgc 123360
accaaatcct tagctctaaa cttctttctt tgttgcttga cctggacata gaaagtcagg 123420
ttctaagccc ttcaggatca gtgggttaga ctcagggcaa accatgtcct gactttatgt 123480
agcacgtatg agtgagcatg tacagatgtg cttgctctct tggtcttggc aacctcaaat 123540
tcacatagtt gtgtgaaggc ttctgaaggg gcgggcctgt gctcacagtc aaagtcactc 123600
atgtcagtct catgtttcag gtgataccac atcataccag tctctgacca tacttgcccg 123660
tgccctggca cagtacctgg tggtgctctc caaagtgcct gctcatttgc accttcctcc 123720

-continued tgagaaggag ggggacacgg tgaagtttgt ggtaatgaca gttgaggtaa gagcagctct 123780
gaaattatgt gtccctgtga ggacaggata tgtgagtagc actaagatga aagtccttga 123840
aaaccgacag tgtggagtac aatagtgcac acattagccc agctgccttg gaggcagagg 123900
cagaattgtg ggttcctggt ctgtaaggat gtgcctgagt atacagctag accctatttg 123960
aataaacagg aaggcaggga atacctattg gcaaagtctg attcacctga tggtacagag 124020
tgcctttcac cctcaccact gggaagcaag gaggtctgta agacatcctg ttatccctac 124080
actataaacc taatgtgggt cctaaataaa atctagacag tgttacattt taaattgggc 124140
agtgaagctg gacatttcac ccagaaacac ttggcccctc aaaatgtatc tatacgtgca 124200
ctatagtttt attaccttgc catgggcatg ctgggaaaga gcctcactgt gccagagctg 124260
tgctgccaat cctgaacaag ggttgacacc ttaccctaag agaagaaagt cagtatcctg 124320
agggtgtatg gtacaaaggc accaggtgaa ccaggctaag ttaggtggtc tttgagcttg 124380
tcttagccca gtgaagacag gaaagcaaat gtgtgtgtaa agtattgggt ggcagctcct 124440
agtcatactc tgcgctgcac aggccatgcc atgacacttg tttcctataa aaactctgtc 124500
cccatttcac acatggggaa agaagctcag agaggttcgg ggacttgcta gaagtcacta 124560
gtcataaatc atactccaaa actcagtgtt gtgactgaga tacaaaacaa aacacattct 124620
gtttctttaa aaaaaaaaaa aaaagtccaa tgttacagga gccctcaaga ccctggctgg 124680
aggctttgta tatggctcag atcaagtttc tatgggcacc catggttcta aaggaaaaag 124740
acacctaggg taaggttggg cattctggca gagggaaggc tggaacttgg ggtataggtg 124800
gatcaggact gaatattaag aaaactagga atgacaacct agaaatgtgg gtcaggggcc 124860
attcttctgc aaggaggttg tctgatctcc tgccctctcc atctatccat ggtcttccat 124920
atcttttatt ggcactgctt ccctagaggt ccctgagata gagtcctggg tgagcattct 124980
aacacagtgc ttccctttag gccctgtcat ggcatttgat ccatgagcag atcccactga 125040
gtctggacct ccaagccggg ctagactgct gctgcctggc actacaggtg cctggcctct 125100
ggggggtgct gtcctcccca gagtacgtga ctcatgcctg ctccctcatc cattgtgtgc 125160
gattcatcct ggaagccagt aagtttttgt ctatgaatga ttttcttgtc ttcacacagc 125220
tcaactgata atcagcaata catgtcaggc tggaatattt tttcttcctg tcttgtattt 125280
cccaagaacc aagttaggac ttggggtgga atggatagat tgtaggtgct gccttcagaa 125340
ggcccatttg tccaccccca gaccttgtca ttacactaga acttaacttg aatttgcttt 125400
tctagctatt ttgttttaga gtttggagtt ctagctctta aaaaatattt tttaagtttt 125460
atccctttga tctttagtct tagttgacta tttgatgttc ttagtcctag atgattataa 125520
gattaataag attacattca atagatgact tctgttagag ttgaagtgtg tgcttgcata 125580
ctgcattgta atgctaatat gttgtaaaat aaaagggatt cattcttttc aaggaacagt 125640
gtcctcaaca agggtcatta gctaaaaatt tttaaaaatt ggacattata gtttacatgt 125700
tagaggatgt tttgaagttt tatgttttca aattaaacat tatagagtgg tgttttgatc 125760
tttcattgtt taaattgttt tcatctgtgc attgtagtca acttggaaac aaagatccag 125820
ggattaattt taaaaagcta ggcttcttag tcaaagtgac gcttttagca gtattgagtt 125880
gtgaatagtc tgataaaaac tctcagggtg gagatggcag acggtgcatt tagaagcctc 125940
agtgcggaag cacaagtctt tgtctgttca tgactagcca aagcactggt gcctgcatct 126000
gctgttctcc agtgcttttc agttttacag aaactgcttc tagaaatcta gccctcagtt 126060
gacctgtcat cgtacgtttc tatgaggctg tacaggcatg aagtacctta agtacaaaga 126120
agagttaaag tttatgttct gctgtaattt cagttgcagt acaacctgga gaccagcttc 126180
tcggtcctga aagcaggtca catactccaa gagctgtcag aaaggaggaa gtagactcag 126240
atatacaaag taagtcttag gaccattttt tccccttctg tgtttctctg gagccttcca 126300
attcattggc aaaagaaact cacgaagtgg actctgggaa acattgctct tgctgtcctg 126360
agggctcatc tagactttaa ggggcaagag ggctttttga ccatggctgc atatatgttc 126420
ctggttttgt aagccctgtt tttctagtga agattcccct ttccttaatc agctggtctg 126480
actcatcctg catccttcct cacaacctgg atttgtacct cttccctgag aagcactgcc 126540 tcaccccccct gtcttagcct cagcacttag gctactttag gataaatatc ttttccttgt 126600
ctgtgctctc aaggttgctg cttggtttgc tgtaagtgac tggcaaatat gtattaaatt 126660
ctgaatgagt aactcaaaat tttaaggaat ttgaagttag tgcagatgct atatgatata 126720
cggtaacctt agtgactatt tcagacatct ctttagtgac atttgttgac atgtttgctt 126780
tgccacaggg tcttcctctg tagcccaggc tgacaatgaa ttcatgactc tcacacctca 126840
acctcttaag tagtagatgc tgtcattact ttgaaaaata ataatgaaat caccatctag 126900
acttaggaac aatgtctttt tctgatcttc cttatgagtc aagggtagct gttatcttag 126960
ttaacgattt ccattgctgt gaagagacac cgtgaccaag gcaagtctta tcaagaacaa 127020
catttaattg gggctggctt acaggttcag aggttcagtc cattatcatc atgggagtaa 127080
gcatggcagt gtgccagcag acatggtgct ggggaaactg agagttctgt gtcttgatcc 127140
aactacaacc aggagagact atctcatgag cagctaggag gagggtctca aagcccacct 127200
ccacagtgac acacttcctc caataaggcc atacctccta atagtgctac tcctggaaca 127260
agcatattga aaccaccaca gctctcttac tgtgacagtt gtggcaaggc caactgagtt 127320
cttgactcct aactgccagg cttctagact ctttttgagt tacttgatct caaaggctca 127380
aatactatag ctacaccact tcttccacaa gcaggtaaca tcgaacatta tttttccttg 127440
ggtcaccagg agcctttgta atcacaagta taaaactgtc tagtcacagc ccaatattat 127500
gacacaggcc tggaaatgca gcactaagga ggccaaagca ggaggatcat gactttgagt 127560
ctactctgag ctatataatg ccagaaacta ttttaaaaga cagggcttcc ctgtctttag 127620
cttttcaatt ctttctcaag attatatagt tgcacagagg cccatgagca acgccatctt 127680
agtacagcct gggctctcac ttggtttctg actggagccc ttcagttcct ggagttcact 127740
tcacctcata gtctggtcgt ttcctgagca acaactcaaa ttattctgtg cttctggtat 127800
gaggataaga cacacataag gaaatcagac catggaaaac actggaataa atgcccacca 127860
tcttgagaat gggtaggtgg gcccagtggc aggagaggac ttaattcagg cagatgaagt 127920
tttgcttatc ctctgtgact tgaggtcagt taatgaagtt ctggtcagaa gaagcaacct 127980
gcattttgct ttaaaaaaaa aaaaaattgg gtttttgttg ttgttgttgt tgttttgttt 128040
tgttttgttt tgttttgttt tgttttttttg agacagggtt tctctgtgta gctctggctg 128100
tcctggaact cactctgaga accagactgg cctcgaactc agaaatcccc ctgcctctgc 128160
ctcctgagtg ctgggattaa aggtgtgcgc caccatgccc ggtgcttttt aaatttttaa 128220
gtcacatcca tagattagca tttttttttta aaaaaatgtt atatgtgagg gtgttttgcc 128280
tgtctgtagg tctgcaccac atgcatgcag tgcccaggga gtccagaaca aagtgctaga 128340
tcccatggga atggagttat acattgttat gagctactat gtgagtgctt ggaattaagc 128400
ccaggtcctc tgaaagagca gacagtgctc ttaaccactg agccatctct cccatctaag 128460
ctggtactac tagaagttag tctgacacac atcatttctt ttagcttggg gctaaattcc 128520
ttaagctcaa aaaggatcct ttttctgtac caggaagtgc ctaaattgtt gaatctcata 128580
gacaagggta actatctgtt tatttaaact ttcaccaact aaacaagttg ttcttaaatt 128640
ctatgctgta tcaagactca gttactatga acagtccctg ccctcaagac tcttacaggg 128700
cagatgggtg gttttcatgc tttctcactc cactgctaga actcccatat acggctgaaa 128760
ctcaagttca aaaccattgc tgtattcctg gtagaaatgg aaagaattgc agggtttaga 128820
tgcatactaa ggaagtaaaa cctcaggcct taagtgagca gcccaaaaat ctgagtcaac 128880
tggaagggct cttaggctgg ggttctctat ggccatgcag aggaagggtg acactgtatt 128940
cttacagact tctctcttta tcaccattgc ctgtgtagac ctcagtcatg tcacttcggc 129000
ctgcgagatg gtggcagaca tggtggaatc cctgcagtca gtgctggcct tgggccacaa 129060
gaggaacagc accctgcctt catttctcac agctgtgctg aagaacattg ttatcagtct 129120
ggcccgactc cccctagtta acagctatac tcgtgtgcct cctctggtaa gttggatctt 129180
gctcaatttg atatgtaacc aggcagcaaa cttgggattc tcctctctac ctcccaaagc 129240
tagaattaca tgcccagctt gtcacatagt cttcattatt gtgacactcc ctgtgatagt 129300
cccagcattt tcatatggtt gtgacactgt gttgtccccc aggcattctg tgtagtaggt 129360
attagtaaaa atactgcatt tcaaaaaact gactgaagta ctaaacttca aaacttcaaa 129420
agtgtcacct ctgaagagat tcgtacagag ctgggcatag tggtacatgc agaggcatgc 129480
agatctctga gttctaggtc agccagagct acatagtgag actctgtcta gagagagaga 129540
gaaagaagga ttgattcata catttaggga caaccactat tgtgggtctt ctcttgaaat 129600
tttcttcatg aatcaactta aaataggctg gttcttaggt tttgttccac ttcacagtca 129660
tggaaatagg gttaacaaca gctaggctga cctcagtctg ctaaaatagc acaccagaca 129720
tattctttcc tacaaaaatc ctcatcaaga aagcaaaggt ggcccgcagc tgatttgaat 129780
catagcgcag agccagacca ggaagccaga taagaaaggg tgatttattc tgcatagata 129840
gggcatatgc ctgctgctgg gccatagcta cagcgtgtgt gtgcttgcat gtaagatcct 129900
agaaaagttc acatctagaa catgacattc attggacctt agagttgctg gggcccagtc 129960
tgagtgctgt gacccaccta tgctggaagt gcttctagaa cagagaggtg tggacattgg 130020
gaagagagca atagaaagcc aagagatcat ctaacactgc tgcatgaggc tcagccctga 130080
gcaggagtat tccttataaa gactgtataa gaaggtggta tggggtcatg gaaggctctt 130140
gtggaatcta cctcataggc tatgtgctgt aggtaaatct ccatcaagag cttttaatcc 130200
aggccaggca gtggtggtgc acgcctttaa tcccagcact tgaaagaccg agacaggtgg 130260
atttctgagt ttgaggacag ccagggctac acagaagaaa ccctgtctca aaaaaacaaa 130320
aaactcttaa tccgatacct tgagtgccct gggcagaaaa gtagctgtag caaacactgc 130380
agaacctccc ctgggcatgc tccagagact tctgtgggtg gtgtaagaga tttatagaag 130440
gttggttgtg ttgtagaaat ctggggaggt tcccttaggt cctcgttgct ttactgaggc 130500
acatagctga gctggctaga tggtcctgcc actggaacag cgtggggtat acctcagggc 130560
ttcctttgtg catggtgctt atctacatat cgaatggcaa aactcagcct ctcacagttg 130620
atagaaatga gcagtggggt tgtccttgag actgaatttc attagtgttt gcctcttttc 130680
caacacactt gatgtttgtg ggtagcagca tttcctacaa ggaatgtggc tgtgtacagg 130740
cagcctgagg ggtgtaacaa gcaggtgatg ggctggcctt gggggagtgg ggggcagggc 130800
agagtgctgg gagtcaagct tggcattgaa ggttctaggc acaagggtgg gagcctctgt 130860
gaaagggcac aggctctgga caaatcagag tagtaaaggg gggggagggc agttgagaga 130920
caagggacac tggacgctgg gggtctcttg tcctcctcat gccatctcca tccacctggc 130980
acgcttttta tcttctcagg tatggaaact cgggtggtca cccaagcctg gaggggattt 131040
tggcacagtg tttcctgaga tccctgtaga gttcctccag gagaaggaga tcctcaagga 131100
gttcatctac cgcatcaaca ccctaggtat cccaccacag tcctcttcag tccccatgtg 131160
ccacctccga gacctgaagc ctcagggtag ggccatcgca ctcggcaact gaaaaggttc 131220
tggggtggta atgatgcagt acaaatagaa ttatggtgaa aagtagacct aggtgtagat 131280
ggatgagtat agtgtggggg ttgcatacca ggcttctttg taactgtcag aggaagccag 131340
ttctgtcttc acattgtcta ttcaaactaa gccatatagg tgggttgggg atgtgcttca 131400
ctgtagtgtt tgtctagcac gaggaagccc aggcgtcagt ctccagagcc gcaacaacag 131460
actaagtagt ggaagtcatg tcctcatgtc ttcctgcttg ccactttgac attgtgttct 131520
cactcgaatc atttttctta tatgcagaat gagcagcttg ggaaaacatg gcaagctagg 131580
tgtcacaggg acagagtgat agaatgaggg aaggtagatt tggccagaca gccctgctca 131640
tccctttgct gacagggtag gatcttcagt gctgtggtcc atagaatgga gactgggtct 131700
atttttatg tttgctacgg atgtgaacat gaaaaataca cttagtgtct cagtaagcag 131760
tagcatgagt agttttcctg tcaggactct tctgctttct gaagcacagt ctaaattgct 131820
gctgctgctg ctgctgctta tcattattat tattatacct cctcctccct ctcttcctcc 131880
tcctccctct cctcttcctc cttctttgat tccttctttt ttgcccattt tctggatgag 131940
ggtgtgtctt ttgtttttgt ttgtttttg tttttgggt tttttgttt ttcaagacag 132000
ggttctctgt gtagccctgg ctgtcctgga actcactctg tagaccaggc tggccttgaa 132060
ctcagaaatc cactttcctc tgcctcccaa gtgctgggat taaaggcgtg cgccaccacc 132120
acctgcctga ggatgtgtct taatcactgt tctgtgaaga gacaccatga ccaaggcaac 132180
tcttatgaag gaaaacattt agttggtggc ttacttatag tttcagaaag ttaattcatt 132240
atcatcatgg cgaaagcaga cagtcatggt gccggagcag tagctgagag ctttacatcc 132300
taatccacag gcagcaggca gagagaggga gatagagata gagagacagg gcctggtgtg 132360
ggcttttcaa acctcaaggc ccagtcacag tgacaaacct cctccagcaa ggccatacct 132420
cctaatcctt cacaaatagt atatcaccta gttaccaagg atgtaaatgt atgagcctat 132480
ggacaccaat ctgacttggt tttgtggtta tagtcctcat agcctttccc ttctggggta 132540
tttcctaaga gtctggtcac cagacccact gcctggtcca agttaggccc tagggattct 132600
tcaagttttc ttattcggat ctcagcaacc tacctctact tcatcactgt gcgcagtaac 132660
tcctgagaag gaatccggca cctcccatga aggacatttt acttccaatc ttagttgctt 132720
ttctgtcgct atgataaaca ccatgaccaa aagcaacttg aggaagaaaa ggtttatttc 132780
tctttatagc ttataagtat atcactgaag gaagccaggg caggaacaca ggacaggaac 132840
ctagaggcag aaacaggagc agaggccata gaggagcgcc acttaccagc ttgctcacca 132900
aggcttgctc agcccgcttt ctcaaagcac tcaggactgt caccccagag gtggttctac 132960
caatataggc tgggccctac cacattgatc actaattaag aaaactccct tcaaacttac 133020
ttataggcca atatttgggg gtagcttttc aactgagagt tcctcttcct agatgattct 133080
agcttgtgtc aagttgacat aactagccag cacattgcct ttgctcctgc ccacttatgc 133140
cttccctggg cagttatcag ttgggtctgt ctcctggtgt cagtattcac ttgaatctga 133200

```
gttataccccc atgttccagg aggtcctagc acttgatgct ctacttttct gctcctcttt 133260
actgcattct ggccttacaa ggagtgctgt agatattttt gggtcttggt gggaacatca 133320
agtgcagcta tttattgaac tttctctgat tggcctccta gactgctaga gtggtcctag 133380
cctgatacca tgcttttttt tttttttttt ttttaaagtc tgtctccggg gtggctttca 133440
ctgtttgcat ttacttactt tgtggaggca ggacccacgt gaacatctca tagtgcagca 133500
tgcacatgga gggcagagga cagctgacag gaattggttc cctcctcctt ccatgtggtc 133560
cctgaattga gaattggact cagattgtca ggcatctcgc tggcagtctg tttaatctca 133620
ctggttttat agagacagaa ttattatctc tatggttctg tggtctgctc tgaggtctca 133680
cttaaggtga gacttttaaa atgcttcgtg ggcaggacta gcctaggtga ttaatgcctt 133740
tgtagacagc ctgtcactgt cctatacagt gggggattga agggcaatct ggcctgtgcc 133800
tcttggcctt gatagcataa ctggtctcca tgtgctgcta tatcctttat gatagatgga 133860
gagaatggca gccctcatgc tgtaggattg ctctgaaggt ggtgtcctag gagcagcact 133920
gatgggatta catcgtcagt gtctcctcat gggtttggcg agtcaggaaa ctaatgtaat 133980
gattgattcc cagggtggac caatcgtacc cagttcgaag aaacttgggc caccctcctt 134040
ggtgtcctgg tgactcagcc cctggtgatg gaacaggaag agagcccacc agaggtgaga 134100
cttccataac tagggggtgg ctaactggaa tcctatagct gtgaaagctg gtgactctgt 134160
gttttgaaac agaaaaacag gctgatcatg taccaactga tggtgcagag taaagacaaa 134220
tgccctgaga ggcttggaga ctgaggcttc cagtagctag gttgtgtctt tcactacata 134280
cattccactc tgatgatcaa tgaactggtt cttcagtact gttatgtttt acttacttac 134340
catgatctga aagaatgtca ttgagctaaa acaaaaaaga caatgaatct aggccatgca 134400
catgtacttg tttggttggg ttttattgct gttgttgttt gtttgtttgt tttaactaac 134460
ttataggttt tgctttgtta gcttaattgc tttgttagta ttaatatgac atgaataacc 134520
gccatatatt tgtaaaatga aggaggttct gaatgttaaa gtactgggat ataagccctt 134580
gattctaaga aatatgtagt aaactgtgga aatgacagag aagaaggtaa atctatatag 134640
atcacaggcc atcagtatta tcttcaaact catctgtaac tgccaggctg ccataggcag 134700
tgttctaaaa tgatgataga atttaagaac aattttctcc aaggtaaatt tctatttgga 134760
gttctatgcc aaacatttgg atactccaag tctcaggtat gtaggtaggt ataaccagtg 134820
ctgagcaaac ttggacttaa gaccctggct gtgggaagcc atagctctta agtgatctga 134880
tattcctgta tgaggccatg tggcctatgg gcactgtgtg aattagaggc aggatgagta 134940
gttggtatct tcttatcatg ttgtcaatgt gtggactgtt tctctaggaa gacacagaaa 135000
gaacccagat ccatgtcctg gctgtgcagg ccatcacctc tctagtgctc agtgcaatga 135060
ccgtgcctgt ggctggcaat ccagctgtaa gctgcttgga gcaacagccc cggaacaagc 135120
cactgaaggc tctcgatacc aggtttgcct gcgttcttat gtgggccagt gcagaggatg 135180
gtgaggtagc ccacttcccc tagccctctc ctttgtaata agaattgatg taacaattaa 135240
ttcttactgg ttctttcagt actgttaatt ttttcgtctg tggccttgcc ctgagataca 135300
gatacaaaag ggatttttgt caatggtgac aactgagaat ttagtctgat atgttatgga 135360
cttcactggg tgttctggct cagacttgtg ggtcaagaat gagcacctac tgaagggttt 135420
gttttttgtt aaaccagctg cttcaggcaa gtgaaagata attcctggtg gctttcactt 135480
ctctgatgtt tgaaggaagc aaacatgttt tttccttggt tctgaatttt agatttggaa 135540
```

-continued gaaagctgag catgatcaga gggattgtag aacaagaaat ccaagagatg gtttcccaga 135600
gagagaatac tgccactcac cattctcacc aggcgtggga tcctgtccct tctctgttac 135660
cagctactac aggtacagga agaagctaga acaatagtgt ggcttaacaa ggaggctttg 135720
tgctgagtgt attgccccca ttcacaagtc tcatgcttcg tctagaccac catgagcatc 135780
agggtgtatc acctcactta aatgaaaagc actttctttc cattgtgtat gttaattgta 135840
caaagttttg tatttcataa ggacattttc atacaagcac ataatgtata ttgaatgagc 135900
cacccccaaa acctccttac cattcccttt gcccatcttc ccttcccttt gctgtcccca 135960
ctatgttatt gttgtacaaa ctgcttccat ctcataatta ctaaattgtt ttaggaattg 136020
tttgttgttg taaatttaag taccttgaag actttatttg ggaaagtttg tgtatggaaa 136080
tgcaatgtgt catttatccc aaaacggttt tggcagcttt gaagtaaaca gagcactgag 136140
actttaaata ctcatgggac ttagaccgtg aggagcttct ttctgtgcag gtagcatggg 136200
tgagaaatgg catacttgct ctggaacgtc ttgagagagg tgtggataga tggcatggca 136260
gctcagagta cagctgtggg gaggacagta gagtaccttg gggggagggtg ggcagtgtga 136320
gatccaatgg agttaacttg aggcagccat cgaagaagag atagtctagt ttgcccactg 136380
ggcctgacag ctcaacaggc tgcaaacgga cagtattcca agacctacag cctctgcata 136440
gctggagtat cctgcctgtg gggagcagtc tcattgggca aatatctgtc caggcaggag 136500
cagggtctca tgcagtgctg tgctgatgtt tggcaggtgc tcttatcagc catgacaagc 136560
tgctgctgca gatcaaccca gagcgggagc caggcaacat gagctacaag ctgggccagg 136620
taggtcagtt ttaccaatcc acacccttct ataaggactg taggctggaa ttataaccac 136680
tttgagcttg agccacatac cacattcaga gaaaagtttt tatgtacttt attctagatt 136740
ttaatatatt ttacatataa gcatacagat gtttataaaa cttgtgagac aggagagaaa 136800
caagaagcat gaaaggtcag ggaggagaga atggagtcag ctgagtgctg tcaggcagat 136860
gcactactga aagtttcctg gctgctagct gagagggtag ctaagtatcc agctcagcag 136920
gcagctggca gttggacagt tcacttcatt cagaacagta gggatagctg acagctactg 136980
actgtagggt cagggagatg tggtacctgc tgcctttcta gacaaactct tctgtgcctt 137040
cctaccttta cagagaaact tccaccctaa gataagtcac agtgatggtt agaatgtgat 137100
gtgcttttga tgcagtgttt ctgaagatga ggtgatgagt aagatgcctg gggctcctgg 137160
gcacatgatc atattctagg ttccatgtcc ctgttgtcac attgtccctt atggctgtgt 137220
tgaactcatc tgtctgtttc cttcagtact tgaggccagc tccaatgtct gcaacctgaa 137280
tgtagtagga ctgtgtgggg ccaaagtata gatttagccc tgccttgcct gggatacctg 137340
ccagctatta aaaaaaactg ccgggctgcg ctgccactcc attttgggga aagagatggt 137400
agaaggggct gggcatggag aacactggca cctggagtca cagctcacag cttgtcttca 137460
ctgaagctga gatctgagat cataaggaaa aatgcaggag gatttgtaga ggagcaatca 137520
aaacggaagt cactgttcat cctgagaatg caaagaccac ttcatctgca actacattta 137580
ggagcttggg gctcttggct gctccttata ccttcctaaa acaaacgcat ctccttctgc 137640
atccttggag aaatttctgt aaccaagcag cccagaaaat caggttttat aattggaaaa 137700
cacaaatgag tgggaccagg tgtataaaat ccatgtatgg gcattctctc cagggtgtgg 137760
tcagctgtca cttagaagca cttagtgtca ctctttggtg ttgcttttac ttcataccct 137820
ctccagacac tcattcaggc tttgaacctg aggtcagaca ttggagctgg cctcaagtac 137880
tgaaggaaac agacagatga gttcaacaca gccataaggg acaatgtgac aacagggaca 137940

-continued tggaacctag aatatgatca tgtgcccagg agccccaggc atcttactca tcacctgcca 138000
acagtttaga acatttacct tactacccag gggttccact gatagtaaca tttgggtctg 138060
agtgaatcat tactgtggcc atatgtgctc agaccaggaa gacctgattg tacctaccca 138120
agaagaacct gaggccttta cctatgtcct tatctctggt gcctgcttct atgacaggtg 138180
tccatacact ccgtgtggct gggaaataac atcacacccc tgagagagga ggaatgggat 138240
gaggaagaag aggaagaaag tgatgtccct gcaccaacgt caccacctgt gtctccagtc 138300
aattccaggt ttactggctc tttttttttt tttttttttt ttaataagaa atttgagatt 138360
tcttctcagt cacttatttg ggtcctcttt gaggctaacc tctcatttct gtatggggaa 138420
aatatccatg tttcacactc tgcagaaaac accgtgccgg ggttgatatt cactcctgtt 138480
cgcagtttct gcttgaattg tacagccgat ggatcctgcc atccagtgca gccagaagga 138540
cccccgtcat cctgatcagt gaagtggttc gatctgtaag tttgctttcc cctcacccag 138600
aggcatctgt acaccataca cacacacttg aacgtgtgca tacacacaca cacaatcatg 138660
cacaggcaca tatgcacaca cgtgtactaa atacaagcga cagacacatt acacaaactt 138720
cacctatatg caccagatac catatacata aatacacaca tgtgccatgc attcaccaaa 138780
tagatacaca gacacataca cacacaaata tatacaaata aacaagcaca cacagatacg 138840
cacacataga cacatacaca cctcatctct aatgtctcag aacctgtaaa ggactcctgc 138900
aggcctccca ggtatggagg gacagaatgt gtgaagttgg tggcgagaca gatatttttt 138960
tttcagatcc agatcaggta aatactctga aatgtaacag cagtgagtgg tgtgccttcc 139020
agagacccag cgtgtctctc tcttccagag tagtaacaaa caactgtgtg ccttatcctt 139080
ctaagccaat actctccaag aagcactggt tcagaagagc agtgtcagag aaggagtagt 139140
ctcattatac ttcactactc cacacttccc gacagtccca aacaaagggt cgtcagtgac 139200
atctttcaat atcgtcaggg ctggatcgaa aggctctaag acactgactt ggtctgaaag 139260
tgatagaggg agctggagag agtggtagtt aagaggacaa cagctgcttt tctgaaggac 139320
ccggatctgt tcccagaact tacacagggg ctcacatttt aggctgcctt tctaacatcc 139380
ctccaggtgt aattcttgtt ctgattctcc atgtctccag cttcttgtag tgtcagactt 139440
attcaccgaa cgtacccagt ttgaaatgat gtatctgacg ctgacagaac tacggagagt 139500
gcacccttca gaagatgaga tcctcattca gtacctggtg cctgccacct gtaaggcagc 139560
tgctgtcctt ggaatggtga gtgagggtag tgcagaggcc gcccccattg aagctgcttg 139620
ggactgcact gctttgggac cttgtattgg tcacatgtgc tacatgcatc tgcatagttc 139680
agagtcctgt cccaagccaa gctccctggc acatgtggac catggctctg gtcagctaaa 139740
agacttcggt gccttttggt gctgttccca cagagactgg gatgtggtga gcatggctgg 139800
agtacttgtc tcccttggct cactgtatgc tgttacagtg agcacctctc cagaatacag 139860
aatgcagaag gtatggtagc actaggacag cacagagtga aactgggtca cacttctgcc 139920
agtctgtcac ttggcagccc cactccattt ctctggtggg gtctagctcc cactgtactg 139980
ctcagcctac acaggcttcc ctggtgagct tgttgtcata gtaacctttc acttctactt 140040
tgagaaatgt agatcttgat ccttaacatc atgattttct tggtctagtt gtgttgctgt 140100
cacaaaacac cttagacagg gtaaataaac aacagatagg aactgcttat aattctcgag 140160
actgggaagc cccaaatcaa ggtgctctgg gacgcctggt gtgcacctcc tggcttctcc 140220
agctcatcgg catttcccat tattttgctg ccgagttatc agcatttagc tagtactact 140280

```
tggttgtctt tcatatgtac atatttttag gtgcttctca gaacatggtt cagacataca 140340
cgtgaaagta atcgcctatg ggttctgcct cttgttggag catattggag ggcatcaaca 140400
ctcaggaaag ggacagacc ttagactgtt gatattggct cttttgtcct gtcacttact 140460
attaaattat tattgtgttt ttaaattatg ttaaaatgtt atcattaaat gttgaaaatt 140520
atcatgtttt taatctctgt ttcctgggat ccaattttgt gacaacataa gaaactgttt 140580
agggattgga aagatggctc agtggttaag agcacttggt tctcttacag aatatctggg 140640
ttcattctta gcactcacat tgtcagctca taaccggcac cctcttctgg cttctacaag 140700
tacacatgca tatttaccat gtggacacat acatgtatac cacatataaa aataagagta 140760
attttaataa ggaaacttct ttgttcatag acacgtgagt ggctgctatg tgtgatgtag 140820
ttaggactgc tggcaggagt agtgtggaag agcctgctgg ggaccattcc ccatgggtca 140880
tatgtgccat gccctctctt gttagtaaga cagtgctatt atcactgtgg ccacaattat 140940
ctgatggcat cttttacata cctgtgtaac cctgtgcagt ctcacagagc agcagtacac 141000
atagatcatg gcacagcatg actcccacct ctccttactg ctctgctaga ggatctgttg 141060
tcactgaacc taggggctag aacaggtata cagcatgggt ggccatagca ccatccagag 141120
aacaggaaca atgagcactt agtcccccta tgtgagcaca ctcttcaaag caggcgtcct 141180
ctgggtgctg tcaggactga ccgtgtgctt gtgggaggtc cattttcctt cttggggtgg 141240
cttcagtggc ttaactttcc ttgtaactgt ggttttgtgc tcaagcccaa gttcctcagg 141300
caaaatgtaa atcaaatgca tcaggcaaat aaagaatggt catttttaag aaacgacccc 141360
aaggcagaat ggcaaatggc tccagttccc agctctgtgt atacaagcag cttgcttgaa 141420
ggcagtgtct tctgagaggc ttccagcctg ttttgtgctg ctacaagctg tgctgcattg 141480
cttttccagg ggaaagggac gctcacctca gatgcgctac tgatgatcca agcccagctt 141540
gtgaatcact gtattaactg gctttcctca taggaacttg agtgaaggct tatttattgg 141600
agctgaggga ccccaaaaca gctgcatact aaaaaattct accacggcat gggtgataat 141660
actcccaaag ctacataaat agagtcatag tctcctcctt cacttaacct ttcccaagac 141720
caggtgcagt gggggcagga tggtgtgcag catctgataa gggaacacta gaatcctgtg 141780
cttgggagag agagtctggt aggaatacag gtaatcccag ctcctctgat ttctagatgg 141840
cataaccatg tcatgtccag aggacagtgt ttcacagtat gtgtcagatt gtcacttttc 141900
tttgcccgtc attagatctg cagccttcaa caacgtatcc tgatgttatg cttgcaggag 141960
tgtggccaga gccctaggtt gtactgtcct taggaaggac tcacagctca atggggatag 142020
cctgggaagg gggatgagaa ggaagtaact ggcaaagact gttaaccctc tttagcctga 142080
caccatcaga tacagactcc cctggagggc tagatgacca gaaggcctct tacatcatga 142140
gatcaaatga gtccttagcc agcctttcct gggggtgggg cagtcagaca atgaaatgct 142200
gcccttggat tgcagaacac aacagcagtc ttcagtgctg aaggagtcat gtttcaaggt 142260
gtgtactccc acatttagaa aacctagtgg aagtgatacc atgtcagtca aggttagcac 142320
aaattaatgt caggagcttc acaactacca acagaggatc cagaccaagg tttattatag 142380
tgaagagaca tgaggcaaaa atcagctgaa ggagaaggtt cctgggtaaa gcctagaaaa 142440
ccagtgtgaa tactattcct gaatagtcat acagatcaca aatcatccag taggtagaca 142500
aggagcagac aacatatatg agctgttgct acaggggcca gcagaactca gaatccaggg 142560
ttgttagaag tagcaggtta caggaacacc cgctgcccag cacataccac agctccaaaa 142620
gagaaagtaa gtgtggtcac aaatcacatt ttcttcataa ggtaaaccct ctctcaactt 142680
```

gaagtgttta gatagggttg gcactgtaca ccaacatctc ctggatgaat ttcaatcatt 142740
ttgtggactc tgctatgtgc gcaactattg ctaggctctt tcaacctcag ggaagcaggc 142800
tgttggcaat cagccatcag tctgcctcca acagctcatg tctgtgcttg tatccaggac 142860
aaaactgtgg cagagccagt cagccgccta ctggagagca cactgaggag cagccacctg 142920
cccagccaga tcggagccct gcacggcatc ctctatgtgt tggagtgtga cctcttggat 142980
gacactgcaa agcagctcat tccagttgtt agtgactatc tgctgtccaa cctcaaagga 143040
atagcccagt gagtggggct ggttgggtgg gctacaggct ttggtgtggt cttaacaaaa 143100
acagaaaaaa gaaaaaagaa aataaaagtc tctaattcga ttttcaaagt atatgccaga 143160
acagacatgg taacaaatgc ttatgatcca gcatttaaga aacgaaggca ggccaggtgg 143220
tggtggcgca cacctttgat cccagcactc gggaggcaga ggcaggcaga tttctgagtt 143280
tgaggccagc ctggtctaca aagtgagttc cagtacagcc agcagagcta tacagaaaaa 143340
ccctgtctcg aaaaaccaaa aagaaagaaa gaaagaaaga aagaaagaaa gaaagaaaga 143400
aagaaagaaa gaaagaaaga aagaaagaag gaaggaaagg aaggaaagga aggaaaggaa 143460
ggaaaggaag gaaaggaagg aaaggaagga aggaaggaag gaaggaagga aggaaggaag 143520
gaaggaagga aggaaggaag gaaaggcagg aaaattgaca taagcttgaa accagccagg 143580
gctacagatg agatcctgtc ccaaaaagag taacagagtg tatgccaggt cctggtaagt 143640
agcagacagg aaacccaggg aaatagtagt tatgagacac aggacacaaa tctacatcag 143700
atggtttctt ggatttttct agcaagatgc tctccactgg cacttagcac actgctgtgt 143760
ggatagcagc cttatcccgt gctgccagac tcagcctcct cttcagttta tgatcagcac 143820
cttgtttcct gtgaggccct tttccctgct ctgatctccc acctccccct aaagacagct 143880
cacatgcagc tgtacctgga tatgttgctg gtccttttga aaatacgttg ggtccatcac 143940
agctctatct tagaagcaga aggaggtgtt atggtgtgat ggagcatagc taggcactca 144000
gaggcacgag ctagggatgc aacgggtctt ggaggaaaag tccaggtgtt ctgtgacggg 144060
attgtagatt gagaggtgga gagtaaattt ggagatggta aagtcttagg ctgacagaca 144120
gctactggga ggaggtggca ttctgacaga tgatcagaag tgcattttgg gggcccaaca 144180
ggcagtggca agttgaactg gaacagagat agtggcttgt agccagcctt ccttgtagtc 144240
cttggctgaa tagtaaccta ctatgtacag ggtgggcaag cagccaccca ttgcccctgt 144300
gatcacacat cctggcctgg agcagatttg ggtaggttct gtgaaatcat aatctgtgct 144360
aaggaatgaa gaggacacag aggactgaag acaggtagga ggagcttaca agtccaaatc 144420
agataatcac atagaccttg ctcaatgctt tgggcagagg gtcctgtaca aaacagtggc 144480
cagttcctag gagtggcagt gtcatttgaa cagatctgaa agggggtaga agagatagag 144540
tgtggctcct ttgtttatgg tgccattggt ctaactcata ttccagccag gcccctgctg 144600
ctgccattgg gcaaagaggc accaactgga gatcccatga gttagagtgt tacaagttag 144660
caaatgcatg gagcaaacag acaccctgaa gaaccctgac taagaacata aagaatgttc 144720
agggagagtg aagtggtcta tggacaggta cagaattgga gatggcatgc taagctaagg 144780
ccatgcagct ctggagtgta atccctaggc catccaggtg aaaaggcctg gagaagctga 144840
catgacccca gagctctgta ctcaatagat gtgggtggat aatgctttaa aactgtcccc 144900
tctgcagaca ggcaggggct gctgtatgtg actgggtatg attatgtgtc tcccattctt 144960
agctgcgtga acattcacag ccagcagcat gtgctggtaa tgtgtgccac tgctttctac 145020

-continued ctgatggaaa actaccctct ggatgtggga ccagaatttt cagcatctgt gatacaggtg 145080
agagggctct attgaacata ggcaggttac catattaact gtaccagtgg gtcattgtgc 145140
ttttggggaa gataagaata agcctttctt cttgtctaga tgtgtggagt aatgctgtct 145200
ggaagtgagg agtccacccc ctccatcatt taccactgtg ccctccgggg tctggagcgg 145260
ctcctgctgt ctgagcagct atctcggcta gacacagagt ccttggtcaa gctaagtgtg 145320
gacagagtga atgtacaaag cccacacagg gccatggcag ccctaggcct gatgctcacc 145380
tgcatgtaca caggtgagtg agttgtaagg gtcatagact cacccaaaga ctcaagccag 145440
gcctcatggt gtggcagtct tagtgtggcc ctaagacatc ctggtcacct ttccagaaat 145500
ttagggctca aggcaagaga gtagctcaca tgatatcacc aagtattgat atcagagctg 145560
cctctggcca ctgcatccct gagagttgga agaaagttgg gctgggtcct gccttgctag 145620
ggactgtaat cacctgtttt tgaaggatct ctgcctatct ggtaaagtcc tgtttgagcc 145680
actgagtgca gatttcaaaa ctcttgggct tctgttctgt atagcctact tagtgttttt 145740
gtttcaggaa aggaaaaagc cagtccaggc agagcttctg accccagccc tgctacacct 145800
gacagcgagt ctgtgattgt agctatggag cgagtgtctg ttctctttga taggtaagac 145860
atgcagcaaa tctctacctc taacctcagt agtcattgac tgccctagag ccacagccag 145920
agcagttctt ctgtgtgtat ttgttcattc tcttgaactc taaaatgtat ctttgcagcc 145980
atttttccag tgcatgcata ttcacagagc accacctgca aaccagactc agagacaact 146040
ggacccatgc aggtgtacaa ccaaaccact gccctggtgg atcccatagg ccactgctga 146100
ggaaatagat actcctggag tatagccaag tgctgtggtg gggctcaggc catatccaca 146160
ggaaggaggc atggctaagg gtctgagtca cttgtgtact tctcagctgt ataccacagt 146220
tgtgtggcat tagtggaata atcataggtc agcggtcttt aaggatgctg ctgaggtaag 146280
ggtaaagtgt tggatgttga gagaagaatc aacaggagca tagatgggtg tccaattttg 146340
aagggaagaa aagttgctga ttgacagtag tactctgggt attaggacat acaacagtga 146400
aaagttttgg tacattttga tgtggagagt ctcttcagta atatcaccac cccacccttt 146460
tgctgctatt cctttacaag gctgtcccac aactgcatta ttctccccag agtgggaaag 146520
atcaccttgt gcccagatca atcagggcag caaaagaaca gcctggatat catctttggc 146580
ttttaaaact catacctag ttgtggtctg agccccactt ggaacattcc tgtgggtcaa 146640
ggacctctga gccttagtcc atgatggctc tatgggcaag gttgagaggc caagagccag 146700
ggtgaggctc aaatcagctc ctctcatttc aggatccgca agggatttcc ctgtgaagcc 146760
agggttgtgg caaggatcct gcctcagttc ctagatgact tctttccacc tcaagatgtc 146820
atgaacaaag tcattggaga gttcctgtcc aatcagcagc catacccaca gttcatggcc 146880
actgtagttt acaaggtgag ggtgtacttg ccttgtgggg taaggacaga gcaggaggag 146940
gaagggggag ccaatcccac acttgccgta ggcctgtcat cagggctaga ctcatccttt 147000
aagatgagtg gcagctgtgg ccccagtccc ctcaccccac cccacagtct gaccctgtgc 147060
tcagggctct cttgtcccta ggtttttcag actctgcaca gtgctgggca gtcatccatg 147120
gtccgggact gggtcatgct gtccctgtcc aacttcacac aaagaactcc agttgccatg 147180
gccatgtgga gcctctcctg cttccttgtt agcgcatcta ccagcccatg ggtttctgcg 147240
atgtatcctt ccttccatgg gactttggcc aggttccttg ttcacttagc atccagttca 147300
ggtttcactg aatgttttca aacctaaact ctaaagaacc tcacaggtgg gtggtggtgg 147360
cgcacgcctt taatcccagc acttgggagg cagaggcagg aggacttctg agttccaggc 147420
cagcctggtc tacagagtga gttccaggac agccagggct acacagagaa accctgtctc 147480
aaaaaaacaa gaaccccaca ggtgatgctt acccttccct aaaatgttga cagggacacg 147540
aaacagaagg tctaaccatt tgccagccag ggtttatggc agttttactg ctgagggaaa 147600
gggaagtcca aagggaggca gggcagctca ggccagccag ccactggccc tgcggctgcc 147660
ccatcatctg gcataatctg tccctctgag gttttctcaa tgctgcttct cattagctct 147720
catctttacg ctgtggtcac cctcctgggg aaagccgtaa gtaaagctgc agttcccgcc 147780
ctaacagtga tgccaggagt tcctcttggc agcctccttc tcagtagacc acaagagtta 147840
ctagcagcaa agctgtcttg gtggtgacag tacagcctca ccctaagtac tgggaaagcc 147900
ttgcaggcag ggtgctagct agctctgccc tccctgcact ggagcagttt gagcaggaac 147960
accagccact agcactgtgt ggggagcaca gcccaggtaa gtgctgttgt gcagagcact 148020
gggaaccagc atcctgtctg cactgcatga ctcccacttc ctgggcctct ctgcctaccc 148080
acccctgtcc tcctgggcag acagcaagct gcagctgaga aaggattaca ggcagctgct 148140
gctgttaatg tggtctaggc tgccctctat tttggttgcc ctcagtcttc cctgggcctc 148200
ttggtggact taggagggga accgcttggg gaggctgtct ttccaccctt gccatcgttc 148260
ctccttaact cttctaccag ccttccacat gtcatcagca ggatgggcaa actggaacag 148320
gtggatgtga acctttttctg cctggttgcc acagacttct acagacacca gatagaggag 148380
gaattcgacc gcagggcttt ccagtctgtg tttgaggtgg tggctgcacc aggaagtcca 148440
taccacaggc tgcttgcttg tttgcaaaat gttcacaagg tcaccacctg ctgagtagtg 148500
cctgtgggac aaaaggctga aagaaggcag ctgctggggc ctgagcctcc aggagcctgc 148560
tccaagcttc tgctggggct gccttggccg tgcaggcttc cacttgtgtc aagtggacag 148620
ccaggcaatg gcaggagtgc tttgcaatga gggctatgca gggaacatgc actatgttgg 148680
ggttgagcct gagtcctggg tcctggcctc gctgcagctg gtgacagtgc taggttgacc 148740
aggtgtttgt ctttttccta gtgttcccct ggccatagtc gccaggttgc agctgccctg 148800
gtatgtggat cagaagtcct agctcttgcc agatggttct gagcccgcct gctccactgg 148860
gctggagagc tccctcccac atttacccag taggcatacc tgccacacca gtgtctggac 148920
acaaaatgaa tggtgtgtgg ggctgggaac tggggctgcc aggtgtccag caccattttc 148980
ctttctgtgt tttcttctca ggagttaaaa tttaattata tcagtaaaga gattaatttt 149040
aatgtaactt ttcctatgcc cgtgtaaagt gtgtgacttg gcaaggcctg tgctgcatgt 149100
gacaaagttt atggaagtgg aggggccttc tggccgccac tccctctcct gtagctactc 149160
agtctagtcg ggcaggtccc tcctgtagcc ctcccaacac cctgtggcac ttgcacttca 149220
tacagctccc ttttcttatg cattccatta agccagcaca gagagaggtg ttggtattga 149280
ctgcctgtgt gagaatcctg cctgtggcct aactgaggaa ctgaaaaact gacttccact 149340
gttagagtta taagaggctt gccctgtggc agctgccctc ctctcccctt cccaggcatg 149400
actgtcaagc tatctcctcc ctggtgttga tgcactctcc tagtctctca gcctgggtag 149460
aaacagcatc tgctggaccc aaagtggcta tcccaataac ctcatccctg gttgtggctg 149520
acctgcactg tagcctgccc acacaccagc tgaccattgt ggatgctgtc tgtccctttg 149580
tatcttctgc atggttggga cctgagaagt gctgacctga ttaccccaaa ggtgtctctg 149640
agctatggtt tgttggtttg tctcagtttc tcatagtcaa gggaaagctt ggtgtcctag 149700
caacagttaa gaatggaccc agagcctctt ttgccccttc ccatcttgcc ttctgtcagc 149760

-continued

```
ccagtagagt acagacctat gcctgtcaga gcccagggag gactcagctg acaagatgag 149820
gcaccaaagg gaaggttcaa aatcaggtca gcctctggcc tcagacagct tcccatgctg 149880
gtcagagcca cctcttccca aagcccaagc ccagagtaac caggtcatgt taatgaaaat 149940
gagctacctt catttcctgg cttggtttgg gaactctgtt tgctgtttga ctatatgacc 150000
aagcagattt tctgctgttc cgctaagtca tatctgtatt tctcagctgt agagtagggg 150060
agtggaatag tttggagatg tttctaggct acacaggagg aaagagcttg cagcctgtga 150120
ttaactaact gtgcttcagt ccatggattg ctttcttgag acccttgaat ttccctctat 150180
ctttccatca tgacaagtag ccttgctgct gggatgcaag gttccctacc aaacacaggt 150240
tgtggggagc ctcacacttg gcctgactct cctcctatct gccctggcaa aaaccacccc 150300
aaggcgtggt aacaggaaca gtggacatgg attaggtctt tcaagaggac gttaagggaa 150360
gctactgaat tttaatgaaa gaaattcacc aatgcccctt tgctgattta gggcttcttc 150420
ttgtcaccct caatttcccg cctagaagtg ctcggggacc atgtgaaagt tcttacagtg 150480
ctgctgccac actctgaggt tggtccaacc gctctgagat gagcatggtg caggcctgat 150540
tactcctcat ggtagatgtt cataaggaaa ctcaatataa aatctagagc cattcaccag 150600
gggattatat cagtgagctc aacctcaagt ttagttggcc tcttgtttag tgtgatcaga 150660
aacaattctt agtatggggc aaggacagcc tctgccacaa agttgttgtc tgctcatggg 150720
tgccacaacc tagagatgca cctgggtaca ggcaggtatg tatttgtgta cacacataaa 150780
cacacacaca atcctcaaag acatatgcaa ggcctctaaa aatgcctgcc tgtttttttct 150840
gaaagcagac ttttcttgca actgccacat acagtcagct ttgtgagtct agcatctgag 150900
aatgggactc aatttttaaa agtccatagc tcattaaagt ctcactggag acattgcccc 150960
acctgtctaa ctgcaggagg gactaaaact ttttatcaaa ttcctcaaaa atctaaagat 151020
ttccaagctt tatttaaaaa caaaagttat tttgactatg aggttttagg ggtaggaggt 151080
gggatgttgt ttctgtttcc atggtggtac tgtcaggaaa gattttaata aaaccagggt 151140
agaacttttg gcaatgcact tcagcatgtt tcttctccaa aatgtgcctc cctccctccc 151200
actgatggcc cccttgacat gtaggtgact tagccactgc caagtgccct ttatggttct 151260
ctcattttgt ctgcacatgt acccttcagg agggaagaac tggagtggaa ccacctcctg 151320
ccctgtagaa tgcagtgcca gggaagggac caatcctaac aggtgccttc cctggcagga 151380
agtaccttcc cgtgagtgag tgaagcagct ctgcttccgg ctcatgggac aggttttata 151440
cagcaatagc ttgtctcaca gccacgtcac aaggagtctt gcctcccatt gtggggctgc 151500
agaattggtc tccttgccac ctgtgagcat ccttccccac acagtctcct tccctccctc 151560
cttccctccc tccctccctc cctccctccg tccctccctc cctccctcag cattgagcac 151620
taggatcatg gctgctacca ggacaggcat gaagctgtcc tccagggatt ggtatgtggg 151680
agtcgaagac actgagctgc tgatgctggg tgtgggctca ggatatcatg gttgggaaaa 151740
gaattgttcc tcagtgggtc tggagcctcc aggaaagaag aaccaatgct gagcagtgtg 151800
acaactaaag atgatatcaa ggttcagggc caccctccat gtgtgcttgt cacactctag 151860
agccatcgaa ggaactgctc ccctcaagtg tctctggaaa caccctctgc cgcaagctgg 151920
gtgtaagata ataggtggca gagacctatc tgcagagatt tggctgcatt ctagggggct 151980
cctgtccaag ccttgctgct gtatgccatg ggcttcactg ggaactagga gggctgtgat 152040
gggtgtgccc cggagcccag cctagacctg gctgtccatt tccaaaagga aggactgaca 152100
tgaaatgtat atttaaaatt tttaaattgc agatattgta cagttgaatt aaagaagcga 152160
```

ttaaaccacc tgttgttgct gtttgaggct tgctttactt ataaaacctc ctttctagca 152220
tttgaggaga gcatcctgct tatctccagt ggggcaagga tactaccagc agccatcttg 152280
acactgtaaa gatcaggcaa tactaggtat agaatgagac tgtgtgcctg gaattgggac 152340
caggcctagg agtattcgca gaccctattg aagtggtctc cctgtctggg agatatggtg 152400
tgccaagttc tcatagttat tggcatttta agcctgtcgt gtgagatcct aggtattgtt 152460
tcagcttcca cacattgctc cagggttcta gaggggtggt gaggctctgt cctcacacag 152520
gacacagtta gtagtccttg gagtctttgc atgctctcca ccagcccttc tgcctttctg 152580
gacatgctcc tgatccacat ggatcctctt ctgcccttca acatgactgg tcttaccacc 152640
tttgtcctgc tgtgtctgca acacctaccc tgtcctttgt aggttacaac ttcttttagg 152700
ttgtctatga cattgcctgt cttaccaggt cccttcttta gtatctgggc taaacctgaa 152760
atgcaggtac ttcatccacc aacctgcagg aacaaggctg tttggggaac actttctaaa 152820
ggcctgtcaa gtttcagttg tgaggcagga gttgtctacc tgatccttca acccaccaga 152880
ccctgacgtt agtgccagga taactcttgg gagtcttata gagcccagtg catgccacta 152940
tcccttctag gacatggcac agggtctgtt ctctgtacaa gataatgaac ctttggcagg 153000
aagggcctgg taggtgcccc accatgttta ggtctttgcc cagtaactca agcatttgat 153060
ggcagcatgg atgttattgc ttcaactccc tgaatctacc tcagcagtcc tctctaggac 153120
tacggtgata ttgcccttaa ggtcttcatc aacgccgggc atggtggcac acacctttaa 153180
tcccatcact tgggagggat ttctgagttt gaggccagcc tggtctacaa tgtgagttcc 153240
aggacagcca gggctataca gagaaaccct gtctacaaaa acaaaaacaa aaagatcttc 153300
atcaacactt gagttttgct cacttcagga aaatgaagta cccctgccct cctggtggat 153360
agccagacct ttgacctaac aggcatgggt ggtattccag aaaggataag gtaagcctcc 153420
ctggggtatt ggcagcacat tattccttct agccactaaa gcagaacgca agccctcacc 153480
atagcaagtc cagccctcct gcctggggaa tgtaggagca catgacttga ggtacccctc 153540
agcctcattg tggtgtttgt ctccagtttt tccaaaaagc attctgaagg agcttgaaga 153600
agcagcctga ttgtgttgaa tacggggatg ggtagtcatg gtatgtgtgc catttgtggc 153660
catatgtgtc cacatattga gtggacaggg tccaagtttc ctggagttat atccaggctt 153720
cctaggatgt gagcctcacc tccatacaag gtggcaaagc tcagccaaat caagaagacc 153780
tacttgggta gcccagggaa ggctcatgag cagaggtgga cccaggtact tgagaatcac 153840
tgagaccttc ctgggatcca cacacatcct tagccctgaa agcctgagtc tcatcttcct 153900
ccatgttgtg gtcctgaaag agatgcctgc ttcacttcaa gctcagggtg gacatttggg 153960
acatagctgg ggtgggaaga gctggccaca aaggcagagt g 154001

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
cgtgtgtctg tgctagtccc 20

<210> SEQ ID NO 13
<211> LENGTH: 20
<212> TYPE: DNA

-continued

<213> ORGANISM: Artificial Sequence
<220> FEATURE:
<223> OTHER INFORMATION: Oligomeric Compound

<400> SEQUENCE: 13
ggcaacgtga acaggtccaa 20

<210> SEQ ID NO 14
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 14
gcccattgct ggacatgc 18

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
agcccattgc tggacatgca 20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
ttgtcccagt cccaggcctc 20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
ctttccgttg gacccctggg 20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18
gtgcgcgcga gcccgaaatc 20

<210> SEQ ID NO 19
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 19
atccaagtgc tactgtagta 20

<210> SEQ ID NO 20
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-20
<223> OTHER INFORMATION: n is a, c, g, or t

<400> SEQUENCE: 20
nnnnnnnnnn nnnnnnnnnn 20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
gccctccatg ctggcacagg 20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
agcaaaagat caatccgtta 20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
tacagaaggc tgggccttga 20

<210> SEQ ID NO 24
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 24
atgcattctg cccccaagga 20

<210> SEQ ID NO 25
<211> LENGTH: 21
<212> TYPE: DNA
<213> ORGANISM: Artificial Sequence
<220> FEATURE:
<223> OTHER INFORMATION: Forward Primer

<400> SEQUENCE: 25
caacggattt ggtcgtattg g 21

<210> SEQ ID NO 26

<211> LENGTH: 26
<212> TYPE: DNA
<213> ORGANISM: Artificial Sequence
<220> FEATURE:
<223> OTHER INFORMATION: Reverse Primer

<400> SEQUENCE: 26
ggcaacaata tccactttac cagagt 26

<210> SEQ ID NO 27
<211> LENGTH: 21
<212> TYPE: DNA
<213> ORGANISM: Artificial Sequence
<220> FEATURE:
<223> OTHER INFORMATION: Probe

<400> SEQUENCE: 27
cgcctggtca ccagggctgc t 21

<210> SEQ ID NO 28
<211> LENGTH: 19
<212> TYPE: DNA
<213> ORGANISM: Artificial Sequence
<220> FEATURE:
<223> OTHER INFORMATION: Forward Primer

<400> SEQUENCE: 28
gaaggtgaag gtcggagtc 19

<210> SEQ ID NO 29
<211> LENGTH: 20
<212> TYPE: DNA
<213> ORGANISM: Artificial Sequence
<220> FEATURE:
<223> OTHER INFORMATION: Reverse Primer

<400> SEQUENCE: 29
gaagatggtg atgggatttc 20

<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30
caagcttccc gttctcagcc 20

<210> SEQ ID NO 31
<211> LENGTH: 20
<212> TYPE: DNA
<213> ORGANISM: Artificial Sequence
<220> FEATURE:
<223> OTHER INFORMATION: Probe

<400> SEQUENCE: 31
tggaatcata ttggaacatg 20

<210> SEQ ID NO 32
<211> LENGTH: 20
<212> TYPE: DNA
<213> ORGANISM: Artificial Sequence
<220> FEATURE:
<223> OTHER INFORMATION: Forward Primer

<400> SEQUENCE: 32
ggcaaattca acggcacagt 20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer

<400> SEQUENCE: 33
gggtctcgct cctggaagat 20

<210> SEQ ID NO 34
<211> LENGTH: 27
<212> TYPE: DNA
<213> ORGANISM: Artificial Sequence
<220> FEATURE:
<223> OTHER INFORMATION: Probe

<400> SEQUENCE: 34
aaggccgaga atgggaagct tgtcatc 27

<210> SEQ ID NO 35
<211> LENGTH: 23
<212> TYPE: DNA
<213> ORGANISM: Artificial Sequence
<220> FEATURE:
<223> OTHER INFORMATION: Forward Primer

<400> SEQUENCE: 35
tgttctagag acagccgcat ctt 23

<210> SEQ ID NO 36
<211> LENGTH: 21
<212> TYPE: DNA
<213> ORGANISM: Artificial Sequence
<220> FEATURE:
<223> OTHER INFORMATION: Reverse Primer

<400> SEQUENCE: 36
caccgacctt caccatcttg t 21

<210> SEQ ID NO 37
<211> LENGTH: 24
<212> TYPE: DNA
<213> ORGANISM: Artificial Sequence
<220> FEATURE:
<223> OTHER INFORMATION: Probe

<400> SEQUENCE: 37
ttgtgcagtg ccagcctcgt ctca 24

<210> SEQ ID NO 38
<211> LENGTH: 20
<212> TYPE: DNA
<213> ORGANISM: Artificial Sequence
<220> FEATURE:
<223> OTHER INFORMATION: Forward Primer

<400> SEQUENCE: 38
ctccgtccgg tagacatgct 20

<210> SEQ ID NO 39
<211> LENGTH: 23
<212> TYPE: DNA

<213> ORGANISM: Artificial Sequence
<220> FEATURE:
<223> OTHER INFORMATION: Reverse Primer

<400> SEQUENCE: 39
ggaaatcaga accctcaaaa tgg 23

<210> SEQ ID NO 40
<211> LENGTH: 29
<212> TYPE: DNA
<213> ORGANISM: Artificial Sequence
<220> FEATURE:
<223> OTHER INFORMATION: Probe

<400> SEQUENCE: 40
tgagcactgt tcaactgtgg atatcggga 29

<210> SEQ ID NO 41
<211> LENGTH: 21
<212> TYPE: DNA
<213> ORGANISM: Artificial Sequence
<220> FEATURE:
<223> OTHER INFORMATION: Forward Primer

<400> SEQUENCE: 41
cagagctggt caaccgtatc c 21

<210> SEQ ID NO 42
<211> LENGTH: 21
<212> TYPE: DNA
<213> ORGANISM: Artificial Sequence
<220> FEATURE:
<223> OTHER INFORMATION: Reverse Primer

<400> SEQUENCE: 42
ggcttaaaca gggagccaaa a 21

<210> SEQ ID NO 43
<211> LENGTH: 26
<212> TYPE: DNA
<213> ORGANISM: Artificial Sequence
<220> FEATURE:
<223> OTHER INFORMATION: Probe

<400> SEQUENCE: 43
acttcatgat gagctcggag ttcaac 26

<210> SEQ ID NO 44
<211> LENGTH: 13210
<212> TYPE: DNA
<213> ORGANISM: H. sapiens

<400> SEQUENCE: 44
gcactcgccg cgagggttgc cgggacgggc ccaagatggc tgagcgcctt ggttccgctt 60
ctgcctgccg cgcagagccc cattcattgc cttgctgcta agtggcgccg cgtagtgcca 120
gtaggctcca agtcttcagg gtctgtccca tcgggcagga agccgtcatg gcaaccctgg 180
aaaagctgat gaaggctttc gagtcgctca agtcgtttca gcagcaacag cagcagcagc 240
caccgccgca ggcgccgccg ccaccgccgc cgccgcctcc gcctcaaccc cctcagccgc 300
cgcctcaggg gcagccgccg ccgccaccac cgccgctgcc aggtccggca gaggaaccgc 360
tgcaccgacc aaagaaggaa ctctcagcca ccaagaaaga ccgtgtgaat cattgtctaa 420
caatatgtga aaacattgtg gcacagtctc tcagaaattc tccagaattt cagaaactct 480

-continued

```
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaaagaatgg tgctcctcga agtttgcgtg    660
ctgccctgtg gaggtttgct gagctggctc acctggttcg acctcagaag tgcaggcctt    720
acctggtgaa tcttcttcca tgcctgaccc gaacaagcaa aagaccggag gaatcagttc    780
aggagacctt ggctgcagct gttcctaaaa ttatggcttc ttttggcaat ttcgcaaatg    840
acaatgaaat taaggttctg ttgaaagctt tcatagcaaa tctgaagtca agctctccca    900
ccgtgcggcg gacagcagcc ggctcagccg tgagcatctg ccaacattct aggaggacac    960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagcacca agaccacaat gtggtgacag gggcactgga gctcctgcag cagctcttcc   1260
gtacccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
tgaggaccga actgctggac actctggcag agattgactt caggctcgtg agtttttttgg   2760
aggcaaaagc agaaagttta caccgagggg ctcatcatta tacagggttt ctaaaactac   2820
```

-continued

```
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa accccccttc tctaagtcct attcgacgga   3660
aagggaagga gaaagaacct ggagaacaag cttctactcc aatgagtccc aagaaagttg   3720
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca accccagcaa gtctcagtgc cgagctcagc   4140
gccttggctc ttcaagtgtg aggcccggct tatatcacta ctgcttcatg gcaccataca   4200
cgcacttcac acaggccttg gctgacgcaa gcctgaggaa catggtgcag gcggagcagg   4260
agcgtgatgc ctcggggtgg tttgatgtac tccagaaagt gtctgcccaa ttgaagacga   4320
acctaacaag cgtcacaaag aaccgtgcag ataagaatgc tattcataat cacattaggt   4380
tatttgagcc tcttgttata aaagcattga agcagtacac cacgacaaca tctgtacaat   4440
tgcagaagca ggttttggat ttgctggcac agctggttca gctacgggtc aattactgtc   4500
tactggattc agaccaggtg ttcatcgggt ttgtgctgaa gcagtttgag tacattgaag   4560
tgggccagtt cagggaatca gaggcaatta ttccaaatat atttttcttc ctggtattac   4620
tgtcttatga gcgctaccat tcaaaacaga tcattggaat tcctaaaatc atccagctgt   4680
gtgatggcat catggccagt ggaaggaagg ccgttacaca tgctatacct gctctgcagc   4740
ccattgtcca tgacctcttt gtgttacgag gaacaaataa agctgatgca gggaaagagc   4800
ttgagacaca gaaggaggtg gtggtctcca tgctgttacg actcatccag taccatcagg   4860
tgctggagat gttcatcctt gtcctgcagc agtgccacaa ggagaatgag gacaagtgga   4920
aacggctctc tcggcaggtc gcagacatca tcctgcccat gttggccaag cagcagatgc   4980
atattgactc tcatgaagcc cttggagtgt taaatacctt gtttgagatt ttggctcctt   5040
cctccctacg tcctgtggac atgcttttgc ggagtatgtt catcactcca agcacaatgg   5100
catctgtaag cactgtgcag ctgtggatat ctggaatcct cgccattctg agggttctca   5160
tttcccagtc aaccgaggac attgttcttt gtcgtattca ggagctctcc ttctctccac   5220
```

```
acttgctctc ctgtccagtg attaacaggt taaggggtgg aggcggtaat gtaacactag   5280
gagaatgcag cgaagggaaa caaaagagtt tgccagaaga tacattctca aggtttcttt   5340
tacagctggt tggtattctt ctagaagaca tcgttacaaa acagctcaaa gtggacatga   5400
gtgaacagca gcatacgttc tactgccaag agctaggcac actgctcatg tgtctgatcc   5460
acatattcaa atctggaatg ttccggagaa tcacagcagc tgccactaga ctcttcacca   5520
gtgatggctg tgaaggcagc ttctatactc tagagagcct gaatgcacgg gtccgatcca   5580
tggtgcccac gcacccagcc ctggtactgc tctggtgtca gatcctactt ctcatcaacc   5640
acactgacca ccggtggtgg gcagaggtgc agcagacacc caagagacac agtctgtcct   5700
gcacgaagtc acttaacccc cagaagtctg gcgaagagga ggattctggc tcggcagctc   5760
agctgggaat gtgcaataga gaaatagtgc gaagaggggc ccttattctc ttctgtgatt   5820
atgtctgtca gaatctccat gactcagaac acttaacatg gctcattgtg aatcacattc   5880
aagatctgat cagcttgtct catgagcctc cagtacaaga ctttattagt gccattcatc   5940
gtaattctgc agctagtggt ctttttatcc aggcaattca gtctcgctgt gaaaatcttt   6000
caacgccaac cactctgaag aaaacacttc agtgcttgga aggcatccat ctcagccagt   6060
ctggtgctgt gctcacacta tatgtggaca ggctcctggg cacccccttc cgtgcgctgg   6120
ctcgcatggt cgacaccctg gcctgtcgcc gggtagaaat gcttttggct gcaaatttac   6180
agagcagcat ggcccagttg ccagaggagg aactaaacag aatccaagaa cacctccaga   6240
acagtgggct tgcacaaaga caccaaaggc tctattcact gctggacaga ttccgactct   6300
ctactgtgca ggactcactt agccccttgc cccagtcac ttcccaccca ctggatgggg    6360
atgggcacac atctctggaa acagtgagtc cagacaaaga ctggtacctc cagcttgtca   6420
gatcccagtg ttggaccaga tcagattctg cactgctgga aggtgcagag ctggtcaacc   6480
gtatccctgc tgaagatatg aatgacttca tgatgagctc ggagttcaac ctaagccttt   6540
tggctccctg tttaagcctt ggcatgagcg agattgctaa tggccaaaag agtcccctct   6600
ttgaagcagc ccgtggggtg attctgaacc gggtgaccag tgttgttcag cagcttcctg   6660
ctgtccatca agtcttccag cccttcctgc ctatagagcc cacggcctac tggaacaagt   6720
tgaatgatct gcttggtgat accacatcat accagtctct gaccatactt gcccgtgccc   6780
tggcacagta cctggtggtg ctctccaaag tgcctgctca tttgcacctt cctcctgaga   6840
aggaggggga cacggtgaag tttgtggtaa tgacagttga ggccctgtca tggcatttga   6900
tccatgagca gatcccactg agtctggacc tccaagccgg gctagactgc tgctgcctgg   6960
cactacaggt gcctggcctc tggggggtgc tgtcctcccc agagtacgtg actcatgcct   7020
gctccctcat ccattgtgtg cgattcatcc tggaagccat tgcagtacaa cctggagacc   7080
agcttctcgg tcctgaaagc aggtcacata ctccaagagc tgtcagaaag gaggaagtag   7140
actcagatat acaaaaacctc agtcatgtca cttcggcctg cgagatggtg gcagacatgg  7200
tggaatccct gcagtcagtg ctggccttgg gccacaagag gaacagcacc ctgccttcat   7260
ttctcacagc tgtgctgaag aacattgtta tcagtctggc ccgactcccc ctagttaaca   7320
gctatactcg tgtgcctcct ctggtatgga aactcgggtg gtcacccaag cctggagggg   7380
attttggcac agtgtttcct gagatccctg tagagttcct ccaggagaag gagatcctca   7440
aggagttcat ctaccgcatc aacaccctag ggtggaccaa tcgtacccag ttcgaagaaa   7500
cttgggccac cctccttggt gtcctggtga ctcagcccct ggtgatggaa caggaagaga   7560
```

-continued

```
gcccaccaga ggaagacaca gaaagaaccc agatccatgt cctggctgtg caggccatca   7620
cctctctagt gctcagtgca atgaccgtgc ctgtggctgg caatccagct gtaagctgct   7680
tggagcaaca gccccggaac aagccactga aggctctcga taccagattt ggaagaaagc   7740
tgagcatgat cagagggatt gtagaacaag aaatccaaga gatggtttcc cagagagaga   7800
atactgccac tcaccattct caccaggcgt gggatcctgt cccttctctg ttaccagcta   7860
ctacaggtgc tcttatcagc catgacaagc tgctgctgca gatcaaccca gagcgggagc   7920
caggcaacat gagctacaag ctgggccagg tgtccataca ctccgtgtgg ctgggaaata   7980
acatcacacc cctgagagag gaggaatggg atgaggaaga agaggaagaa agtgatgtcc   8040
ctgcaccaac gtcaccacct gtgtctccag tcaattccag aaaacaccgt gccggggttg   8100
atattcactc ctgttcgcag tttctgcttg aattgtacag ccgatggatc ctgccatcca   8160
gtgcagccag aaggaccccc gtcatcctga tcagtgaagt ggttcgatct cttcttgtag   8220
tgtcagactt attcaccgaa cgtacccagt ttgaaatgat gtatctgacg ctgacagaac   8280
tacggagagt gcacccttca gaagatgaga tcctcattca gtacctggtg cctgccacct   8340
gtaaggcagc tgctgtcctt ggaatggaca aaactgtggc agagccagtc agccgcctac   8400
tggagagcac actgaggagc agccacctgc ccagccagat cggagccctg cacggcatcc   8460
tctatgtgtt ggagtgtgac ctcttggatg acactgcaaa gcagctcatt ccagttgtta   8520
gtgactatct gctgtccaac ctcaaaggaa tagcccactg cgtgaacatt cacagccagc   8580
agcatgtgct ggtaatgtgt gccactgctt tctacctgat ggaaaactac cctctggatg   8640
tgggaccaga attttcagca tctgtgatac agatgtgtgg agtaatgctg tctggaagtg   8700
aggagtccac cccctccatc atttaccact gtgccctccg gggtctggag cggctcctgc   8760
tgtctgagca gctatctcgg ctagacacag agtccttggt caagctaagt gtggacagag   8820
tgaatgtaca aagcccacac agggccatgg cagccctagg cctgatgctc acctgcatgt   8880
acacaggaaa ggaaaaagcc agtccaggca gagcttctga ccccagccct gctacacctg   8940
acagcgagtc tgtgattgta gctatggagc gagtgtctgt tctctttgat aggatccgca   9000
agggatttcc ctgtgaagcc agggttgtgg caaggatcct gcctcagttc ctagatgact   9060
tctttccacc tcaagatgtc atgaacaaag tcattggaga gttcctgtcc aatcagcagc   9120
catacccaca gttcatggcc actgtagttt acaaggtttt tcagactctg cacagtgctg   9180
ggcagtcatc catggtccgg gactgggtca tgctgtccct gtccaacttc acacaaagaa   9240
ctccagttgc catggccatg tggagcctct cctgcttcct tgttagcgca tctaccagcc   9300
catgggtttc tgcgatcctt ccacatgtca tcagcaggat gggcaaactg gaacaggtgg   9360
atgtgaacct tttctgcctg gttgccacag acttctacag acaccagata gaggaggaat   9420
tcgaccgcag ggctttccag tctgtgtttg aggtggtggc tgcaccagga agtccatacc   9480
acaggctgct tgcttgtttg caaaatgttc acaaggtcac cacctgctga gtagtgcctg   9540
tgggacaaaa ggctgaaaga aggcagctgc tggggcctga gcctccagga gcctgctcca   9600
agcttctgct ggggctgcct tggccgtgca ggcttccact tgtgtcaagt ggacagccag   9660
gcaatggcag gagtgctttg caatgagggc tatgcaggga acatgcacta tgttggggtt   9720
gagcctgagt cctgggtcct ggcctcgctg cagctggtga cagtgctagg ttgaccaggt   9780
gtttgtcttt ttcctagtgt tcccctggcc atagtcgcca ggttgcagct gccctggtat   9840
gtggatcaga agtcctagct cttgccagat ggttctgagc ccgcctgctc cactgggctg   9900
gagagctccc tcccacattt acccagtagg catacctgcc acaccagtgt ctggacacaa   9960
```

-continued

```
aatgaatggt gtgtggggct gggaactggg gctgccaggt gtccagcacc attttccttt  10020
ctgtgttttc ttctcaggag ttaaaattta attatatcag taaagagatt aattttaatg  10080
taacttttcc tatgcccgtg taaagtgtgt gacttggcaa ggcctgtgct gcatgtgaca  10140
aagtttatgg aagtggaggg gccttctggc cgccactccc tctcctgtag ctactcagtc  10200
tagtcgggca ggtccctcct gtagccctcc caacaccctg tggcacttgc acttcataca  10260
gctccctttt cttatgcatt ccattaagcc agcacagaga gaggtgttgg tattgactgc  10320
ctgtgtgaga atcctgcctg tggcctaact gaggaactga aaaactgact tccactgtta  10380
gagttataag aggcttgccc tgtggcagct gccctcctct ccccttccca ggcatgactg  10440
tcaagctatc tcctccctgg tgttgatgca ctctcctagt ctctcagcct gggtagaaac  10500
agcatctgct ggacccaaag tggctatccc aataacctca tccctggttg tggctgacct  10560
gcactgtagc ctgcccacac accagctgac cattgtggat gctgtctgtc cctttgtatc  10620
ttctgcatgg ttgggacctg agaagtgctg acctgattac cccaaaggtg tctctgagct  10680
atggtttgtt ggtttgtctc agtttctcat agtcaaggga aagcttggtg tcctagcaac  10740
agttaagaat ggacccagag cctcttttgc cccttcccat cttgccttct gtcagcccag  10800
tagagtacag acctatgcct gtcagagccc agggaggact cagctgacaa gatgaggcac  10860
caaagggaag gttcaaaatc aggtcagcct ctggcctcag acagcttccc atgctggtca  10920
gagccacctc ttcccaaagc ccaagcccag agtaaccagg tcatgttaat gaaaatgagc  10980
taccttcatt tcctggcttg gtttgggaac tctgtttgct gtttgactat atgaccaagc  11040
agattttctg ctgttccgct aagtcatatc tgtatttctc agctgtagag taggggagtg  11100
gaatagtttg gagatgtttc taggctacac aggaggaaag agcttgcagc ctgtgattaa  11160
ctaactgtgc ttcagtccat ggattgcttt cttgagaccc ttgaatttcc ctctatcttt  11220
ccatcatgac aagtagcctt gctgctggga tgcaaggttc cctaccaaac acaggttgtg  11280
gggagcctca cacttggcct gactctcctc ctatctgccc tggcaaaaac caccccaagg  11340
cgtggtaaca ggaacagtgg acatggatta ggtctttcaa gaggacgtta agggaagcta  11400
ctgaatttta atgaaagaaa ttcaccaatg cccctttgct gatttagggc ttcttcttgt  11460
caccctcaat ttcccgccta gaagtgctcg gggaccatgt gaaagttctt acagtgctgc  11520
tgccacactc tgaggttggt ccaaccgctc tgagatgagc atggtgcagg cctgattact  11580
cctcatggta gatgttcata aggaaactca atataaaatc tagagccatt caccagggga  11640
ttatatcagt gagctcaacc tcaagtttag ttggcctctt gtttagtgtg atcagaaaca  11700
attcttagta tggggcaagg acagcctctg ccacaaagtt gttgtctgct catgggtgcc  11760
acaacctaga gatgcacctg ggtacaggca ggtatgtatt tgtgtacaca cataaacaca  11820
cacacaatcc tcaaagacat atgcaaggcc tctaaaaatg cctgcctgtt ttttctgaaa  11880
gcagactttt cttgcaactg ccacatacag tcagctttgt gagtctagca tctgagaatg  11940
ggactcaatt tttaaaagtc catagctcat taaagtctca ctggagacat tgccccacct  12000
gtctaactgc aggagggact aaaacttttt atcaaattcc tcaaaaatct aaagatttcc  12060
aagctttatt taaaaacaaa agttattttg actatgaggt tttaggggta ggaggtggga  12120
tgttgtttct gtttccatgg tggtactgtc aggaaagatt ttaataaaac cagggtagaa  12180
cttttggcaa tgcacttcag catgtttctt ctccaaaatg tgcctccctc cctcccactg  12240
atggccccct tgacatgtag gtgacttagc cactgccaag tgccctttat ggttctctca  12300
```

ttttgtctgc acatgtaccc ttcaggaggg aagaactgga gtggaaccac ctcctgccct 12360
gtagaatgca gtgccaggga agggaccaat cctaacaggt gccttccctg gcaggaagta 12420
ccttcccgtg agtgagtgaa gcagctctgc ttccggctca tgggacaggt tttatacagc 12480
aatagcttgt ctcacagcca cgtcacaagg agtcttgcct cccattgtgg ggctgcagaa 12540
ttggtctcct tgccacctgt gagcatcctt ccccacacag tctccttccc tccctccttc 12600
cctccctccc tccctccctc cctccgtccc tccctccctc cctcagcatt gagcactagg 12660
atcatggctg ctaccaggac aggcatgaag ctgtcctcca gggattggta tgtgggagtc 12720
gaagacactg agctgctgat gctgggtgtg ggctcaggat atcatggttg ggaaaagaat 12780
tgttcctcag tgggtctgga gcctccagga aagaagaacc aatgctgagc agtgtgacaa 12840
ctaaagatga tatcaaggtt cagggccacc ctccatgtgt gcttgtcaca ctctagagcc 12900
atcgaaggaa ctgctcccct caagtgtctc tggaaacacc ctctgccgca agctgggtgt 12960
aagataatag gtggcagaga cctatctgca gagatttggc tgcattctag ggggctcctg 13020
tccaagcctt gctgctgtat gccatgggct tcactgggaa ctaggagggc tgtgatgggt 13080
gtgccccgga gcccagccta gacctggctg tccatttcca aaaggaagga ctgacatgaa 13140
atgtatattt aaaattttta aattgcagat attgtacagt tgaattaaag aagcgattaa 13200
accacctgtt 13210

<210> SEQ ID NO 45
<211> LENGTH: 1876
<212> TYPE: DNA
<213> ORGANISM: Mus musculus

<400> SEQUENCE: 45
cgcccaccct ctccccgtgc agagagcccc gcagctggct ccccgcaggg ctgtccgggt 60
gagtatggct ctggccacgg gccagtgtgg cgggagggca aaccccaagg ccacctcggc 120
tcagagtcca cggccggctg tcgccccgct ccaggcgtcg gcgggggatc ctttccgcat 180
gggcctgcgc ccgcgctcgg cgccccctcc acggccccgc cccgtccatg gccccgtcct 240
tcatgggcga gcccctccat ggccctgccc ctccgcgccc caccccctccc tcgccccacc 300 tctcaccttc ctgccccgcc cccagcctcc ccaaccctca ccggccagtc ccctccccta 360
tcccgtccgc ccctcagccg ccccgcccct cagccggcct gcctaatgtc cccgtcccca 420
gcatcgcccc gccccgcccc cgtctcgccc cgcccctcag gcggcctccc tgctgtgccc 480
cgccccggcc tcgccacgcc cctacctcac cacgcccccc gcatcgccac gccccccgca 540
tcgccacgcc tcccttacca tgcagtcccg ccccgtccct tcctcgtccc gcctcgccgc 600
gacacttcac acacagcttc gcctcacccc attacagtct caccacgccc cgtcccctct 660
ccgttgagcc ccgcgccttc gcccgggtgg ggcgctgcgc tgtcagcggc cttgctgtgt 720
gaggcagaac ctgcgggggc aggggcgggc tggttccctg gccagccatt ggcagagtcc 780
gcaggctagg gctgtcaatc atgctggccg gcgtggcccc gcctccgccg gcgcggcccc 840
gcctccgccg gcgcagcgtc tgggacgcaa ggcgccgtgg gggctgccgg gacgggtcca 900
agatggacgg ccgctcaggt tctgctttta cctgcggccc agagccccat tcattgcccc 960
ggtgctgagc ggcgccgcga gtcggcccga ggcctccggg gactgccgtg ccgggcggga 1020
gaccgccatg gcgaccctgg aaaagctgat gaaggccttc gagtccctca agtccttcca 1080
gcagcagcag cagcagcagc agcagcagca gcagcagcag cagcagcagc agcagcaaca 1140
gcagcagcag cagcagcagc agcagcagca gcagcagcag cagcagcagc agcagcagca 1200
gcagcagcag cagcagcagc agcagcagca gcagcagcag cagcagcagc agcagcagca 1260
gcagcagcag cagcagcagc agcagcagca gcagcagcag cagcagcagc agcagcagca 1320
gcagcagcag cagcagcagc agcagcagca gcagcagcag cagcagcagc agcagcagca 1380
gcagcagcag cagcagcagc agcagcagca gcagcagcag cagcagcagc agcagcagca 1440
gcagcagcag cagcagcagc agcagcagcc gccaccgccg ccgccgccgc cgccgcctcc 1500
tcagcttcct cagccgccgc cgcaggcaca gccgctgctg cctcagccgc agccgccccc 1560
gccgccgccc ccgccgccac ccggcccggc tgtggctgag gagccgctgc accgaccgtg 1620
agtttgggcc cgctgcagct ccctgtcccg gcgggtccca ggctacggcg gggatggcgg 1680
taaccctgca gcctgcgggc cggcgacacg aacccccggc cccgcagaga cagagtgacc 1740
cagcaaccca gagcccatga gggacacccg ccccctcctg gggcgaggcc ttcccccact 1800
tcagccccgc tccctcactt gggtcttccc ttgtcctctc gcgaggggag gcagagcctt 1860
gttggggcct gtcctg 1876

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
caggtaaaag cagaacctga 20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
gccttcatca gcttttccag 20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
gctgctgctg ctgctggaag 20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
tgctgctgct gctgctgctg 20

<210> SEQ ID NO 50
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 50
ctgctgctgt tgctgctgct 20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
ctgctgctgc tgctgctgct 20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
gctgctgctg ctgctgctgc 20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
tggcggctgc tgctgctgct 20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
gcggcggcgg cggtggcggc 20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
atgattcaca cggtctttct 20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
aaattctgga gaatttctga 20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
agtttctgaa attctggaga 20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
gaatccatca aagctttgat 20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
ccttggaaga ttagaatcca 20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
gagccagctc agcaaacctc 20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
gaaccaggtg agccagctca 20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
ttcaccaggt aaggcctgca 20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
acagctgcag ccaaggtctc 20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
ccaaaagaag ccataatttt 20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
aaccttaatt tcattgtcat 20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
gtagccaact atagaaatat 20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
atttagtagc caactataga 20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
agagacttcc atttctttcc 20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
agaaggagag acttccattt 20

<210> SEQ ID NO 70
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 70
tgctctgcag aaggagagac 20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
cataaacctg gacaagctgc 20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
gtcagttcat aaacctggac 20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
acattgtggt cttggtgctg 20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
aagagcactt tgccttttg 20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
tgctgaccct ggagtggaaa 20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
tggccagatc cactgagtcc 20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
tcattcaggt ccatggcagg 20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
ggtcccatca ttcaggtcca 20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
ctaacacaat ttcagaactg 20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
tggaagagtt cctgaaggcc 20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
gtttttcaat aaatgtgcct 20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
gcagtgactc atgtttttca 20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
tgcctgcagt gactcatgtt 20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
gtcaagagga actttataga 20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
atcgatgtag ttcaagatgt 20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
gtcccacaga gaatggcagt 20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
tgatcagctg cagtcctaac 20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
tgtataatga tgagcccctc 20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
gatcagcttg tccttggtca 20

-continued

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
tctggtggtt gatgtgatta 20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
tgagtgctct ggtggttgat 20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
cagcatccaa atgtgagtgc 20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
gcttcacagc atccaaatgt 20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gaaggcagtg gaaagaagac 20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
agagaaggca aggctgcctt 20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
ggtttgttag agaaggcaag 20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
acatcatgca gtttgaggta 20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
gctttcagga catcatgcag 20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
aagcaggatt tcaggtatcc 20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
ctcgactaaa gcaggatttc 20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
acagttgcca tcattggttc 20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
attgttgaac acaaacagtt 20

<210> SEQ ID NO 103

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
ttggaagata agccatcaaa 20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
tgcaccatgt tcctcaggct 20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
cgcctgcacc atgttcctca 20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
aatagcattc ttatctgcac 20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
aatgtgatta tgaatagcat 20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
taactgcaca catgttgtag 20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
aacacctgat ctgaatccag 20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
gtttcaatac aaagccaata 20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
aactggccca cttcaatgta 20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
tgattccctg aactggccca 20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
ttaggaattc caatgatctg 20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
atgattttag gaattccaat 20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
ctggccatga tgccatcaca 20

<210> SEQ ID NO 116
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 116
ttccttccac tggccatgat 20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
gcatcagctt tatttgttcc 20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
ctcagtaaca ttgacaccac 20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
tactggatga gtctcagtaa 20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
ctgatggtac tggatgagtc 20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
tggcactgct gcaggacaag 20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
tcctgaatac gagaaagaac 20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
tttggctgcc aagtcagaat 20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
tccaagtttg gctgccaagt 20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
tctctattgc acattccaag 20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
ctgacagaca taatcacaga 20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
tgatcagatc ttgaatgtga 20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
cgagactgaa ttgcctggat 20

<210> SEQ ID NO 129
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 129
gaatagagcc tttggtgtct 20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
gtcttgcatg gtggagagac 20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
aatctgacct ggtccaacac 20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
agcagtgcag aatctgacct 20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
tctgcacctt ccagcagtgc 20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
accagaaatt tcactcatcc 20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
ctggccacca gaaatttcac 20

-continued

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
cagcatcccc aaacagatca 20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
acagtgcagc atccccaaac 20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
ggactgatac agtgcagcat 20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
ttctcaggag gaaggtgcaa 20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
ctgctcatgg atcaaatgcc 20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
gtgtgtttgg atctacttcc 20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
gcagtgatat acttaggatt 20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
tcacaggctg cagtgatata 20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
tgatgttcct gagcaatggc 20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
tccaagcttc cacaccagtg 20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
tgttgatgcg gtagatgaac 20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
gtcaccagga caccaaggag 20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
tccaagcagc ttacagctgg 20

<210> SEQ ID NO 149
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 149
ttgaaaccat tgcttgaatc 20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
atgcctgata taaatgatgg 20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151
gttgatctgc agcagcagct 20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
gagtgtatgg acacctggcc 20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
tgttccccag ccacacggag 20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
gtggcaggca ccaggtactg 20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
atagttctca atgaggtaaa 20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
acagtggtaa atgatggagg 20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
atgcaggtga gcatcaggcc 20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
tgtgtacatg caggtgagca 20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
aggaaagcct ttcctgatcc 20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
tatggctgct ggttggacag 20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
cagcatgacc cagtcccgga 20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
ggacagcatg acccagtccc 20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
cccatcctgc tgatgacatg 20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
accaggcaga aaaggttcac 20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
tcagcaggtg gtgaccttgt 20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
tctgccacat ggcagagaca 20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
aaagagcact tctgccacat 20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
gccactgcca caaagagcac 20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
caccaggact gcagacactc 20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
tggaaggcct caggctcagc 20

<210> SEQ ID NO 171
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 171
ggacctggtc acccacatgg 20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
ggcaacaacc agcaggtgac 20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
tgcaacctgg caacaaccag 20

<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
cccagatgca agagcagctg 20

<210> SEQ ID NO 175
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 175
aacagccagc ctgcaggagg 20

<210> SEQ ID NO 176
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
tctactgcag gacagcagag 20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
tgttcccaaa gcctgctcac 20

<210> SEQ ID NO 178
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
ccaggccagt gttcccaaag 20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
ggagacccag gccagtgttc 20

<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
agcacaggcc atggcatctg 20

<210> SEQ ID NO 181
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 181
ctggcccagc acaggccatg 20

<210> SEQ ID NO 182

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 182
actgatataa ttaaatttta 20

<210> SEQ ID NO 183
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 183
ggctatgcca gtggctacag 20

<210> SEQ ID NO 184
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 184
tgtgaatgca taaacaggaa 20

<210> SEQ ID NO 185
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 185
ctagcaagga acaggagtgg 20

<210> SEQ ID NO 186
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 186
ccatggagca gcaggtccca 20

<210> SEQ ID NO 187
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 187
gcatgcatcc atggagcagc 20

<210> SEQ ID NO 188
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 188
actaacagtg ccaagacacc 20

<210> SEQ ID NO 189
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 189
ccattttaat gacttggctc 20

<210> SEQ ID NO 190
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 190
aggaagcaga gcccctgcct 20

<210> SEQ ID NO 191
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 191
ggcagcacct gcacagagtt 20

<210> SEQ ID NO 192
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 192
gcatacaagt ccacatctca 20

<210> SEQ ID NO 193
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 193
catacaggcc tggcagaggc 20

<210> SEQ ID NO 194
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 194
aagaatggtg attttcttac 20

<210> SEQ ID NO 195
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 195
tctagccagg aacaacatct 20

<210> SEQ ID NO 196
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 196
atgtaaacat ctagccagga 20

<210> SEQ ID NO 197
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 197
aatgagctca tattcatctc 20

<210> SEQ ID NO 198
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 198
gaatgagccc tgccctgacc 20

<210> SEQ ID NO 199
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 199
gcaatgaatg agccctgccc 20

<210> SEQ ID NO 200
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 200
agctgatatg gagaccatct 20

<210> SEQ ID NO 201
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 201
ggtgcttgcc acagattttt 20

<210> SEQ ID NO 202
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 202
tgcattgcca aacaattcta 20

<210> SEQ ID NO 203
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 203
ttggcagctg gaaacatcac 20

<210> SEQ ID NO 204
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 204
tccaagtcta ccctggccag 20

<210> SEQ ID NO 205
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 205
gttgccttca gttgtcatgc 20

<210> SEQ ID NO 206
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 206
ttccaggttg ccttcagttg 20

<210> SEQ ID NO 207
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 207
cagttaccac ccagattgca 20

<210> SEQ ID NO 208
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 208
gagacctgga caaggaggcc 20

<210> SEQ ID NO 209
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 209
tgtaattaca gaatttgtat 20

<210> SEQ ID NO 210
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 210
acattccatg aattccattt 20

<210> SEQ ID NO 211
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 211
gttaatttag agaaaattca 20

<210> SEQ ID NO 212
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 212
cagaagcatc caaaccagta 20

<210> SEQ ID NO 213
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 213
caagagggtt gcatagaaac 20

<210> SEQ ID NO 214
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 214
caaagtataa acagtttgag 20

<210> SEQ ID NO 215
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 215
cccagtgcag ttcacattca 20

<210> SEQ ID NO 216
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 216
tattataaaa tacatgtttc 20

<210> SEQ ID NO 217
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 217
attagagatt catcatattg 20

<210> SEQ ID NO 218
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 218
ggtatggaaa ggttcaacat 20

<210> SEQ ID NO 219
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 219
tggaaggtga gggacaaaaa 20

<210> SEQ ID NO 220
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 220
agcagaaaca agtattccat 20

<210> SEQ ID NO 221
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 221
caaattcaca tagggttggt 20

<210> SEQ ID NO 222
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 222
acatgagcaa tgaaggacag 20

<210> SEQ ID NO 223
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 223
gcaatgtgtg atttaccaca 20

<210> SEQ ID NO 224
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 224
accacatcat aatttgtcat 20

<210> SEQ ID NO 225
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 225
attatttaag aagtacccac 20

<210> SEQ ID NO 226
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 226
tgccccaaaa agtggaacca 20

<210> SEQ ID NO 227
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 227
acatttccaa gaggttttga 20

<210> SEQ ID NO 228
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 228
tcagccccaa tttgtagcag 20

<210> SEQ ID NO 229
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 229
gacataaagt ttagaggtat 20

<210> SEQ ID NO 230
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 230
gaaggaccca cagaggtttg 20

<210> SEQ ID NO 231
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 231
tgaaaaggaa gtgacatcat 20

<210> SEQ ID NO 232
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 232
cagtgtcagg agaagcccag 20

<210> SEQ ID NO 233
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 233
gataaaacac cttgttaatg 20

<210> SEQ ID NO 234
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 234

```
ggagcagtac cttatagttg                                                    20


<210> SEQ ID NO 235
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 235

atagctgctg cacacagaca                                                    20


<210> SEQ ID NO 236
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 236

gcatcagtac ctgaactggc                                                    20


<210> SEQ ID NO 237
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 237

gagtggttgg ctaatgttga                                                    20


<210> SEQ ID NO 238
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 238

cagttttgtc ctggatacaa                                                    20


<210> SEQ ID NO 239
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 239

ggagccagtt gtagaagtac                                                    20


<210> SEQ ID NO 240
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 240

cctggtgtgg tcagtgcttg                                                    20


<210> SEQ ID NO 241
<211> LENGTH: 20
<212> TYPE: DNA
<213> ORGANISM: Artificial Sequence
```

<220> FEATURE:
<223> OTHER INFORMATION: Oligomeric Compound

<400> SEQUENCE: 241
cagagtgagc tgcccaagcc 20

<210> SEQ ID NO 242
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 242
tcttcttgaa ccagagtgag 20

<210> SEQ ID NO 243
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 243
gtttctgaaa acatctgaga 20

<210> SEQ ID NO 244
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 244
ctatggccca ttctttccaa 20

<210> SEQ ID NO 245
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 245
taagcagttg taatcccaag 20

<210> SEQ ID NO 246
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 246
ggactcattg gagtagaagc 20

<210> SEQ ID NO 247
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 247
aagaccacta gctgcagaat 20

-continued

<210> SEQ ID NO 248
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 248
tggtatgatg tggtatcacc 20

<210> SEQ ID NO 249
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 249
gtcattacca caaacttcac 20

<210> SEQ ID NO 250
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 250
gactgaggtt ttgtatatct 20

<210> SEQ ID NO 251
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 251
acaatgttct tcagcacagc 20

<210> SEQ ID NO 252
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 252
cagcagatag tcactaacaa 20

<210> SEQ ID NO 253
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 253
actggagttc tttgtgtgaa 20

<210> SEQ ID NO 254
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 254
ggcactactc agcaggtggt 20

<210> SEQ ID NO 255
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 255
cttttgtccc acaggcacta 20

<210> SEQ ID NO 256
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 256
cttgacacaa gtggaagcct 20

<210> SEQ ID NO 257
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 257
gcatagccct cattgcaaag 20

<210> SEQ ID NO 258
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 258
tagtgcatgt tccctgcata 20

<210> SEQ ID NO 259
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 259
aaccccaaca tagtgcatgt 20

<210> SEQ ID NO 260
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 260
aagacaaaca cctggtcaac 20

<210> SEQ ID NO 261

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 261
aaccatctgg caagagctag 20

<210> SEQ ID NO 262
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 262
tgtggcaggt atgcctactg 20

<210> SEQ ID NO 263
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 263
gacactggtg tggcaggtat 20

<210> SEQ ID NO 264
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 264
cttgccaagt cacacacttt 20

<210> SEQ ID NO 265
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 265
acttccataa actttgtcac 20

<210> SEQ ID NO 266
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 266
gactgagtag ctacaggaga 20

<210> SEQ ID NO 267
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 267
tgctggctta atggaatgca 20

<210> SEQ ID NO 268
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 268
ggattctcac acaggcagtc 20

<210> SEQ ID NO 269
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 269
gttaggccac aggcaggatt 20

<210> SEQ ID NO 270
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 270
cagtttttca gttcctcagt 20

<210> SEQ ID NO 271
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 271
ttataactct aacagtggaa 20

<210> SEQ ID NO 272
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 272
ctaggagagt gcatcaacac 20

<210> SEQ ID NO 273
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 273
tttctaccca ggctgagaga 20

<210> SEQ ID NO 274
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 274
ctacagtgca ggtcagccac 20

<210> SEQ ID NO 275
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 275
catccacaat ggtcagctgg 20

<210> SEQ ID NO 276
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 276
cccaaccatg cagaagatac 20

<210> SEQ ID NO 277
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 277
ggtcagcact tctcaggtcc 20

<210> SEQ ID NO 278
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 278
ttaacatgac ctggttactc 20

<210> SEQ ID NO 279
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 279
cccaaaccaa gccaggaaat 20

<210> SEQ ID NO 280
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 280
cttggtcata tagtcaaaca 20

<210> SEQ ID NO 281
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 281
taatcacagg ctgcaagctc 20

<210> SEQ ID NO 282
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 282
aagcaatcca tggactgaag 20

<210> SEQ ID NO 283
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 283
gtcatgatgg aaagatagag 20

<210> SEQ ID NO 284
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 284
aaccttgcat cccagcagca 20

<210> SEQ ID NO 285
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 285
ggcagatagg aggagagtca 20

<210> SEQ ID NO 286
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 286
ggtgaatttc tttcattaaa 20

<210> SEQ ID NO 287
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 287
ttggaccaac ctcagagtgt 20

<210> SEQ ID NO 288
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 288
gtaatcaggc ctgcaccatg 20

<210> SEQ ID NO 289
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 289
catctaccat gaggagtaat 20

<210> SEQ ID NO 290
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 290
aatggctcta gattttatat 20

<210> SEQ ID NO 291
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 291
ttctgatcac actaaacaag 20

<210> SEQ ID NO 292
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 292
ctaggttgtg gcacccatga 20

<210> SEQ ID NO 293
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 293
gtacccaggt gcatctctag 20

<210> SEQ ID NO 294
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 294
tgtatgtggc agttgcaaga 20

<210> SEQ ID NO 295
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 295
acttttaaaa attgagtccc 20

<210> SEQ ID NO 296
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 296
ttaaataaag cttggaaatc 20

<210> SEQ ID NO 297
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 297
tgacagtacc accatggaaa 20

<210> SEQ ID NO 298
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 298
gtgcattgcc aaaagttcta 20

<210> SEQ ID NO 299
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 299
aagtcaccta catgtcaagg 20

<210> SEQ ID NO 300
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 300
acttggcagt ggctaagtca 20

<210> SEQ ID NO 301
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 301
gttaggattg gtcccttccc 20

<210> SEQ ID NO 302
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 302
gaccaattct gcagccccac 20

<210> SEQ ID NO 303
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 303
ccatgatcct agtgctcaat 20

<210> SEQ ID NO 304
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 304
ccacatacca atccctggag 20

<210> SEQ ID NO 305
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 305
ccagcatcag cagctcagtg 20

<210> SEQ ID NO 306
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 306
tttcccaacc atgatatcct 20

<210> SEQ ID NO 307
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 307
ccctgaacct tgatatcatc 20

<210> SEQ ID NO 308
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 308
tgcagatagg tctctgccac 20

<210> SEQ ID NO 309
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 309
tacagcagca aggcttggac 20

<210> SEQ ID NO 310
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 310
ggaaatggac agccaggtct 20

<210> SEQ ID NO 311
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 311
aggttctgcc tcacacagca 20

<210> SEQ ID NO 312
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 312
cccgcaggtt ctgcctcaca 20

<210> SEQ ID NO 313
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 313
agggaaccag cccgcccctg 20

<210> SEQ ID NO 314
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 314
tggccaggga accagcccgc 20

<210> SEQ ID NO 315
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 315
atggctggcc agggaaccag 20

<210> SEQ ID NO 316
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 316
tgccaatggc tggccaggga 20

<210> SEQ ID NO 317
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 317
gacagcccta gcctgcggac 20

<210> SEQ ID NO 318
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 318
gattgacagc cctagcctgc 20

<210> SEQ ID NO 319
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 319
gcatgattga cagccctagc 20

<210> SEQ ID NO 320
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 320
atcttggacc cgtcccggca 20

<210> SEQ ID NO 321
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 321
cgtccatctt ggacccgtcc 20

<210> SEQ ID NO 322
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 322
agcggccgtc catcttggac 20

<210> SEQ ID NO 323
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 323
aacctgagcg gccgtccatc 20

<210> SEQ ID NO 324
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 324
gcagaacctg agcggccgtc 20

<210> SEQ ID NO 325
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 325
aaaagcagaa cctgagcggc 20

<210> SEQ ID NO 326
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 326
ggtaaaagca gaacctgagc 20

<210> SEQ ID NO 327
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 327
ggccgcaggt aaaagcagaa 20

<210> SEQ ID NO 328
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 328
gctctgggcc gcaggtaaaa 20

<210> SEQ ID NO 329
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 329
agtccccgga ggcctcgggc 20

<210> SEQ ID NO 330
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 330
ggcacggcag tccccggagg 20

<210> SEQ ID NO 331
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 331
agggtcgcca tggcggtctc 20

<210> SEQ ID NO 332
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 332
ttttccaggg tcgccatggc 20

<210> SEQ ID NO 333
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 333
tcagcttttc cagggtcgcc 20

<210> SEQ ID NO 334
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 334
ttcatcagct tttccagggt 20

<210> SEQ ID NO 335
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 335
aaggccttca tcagcttttc 20

<210> SEQ ID NO 336
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 336
actcgaaggc cttcatcagc 20

<210> SEQ ID NO 337
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 337
gagggactcg aaggccttca 20

<210> SEQ ID NO 338
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 338
ggacttgagg gactcgaagg 20

<210> SEQ ID NO 339
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 339
ctgaggaagc tgaggaggcg 20

<210> SEQ ID NO 340

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 340
tgtgcctgcg gcggcggctg 20

<210> SEQ ID NO 341
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 341
ggcagcagcg gctgtgcctg 20

<210> SEQ ID NO 342
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 342
caaactcacg gtcggtgcag 20

<210> SEQ ID NO 343
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 343
gcgggcccaa actcacggtc 20

<210> SEQ ID NO 344
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 344
ggagctgcag cgggcccaaa 20

<210> SEQ ID NO 345
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 345
gccgtagcct gggacccgcc 20

<210> SEQ ID NO 346
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 346
gcagggttac cgccatcccc 20

<210> SEQ ID NO 347
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 347
aggctgcagg gttaccgcca 20

<210> SEQ ID NO 348
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 348
cccgcaggct gcagggttac 20

<210> SEQ ID NO 349
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 349
gccggcccgc aggctgcagg 20

<210> SEQ ID NO 350
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 350
aaggcctcgc cccaggaggg 20

<210> SEQ ID NO 351
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 351
agacccaagt gagggagcgg 20

<210> SEQ ID NO 352
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 352
aagggaagac ccaagtgagg 20

<210> SEQ ID NO 353
<211> LENGTH: 20
<212> TYPE: DNA

-continued

<213> ORGANISM: Artificial Sequence
<220> FEATURE:
<223> OTHER INFORMATION: Oligomeric Compound

<400> SEQUENCE: 353
ggacaaggga agacccaagt 20

<210> SEQ ID NO 354
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 354
tcgcgagagg acaagggaag 20

<210> SEQ ID NO 355
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 355
tcccctcgcg agaggacaag 20

<210> SEQ ID NO 356
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 356
ggccccaaca aggctctgcc 20

<210> SEQ ID NO 357
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 357
ggacaggccc caacaaggct 20

<210> SEQ ID NO 358
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 3
<223> OTHER INFORMATION: n = A or T

<400> SEQUENCE: 358
cgnctgcacc atgttcctca 20

<210> SEQ ID NO 359
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 5
<223> OTHER INFORMATION: n = C or G

<400> SEQUENCE: 359
cgccngcacc atgttcctca 20

<210> SEQ ID NO 360
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 12
<223> OTHER INFORMATION: n = C or G

<400> SEQUENCE: 360
cgcctgcacc angttcctca 20

<210> SEQ ID NO 361
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 17
<223> OTHER INFORMATION: n = A or T

<400> SEQUENCE: 361
cgcctgcacc atgttcntca 20

<210> SEQ ID NO 362
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 3
<223> OTHER INFORMATION: n = A or T

<400> SEQUENCE: 362
gcngtagcct gggacccgcc 20

<210> SEQ ID NO 363
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 9, 14
<223> OTHER INFORMATION: n = C or G

<400> SEQUENCE: 363
gccgtagcnt gggncccgcc 20

<210> SEQ ID NO 364
<211> LENGTH: 20
<212> TYPE: DNA
<213> ORGANISM: Artificial Sequence
<220> FEATURE:

<223> OTHER INFORMATION: Oligomeric Compound
<220> FEATURE:
<221> NAME/KEY: misc_feature
<222> LOCATION: 18
<223> OTHER INFORMATION: n = A or T

<400> SEQUENCE: 364
gccgtagcct gggacccncc 20

<210> SEQ ID NO 365
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 20
<223> OTHER INFORMATION: n = A or T

<400> SEQUENCE: 365
gccgtagcct gggacccgcn 20

<210> SEQ ID NO 366
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 3
<223> OTHER INFORMATION: n = C or G

<400> SEQUENCE: 366
tcnctattgc acattccaag 20

<210> SEQ ID NO 367
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 8
<223> OTHER INFORMATION: n = C or G

<400> SEQUENCE: 367
tctctatngc acattccaag 20

<210> SEQ ID NO 368
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 12
<223> OTHER INFORMATION: n = A or T

<400> SEQUENCE: 368
tctctattgc anattccaag 20

<210> SEQ ID NO 369
<211> LENGTH: 20
<212> TYPE: DNA
<213> ORGANISM: Artificial Sequence -continued

```
<220> FEATURE:
<223> OTHER INFORMATION: Oligomeric Compound
<220> FEATURE:
<221> NAME/KEY: misc_feature
<222> LOCATION: 17
<223> OTHER INFORMATION: n = A or T

<400> SEQUENCE: 369

tctctattgc acattcnaag                                    20
```

COMPOSITIONS AND THEIR USES DIRECTED TO HUNTINGTIN

CROSS-REFERENCE TO RELATED APPLICATIONS

This application is a continuation of U.S. patent application Ser. No. 12/618,470, filed Nov. 13, 2009, which is a continuation of U.S. patent application Ser. No. 11/627,921, filed Jan. 26, 2007, which claims priority to U.S. Provisional Application Ser. No. 60/836,290, filed Aug. 7, 2006, and U.S. Provisional Application Ser. No. 60/762,954, filed Jan. 26, 2006, each of which is incorporated herein by reference.

SEQUENCE LISTING

The present application is being filed along with a Sequence Listing in electronic format. The Sequence Listing is provided as a file entitled RTS0838US2C3SEQ.txt, created on Dec. 7, 2012 which is 576 Kb in size. The information in the electronic format of the sequence listing is incorporated herein by reference in its entirety.

BACKGROUND OF THE INVENTION

Huntington's disease (HD) is a neurodegenerative disorder caused by the mutation of the huntingtin gene. Alteration of this widely expressed single gene results in a progressive, neurodegenerative disorder with a large number of characteristic symptoms. Huntington's disease is an autosomal dominant disorder, with an onset generally in mid-life, although cases of onset from childhood to over 70 years of age have been documented. An earlier age of onset is associated with paternal inheritance, with 70% of juvenile cases being inherited through the father. Symptoms have an emotional, motor and cognitive component. Chorea is a characteristic feature of the motor disorder and is defined as excessive spontaneous movements which are irregularly timed, randomly distributed and abrupt. It can vary from being barely perceptible to severe. Other frequently observed abnormalities include dystonia, rigidity, bradykinesia, ocularmotor dysfunction and tremor. Voluntary movement disorders include fine motor incoordination, dysathria, and dysphagia. Emotional disorders commonly include depression and irritability, and cognitive component comprises subcortical dementia (Mangiarini et al., 1996. *Cell* 87:493-506). Changes in HD brains are widespread and include neuronal loss and gliosis, particularly in the cortex and striatum (Vonsattel and DiFiglia. 1998. *J. Neuropathol. Exp. Neurol.,* 57:369-384).

The HD mutation is a CAG expansion that results in the expansion of a poly-glutamine tract in the huntingtin protein, a 350 kDa protein of unknown function (Huntington Disease Collaborative Research Group, 1993. *Cell.* 72:971-83). The normal and expanded HD allele size have been found to be $CAG_{6-37}$ and $CAG_{35-121}$ repeats, respectively. Longer repeat sequences are associated with earlier disease onset. The mechanism by which the expansion results in pathology is unknown. However, the absence of an HD phenotype in individuals deleted for one copy of huntingtin, or increased severtity of disease in those homozygous for the expansion suggests that the mutation does not result in a loss of function (Trottier et al., 1995, *Nature Med.,* 10:104-110). Transcriptional deregulation and loss of function of transcriptional coactivator proteins have been implicated in HD pathogenesis. Mutant huntingtin has been shown specifically to disrupt activator-dependent transcription in the early stages of HD pathogenesis (Dunah et al., 2002. *Science* 296:2238-2243). Gene profiling of human blood has identified 322 mRNAs that show significantly altered expression in HD blood samples as compared to normal or presymptomatic individuals. Expression of marker genes was similarly substantially altered in post-mortem brain samples from HD caudate, suggesting that upregulation of genes in blood samples reflects disease mechanisms found in brain. Monitoring of gene expression may provide a sensitive and quantitative method to monitor disease progression, especially in the early stages of disease in both animal models and human patients (Borovecki et al., 2005, *Proc. Natl. Acad. Sci. USA* 102: 11023-11028).

Identification of the gene has allowed for the development of animal models of the disease, including transgenic mice carrying mutated human or mouse forms of the gene. Models include mice carrying a fragment of the human gene, typically the first one or two exons, which contains the glutamine expansion, in addition to the undisrupted wild-type, endogenous, mouse gene; mice carrying the full length human huntingtin with an expanded glutamine repeat region, again with the endogenous mouse gene; and mice with pathogenic CAG repeats inserted into the CAG repeat region. All of the models have at least some shared features with the human disease. These mice have allowed for the testing of a number of different therapeutic agents for the prevention, amelioration and treatment of HD (see, e.g., Hersch and Ferrante, 2004. *NeuroRx.* 1:298-306) using a number of endpoints. The compounds are believed to function by a number of different mechanisms including transcription inhibition, caspace inhibition, histone deacetylase inhibition, antioxidant, huntingtin inhibition/antioxidant, biogenergetic/antioxidant, antiexcitotoxic, and antiapoptotic.

A number of authors have reported that the repression of the mutant huntingtin transgene in animal models of HD reduces the symptoms associated with the disease, (see e.g. Diaz-Hernandez et al., (2005. *J. Neurosci.* 25:9773-81; incorporated herein by reference). Wang et al., (2005. *Nuerosci. Res.* 53:241-9; incorporated herein by reference) report that small interfering RNAs (siRNAs) directed against the huntingtin gene in the mouse model R6/2 inhibited transgenic huntingtin expression and significantly prolonged longevity, improved motor function and slowed loss of body weight.

Machida et al., (2006. *Biochem. Biophys. Res. Commun.* 343:190-7; incorporated herein by reference), report that recombinant adeno-associated virus (rAAV)-mediated delivery of RNA interference (RNAi) into the striatum of a HD mouse model ameliorated neuropathological abnormalities associated with HD, such as insoluable protein accumulation and down-regulation of DARPP-32 expression. Importantly, the authors state that neuronal aggregates in the striatum were reduced after RNAi transduction in the animals compared to those at the time point of RNAi transduction.

Harper et al., (2005. *PNAS* 102:5820-25; incorporated herein by reference), found that RNAi directed to huntingtin reduced huntingtin mRNA and protein expression in cell culture and a HD mouse model. The authors report that huntingtin gene silencing improved behavioral and neuropathological abnormalities associated with HD.

Rodrigues-Lebron et al., (2005. *Mol. Ther.* 12:618-33; incorporated herein by reference), report that a recombinant adeno-associated viral serotype 5 (rAAV5) gene transfer of RNAi to suppress the levels of striatal mutant huntingtin in the R6/1 HD transgenic mouse resulted in reduced levels of huntingitin mRNA and protein. The reduction in huntingtin was concomitant with a reduction in the size and number of neuronal intranuclear inclusions and other markers of HD, and resulted in delayed onset of the rear paw clasping phenotype exhibited by the R6/1 mice.

Nguyen et al., (2005. *PNAS,* 102:11840-45; incorporated herein by reference), used the metal-binding compound clioquinol to treat PC12 cells expressing the mutant huntingtin gene and found reduced accumulation of mutant protein. Treating the HD mouse model R6/2 with clioquinol resulted in improved behavioral and pathologic phenotypes, including decreased huntingtin aggregate accumulation, decreased striatal atrophy, improved rotarod performance, reduction of weight loss, normalization of blood glucose and insulin levels, and extension of lifespan, supporting the conclusion that reduction in mutant huntingtin protein is therapeutic for HD.

Based on these and other studies, one of skill in the art recognizes that reducing the expression of the mutant huntingtin gene will be therapeutic for HD.

SUMMARY OF THE INVENTION

One embodiment of the invention is an antisense oligonucleotide 12 to 35 nucleotides in length comprising at least 12 consecutive nucleotides of a nucleotide sequence selected from the group consisting of SEQ ID NOs 46-357. In a preferred embodiment, the nucleotide sequence is selected from the group consisting of SEQ ID NOs: 50, 93, 100, 105, 110, 125, 137, 345, 346, and 353. In a further embodiment, the antisense oligonucleotide has at least 95% or 100% complementarity to SEQ ID NO: 4. In a further embodiment, the antisense oligonucleotide has at least one modified internucleoside linkage, sugar moiety, or nucleobase. In a further embodiment, the antisense oligonucleotide comprises a chimeric oligonucleotide having a gap segment positioned between 5' and 3' wing segments, and in some embodiments, the gap segment of the chimeric oliognucleotide is comprised of 2'-deoxynucleotides and the wing segments are comprised of nucleotides having modified sugar moieties. Is still other embodiments, the modified sugar moiety is 2'-OMe or a bicyclic nucleic acid. In a preferred embodiment, the gap segment of the chimeric oligonucleotide consists of ten 2'-deoxynucleotides and each wing segment consists of five 2'-O-methoxyethyl-modified nucleotides, and in a more preferred embodiment said antisense oligonucleotide is 20 nucleotides in length.

In another embodiment each internucleoside linkage of the antisense oligonucleotide is a phosphorothioate internucleoside linkage.

In another embodiment each cytosine of the antisense oligonucleotide is a 5-methylcytosine.

In another embodiment, the antisense oligonucleotide is 17 to 25 nucleotides in length. In another embodiment, the antisense oligonucleotide is 19 to 23 nucleotides in length. In another embodiment the antisense oligonucleotide is 20 nucleotides in length.

Another embodiment of the invention is a pharmaceutical composition comprising any of the antisense oligonucleotide described herein and a pharmaceutically acceptable diluent.

Another embodiment is a method of treating an individual at risk of suffering from or currently suffering from Huntington's Disease (HD) comprising administering to the individual a therapeutically effective amount of a pharmaceutical composition comprising an antisense compound 12 to 35 nucleobases in length having at least 90% complementarity to nucleotides 1650-1704, 1807-1874, 3183-3228, 4010-4087, 4265-4288, 4553-4608, 5781-5820, and 6793-6796 of SEQ ID NO: 4, where the administration treats the individual. In a some embodiments, the administering comprises intrathecal delivery, intracerebroventricular delivery, or intraparenchymall delivery. In a some embodiments, the administering comprises administration into the cerebrospinal fluid of the individual by intrathecal infusion. In some embodiments, the treatment comprises improvement in one or more indicators of HD. In some embodiments, the treatment comprises increasing the survival time of the individual. In some embodiments, the treatment comprises delaying the onset of HD. In some embodiments, the antisense compound has at least at least 95%, or 100%, complementarity to nucleotides 1650-1704, 1807-1874, 3183-3228, 4010-4087, 4265-4288, 4553-4608, 5781-5820, and 6793-6796 of SEQ ID NO: 4.

In some embodiments, the antisense compound is an antisense oligonucleotide. In some embodiments, the antisense oligonucleotide has at least one modified internucleoside linkage, sugar moiety, or nucleobase. In some embodiments, the oligonucleotide comprises a chimeric oligonucleotide having a gap segment positioned between 5' and 3' wing segments. In some embodiments, the gap segment of the chimeric oliognucleotide is comprised of 2'-deoxynucleotides and the wing segments are comprised of nucleotides having modified sugar moieties. In some embodiments, the modified sugar moiety is 2'-OMe or a bicyclic nucleic acid. In some embodiments, the gap segment of the chimeric oligonucleotide consists of ten 2'-deoxynucleotides and each wing segment consists of five 2'-O-methoxyethyl-modified nucleotides. In some embodiments, each internucleoside linkage is a phosphorothioate internucleoside linkage. In some embodiments, each cytosine is a 5-methylcytosine. In some embodiments, the compound comprises 17 to 25 nucleotides, in others 19 to 23 nucleotides, in others, 20 nucleotides.

In some embodiments, the method further comprises selecting an individual suffering from HD. In some embodiments, the method further comprises selecting an individual susceptible to HD.

Another embodiment is a method of treating an individual at risk of suffering from or currently suffering from Huntington's Disease (HD) comprising administering to the individual a therapeutically effective amount of a pharmaceutical composition comprising an antisense oligonucleotide 12 to 35 nucleotides in length comprising at least 12 consecutive nucleotides of a nucleotide sequence selected from the group consisting of SEQ ID NOs 46-357. In some embodiments, the nucleotide sequence is selected from the group consisting of SEQ ID NOs: 50, 93, 100, 105, 110, 125, 137, 345, 346, and 353.

Another embodiment is the use of any of the antisense compounds or oligonucleotides disclosed herein in the manufacture of a medicament for treatment of HD. One embodiment is use of an antisense oligonucleotide 12 to 35 nucleotides in length comprising at least 12 consecutive nucleotides of a nucleotide sequence selected from the group consisting of SEQ ID NOs 46-357 in the preparation of a medicament for treating HD. Another embodiment is the use of an antisense oligonucleotide 12 to 35 nucleotides in length comprising at least 12 consecutive nucleotides of a nucleotide sequence selected from the group consisting of SEQ ID NOs: 50, 93, 100, 105, 110, 125, 137, 345, 346, and 353 in the preparation of a medicament for treating HD. In a further embodiment, the treatment of HD is the slowing of HD progression in an individual suffering from HD. In a further embodiment, the treatment of HD is preventing the onset of HD in an individual susceptible to HD. In a further embodiment, the treatment of HD comprises increasing survival time of the individual.

DETAILED DESCRIPTION OF THE INVENTION

Overview

Huntington's disease is a progressive, neurodegenerative disease caused by mutation of a widely expressed, single gene, huntingtin. The mutation is an expansion of a CAG repeat region, wherein a larger expansion results in greater severity of the disease and an earlier age of onset. The mutation results in a variety of motor, emotional and cognitive symptoms, and results in the formation of huntingtin aggregates in brain. The absence of a phenotype for a single gene deletion, and an increase in disease severity in individuals carrying two mutated copies of the huntingtin gene suggests that the mutation does not result in a loss of function.

Antisense technology provides a mechanism for the development of therapeutic agents for a variety of diseases, including Huntinton's Disease. The principle behind antisense technology is that an antisense compound, which hybridizes to a target nucleic acid, modulates gene expression activities such as transcription or translation. This sequence specificity makes antisense compounds extremely attractive as tools for target validation and gene functionalization, as well as therapeutics to selectively modulate the expression of genes involved in disease.

The present invention is directed to antisense compounds, especially nucleic acid and nucleic acid-like oligomers, which are targeted to a nucleic acid encoding huntingtin, and which modulate the expression of huntingtin. In a preferred embodiment, the antisense compound is targeted to human huntingtin (SEQ ID NOs 1-5 and 45). Pharmaceutical and other compositions comprising the compounds of the invention are also provided. Further provided are methods of slowing HD progression, and methods of ameliorating or delaying the onset of HD symptoms. Such methods employ antisense compounds which modulate the expression of huntingtin.

Therapeutics

Provided herein are methods for treating an individual suffering from Huntington's Disease (HD). Treatment encompasses slowing of disease progression in an individual suffering from Huntington's Disease (HD) as well as delaying the onset of HD in an individual susceptible to HD. In some embodiments, such treatment methods comprise the administration to the cerebrospinal fluid of the individual a therapeutically effective amount of a pharmaceutical composition comprising an antisense compound or oligonucleotide targeted to huntingtin. Such treatment methods further comprise increasing the survival time of an individual suffering from HD, or increasing the survival time of an individual susceptible to HD. Slowing of disease progression is indicated by a lack of measurable change in, or an improvement of, one or more indicators of HD, including molecular markers or symptoms of the disease. The delaying of the onset of HD is indicated by a lack of clinical presentation of indicators of HD.

The present invention employs antisense compounds, particularly antisense oligonucleotides, for use in modulating the function of nucleic acid molecules encoding huntingtin, ultimately modulating the amount of huntingtin protein produced. A suitable form of modulation is inhibition of nucleic acid molecules encoding huntingtin, which is evidenced by a reduction in the levels of nucleic acids encoding huntingtin. Accordingly, disclosed herein are antisense compounds, including antisense oligonucleotides, for use in inhibiting the expression of nucleic acid molecules encoding huntingtin, i.e. reducing the levels of nucleic acid molecules encoding huntingtin. As used herein, the terms "target nucleic acid" and "nucleic acid molecule encoding huntingtin" have been used for convenience to encompass DNA encoding huntingtin, RNA (including pre-mRNA and mRNA or portions thereof) transcribed from such DNA, and also cDNA derived from such RNA. Antisense oligonucleotides which hybridize to and modulate the expression of one or more nucleic acids encoding huntingtin are considered to be "targeted to huntingtin." Antisense oligonucleotides of the present invention do not necessarily distinguish between wild-type huntingtin target nucleic acids and mutant huntingtin target nucleic acids. It is clinically desirable to reduce the levels of mutant huntingtin target nucleic acids, without introducing adverse effects due to reduction of the levels of wild-type huntingtin target nucleic acids.

In one embodiment, antisense oligonucleotides at least 90% complementary to exon 30 of SEQ ID NO: 4, which encompasses nucleotides 4010-4087 of SEQ ID NO: 4. Thus, antisense oligonucleotides are at least 90% complementary to nucleotides 4010-4087 of SEQ ID NO: 4. This embodiment includes antisense oligonucleotides comprising a sequence selected from SEQ ID NOs: 99, 100, 101, or 102.

In another embodiment, antisense oligonucleotides are at least 90% complementary to nucleotides 4028-4146 of SEQ ID NO: 4. In one embodiment, the antisense oligonucleotides include those comprising a sequence selected from SEQ ID NOs: 99, 100, 101, 102, or 103.

In another embodiment, antisense oligonucleotides are at least 90% complementary to nucleotides 4538-4615 of SEQ ID NO: 4. This embodiment includes antisense oligonucleotides comprising a sequence selected from SEQ ID NOs: 109, 110, 111, or 112.

In another embodiment, antisense oligonucleotides are at least 90% complementary to exon 34 of SEQ ID NO: 4, which encompasses nucleotides 4553-4608 of SEQ ID NO: 4. Thus, in this embodiment, the antisense oligonucleotides are at least 90% complementary to nucleotides 4553-4608 of SEQ ID NO: 4. This embodiment includes antisense oligonucleotides comprising a sequence selected from SEQ ID NOs: 110 or 112.

In another embodiment, antisense oligonucleotides are at least 90% complementary to nucleotides 5781-5820 of SEQ ID NO: 4. In one embodiment, the antisense oligonucleotides comprise a sequence selected from SEQ ID NOs: 123, 124, or 125.

In another embodiment, antisense oligonucleotides are at least 90% complementary to exon 42 of SEQ ID NO: 4, which encompasses nucleotides 5722-5863 of SEQ ID NO: 4. Thus, in one embodiment, antisense oligonucleotides are at least 90% complementary to nucleotides 5722-5863 of SEQ ID NO: 4. In one embodiment, antisense oligonucleotides comprise a sequence selected from SEQ ID NOs: 123, 124, or 125.

In another embodiment, antisense oligonucleotides are at least 90% complementary to nucleotides 6763-6796 of SEQ ID NO: 4. In one embodiment, the antisense oligonucleotides comprise a sequence selected from SEQ ID NOs: 136, 137, or 138.

In another embodiment, antisense oligonucleotides are at least 90% complementary to a region comprising both exon 48 of SEQ ID NO: 4, which encompasses nucleotides 6560-6773 of SEQ ID NO: 4, and exon 49 of SEQ ID NO: 4, which encompasses nucleotides 6774-6919 of SEQ ID NO: 4. Accordingly, antisense oligonucleotides are at least 90% complementary to nucleotides 6560-6919 of SEQ ID NO: 4. In one embodiment, antisense oligonucleotides comprise a sequence selected from SEQ ID NOs: 134, 135, 136, 137, 138, or 151.

In another embodiment, antisense oligonucleotides are at least 90% complementary to nucleotides 3183-3253 of SEQ ID NO: 4. In one embodiment, antisense oligonucleotides comprise a sequence selected from SEQ ID NOs: 90, 91, 92, 93, and 94. In a further embodiment, antisense oligonucleotides are at least 90% complementary to nucleotides 3183-3228 of SEQ ID NO: 4. This aspect encompasses antisense oligonucleotides comprising a sequence selected from SEQ ID NOs: 90, 91, 92, or 93.

In another embodiment, antisense oligonucleotides are at least 90% complementary to a region comprising both exon 23 of SEQ ID NO: 4, which encompasses nucleotides 3019-3211 of SEQ ID NO:4, and exon 24 of SEQ ID NO: 4, which encompasses nucleotides 3212-3288 of SEQ ID NO: 4. Thus, in one embodiment, antisense oligonucleotides are at least 90% complementary to nucleotides 3091-3288 of SEQ ID NO: 4. This embodiment encompasses antisense oligonucleotides comprising a sequence selected from SEQ ID NOs: 90, 91, 92, 93, or 94.

In another embodiment, antisense oligonucleotides are at least 90% complementary to nucleotides 4265-4288 of SEQ ID NO: 4. This embodiment encompasses antisense oligonucleotides comprising a sequence selected from SEQ ID NOs: 104 or 105.

In another embodiment, antisense oligonucleotides are at least 90% complementary to exon 31 of SEQ ID NO: 4, which encompasses nucleotides 4088-4311 of SEQ ID NO: 4. Thus, in this embodiment, the antisense oligonucleotides are at least 90% complementary to nucleotides 4088-4311 of SEQ ID NO: 4. This embodiment encompasses the antisense oligonucleotides comprising a sequence selected from SEQ ID NOs: 103, 104, or 105.

In another embodiment, the antisense oligonucleotides are at least 90% complementary to nucleotides 1607-1704 of SEQ ID NO: 45. This embodiment encompasses antisense oligonucleotides comprising a sequence selected from SEQ ID NOs: 342, 343, 344, 345, 346, 347, 348, or 349. In one aspect, antisense oligonucleotides are at least 90% complementary to nucleotides 1650-1704 of SEQ ID NO: 45. This aspect encompasses antisense oligonucleotides comprising a sequence selected from SEQ ID NOs: 345, 346, 347, 348, or 349.

In another embodiment, antisense oligonucleotides are at least 90% complementary to nucleotides 1807-1874 of SEQ ID NO: 45. This embodiment encompasses antisense oligonucleotides comprising a sequence selected from SEQ ID NOs: 351, 352, 353, 354, 355, 356, or 357.

In another embodiment, antisense oligonucleotides are at least 90% complementary to nucleotides 985-1580 of SEQ ID NO: 45. This embodiment encompasses antisense oligonucleotides comprising a sequence selected from SEQ ID NOs: 329, 330, 331, 332, 333, 334, 335, 336, 337, 338, 339, 340, 341, 47, 48, 49, 50, 51, 52, 53, or 54.

In another embodiment, antisense oligonucleotides are at least 90% complementary to nucleotides 1079-1459 of SEQ ID NO: 45, which comprises a plurality of CAG repeats. This embodiment encompasses antisense oligonucleotides comprising a sequence selected from SEQ ID NOs: 48, 49, 50, 51, 52, or 53.

In another embodiment, antisense oligonucleotides are at least 90% complementary to nucleotides 1055-1477 of SEQ ID NO: 45. This region comprises a plurality of CAG repeats. This embodiment encompasses antisense oligonucleotides comprising a sequence selected from SEQ ID NOs: 338, 48, 49, 50, 51, 52, or 53.

In another embodiment, antisense oligonucleotides are at least 90% complementary to nucleotides 1019-1542 of SEQ ID NO: 45. This embodiment encompasses antisense oligonucleotides comprising a sequence selected from SEQ ID NOs: 331, 332, 333, 334, 335, 336, 337, 338, 339, 340, 341, 48, 49, 50, 51, 52, 53, or 54.

In further embodiments, antisense oligonucleotides are at least 95% complementary to a nucleotide region recited herein. In additional embodiments, antisense oligonucleotides are at least 96%, 97%, 98%, 99% or 100% complementary to a nucleotide region recited herein.

As used herein, an "individual suffering from Huntington's Disease (HD)" is an individual who has received from a health professional, such as a physician, a diagnosis of HD. Relevant diagnostic tests are well known in the art and are understood to include, without limitation, genetic testing to determine the presence of a mutation in the huntingtin gene, neurological examination, and brain imaging. Genetic testing for mutations in the huntingtin gene is a particularly accurate diagnostic test for the presence of HD.

An "individual susceptible to Huntington's Disease (HD)" is understood to include an individual who, based on genetic testing and/or family history, is likely to develop HD. Genetic testing for mutations in the huntingtin gene is a particularly accurate diagnostic test for susceptibility to HD. Indicators of HD may also be employed in the identification of an individual susceptible to HD.

In order for antisense inhibition of huntingtin to have a clinically desirable effect, it is beneficial to deliver an antisense oligonucleotide targeted to huntingtin to the central nervous system (CNS) of an individual, and in particular to the regions of the CNS affected by HD. As the blood-brain barrier is generally impermeable to antisense oligonucleotides administered systemically, a preferred method of providing antisense oligonucleotides targeted to huntingtin to the tissues of the CNS is via administration of the antisense oligonucleotides directly into the cerebrospinal fluid (CSF). Means of the delivery to the CSF and brain include intrathecal (IT), intracerebroventricular (ICV), and intraparenchymal administration. IT or ICV administration may be achieved through the use of surgically implanted pumps that infuse a therapeutic agent into the cerebrospinal fluid. Intraparenchymal delivery may be achieved by the surgical placement of a catheter into the brain. As used herein, "delivery to the CSF" and "administration to the CSF" encompass the IT infusion or ICV infusion of antisense oligonucleotides targeted to huntingtin through the use of an infusion pump. In some embodiments, IT infusion is a suitable means for delivery to the CSF. In other embodiments, the antisense oligonucleotide is continuously infused into the CSF for the entire course of treatment; such administration is referred to as "continuous infusion" or, in the case of IT infusion, "continuous IT infusion." Also contemplated is continuous intraparenchymal infusion using a pump.

In some embodiments, an infusion pump such as, for example, the Medtronic SyncroMed® II pump, is employed to deliver antisense oligonucleotides targeted to huntingtin to the CNS. The SyncroMed® II pump is surgically implanted according the procedures set forth by the manufacturer. The pump contains a reservoir for retaining a drug solution, which is pumped at a programmed dose into a catheter that is surgically implanted. For intrathecal administration of a drug, the catheter is surgically intrathecally implanted. In the context of the methods provided herein, the drug is the pharmaceutical composition comprising an antisense oligonucleotide targeted to huntingtin.

As used herein, a "pharmaceutical composition comprising an antisense oligonucleotide" refers to a composition comprising an antisense oligonucleotide targeted to huntingtin in a pharmaceutically acceptable diluent. By way of example, a suitable pharmaceutically acceptable diluent is phosphate-buffered saline. As provided herein, an ISIS Number represents the nonadecasodium salt of the antisense oligonucleotide having the provided nucleobase sequence, where nucleosides 1 to 5 and 16 to 20 have 2'-O-methoxyethyl sugar moieties, nucleosides 6 to 15 are 2'-deoxynucleotides, each internucleoside linkage is a phosphorothioate linkage, and each cytosine is a 5-methylcytosine.

As used herein, a "therapeutically effective amount" is an amount of a compound that provides a therapeutic benefit to an individual. For example, a therapeutically effective amount of an antisense compound targeted to huntingtin, such as an antisense oligonucleotide, is an amount that slows, or prevents the progression of HD, or prevents or delays the onset of HD. In one embodiment, a therapeutically effective amount of an antisense oligonucleotide that will result in an improvement to, or prevents or slows the worsening of, one or more indicators or symptoms of HD, such as those described herein. In some embodiments, a therapeutically effective amount of an antisense oligonucleotide targeted to huntingtin ranges from 8 mg to 12 mg of antisense oligonucleotide. In other embodiments, a therapeutically effect amount of an antisense oligonucleotide targeted to huntingtin is 10 mg. As used herein, "treating" a patient with HD includes administering a therapeutically effective amount of a compound of the invention.

As used herein, "slowing disease progression" means the prevention of, or delay in, a clinically undesirable change in one or more clinical parameters in an individual suffering from HD, such as those described herein. It is well within the abilities of a physician to identify a slowing of disease progression in an individual suffering from HD, using one or more of the disease assessment tests described herein. Additionally, it is understood that a physician may administer to the individual diagnostic tests other than those described herein to assess the rate of disease progression in an individual suffering from HD.

As used herein, "delaying the onset of HD" means delaying undesirable changes in one or more indicators of HD that were previously negative for HD. A physician may use family history of HD to determine an approximate age of HD onset in an individual susceptible to HD to determine if onset of HD is delayed.

As used herein, "indicators of HD," are parameters employed by a medical professional, such as a physician, to diagnose or measure the progression of HD, and include, without limitation, genetic testing, hearing, eye movements, strength, coordination, chorea (rapid, jerky, involuntary movements), sensation, reflexes, balance, movement, mental status, dementia, personality disorder, family history, weight loss, and degeneration of the caudate nucleus. Degeneration of the caudate nucleaus is assessed via brain imaging techniques such as magnetic resonance imaging (MRI) or computed tomography (CT) scan.

As used herein, an "improvement in an indicator of HD" refers to the absence of an undesirable change, or the presence of a desirable change, in one or more indicators of HD. In one embodiment, an improvement in an indicator of HD is evidenced by the absence of a measureable change in one or more indicators of HD. In another embodiment, an improvement in an indicator of HD is evidenced by a desirable change in one or more indicators of HD.

A slowing of disease progression may further comprise an increase in survival time in an individual suffering from HD. An "increase in survival time" is understood to mean increasing the survival of an individual suffering from HD, relative to an approximate survival time based upon HD progression and/or family history of HD. A physician can use one or more of the disease assessment tests described herein to predict an approximate survival time of an individual suffering from HD. A physician may additionally use the family history of an individual suffering from HD to predict survival time.

Antisense compounds targeted to huntingtin can be used to modulate the expression of huntingtin in an animal, such as a human, including humans suffering from, or susceptible to, HD. In one embodiment, the antisense compounds effectively inhibit the levels or function of huntingtin RNA. Because reduction in huntingtin mRNA levels can lead to alteration in huntingtin protein products of expression as well, such resultant alterations can also be measured. Antisense compounds of the present invention that effectively inhibit the level or function of huntingtin RNA or protein products of expression are considered an active antisense compound. In one embodiment, the antisense compounds of the invention inhibit the expression of huntingtin causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

The reduction of the expression of huntingtin can be measured in a bodily fluid, tissue or organ of the animal. Methods of obtaining samples for analysis, such as body fluids or tissues, and methods of preparation of the samples to allow for analysis are well known to those skilled in the art. Methods for analysis of RNA and protein levels are discussed above and are well known to those skilled in the art. The effects of treatment using the compounds of the invention can be assessed by measuring biomarkers associated with the target gene expression in the aforementioned fluids, tissues or organs, collected from an animal contacted with one or more compounds of the invention, by routine clinical methods known in the art. Biomarkers of huntingtin include but are not limited to the accumulation of huntingtin positive neuronal inclusions, loss of certain neuronal tissue, etc.

In addition, a subject's systemic response to treatment can be assessed by monitoring clinically relevant measures that include but are not limited to: liver transaminases, bilirubin, albumin, blood urea nitrogen, creatine and other markers of kidney and liver function; interleukins, tumor necrosis factors, intracellular adhesion molecules, C-reactive protein and other markers of inflammation.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of huntingtin expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

In one embodiment, provided are uses of a compound of an isolated double stranded RNA oligonucleotide in the manufacture of a medicament for inhibiting huntingtin expression or overexpression. Thus, provided herein is the use of an isolated double stranded RNA oligonucleotide targeted to huntingtin in the manufacture of a medicament for the treatment of a disease or disorder by means of the method described above.

Pharmaceutical Compositions

Antisense compounds targeted to huntingtin can be utilized in pharmaceutical compositions by adding an effective amount of a compound to a suitable pharmaceutically acceptable diluent or carrier. Acceptable carriers and dilutents are well known to those skilled in the art. Selection of a dilutent or carrier is based on a number of factors, including, but not limited to, the solubility of the compound and the route of administration. Such considerations are well understood by those skilled in the art. In one aspect, the antisense compounds of the present invention inhibit the expression of huntingtin.

Antisense compounds targeted to huntingtin can also be used in the manufacture of a medicament for the treatment of diseases and disorders related to huntingtin expression. In one embodiment, the disease or disorder is Huntinton's disease.

The antisense compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including but not limited to ophthalmic and to mucous membranes including vaginal and rectal delivery), pulmonary, e.g., by inhalation or insufflation of powders or aerosols, including by nebulizer (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Sites of administration are known to those skilled in the art. Oligonucleotides with at least one 2'-O-methoxyethyl modification are believed to be useful for oral administration.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property.

Oral compositions for administration of non-parenteral oligomeric compounds can be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. Such oral oligomeric compound compositions can be referred to as "mucosal penetration enhancers."

Oligomeric compounds, such as oligonucleotides, may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, which are herein incorporated by reference.

In one embodiment, oral oligomeric compound compositions comprise at least one member of the group consisting of surfactants, fatty acids, bile salts, chelating agents, and non-chelating surfactants. Such formulations are well known to those skilled in the art.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Oral oligomeric compositions may additionally contain other adjunct components conventionally found in pharmaceutical compositions, at their art-established usage levels.

One of skill in the art will recognize that formulations are routinely designed according to their intended route of administration.

Combinations

Compositions of the invention can contain two or more oligomeric compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially.

Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound. The compounds of the instant invention are non-catalytic.

An "antisense oligonucleotide" is an antisense compound that is a nucleic acid-based oligomer, but does not include siRNA duplexes. In a preferred embodiment, and in any of the embodiments disclosed herein, the "antisense oligonucleotide" can be a single-stranded nucleic acid molecule. An antisense oligonucleotide can be chemically modified.

Antisense compounds comprise from about 12 to about 35 linked nucleotides. This embodies antisense compounds of 12, 13, 14, 15, 16, 17, 18, 19, 20, 21, 22, 23, 24, 25, 26, 27, 28, 29, 30, 31, 32, 33, 34, or 35 nucleotides in length.

In one embodiment, the antisense compounds are 15 to 30 linked nucleotides in length, as exemplified above.

In one embodiment, the antisense compounds are 17 to 25 linked nucleotides in length, as exemplified herein.

In one embodiment, the antisense compounds are 19, 20, 21, 22, 23, or 24 linked nucleotides in length, or alternatively the oligomeric compounds range from 19 to 24 linked nucleotides in length.

In one embodiment, the antisense compounds are 21, 22, 23, or 24 linked nucleotides in length, or alternatively the oligomeric compounds range from 21 to 24 linked nucleotides in length.

In one embodiment, the antisense compounds are 20 linked nucleotides in length.

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary. The ends of the strands may be modified by the addition of one or more natural or modified nucleobases to form an overhang. In one nonlimiting example, the first strand of the siRNA is antisense to the target nucleic acid, while the second strand is complementary to the first strand. Once the antisense strand is designed to target a particular nucleic acid target, the sense strand of the siRNA can then be designed and synthesized as the complement of the antisense strand and either strand may contain modifications or additions to either terminus. For example, in one embodiment, both strands of the siRNA duplex would be complementary over the central nucleobases, each having overhangs at one or both termini. It is possible for one end of a duplex to be blunt and the other to have overhanging nucleobases. In one embodiment, the number of overhanging nucleobases is from 1 to 6 on the 3' end of each strand of the duplex. In another embodiment, the number of overhanging nucleobases is from 1 to 6 on the 3' end of only one strand of the duplex. In a further embodiment, the number of overhanging nucleobases is from 1 to 6 on one or both 5' ends of the duplexed strands. In another embodiment, the number of overhanging nucleobases is zero.

In one embodiment of the invention, double-stranded antisense compounds are canonical siRNAs. As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

Each strand of the siRNA duplex may be from about 12 to about 35 nucleobases. In a preferred embodiment, each strand of the siRNA duplex is about 17 to about 25 nucleobases. The central complementary portion may be from about 12 to about 35 nucleobases in length. In a preferred embodiment, the central complimentary portion is about 17 to about 25 nucleobases in length. It is understood that each the strand of the siRNA duplex and the central complementary portion may be about 12, 13, 14, 15, 16, 17, 18, 19, 20, 21, 22, 23, 24, 25, 26, 27, 28, 29, 30, 31, 32, 33, 34, or 35 nucleobases in length. The terminal portions can be from 1 to 6 nucleobases. It is understood that the terminal portions can be about 1, 2, 3, 4, 5, or 6 nucleobases in length. The siRNAs may also have no terminal portions. The two strands of an siRNA can be linked internally leaving free 3' or 5' termini, or can be linked to form a continuous hairpin structure or loop. The hairpin structure may contain an overhang on either the 5' or 3' terminus producing an extension of single-stranded character.

In another embodiment, the double-stranded antisense compounds are blunt-ended siRNAs. As used herein the term "blunt-ended siRNA" is defined as an siRNA having no terminal overhangs. That is, at least one end of the double-stranded compound is blunt. siRNAs, whether canonical or blunt, act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, the compounds can take the form of a self-complementary hairpin-type molecule that doubles back on itself to form a duplex. Thus, the compounds can be fully or partially double-stranded. When formed from two strands, or a single strand that takes the form of a self-complementary hairpin-type molecule doubled back on itself to form a duplex, the two strands (or duplex-forming regions of a single strand) are complementary when they base pair in Watson-Crick fashion.

The antisense compounds in accordance with this invention may comprise a complementary antisense compound from about 12 to about 35 nucleobases (i.e. from about 12 to about 35 linked nucleosides). In other words, a single-stranded antisense compound of the invention comprises from about 12 to about 35 nucleobases, and a double-stranded antisense compound of the invention (such as a siRNA, for example) comprises two strands, each of which is from about 12 to about 35 nucleobases. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that this comprehends antisense portions of 12, 13, 14, 15, 16, 17, 18, 19, 20, 21, 22, 23, 24, 25, 26, 27, 28, 29, 30, 31, 32, 33, 34, or 35 nucleobases.

In one embodiment, the antisense compounds of the invention have antisense portions of 12 to 35 nucleobases. It is understood that the antisense portion may be about 12, 13, 14, 15, 16, 17, 18, 19, 20, 21, 22, 23, 24, 25, 26, 27, 28, 29, 30, 31, 32, 33, 34, or 35 nucleobases in length.

Antisense compounds 12 to 35 nucleobases in length comprising a stretch of at least 8, preferably at least 12, more preferably at least 17 consecutive nucleobases selected from within the illustrative antisense compounds are considered to be suitable antisense compounds as well. Also contemplated are antisense compounds 12 to 35 nucleobases in length comprising a stretch of at least 8, 9, 10, 11, 12, 13, 14, 15, 16, 17, 18, or 19 nucl nucleobases selected from within the illustrative antisense compounds are considered to be suitable antisense compounds as well.

Antisense compounds of the invention include antisense compound sequences that comprise at least the 8 (or 9-19) consecutive nucleobases from the 5'-terminus of one of the illustrative antisense compounds (the remaining nucleobases being a consecutive stretch of the same antisense beginning immediately upstream of the 5'-terminus of the antisense compound which is specifically hybridizable to the target nucleic acid and continuing until the antisense contains about 12 to 35 nucleobases). Other antisense compounds are represented by antisense compound sequences that comprise at least the 8 (or 9-19) consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the antisense compound contains about 12 to about 35 nucleobases). It is also understood that antisense compounds may be represented by antisense compound sequences that comprise at least 8 (or 9-19) consecutive nucleobases from an internal portion of the sequence of an illustrative compound, and may extend in either or both directions until the antisense contains about 12 to about 35 nucleobases.

One having skill in the art armed with the antisense compounds illustrated herein will be able, without undue experimentation, to identify further antisense compounds.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages

Oligomeric compounds may comprise modified internucleoside linkages, e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds, including antisense compounds and antisense oligonucleotides, can have one or more modified internucleoside linkages. Modified oligonucleotide backbones containing a phosphorus atom therein include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al., *Nucleic Acids Research,* 2003, 31(14), 4109-4118 and Dellinger et al., *J. Am. Chem. Soc.,* 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.,* 1994, 116, 3143-3144). N3'-P5'-phosphoramidates have been studied with some success in vivo to specifically down regulate the expression of the c-myc gene (Skorski et al., *Proc. Natl. Acad. Sci.,* 1997, 94, 3966-3971; and Faira et al., *Nat. Biotechnol.,* 2001, 19, 40-44).

In some embodiments, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene(methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(═O)(OH)—O—$CH_2$—).

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Modified Sugars

Oligomeric compounds may also contain one or more substituted sugar moieties. Suitable compounds can comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy(2'-O—$CH_2CH_2OCH_3$, also known as 2'-O-(2-methoxyethyl) or 2'-MOE) (Martin et al., *Helv. Chim. Acta,* 1995, 78, 486-504), i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$(CH_2)_2$—O—$(CH_2)_2$—$N(CH_3)_2$, also described in examples hereinbelow.

Other modifications include 2'-methoxy(2'-O—$CH_3$), 2'-aminopropoxy(2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro(2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

A further modification includes bicyclic sugar moieties referred to as "bicyclic nucleic acids" or "BNAs" in which the 2'-hydroxyl group of the ribosyl sugar ring is linked to the 4' carbon atom of the sugar ring to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr. Opinion Mol. Ther.,* 2001, 3, 239-243; see also U.S. Pat. Nos. 6,268,490 and 6,670,461). The linkage can be a methylene (—$CH_2$—) group bridging the 2' oxygen atom and the 4' carbon atom, or can be an ethylene group. The alpha-L isomer of the bicyclic nucleic acid moiety wherein the linkage is a methylene group is an additional modified sugar moiety. Another bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

Oligonucleotide Mimetics

Another group of oligomeric compounds includes oligonucleotide mimetics. The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. Oligonucleotide mimetics include peptide nucleic acid (PNA) compounds (Nielsen et al., *Science,* 1991, 254, 1497-1500), morpholino-based compounds (see, for example, U.S. Pat. No. 5,034,506), cyclohexene nucleic acids (CeNA). In CeNA oligonucleotides (Wang et al., *J. Am. Chem. Soc.,* 2000, 122, 8595-8602), and phosphonomonoester nucleic acids.

Modified and Alternate Nucleobases

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido (5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Certain nucleobase modifications increase the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Conjugates

Oligomeric compounds may be chemically linked to one or more moieties or conjugates which enhance the oligomeric compound properties such as activity, cellular distribution or cellular uptake. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Additional conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides. These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at the 5' end of native mRNA molecules.

In non-limiting examples, the 5'-cap includes inverted abasic residue (moiety), 4',5'-methylene nucleotide; 1-(beta-D-erythrofuranosyl)nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

1. Chimeric Compounds

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotide Synthesis

Oligomeric compounds and phosphoramidites are made by methods well known to those skilled in the art. Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. Alternatively, oligomers may be purchased from various oligonucleotide synthesis companies such as, for example, Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed (including solution phase synthesis).

Methods of isolation and analysis of oligonucleotides are well known in the art. A 96-well plate format is particularly useful for the synthesis, isolation and analysis of oligonucleotides for small scale applications.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Complementarity

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

As used herein, an antisense oligonucleotide is "fully complementary" to a target nucleic acid when each nucleobase of the antisense oligonucleotide is capable of undergoing precise base pairing with an equal number of nucleobases in the target nucleic acid. It is understood in the art that the sequence of the antisense oligonucleotide need not be fully complementary to that of its target nucleic acid to be active in inhibiting the activity of the target nucleic acid. In some embodiments there are "non-complementary" positions, also known as "mismatches", between the antisense oligonucleotide and the target nucleic acid, and such non-complementary positions may be tolerated between an antisense oligonucleotide and the target nucleic acid provided that the antisense oligonucleotide remains specifically hybridizable to the target nucleic acid. For example, as demonstrated herein, 387916, having one non-complementary nucleobases with respect to mouse huntingtin, is capable of reducing mouse huntingtin mRNA levels in vitro and in vivo. A "non-complementary nucleobase" means a nucleobase of an antisense oligonucleotide that is unable to undergo precise base pairing with a nucleobase at a corresponding position in a target nucleic acid. As used herein, the terms "non-complementary" and "mismatch" are interchangable. In some embodiments antisense oligonucleotides having no more than three non-complementary nucleobases with respect to a nucleic acid encoding huntingtin are considered "complementary" to a nucleic acid encoding huntingtin. In other embodiments, antisense oligonucleotides contain no more than two non-complementary nucleobases with respect to a nucleic acid encoding huntingtin. In further embodiments, antisense oligonucleotides contain no more than one non-complementary nucleobase with respect to a nucleic acid encoding huntingtin.

The location of a non-complementary nucleobase may be at the 5' end or 3' end of the antisense oligonucleotide. Alternatively, the non-complementary nucleobase may be at an internal position in the antisense oligonucleotide. When two or more non-complementary nucleobases are present, they may be contiguous (i.e. linked) or non-contiguous.

In other embodiments of the invention, the antisense oligonucleotides comprise at least 90% sequence complementarity to a huntingtin target nucleic acid. In further embodiments of the invention, the antisense oligonucleotides comprise at least 95% sequence complementarity to a huntingtin target nucleic acid. In further embodiments of the invention, the antisense oligonucleotides comprise at least 96%, 97%, 98% or 99% sequence complementarity to a huntingtin target nucleic acid.

Examples of oligonucleotides having mismatches or less than 100% sequence complementarity are shown in Table 1 below where the mismatch is designated by the letter X in the sequence.

TABLE 1

| Isis No. | SEQ ID NO: | Sequence (5' to 3') | X is |
|---|---|---|---|
| 387902 | 105 | CGCCTGCACCATGTTCCTCA | |
| | 358 | CGXCTGCACCATGTTCCTCA | A or T |
| | 359 | CGCCXGCACCATGTTCCTCA | C or G |
| | 360 | CGCCTGCACCAXGTTCCTCA | C or G |
| | 361 | CGCCTGCACCATGTTCXTCA | A or T |
| 388816 | 345 | GCCGTAGCCTGGGACCCGCC | |
| | 362 | GCXGTAGCCTGGGACCCGCC | A or T |
| | 363 | GCCGTAGCXTGGGXCCCGCC | C or G |
| | 364 | GCCGTAGCCTGGGACCCXCC | A or T |
| | 365 | GCCGTAGCCTGGGACCCGCX | A or T |
| 387916 | 125 | TCTCTATTGCACATTCCAAG | |
| | 366 | TCXCTATTGCACATTCCAAG | C or G |
| | 367 | TCTCTATXGCACATTCCAAG | C or G |
| | 368 | TCTCTATTGCAXATTCCAAG | A or T |
| | 369 | TCTCTATTGCACATTCXAAG | A or T |

Identity

Oligomeric compounds, or a portion thereof, may have a defined percent identity to a SEQ ID NO, or a compound having a specific Isis number. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO.). It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (i.e., one base replaced with another) versions of the oligonucleotides taught herein fall within the scope of the invention. Percent identity is calculated according to the number of bases that are identical to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. In the context of the invention, the full length of the modified sequence may constitute a single portion.

It is well known by those skilled in the art that it is possible to increase or decrease the length of an antisense oligonucleotide and/or introduce mismatch bases without eliminating activity. For example, in Woolf et al. (Proc. Natl. Acad. Sci. USA 89:7305-7309. 1992, incorporated herein by reference), a series of oligomers 13-25 nucleobases in length were tested for their ability to induce cleavage of a target RNA in an oocyte injection model. Oligonucleotides 25 nucleobases in length with 8 or 11 mismatch bases near the ends of the oligonucleotide were able to direct specific cleavage of the target mRNA, albeit to a lesser extent than the oligonucleotide that contained no mismatches. Similarly, target specific cleavage was achieved using a 13 nucleobase oligomer, including those with 1 or 3 mismatches. Maher and Dolnick (Nuc. Acid. Res. 16:3341-3358. 1988, incorporated herein by reference) tested a series of tandem 14 nucleobase oligonucleotides, and a 28 and 42 nucleobase oligonucleotide comprised of the sequence of two or three of the tandem oligonucleotides, respectively, for their ability to arrest translation of human DHFR in a rabbit reticulocyte assay. Each of the three 14 nucleobase oligonucleotides alone were able to inhibit translation, albeit at a more modest level, than the 28 or 42 nucleobase oligonucleotide. Interestingly, a mixture of the tandem 14 nucleobase oligonucleotides was as effective at inhibiting translation as the 28 nucleobase oligonucleotide targeted to the same region.

Target Nucleic Acids

"Targeting" an oligomeric compound to a particular target nucleic acid molecule can be a multistep process. The process usually begins with the identification of a target nucleic acid whose expression is to be modulated. As used herein, the terms "target nucleic acid" and "nucleic acid encoding huntingtin" encompass DNA encoding huntingtin, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes huntingtin.

2. Target Regions, Segments, and Sites

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Target regions include, but are not limited to, contiguous nucleotide sequences, translation initiation and termination regions, coding regions, open reading frames, introns, exons, 3'-untranslated regions (3'-UTR), and 5'-untranslated regions (5'-UTR). Within regions of target nucleic acids are target segments. As used herein, a "target segment" means a sequence of a huntingtin target nucleic acid to which one or more antisense oligonucleotides are complementary. The term "5' target site" is defined as the 5'-most nucleobase of a target segment to which an antisense oligonucleotide is complementary. Likewise, a "3' target site" is defined as the 3'-most nucleobase of a target segment to which an antisense oligonucleotide is complementary.

3. Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Oligonucleotides to such variants are within the scope of the instant invention.

4. Target Names and Synonyms

In accordance with the present invention are compositions and methods for modulating the expression of genes which are presented in Table 2. Listed in Table 2 are the gene target names, as well as GENBANK® accession numbers used to design oligomeric compounds targeted to each gene.

TABLE 2

Gene Target Names and Sequences

| Species | Genbank # | SEQ ID NO |
|---|---|---|
| Human | AB209506.1 | 1 |
| Human | BE378835.1 | 2 |
| Human | L12392.1 | 3 |
| Human | NM_002111.5 | 4 |
| Human | nucleotides 462000 to 634000 of NT_006081.17 | 5 |
| Mouse | AK042204.1 | 6 |
| Mouse | AK049546.1 | 7 |
| Mouse | L23312.1 | 8 |
| Mouse | L23313.1 | 9 |
| Mouse | NM_010414.1 | 10 |
| Mouse | nucleotides 2036000 to 2190000 of NT_039302.4 | 11 |

TABLE 2-continued

Gene Target Names and Sequences

| Species | Genbank # | SEQ ID NO |
|---|---|---|
| Mouse | NM_010414.1 (mouse short form)* | 44 |
| Human | cut from genomic ad Sac1 and EcoR1 sites surrounding exon 1, expanded CAG to results in 130 gln in this region | 45 |

*NM_010414.1 (mouse short form) extended with mouse genomic sequence to create transcript orthologous to human long form (NM_002111.5). Much of this extension is supported by mouse ESTs but the most 3' end is supported only by homology to the human mRNA Modulation of Target Expression Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of HUNTINGTINα. Thus, in one embodiment modulation of expression can mean increase or decrease in target RNA or protein levels. In another embodiment modulation of expression can mean an increase or decrease of one or more RNA splice products, or a change in the ratio of two or more splice products.

Cultured Cells

The effect of oligomeric compounds of the present invention on target nucleic acid expression can be tested in any of a variety of cell types provided that the target nucleic acid is present at measurable levels. The effect of oligomeric compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and are well known to those skilled in the art. Primary cells, or those cells which are isolated from an animal and not subjected to continuous culture, can be prepared according to methods known in the art or obtained from various commercial suppliers. Additionally, primary cells include those obtained from donor human subjects in a clinical setting (i.e. blood donors, surgical patients).

Cells isolated from Huntington's disease patients are also used to test the effects of antisense compounds targeted to huntingtin. In such cells, the mutant huntingtin gene may be present in a heterozygous or homozygous form. Such cells are available from National Institute of General Medical Sciences (NIGMS) Human Genetic Cell Repository, examples of which include fibroblasts having repository number GMO4281 or GMO4478. Cells from Huntington's disease patients are cultured according to procedures recommended by the supplier.

The pharmacological effects of antisense inhibition of huntingtin can be assessed in cell lines isolated from neuronal cells expressing either wild-type or mutant forms of the huntingtin gene. The mutant forms of huntingtin are associated with particular phenotypes, and the effects on these phenotypes are evaluated following antisense inhibition of huntintin. An example of such cells are striatal cells established from $Hdh^{Q111}$ knock-in mice, which bear 111 CAG repeats inserted into the mouse huntingtin locus. Establishment of striatal cell lines isolated from $Hdh^{Q111}$ mice has been described by Trettel et al. (Human Mol. Genet., 2000, 9, 2799-2809). Striatal cell lines established from mice bearing a wild-type huntingtin gene are used for comparison studies.

Assaying Modulation of Expression

Modulation of huntingtin expression can be assayed in a variety of ways known in the art. Huntingtin mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by huntingtin can be quantitated in a variety of ways well known in the art, such as immunoprecipitation, Western blot analysis (immunoblotting), ELISA or fluorescence-activated cell sorting (FACS). Antibodies directed to a protein encoded by huntingtin can be identified and obtained from a variety of sources, such as the MSRS catalog of antibodies (Aerie Corporation, Birmingham, Mich.).

Validated Target Segments

The locations on the target nucleic acid to which active oligomeric compounds hybridize are hereinbelow referred to as "validated target segments." In one embodiment, a validated target segment includes at least an 8-nucleobase portion of a target region. I n another embodiment, a validated target segment includes at least a 12-nucleobase portion of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8, or at least the 12, consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 12 to about 35 nucleobases). Similarly validated target segments are represented by DNA or RNA sequences that comprise at least the 8, or at least the 12 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 12 to about 35 nucleobases). It is also understood that a validated oligomeric target segment can be represented by DNA or RNA sequences that comprise at least 8, or at least the 12, consecutive nucleobases from an internal portion of the sequence of a validated target segment, and can extend in either or both directions until the oligonucleotide contains about 12 to about 35 nucleobases.

Screening for Modulator Compounds

In another embodiment, the validated target segments identified herein can be employed in a screen for additional compounds that modulate the expression of huntingtin. "Modulators" are those compounds that modulate the expression of huntingtin and which comprise at least an 8-nucleobase portion which is complementary to a validated target segment. The screening method comprises the steps of contacting a validated target segment of a nucleic acid molecule encoding huntingtin with one or more candidate modulators, and selecting for one or more candidate modulators which perturb the expression of a nucleic acid molecule encoding huntingtin. Once it is shown that the candidate modulator or modulators are capable of modulating the expression of a nucleic acid molecule encoding huntingtin, the modulator can then be employed in further investigative studies of the function of huntingtin, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

In Vivo Testing of Antisense Compounds Targeted to Huntingtin

Antisense compounds targeted to huntingtin are tested in experimental animal models. In one embodiment, the antisense compounds are targeted to the human hungtingtin gene alone. Such antisense compounds have, for example, less than four mismatches to human huntingtin and four or more mismatches to non-human huntingtin. In another embodiment, antisense compounds are targeted to both human and non-human huntingtin. Such antisense compounds have, for example, less than four mismatches to human huntingtin and less than four mismatches to non-human huntingtin.

Normal Animals

Normal, wild-type animals may be used to perform toxicity studies of antisense oligonucleotides targeted to huntingtin. The antisense compounds are administered systemically (e.g. via intraperitoneal injection) at doses of 25, 50, 75, or 100 mg/kg. Animals are monitored for any clinical changes, including changes in body weight. Serum is collected periodically, for example every week or every two weeks, during the dosing period and subjected to analysis using a clinical analyzer to detect any changes in serum chemistry profiles. At the end of the study, the animals are sacrificed. Blood is collected and analyzed for white blood cell count, platelet count, and serum chemistry. The weights of major organs are determined, and histological analyses are performed on spleen, liver, kidney and pancreas.

Huntington's Disease Models

Antisense compounds targeted to huntingtin may be tested in experimental non-human models of Huntington's disease. Several non-human models have been developed and characterized.

The R6/2 transgenic mouse model has integrated into its genome 1 kilobase of the human huntingtin gene, including the 5'-UTR exon 1 and the first 262 basepairs of intron 1 (Mangiarin L. et al., *Cell,* 1996, 87, 493-506). This transgene has 144 CAG repeats. The transgene encodes for approximately 3% of the N-terminal region of the huntingtin protein, expression of which is driven by the human huntingtin promoter. Expression levels of this truncated version of human huntingtin protein are approximately 75% of the endogenous mouse huntingtin protein levels. The R6/2 transgenic mice exhibit symptoms of human Huntington's disease and brain dysfunction.

The YAC128 transgenic mice harbor a yeast artificial chromosome (YAC) carrying the entire huntingtin gene, including the promoter region and 128 CAG repeats (Hodgson J. G. et al., *Human Mol. Genet.,* 1998, 5, 1875). This YAC expresses all but exon 1 of the human gene. These transgenic mice do not express endogenouse mouse huntingtin.

The endogenous mouse huntingtin gene of the Q111 mice has 111 CAG repeats inserted into exon 1 of the gene (Wheeler V. C. et al., *Human Mol. Genet.,* 8, 115-122).

In the Q150 transgenic mice, the CAG repeat in exon 1 of the wild-type mouse huntingtin gene is replaced with 150 CAG repeats (Li C. H. et al., *Human Mol. Genet.,* 2001, 10, 137).

Antisense compounds targeted to huntingtin are administered to the non-human experimental model, for example to transgenic mice that are used as models of Huntington's disease.

Antisense compounds may be administered directly into the central nervous system of the experimental animal, for example through intracerebroventricular (ICV), intrathecal (IT) or intraparenchymal administration. Dosages of antisense compounds administered may be 25, 50, 75, or 100 ug/day, and administration may be accomplished through continuous infusion using a surgically implanted osmotic pump (e.g. an Alzet mini-pump). 0.25, 0.5, or 1 uL/hour. Each dosage is administered to groups of 4 to 6 animals. Control groups of animals may receive saline infusion, or infusion of an antisense compound having a sequence not targeted to any known gene.

Animals are treated for several weeks, for example 1, 2, 4, or 8 weeks. Animals are monitored for any clinical changes, including changes in body weight. At the end of the treatment period, animals are sacrificed. The brains are dissected into three regions: forebrain, basal ganglion, and cerebellum. Brain regions undergo histological assessment, including hemotoxylin/eosin staining, GFAP staining (to assess glial cell activation) and FluoroJ staining (to assess neurodegenerative changes). Huntingtin mRNA levels are measured by real-time PCR, and huntingtin protein levels are measured by immunoblotting (western blotting).

The duration of action of antisense compounds targeting huntingtin may also be evaluated. For such analyses, animals are dosed for 2, 4, 6, or 8 weeks with antisense compounds targeting huntingtin. At the end of the dosing period, the osmotic pumps are removed and animals are sacrificed 0, 1, 2, 4, 6, or 8 weeks following dosing termination. The brains are dissected into three regions: forebrain, basal ganglion, and cerebellum. Brain regions undergo histological assessment, including hemotoxylin/eosin staining, GFAP staining (to assess glial cell activation) and FluoroJ staining (to assess neurodegenerative changes). Huntingtin mRNA levels are measured by real-time PCR, and huntingtin protein levels are measured by immunoblotting (western blotting).

Kits, Research Reagents, and Diagnostics

The oligomeric compounds of the present invention can be utilized for diagnostics, research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns. By way of example, gene expression patterns may be identified by microarray analysis.

Nonlimiting Disclosure and Incorporation by Reference

While certain compounds, compositions and methods of the present invention have been described with specificity in accordance with certain embodiments, the following examples serve only to illustrate the compounds of the invention and are not intended to limit the same. Each of the references, GENBANK® accession numbers, and the like recited in the present application is incorporated herein by reference in its entirety.

EXAMPLE 1

Antisense Inhibition of Huntingtin in Culture Cells

The effect of oligomeric compounds on target nucleic acid expression was tested in cultured cells, for example A549 cells or HD patient fibroblasts for compounds targeted to human huntingtin, and in b.END cells for compounds targeted to mouse huntingtin.

When cells reached 65-75% confluency, the transfection reagent LIPOFECTIN® was used to introduce oligonucleotide into cells. Other methods of transfection are well known to those skilled in the art. The method of screening is not a limitation of the instant invention.

Oligonucleotide was mixed with LIPOFECTIN® Invitrogen Life Technologies, Carlsbad, Calif.) in OPTI-MEM®-1 reduced serum medium (Invitrogen Life Technologies, Carlsbad, Calif.) to achieve the desired concentration of oligonucleotide and a LIPOFECTIN® concentration of 2.5 or 3 μg/mL per 100 nM oligonucleotide. This transfection mixture was incubated at room temperature for approximately 0.5 hours. For cells grown in 96-well plates, wells were washed once with 100 μL OPTI-MEM®-1 and then treated with 130 μL of the transfection mixture. Cells are treated and data were obtained in duplicate or triplicate. After approximately 4-7 hours of treatment at 37° C., the medium containing the transfection mixture was replaced with fresh culture medium. Cells were harvested 16-24 hours after oligonucleotide treatment.

For culture chambers other than 96-well plates, the cells may be treated similarly, using appropriate volumes of medium and oligonucleotide.

EXAMPLE 2

Real-time Quantitative PCR Analysis of Huntingtin mRNA Levels

Quantitation of huntingtin mRNA levels was accomplished by real-time quantitative PCR using the ABI PRISM® 7600, 7700, or 7900 Sequence Detection System (PE-Applied Biosystems, Foster City, Calif.) according to manufacturer's instructions.

After isolation from cells or tissues, RNA was subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RIBOGREEN® (Molecular Probes, Inc. Eugene, Oreg.). GAPDH expression was quantified by RT, real-time PCR, by being run simultaneously with the target, multiplexing, or separately. Total RNA was quantified using RIBOGREEN® RNA quantification reagent (Molecular Probes, Inc. Eugene, Oreg.) according to the manufacturer's instructions.

Probes and primers for use in real-time PCR were designed to hybridize to target-specific sequences. The primers and probes and the target nucleic acid sequences to which they hybridize are presented in Table 3. The target-specific PCR probes have FAM covalently linked to the 5' end and TAMRA or MGB covalently linked to the 3' end, where FAM is the fluorescent dye and TAMRA or MGB is the quencher dye.

TABLE 3

Gene target-specific primers and probes for use in real-time PCR

| Species | Target SEQ ID NO | Sequence Description | Sequence (5' to 3') | SEQ ID NO |
|---|---|---|---|---|
| Human | 4 | Forward Primer | CTCCGTCCGGTAGACATGCT | 38 |
| Human | 4 | Reverse Primer | GGAAATCAGAACCCTCAAAATGG | 39 |
| Human | 4 | Probe | TGAGCACTGTTCAACTGTGGATATCGGGA | 40 |
| Mouse | 10 | Forward Primer | CAGAGCTGGTCAACCGTATCC | 41 |
| Mouse | 10 | Reverse Primer | GGCTTAAACAGGGAGCCAAAA | 42 |
| Mouse | 10 | Probe | ACTTCATGATGAGCTCGGAGTTCAAC | 43 |

EXAMPLE 3

Antisense Inhibition of the Huntingtin Gene

Human Huntingtin

Antisense oligonucleotides were designed to target different regions of the human huntingtin gene, using published sequences cited in Table 2. The sequences and corresponding SEQ ID NOs are shown in Table 4. All compounds in Table 4 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl)nucleotides, also known as 2'-MOE nucleotides. The internucleoside (backbone) linkages are phosphorothioate throughout the oligonucleotide. All cytidine residues are 5-methylcytidines.

The antisense oligonucleotides were analyzed for their effect on huntingtin mRNA levels in A549 cells by quantitative real-time PCR as described in other examples herein. The data presented in Table 4 represent percent inhibition of huntingtin mRNA levels relative to untreated cells. Data are averages from experiments in which cultured cells were treated with the disclosed antisense oligonucleotides, If the huntingtin mRNA level in antisense oligonucleotide-treated cells was equal to or higher than in control cells, percent inhibition is expressed as zero inhibition. If present, "N.D." indicates "not determined." The target regions to which these antisense oligonucleotides are inhibitory are herein referred to as "validated target segments."

TABLE 4

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388224 | 4 | 33 | CAGGTAAAAGCAGAACCTGA | 0 | 46 |
| 387865 | 4 | 155 | GCCTTCATCAGCTTTTCCAG | 65 | 47 |
| 388829 | 4 | 193 | GCTGCTGCTGCTGCTGGAAG | 46 | 48 |
| 388830 | 4 | 194 | TGCTGCTGCTGCTGCTGCTG | 46 | 49 |
| 388833 | 4 | 195 | CTGCTGCTGTTGCTGCTGCT | 62 | 50 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388831 | 4 | 195 | CTGCTGCTGCTGCTGCTGCT | 56 | 51 |
| 388832 | 4 | 196 | GCTGCTGCTGCTGCTGCTGC | 36 | 52 |
| 388834 | 4 | 198 | TGGCGGCTGCTGCTGCTGCT | 62 | 53 |
| 388835 | 4 | 259 | GCGGCGGCGGCGGTGGCGGC | 52 | 54 |
| 387866 | 4 | 432 | ATGATTCACACGGTCTTTCT | 76 | 55 |
| 387867 | 4 | 489 | AAATTCTGGAGAATTTCTGA | 31 | 56 |
| 387868 | 4 | 497 | AGTTTCTGAAATTCTGGAGA | 58 | 57 |
| 387869 | 4 | 608 | GAATCCATCAAAGCTTTGAT | 53 | 58 |
| 387870 | 4 | 621 | CCTTGGAAGATTAGAATCCA | 45 | 59 |
| 387871 | 4 | 709 | GAGCCAGCTCAGCAAACCTC | 65 | 60 |
| 387872 | 4 | 718 | GAACCAGGTGAGCCAGCTCA | 37 | 61 |
| 387873 | 4 | 749 | TTCACCAGGTAAGGCCTGCA | 33 | 62 |
| 387874 | 4 | 821 | ACAGCTGCAGCCAAGGTCTC | 60 | 63 |
| 387875 | 4 | 845 | CCAAAAGAAGCCATAATTTT | 63 | 64 |
| 387876 | 4 | 876 | AACCTTAATTTCATTGTCAT | 75 | 65 |
| 388225 | 4 | 1000 | GTAGCCAACTATAGAAATAT | 53 | 66 |
| 388226 | 4 | 1005 | ATTTAGTAGCCAACTATAGA | 26 | 67 |
| 387877 | 4 | 1170 | AGAGACTTCCATTTCTTTCC | 81 | 68 |
| 387878 | 4 | 1176 | AGAAGGAGAGACTTCCATTT | 41 | 69 |
| 387879 | 4 | 1184 | TGCTCTGCAGAAGGAGAGAC | 46 | 70 |
| 387880 | 4 | 1201 | CATAAACCTGGACAAGCTGC | 79 | 71 |
| 387881 | 4 | 1208 | GTCAGTTCATAAACCTGGAC | 72 | 72 |
| 387882 | 4 | 1241 | ACATTGTGGTCTTGGTGCTG | 51 | 73 |
| 387883 | 4 | 1460 | AAGAGCACTTTGCCTTTTTG | 66 | 74 |
| 388227 | 4 | 1596 | TGCTGACCCTGGAGTGGAAA | 78 | 75 |
| 388228 | 4 | 1666 | TGGCCAGATCCACTGAGTCC | 30 | 76 |
| 387884 | 4 | 1775 | TCATTCAGGTCCATGGCAGG | 61 | 77 |
| 387885 | 4 | 1782 | GGTCCCATCATTCAGGTCCA | 68 | 78 |
| 387886 | 4 | 1876 | CTAACACAATTTCAGAACTG | 73 | 79 |
| 388229 | 4 | 1990 | TGGAAGAGTTCCTGAAGGCC | 29 | 80 |
| 388230 | 4 | 2022 | GTTTTTCAATAAATGTGCCT | 58 | 81 |
| 388231 | 4 | 2034 | GCAGTGACTCATGTTTTTCA | 60 | 82 |
| 388232 | 4 | 2039 | TGCCTGCAGTGACTCATGTT | 37 | 83 |
| 388233 | 4 | 2346 | GTCAAGAGGAACTTTATAGA | 55 | 84 |
| 387887 | 4 | 2400 | ATCGATGTAGTTCAAGATGT | 29 | 85 |
| 387888 | 4 | 2447 | GTCCCACAGAGAATGGCAGT | 73 | 86 |
| 388234 | 4 | 2677 | TGATCAGCTGCAGTCCTAAC | 1 | 87 |
| 387889 | 4 | 2820 | TGTATAATGATGAGCCCCTC | 76 | 88 |
| 387890 | 4 | 2971 | GATCAGCTTGTCCTTGGTCA | 81 | 89 |
| 388235 | 4 | 3183 | TCTGGTGGTTGATGTGATTA | 63 | 90 |
| 388236 | 4 | 3190 | TGAGTGCTCTGGTGGTTGAT | 26 | 91 |
| 387891 | 4 | 3203 | CAGCATCCAAATGTGAGTGC | 82 | 92 |
| 387892 | 4 | 3209 | GCTTCACAGCATCCAAATGT | 89 | 93 |
| 388237 | 4 | 3234 | GAAGGCAGTGGAAAGAAGAC | 62 | 94 |
| 387893 | 4 | 3641 | AGAGAAGGCAAGGCTGCCTT | 60 | 95 |
| 387894 | 4 | 3649 | GGTTTGTTAGAGAAGGCAAG | 63 | 96 |
| 387895 | 4 | 3851 | ACATCATGCAGTTTGAGGTA | 68 | 97 |
| 387896 | 4 | 3860 | GCTTTCAGGACATCATGCAG | 51 | 98 |
| 387897 | 4 | 4028 | AAGCAGGATTTCAGGTATCC | 78 | 99 |
| 387898 | 4 | 4036 | CTCGACTAAAGCAGGATTTC | 90 | 100 |
| 387899 | 4 | 4055 | ACAGTTGCCATCATTGGTTC | 67 | 101 |
| 388238 | 4 | 4069 | ATTGTTGAACACAAACAGTT | 50 | 102 |
| 387900 | 4 | 4127 | TTGGAAGATAAGCCATCAAA | 82 | 103 |
| 387901 | 4 | 4265 | TGCACCATGTTCCTCAGGCT | 79 | 104 |
| 387902 | 4 | 4269 | CGCCTGCACCATGTTCCTCA | 90 | 105 |
| 387903 | 4 | 4380 | AATAGCATTCTTATCTGCAC | 84 | 106 |
| 387904 | 4 | 4392 | AATGTGATTATGAATAGCAT | 64 | 107 |
| 388239 | 4 | 4458 | TAACTGCACACATGTTGTAG | 54 | 108 |
| 387905 | 4 | 4538 | AACACCTGATCTGAATCCAG | 78 | 109 |
| 388240 | 4 | 4558 | GTTTCAATACAAAGCCAATA | 78 | 110 |
| 387906 | 4 | 4586 | AACTGGCCCACTTCAATGTA | 78 | 111 |
| 387907 | 4 | 4596 | TGATTCCCTGAACTGGCCCA | 77 | 112 |
| 387908 | 4 | 4682 | TTAGGAATTCCAATGATCTG | 76 | 113 |
| 387909 | 4 | 4688 | ATGATTTTAGGAATTCCAAT | 77 | 114 |
| 387910 | 4 | 4715 | CTGGCCATGATGCCATCACA | 86 | 115 |
| 387911 | 4 | 4724 | TTCCTTCCACTGGCCATGAT | 77 | 116 |
| 387912 | 4 | 4805 | GCATCAGCTTTATTTGTTCC | 70 | 117 |
| 388241 | 4 | 4856 | CTCAGTAACATTGACACCAC | 71 | 118 |
| 388242 | 4 | 4868 | TACTGGATGAGTCTCAGTAA | 49 | 119 |
| 387913 | 4 | 4875 | CTGATGGTACTGGATGAGTC | 59 | 120 |
| 387914 | 4 | 4913 | TGGCACTGCTGCAGGACAAG | 71 | 121 |
| 387915 | 4 | 5219 | TCCTGAATACGAGAAAGAAC | 86 | 122 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388243 | 4 | 5781 | TTTGGCTGCCAAGTCAGAAT | 52 | 123 |
| 388244 | 4 | 5787 | TCCAAGTTTGGCTGCCAAGT | 48 | 124 |
| 387916 | 4 | 5801 | TCTCTATTGCACATTCCAAG | 91 | 125 |
| 387917 | 4 | 5850 | CTGACAGACATAATCACAGA | 61 | 126 |
| 387918 | 4 | 5911 | TGATCAGATCTTGAATGTGA | 41 | 127 |
| 387919 | 4 | 6005 | CGAGACTGAATTGCCTGGAT | 59 | 128 |
| 387920 | 4 | 6296 | GAATAGAGCCTTTGGTGTCT | 56 | 129 |
| 388245 | 4 | 6333 | GTCTTGCATGGTGGAGAGAC | 39 | 130 |
| 387921 | 4 | 6466 | AATCTGACCTGGTCCAACAC | 65 | 131 |
| 387922 | 4 | 6476 | AGCAGTGCAGAATCTGACCT | 53 | 132 |
| 387923 | 4 | 6488 | TCTGCACCTTCCAGCAGTGC | 62 | 133 |
| 388246 | 4 | 6600 | ACCAGAAATTTCACTCATCC | 50 | 134 |
| 388247 | 4 | 6606 | CTGGCCACCAGAAATTTCAC | 21 | 135 |
| 388248 | 4 | 6763 | CAGCATCCCCAAACAGATCA | 65 | 136 |
| 388249 | 4 | 6769 | ACAGTGCAGCATCCCCAAAC | 72 | 137 |
| 388250 | 4 | 6777 | GGACTGATACAGTGCAGCAT | 65 | 138 |
| 387924 | 4 | 6860 | TTCTCAGGAGGAAGGTGCAA | 61 | 139 |
| 387925 | 4 | 6930 | CTGCTCATGGATCAAATGCC | 78 | 140 |
| 388251 | 4 | 7177 | GTGTGTTTGGATCTACTTCC | 67 | 141 |
| 388252 | 4 | 7199 | GCAGTGATATACTTAGGATT | 46 | 142 |
| 388253 | 4 | 7208 | TCACAGGCTGCAGTGATATA | 29 | 143 |
| 388254 | 4 | 7312 | TGATGTTCCTGAGCAATGGC | 51 | 144 |
| 388255 | 4 | 7383 | TCCAAGCTTCCACACCAGTG | 67 | 145 |
| 387926 | 4 | 7489 | TGTTGATGCGGTAGATGAAC | 29 | 146 |
| 387927 | 4 | 7556 | GTCACCAGGACACCAAGGAG | 70 | 147 |
| 387928 | 4 | 7709 | TCCAAGCAGCTTACAGCTGG | 69 | 148 |
| 388256 | 4 | 7816 | TTGAAACCATTGCTTGAATC | 64 | 149 |
| 388257 | 4 | 7855 | ATGCCTGATATAAATGATGG | 52 | 150 |
| 387942 | 4 | 7932 | GTTGATCTGCAGCAGCAGCT | 39 | 151 |
| 387929 | 4 | 7988 | GAGTGTATGGACACCTGGCC | 49 | 152 |
| 387930 | 4 | 8005 | TGTTCCCCAGCCACACGGAG | 85 | 153 |
| 387931 | 4 | 8363 | GTGGCAGGCACCAGGTACTG | 65 | 154 |
| 388258 | 4 | 8655 | ATAGTTCTCAATGAGGTAAA | 72 | 155 |
| 387932 | 4 | 8757 | ACAGTGGTAAATGATGGAGG | 41 | 156 |
| 387933 | 4 | 8903 | ATGCAGGTGAGCATCAGGCC | 29 | 157 |
| 387934 | 4 | 8910 | TGTGTACATGCAGGTGAGCA | 37 | 158 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388259 | 4 | 9036 | AGGAAAGCCTTTCCTGATCC | 31 | 159 |
| 387935 | 4 | 9149 | TATGGCTGCTGGTTGGACAG | 57 | 160 |
| 387936 | 4 | 9240 | CAGCATGACCCAGTCCCGGA | 63 | 161 |
| 387937 | 4 | 9243 | GGACAGCATGACCCAGTCCC | 68 | 162 |
| 387938 | 4 | 9368 | CCCATCCTGCTGATGACATG | 69 | 163 |
| 387939 | 4 | 9407 | ACCAGGCAGAAAAGGTTCAC | 63 | 164 |
| 387940 | 4 | 9555 | TCAGCAGGTGGTGACCTTGT | 64 | 165 |
| 388260 | 4 | 9714 | TCTGCCACATGGCAGAGACA | 25 | 166 |
| 388261 | 4 | 9724 | AAAGAGCACTTCTGCCACAT | 56 | 167 |
| 388262 | 4 | 9735 | GCCACTGCCACAAAGAGCAC | 60 | 168 |
| 388263 | 4 | 9763 | CACCAGGACTGCAGACACTC | 65 | 169 |
| 388264 | 4 | 9785 | TGGAAGGCCTCAGGCTCAGC | 65 | 170 |
| 388265 | 4 | 9831 | GGACCTGGTCACCCACATGG | 22 | 171 |
| 388266 | 4 | 9863 | GGCAACAACCAGCAGGTGAC | 54 | 172 |
| 388267 | 4 | 9871 | TGCAACCTGGCAACAACCAG | 32 | 173 |
| 388268 | 4 | 9889 | CCCAGATGCAAGAGCAGCTG | 65 | 174 |
| 388269 | 4 | 9921 | AACAGCCAGCCTGCAGGAGG | 25 | 175 |
| 388270 | 4 | 9946 | TCTACTGCAGGACAGCAGAG | 20 | 176 |
| 388271 | 4 | 9973 | TGTTCCCAAAGCCTGCTCAC | 43 | 177 |
| 388272 | 4 | 9982 | CCAGGCCAGTGTTCCCAAAG | 41 | 178 |
| 388273 | 4 | 9988 | GGAGACCCAGGCCAGTGTTC | 44 | 179 |
| 388274 | 4 | 10047 | AGCACAGGCCATGGCATCTG | 43 | 180 |
| 388275 | 4 | 10054 | CTGGCCCAGCACAGGCCATG | 33 | 181 |
| 387941 | 4 | 10133 | ACTGATATAATTAAATTTTA | 0 | 182 |
| 388276 | 4 | 10274 | GGCTATGCCAGTGGCTACAG | 29 | 183 |
| 388277 | 4 | 10329 | TGTGAATGCATAAACAGGAA | 61 | 184 |
| 388278 | 4 | 10579 | CTAGCAAGGAACAGGAGTGG | 15 | 185 |
| 388279 | 4 | 10639 | CCATGGAGCAGCAGGTCCCA | 28 | 186 |
| 388280 | 4 | 10647 | GCATGCATCCATGGAGCAGC | 31 | 187 |
| 388281 | 4 | 10726 | ACTAACAGTGCCAAGACACC | 45 | 188 |
| 388282 | 4 | 10923 | CCATTTTAATGACTTGGCTC | 60 | 189 |
| 388283 | 4 | 11023 | AGGAAGCAGAGCCCCTGCCT | 48 | 190 |
| 388284 | 4 | 11150 | GGCAGCACCTGCACAGAGTT | 57 | 191 |
| 388285 | 4 | 11225 | GCATACAAGTCCACATCTCA | 54 | 192 |
| 388286 | 4 | 11293 | CATACAGGCCTGGCAGAGGC | 49 | 193 |
| 388287 | 4 | 11449 | AAGAATGGTGATTTTCTTAC | 46 | 194 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388288 | 4 | 11637 | TCTAGCCAGGAACAACATCT | 47 | 195 |
| 388289 | 4 | 11646 | ATGTAAACATCTAGCCAGGA | 24 | 196 |
| 388290 | 4 | 11854 | AATGAGCTCATATTCATCTC | 20 | 197 |
| 388291 | 4 | 12076 | GAATGAGCCCTGCCCTGACC | 38 | 198 |
| 388292 | 4 | 12081 | GCAATGAATGAGCCCTGCCC | 57 | 199 |
| 388293 | 4 | 12122 | AGCTGATATGGAGACCATCT | 35 | 200 |
| 388294 | 4 | 12177 | GGTGCTTGCCACAGATTTTT | 65 | 201 |
| 388295 | 4 | 12324 | TGCATTGCCAAACAATTCTA | 57 | 202 |
| 388296 | 4 | 12409 | TTGGCAGCTGGAAACATCAC | 52 | 203 |
| 388297 | 4 | 12873 | TCCAAGTCTACCCTGGCCAG | 40 | 204 |
| 388298 | 4 | 13044 | GTTGCCTTCAGTTGTCATGC | 34 | 205 |
| 388299 | 4 | 13050 | TTCCAGGTTGCCTTCAGTTG | 59 | 206 |
| 388300 | 4 | 13167 | CAGTTACCACCCAGATTGCA | 46 | 207 |
| 388301 | 4 | 13251 | GAGACCTGGACAAGGAGGCC | 30 | 208 |
| 388842 | 5 | 3535 | TGTAATTACAGAATTTGTAT | 60 | 209 |
| 388852 | 5 | 16048 | ACATTCCATGAATTCCATTT | 43 | 210 |
| 388846 | 5 | 17007 | GTTAATTTAGAGAAAATTCA | 1 | 211 |
| 388845 | 5 | 24805 | CAGAAGCATCCAAACCAGTA | 40 | 212 |
| 388844 | 5 | 31595 | CAAGAGGGTTGCATAGAAAC | 17 | 213 |
| 388848 | 5 | 41489 | CAAAGTATAAACAGTTTGAG | 32 | 214 |
| 388839 | 5 | 41869 | CCCAGTGCAGTTCACATTCA | 54 | 215 |
| 388859 | 5 | 46461 | TATTATAAAATACATGTTTC | 26 | 216 |
| 388856 | 5 | 58668 | ATTAGAGATTCATCATATTG | 46 | 217 |
| 388857 | 5 | 59960 | GGTATGGAAAGGTTCAACAT | 58 | 218 |
| 388858 | 5 | 64678 | TGGAAGGTGAGGGACAAAAA | 57 | 219 |
| 388862 | 5 | 71659 | AGCAGAAACAAGTATTCCAT | 56 | 220 |
| 388853 | 5 | 86173 | CAAATTCACATAGGGTTGGT | 60 | 221 |
| 388860 | 5 | 97067 | ACATGAGCAATGAAGGACAG | 48 | 222 |
| 388840 | 5 | 98221 | GCAATGTGTGATTTACCACA | 67 | 223 |
| 388850 | 5 | 118154 | ACCACATCATAATTTGTCAT | 41 | 224 |
| 388855 | 5 | 120499 | ATTATTTAAGAAGTACCCAC | 36 | 225 |
| 388861 | 5 | 121068 | TGCCCCAAAAAGTGGAACCA | 55 | 226 |
| 388847 | 5 | 126660 | ACATTTCCAAGAGGTTTTGA | 48 | 227 |
| 388854 | 5 | 128596 | TCAGCCCCAATTTGTAGCAG | 59 | 228 |
| 388841 | 5 | 140692 | GACATAAAGTTTAGAGGTAT | 50 | 229 |
| 388843 | 5 | 142578 | GAAGGACCCACAGAGGTTTG | 53 | 230 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388851 | 5 | 146457 | TGAAAAGGAAGTGACATCAT | 17 | 231 |
| 388849 | 5 | 165574 | CAGTGTCAGGAGAAGCCCAG | 46 | 232 |
| 388785 | 45 | 713 | AGGTTCTGCCTCACACAGCA | 57 | 311 |
| 388786 | 45 | 718 | CCCGCAGGTTCTGCCTCACA | 33 | 312 |
| 388787 | 45 | 740 | AGGGAACCAGCCCGCCCCTG | 56 | 313 |
| 388788 | 45 | 745 | TGGCCAGGGAACCAGCCCGC | 47 | 314 |
| 388789 | 45 | 750 | ATGGCTGGCCAGGGAACCAG | 25 | 315 |
| 388790 | 45 | 755 | TGCCAATGGCTGGCCAGGGA | 7 | 316 |
| 388791 | 45 | 777 | GACAGCCCTAGCCTGCGGAC | 19 | 317 |
| 388792 | 45 | 781 | GATTGACAGCCCTAGCCTGC | 0 | 318 |
| 388793 | 45 | 785 | GCATGATTGACAGCCCTAGC | 9 | 319 |
| 388794 | 45 | 885 | ATCTTGGACCCGTCCCGGCA | 63 | 320 |
| 388795 | 45 | 890 | CGTCCATCTTGGACCCGTCC | 53 | 321 |
| 388796 | 45 | 896 | AGCGGCCGTCCATCTTGGAC | 45 | 322 |
| 388797 | 45 | 902 | AACCTGAGCGGCCGTCCATC | 54 | 323 |
| 388798 | 45 | 906 | GCAGAACCTGAGCGGCCGTC | 62 | 324 |
| 388799 | 45 | 910 | AAAAGCAGAACCTGAGCGGC | 56 | 325 |
| 388800 | 45 | 913 | GGTAAAAGCAGAACCTGAGC | 36 | 326 |
| 388801 | 45 | 920 | GGCCGCAGGTAAAAGCAGAA | 65 | 327 |
| 388802 | 45 | 926 | GCTCTGGGCCGCAGGTAAAA | 64 | 328 |
| 388803 | 45 | 985 | AGTCCCCGGAGGCCTCGGGC | 56 | 329 |
| 388804 | 45 | 993 | GGCACGGCAGTCCCCGGAGG | 57 | 330 |
| 388805 | 45 | 1019 | AGGGTCGCCATGGCGGTCTC | 35 | 331 |
| 388806 | 45 | 1025 | TTTTCCAGGGTCGCCATGGC | 33 | 332 |
| 388807 | 45 | 1030 | TCAGCTTTTCCAGGGTCGCC | 63 | 333 |
| 388808 | 45 | 1034 | TTCATCAGCTTTTCCAGGGT | 54 | 334 |
| 388809 | 45 | 1040 | AAGGCCTTCATCAGCTTTTC | 48 | 335 |
| 388810 | 45 | 1045 | ACTCGAAGGCCTTCATCAGC | 57 | 336 |
| 388811 | 45 | 1050 | GAGGGACTCGAAGGCCTTCA | 51 | 337 |
| 388812 | 45 | 1056 | GGACTTGAGGGACTCGAAGG | 62 | 338 |
| 388836 | 45 | 1494 | CTGAGGAAGCTGAGGAGGCG | 45 | 339 |
| 388837 | 45 | 1511 | TGTGCCTGCGGCGGCGGCTG | 61 | 340 |
| 388838 | 45 | 1523 | GGCAGCAGCGGCTGTGCCTG | 53 | 341 |
| 388813 | 45 | 1607 | CAAACTCACGGTCGGTGCAG | 58 | 342 |
| 388814 | 45 | 1614 | GCGGGCCCAAACTCACGGTC | 51 | 343 |
| 388815 | 45 | 1623 | GGAGCTGCAGCGGGCCCAAA | 39 | 344 |

TABLE 4-continued

Inhibition of huntingtin mRNA levels by chimeric oligonucleotides having 2'-MOE wings and deoxy gap

| ISIS # | Target SEQ ID NO | 5' Target Site | Sequence (5' to 3') | % Inhib | SEQ ID NO |
|---|---|---|---|---|---|
| 388816 | 45 | 1650 | GCCGTAGCCTGGGACCCGCC | 77 | 345 |
| 388817 | 45 | 1670 | GCAGGGTTACCGCCATCCCC | 70 | 346 |
| 388818 | 45 | 1675 | AGGCTGCAGGGTTACCGCCA | 66 | 347 |
| 388819 | 45 | 1680 | CCCGCAGGCTGCAGGGTTAC | 53 | 348 |
| 388820 | 45 | 1685 | GCCGGCCCGCAGGCTGCAGG | 49 | 349 |
| 388821 | 45 | 1773 | AAGGCCTCGCCCCAGGAGGG | 46 | 350 |
| 388822 | 45 | 1807 | AGACCCAAGTGAGGGAGCGG | 65 | 351 |
| 388823 | 45 | 1813 | AAGGGAAGACCCAAGTGAGG | 44 | 352 |
| 388824 | 45 | 1817 | GGACAAGGGAAGACCCAAGT | 68 | 353 |
| 388825 | 45 | 1825 | TCGCGAGAGGACAAGGGAAG | 24 | 354 |
| 388826 | 45 | 1830 | TCCCCTCGCGAGAGGACAAG | 59 | 355 |
| 388827 | 45 | 1850 | GGCCCCAACAAGGCTCTGCC | 58 | 356 |
| 388828 | 45 | 1855 | GGACAGGCCCCAACAAGGCT | 61 | 357 |

Mouse Huntingtin

Antisense oligonucleotides were designed to target different regions of the mouse huntingtin gene, using published sequences cited in Table 2. The sequences and corresponding SEQ ID NOs are shown in Table 5. All compounds in Table 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl)nucleotides, also known as 2'-MOE nucleotides. The internucleoside (backbone) linkages are phosphorothioate throughout the oligonucleotide. All cytidine residues are 5-methylcytidines.

The antisense oligonucleotides were analyzed for their effect on huntingtin mRNA levels in b.END cells by quantitative real-time PCR as described in other examples herein. The data presented in Table 5 represent percent inhibition of huntingtin mRNA levels relative to untreated cells. Data are averages from experiments in which cultured cells were treated with the disclosed antisense oligonucleotides.

If the huntingtin mRNA level in antisense oligonucleotide-treated cells was equal to or higher than in control cells, percent inhibition is expressed as zero inhibition. If present, "N.D." indicates "not determined." The target regions to which these antisense oligonucleotides are inhibitory are herein referred to as "validated target segments."

TABLE 5

Inhibition of mouse huntingtin mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 387869 | 8 | 517 | GAATCCATCAAAGCTTTGAT | 46 | 58 |
| 387884 | 8 | 1684 | TCATTCAGGTCCATGGCAGG | 54 | 77 |
| 387913 | 8 | 4787 | CTGATGGTACTGGATGAGTC | 32 | 120 |
| 387865 | 10 | 177 | GCCTTCATCAGCTTTTCCAG | 35 | 47 |
| 387866 | 10 | 394 | ATGATTCACACGGTCTTTCT | 38 | 55 |
| 387867 | 10 | 451 | AAATTCTGGAGAATTTCTGA | 22 | 56 |
| 387868 | 10 | 459 | AGTTTCTGAAATTCTGGAGA | 39 | 57 |
| 387870 | 10 | 583 | CCTTGGAAGATTAGAATCCA | 41 | 59 |
| 387871 | 10 | 671 | GAGCCAGCTCAGCAAACCTC | 34 | 60 |
| 387872 | 10 | 680 | GAACCAGGTGAGCCAGCTCA | 23 | 61 |
| 387874 | 10 | 783 | ACAGCTGCAGCCAAGGTCTC | 52 | 63 |
| 387875 | 10 | 807 | CCAAAAGAAGCCATAATTTT | 19 | 64 |
| 387876 | 10 | 838 | AACCTTAATTTCATTGTCAT | 42 | 65 |
| 387877 | 10 | 1132 | AGAGACTTCCATTTCTTTCC | 51 | 68 |
| 387878 | 10 | 1138 | AGAAGGAGAGACTTCCATTT | 24 | 69 |
| 387879 | 10 | 1146 | TGCTCTGCAGAAGGAGAGAC | 17 | 70 |
| 387880 | 10 | 1163 | CATAAACCTGGACAAGCTGC | 34 | 71 |
| 387882 | 10 | 1203 | ACATTGTGGTCTTGGTGCTG | 70 | 73 |
| 387883 | 10 | 1422 | AAGAGCACTTTGCCTTTTTG | 52 | 74 |
| 387885 | 10 | 1744 | GGTCCCATCATTCAGGTCCA | 44 | 78 |
| 387887 | 10 | 2365 | ATCGATGTAGTTCAAGATGT | 39 | 85 |
| 387888 | 10 | 2412 | GTCCCACAGAGAATGGCAGT | 31 | 86 |
| 387889 | 10 | 2785 | TGTATAATGATGAGCCCCTC | 48 | 88 |
| 387890 | 10 | 2936 | GATCAGCTTGTCCTTGGTCA | 55 | 89 |
| 387891 | 10 | 3168 | CAGCATCCAAATGTGAGTGC | 52 | 92 |
| 387892 | 10 | 3174 | GCTTCACAGCATCCAAATGT | 46 | 93 |
| 387893 | 10 | 3606 | AGAGAAGGCAAGGCTGCCTT | 46 | 95 |
| 387894 | 10 | 3614 | GGTTTGTTAGAGAAGGCAAG | 43 | 96 |
| 387895 | 10 | 3816 | ACATCATGCAGTTTGAGGTA | 57 | 97 |
| 387896 | 10 | 3825 | GCTTTCAGGACATCATGCAG | 38 | 98 |
| 387897 | 10 | 3993 | AAGCAGGATTTCAGGTATCC | 60 | 99 |
| 387898 | 10 | 4001 | CTCGACTAAAGCAGGATTTC | 48 | 100 |
| 387899 | 10 | 4020 | ACAGTTGCCATCATTGGTTC | 35 | 101 |
| 387900 | 10 | 4092 | TTGGAAGATAAGCCATCAAA | 41 | 103 |
| 387901 | 10 | 4230 | TGCACCATGTTCCTCAGGCT | 64 | 104 |
| 387902 | 10 | 4234 | CGCCTGCACCATGTTCCTCA | 47 | 105 |

TABLE 5-continued

Inhibition of mouse huntingtin mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 387903 | 10 | 4345 | AATAGCATTCTTATCTGCAC | 46 | 106 |
| 387904 | 10 | 4357 | AATGTGATTATGAATAGCAT | 25 | 107 |
| 387905 | 10 | 4503 | AACACCTGATCTGAATCCAG | 29 | 109 |
| 387906 | 10 | 4551 | AACTGGCCCACTTCAATGTA | 64 | 111 |
| 387908 | 10 | 4647 | TTAGGAATTCCAATGATCTG | 74 | 113 |
| 387909 | 10 | 4653 | ATGATTTTAGGAATTCCAAT | 28 | 114 |
| 387910 | 10 | 4680 | CTGGCCATGATGCCATCACA | 27 | 115 |
| 387911 | 10 | 4689 | TTCCTTCCACTGGCCATGAT | 38 | 116 |
| 387912 | 10 | 4770 | GCATCAGCTTTATTTGTTCC | 45 | 117 |
| 387914 | 10 | 4878 | TGGCACTGCTGCAGGACAAG | 73 | 121 |
| 387915 | 10 | 5184 | TCCTGAATACGAGAAAGAAC | 8 | 122 |
| 387916 | 10 | 5763 | TCTCTATTGCACATTCCAAG | 59 | 125 |
| 387917 | 10 | 5812 | CTGACAGACATAATCACAGA | 55 | 126 |
| 387918 | 10 | 5873 | TGATCAGATCTTGAATGTGA | 69 | 127 |
| 387919 | 10 | 5967 | CGAGACTGAATTGCCTGGAT | 73 | 128 |
| 387920 | 10 | 6258 | GAATAGAGCCTTTGGTGTCT | 53 | 129 |
| 387921 | 10 | 6428 | AATCTGACCTGGTCCAACAC | 4 | 131 |
| 387922 | 10 | 6438 | AGCAGTGCAGAATCTGACCT | 16 | 132 |
| 387924 | 10 | 6822 | TTCTCAGGAGGAAGGTGCAA | 26 | 139 |
| 387925 | 10 | 6892 | CTGCTCATGGATCAAATGCC | 43 | 140 |
| 387926 | 10 | 7445 | TGTTGATGCGGTAGATGAAC | 8 | 146 |
| 387927 | 10 | 7512 | GTCACCAGGACACCAAGGAG | 47 | 147 |
| 387928 | 10 | 7665 | TCCAAGCAGCTTACAGCTGG | 31 | 148 |
| 387942 | 10 | 7888 | GTTGATCTGCAGCAGCAGCT | 54 | 151 |
| 387930 | 10 | 7961 | TGTTCCCCAGCCACACGGAG | 53 | 153 |
| 387931 | 10 | 8319 | GTGGCAGGCACCAGGTACTG | 62 | 154 |
| 387932 | 10 | 8713 | ACAGTGGTAAATGATGGAGG | 51 | 156 |
| 387933 | 10 | 8859 | ATGCAGGTGAGCATCAGGCC | 64 | 157 |
| 387934 | 10 | 8866 | TGTGTACATGCAGGTGAGCA | 45 | 158 |
| 387935 | 10 | 9105 | TATGGCTGCTGGTTGGACAG | 43 | 160 |
| 387936 | 10 | 9196 | CAGCATGACCCAGTCCCGGA | 53 | 161 |
| 387937 | 10 | 9199 | GGACAGCATGACCCAGTCCC | 34 | 162 |
| 387938 | 10 | 9324 | CCCATCCTGCTGATGACATG | 41 | 163 |
| 387939 | 10 | 9363 | ACCAGGCAGAAAAGGTTCAC | 28 | 164 |
| 387940 | 10 | 9511 | TCAGCAGGTGGTGACCTTGT | 54 | 165 |
| 387941 | 10 | 10042 | ACTGATATAATTAAATTTTA | 3 | 182 |

TABLE 5-continued

Inhibition of mouse huntingtin mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 387873 | 11 | 39021 | TTCACCAGGTAAGGCCTGCA | 28 | 62 |
| 387881 | 11 | 46216 | GTCAGTTCATAAACCTGGAC | 57 | 72 |
| 387886 | 11 | 52829 | CTAACACAATTTCAGAACTG | 25 | 79 |
| 388535 | 11 | 64098 | GATAAAACACCTTGTTAATG | 0 | 233 |
| 388536 | 11 | 74028 | GGAGCAGTACCTTATAGTTG | 0 | 234 |
| 388467 | 11 | 85701 | ATAGCTGCTGCACACAGACA | 37 | 235 |
| 387907 | 11 | 90911 | TGATTCCCTGAACTGGCCCA | 77 | 112 |
| 388534 | 11 | 90914 | GCATCAGTACCTGAACTGGC | 18 | 236 |
| 388532 | 11 | 116664 | GAGTGGTTGGCTAATGTTGA | 26 | 237 |
| 387923 | 11 | 119259 | TCTGCACCTTCCAGCAGTGC | 25 | 133 |
| 387929 | 11 | 138172 | GAGTGTATGGACACCTGGCC | 64 | 152 |
| 388533 | 11 | 142848 | CAGTTTTGTCCTGGATACAA | 0 | 238 |
| 388459 | 44 | 962 | GGAGCCAGTTGTAGAAGTAC | 4 | 239 |
| 388460 | 44 | 1284 | CCTGGTGTGGTCAGTGCTTG | 39 | 240 |
| 388461 | 44 | 1306 | CAGAGTGAGCTGCCCAAGCC | 18 | 241 |
| 388462 | 44 | 1317 | TCTTCTTGAACCAGAGTGAG | 29 | 242 |
| 388463 | 44 | 1948 | GTTTCTGAAAACATCTGAGA | 13 | 243 |
| 388464 | 44 | 1998 | CTATGGCCCATTCTTTCCAA | 33 | 244 |
| 388465 | 44 | 2642 | TAAGCAGTTGTAATCCCAAG | 7 | 245 |
| 388466 | 44 | 3690 | GGACTCATTGGAGTAGAAGC | 34 | 246 |
| 388468 | 44 | 5944 | AAGACCACTAGCTGCAGAAT | 29 | 247 |
| 388469 | 44 | 6735 | TGGTATGATGTGGTATCACC | 53 | 248 |
| 388470 | 44 | 6855 | GTCATTACCACAAACTTCAC | 20 | 249 |
| 388471 | 44 | 7145 | GACTGAGGTTTTGTATATCT | 19 | 250 |
| 388472 | 44 | 7269 | ACAATGTTCTTCAGCACAGC | 24 | 251 |
| 388473 | 44 | 8515 | CAGCAGATAGTCACTAACAA | 20 | 252 |
| 388474 | 44 | 9228 | ACTGGAGTTCTTTGTGTGAA | 25 | 253 |
| 388475 | 44 | 9519 | GGCACTACTCAGCAGGTGGT | 49 | 254 |
| 388476 | 44 | 9532 | CTTTTGTCCCACAGGCACTA | 20 | 255 |
| 388477 | 44 | 9630 | CTTGACACAAGTGGAAGCCT | 15 | 256 |
| 388478 | 44 | 9676 | GCATAGCCCTCATTGCAAAG | 40 | 257 |
| 388479 | 44 | 9691 | TAGTGCATGTTCCCTGCATA | 45 | 258 |
| 388480 | 44 | 9701 | AACCCCAACATAGTGCATGT | 16 | 259 |
| 388481 | 44 | 9770 | AAGACAAACACCTGGTCAAC | 13 | 260 |
| 388482 | 44 | 9855 | AACCATCTGGCAAGAGCTAG | 23 | 261 |
| 388483 | 44 | 9924 | TGTGGCAGGTATGCCTACTG | 14 | 262 |

TABLE 5-continued

Inhibition of mouse huntingtin mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 388484 | 44 | 9932 | GACACTGGTGTGGCAGGTAT | 36 | 263 |
| 388485 | 44 | 10102 | CTTGCCAAGTCACACACTTT | 19 | 264 |
| 388486 | 44 | 10135 | ACTTCCATAAACTTTGTCAC | 7 | 265 |
| 388487 | 44 | 10181 | GACTGAGTAGCTACAGGAGA | 40 | 266 |
| 388488 | 44 | 10275 | TGCTGGCTTAATGGAATGCA | 34 | 267 |
| 388489 | 44 | 10315 | GGATTCTCACACAGGCAGTC | 39 | 268 |
| 388490 | 44 | 10330 | GTTAGGCCACAGGCAGGATT | 30 | 269 |
| 388491 | 44 | 10348 | CAGTTTTTCAGTTCCTCAGT | 51 | 270 |
| 388492 | 44 | 10370 | TTATAACTCTAACAGTGGAA | 24 | 271 |
| 388493 | 44 | 10460 | CTAGGAGAGTGCATCAACAC | 38 | 272 |
| 388494 | 44 | 10480 | TTTCTACCCAGGCTGAGAGA | 30 | 273 |
| 388495 | 44 | 10550 | CTACAGTGCAGGTCAGCCAC | 42 | 274 |
| 388496 | 44 | 10582 | CATCCACAATGGTCAGCTGG | 30 | 275 |
| 388497 | 44 | 10616 | CCCAACCATGCAGAAGATAC | 17 | 276 |
| 388498 | 44 | 10634 | GGTCAGCACTTCTCAGGTCC | 50 | 277 |
| 388499 | 44 | 10950 | TTAACATGACCTGGTTACTC | 27 | 278 |
| 388500 | 44 | 10988 | CCCAAACCAAGCCAGGAAAT | 19 | 279 |
| 388501 | 44 | 11020 | CTTGGTCATATAGTCAAACA | 43 | 280 |
| 388502 | 44 | 11140 | TAATCACAGGCTGCAAGCTC | 28 | 281 |
| 388503 | 44 | 11170 | AAGCAATCCATGGACTGAAG | 52 | 282 |
| 388504 | 44 | 11211 | GTCATGATGGAAAGATAGAG | 35 | 283 |
| 388505 | 44 | 11240 | AACCTTGCATCCCAGCAGCA | 12 | 284 |
| 388506 | 44 | 11300 | GGCAGATAGGAGGAGAGTCA | 19 | 285 |
| 388507 | 44 | 11407 | GGTGAATTTCTTTCATTAAA | 53 | 286 |
| 388508 | 44 | 11525 | TTGGACCAACCTCAGAGTGT | 45 | 287 |
| 388509 | 44 | 11560 | GTAATCAGGCCTGCACCATG | 41 | 288 |
| 388510 | 44 | 11575 | CATCTACCATGAGGAGTAAT | 15 | 289 |
| 388511 | 44 | 11611 | AATGGCTCTAGATTTTATAT | 33 | 290 |
| 388512 | 44 | 11678 | TTCTGATCACACTAAACAAG | 31 | 291 |
| 388513 | 44 | 11750 | CTAGGTTGTGGCACCCATGA | 47 | 292 |
| 388514 | 44 | 11766 | GTACCCAGGTGCATCTCTAG | 52 | 293 |
| 388515 | 44 | 11890 | TGTATGTGGCAGTTGCAAGA | 51 | 294 |
| 388516 | 44 | 11940 | ACTTTTAAAAATTGAGTCCC | 17 | 295 |
| 388517 | 44 | 12054 | TTAAATAAAGCTTGGAAATC | 8 | 296 |
| 388518 | 44 | 12132 | TGACAGTACCACCATGGAAA | 27 | 297 |
| 388519 | 44 | 12176 | GTGCATTGCCAAAAGTTCTA | 41 | 298 |
| 388520 | 44 | 12248 | AAGTCACCTACATGTCAAGG | 22 | 299 |
| 388521 | 44 | 12262 | ACTTGGCAGTGGCTAAGTCA | 21 | 300 |
| 388522 | 44 | 12377 | GTTAGGATTGGTCCCTTCCC | 18 | 301 |
| 388523 | 44 | 12527 | GACCAATTCTGCAGCCCCAC | 28 | 302 |
| 388524 | 44 | 12648 | CCATGATCCTAGTGCTCAAT | 42 | 303 |
| 388525 | 44 | 12696 | CCACATACCAATCCCTGGAG | 38 | 304 |
| 388526 | 44 | 12726 | CCAGCATCAGCAGCTCAGTG | 40 | 305 |
| 388527 | 44 | 12756 | TTTCCCAACCATGATATCCT | 7 | 306 |
| 388528 | 44 | 12846 | CCCTGAACCTTGATATCATC | 2 | 307 |
| 388529 | 44 | 12971 | TGCAGATAGGTCTCTGCCAC | 16 | 308 |
| 388530 | 44 | 13020 | TACAGCAGCAAGGCTTGGAC | 29 | 309 |
| 388531 | 44 | 13100 | GGAAATGGACAGCCAGGTCT | 44 | 310 |

Isis numbers 387865-387942 are targeted to both human and mouse huntingtin.

EXAMPLE 4

Antisense Inhibition of Human Huntingtin in A549 Cells

Several antisense oligonucleotides were selected for additional testing in A549 cells. Cells in multi-well plates were treated with various amounts of the selected antisense oligonucleotides, as indicated in the following table (n=6 treatments per antisense oligonucleotide). Following the end of the treatment period, RNA was isolated from the cells, and human huntingtin mRNA levels in each individual cell culture well were measured by quantitative, real-time PCR. The data presented in the following table (Table 6) represent the average percent inhibition for each antisense oligonucleotide (n=6 treatments), relative to untreated cells. Control oligonucleotides, having randomized nucleotide sequences not targeted to any known gene, were also tested.

TABLE 6

Dose response inhibition of human huntingtin in A549 cells

| Isis No. | 6.25 nM | 12.5 nM | 25 nM | 50 nM | 100 nM | 200 nM |
|---|---|---|---|---|---|---|
| 387892 | 97 | 91 | 77 | 68 | 45 | 28 |
| 387898 | 85 | 86 | 69 | 47 | 35 | 21 |
| 387902 | 91 | 104 | 67 | 47 | 23 | 9 |
| 387916 | 88 | 100 | 100 | 51 | 32 | 19 |
| 388227 | 86 | 92 | 114 | 80 | 69 | 58 |
| 388240 | 117 | 126 | 83 | 65 | 24 | 22 |
| 388249 | 101 | 100 | 106 | 54 | 35 | 24 |
| 388816 | 101 | 132 | 77 | 59 | 38 | 26 |
| 388817 | 92 | 97 | 84 | 69 | 50 | 30 |
| 388824 | 78 | 87 | 85 | 69 | 41 | 27 |
| 388833 | 81 | 82 | 68 | 65 | 47 | 41 |
| Control #1 | 115 | 102 | 96 | 77 | 71 | 57 |

These results demonstrate that the antisense oligonucleotides targeted to huntingtin reduced huntingtin mRNA levels in A549 cells. The control oligonucleotides were not able to effectively inhibit huntingtin mRNA levels, particularly at lower doses. The target regions to which these inhibitory antisense oligonucleotides are complementary are herein referred to as "validated target segments."

EXAMPLE 5

Antisense Inhibition of Human Huntingtin in HD Patient Cells

GMO4281

Several antisense oligonucleotides were selected for additional testing in GMO4281 fibroblasts, which originated from an HD patient. Cells in multi-well plates were treated with various amounts of the selected antisense oligonucleotides, as indicated in the following table (n=6 treatments per antisense oligonucleotide). Control oligonucleotides, having randomized nucleotide sequences not targeted to any known gene, were also tested.

Following the end of the treatment period, RNA was isolated from the cells, and human huntingtin mRNA levels in each individual cell culture well were measured by quantitative, real-time PCR. The data presented in the following table represent the average huntingtin mRNA level (n=6), relative to untreated cells, i.e. the data are expressed as percentage of control cell huntingtin mRNA levels. Percent control less than 100 indicates a reduction in huntingtin mRNA levels, whereas percent control greater than 100 indicates an increase in huntingtin mRNA levels. Percent inhibition can be calculated by subtracting the percentage of control from 100.

TABLE 7

Dose response inhibition of human huntingtin in GMO4281 fibroblasts

| | Oligonucleotide Treatment Concentration | | | | | |
|---|---|---|---|---|---|---|
| Isis # | 9.375 nM | 18.75 nM | 37.5 nM | 75.0 nM | 150.0 nM | 300.0 nM |
| 387892 | 77 | 55 | 47 | 33 | 22 | 21 |
| 387898 | 77 | 61 | 49 | 25 | 17 | 13 |
| 387902 | 87 | 58 | 52 | 27 | 17 | 13 |
| 387916 | 104 | 75 | 50 | 25 | 14 | 12 |
| 388240 | 81 | 74 | 57 | 26 | 17 | 16 |
| 388249 | 96 | 74 | 55 | 32 | 18 | 14 |
| 388816 | 86 | 61 | 48 | 26 | 14 | 12 |
| 388817 | 84 | 76 | 51 | 35 | 26 | 18 |
| 388824 | 86 | 78 | 59 | 38 | 24 | 20 |
| 388833 | 84 | 79 | 60 | 33 | 19 | 13 |
| Control #1 | 99 | 95 | 106 | 67 | 63 | 48 |
| Control #2 | 100 | 102 | 88 | 77 | 64 | 49 |

GMO4478 Cells

Several antisense oligonucleotides targeted to huntingtin were selected for additional testing in GMO4478 cells, which are fibroblasts derived from and HD patient. The testing was performed according to the procedure used for GMO4281 cells. The results are shown in the following table as average percent inhibition, relative to untreated cells.

TABLE 8

Dose response inhibition of human huntingtin in GMO4478 fibroblasts

| | Oligonucleotide Treatment Concentration | | | | |
|---|---|---|---|---|---|
| Isis No. | 9.375 nM | 18.75 nM | 37.5 nM | 75.0 nM | 150.0 nM |
| 387892 | 45 | 29 | 17 | 10 | 7 |
| 387898 | 50 | 27 | 9 | 2 | 2 |
| 387902 | 40 | 22 | 9 | 3 | 2 |
| 387916 | 60 | 39 | 18 | 6 | 3 |
| 388240 | 60 | 34 | 16 | 5 | 6 |
| 388249 | 78 | 56 | 34 | 13 | 7 |
| 388816 | 75 | 48 | 26 | 8 | 7 |
| 388817 | 70 | 52 | 37 | 38 | 32 |
| 388824 | 65 | 42 | 21 | 9 | 8 |
| 388833 | 43 | 31 | 16 | 7 | 3 |
| Control #1 | 95 | 88 | 73 | 58 | 48 |
| Control #2 | 101 | 94 | 90 | 64 | 56 |

Each of the antisense oligonucleotides targeted to human huntingtin efficiently reduced huntingtin mRNA levels, in both GMO4478 and GMO4281 fibroblasts. The control oligonucleotides were not able to effectively inhibit huntingtin mRNA levels, particularly at lower doses.

The potency of antisense oligonucleotides targeted to huntingtin is summarized in Table 9. The potency is illustrated as $IC_{50}$, which is the concentration at which a 50% reduction in huntingtin mRNA levels is observed. This table also indicates the huntingtin sequence to which the antisense oligonucleotides are complementary, as well as the corresponding 5' target site. Particular features of the region of the huntingtin sequence to which the antisense oligonucleotides are complementary are also shown. Additionally indicated is the species of huntingtin gene to which the antisense oligonucleotides are targeted. The target regions to which these inhibitory antisense oligonucleotides are complementary are herein referred to as "validated target segments."

TABLE 9

Summary of potent antisense oligonucleotides targeted to huntingtin

| | | $IC_{50}$ | | | | | |
|---|---|---|---|---|---|---|---|
| Isis No | A549 | GM04281 | GM04478 | Target SEQ ID NO | 5' Target Site | Target nucleic acid specifity | Target region within human huntingtin gene |
| 387892 | 84 | 32 | 5 | 4 | 3209 | Human-Mouse | exon 23:exon 24 |
| 387898 | 47 | 31 | 8 | 4 | 4036 | Human-Mouse-Rat | exon 30 |
| 387902 | 39 | 35 | 5 | 4 | 4269 | Human-Mouse | exon 31 |
| 387916 | 61 | 42 | 13 | 4 | 5801 | Human-Rat | exon 42 |
| 388240 | 63 | 39 | 12 | 4 | 4558 | Human; >4 mm to rodent | exon 34 |
| 388249 | 63 | 45 | 24 | 4 | 6769 | human; >5 mm to rodent | exon 48:exon 49 |
| 388816 | 69 | 34 | 19 | 45 | 1650 | targets R6/2 insert; >5 mm to mouse | intron 1 |

TABLE 9-continued

| Summary of potent antisense oligonucleotides targeted to huntingtin | | | | | | | |
|---|---|---|---|---|---|---|---|
| Isis No | A549 | $IC_{50}$ GM04281 | GM04478 | Target SEQ ID NO | 5' Target Site | Target nucleic acid specifity | Target region within human huntingtin gene |
| 388817 | 98 | 48 | 25 | 45 | 1670 | targets R6/2 insert; >5 mm to mouse | intron 1 |
| 388824 | 81 | 50 | 15 | 45 | 1817 | targets R6/2 insert; 5 mm to mouse | intron 1 |
| 388833 | 103 | 48 | 5 | 45 | 1128 | targets CAG repeat region | exon 1 |

As the antisense oligonucleotides reduced huntingtin mRNA levels in cells isolated from HD patients, the antisense oligonucleotides are candidate therapeutic agents for the reduction of huntingtin mRNA levels in vivo. In one embodiment, the antisense oligonucleotides, having demonstrated potency in vitro, are further tested in experimental animal models, including experimental models of Huntington's disease, to identify antisense oligonucleotides that may reduce huntingtin mRNA in humans. Accordingly, in one embodiment, the antisense oligonucleotides are administered at therapeutically effect amounts to a human, for the treatment or amelioration of Huntington's disease. In another embodiment, the antisense oligonucleotides are administered at therapeutically effective amounts, to delay the onset of Huntington's disease.

EXAMPLE 6

Antisense Inhibition of Huntingtin in Neuronal Cell Lines

Several antisense oligonucleotides targeted to huntingtin were selected for additional testing in huntingtin neuronal cell lines. Mouse striatum cell lines with wild-type huntingtin, STHdhQ7/7 (Q7/7), and mutant huntingtin, STHdhQ111/111 (Q111/111) were transfected with various doses of oligos 387902 and 387916, ranging from approximately 0.05 μM, to 10 μM. A 200V, 2 msec pulse in a 2 mm gap cuvette was used for electroploration transfection. One million cells were electroporated in the presence of the indicated amount of oligonucleotide. Following electroporation, the cells were plated at a density of $5\times10^4$ cells per well. The results are reported in the Table 10 as percent huntingtin mRNA as compared to no oligo control, with each concentration performed in triplicate.

TABLE 10

| Inhibition of huntingtin in mouse neuronal cell lines | | | | |
|---|---|---|---|---|
| | Q7/7 | | Q111/111 | |
| [Oligo] μM | 387902 % mHtt | 387916 % mHtt | 387902 % mHtt | 387916 % mHtt |
| 0 | 100.0 | 100.0 | 100.0 | 100.0 |
| 0.675 | 85.9 | 36.5 | 156.4 | 59.3 |
| 1.25 | 50.2 | 34.5 | 103.4 | 31.4 |
| 3 | 31.4 | 11.0 | 38.9 | 18.8 |
| 5 | 12.2 | 1.6 | 16.5 | 6.4 |
| 10 | 5.5 | 2.7 | 6.8 | 3.1 |

In subsequent studies, cells are evaluated for phenotypic response by measuring caspase activity using the Promega Apo-ONE® Homogeneous Caspase-3/7 commercial assay. Briefly, cells are plated and Lipofectin® transfected the next day. After 48 hours the media is changed to serum-free DMEM for 24 h prior to the caspase assay.

EXAMPLE 7

In vivo Antisense Inhibition of Huntingtin

In order to evaluate the effects of antisense inhibition of a gene in the central nervous system, it is beneficial to deliver antisense oligonucleotides directly to the central nervous system, for example, by intracerebroventricular (ICV), intrathecal (IT), or intraparenchymal administration. To evaluate the effects of antisense inhibition of huntingtin in the central nervous system of animals, antisense oligonucleotides targeted to huntingtin were administered to mice via ICV delivery.

ISIS 387902, 387916, 387918, 388249, 388503, 388509, and 388816 were selected for in vivo testing. Saline-treated mice were used as control animals. Each treatment or control group included four animals. Surgically implanted Alzet mini-pumps continuously infused antisense oligonucleotides into mice at a dose of 100 ug/day over a two-week period. During the treatment period, mice were monitored for any clinical changes, such as body weight changes. At the end of the treatment period, mice were sacrificed and major organs were isolated. RNA was prepared from brain and liver tissues, and subjected to quantitative real-time PCR analysis to measure the reduction in mouse huntingtin mRNA levels.

Each antisense oligonucleotide targeted to huntingtin reduced huntingtin mRNA levels in mouse brain, as shown in the following table. The species of huntingtin nucleic acid to which each antisense oligonucleotide is targeted is also shown. Mouse huntingtin mRNA levels represent the average for each treatment group and are expressed as percentage of saline control (% saline control).

TABLE 11

| In vivo antisense inhibition of mouse huntingtin | | | |
|---|---|---|---|
| Isis No. | SEQ ID NO: | Huntingtin nucleic acid target species | Huntingtin mRNA levels, % of saline control |
| 387902 | | human, mouse | 37% |
| 387916 | | human, rat (single mismatch to mouse) | 32% |
| 387918 | | human, mouse, rat | 35% |
| 388503 | | mouse | 30% |
| 388509 | | mouse | 34% |

Each of the antisense oligonucleotides shown in Table 11 reduced huntingtin mRNA levels in mouse brain following the ICV infusion period. Furthermore, ISIS 387916, which has one mismatch to mouse huntingtin, was able to reduce mouse huntingtin mRNA levels in vivo.

EXAMPLE 8

In vivo Antisense Inhibition in Models of Huntington's Disease

To evaluate the effects of antisense inhibition of huntingtin in the central nervous system of an animal model of HD, antisense oligonucleotides targeted to huntingtin are administered to R6/2 transgenic mice via ICV delivery.

ISIS 387902, 387916, 387918, 388249, 388503, 388509, and 388816 are selected for in vivo testing. Saline-treated mice are used as control animals. Each treatment or control group includes four animals. Surgically implanted Alzet mini-pumps continuously infuse antisense oligonucleotides into mice at a dose of 100 ug/day over a two-week period. During the treatment period, mice are monitored for any clinical changes, such as body weight changes as well as phenotypical behaviors related to the huntingtin transgene. At the end of the treatment period, mice are sacrificed and major organs are isolated. RNA is prepared from brain and liver tissues, and is subjected to quantitative real-time PCR analysis to measure the reduction in mouse huntingtin mRNA levels. Huntingtin protein expression in the tissue is also measured using standard Western blotting techniques.

EXAMPLE 9

Administration of Antisense Oligonucleotides to Individuals Suffering from Huntington's Disease Provided herein are methods of treating an individual suffering from Huntington's Disease (HD). Such methods comprise the administration to the cerebrospinal fluid or brain tissue of the individual a pharmaceutical composition comprising an antisense oligonucleotide targeted to huntingtin. Delivery of the pharmaceutical composition to the cerebrospinal fluid allows for contact of the antisense oligonucleotide with the cells of central nervous system tissues, including tissues affected by HD.

Individuals suffering from HD receive a diagnosis of HD from a physician. The physician's assessment includes the genetic testing of the HD gene, and a neurological examination.

A surgically implanted pump (e.g, a Medtronic SyncroMed® II pump) is used to deliver a pharmaceutical composition comprising an antisense oligonucleotide targeted to huntingtin to the cerebrospinal fluid or brain of an individual suffering from HD. The pump is surgically implanted per the procedures outlined by the manufacturer. Drug is retained in the reservoir of the pump, and is pumped at a programmed dose preferably into a catheter that is surgically intrathecally implanted.

The reservoir is loaded with a pharmaceutical composition comprising an antisense oligonucleotide targeted to huntingtin. The pharmaceutical composition is administered at an amount that yields an infusion of 8 mg to 12 mg of antisense oligonucleotide into the cerebrospinal fluid. In some embodiments, the amount of antisense oligonucleotide infused is 10 mg. Administration is for a period of at least 28 days. Individuals are monitored by a medical professional, who evaluates indicators of HD. It is clinically desirable for the administration to slow or halt the progression of HD, or prevent or slow the worsening of, or improve, a symptom or marker of HD.

EXAMPLE 10

Administration of Antisense Oligonucleotides to Individuals Susceptible to Huntington's Disease Provided herein are methods of preventing or delaying the onset of Huntington's Disease (HD) in individuals susceptible to HD. Such methods comprise the administration to the cerebrospinal fluid or brain of the individual a pharmaceutical composition comprising an antisense oligonucleotide targeted to huntingtin. Delivery of the pharmaceutical composition to the cerebrospinal fluid allows for contact of the antisense oligonucleotide with the cells of central nervous system tissues, including tissues affected by HD.

Individuals susceptible to HD are identified by a physician following genetic testing of the HD gene, and a neurological examination.

A surgically implanted pump (e.g, a Medtronic SyncroMed® II pump) is used to deliver a pharmaceutical composition comprising an antisense oligonucleotide targeted to huntingtin to the cerebrospinal fluid or brain of an individual susceptible to HD. The pump is surgically implanted per the procedures outlined by the manufacturer. Drug is retained in the reservoir of the pump, and is pumped at a programmed dose preferably into a catheter that is surgically intrathecally implanted.

The reservoir is loaded with a pharmaceutical composition comprising an antisense oligonucleotide targeted to huntingtin. The pharmaceutical composition is administered at an amount that yields an infusion of 8 mg to 12 mg of antisense oligonucleotide into the cerebrospinal fluid. In some embodiments, the amount of antisense oligonucleotide infused is 10 mg. Administration is for a period of at least 28 days. Individuals are monitored by a medical professional, who evaluates indicators of HD. It is clinically desirable for the administration to prevent or delay the onset of symptoms of HD.

What is claimed is:

1. A method of reducing expression of mutant huntingtin mRNA in a cell, comprising contacting a cell in the central nervous system of a subject with a modified oligonucleotide 12 to 35 nucleobases in length, wherein the modified oligonucleotide comprises at least 12 consecutive nucleobases of a nucleotide sequence selected from the group consisting of SEQ ID NOs 48-52, and wherein the modified oligonucleotide is 100% complementarity to SEQ ID NO. 4.

2. The method of claim 1, wherein at least one internucleoside linkage of the modified oligonucleotide is a modified internucleoside linkage.

3. The method of claim 1, wherein at least one internucleoside linkage of the modified oligonucleotide is a phosphorothioate internucleoside linkage.

4. The method of claim 1, wherein each internucleoside linkage is a phosphorothioate internucleoside linkage.

5. The method of claim 1, wherein at least one nucleoside comprises a modified sugar.

6. The method of claim 5, wherein at least one modified sugar is a bicyclic sugar.

7. The method of claim 5, wherein at least one modified sugar comprises a 2'-O-methoxyethyl moiety.

8. The method of claim 1, wherein at least one nucleoside comprises a modified nucleobase.

9. The method of claim 8, wherein the modified nucleobase is a 5-methylcytosine.

10. The method of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

11. The method of claim 10, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; and wherein each internucleoside linkage of said modified oligonucleotide is a phosphorothioate linkage.

12. The method of claim 11, wherein the modified oligonucleotide consists of 20 linked nucleosides.

13. The method of claim 1, wherein said modified oligonucleotide consists of 17 to 25 linked nucleosides.

14. The method of claim 1, wherein said modified oligonucleotide consists of 19 to 23 linked nucleosides.

15. The compound of method of claim 1, wherein said modified oligonucleotide consists of 20 linked nucleosides.

16. The method of claim 1, wherein said modified oligonucleotide comprises a nucleobase sequence selected from the group consisting of SEQ ID NO: 49, 50, and 52.

17. The method of claim 11, wherein said modified oligonucleotide comprises a nucleobase sequence selected from the group consisting of SEQ ID NO: 49, 50, and 52.

* * * * *